US012241069B2

(12) United States Patent
Farhadi et al.

(10) Patent No.: US 12,241,069 B2
(45) Date of Patent: *Mar. 4, 2025

(54) GAS VESICLE EXPRESSION SYSTEMS, GAS VESICLE CONSTRUCTS AND RELATED GENETIC CIRCUITS, VECTORS, MAMMALIAN CELLS, HOSTS, COMPOSITIONS, METHODS AND SYSTEMS

(71) Applicant: CALIFORNIA INSTITUTE OF TECHNOLOGY, Pasadena, CA (US)

(72) Inventors: Arash Farhadi, Pasadena, CA (US); Gabrielle H Ho, Pasadena, CA (US); Daniel P Sawyer, Pasadena, CA (US); Mikhail Shapiro, Pasadena, CA (US); Robert C. Hurt, Pasadena, CA (US); Mengtong Duan, Pasadena, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/317,915

(22) Filed: May 15, 2023

(65) Prior Publication Data
US 2023/0357780 A1 Nov. 9, 2023

Related U.S. Application Data

(63) Continuation of application No. 16/736,683, filed on Jan. 7, 2020, now Pat. No. 11,761,008.

(60) Provisional application No. 62/789,295, filed on Jan. 7, 2019, provisional application No. 62/895,553, filed on Sep. 4, 2019.

(51) Int. Cl.
*C12N 15/67* (2006.01)
*C07K 14/195* (2006.01)

(52) U.S. Cl.
CPC ............ *C12N 15/67* (2013.01); *C07K 14/195* (2013.01); *C12N 2510/02* (2013.01)

(58) Field of Classification Search
CPC .................................................. C12N 15/67
See application file for complete search history.

(56) References Cited

U.S. PATENT DOCUMENTS

| | | | |
|---|---|---|---|
| 11,504,438 B2 | 11/2022 | Lakshmanan et al. | |
| 11,761,008 B2 | 9/2023 | Farhadi et al. | |
| 11,786,218 B2 | 10/2023 | Sawyer et al. | |
| 12,109,440 B2 | 10/2024 | Bar-Zion et al. | |
| 2018/0030501 A1* | 2/2018 | Bourdeau | C12Q 1/10 |
| 2020/0291409 A1 | 9/2020 | Farhadi et al. | |
| 2023/0139561 A1 | 5/2023 | Bar-Zion et al. | |
| 2023/0277695 A1 | 9/2023 | Lakshmanan et al. | |

OTHER PUBLICATIONS

Aguino, Carmen F. et al; "Single component biohybrid light-emitting diodes using a white-emitting fused protein." ACS Omega (2018) 3, p. 15829-15836.
Andreev, Y., et al., "Cyanogen Bromide Cleavage of Proteins in Salt and Buffer Solutions." *Analytical Biochemistry*, 2010. 1;407(1), p. 144-146. 3 pages.
Cesaratto, Francesca et al; "Engineered tobacco etch virus (TEV) protease active in the secretory pathway of mammalian cells." J. Biotech. (2015) 212, p. 159-166.
Ciechanover, A., et al., "Ubiquitin-Mediated Proteolysis: Biological Regulation via Destruction." *BioEssays*, 2000. 22(5), p. 442-451. 10 pages.
Corrected Notice of Allowability for U.S. Appl. No. 16/656,417, filed Oct. 17, 2019, on behalf of California Institute of Technology. Mail Date: Oct. 20, 2022. 4 Pages.
Corrected Notice of Allowability issued for U.S. Appl. No. 16/736,683, filed Jan. 7, 2020, on behalf of California Institute of Technology. Mail Date: Aug. 3, 2023. 7 Pages.
Corrected Notice of Allowability issued for U.S. Appl. No. 16/736,683, filed Jan. 7, 2020, on behalf of California Institute of Technology. Mail Date: Feb. 23, 2023. 7 Pages.
Dutka, P. et al., Structure of Anabaena flos-aquae gas vesicles revealed by cryo-ET. Structure, 31, 518-528. 18 pages. May 4, 2023. Website: doi.org/10.1016/j.str.2023.03.011.
"Enzyme" definition and meaning from Merriam Webster dictionary website. (Last updated Nov. 4, 2023).
"Enzyme" Definition, Mechanisms, and Nomenclature. Last updated on Dec. 10, 2023. 13 pages. Downloaded from website: www.britannica.com/science/enzyme.
"Enzyme" from NIH: National Human Genome Research Institute. Downloaded through The Wayback Machine with a date of Jul. 9, 2019. 1 page.
Final Office Action issued for U.S. Appl. No. 17/006,591, filed Aug. 28, 2020, on behalf of California Institute of Technology. (Mail Date: Nov. 9, 2023). 21 Pages.
Herrmann, Joerg et al; "Ubiquitin and ubiquitin-like proteins in protein regulation." Circulation Research (May 2007) 100, p. 1276-1291.
Jiang et al., "Tumor imaging by means of proteolytic activation of cell penetrating peptides," PNAS vol. 101 No. 51, Dec. 21, 2004. 17862-17872 (6 pages).
Lux, Jacques et al.; "Thrombin-activatable microbubbles as potential ultrasound contrast agents for the detection of acute thrombosis." ACS Appl. Mater. Interfaces (Nov. 2017) 9(43), p. 37587-37596. 22 pages.
Non-Final Office Action for U.S. Appl. No. 17/334,953, filed May 31, 2021 on behalf of California Institute of Technology. Mailed on Oct. 19, 2023. 20 pages.

(Continued)

*Primary Examiner* — Suzanne M Noakes
(74) *Attorney, Agent, or Firm* — Steinfl + Bruno LLP

(57) ABSTRACT

Provided herein are genetically engineered gas vesicle expression systems (GVES) that are configured to express gas vesicles (GVs) in a mammalian cell, related gas vesicle polynucleotide constructs, gas vesicle reporting genetic circuits, vectors, genetically engineered mammalian cells, non-human mammalian hosts, compositions, methods and systems, which in several embodiments can be used together with contrast-enhanced imaging techniques to detect and report biological events in an imaging target site comprising a mammalian cell and/or organism.

32 Claims, 27 Drawing Sheets

Specification includes a Sequence Listing.

(56) References Cited

OTHER PUBLICATIONS

Non-Final Office Action issued for U.S. Appl. No. 16/736,683, filed Jan. 7, 2020, on behalf of California Institute of Technology. Mail Date: Apr. 8, 2022. 36 Pages.

Non-Final Office Action issued for U.S. Appl. No. 17/006,591, filed Aug. 28, 2020, on behalf of California Institute of Technology. Mail Date: Apr. 14, 2023. 39 Pages.

Notice of Allowability for U.S. Appl. No. 16/736,581, filed Jan. 7, 2020 on behalf of California Institute of Technology Mail Date: Jul. 19, 2023 8 pages.

Notice of Allowance for U.S. Appl. No. 16/736,581, filed Jan. 7, 2020 on behalf of California Institute of Technology Mail Date: Jun. 16, 2023. 11 pages.

Notice of Allowance for U.S. Appl. No. 17/816,373, filed Jul. 29, 2022 on behalf of California Institute of Technology, mailed on Jun. 8, 2023. 13 pages.

Notice of Allowance issued for U.S. Appl. No. 16/736,683, filed Jan. 7, 2020, on behalf of California Institute of Technology. Mail Date: Jan. 6, 2023. 11 Pages.

Notice of Allowance issued for U.S. Appl. No. 16/736,683, filed Jan. 7, 2020, on behalf of California Institute of Technology. Mail Date: May 31, 2023. 11 Pages.

Notice of Allowance issued for U.S. Appl. No. 17/816,373, filed Jul. 29, 2022 on behalf of California Institute of Technology. Mail Date: Dec. 4, 2023. 10 pages.

Perona, J. et al. "Structural basis of substrate specificity in the serine proteases", Protein Science, (1995), 4, 337-360. Cambridge University Press.

Restriction Requirement for U.S. Appl. No. 16/736,683, filed Jan. 7, 2020 on behalf of California Institute of Technology Mail Date: Sep. 14, 2021 8 pages.

Supplemental Notice of Allowability for U.S. Appl. No. 16/736,581, filed Jan. 7, 2020 on behalf of California Institute of Technology Mail Date: Feb. 13, 2023 3 pages.

The PubChem database entry for "Cyanogen Bromide", (downloaded Nov. 2, 2023). 89 pages.

"Thrombin" from Wikipedia, the online encyclopedia, downloaded from The Wayback Machine for Mar. 23, 2018. 24 pages.

To, Tsz-Leung et al; "Rationally designed fluorogenic protease reporter visualizes spatiotemporal dynamics of apoptosis in vivo." PNAS (Mar. 2015) 112(11), p. 3338-3343.

Waldner, B.J. et al. "Electrostatic recognition in substrate binding to serine proteases", Journal of Molecular Recognition 31, e2727.10 (2018), 12 pages. Website: doi.org/10/1002/jmr.2727.

Carson, M., et al., "His-tag impact on structure," Acta Cryst. (2007). D63, 295-301. 7 pages.

"Enzyme" Definition, Mechanisms, and Nomenclature. Last updated on Mar. 4, 2024. 13 pages. Downloaded from website: www.britannica.com/science/enzyme. Retrieved Mar. 29, 2024.

Final Office Action for U.S. Appl. No. 17/334,953, filed May 31, 2021 on behalf of California Institute of Technology. Mailed on Mar. 7, 2024. 16 pages.

National Human Genome Research Institute, "Enzyme-less DNA base discrimination using solid-state nanopores with high-frequency integrated detection electronics" Project Description (Project End date: Jun. 30, 2019). Retrieved Mar. 29, 2024. Abstract Only. 5 pages.

Anderson, Caleb F. et al, "Protease sensitive nanomaterials for cancer therapeutics and imaging." Ind. Eng. Chem. Res. (Apr. 24, 2017) 56, pp. 5761-5777. 17 Pages.

Certification Statement and List—37 CFR 1.98(d)(1) filed in U.S. Appl. No. 18/317,915, filed May 15, 2023 on behalf of California Institute of Technology. 1 page.

Dos Santos, Nancy, et al, "Influence of poly(ethylene glycol) grafting density and polymer length on liposomes: relating plasma circulation lifetimes to protein binding." Biochim. Biophys. Acta (2007) 1768, p. 1367-1377. 11 pages.

Dutka, P. et al., Supplemental Information—Structure of Anabaena flos-aquae gas vesicles revealed by cryo-ET. Structure, 31, 20 pages. May 4, 2023.

"Enzyme" Definition, Mechanisms, and Nomenclature, from Encyclopaedia Britannica (Britannica.com). 3 pages. Downloaded through the Wayback Machine for Jun. 29, 2019.

Final Office Action issued for U.S. Appl. No. 17/006,591, filed Aug. 28, 2020, on behalf of California Institute of Technology. Mail Date: Jul. 18, 2024. 24 Pages.

Green, Anthony et al, "In vitro testing of a protease sensitive contrast agent for optoacoustic imaging." J. Biomed. Optics (Mar./Apr. 2010) 15(2) 021315. 8 pages.

Law, Benedict et al., "Protease sensitive fluorescent nanofibers." Bioconj. Chem. (2007) 18, p. 1701-1704.

Non-Final Office Action for U.S. Appl. No. 18/046,881, filed Oct. 14, 2022 on behalf of California Instititute of Technology. Mailed on Jul. 15, 2024. 14 pages.

Non-Final Office Action for U.S. Appl. No. 17/816,373, filed Jul. 29, 2022 on behalf of California Institute of Technology. Mailed on Jul. 15, 2024. 14 pages. Notice of Allowability issued for U.S. Appl. No. 17/816,373, filed Jul. 29, 2022 on behalf of California Institute of Technology. Mail Date: Jun. 25, 2024. 5 pages.

Notice of Allowability issued for U.S. Appl. No. 17/816,373, filed Jul. 29, 2022 on behalf of California Institute of Technology. Mail Date: Sep. 13, 2024. 5 pages.

Notice of Allowance for U.S. Appl. No. 17/334,953, filed May 31, 2021 on behalf of California Institute of Technology. Mailed on Sep. 27, 2024. 9 pages.

Notice of Allowance issued for U.S. Appl. No. 17/816,373, filed Jul. 29, 2022 on behalf of California Institute of Technology. Mail Date: Jun. 4, 2024. 11 pages.

Sciencelearn web page on enzymes in laundry detergent: website web.archive.org/web/20170521005639/https://www.sciencelearn.org.nz/resources/1947- enzymes-in-washing-powders. According to USPTO examiner in U.S. Appl. No. 17/006,591, available at least by 2017. 4 pages.

Tang, Haichao et al, "The analysis of key factors related to ADSs structural design." Front. Pharmacol. (Apr. 2019) 10:373. 11 pages.

* cited by examiner

γ-Proteobacteria

*Serratia sp.* ATCC39006

*Psychromonas ingrahamii* 37

*Legionella drancourtii* LLAP12

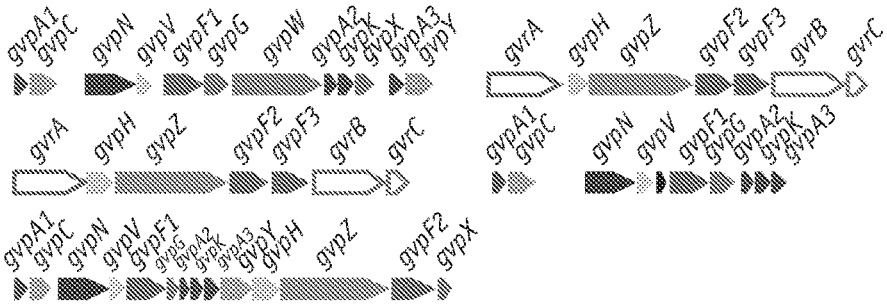

δ-Proteobacteria

*Desulfomonile tiedjei* DCB-1

β-Proteobacteria

*Burkholderia thailandensis* MSMB43

α-Proteobacteria

*Bradyrhizobium oligotrophicum* S58

*Rhodobacter capsulatus* SB1003

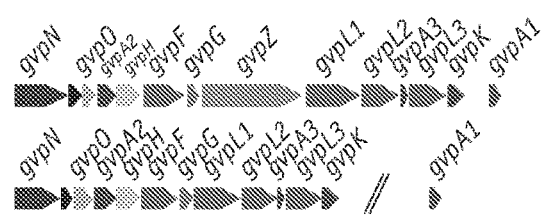

Cyanobacteria

*Anabaena flos-aquae* CCAP 1403/13F

1 kb

Firmicutes

*Bacillus megaterium* DSM319

Actinobacteria

*Rhodococcus jostii* RHA1

*Streptomyces coelicolor* A3(2)

Archaea

*Halobacterium salinarum* PHH1

FIG. 5

Archaea
Halobacterium sp. NRC-1 pNRC200
Halobacterium sp. NRC-1 pNRC100
Halobacterium mediterranei c-vac
Natronobacterium vacuolatum
Methanosarcina barkeri

Cyanobacteria
Anabaena flos-aquae
Nostoc sp. ATCC29413
Pseudoanabaena sp. PCC6901
Microcystis aeruginosa
Trichodesmium erythraeum

Actinomycetes
Streptomyces coelicolor gvp1
Streptomyces coelicolor gvp2
Streptomyces avermitilis gvp1
Streptomyces avermitilis gvp2
Streptomyces avermitilis gvp3
Streptomyces scabies gvp1
Streptomyces scabies gvp2
Streptomyces peucetius gvp1
Streptomyces peucetius gvp2
Streptomyces diversea™ gvp1
Streptomyces diversa™ gvp2
Saccharopolyspora erythraea
Frankia alni
Frankia sp. EAN1pec
Frankia sp. Ccl3
Rhodococcus sp. RHA1 gvp1
Rhodococcus sp. RHA1 gvp2
Rhodococcus equi

Other bacteria
Bacillus megaterium
Rhodobacter sphaeroides
Ancylobacter aquaticus

*FIG. 6*

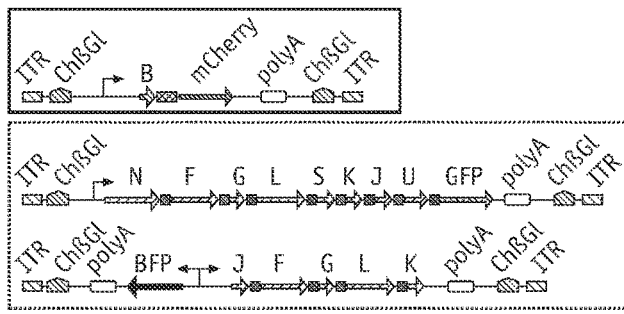
FIG. 11A
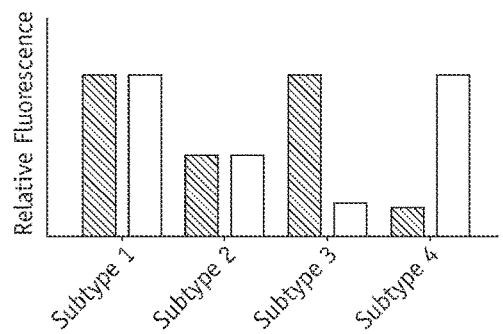
FIG. 11C
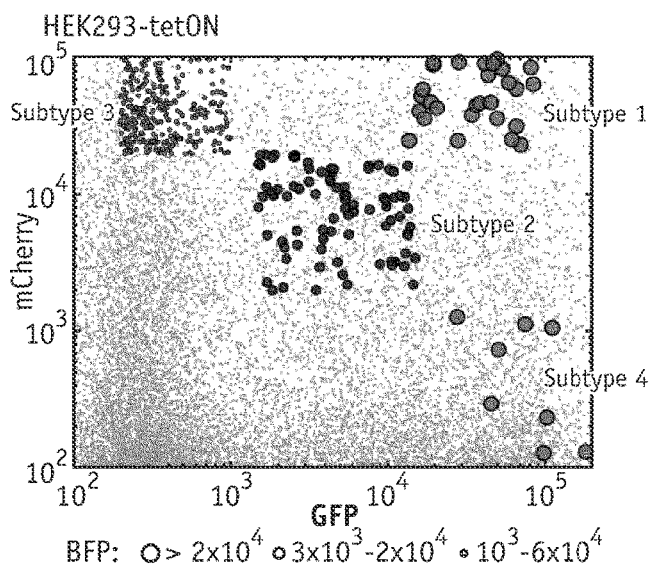
FIG. 11B
| Subtype 1 (GV/Cell) | Subtype 2 (GV/Cell) | Subtype 3 (GV/Cell) | Subtype 4 (GV/Cell) |
|---|---|---|---|
| ~0.25 | ~0.002 | ~0.001 | ~0.0005 |
FIG. 11D
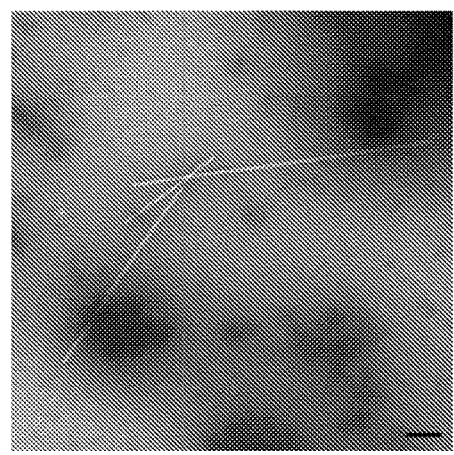
FIG. 11F
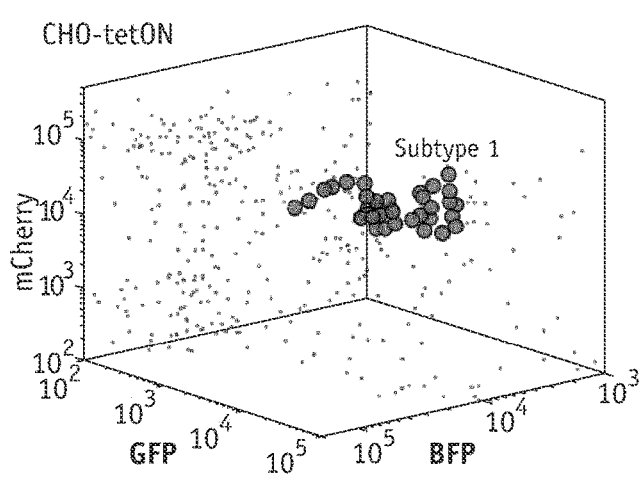
FIG. 11E
| Subtype 1 (GV/Cell) |
|---|
| ~0.1 |
FIG. 11G

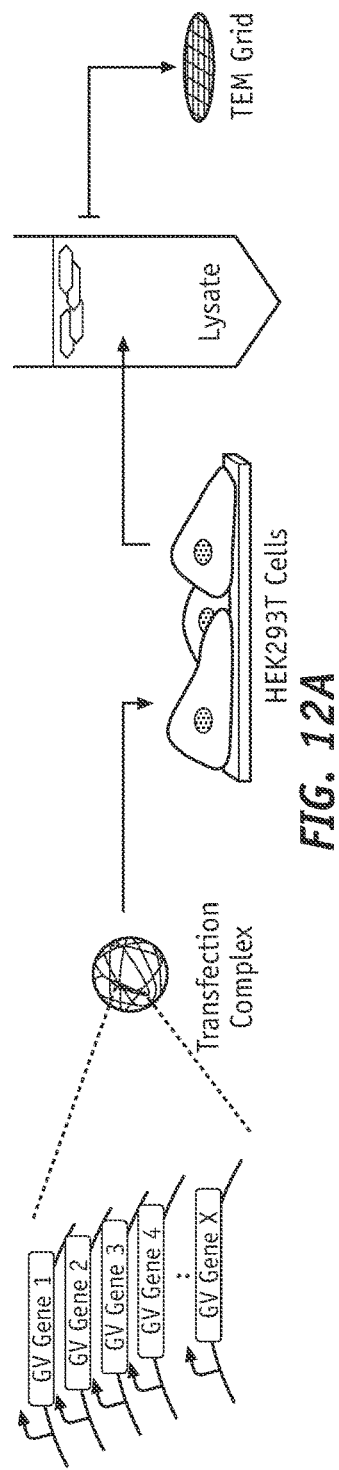
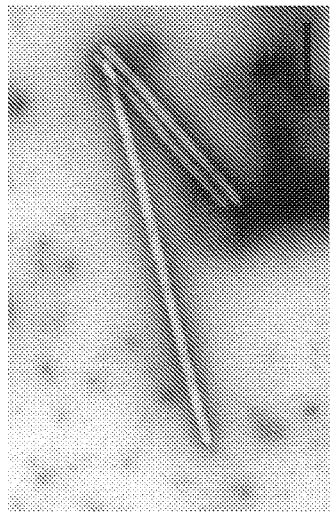
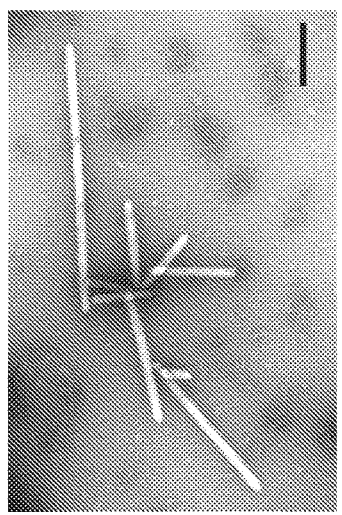
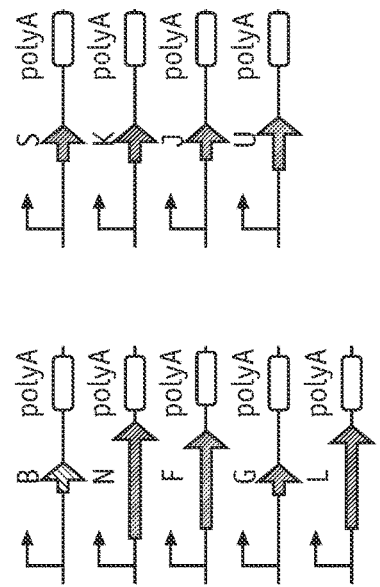
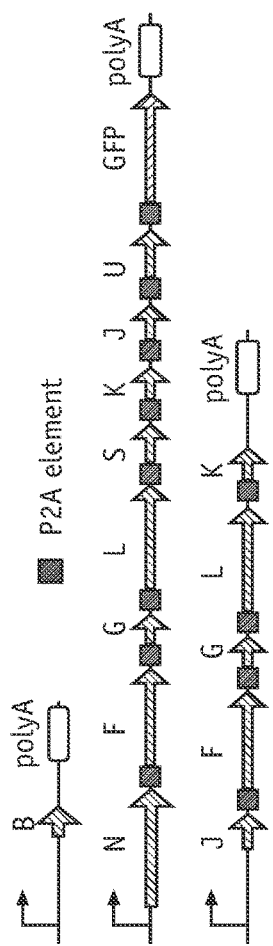
FIG. 12A
FIG. 12B
FIG. 12C
FIG. 12D
FIG. 12E

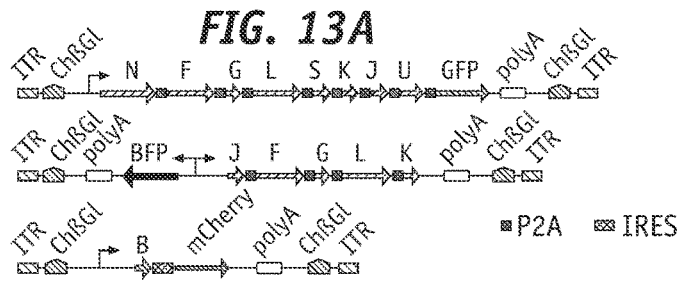
FIG. 13A
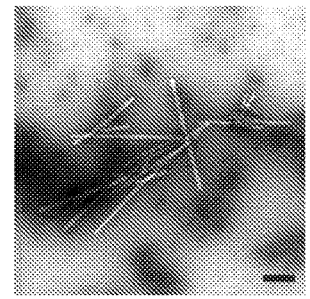
FIG. 13B
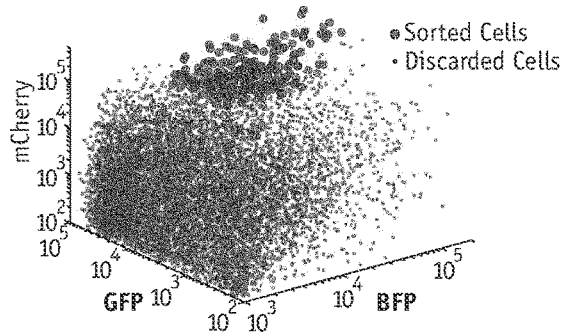
FIG. 13C
FIG. 13D
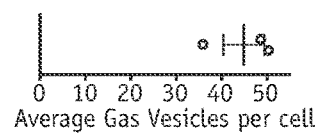
FIG. 13E
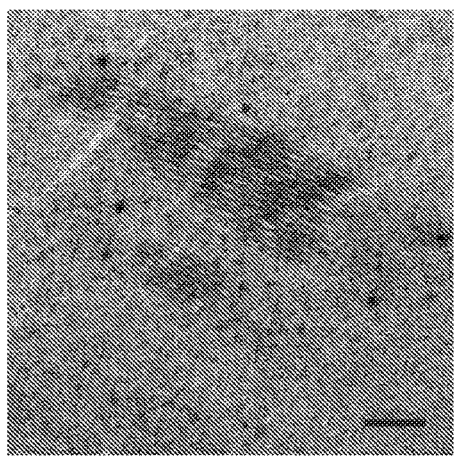
FIG. 13F
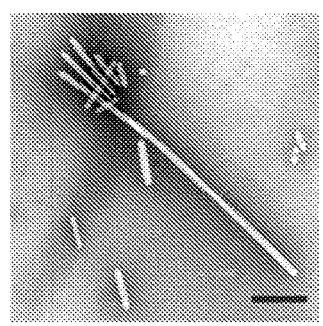
FIG. 13G
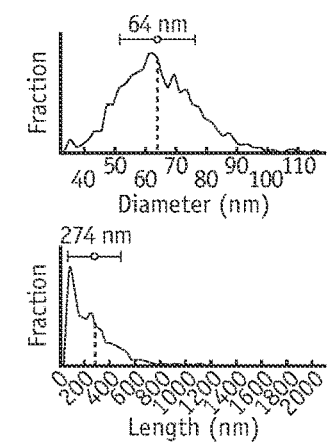
FIG. 13H
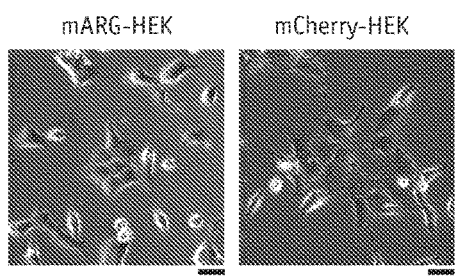
FIG. 13I
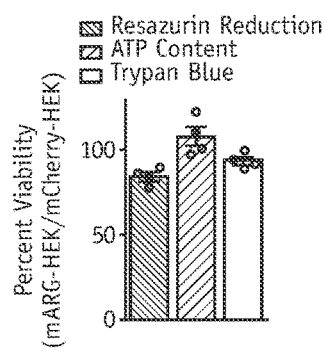
FIG. 13J
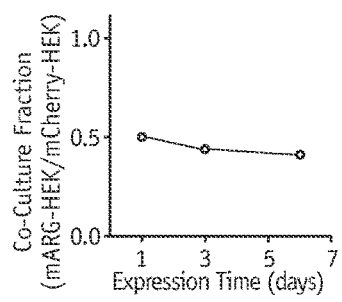
FIG. 13K

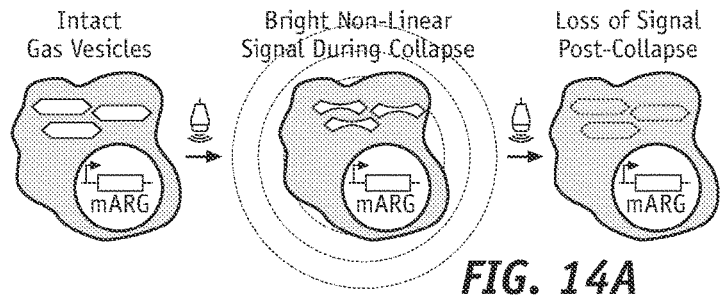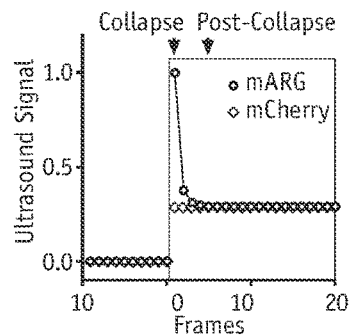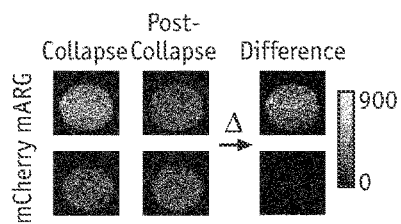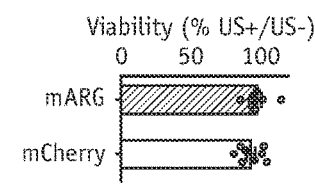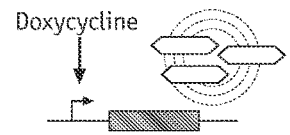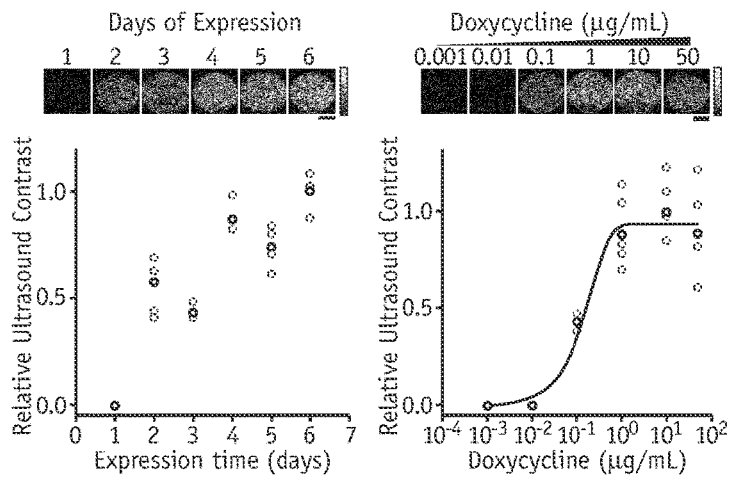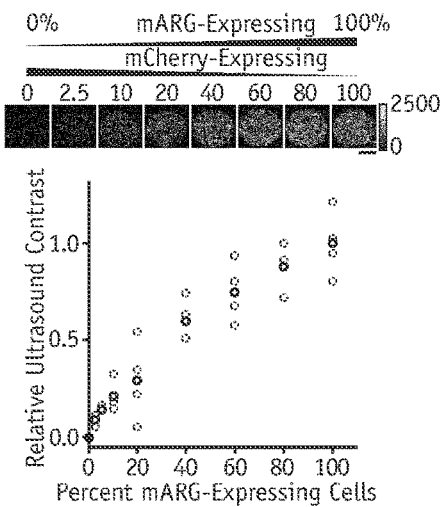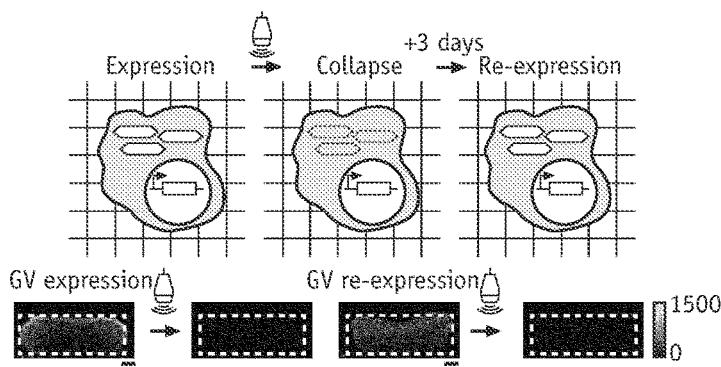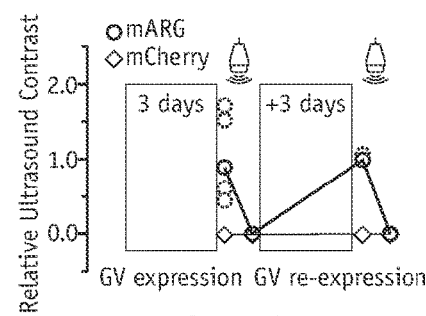
FIG. 14A
FIG. 14B
FIG. 14C
FIG. 14D
FIG. 14E
FIG. 14F
FIG. 14G
FIG. 14H
FIG. 14I
FIG. 14J

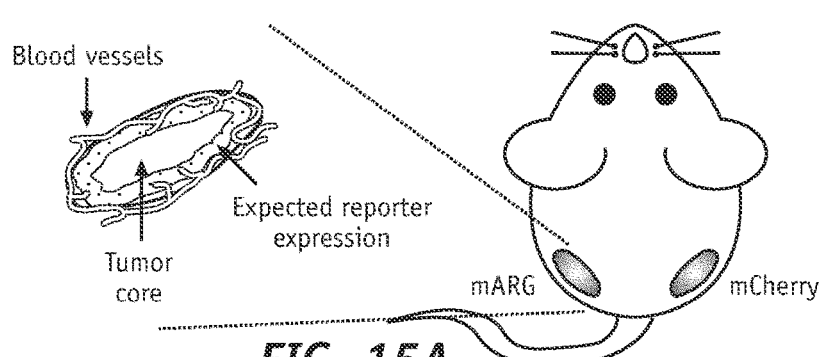
FIG. 15A
FIG. 15B
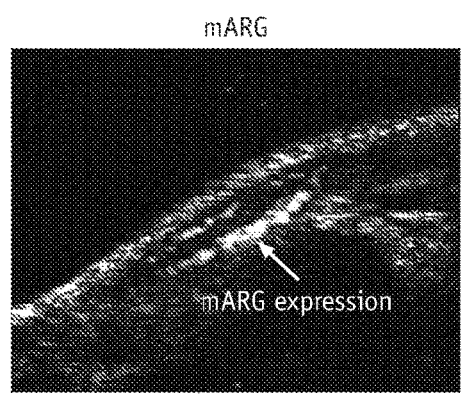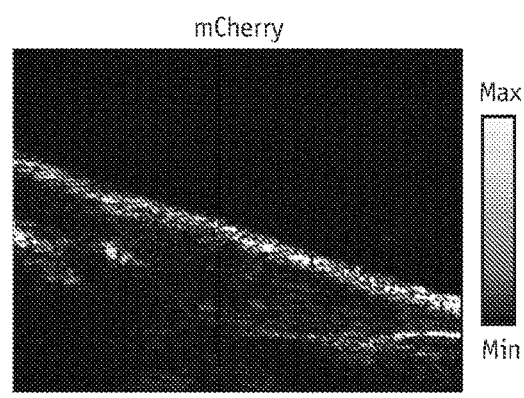
FIG. 15C
FIG. 15D
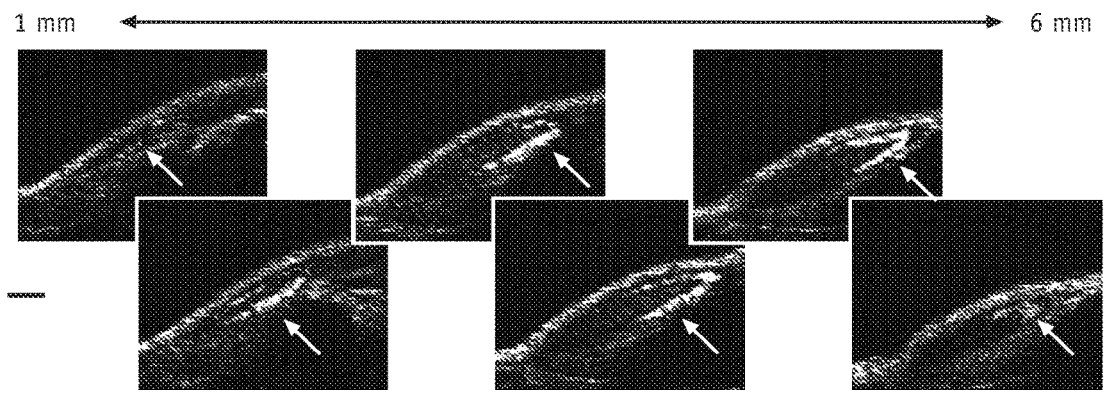
FIG. 15E
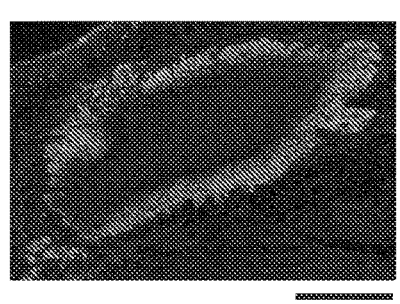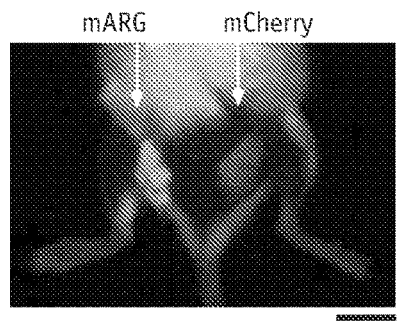
FIG. 15F
FIG. 15G

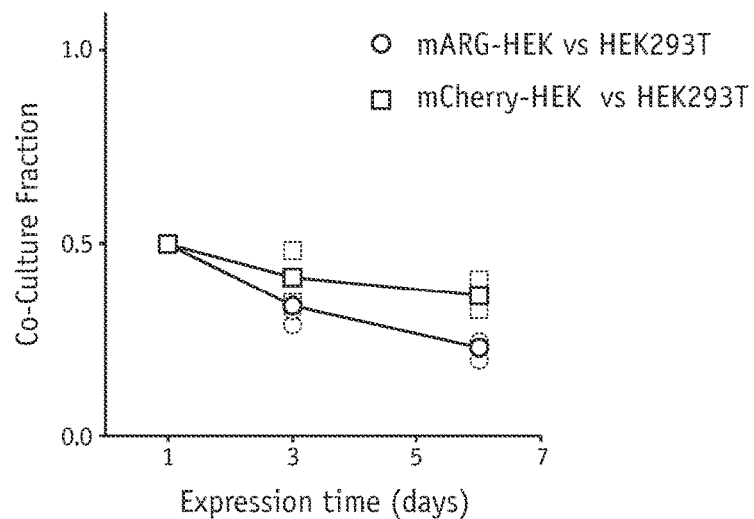
FIG. 16
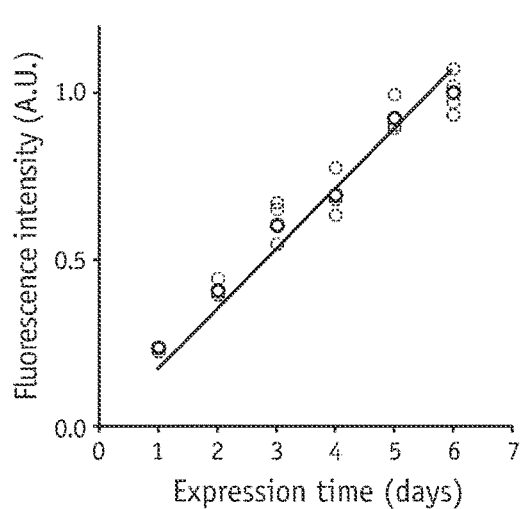
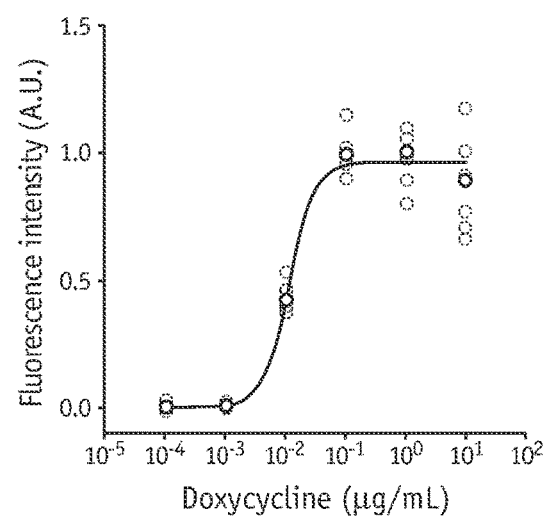
FIG. 17A  FIG. 17B

Ana-gvpA, Ana-gvpC, Ana-gvpN, Ana-gvpJ,
Ana-gvpK, Ana-gvpF, Ana-gvpG, Ana-gvpV, Ana-gvpW Ana-gvpA, Ana-gvpN, Ana-gvpJ, Ana-gvpK,
Ana-gvpF, Ana-gvpG, Ana-gvpV, Ana-gvpW Ana-gvpA, Ana-gvpN, Ana-gvpJ, Ana-gvpK,
Ana-gvpF, Ana-gvpV, Ana-gvpW BURST Ultrasound Imaging For panels A and B, sample on the left:
Ana-gvpA, Ana-gvpC, Ana-gvpN Ana-gvpJ,
Ana-gvpK, Ana-gvpF, Ana-gvpG, Ana-gvpV, Ana-gvpW
and right:
Ana-gvpA, Ana-gvpN Ana-gvpJ, Ana-gvpK,
Ana-gvpF, Ana-gvpG, Ana-gvpV, Ana-gvpW Amplitude Modulation Ultrasound Imaging

GAS VESICLE EXPRESSION SYSTEMS, GAS VESICLE CONSTRUCTS AND RELATED GENETIC CIRCUITS, VECTORS, MAMMALIAN CELLS, HOSTS, COMPOSITIONS, METHODS AND SYSTEMS

CROSS REFERENCE TO RELATED APPLICATIONS

The present application is a continuation of U.S. patent application Ser. No. 16/736,683 filed on Jan. 7, 2020, incorporated herein by reference, which, in turn, claims priority to U.S. Provisional Application No. 62/789,295, entitled "Mammalian Expression Of Gas Vesicles As Acoustic Reporter Genes" filed on Jan. 7, 2019, with docket number CIT 8165-P, and to U.S. Provisional Application No. 62/895,553, entitled "Burst Ultrasound Reconstruction With Signal Templates" filed on Sep. 4, 2019, with docket number CIT 8337-P, both of which are incorporated herein by reference in its entirety. The present application is also related to U.S. application Ser. No. 16/736,581 entitled "BURST Ultrasound Reconstruction with Signal Templates and related Methods and Systems" filed on Jan. 7, 2020 with docket number P2443-US and PCT Application Number PCT/US2020/012557 entitled "BURST Ultrasound Reconstruction with Signal Templates and related Methods and Systems" filed on Jan. 7, 2020 with the docket number P2443-PCT, the content of each of which is also incorporated by reference in its entirety.

STATEMENT OF GOVERNMENT GRANT

This invention was made with government support under Grant No. EB018975 awarded by the National Institutes of Health. The government has certain rights in the invention.

INCORPORATION-BY-REFERENCE OF MATERIAL SUBMITTED AS AN XML FILE VIA THE PATENT ELECTRONIC SYSTEM

Further, the computer readable form of the sequence listing of the XML text file "P2420-USC-2023-08-01-Sequence-Listing.xml", created on Aug. 1, 2023, with a size of 614,917 bytes measured on Windows Server 2019 Datacenter, is incorporated herein by reference in its entirety.

FIELD

The present disclosure relates to gas-filled structures, and in particular genetically engineered gas vesicle gene expression systems, engineered gas vesicle polynucleotide construct and related genetic circuits, vectors, mammalian cells, hosts, compositions, methods and systems and in particular related methods and systems to produce gas filled structures and/or to image biological events in a target site.

BACKGROUND

Reporting biological events, such as a gene expression, proteolysis, biochemical reactions as well as cell location and function, is currently primarily based on fluorescent reporter genes.

Challenges remain for identifying, producing and/or developing biocompatible reporters that can be imaged in deep tissues, enable multiplexed imaging of biological events, are genetically modifiable, are capable of enabling detection at nanomolar concentrations and/or produce dynamic contrast in response to local molecular signals.

SUMMARY

Provided herein are genetically engineered gas vesicle expression systems (GVES) that are configured to express gas vesicles (GVs) in a mammalian cell. Provided herein are also related genetic circuits, vectors, genetically engineered mammalian cells, compositions, methods and systems, which in several embodiments can be used together with ultrasound and/or contrast-enhanced imaging techniques to detect and report biological events in an imaging target site comprising a mammalian cell and/or organism.

According to a first aspect, a genetically engineered Gas Vesicle Expression System (GVES) is described, configured for expressing in a mammalian cell, a gene cluster of gyp genes (GVGC) encoding GV proteins capable of forming a GV type. The Gas Vesicle expression system comprises:

a gvpA/B gene expression cassette comprising a gvpA/B gene under control of a mammalian promoter and additional mammalian regulatory regions in a configuration allowing expression of a gvpA/B protein in the mammalian cell; and one or more additional gyp gene expression cassettes comprising the gyp genes of the GV gene cluster other than gvpB, under control of a mammalian promoter and additional regulatory regions in a configuration allowing expression of the GV proteins other than the gvpA/B in the mammalian cell.

In the Gas Vesicle expression system, each of the one or more additional gyp gene expression cassette, when comprising two or more gyp genes, further comprises a separation element between the two or more gyp genes configured to provide a separate expression of the corresponding GV protein.

In the Gas Vesicle expression system, the GVPB cassette and the one or more additional GVP cassettes are operably linked by regulatory sequences allowing co-expression of the GV proteins and formation of the GV type in the mammalian cell.

According to a second aspect, a Gas Vesicle Polynucleotide Construct (GVPC) is described, comprising a single gyp gene cassette comprising
two or more gyp genes other than gvpA/B, of a GV gene cluster encoding GV proteins configured to form a GV type,
a separation elements located between the two or more gyp genes; and
a mammalian promoter; and
additional mammalian regulatory regions;
wherein the two or more gyp genes are under control of the mammalian promoter and the additional mammalian regulatory regions in a configuration allowing expression of GV proteins encoded by the two or more gyp genes in the mammalian cell and formation of the GV type in combination with a gvpA/B protein in the mammalian cell.

According to a third aspect, a genetically engineered mammalian Gas Vesicle Reporting molecular component (GVRMC) is described. The gas vesicle reporting molecular component comprises at least one of the Gas Vesicle expression system (GVES) and the Gas Vesicle polynucleotide construct (GVPC) herein described in which the mammalian regulatory regions comprise a gas vesicle reporting (GVR) target region configured to be activated and/or inhibited by a molecular component of a genetic circuit;

wherein the gyp genes and mammalian regulatory regions are in a configuration allowing expression of GV proteins encoded by the gyp genes through activation and/or inhibition of the gas vesicle reporting (GVR) target region, when the genetic circuit operates according to the circuit design in the mammalian cell.

According to a fourth aspect, a genetically engineered gas vesicle reporting (GVR) genetic circuit (GVRGC) configured for expression in a mammalian cell is described. In the GVR genetic circuit molecular components are connected one to another in a mammalian cell in accordance with a circuit design by activating, inhibiting, binding or converting reactions to form a fully connected network of interacting components.

The GVR genetic circuit comprises a mammalian Gas Vesicle Reporting Molecular Component (GVRMC) herein described in a configuration in which GV proteins encoded by the gyp genes of the GVRMC are expressed and a gas vesicle (GV) type is provided when the genetic circuit operates according to the circuit design.

According to a fifth aspect, a method to express a Gas Vesicles in a mammalian cell is described. The method comprises introducing into the mammalian cell a genetically engineered Gas Vesicle expression system (GVES) herein described for a time and under condition to allow expression of GV proteins encoded by the gyp genes of the GVES and production of the Gas vesicle type in the mammalian cell.

According to a sixth aspect, a genetically engineered mammalian cell is described comprising the Gas Vesicle expression system (GVES) and/or Gas Vesicle Polynucleotide Construct (GVPC) herein described, configured for expression in the genetically engineered mammalian cell.

According to a seventh aspect, a method to provide a gas vesicle in a mammalian host is described. The method comprises introducing into a cell of the mammalian host the genetically engineered Gas Vesicle expression system (GVES), the introducing performed for a time and under condition to allow expression of the GV proteins encoded by the gyp genes of the GVES and the production of the Gas Vesicle type in the mammalian cell.

According to an eighth aspect, a genetically engineered non-human mammalian host is described comprising the Gas Vesicle expression system (GVES) and/or Gas Vesicle Polynucleotide Construct (GVPC) herein described, configured for expression in a mammalian cell of the GV proteins encoded by the gyp genes of the GVES and the production of the Gas Vesicle type in the genetically engineered non-human mammalian host.

According to a ninth aspect, a method and system to provide a genetically engineered a mammalian cell comprising a GVR genetic circuit is described, the method comprising:
genetically engineering the mammalian cell to introduce into the mammalian cell one or more genetically engineered Gas Vesicle Reporting Molecular Components (GVRMC) herein described wherein at least one of the gvpB gene expression cassette and one or more additional gyp gene expression cassettes comprise a gas vesicle reporting (GVR) target region configured to be activated and/or inhibited by a molecular component of the GVR genetic circuit, to provide a Gas Vesicle Reporting Genetic Circuit (GVRGC) herein described.

According to a tenth aspect, a method is described to image a biochemical event in a mammalian cell comprised in an imaging target site, the method comprising:
introducing into the mammalian cell a Gas Vesicle Reporting Molecular Components (GVRMC) herein described to provide a GVR genetic circuit in which expression of GV proteins encoded by the gyp genes of the GVRMC and production of the the GV type or an intracellular spatial translocation of the GV type occurs when the GVR genetic circuit operates according to the circuit design in response to the biochemical event, the introducing performed for a time and under conditions allowing expression of the GV proteins and production of the GV type or an intracellular spatial translocation of the GV type in response to the biochemical event; and imaging the target site comprising the mammalian host by applying a magnetic field and/or ultrasound to obtain an MRI and/or an ultrasound image of the target site.

The system comprises the genetically engineered Gas Vesicle expression system (GVES), Gas Vesicle Polynucleotide Construct (GVPC), Gas Vesicle Reporting Molecular Components (GVRMC) and/or GVR genetic circuits (GVRGC), related components and/or mammalian host cells in a combination for simultaneous combined or sequential use in the imaging methods herein described.

According to an eleventh aspect, a method is described to label a target mammalian host, the method comprising:
introducing into the mammalian cell a Gas Vesicle Reporting Molecular Components (GVRMC) herein described to provide a GVR genetic circuit in which expression of GV proteins encoded by the gyp genes of the GVRMC and production of the GV type or an intracellular spatial translocation of the GV type occurs when the GVR genetic circuit operates according to the circuit design in response to a trigger molecular component;

In the method, the introducing is performed under conditions resulting in presence of the trigger molecular component in the target mammalian host.

In some embodiments, the method can further comprise imaging the target site comprising the target mammalian host, by applying a magnetic field and/or ultrasound to obtain an MRI and/or an ultrasound image of the target site.

The system comprises the genetically engineered GVES, GVPC, related polynucleotide constructs, GVR genetic circuits, related components and/or mammalian host cells in a combination for simultaneous combined or sequential use in the imaging methods herein described.

According to a twelfth aspect, a composition is described. The composition comprises a genetically engineered Gas Vesicle expression system (GVES), Gas Vesicle Polynucleotide Construct (GVPC), Gas Vesicle Reporting Molecular Components (GVRMC) and/or GVR genetic circuits (GVRGC) of the disclosure, vectors, and/or genetically engineered mammalian cells described herein together with a suitable vehicle.

The Gas Vesicle expression system (GVES), Gas Vesicle Polynucleotide Construct (GVPC), Gas Vesicle Reporting Molecular Components (GVRMC) GVR genetic circuits (GVRGC), related vectors, genetically engineered mammalian cells, compositions, methods and systems can be used in several embodiments for reporting biochemical events in a mammalian cell in vitro, or in vivo, and in particular can be used for non-invasive reporting of biochemical events in mammalian cells using contrast-enhanced imaging techniques such as MRI and/or ultrasound, two widely available techniques with high resolution and deep tissue penetration.

In particular, in several embodiments described herein, the Gas Vesicle expression system (GVES), Gas Vesicle Polynucleotide Construct (GVPC), Gas Vesicle Reporting Molecular Components (GVRMC) GVR genetic circuits (GVRGC), related vectors, genetically engineered mammalian cells, compositions, methods and systems can be used to report the location of mammalian cells configured to express one or more GV types within an imaging target site, and/or sense and report one or more biochemical events in a mammalian cell configured to express one or more GV types within an imaging target site.

The GVES, and related GV polynucleotide constructs, GV reporting molecular components, GVR genetic circuits, vectors, genetically engineered mammalian cells, genetically engineered non-human mammals, compositions, methods and systems herein described, can be used in several embodiments to allow multiplexed imaging of a mammalian cell using parametric MRI, and differential acoustic sensitivity and background-free MRI when combined with ultrasound detection.

The GVES, and related GV polynucleotide constructs, GV reporting molecular components, GVR genetic circuits, vectors, genetically engineered mammalian cells, genetically engineered non-human mammals, compositions, methods and systems herein described, can be used in several embodiments to detect events such as multiple gene expression, proteolysis and/or biochemical reactions by clustering-induced changes in MRI contrast also enable the design of dynamic molecular sensors.

The GVES, and related GV polynucleotide constructs, GV reporting molecular components, GVR genetic circuits, vectors, genetically engineered mammalian cells, genetically engineered non-human mammals, compositions, methods and systems herein described, can be used in several embodiments to report biochemical events in mammalian cells and/or host through multiplexing, multimodal MRI and/or ultrasound detection.

The GVES, and related GV polynucleotide constructs, GV reporting molecular components, GVR genetic circuits, vectors, genetically engineered mammalian cells, genetically engineered non-human mammals, compositions, methods and systems herein described, can be used in several embodiments to produce dynamic contrast in response to local molecular signals in mammalian cells and/or host The GVES, and related GV polynucleotide constructs, GV reporting molecular components, GVR genetic circuits, vectors, genetically engineered mammalian cells, genetically engineered non-human mammals, compositions, methods and systems herein described, can be used in several embodiments to provide ultrasound imaging of mammalian cells llowing for sensitive and selective ultrasound imaging in order to detect gas vesicle-expressing cells at volumetric concentrations below 0.5% in vitro, and/or to image gene expression in mammals in vivo using ultrasound.

The GVES, and related GV polynucleotide constructs, GV reporting molecular components, GVR genetic circuits, vectors, genetically engineered mammalian cells, genetically engineered non-human mammals, compositions, methods and systems herein described, can be used in several embodiments to track movement of mammalian cells in target sites of interest such as mammalian tumor cells, immune cells, red blood cells, and stem cells within the body of an individual or other environments.

The GVES, and related GV polynucleotide constructs, GV reporting molecular components, GVR genetic circuits, vectors, genetically engineered mammalian cells, genetically engineered non-human mammals, compositions, methods and systems herein described, can in some embodiments be used to allow measures of fluid flows within blood and lymphatic circulation systems by detecting the spatial location of the ultrasound contrast produced the by the cells in an image and tracking the spatial changes of that contrast over time as well as measuring movement of cells inside a tissue as will be understood by a skilled person.

The GVES, and related GV polynucleotide constructs, GV reporting molecular components, GVR genetic circuits, vectors, genetically engineered mammalian cells, genetically engineered non-human mammals, compositions, methods and systems herein described can be used in connection with various applications wherein reporting of biological events, labeling of mammalian cells, and/or tracking of their movement in a target site is desired.

For example, the GVES, and related GV polynucleotide constructs, GV reporting molecular components, GVR genetic circuits, vectors, genetically engineered mammalian cells, genetically engineered non-human mammals, compositions, methods and systems herein described, can be used for visualization of biological events, such as a gene expression, proteolysis, biochemical reactions, such as production of signaling molecule and ion concentration changes, as well as cell location on a target site (e.g. tumor cells inside a host individual, such as mammalian hosts).

The GVES, and related GV polynucleotide constructs, GV reporting molecular components, GVR genetic circuits, vectors, genetically engineered mammalian cells, genetically engineered non-human mammals, compositions, methods and systems herein described, can also be used in developmental biology, the development and monitoring of diagnostic and therapeutic cellular agents and/or of genetic therapeutic circuits (for example to correct or modify genetic disorders) in medical applications, as well diagnostics applications, such as monitoring of therapeutic cell/agent efficacy and safety during developmental stages and clinical usage.

Additional exemplary applications include uses of the GVES, and related polynucleotide constructs, GVR genetic circuits, vectors, genetically engineered mammalian cells, genetically engineered non-human mammals, compositions, methods and systems herein described in several fields including basic biology research, applied biology, bio-engineering, bio-energy, medical research, medical diagnostics, therapeutics, and in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

FIG. 5 shows diagrams illustrating the organization of exemplary gas vesicle gene clusters. Gas vesicle gene clusters from the indicated organisms are shown, with genes shown as block-shaped arrows, and genes of predicted similar function indicated in the same shade of grey. The direction of the transcription of genes within a gene cluster is indicated by the direction of the block-shaped arrows, and genes grouped together having block arrows pointed in the same direction are typically organized in the same operon. The scale bar indicates 1 kb. [1]

FIG. 6 shows diagrams illustrating organization of exemplary gyp gene clusters, wherein each letter indicates a gyp gene, and an arrow beneath a group of letters indicates an operon, with the direction of the arrow indicating the direction of transcription. [2]

FIG. 7 bottom panel shows representative whole cell TEM images of *E. coli* Rosetta 2(DE3)pLysS cells after expression of gas vesicles genes for 22 hours. Scale bars represent 500 nm. Expression performed as in Farhadi et al. 2018 (21) and TEM imaging as in Bourdeau et al. *Nature*, 2018 (13). The results indicate that gvpR and gvpT genes in the *B. megaterium* gene cluster are not necessary for gas vesicle formation.

FIG. 9A shows a schematic representation of the experimental approach. FIG. 9B shows a chart reporting a qualitative estimate of the relative number of gas vesicles produced when each indicated gene was supplied solely by the polycistronic plasmid. FIG. 9C shows representative TEM images of gas vesicles in the lysate of HEK293T cells for all 8 assays. Scale bars represent 500 nm.

FIG. 10A shows a schematic representation of a genetic construct including exemplary regulatory regions usable in polynucleotide constructs of the present disclosure. FIG. 10B shows a diagram reporting FACS of mCherry cells, with selected cells indicated with dark gray dots.

FIGS. 11A-11G illustrate results of fluorescence activated cell sorting of HEK293-tetON and CHO-tetON cells transfected with integrating mARG constructs herein described.

FIG. 11A shows a schematic representation of the integrating constructs used to generate polyclonal cell lines. FIG. 11B shows a chart illustrating FACS of mARG-expressing HEK293-tetON cells. The cells are sorted for each group (subtype 1, subtype 2, subtype, 3, subtype 4) as indicated with the remaining smaller gray dots indicating unsorted population. FIG. 11C shows a chart illustrating the relative fluorescence of the four polyclonal subtypes sorted. Dark gray bars indicate mCherry expression; light gray bars indicate EmGFP and eBFP2 expression. FIG. 11D shows a chart reporting the approximate gas vesicle yield from polyclonal cells in each subtype.

FIG. 11E shows a chart reporting FACS of mARG-expressing CHO-tetON cells. Dark gray data indicate cells sorted in subtype 1 and small light gray dots are unsorted cells. FIG. 11F shows representative TEM image of buoyancy-enriched lysate from CHO-tetON cells sorted as indicated in FIG. 11E. Scale bar represents 500 nm. FIG. 11G shows a chart reporting the approximate gas vesicle yield for the sorted mARG-expressing CHO-tetON cells.

FIGS. 12A-12E illustrate an approach for engineering a mammalian cell through transformation of the cell with an exemplary GVES of the disclosure. In particular FIG. 12A shows a schematic illustration of the transient co-transfection assay used to identify combinations of genes capable of producing gas vesicles in mammalian cells. FIG. 12B shows a schematic representation of nine expression cassettes comprising genes from *B. megaterium* capable of encoding gas vesicle expression in mammalian cells. Thin arrow denotes CMV promoter. polyA denotes SV40 polyadenylation element. FIG. 12C shows Representative TEM image of purified gas vesicles expressed in HEK293T cells. FIG. 12D shows a schematic representation of gene cassettes comprising the mammalian acoustic reporter gene construct, mARG. FIG. 12E shows representative TEM image of gas vesicles purified from HEK293T cells transiently transfected with mARGs for 72 hours. All scale bars represent 500 nm.

FIGS. 13A-13K illustrates formation, properties and non-toxicity of gas vesicles in cells with genome-integrated mammalian acoustic reporter genes. FIG. 13A shows a schematic representation of mARG constructs used for genomic integration into cells with the piggyBac transposase system. ITR, inverted terminal repeat; ChβGI, Chicken beta-globin insulator; GFP, Emerald green fluorescent protein; BFP, enhanced blue fluorescent protein 2. FIG. 13B shows representative TEM image of buoyancy-enriched lysate from HEK293-tetON cells transfected with the constructs in FIG. 13A and sorted for high expression of all three operons. FIG. 13C shows fluorescence-activated cell sorting of HEK293-tetON cells transfected with the constructs in FIG. 13A. Large gray circles denote individual cells selected by sorting to form monoclonal cell lines. FIG. 13D shows a flowchart illustrating a selection process for monoclonal cell lines, including assays for viability, fluorescence intensity and gas vesicle yield. FIG. 13E shows a chart illustrating the number of gas vesicles expressed by monoclonal HEK293-tetON cells after 72 hours of induced expression, as counted in lysates using TEM. Bar represents the mean and the shaded area represents SEM (n=3, each from two technical replicates). FIG. 13F shows Representative TEM image of a 60-nm section through an mARG-HEK cell showing an angled slice through two bundles of gas vesicles in the cytosol. FIG. 13G shows representative TEM image of gas vesicles purified from mARG-HEK cells. FIG. 13H shows Size distribution of gas vesicles expressed in mARG-HEK cells. The mean and standard deviation of both distributions is illustrated as a circle and with error bars. (n=1828) FIG. 13I shows phase contrast images of mARG-HEK and mCherry-HEK cells 72 hours after induction with 1 μg/mL doxycycline and 5 mM sodium butyrate. FIG. 13J shows a diagram reporting cell viability of mARG-HEK cells relative to mCherry-HEK cells after 72 hours of gene expression. Error bars indicate SEM. FIG. 13K shows a chart reporting a fraction of mARG-HEK cells in co-culture with mARG-mCherry cells seeded in equal numbers over 6 days of gene expression (n=3 biological replicates, each from 4 technical replicates, with darker symbols showing the mean). Scale bars in B, F, G represent 500 nm. Scale bar in I represents 20 µm.

FIGS. 14A-14J illustrate an exemplary ultrasound imaging of mammalian gene expression in vitro. FIG. 14A shows a schematic illustration of the collapse-based ultrasound imaging paradigm used to generate gas vesicle-specific ultrasound contrast from mARG-expressing cells. FIG. 14B shows a chart reporting a representative non-linear signal recorded during a step change in the incident acoustic pressure, from 0.27 MPa in the white-shaded region to 1.57 MPa in the grey-shaded region, exemplifying BURST ultrasound imaging. FIG. 14C shows a grayscale version of representative collapse and post-collapse ultrasound images of mARG-HEK and mCherry-HEK cells acquired during this ultrasound imaging paradigm and their difference, indicating gas vesicle-specific contrast. FIG. 14D shows a chart reporting cellular viability after being insonated under 3.2 MPa acoustic pressures, as measured using the MTT assay. FIG. 14E shows a schematic representation of a chemically inducible gene circuit with mARG expression as its output. All three mARG cassettes in mARG-HEK cells are under the control of the doxycycline-inducible TRE3G promoter (TRE), with expression triggered by incubation with doxycycline. FIG. 14F shows a grayscale version of representative ultrasound images and contrast measurements in mARG-HEK cells as a function of time following induction with 1 µg/mL of doxycycline and 5 mM sodium butyrate (n=6, with the darker dots showing the mean). FIG. 14G shows a grayscale version of representative ultrasound images and contrast measurements in mARG-HEK cells as a function of doxycycline induction concentrations. Cells were allowed to express gas vesicles for 72 hours in the presence of 5 mM sodium butyrate. (n=6, with the darker dots showing the mean). A sigmoidal function is fitted as a visual guide. FIG. 14H shows a grayscale version of representative ultrasound images and contrast measurements in mARG-HEK cells mixed with mCherry-HEK cells in varying proportions. Cells were induced with 1 µg/mL of doxycycline and 5 mM sodium butyrate for 72 hours prior to imaging. (n=4, with the darker dots showing the mean) FIG. 14I shows schematic representative and a grayscale version of representative ultrasound images from mARG-HEK cells in Matrigel re-expressing gas vesicles after acoustic collapse. Cells were induced with 1 µg/mL of doxycycline and 5 mM sodium butyrate for 72 hours before and after 3.2 MPa acoustic insonation. Ultrasound images were acquired after an additional 72 hours in culture following collapse. FIG. 14J shows a chart reporting results of ultrasound contrast in mARG-HEK and mCherry-HEK cells after initial expression, after collapse, after re-expression and after second collapse. (n=7, with the darker dots showing the mean). GV, gas vesicles. All scale bars represent 1 mm.

FIGS. 15A-15G illustrate an exemplary ultrasound imaging of mammalian gene expression in vivo. FIG. 15A shows a schematic illustration of an approach wherein a mouse implanted with a subcutaneous tumor model, and the related expected spatial pattern of vascularization and doxycycline-induced reporter gene expression. FIG. 15B shows a chart reporting an exemplary experimental timeline. FIG. 15C shows a grayscale version of representative ultrasound image of tumors containing mARG-HEK cells after 4 days of doxycycline administration, arrow indicates mARG-specific BURST ultrasound image. mARG-specific contrast shown in the grayscale version of the hot colormap is overlaid on an anatomical B-mode image showing the background anatomy. FIG. 15D shows a grayscale version of representative ultrasound image of tumors containing mCherry-HEK cells after 4 days of doxycycline administration. FIG. 15E shows a grayscale version of ultrasound images of adjacent planes in the mARG-HEK tumor acquired at 1 mm intervals. The minimum and maximum values of scale bars in the original ultrasound images of FIGS. 15C-15E are 4000 and 40000 au, respectively. FIG. 15F shows a grays scale version of representative fluorescence image of a histological tissue section of a mARG-HEK tumor. The light gray color shows the GFP and mCherry fluorescence around the periphery of the tumor. FIG. 15G shows a grayscale version of a fluorescence image of a mouse implanted with mARG-HEK and mCherry-HEK tumors on the left and right flanks, respectively, as outlined with arrows, after 4 days of expression. Scale bars for are 1 mm for C-F and 1 cm for G.

FIG. 16 shows a graph illustrating the co-culture of reporter gene expressing cells with HEK293T cells. Fraction of mARG-HEK cells in co-culture with HEK293T cells (circle) or mARG-mCherry cells in co-culture with HEK293T cells (square) seeded in equal numbers over 6 days of gene expression (n=3 biological replicates, each from 4 technical replicates, with darker dots showing the mean).

FIGS. 17A-17B show fluorescence measurements of gene expression as a function of time and inducer concentration in mARG-HEK cells. FIG. 17A shows a chart illustrating mCherry fluorescence of mARG-HEK cells induced with 1 µg/mL doxycycline and 5 mM sodium butyrate at the indicated times after induction (n=4, with the darker dots showing the mean).

FIG. 17B shows a chart reporting mCherry fluorescence of mARG-HEK cells with the indicated inducer concentration and 5 mM sodium butyrate after 72 hours of induction (n=7, with the darker dots showing the mean).

In FIG. 22B, the left column shows ultrasound images of tumors containing mARG-HEK cells re-expressing gas vesicles after an additional 4 days of doxycycline administration. The right column shows ultrasound images of tumors containing mCherry-HEK cells after an additional 4 days of doxycycline administration. Difference heatmap of nonlinear signal between frame 1 and frame 4 is overlaid on a grayscale anatomical ultrasound image. Min and max on color bar represent 4000 and 40000, respectively. White arrows indicate location of mARG-specific BURST ultrasound signal. Scale bars represent 1 mm.

FIG. 24A shows a schematic representation of two gene cassettes integrated to the genome of HEK293-tetON cells. In the top construct gvpB is separated from gvpN by an internal ribosome entry sequence (shown as box between gvpB and gvpN). The promoters, as illustrated by thin arrows are TRE3G doxycycline-inducible promoters. FIG. 24B shows representative TEM image of GVs in the lysate of HEK293-tetON cells transfected with the constructs in (FIG. 24A) and induced with 1 μg/mL doxycycline. FIG. 24C illustrates an alternative consolidated mARG construct comprising of 2 gene cassettes enabling mammalian GV expression. In the top construct gvpB is separated from gvpF by an IRES. The promoters, as illustrated by thin arrows are CMV promoters. FIG. 24D shows a representative BUST ultrasound of HEK293T cells expressing the constructs in FIG. 24C. HEK293T control without GV genes do not produce BURST ultrasound signal.

FIG. 27A shows representative BURST ultrasound images of HEK293T cells expressing Ana-gvpA, Ana-gvpC, Ana-gvpN, Ana-gpvJ, Ana-gvpK, Ana-gvpF, Ana-gvpG, Ana-gvpV, Ana-gvpW on the left and Ana-gvpA, Ana-gvpN, Ana-gpvJ, Ana-gvpK, Ana-gvpF, Ana-gvpG, Ana-gvpV, Ana-gvpW on the right. FIG. 27B shows representative nonlinear signals with amplitude modulation ultrasound images of HEK293T cells expressing Ana-gvpA, Ana-gvpC, Ana-gvpN, Ana-gpvJ, Ana-gvpK, Ana-gvpF, Ana-gvpG, Ana-gvpV, Ana-gvpW on the left and Ana-gvpA, Ana-gvpN, Ana-gpvJ, Ana-gvpK, Ana-gvpF, Ana-gvpG, Ana-gvpV, Ana-gvpW on the right.

DETAILED DESCRIPTION

Figure 1:
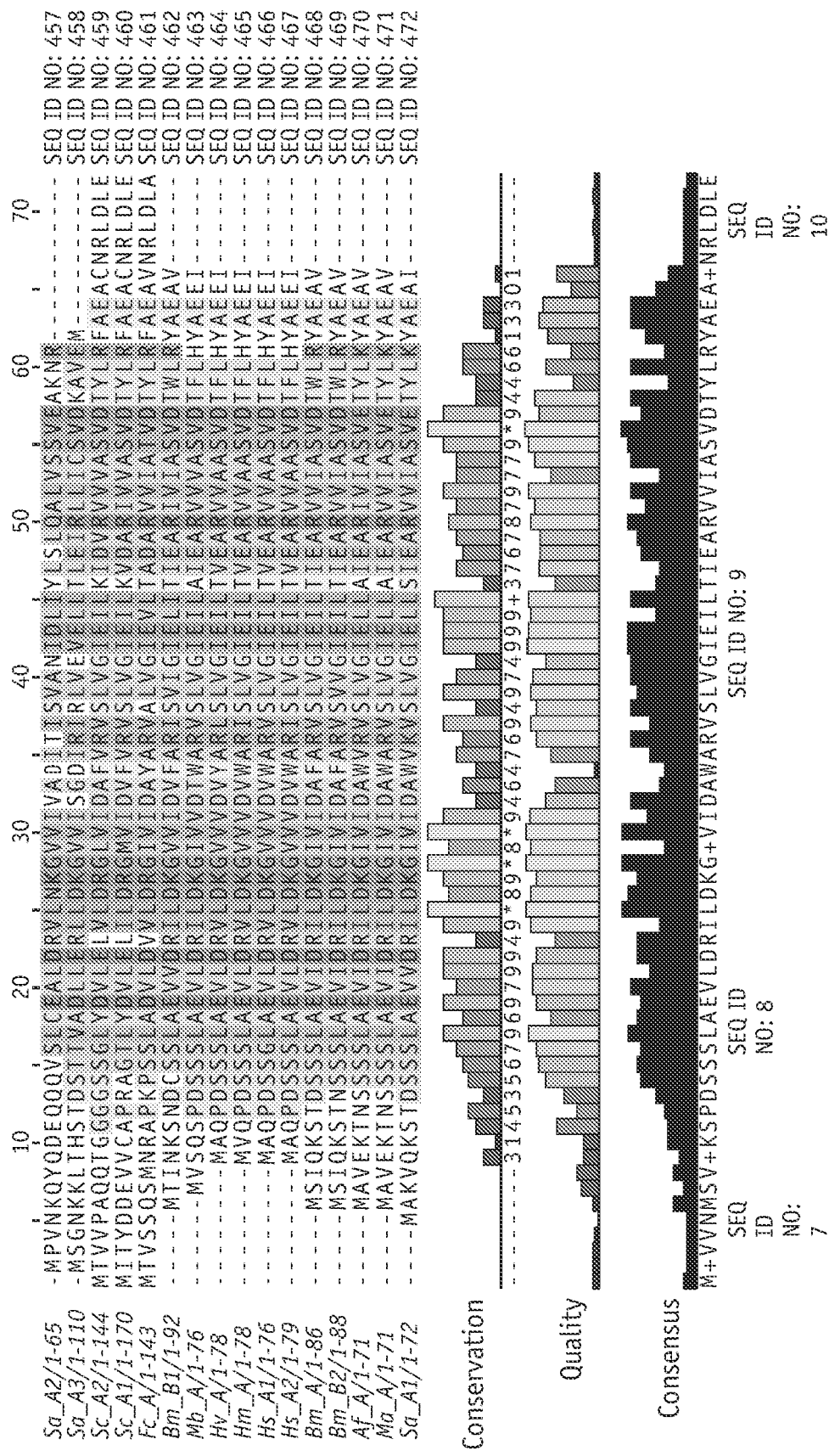
FIG. 1 shows an exemplary Clustal omega alignment of amino acid sequences of selected exemplary gvpA and gvpB proteins (SEQ ID NO: 7-10 and 457-472).

Provided herein are genetically engineered gas vesicle expression systems (GVES) and related polynucleotide constructs configured for expression of a gas vesicle (GV) in a mammalian cell, and related gas vesicle gene clusters, gas vesicles, genetic circuits, vectors, genetically engineered mammalian cells, compositions, methods and systems.

The wordings "gas vesicles", GV", "gas vesicles protein structure", or "GVPS", refer to a gas-filled protein structure natively intracellularly expressed by certain bacteria or archaea as a mechanism to regulate cellular buoyancy in aqueous environments [3]. In particular, gas vesicles are protein structures natively expressed almost exclusively in microorganisms from aquatic habitats, to provide buoyancy by lowering the density of the cells [3]. GVs have been found in over 150 species of prokaryotes, comprising cyanobacteria and bacteria other than cyanobacteria [4, 5], from at least 5 of the 11 phyla of bacteria and 2 of the phyla of archaea described by Woese (1987) [6]. Exemplary microorganisms expressing or carrying gas vesicle protein structures and/or related genes include cyanobacteria such as *Microcystis aeruginosa, Aphanizomenon flos aquae Oscillatoria agardhii, Anabaena, Microchaete diplosiphon* and *Nostoc*; phototropic bacteria such as *Amoebobacter, Thiodiclyon, Pelodiclyon, and Ancalochloris*; non phototropic bacteria such as *Microcyclus aquaticus*; Gram-positive bacteria such as *Bacillus megaterium* Gram-negative bacteria such as *Serratia*; and archaea such as *Haloferax mediterranei, Methanosarcina barkeri*, and *Halobacteria salinarium*, as well as additional microorganisms identifiable by a skilled person.

In particular, a GV in the sense of the disclosure is an intracellularly expressed structure forming a hollow structure wherein a gas is enclosed by a protein shell, which is a shell substantially made of protein (at least 95% protein). In gas vesicles in the sense of the disclosure, the protein shell is formed by a plurality of proteins herein also indicated as GV proteins or gvps, which form in the cytoplasm a gas permeable and liquid impermeable protein shell configuration encircling gas. Accordingly, a protein shell of a GV is permeable to gas but not to surrounding liquid such as water. In particular, GV protein shells exclude water but permit gas to freely diffuse in and out from the surrounding media [7] making them physically stable despite their usual nanometer size, unlike microbubbles, which trap pre-loaded gas in an unstable configuration.

GV structures are typically nanostructures with widths and lengths of nanometer dimensions (in particular with widths of 45-250 nm and lengths of 100-800 nm) but can have lengths up to 2 m in prokaryotes but can have larger dimensions such as up to 8-10 μm as will be understood by a skilled person upon reading of the present disclosure. In certain embodiments, the gas vesicles protein structure have average dimensions of 1000 nm or less, such as 900 nm or less, including 800 nm or less, or 700 nm or less, or 600 nm or less, or 500 nm or less, or 400 nm or less, or 300 nm or less, or 250 nm or less, or 200 nm or less, or 150 nm or less, or 100 nm or less, or 75 nm or less, or 50 nm or less, or 25 nm or less, or 10 nm or less. For example, the average diameter of the gas vesicles may range from 10 nm to 1000 nm, such as 25 nm to 500 nm, including 50 nm to 250 nm, or 100 nm to 250 nm. By "average" is meant the arithmetic mean.

GVs in the sense of the disclosure have different shapes depending on their genetic origins [7]. For example, GVs in the sense of the disclosure can be substantially spherical, ellipsoid, cylindrical, or have other shapes such as football shape or cylindrical with cone shaped end portions depending on the type of bacteria providing the gas vesicles.

Representative examples of endogenously expressed GVs native to bacterial or archaeal species are the gas vesicle protein structure produced by the Cyanobacterium *Anabaena flos-aquae* (Ana GVs) [3], and the *Halobacterium Halobacterium salinarum* (Halo GVs) [8]. In particular, Ana GVs are cone-tipped cylindrical structures with a diameter of approximately 140 nm and length of up to 2 m and in particular 200-800 nm or longer. Halo GVs are typically spindle-like structures with a maximal diameter of approximately 250 nm and length of 250-600 nm.

In bacteria or archaea expressing GVs, the genes (herein also gyp genes) encoding for the proteins forming the GVs (herein also GV proteins), are organized in a gas vesicle gene cluster of 8 to 14 different genes depending on the host bacteria or archaea, as will be understood by a skilled person.

The term "Gas Vesicle Genes Cluster" or "GVGC" as described herein indicates a gene cluster encoding a set of GV proteins capable of providing a GV upon expression within a bacterial or archaeal cell Since the ability of expressed GV proteins to assemble in a GV depends on the cell environment where GV proteins are expressed and a same group of gyp genes may or may not form a GV upon expression in a cell, gyp genes provide GVGCs in a cell dependent manner as will be understood by a skilled person (see on point US application 15/663,635 published as US 2018/0030501).

The term "gene cluster" as used herein means a group of two or more genes found within an organism's DNA that encode two or more polypeptides or proteins, which collectively share a generalized function or are genetically regulated together to produce a cellular structure and are often located within a few thousand base pairs of each other. The size of gene clusters can vary significantly, from a few genes to several hundred genes [9]. Portions of the DNA sequence of each gene within a gene cluster are sometimes found to be similar or identical; however, the resulting protein of each gene is distinctive from the resulting protein of another gene within the cluster. Genes found in a gene cluster can be observed near one another on the same chromosome or native plasmid DNA, or on different, but homologous chromosomes. An example of a gene cluster is the Hox gene, which is made up of eight genes and is part of the Homeobox gene family. In the sense of the disclosure, gene clusters as described herein also comprise gas vesicle gene clusters, wherein the expressed proteins thereof together are able to form gas vesicles.

The term "gene" as used herein indicates a polynucleotide encoding for a protein that in some instances can take the form of a unit of genomic DNA within a bacteria, plant, or other organism. The term gene as used herein incudes naturally occurring polynucleotide encoding for a protein as well as engineered polynucleotide whose sequences have been modified from the original sequence for example to optimize expression, e.g. through codon changes (see Examples section) and/or through introduction of modified N- and/or C-terminal modifications, while still maintaining the ability to encode for the protein encoded by the naturally occurring polynucleotide or a or a functional variant thereof.

The term "polynucleotide" as used herein indicates an organic polymer composed of two or more monomers including nucleotides, nucleosides or analogs thereof. The term "nucleotide" refers to any of several compounds that consist of a ribose or deoxyribose sugar joined to a purine or pyrimidine base and to a phosphate group and that are the basic structural units of nucleic acids. The term "nucleoside" refers to a compound (as guanosine or adenosine) that consists of a purine or pyrimidine base combined with deoxyribose or ribose and is found especially in nucleic acids. The term "nucleotide analog" or "nucleoside analog" refers respectively to a nucleotide or nucleoside in which one or more individual atoms have been replaced with a different atom or a with a different functional group. Accordingly, the term polynucleotide includes nucleic acids of any length, and in particular DNA RNA analogs and fragments thereof.

The term "protein" as used herein indicates a polypeptide with a particular secondary and tertiary structure that can interact with another molecule and in particular, with other biomolecules including other proteins, DNA, RNA, lipids, metabolites, hormones, chemokines, and/or small molecules. The term "polypeptide" as used herein indicates an organic linear, circular, or branched polymer composed of two or more amino acid monomers and/or analogs thereof. The term "polypeptide" includes amino acid polymers of any length including full-length proteins and peptides, as well as analogs and fragments thereof. A polypeptide of three or more amino acids is also called a protein oligomer, peptide, or oligopeptide. In particular, the terms "peptide" and "oligopeptide" usually indicate a polypeptide with less than 100 amino acid monomers. In particular, in a protein, the polypeptide provides the primary structure of the protein, wherein the term "primary structure" of a protein refers to the sequence of amino acids in the polypeptide chain covalently linked to form the polypeptide polymer. A protein "sequence" indicates the order of the amino acids that form the primary structure. Covalent bonds between amino acids within the primary structure can include peptide bonds or disulfide bonds, and additional bonds identifiable by a skilled person. Polypeptides in the sense of the present disclosure are usually composed of a linear chain of alpha-amino acid residues covalently linked by peptide bond or a synthetic covalent linkage. The two ends of the linear polypeptide chain encompassing the terminal residues and the adjacent segment are referred to as the carboxyl terminus (C-terminus) and the amino terminus (N-terminus) based on the nature of the free group on each extremity. Unless otherwise indicated, counting of residues in a polypeptide is performed from the N-terminal end ($NH_2$-group), which is the end where the amino group is not involved in a peptide bond to the C-terminal end (—COOH group) which is the end where a COOH group is not involved in a peptide bond. Proteins and polypeptides can be identified by x-ray crystallography, direct sequencing, immunoprecipitation, and a variety of other methods as understood by a person skilled in the art. Proteins can be provided in vitro or in vivo by several methods identifiable by a skilled person. In some instances where the proteins are synthetic proteins in at least a portion of the polymer two or more amino acid monomers and/or analogs thereof are joined through chemically-mediated condensation of an organic acid (—COOH) and an amine (—$NH_2$) to form an amide bond or a "peptide" bond.

As used herein the term "amino acid", "amino acid monomer", or "amino acid residue" refers to organic compounds composed of amine and carboxylic acid functional groups, along with a side-chain specific to each amino acid. In particular, alpha- or α-amino acid refers to organic compounds composed of amine (—NH2) and carboxylic acid (—COOH), and a side-chain specific to each amino acid connected to an alpha carbon. Different amino acids have different side chains and have distinctive characteristics, such as charge, polarity, aromaticity, reduction potential, hydrophobicity, and pKa. Amino acids can be covalently linked to form a polymer through peptide bonds by reactions between the amine group of a first amino acid and the carboxylic acid group of a second amino acid. Amino acid in the sense of the disclosure refers to any of the twenty naturally occurring amino acids, non-natural amino acids, and includes both D an L optical isomers.

In embodiments herein described identification of a gene cluster encoding GV proteins naturally expressed in bacteria or archaea as described herein can be performed for example by isolating the GVs from the bacteria or archaea, isolating the protein for the protein shell of the GV and deriving the related amino acidic sequence with methods and techniques identifiable by a skilled person (see e.g. procedures described in [10] [11]). The sequence of the genes encoding for the GV proteins can then be identified by methods and techniques identifiable by a skilled person. For example, gas vesicle gene clusters can also be identified by persons skilled in the art by performing gene sequencing or partial- or whole-genome sequencing of organisms using wet lab and in silico molecular biology techniques known to those skilled in the art. As understood by those skilled in the art, gas vesicle gene clusters can be located on the chromosomal DNA or native plasmid DNA of microorganisms. After performing DNA or cDNA isolation from a microorganism, the polynucleotide sequences or fragments thereof or PCR-amplified fragments thereof can be sequenced using DNA sequencing methods such as Sanger sequencing, DNASeq, RNASeq, whole genome sequencing, and other methods known in the art using commercially available DNA sequencing reagents and equipment, and then the DNA sequences analyzed using computer programs for DNA sequence analysis known to skilled persons.

In some embodiments, identification of a gene cluster encoding for GV proteins [8, 12, 13] can also be performed by screening DNA sequence databases such as GenBank, EMBL, DNA Data Bank of Japan, and others. Gas vesicle gene cluster gene sequences in databases such as those above can be searched using tools such as NCBI Nucleotide BLAST and the like, for gas vesicle gene sequences and homologs thereof, using gene sequence query methods known to those skilled in the art. For example, genes of the gene cluster for the exemplary haloarchael GVs (which have the largest number of different gyp genes) and their predicted function and features are illustrated in Example 26 of related U.S. application Ser. No. 15/613,104, filed on Jun. 2, 2017 which is incorporated herein by reference in its entirety. GV gene clusters can also be identified using a combination of genomic vicinity (e.g. antiSMASH), protein homology and prior GV gene annotation as will be understood by a skilled person.

A GV gene cluster encoding for GV proteins typically comprises Gas Vesicle Assembly (GVA) genes and Gas Vesicle Structural (GVS) genes.

The term Gas Vesicle Structural (GVS) proteins as used herein indicates proteins forming part of a gas-filled protein structure intracellularly expressed by certain bacteria or archaea and can be used as a mechanism to regulate cellular buoyancy in aqueous environments [7]. In particular, GVS shell comprises a GVS identified as gvpA or gvpB (herein also referred to as gvpA/B) and optionally also a GVS identified as gvpC.

In particular, gvpB gene is a gene encoding for gas vesicle structural protein B. gvpB genes is highly homologous to gvpA gene encoding for gas vesicle structural protein A. A gyp A/B is a protein of the GV shell that has a higher than 60% and possibly higher than 70% identity to the following consensus sequence:

(SEQ ID NO: 3)
SSSLAEVLDRILDKGXVIDAWARVSLVGIEILTIEARVVIASVDTYLR wherein X can be any amino acid. In particular in a gvpA/B of prokaryotes, the consensus sequence of SEQ ID NO: 3 typically forms a conserved secondary structure having an alpha-beta-beta-alpha structural motif formed by portions of the consensus sequence comprising the amino acids LDRILD (SEQ ID NO:4) having an alpha helical structure, RILDKGXVIDAWARVS (SEQ ID NO:5) wherein X can be any amino acid, having a beta strand, beta strand structure, and DTYLR (SEQ ID NO:6) having an alpha helical structure, as will be understood by a skilled person.

As used herein, "homology", "sequence identity" or "identity" in the context of two nucleic acid or polypeptide sequences makes reference to the nucleotide bases or residues in the two sequences that are the same when aligned for maximum correspondence over a specified comparison window. When percentage of sequence identity or similarity is used in reference to proteins, it is recognized that residue positions which are not identical often differ by conservative amino acid substitutions, where amino acid residues are substituted with a functionally equivalent residue of the amino acid residues with similar physiochemical properties and therefore do not change the functional properties of the molecule.

A functionally equivalent residue of an amino acid used herein typically refers to other amino acid residues having physiochemical and stereochemical characteristics substantially similar to the original amino acid. The physiochemical properties include water solubility (hydrophobicity or hydrophilicity), dielectric and electrochemical properties, physiological pH, partial charge of side chains (positive, negative or neutral) and other properties identifiable to a person skilled in the art. The stereochemical characteristics include spatial and conformational arrangement of the amino acids and their chirality. For example, glutamic acid is considered to be a functionally equivalent residue to aspartic acid in the sense of the current disclosure. Tyrosine and tryptophan are considered as functionally equivalent residues to phenylalanine. Arginine and lysine are considered as functionally equivalent residues to histidine.

A person skilled in the art would understand that similarity between sequences is typically measured by a process that comprises the steps of aligning the two polypeptide or polynucleotide sequences to form aligned sequences, then detecting the number of matched characters, i.e. characters similar or identical between the two aligned sequences, and calculating the total number of matched characters divided by the total number of aligned characters in each polypeptide or polynucleotide sequence, including gaps. The similarity result is expressed as a percentage of identity.

As used herein, "percentage of sequence identity" means the value determined by comparing two optimally aligned sequences over a comparison window, wherein the portion of the polynucleotide sequence in the comparison window may comprise additions or deletions (gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length protein or protein fragment. A reference sequence can comprise, for example, a sequence identifiable a database such as GenBank and UniProt and others identifiable to those skilled in the art.

As understood by those skilled in the art, determination of percent identity between any two sequences can be accomplished using a mathematical algorithm. Non-limiting examples of such mathematical algorithms are the algorithm of Myers and Miller [14], the local homology algorithm of Smith et al. [15]; the homology alignment algorithm of Needleman and Wunsch [16]; the search-for-similarity-method of Pearson and Lipman [17]; the algorithm of Karlin and Altschul [18], modified as in Karlin and Altschul [19]. Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA [17], and TFASTA in the Wisconsin Genetics Software Package, Version 8 (available from Genetics Computer Group (GCG), 575 Science Drive, Madison, Wis., USA). Alignments using these programs can be performed using the default parameters.

Thus, a gvpA/B protein in a prokaryote of interest can be identified for example by isolating GVs from a prokaryote of interest, isolating the protein from the protein shell of the GV and obtaining the amino acid sequence of the isolated protein. In addition or in the alternative to the isolating the GVs and isolating the protein, the method can include obtaining amino acidic sequences of the shell proteins of the GV of the prokaryote of interest from available database. The method further comprises performing a sequence alignment of the obtained amino acidic sequences against the gvpA/B protein consensus sequence of SEQ ID NO:3.

In particular the isolating GVs from a prokaryote of interest can be performed following methods to isolate gas vesicles as described in U.S. application Ser. No. 15/613,104, filed on Jun. 2, 2017. The isolating the protein for the protein shell of the GV and obtaining the related amino acidic sequence can be performed with tandem liquid chromatography mass-spectrometry alone or in combination with obtaining amino acid sequences of the isolated protein with wet lab techniques or from available databases comprising the sequences of the prokaryote of interest as well as additional techniques and approaches identifiable by a skilled person. Obtaining amino acid sequences of GV shell proteins of the prokaryote of interest can be performed by screening available databases of gene and protein sequences identifiable by a skilled person. Performing a sequence alignment of the sequences of the isolated GV proteins or proteins encoded in the genome of a prokaryote of interest can be performed (using Protein BLAST or other alignment algorithms known in the art) against the gvpA/B protein consensus sequence of SEQ ID NO:3. In particular, a sequence alignment can be performed using gvpA/B protein sequences from the closest phylogenetic relative to the prokaryote of interest. Reference is made to Example 1 showing exemplary phylogenetic relationships between gvpA/B proteins of exemplary prokaryotic species.

The optional gvpC gene encodes for a gvpC protein which is a hydrophilic protein of a GV shell, including repetitions of one repeat region flanked by an N-terminal region and a C terminal region. The term "repeat region" or "repeat" as used herein with reference to a protein refers to the minimum sequence that is present within the protein in multiple repetitions along the protein sequence without any gaps. Accordingly, in a gvpC multiple repetitions of a same repeat is flanked by an N-terminal region and a C-terminal region. In a same gvpC, repetitions of a same repeat in the gvpC protein can have different lengths and different sequence identity one with respect to another.

Repeat regions within any given gvpC sequence 'X' from organism 'Y' can be identified by comparing the related sequence with the sequence of a known gvpC (herein e.g. reference gvpC sequence "Z"). In particular, the comparing can be performed by aligning sequence 'X' to the reference gvpC sequence 'Z' using a sequence alignment tools such as BLASTP or other sequence alignment tools identifiable by a skilled person at the date of filing of the application upon reading of the present disclosure. In particular, a reference sequence 'Z' is chosen from a host that is the closest phylogenetic relative of 'Y', from a list of *Anabaena flosaquae, Halobacterium salinarum, Haloferax mediditerranei, Microchaetae diplosiphon* and *Nostoc* sp. The sequence alignment of 'X' and 'Z' (e.g. a BLASTP) is performed by performing a first alignment of sequence X and sequence Z to identify a beginning and an end of a repeat in 'X as well as a number of repetition of the identified repeat, in accordance with the known repeats in 'Z'. The first alignment results in at least one first aligned portion of X with respect to reference sequence Z. The aligning can also comprises performing a second alignment between the at least one first aligned portion of X identified following the first alignment and additional portions of X to identify at least one repeat 'R1' in X. Other repeats in 'X' (i.e. R2, R3, R4 . . . ) can subsequently be identified with respect to R1.

In performing alignment steps sequence are identified as repeat when the sequence shows at least 3 or more of the characteristics described in US application 15,663,635 published as US 2018/0030501 (incorporated herein by reference in its entirety) which also include additional features of of gvpC proteins and the related identification.

In a GVGC, the GVS genes are comprised with Gas Vesicle Assembly genes. The Gas Vesicle Assembly genes are genes encoding for GVA proteins. GVA proteins comprise proteins with various putative functions such as nucleators and/or chaperons as well as proteins with an unknown specific function related to the assembly of the GV.

In a prokaryotic cell GVA genes are all the genes within one or more operons comprising at least one of a gvpN and a gvpF excluding any gvpA/B and gvpC gene possibly present within said one or more operons. Therefore GVA genes can be identified by identifying an operon in a prokaryote including at least one of a gvpN and a gvpF excluding any gvpA/B and gvpC gene.

Preferably the one or more operons comprising all the GVA genes of a prokaryote can be identified and detected by detecting a gvpN gene encoding for a GV protein consensus sequence RALXYLQAGYXVHXRGPAGTGKTTLAM-HLAXXLXRPVMLIXGDDEFXTSDLIGSESGY XXKKVVDNYIHSVVKVEDELRQNWVDNRLTXA-CREGFTLVYDEFNRSRPEXNNVLLS VLEEKILXLP (SEQ ID NO: 1) wherein X indicates any amino acid or a sequence of any length having at least 50%, and more preferably 60% or higher, most preferably from 50% to 83% identity.

gvpN genes of various microorganisms have a sequence encoding for a gvpN protein within the consensus SEQ ID NO: 1. In particular, gvpN gene in the sense of the disclosure can be a gene encoding for sequence MTVLTDKRKKGSGAFIQDDETKEVLSRAL-SYLKSGYSIHFTGPAGGGKTSLARALAKKR KRPVMLMHGN-HELNNKDLIGDFTGYTSKKVIDQYVRSVYKKD-EQVSENWQDGRLLEA VKNGYTLIYDEFTRSKPATN-NIFLSILEEGVLPLYGVKMTDPFVRVHPDFRVIF TSNPAEY AGVYDTQDALLDRLITMFIDYKDI-DRETAILTEKTDVEEDEARTIVTLVANVRNRSGDEN SSGLSLRASLMIATLATQQDIPIDGSDEDFQTLCI-DILHHPLTKCLDEENAKSKAEKIILEE CKNIDTEEK (SEQ ID NO: 11) or a sequence of any length having at least 30% sequence identity with respect to SEQ ID NO:11, preferably at least 50%, and more preferably 60% or higher, and gvpF gene in the sense of the disclosure can be a gene encoding for sequence MSETNETGIYIFSAI-QTDKDEEFGAVEVEGTKAETFLIRYK-DAAMVAAEVPMKIYHPNR QNLLMHQ-NAVAAIMDKNDTVIPISFGNVFKSKEDVKVLLE NLYPQFEKLFPAIKGKIEVG LKVIGKKEW-LEKKVNENPELEKVSASVKGKSEAAGYYERIQLGG-MAQKMFTSLQKEV KTDVFSPLEEAAEAAKANEPT-GETMLLNASFLINREDEAKFDEKVNEAHENW KDKADF HYSGPWPAYNFVNIRLKVEEK (SEQ ID NO: 12) or a sequence of any length having at least 20% sequence identity with respect to SEQ ID NO:12, preferably at least 50%, more preferably 60%, and at least 70% or higher.

The term "operon" as described herein indicates a group of genes arranged in tandem in a prokaryotic genome as will be understood by a skilled person. Operons typically encode proteins participating in a common pathway are organized together as understood by those skilled in the art. Typically, genes of an operon are transcribed together into a single mRNA molecule referred to as polycistronic mRNA. Polycistronic mRNA comprises several open reading frames (ORFs), each of which is translated into a polypeptide. These polypeptides usually have a related function and their coding sequence is grouped and regulated together in a regulatory region, containing a promoter and an operator. Typically, repressor proteins bound to the operator sequence can physically obstruct the RNA polymerase enzyme from binding the promoter, preventing transcription. An example of a prokaryotic operon is the lac operon, which natively regulates transport and metabolism of lactose in *E. coli* and many other enteric bacteria.

In an operon, each ORF typically has its own ribosome binding site (RBS) so that ribosomes simultaneously translate ORFs on the same mRNA. Some operons also exhibit translational coupling, where the translation rates of multiple ORFs within an operon are linked. This can occur when the ribosome remains attached at the end of an ORF and translocates along to the next ORF without the need for a new RBS. Translational coupling is also observed when translation of an ORF affects the accessibility of the next RBS through changes in RNA secondary structure.

In some embodiments, a GV cluster comprises one of gvpN or gvpF. In several embodiments GV clusters include both gvpN and gvpF as will be understood by a skilled person. In this connection, reference is made to Example 12 and FIGS. 20 and 21 of related application US application 15,663,635 published as US 2018/0030501 incorporated herein by reference in its entirety, showing exemplary gas vesicle gene clusters operons [1, 2] comprising GVS and GVA genes and related exemplary configuration. In particular, as shown in Example 12 of related application US application 15,663,635 published as US 2018/0030501, typically a native GV gene cluster has GVA genes comprising both gvpN and gvpF genes, even if native GV gene clusters are known having a gvpN gene or a gvpF gene, as understood by skilled persons.

Accordingly, for a certain prokaryote, GVA genes in the sense of the disclosure indicate all the genes that are comprised in the one or more operons having at least one of a gvpN and/or a gvpF herein described and excluding any Gas Vesicle Structural (GVS) genes of the prokaryotes possibly comprised within the one or more operons.

Thus, GVA genes comprised in a gas vesicle gene cluster in a prokaryote can be identified for example by obtaining genome sequence of the prokaryote of interest and performing a sequence alignment of the protein sequences encoded in the genome of the prokaryote of interest against a gvpN protein sequence and/or a gvpF protein sequence.

In particular, obtaining the genome sequence of the prokaryote of interest, can be performed either using wet lab techniques identifiable by a skilled person upon reading of the present disclosure, or obtained from databases of gene and protein sequences also identifiable by a skilled person upon reading of the present disclosure. Performing a sequence alignment of the protein sequences encoded in the genome of the prokaryote of interest can per performed using Protein BLAST or other alignment algorithms identifiable by a skilled person. Exemplary gvpN protein sequence and/or a gvpF protein sequence, that can be used in performing the alignment are sequences SEQ ID NO:11 and/or SEQ ID NO:12. In particular, a sequence alignment can be performed using gvpN and/or gvpF protein sequences from the closest phylogenetic relative to the prokaryote of interest. Reference is made to Example 2 showing exemplary phylogenetic relationships between gvpF and gvpN proteins of exemplary prokaryotic species. Accordingly, one or more operons that comprise the gvpN and/or gvpF genes can be identified, and any other gvps within the one or more operons can also be identified, wherein the other gvps are comprised in ORFs within the one or more operons, excluding any ORFs encoding gvpA/B or gvpC genes comprised in the one or more operons of the GV gene cluster.

Accordingly, GVA genes can also be identified based on the configuration of operon and Gene Clusters identified through homology (see e.g. Example 1), phylogenesis (see e.g. Example 2) also using the gvpA/B, gvpN and/or gvpF consensus of SEQ ID Nos: 1, 3, and 11-12 herein provided, preferably gvpA/B consensus of SEQ ID NO: 3 and gvpN consensus of SEQ ID NO: 1. Reference is also made in this connection to the indication of Example 3 reporting exemplary GVGC configurations of naturally occurring Gas Vesicle gene clusters identified with method herein described and additional methods identifiable by a skilled person.

GVS genes of a GVGC of the disclosure, identified with methods herein indicated, typically comprise gvpA or gvpB which have similar sequences and are equivalent in their purpose and optionally gvpC. Exemplary sequences for gvpA and gvpB genes of GV gene clusters in the sense of the disclosure, which can also be used to identify additional GVS and GVGC through homology and alignment in addition to the use of the consensus sequence SEQ ID NO: 3, are reported in Example 4.

GVA genes of a GVGC of the disclosure, identified with methods herein indicated, typically comprise proteins identified as gvpF, gvpG, gvpL, gvpS, gvpK, gvpJ, and gvpU. GVA genes and proteins can also comprise gvpR and gvpT (see e.g. *B. megaterium* GVA) gvpV, gvpW (see *Anaboena flos aque* and *Serratia* GVA) and/or gyp X, gyp Y and gyp Z (see e.g. *Serratiai* GVA. Preferably GVGC of the disclosure further comprise gvpN which result in a more robust detection with many detection methods herein described. Exemplary sequences for GVA genes of GV gene clusters in the sense of the disclosure which can also be used to identify additional GVAs and GVGC through homology and alignment are reported in Example 4.

In GVGC herein described co-expression of the GVS genes and the GVA genes in connection with regulatory sequence capable of operating in a host cell are configured to provide a GV type, with a different GVGC typically resulting in a different GV type.

The wording "GV type" in the sense of the disclosure indicates a gas vesicle having dimensions and shape resulting in distinctive mechanical, acoustic, surface and/or magnetic properties as will be understood by a skilled person upon reading of the present disclosure. In particular, a skilled person will understand that different shapes and dimensions will result in different properties in view of the indications in provided in U.S. Applicant Ser. No. 15/613, 104 published as US2018/0028693 and U.S. Ser. No. 15/663,600 published as US2018/0038922 and additional indications identifiable by a skilled person Typically, larger volume results in stronger per-particle scattering, smaller diameter generally results in higher collapse pressure after removal of gvpC, and different dimensions result in different ratios of T2/T2* relaxivity per volume-averaged magnetic susceptibility ([20]).

Accordingly, in embodiments herein described, GVGC can be selected based on desired properties of the corresponding GV type. In particular, to this extent, a skilled person can use naturally occurring GVGC, can provide engineered GVGC wherein some of the naturally occurring gyp genes are omitted, and/or can provide hybrid GVGC in which GVAs and GVS genes of naturally occurring GVGCs are combined to provide GV types having the shape and dimensions resulting in the desired properties.

The term "hybrid gene cluster" or "hybrid cluster" as used herein indicates a cluster comprising at least two genes native to different species and resulting in a cluster not natively in any organisms. Typically, a hybrid gene cluster comprises a subset of gas vesicle genes native to a first bacterial species and another subsets of gas vesicle genes native to one or more bacterial species, with at least one of the one or more bacterial species different from the first bacterial specie Accordingly, a hybrid GV gene clusters includes a combination of GV genes which is not native in any naturally occurring prokaryotes.

In particular, identification of a desired GVGC for a target cell and therefore of the ability of the corresponding gyp genes combination to result in production of functional GV proteins capable of assembling in a GV thus providing a corresponding detectable GV type can be performed through a testing method also directed to verify detectability of the GV by a detection method of choice. The testing method can be performed in the target cell where detection of the GV type is desired or in testing cells having a cell environment equivalent to the cell environment of the target cell in terms of expression of GV genes and GV formation and thus provide a model to verify ability of the gyp genes to provide a GVGC for the target cells. In the method to identify a desired GVGC the introducing can be performed using engineered polynucleotide constructs contacted with the target cell or testing cell for a time and under conditions to allow expression of the GVGC and formation of the GV type (e.g. using the methods described in US application 15,663, 635 published as US 2018/0030501 incorporated herein by reference). The method further comprises detecting formation of a gas vesicle in the target cell or testing cell following the introducing with a pre-set method of detection. Preset methods of detection can be directed to detect acoustic and/or magnetic properties that are of interest in desired applications of the corresponding GV type. Preferably the testing can be performed in a target cell or testing cell, that have been modified, either chemically or genetically, to have the same cellular turgor pressure as mammalian cells according to methods identifiable by a skilled person.

Experiments performed with GVGC herein described provide proof of principle that *E. coli* is an effective model for ability of a GVGC to correctly assemble in mammalian cell environment and that therefore can be used as a testing cell GVGC capable of mammalian cells. Accordingly, detecting expression of a candidate GVGC in *E. coli* with a pre-set method is indicative of the ability of the corresponding GV proteins to form a GV type and of the GV type to correctly assemble and be detectable with the pre-set method in a mammalian cell.

Experiments performed with GVGC herein described provide proof of principle that *E. coli* is an effective model for ability of a GVGC to correctly assemble in mammalian cell environment and that detecting expression of a candidate GVGC in *E. coli* with a pre-set method is indicative of the ability of the corresponding GV type to correctly assemble and be detectable with the pre-set method in a mammalian cell.

In exemplary embodiments where a GV type is to be used in differential ultrasound imaging or image-subtracted ultrasound, the pre-set method of detection can comprise imaging with ultrasound a target site comprising the cell following the introduction of the GVGC, applying acoustic pressure to the target site at a pressure expected to collapse the GVs and then imaging the target site with ultrasound again, and the difference of the images (before and after collapse) shows if collapsing GVs (having a collapse threshold below the acoustic pressure) were present at the target site.

In exemplary embodiments where a GV type is to be used in MRI (magnetic resonance imaging), imaging, the pre-set method of detection can comprise imaging with MRI a target site comprising the cell following the introduction of the GVGC, applying hydrostatic pressure to the target site at a pressure expected to collapse the GVs. The target site is then imaged with MRI again, and the difference of the images (before and after collapse) shows if collapsing GVs (having a collapse threshold below the hydrostatic pressure) were present at the target site.

In exemplary embodiments where a GV type is to be used in BURST (burst ultrasound reconstruction with signal templates) imaging described herein and in U.S. application Ser. No. 16/736,581 filed on Jan. 7, 2020 and herein incorporated by reference in its entirety, the pre-set method of detection can comprise imaging with ultrasound a target site comprising the cell following the introduction of the GVGC, over successive frames, at a peak positive pressure (PPP) well below the expected collapse threshold pressure for the GVs. While the frames are being taken, increasing the PPP step-wise to a value over the expected collapse threshold pressure for at least 9 half-cycles. Frames from before, during, and after the application of the increased pressure undergo template mixing to detect a BURST signal from the collapsing GVs, if present.

Additional methods of detection such as Transmission Electron Microscopy (TEM) and optical scattering, optical phase detection, xenon hyperCEST MRI can be used.

An exemplary method of detection of a functional GVGC in the sense of the disclosure performed in *E. coli* is reported in Example 5 of the present disclosure. Additional methods to be performed other prokaryotic cells and/or mammalian cells using the GVES of the disclosure can be identified by a skilled person upon reading of the present disclosure.

Several detectable GVGC with one or more detection method of interests have been identified and can be used for production of GV types in various cells through various genetically engineered constructs as will be understood by a skilled person upon reading of the present disclosure and US application 15/663,635 published as US 2018/0030501 herein incorporated by reference in its entirety.

In some embodiments described herein GVGC of the instant disclosure can be naturally occurring combination of gyp genes which can have a naturally occurring sequence or a sequence modified to optimize the expression in the cell where detection is to be performed. For example GVGC clusters of the instant disclosure comprise a GVGC of *B. megaterium* formed by the gvpA or gvpB genes, gvpR, gvpN gvpF, gvpG, gvpL gvpS, gvpK, gvpJ, gvpT, gvpU of *B. megaterium*, or the GVGC of *Anaboena Flos Aquae* formed by the gvpA or gvpB genes of *Anaboena Flos Aquae* (see e.g. the sequences in Table 6 of Example 4) and the GVA gvpC, gvpN, gvpJ, gvpK, gvpF, gvpG, gvpV, gvpW of *Anaboena Flos Aquae* (see e.g. sequences in Table 10 of Example 4).

The gyp genes in one or more genes of the GVGC cluster of the present disclosure can have a naturally occurring sequence or a sequence modified to optimize the expression in the cell where detection is to be performed. For example a *B. megaterium* GVGC can have a gvpA or gvpB genes having the sequences in Table 6 of Example 4, and/or any one of the gvpR, gvpN gvpF, gvpG, gvpL gvpS, gvpK, gvpJ, gvpT, gvpU genes having the sequences in Table 8 of Example 4. Similarly, an *Anaboena Flos Aquae* GVGC can have the gvpA or gvpB genes having the sequences reported in Table 6 of Example 4 and/or any one of the gvpC, gvpN, gvpJ, gvpK, gvpF, gvpG, gvpV, gvpW having the. sequences reported in Table 10 of Example 4.

In some embodiments, described herein, GVGC of the instant disclosure can be modified version of naturally occurring GV gene clusters. An example is provided by the. GVGC of *B. megaterium* comprising gvpB, gvpR, gvpN gvpF, gvpG, gvpL gvpS, gvpK, gvpJ, gvpT, gvpU wherein the gvpR and gvpT genes of the naturally occurring GVGC from *B. megaterium* have been omitted (see e.g. the sequences reported in Example 6 and Table 9 of the instant disclosure). Another example is provided by GV gene clusters comprising gvpA, Ana-gvpC gvpN, gpvJ, gvpK, gvpF, gvpG, gvpW, and gvpV from *Anabaena flos-aquae* or GV gene clusters comprising gvpA+gvpN, gpvJ, gvpK, gvpF, gvpG, gvpW, gvpV from *Anabaena flos-aquae* (see *Anabaena flos-aquae* genes in Table 4 and Table 10 of Example 4 of the present disclosure).

In other embodiments described herein, GVGC of the instant disclosure can be a hybrid GV gene cluster in a Gas Vesicle expression system of the disclosure, can comprise a combination of genes from *A. flos-aquae* (herein also Ana-gvp) and genes from *B. megaterium* (herein also Mega-gvp). In particular, in exemplary embodiments, the hybrid GV gene cluster can comprise *B. megaterium* GVA assembly genes gvpR, gvpN, gvpF, gvpG, gvpL, gvpS, gvpK, gvpJ, gvpT and gvpU and further comprise structural gvpA gene from *Anabaena flos-aquae*. In some of those embodiments, the hybrid GV gene cluster can comprise gvpA, gvpC from *Anabaena flos-aquae* and GVA genes from *B. megaterium* possibly excluding gvpR and/or gvpT. In some of those embodiments, the hybrid GV gene cluster can comprise Ana-gvpA and mega GVA genes possibly excluding gvpR and/or gvpT. In some embodiments GVGC of the instant disclosure can include gvpA, gvpC, gvpN from *Anabaena flos-aquae* and GVA genes from *B. megaterium*, as well as other combinations identifiable by a skilled person upon reading of the present disclosure.

In some embodiments herein described, a GVGC comprising gyp genes A/B, C and N (gvpA/B, gvpC, gvpN genes) from a same or different prokaryote. Preferably the GVGC comprises a gvpN gene as presence of gvpN protein results in an increased detectability of the related GV type.

For example, in one exemplary embodiment, all the gyp genes B, N, F, G, L, S, K, J and U are from *B. megaterium*. GVs from *B. megaterium* are typically cone-tipped cylindrical structures with a diameter of approximately 73 nm and length of 100-600 nm, encoded by a cluster of eleven or fourteen different genes, including the primary structural protein, gvpB, and several putative minor components and putative chaperones [21, 22] as would be understood by a person skilled in the art.

In some embodiments, some of the set of nine gyp genes can be from *Bacillus megaterium* and the rest genes are from *Anabaena flos-aquae* such as the GVGC comprising Ana-A, Ana-C, Ana-N, mega: gvpF, gvpG, gvpL, gvpS, gvpK, gvpJ, gvpT and gvpU with/without gvpR and gvpT, and additional examples identifiable by a skilled person upon reading of the present disclosure (see Example 4 and Example 5 of the present disclosure).

In embodiments herein described, the sequences of at least one gyp gene can be modified with respect to the natural occurring sequence to improve the related expression (e.g. to be codon optimized) and/or the inclusion in the GVES of the disclosure (e.g. by modification of the N- and/or C-terminal portions to allow the use of linker or other elements to be included in a cassette or construct of the disclosure).

In some embodiments, the GVGC can comprise *Serratia* gyp genes as *Serratia* GVs can express functional GV proteins in *E. coli*, as reported in literature ([23] [24]).

GVES and related constructs have been herein provided based on the surprising finding that a naturally occurring, or engineered GVGC (e.g. modified to remove or add gyp genes, to include one or more gyp genes with a modified sequence, and/or to include gyp genes from different prokaryotes to provide a hybrid cluster) which is functional in *E. Coli* can be expressed in mammalian cells on an engineered polynucleotide construct specifically configured to allow expression in the mammalian cell of GV proteins encoded by the GVGC resulting in formation of a corresponding GV type in the mammalian cell.

The term "mammalian cell" refers to cells from a mammal tissue comprising cell within a mammal host and cell isolated from and expanded in culture for use as therapeutic and research tools. Exemplary mammalian cells that can express GVES of the disclosure are primary cells (cells that are directly harvested from an animal and genetically engineered with GVs. Exemplary mammalian cell culture that can be genetically engineered with GV constructs described herein configured to allow expression of GVs comprise HEK 293T, CHO-K1 cells, HEK293, CHO-K1, N2A cells, HeLa, Jurkat, NIH3T3, and other identifiable by those skilled in the art.

In particular, in accordance with the disclosure it has been surprisingly found that naturally occurring, modified and/or hybrid GVGC can be expressed in a mammalian cells if expression of gvpA or gvpB gene is performed in a gene expression cassette separated from the one or more gene expression cassettes used to express the remaining GV genes of the GV gene cluster to be expressed. Also, it has surprisingly be found that gyp genes of a GVgene cluster other than gvpA and/or B can be expressed in a mammalian cells in a single gene expression cassette providing that each gyp gene is separated from another in the same cassette by a separation element encoding a separation peptide possibly in combination with at least one booster cassettes to increase expression of bottleneck genes in the GVGC cluster.

The term "gene cassette" as used herein indicated a mobile genetic element that contains at least one gene and a recombination site. Accordingly, a gene cassette can contain a single gene or multiple genes possibly organized in an operon structure A gene cassette can be transferred from one DNA sequence (usually on a vector) to another by 'cutting' the fragment out using restriction enzymes or transposase, cripr, viral and/or recombinase enzymes and other nucleases and 'pasting' it back into the new context or other molecular biology and cloning techniques (e.g. pcr, CRISPR, TALENs, ZFN). Gene cassettes can move around within an organism's genome or be transferred to another organism in the environment via horizontal gene transfer.

A "gene expression cassette" is a gene cassette comprising regulatory sequence to be expressed by a transfected cell. Following transformation, the expression cassette directs the cell's machinery to make RNA and proteins. Some expression cassettes are designed for modular cloning of protein-encoding sequences so that the same cassette can easily be altered to make different proteins. An expression cassette is composed of one or more genes and the sequences controlling their expression. An expression cassette typically comprises at least three components: a promoter sequence, an open reading frame, and a 3' untranslated region that, in eukaryotes, usually contains a polyadenylation site. An expression cassette can be formed by manipulable fragment of DNA carrying, and capable of expressing, one or more genes of interest optionally located between one or more sets of restriction sites Gene expression cassettes as used herein typically comprise further regulatory sequences additional to the prompter to regulated the expression of the gene or genes within the open reading frame herein also indicated as coding region of the cassette.

In particular, in embodiments of the GVES herein described, the gene expression cassettes of the system comprise one or more gyp genes under control of regulatory sequence capable of operating in the mammalian host and are thus configured to provide a GV type in the mammalian cell.

The term "regulatory sequence" or "regulatory regions" as described herein indicate a segment of a nucleic acid molecule which is capable of increasing or decreasing transcription or translation of a gene within an organism either in vitro or in vivo. In particular, coding regions of the GV genes herein described comprise one or more protein coding regions which when transcribed and translated produce a polypeptide. Regulatory regions of a gene herein described comprise promoters, transcription factor binding sites, operators, activator binding sites, repressor binding sites, enhancers, protein-protein binding domains, RNA binding domains, DNA binding domains, silencers, insulators and additional regulatory regions that can alter gene expression in response to developmental and/or external stimuli as will be recognized by a person skilled in the art.

The term "operative connection" as used herein indicate an arrangement of elements in a combination enabling production of an appropriate effect. With respect to genes and regulatory sequences an operative connection indicates a configuration of the genes with respect to the regulatory sequence allowing the regulatory sequences to directly or indirectly increase or decrease transcription or translation of the genes.

Regulatory sequences used in gene expression cassettes herein described identified herein also as mammalian regulatory regions are configured to operate in a mammalian cell.

Exemplary regulatory regions capable of operating in mammalian cells comprise promoters, enhancers, silencers, terminators, regulators, operators, ribosome binding/entry sites, and riboswitches, among others known in the art. Regulatory regions capable of operating in a mammalian host can be selected by a skilled person following selection of the mammalian host of interest. Exemplary constitutive and inducible mammalian promoters and operators suitable for regulating expression of GVs in a mammalian host comprise and others identifiable by those skilled in the art and described herein.

Mammalian regulatory regions comprised in a gene expression cassette herein described, typically comprise a mammalian promoter, 5'UTR regions, 3'UTR regions, and a terminator as will be understood by a skilled person.

A "mammalian promoter" in the sense of the disclosure suitable for gene expression in a mammalian cell is a region of DNA that leads to initiation of transcription of a particular gene. Exemplary are typically located on a same strand and upstream on a DNA sequence (towards the 5' region of the sense strand), adjacent to the transcription start site of the genes whose transcription they initiate. In mammalian cells organisms, promoters typically comprise the eukaryotic TATA (SEQ ID NO:13) box. Promoters are located near the transcription start sties of genes, upstream on the DNA. Promoters can typically be about 100-1000 base pairs long. In particular promoters that can be used in gene expression cassette herein described can be a constitutive promoter or a conditional promoter.

The term "conditional promoter" refers to a promoter with activity regulatable or controlled by endogenous transcription factors or exogenous inputs such as chemical, or thermal inducers or optical induction. Examples of mammalian constitutive promoters include inducible promoters based on exogenous agents such as TET (tetracycline-response elements, TET-ON/TET-OFF), Lac, dCas-transactivator, Zinc-finger-TF, TALENs-ZF Gal4-uas, synNotch and inducible promoters based on endogenous signals TNF-alpha, cFOS and others identifiable to a skilled person.

The term "constitutive promoter" refers to an unregulated promoter that allows for continual transcription of its associated genes. Exemplary mammalian constitutive promoters that can be used for expression in mammalian cell include CMV from human cytomegalovirus, EF1a from human elongation factor 1 alpha, SV40 from the simian vacuolating virus 40, PGK1 from phosphoglycerate kinase gene, Ubc from human ubiquitin C gene, human beta actin, CAAG, SynI and others identifiable to those skilled in the art.

The wording "5'UTR region" refers to the region upstream from the initiation codon as will be understood by a person of ordinary skill in the art and is therefore outside the coding region of the cassette. The 5'UTR region can contain a Kozak sequence. The Kozak sequence used herein refers to a nucleic acid motif that functions as the protein translation initiation site in most eukaryotic mRNA transcripts as will be understood by a person skilled in the art. The Kozak sequence locates approximately 6 nucleotide sequence upstream of the ATG start codon. Exemplary Kozak sequence include GCCACCATG (SEQ ID NO: 475), TTCACCATG (SEQ ID NO: 476), (CCC)TTCACCATG (SEQ ID NO: 477) consensus sequence XXX[A/G]XXATG (SEQ ID NO: 478) wherein X indicates any nucleotide, and additional sequences identifiable by a skilled person.

The "3'UTR region" refers to an untranslated region that immediately follows the translation termination codon and is therefore outside the coding region of the cassette. 3'UTR region often contains regulatory regions that post-transcriptionally influence gene expression. Regulatory regions within the 3'UTR can influence polyadenylation, translation efficiency, localization, and stability of the mRNA as will be understood by a person skilled in the art. In some embodiments, the 3'UTR contains silencer regions which are configured to bind to repressor proteins and inhibit the expression of the mRNA.

A "terminator" as used herein indicates a sequence-based element that defines the end of a transcriptional unit and initiates the process of releasing the synthesized mRNA. Exemplary mammalian terminators include polyadenylation sites. A "polyadenylation site" indicates an element target by the polyadenylation enzymes such as CPSF and typically comprises the sequence AAUAAA (SEQ ID NO: 14) on the RNA. Polyadenylation sites will result in cleavage of the construct 10-30 nucleotides downstream the site, and addition of a poly(A) tail located at the end of 3'UTR as will be understood by a person skilled in the art. In gene expression cassette the poly(A) site can include SV40 polyadenylation element, hGH poly(A) signal, and other poly(A) signal that have the canonical AAUAAA (SEQ ID NO: 14) region as will be understood by a skilled person.

In some embodiments, a gene expression cassette can include additional mammalian regulatory regions configured to increase or decrease the expression of the GV coding regions of the cassette, as will also be understood by a skilled person.

Exemplary mammalian regulatory sequences increasing transcription of the operatively linked gene comprise enhancers that can be located more distally from the transcription start site compared to promoters, and either upstream or downstream from the regulated genes, as understood by those skilled in the art. Enhancers are typically short (50-1500 bp) regions of DNA that can be bound by transcriptional activators to increase transcription of a particular gene. Typically, enhancers can be located up to 1 Mbp away from the gene, upstream or downstream from the start site. An exemplary additional mammalian regulatory regions directed to enhance the expression levels of the GV genes, include Woodchuck Hepatitis Virus Posttranscriptional Regulatory Element (WPRE) placed downstream of the genes between GV gene and the poly(A) tail. The WPRE and WPRE-like (e.g. RE of Hepatitis B virus (HPRE)) element is known to increase transgene expression from a variety of viral vectors.

Exemplary mammalian regulatory sequences decreasing transcription of the operatively linked gene comprise RNAi/miRNA/shRNA sites that can be located upstream or downstream of the GV genes to control mRNA translation or degradation. For example, by binding to specific sites within the 3'UTR, miRNAs can decrease gene expression of various mRNAs by either inhibiting translation or directly causing degradation of the transcript.

Additional mammalian regulatory sequences that can be included in a gene expression cassette include post transcriptional regulatory sequences such as riboswitches typically present in eukaryotic untranslated regions (UTRs) of encoded RNAs. These sequences are configured to switch between alternative secondary structures in the RNA depending on the concentration of key metabolites. The secondary structures then either block or reveal other regulatory sequence regions such as RNA binding proteins. A further examples of additional post transcriptional regulatory sequences regulatory sequences comprise aptazymes fusions composed of an aptamer domain and a self-cleaving ribozyme which can be used for conditional gene expression to control mRNA levels with small molecules (e.g. tetracycline).

In general, selection of promoter and other regulatory sequences to be included in expression polynucleotidic constructs comprised in GVES of the present disclosure can be performed by one or more of the following: detecting functionality of a promoter and/or additional regulatory sequence in the host cells, selecting promoters and/or additional regulatory sequences known to be functional in the host cells; detecting the strength of the promoters and/or additional regulatory sequences in connection with protein production and/or selecting promoter and/or additional regulatory sequences of known strength; and selecting inducible promoters and/or additional regulatory sequence to control GV expression.

Mammalian regulatory sequences can be provided in any configuration which is directed to provide a desired expression of the GV protein in the coding regions. For example, a gene expression cassette can an end of UTR with polyA site only, or can be with WPRE and polyA site, or it can be with WPRE only. A combination of WPRE and polyA tail is expected to result in highest expression (highest copy of translated protein). Additional configuration can be identified by a skilled person.

In embodiments of the GVES herein described GV genes other than gvpA/B can be provided in a single gene expression cassette in various combinations and in any order to the extent that when the cassette comprises two or more gyp genes other than gvpA/B, the two or more gyp genes are configured to have each GV gene linked to another by a separation element.

A separation element used herein refers to an element that can be placed between two adjacent coding genes allowing for a separate transcription or translation of the two adjacent coding genes.

In some embodiments, a separation element can be an internal ribosome entry site ("IRES"). An internal ribosome entry site (IRES) used herein refers to an element that allows for translation initiation in a cap-independent manner. In some embodiments herein described, an IRES element is placed between two coding genes to allow for initiation of translation from an internal region of the mRNA. It allows the coordinated expression of two genes using the same promoter in a single gene cassette as will be understood by a person skilled in the art. Thus, the genes separated by IRES can be expressed from a bicistronic mRNA without requiring either cleavage of a polyprotein or generation of a monocistronic mRNA.

Internal ribosome entry sites are approximately 450 nucleotides in length and are characterized by moderate conservation of primary sequence and strong conservation of secondary structure. The most significant primary sequence feature of the IRES is a pyrimidine-rich site whose start is located approximately 25 nucleotides upstream of the 3' end of the IRES. Detailed information on IRES can be found in Jackson, et al., Trends Biochem. Sci., vol. 15, No. 12, pp. 477-483, 1990.

Examples of IRES known in the art include IRES obtainable from picornavirus and IRES obtainable from viral or cellular mRNA sources such as for example, immunoglobulin heavy-chain binding protein (BiP), the vascular endothelial growth factor (VEGF) (Huez et al. (1998) Mol. Cell. Biol. 18(11):6178-6190), the fibroblast growth factor 2 (FGF-2), and insulin-like growth factor (IGFII), the translational initiation factor eIF4G and yeast transcription factors TFIID and HAP4, the encephelomycarditis virus (EMCV) which is commercially available from Novagen (Duke et al. (1992) J. Virol 66(3):1602-9) and the VEG-FIRES (Huez et al. (1998) Mol Cell Biol 18(11):6178-90). IRES have also been reported in different viruses such as cardiovirus, rhinovirus, aphthovirus, HCV. Friend murine leukemia virus (FrMLV) and Moloney murine leukemia virus (MoMLV). As used herein, IRES encompasses functional variations of IRES sequences as long as the variation is able to promote direct internal ribosome entry to the initiation codon of a cistron.

In some embodiments, a separation element is a post-translation cleavage element comprising a cleavage site sequence. A post-translation cleavage element is typically placed between two adjacent coding genes.

In some embodiments, the post-translation cleavage element comprises a 2A element. The term "2A element" or "2A sequence" refers to a post-translational or co-translational processing cleavage site sequence. The 2A sequence can be a DNA sequence or the peptide expression produce of the DNA sequence. The latter is referred to as the 2A peptide. The 2A peptides are known to function by making the ribosome skip the synthesis of a peptide bond at the C-terminus of a 2A element, leading to separation between the end of the 2A sequence and the next peptide downstream. The cleavage occurs between the Glycine and Proline residues found on the C-terminus meaning the upstream cistron will have a few additional residues added to the end, while the downstream cistron will start with the Proline. The 2A elements used herein are placed between two adjacent GV coding genes. Exemplary 2A peptides are listed in Table 1 below:

TABLE 1

| Exemplary 2A peptide sequences | |
|---|---|
| P2A | ATNFSLLKQAGDVEENPGP (SEQ ID NO: 15) |
| T2A | EGRGSLLTCGDVEENPGP (SEQ ID NO: 16) |
| E2A | QCTNYALLKLAGDVESNPGP (SEQ ID NO: 17) |
| F2A | VKQTLNFDLLKLAGDVESNPGP (SEQ ID NO: 18) |
| BmCPV | DVFRSNYDLLKLCGDIESNPGP (SEQ ID NO: 19) |
| BmIFV | TLTRAKIEDELIRAGIESNPGP (SEQ ID NO: 20) |

In Table 1, the bold residues are the consensus residues among each type of 2A element (P2A, T2A, E2A or F2A). In each 2A element of Table 1, the cleavage occurs between the last G/P. In some embodiments, a linker sequence such as GAPGSG linker (SEQ ID NO: 21) is placed between a GV coding gene and the 2A sequence optionally using a linker, wherein any linker sequences such as GSG, GSGSG (SEQ ID NO: 2), SGS, and other linkers identifiable by a skilled person can be used. For example, a polynucleotide construct can comprise from 5' to 3' GV gene 1-GAPGSG-2A sequence-GV gene 2.

In some embodiments, the post-translation cleavage element comprises a cleavage recognition site that can be targeted and subsequently cleaved by protease enzymes. Exemplary protease enzymes include TEV, HCV NS3/5 protease, HIV protease, CMV protease, and HSV protease.

The term "protease cleavage site" in the sense of the disclosure indicates target sites for proteolytic cleavage by enzymes such as peptidases, proteases or proteolytic cleavage enzymes which break peptide bond between amino acids in proteins. The general nomenclature of cleavage site positions of the substrate were formulated by Schechter and Berger, 1967 [25] and Schechter and Berger, 1968 [26] Accordingly, the cleavage site is designated between P1-P1', incrementing the numbering in the N-terminal direction of the cleaved peptide bond (P2, P3, P4, etc.). On the carboxyl side of the cleavage site the numbering is incremented in the same way (P1', P2', P3' etc.).

Protease cleavage sites that can be inserted in engineered microcompartment proteins of the disclosure comprise regions up to 25 residues. In particular, protease cleavage sites are inserted in a configuration which makes them surface accessible. In some embodiments protease cleavage site are included in an unstructured segment or within an alpha helical or beta sheet secondary structured segment. Exemplary protease cleavage sites that can be inserted in engineered microcompartment proteins herein described comprise TEV protease cleavage sites with sequence ENLYFQG, (SEQ ID NO: 25) which is unstructured and others identifiable by a skilled person upon reading of the present disclosure (see Table 2).

Recognition sequences and cleavage sites of exemplary proteases are shown in Table 2./forward slash (/) indicates where protease cleaves the protein sequence.

TABLE 2

Recognition sequences and cleavage sites of exemplary proteases

| Enzyme Name | Sequence and Cleavage | SEQ ID NO |
|---|---|---|
| Human Rhinovirus (HRV) 3C Protease | LEVLFQ/GP | 22 |
| Enterokinase | DDDDK/ | 23 |
| Factor Xa | IEGR/ | 24 |
| Tobacco etch virus protease (TEV protease) | ENLYFQ/G | 25 |
| Thrombin | LVPR/GS | 26 |
| NS3/4A | DLEVVT/STWV | 27 |
| NS4A/4B | DEMEEC/ASHL | 28 |
| NS4B/5A | DCSTPC/SGSW | 29 |
| NS5A/5B | EDVVCC/SMSY | 30 |
| NS4A/4B | DEMEEC/SQH | 31 |

In some embodiments, the cleavage recognition site comprises a TEV protease cleavable sequence that can be placed between two GV coding genes when the TEV enzymes are co-expressed. The TEV peptide can be cleaved to release the two GV proteins.

In some embodiments, the cleavage recognition site comprises a recognition sequence targeted by one or more non-structural protein NS3, NS4A, NS4B and NS5 sequence.

In some embodiments herein described, post-translation cleavage element comprises an intein or hedgehog family auto-processing domains or variants therefore, inserted in an open reading frame between multiple coding genes. The term "intein" refers to the protein equivalent of gene introns which facilitate protein splicing. The intein element contains the necessary components needed to catalyze protein slicing and often contains an endonuclease domain that participates in intein mobility (Perler, F. B., et al., Nucleic Acids Research 1994, 22, 1127).

The Hedgehog family auto-processing domains used herein comprise the hedgehog protein carboxy-terminal autocatalytic domain HhC. As a person skilled in the art will understand, the hedgehog ("Hh") proteins are composed of two domains, an amino-terminal domain HhN, which has the biological signal activity, and a carboxy-terminal auto-catalytic domain HhC, a carboxy-terminal autocatalytic domain HhC which cleaves Hh into two parts in an intra-molecular reaction and adds a cholesterol moiety to the HhN. HhC has sequence similarity to the self-splicing inteins, the shared region is termed Hint. New classes of proteins containing the Hint domain have been discovered in bacteria and eukaryotes.

As a person skilled in the art will understand, the sequences of the inserted auto-processing polypeptides or cleavage sites can be manipulated to enhance the efficiency of expression of the separate proteins.

Accordingly, in some embodiments, the constructs encoding gvpN, gvpF, gvpG, gvpL, gvpS, gvpK, gvpJ, and gvpU genes are comprised in a single polynucleotide. For example, all of the gvpN, gvpF, gvpG, gvpL, gvpS, gvpK, gvpJ, and gvpU genes can be provided in one open reading frame, operatively connected and under regulatory control of the same promoter. In an exemplary embodiments, gvpN, gvpF, gvpG, gvpL, gvpS, gvpK, gvpJ, and gvpU genes from B. megaterium are comprised in a single polycistronic construct (see e.g. construct of Example 8).

In some embodiments, the construct encoding gvpN, gvpF, gvpG, gvpL, gvpS, gvpK, gvpJ, and gvpU genes are comprised in more than one polynucleotide. For example, a subset of the gvpN, gvpF, gvpG, gvpL, gvpS, gvpK, gvpJ, and gvpU genes are comprised in one cassette in which they are, operatively connected and under regulatory control of a first promoter, whereas another subset of the gvpN, gvpF, gvpG, gvpL, gvpS, gvpK, gvpJ, and gvpU genes are comprised in another construct, operatively connected and under regulatory control of a second promoter. Each construct can be polycistronic construct when comprising two or more coding genes. For example, one subset of Ana gvpN, gvpJ, gvpK, gvpF, gvpG, gvpW, gvpV can be on a polynucleotide and another subset of Ana gvpN, gvpJ, gvpK, gvpF, gvpG, gvpW, gvpV can be on another construct, either as monocistronic constructs or as polycistronic constructs as will be understood by a skilled person.

The term "polycistronic construct" as used herein refers to a construct capable of simultaneously translating multiple genes from a single transcript as will be understood by a person skilled in the art, within a single cassette or in different cassettes on the construct if the cassettes are separated by an internal ribosome entry site.

In some embodiments, the polycistronic construct can be a biocistronic construct which comprises two genes separated by an Internal Ribosome Entry Site (IRES) element which allows for initiation of translation from an internal region of the mRNA. Use of IRES allows for the upstream protein to remain pristine while the downstream protein gets a MATT peptide addition to its N terminus. The second protein may be expressed at a lower level compared with the first protein since the ribosome entry site is less efficient than the 5'cap/UTR as will be understood by a skilled persons.

In some embodiments, some of the gene of a GVGC are expressed at a lower level compared to other gyp genes of the GV gene cluster when expressed under a same promoter and regulatory regions (herein also indicated as bottleneck genes). in those embodiments, the stoichiometry of the expression of the bottleneck genes can be increased to provide an optimal functionality of the GVES in the mammalian cell.

In particular, in some of those embodiments, the polynucleotide construct herein described further comprises a booster construct to elevate the gene expression. For example, the booster construct can contain gyp genes J, F, G, L and K connected with a separation element such as the p2A elements to elevate the expression of these genes. The booster construct containing gyp genes J, F, G, L and K can be comprised in one or more gene cassettes each operatively connected with regulatory sequences to enable the expression of the gyp genes J, F, G, L and K. In those embodiments when comprised in more than one operon, these genes are separated by a joint element such as the P2A element. In some embodiments, gvpJ and gvpK can also be used by themselves as boosters. gvpJ, F, G, L, K can also be on their own separate gene cassettes (e.g. on separate plasmids) and act as boosters.

In some embodiments the booster constructs can be comprised on one or more gene cassettes, where the use of promoter strengths can tune stoichiometry of the translated proteins. Stronger promoters can be used on the booster constructs while relatively weaker promoters can be used for the other cassette.

In some embodiments the booster constructs can be comprised on one or more gene cassettes, where the stability of the transcript can tune stoichiometry of the translated proteins. Regulatory elements that stabilize mRNAs (for example PolyA, WPRE) can be used on the booster constructs. For genes that need to be expressed at lower relative stoichiometries, these stability elements can be removed, or can be conditionally removed using siRNAs/shRNAs/aptazymes/cas9 and etc. While the other GV cassette can include these mRNA stability elements.

In some embodiments the booster constructs can be comprised on one or more gene cassettes, where the use of degradation tags can tune stoichiometry of the translated proteins. Degradation tags target proteins for proteolysis, for example ubiquitin and library of ubiquitin-fusion degradation tags (UbR, UbP, UbW, UbH, UbI, UbK, UbQ, UbV, UbL, UbD, UbN, UbG, UbY, UbT, UbS, UbF, UbA, UbC, UbE, UbM, 3xUbVR, 3xUbVV, 2xUbVR, 2xUbVV, UbAR, UbVV, UbVR, UbAV, 2xUbAR, 2xUbAV), auxin-inducible degraon (AID), D-element, the PEST sequence, unstructured initiation sites, or short sequences rich in acceptor lysines. Genes on the booster constructs will not have these degradation tags while relatively degradation tags can be used for the other genes that need to be expressed to lower levels. This can be used in combination with promoters and transcript stability examples.

Some embodiments the booster constructs can be comprised on one or more gene cassettes, where the use of micro-ORFs upstream of a cassette (ORF encoding gv genes) can be used to reduce the expression of GV proteins. Micro-ORFs are short open reading frames placed up stream of the ORF encoding the protein(s) of interest and results in the suppression of protein expression. They include a kozak/start codon NNNATG, small peptide and stop codon (TGA, TAG, TAA), for example AAAATGGCCGCGCCCAGAGCGTAG (SEQ ID NO: 481), NNNATG(NNN)[TAG/TGA/TAA] (SEQ ID NO: 474) ([27]). For genes that need to be expressed at lower relative stoichiometries, mico-ORFs can be placed upstream of their cassette to reduce the expression level of these GV proteins.

In some embodiments the booster constructs can be comprised on one or more gene cassettes, where the use of different inducible promoters (chemically or otherwise) can tune stoichiometry of translated proteins. Different promoters that are inducible by different stimuli can be used to drive expression of the booster construct and/or other cassettes. A higher amount of inducer can be used to increase the expression of booster constructs. For genes that need to be expressed at lower relative stoichiometries a relatively lower amount of inducer can be used.

In some embodiments the booster constructs can be comprised on one or more gene cassettes, where the presence of enhancing introns can tune stoichiometry of the translated proteins. Intron-mediated enhancement can be used on the booster constructs. For genes that need to be expressed at lower relative stoichiometries, these introns can be omitted, while the other GV cassette can include these introns. ([28], [29])

In some embodiments the booster constructs can be comprised on one or more gene cassettes, where the stoichiometry of the translated proteins can be tuned by different modes of Ribosome entry. Translation of the booster construct can be initiated via the stronger cap-dependent gene expression mediated by the KOZAK sequence and genes that need to be expressed at lower relative stoichiometries can be initiated via Internal Ribosome Entry Site (IRES).

Accordingly, in some of these embodiments, the GVES of the disclosure the polynucleotides comprises at least three cassettes possibly on three different polynucleotides, wherein the first polynucleotide contains gas vesicle gene B, the second polynucleotide is the booster construct containing gas vesicle genes J, F, G, L and K connected with a separation element, and at least a third polynucleotide contains the gas vesicle gene N, F, G, L, S, K, J, and U (gvpN, gvpF, gvpG, gvpL, gvpS, gvpK, gvpJ, and gvpU). These gas vesicle genes N, G, L, S, K, J, and U can be comprised in one or more synthetic operons each operatively connected with regulatory sequences to enable the expression of the gas vesicle genes N, F, G, L, S, K, J, and U.

When comprised in more than one gene expressions cassette, these genes are separated by a separation element such as the P2A element. In embodiments here described the order of gyp genes within one or more cassettes are not important to determine functionality of the system. The co-transfection of these at least three polynucleotides is sufficient for robust expression of gas vesicles in cells, herein referred to as mammalian acoustic reporter gene (mammalian ARG) (see Examples 12 and 13). Additionally, this architecture can be further consolidated by connecting the gas vesicle protein B gene to the polycistronic construct using IRES. When this new architecture is co-transfected to cells with the booster plasmid, it robustly produces gas vesicles.

In some embodiments, the GVES can comprise one cassette that encodes gvpB, one cassette that encodes gvpN, gvpF, gvpG, gvpL, gvpS, gvpK, gvpJ, and gvpU, and a booster with gvpJ, F, G, L, K as a polycistronic cassette and/or as a plurality of monocistronic cassettes. The cassettes can be on separate polynucleotides or on one or more polynucleotides. For example the GVPB cassette can be comprised on a same polynucleotide construct together with the cassette comprising gvpN, gvpF, gvpG, gvpL, gvpS, gvpK, gvpJ, and gvpU, or on a same polynucleotide with one booster cassette comprising gvpJ, F, G, L (see e.g. construct of Example 8).

Additional embodiments with other GVGC clusters e.g. comprising gyp genes from *B. megaterium* and/or genes form *Anabaena flos-aquae* as well as additional clusters are identifiable by a skilled person upon reading of the present disclosure.

In embodiments herein described, the GVES comprising a GVGC in two or more gene cassettes located on one or more polynucleotide construct herein described operatively connected to regulatory sequences can be introduced to a mammalian host allowing expression of the GV constructs and producing of gas vesicles in the mammalian host.

In particular in some embodiments, the method comprises introducing into the mammalian cell a genetically engineered Gas Vesicle expression system (GVES) herein described for a time and under condition to allow expression of the gyp genes in the mammalian cell.

In some embodiments, the method comprises introducing into a cell of the mammalian host a genetically engineered Gas Vesicle expression system (GVES) herein described in which the gyp genes encode for proteins of the gas vesicle type, the introducing performed for a time and under condition to allow expression of the gyp genes in the mammalian cell.

Expression of GV constructs in a mammalian cell can be performed by cloning one or more polynucleotides encoding naturally occurring GV proteins or homologs thereof that are required for production of GVs (comprising gvpB, gvpN, gvpF, gvpG, gvpL, gvpS, gvpK, gvpJ, and gvpU and other proteins known to those skilled in the art and described herein) into one or more suitable constructs configured to express the heterologous GV proteins in the mammalian cell. Polynucleotides encoding GV protein genes can be cloned using commercially available reagents from vendors such as Qiagen, Invitrogen, Applied Biosystems, Promega, New England BioLabs and others, following standard molecular biology methods known in the art, such as those described herein. As would be understood by those skilled in the art, polynucleotides encoding GV protein genes can be obtained from several different sources. For example, polynucleotides encoding GV proteins can be obtained by isolating genomic DNA or cDNA encoding GV proteins from microorganisms whose genomes encode GV proteins genes, and/or express GV proteins RNA. RNA can be isolated from a cell that expresses GV proteins genes, and cDNA produced by reverse transcription using standard techniques and commercial kits. Genomic DNA can be purified from the cell, and cDNA or genomic DNA encoding one or more GV proteins isolated, following methods known to those in the art. In addition or in the alternative, polynucleotides comprising one or more gas vesicle genes can be synthesized using oligonucleotide and polynucleotide synthetic methods known in the art. For example, if rare mammalian codons are identified following purification of genomic DNA from the cell, rare mammalian codons are preferably edited to improve expression in the target cell. PCR-based amplification of one or more GV protein genes can be performed using appropriately designed primer pairs (e.g. using PrimerDesign or other programs known to those skilled in the art). PCR-based amplification can be followed by ligation (e.g. using T4 DNA ligase) of a polynucleotide encoding gas vesicle gene amplicon into an appropriate construct in a plasmid suitable for propagation in bacteria or archaea, such as transformation-competent *E. coli* DH5alpha or other competent *E Coli* type, followed by growth of transformed cell cultures, purification of the plasmid for confirmation of the cloned gene by DNA sequence analysis, among other methods known to those skilled in the art. Expression vectors can comprise plasmid DNA, viral vectors, or non-viral vectors, among others known to those skilled in the art, comprising appropriate regulatory elements such as promoters, enhancers, and post-transcriptional and post-translational regulatory sequences that are compatible with the mammalian cell intended to heterologously express the GV, as would be understood by a skilled person. In particular, in embodiments described herein, expression vectors suitable for regulating heterologous expression of GVs comprise those having promoters and other regulatory elements known to skilled persons that are compatible with mammalian cells, including cell lines, primary cells cultured in vitro such as petri dishes or introduce the GV gene circuits inside the animal to genetically engineer cells directly inside the animal and described above. Promoters can be constitutively active or inducible (and chosen to be selectively expressed in different cell types). Exemplary inducible expression systems comprise tetracycline-inducible expression as shown in Examples 13, and 18.

In particular, in some embodiments described herein, production of a GV gene sequences can be codon-optimized (for example to remove rare mammalian codons) for expression in the mammalian cell type according to methods identifiable by a skilled person. As would be understood by those skilled in the art, the term "codon optimization" as used herein refers to the introduction of synonymous mutations into codons of a protein-coding gene in order to improve protein expression in expression systems of a particular organism, such as human, in accordance with the codon usage bias of that organism. The term "codon usage bias" refers to differences in the frequency of occurrence of synonymous codons in coding DNA. The genetic codes of different organisms are often biased towards using one of the several codons that encode a given amino acid over others, and use the one codon with a greater frequency than expected by chance. Optimized codons in organisms reflect the composition of their respective genomic tRNA pool. The use of optimized codons can help to achieve faster translation rates and high accuracy (and ultimately higher recombinant protein yield).

In some embodiments, one or more statistical methods proposed and used to analyze codon usage bias the field of bioinformatics and computational biology can be used for codon optimization in the sense of the disclosure. Methods such as the 'frequency of optimal codons' (Fop), the Relative Codon Adaptation (RCA) or the 'Codon Adaptation Index' (CAI) are used to predict gene expression levels, while methods such as the 'effective number of codons' (Nc) and Shannon entropy from information theory are used to measure codon usage evenness. Multivariate statistical methods, such as correspondence analysis and principal component analysis, are widely used to analyze variations in codon usage among genes. There are many computer programs to implement the statistical analyses enumerated above, including CodonW, GCUA, INCA, and others identifiable by those skilled in the art. Several software packages are available online for codon optimization of gene sequences, including those offered by companies such as GenScript, EnCor Biotechnology, Integrated DNA Technologies, ThermoFisher Scientific, among others known those skilled in the art. Those packages can be used in providing GV proteins with codon usage ensuring optimized expression in various prokaryotic cell systems as will be understood by a skilled person. In particular, codon optimization in embodiments herein described can be used primarily to remove or limit the use of rare codons, or keep codon usage above ~10%)

Mammalian cell used herein to include a GVES of the disclosure refers to a mammalian cell which can be transduced, infected, transfected or transformed with a vector under certain culture conditions. The vector can be plasmid, a viral particle, or others identifiable to a person skilled in the art. The term mammalian cell refers to cells isolated from an animal (mammal) tissue and expanded in culture for use as therapeutic and research tools.

In some embodiments, the transformed mammalian cells can comprise one or more cells such as T-cells, hematopoietic stem cells, mesenchymal stem cells, neural precursor cells, macrophages, fibroblasts or cardiomyocytes and any cell where one can express reporter genes (e.g. Green fluorescent protein (GFP)).

In some embodiments, the transformed mammalian cells can be part of a tissue in vivo or ex vivo.

In some embodiments, the transformed mammalian cells can be isolated mammalian cells such as mammalian cell lines. Mammalian cell lines used herein refer to human or non-human mammalian recombinant expression systems capable of producing post-translational modifications which closely resemble those in mammalian cells in vivo. Exemplary non-human mammalian cell lines include CHO-K1, mouse myeloma cell lines such as NS0, SP2/0, rat myeloma cell lines such as YB2/0, baby hamster kidney (BHK), N2A cells, HeLa, Jurkat, NIH3T3, and others identifiable to a person skilled in the art. Human mammalian cell lines are immortalized cells propagated in vitro from primary explants of human tissue or body fluid. Exemplary human cell lines include HEK293 and its derivatives, HT-1080, PER.C6, Huh-7 as well as others identifiable to a person skilled in the art.

In some embodiments, the transformation can occur in an individual of a mammalian species such as *Homo sapiens* or *Mus musculus*, for example, among others. In some embodiments, mammalian cells in the sense of the disclosure comprise stem cells, progenitor cells, induced pluripotent stem cells, and others identifiable by a skilled person.

In some embodiments herein described, the GVES herein described can be introduced in a mammalian cell to provide a reportable molecular component (herein GVRMC) of a gas vesicle reporting (GVR) genetic circuit in operative connection with other molecular components of the genetic circuit to report occurrence of a biochemical event in the mammalian cell.

The term "molecular component" as used in connection with the GVR genetic circuits described herein indicates a chemical compound or a structure comprised of a plurality of chemical compounds comprised in a cellular environment. Exemplary molecular components thus comprise polynucleotides, such as ribonucleic acids or deoxyribonucleic acids, polypeptides, polysaccharides, lipids, amino acids, peptides, sugars and/or other small or large molecules and/or polymers that can be found in a cellular environment. In some embodiments described herein, a molecular component of a GVR genetic circuit is a GV type or a cluster thereof.

The term "genetic molecular component" as used herein indicates a molecular unit formed by a gene (possibly comprising or formed by a cluster of genes), an RNA transcribed from the gene or a portion thereof and optionally a polypeptide or a protein translated from the transcribed RNA. In genetic circuits herein described, the biochemical reactions connecting the genetic molecular component to another molecular component of the circuit can involve any one of the gene, the transcribed RNA and/or the polypeptide forming the molecular component.

A gene comprised in a genetic molecular component is a polynucleotide that can be transcribed to provide an RNA and typically comprises coding regions as well as one or more regulatory sequence regions, which is a segment of a nucleic acid molecule which is capable of increasing or decreasing transcription or translation of the gene within an organism either in vitro or in vivo. In particular, coding regions of a gene herein described can comprise one or more protein coding regions which when transcribed and translated produce a polypeptide, or if an RNA is the final product only a functional RNA sequence that is not meant to be translated. Regulatory regions of a gene herein described comprise promoters, transcription factor binding sites, operators, activator binding sites, repressor binding sites, enhancers, protein-protein binding domains, RNA binding domains, DNA binding domains, silencers, insulators and additional regulatory regions that can alter gene expression in response to stimuli as will be recognized by a person skilled in the art.

An RNA of a genetic molecular component comprises any RNA that can be transcribed from a gene, such as a messenger ribonucleic acid (mRNA), short interfering ribonucleic acid, or ribonucleic acid capable of acting as a regulating factor in the cell. mRNA comprised in a genetic molecular component comprises regions coding for the protein as well as regulatory regions. mRNA can have additional control elements encoded, such as riboregulator sequences or a protein binding aptamer sequence placed upstream of the gene so the protein blocks ribosomes and conditionally prevents translation. Other RNAs that serve regulatory roles that can comprise the genetic molecular component include riboswitches, aptamers (e.g. malachite green, Spinach), aptazymes, guide CRISPR RNAs, and other RNAs known to those skilled in the art.

A protein comprised in a molecular component can be proteins with activating, inhibiting, binding, converting, or reporting functions. Proteins that have activating or inhibiting functions typically act on operator sites encoded on DNA, but can also act on other molecular components. Proteins that have binding functions typically act on other proteins, but can also act on other molecular components. Proteins that have converting functions typically act on small molecules, and convert small molecules from one small molecule to another by conducting a chemical or enzymatic reaction. Proteins with converting functions can also act on other molecular components. Proteins with reporting functions have the ability to be easily detectable by commonly used detection methods (absorbance, fluorescence, for example), or otherwise cause a reaction on another molecular component that causes easy detection by a secondary assay (e.g. adjusts the level of a metabolite that can then be assayed for). The activating, inhibiting binding, converting, or reporting functions of a protein typically form the interactions between genetic components of a genetic circuit. Exemplary proteins that can be comprised in a genetic molecular component comprise monomeric proteins and multimeric proteins, proteins with tertiary or quaternary structure, proteins with linkers, proteins with non-natural amino acids, proteins with different binding domains, and other proteins known to those skilled in the art.

The term "cellular molecular component" indicates a molecular component not encoded by a gene, or indicates a molecular component transcribed and/or translated by a gene but comprised in the circuit without the corresponding gene. Exemplary cellular components comprise polynucleotides, polypeptides, polysaccharides, small molecules and additional chemical compounds that are present in a cellular environment and are identifiable by a skilled person. Polysaccharides, small molecules, and additional chemical compounds can include, for example, NAD, FAD, ATP, GTP, CTP, TTP, AMP, GMP, ADP, GDP, Vitamin B1, B12, citric acid, glucose, pyruvate, 3-phosphoglyceric acid, phosphoenolpyruvate, amino acids, PEG-8000, FiColl 400, spermidine, DTT, b-mercaptoethanol maltose, maltodextrin, fructose, HEPES, Tris-Cl, acetic acid, aTc, IPTG, 30C12HSL, 30C6HSL, vanillin, malachite green, Spinach, succinate, tryptophan, and others known to those skilled in the art. Polynucleotides can include RNA regulatory factors (small activating RNA, small interfering RNA), or "junk" decoy DNA that either saturates DNA-binding enzymes (such as exonuclease) or contains operator sites to sequester activator or repressor enzymes present in the system. Polypeptides can include those present in the genetic circuit but not produced by genetic components in the circuit, or those added to affect the molecular components of the circuit.

In embodiments of genetic circuits herein described, one or more molecular components is a recombinant molecular component that can be provided by genetic recombination (such as molecular cloning) and/or chemical synthesis to bring together molecules or related portions from multiple sources, thus creating molecular components that would not otherwise be found in a single source.

In a GVRMC of the disclosure, at least one gene expression cassette of the gene expression cassettes of the GVES of the disclosure comprises a gas vesicle reporting (GVR) target region configured to be activated and/or inhibited by a molecular component of a genetic circuit.

These additional (GVR) target region can include genetic elements that allow control over cellular behavior through various biochemical processes including transcriptional control, translational control, post-translational control and other control processes identifiable to a person skilled in the art.

In some embodiments, the transcriptional control elements can include constitutive promoters, repressor and/or activator sites, recombination sites, inducible and/or tissue-specific promoters, or cell fate regulators. The translational control elements can include RNAi, Riboregulators, RNA secondary structural motifs included in the GVES mRNA, or Ribosome-binding sites. The post-translational control elements can include elements controlling phosphorylation cascades, protein receptor design, protein degradation element, and localization signals. Examples of these regulatory regions and their functional purposes can be found in published review articles such as Purnick et al. ([30]) (for example Table 1 of Purnick) as will be understood by a person skilled in the art.

In embodiments herein described, a genetic circuit comprises at least one genetic molecular component or at least two genetic molecular components, and possibly one or more cellular molecular components, connected one to another in accordance with a circuit design by activating, inhibiting, binding or converting reactions to form a fully connected network of interacting components.

In embodiments of the GVR genetic circuits described herein, the molecular components are connected with one another according to a circuit design in which a molecular component is an input and another molecular component is an output. In particular, a genetic circuit typically has one or more input or start molecular component which activates, inhibits, binds and/or convert another molecular component, one or more output or end molecular component which are activated, inhibited, bound and/or converted by another molecular component, and intermediary molecular components each inhibiting, binding and/or converting another molecular component and being activated, inhibited, bound and/or converted by another molecular component. In some embodiments of the genetic circuits herein described, the input is the biochemical event and/or a trigger molecular component and the output is activation of expression of a GV gene cluster and assembly of a GV type through binding reactions between gvps of the GV type. In other embodiments of the genetic circuits herein described, the input is a biochemical event and/or a trigger molecular component and the output is an intracellular spatial translocation of the GV type, the intracellular spatial translocation occurring typically through one or more converting and/or binding reactions as described herein. The output of GVR circuit herein described can be detected with ultrasound contrast, MRI SWI, light scattering and additional techniques to detect GV identifiable by a skilled person upon reading of the present disclosure.

The term "activating" as used herein in connection with a molecular component of a genetic circuit refers to a reaction involving the molecular component which results in an increased presence of the molecular component in the cellular environment. For example, activation of a genetic molecular component indicates one or more reactions involving the gene, RNA and/or protein of the genetic molecular component resulting in an increased presence of the gene, RNA and/or protein of the genetic molecular component (e.g. by increased expression of the gene of the molecular component, and/or an increased translation of the RNA). An example of "activating" described herein comprises the initiation of expression of a GV gene cluster under the control of the tetracycline-inducible promoter (using reverse tetracycline-controlled transactivator) followed by the ultrasound response of mammalian ARGs (e.g., see Example 13, and 18).

Activation of a molecular component of a genetic circuit by another molecular component of the circuit can be performed by direct or indirect reaction of the molecular components. Examples of a direct activation of a genetic molecular component comprise in a circuit the production of an alternate sigma factor (molecular component of the circuit) that drives the expression of a gene controlled by the alternate sigma factor promoter (other molecular component of the circuit), or the production of a small ribonucleic acid (molecular component of the circuit) that increases expression of a riboregulator-controlled RNA (molecular component of the circuit). Examples of indirect activation of a genetic molecular component comprise the production of a first protein that inhibits an intermediate transcriptional repressor protein, wherein the intermediate transcriptional repressor protein represses the production of a target gene, such that the first protein indirectly activates expression of the target gene.

The term "inhibiting" as used herein in connection with a molecular component of a genetic circuit refers to a reaction involving the molecular component of the genetic circuit and resulting in a decreased presence of the molecular component in the cellular environment. For example, inhibition of a genetic molecular component indicates one or more reactions involving the gene, RNA and/or protein of the genetic molecular component resulting in a decreased presence of the gene, RNA and/or protein (e.g. by decreased expression of the gene of the molecular component, and/or a decreased translation of the RNA). Inhibition of a cellular molecular component indicates one or more reactions resulting in a decreased production or increased conversion, sequestration or degradation of the cellular molecular components (e.g. a polysaccharide or a metabolite) in the cellular environment.

Inhibition can be performed in the genetic circuit by direct reaction of a molecular component of the genetic circuit with another molecular component of the circuit or indirectly by reaction of products of a reaction of the molecular components of the genetic circuit with the another molecular component of the circuit.

The term "binding" as used herein in connection with molecular components of a genetic circuit refers to the connecting or uniting two or more molecular components of the circuit by a bond, link, force or tie in order to keep two or more molecular components together, which encompasses either direct or indirect binding where, for example, a first molecular component is directly bound to a second molecular component, or one or more intermediate molecules are disposed between the first molecular component and the second molecular component another molecular component of the circuit. Exemplary bonds comprise covalent bond, ionic bond, van der Waals interactions and other bonds identifiable by a skilled person.

In some embodiments, the binding can be direct, such as the production of a polypeptide scaffold that directly binds to a scaffold-binding element of a protein. In other embodiments, the binding may be indirect, such as the co-localization of multiple protein elements on one scaffold. In some instances binding of a molecular component with another molecular component can result in sequestering the molecular component, thus providing a type of inhibition of said molecular component. In some instances, binding of a molecular component with another molecular component can change the activity or function of the molecular component, as in the case of allosteric interactions between proteins, thus providing a type of activation or inhibition of the bound component.

The term "converting" as used herein in connection with a molecular component of the circuit refers to the direct or indirect conversion of the molecular component into another molecular component. An example of this is the conversion of chemical X by protein A to chemical Y that is then further converted by protein B to chemical Z.

In the GVR genetic circuits in the sense of the present disclosure, the gyp genes and related cassettes included with a GVES of the disclosure are introduced into a mammalian cell to provide a reportable molecular component connected with other genetic or cellular molecular components according to a circuit design, wherein the GV type is expressed or the GV type is intracellularly spatially translocated when the GVGC genetic circuit operates according to the circuit design in response to a biochemical event and/or to a trigger molecular component.

The term "reportable molecular component" as used herein indicates a molecular component capable of detection in one or more systems and/or environments. The terms "detect" or "detection" as used herein indicates the determination of the existence, presence or fact of a target in a limited portion of space, including but not limited to a sample, a reaction mixture, a molecular complex and a substrate. The "detect" or "detection" as used herein can comprise determination of chemical and/or biological properties of the target, comprising ability to interact, and in particular bind other compounds, ability to activate another compound and additional properties identifiable by a skilled person upon reading of the present disclosure. The detection can be quantitative or qualitative. A detection is "quantitative" when it refers, relates to, or involves the measurement of quantity or amount of the target or signal (also referred as quantitation), which includes but is not limited to any analysis designed to determine the amounts or proportions of the target or signal. A detection is "qualitative" when it refers, relates to, or involves identification of a quality or kind of the target or signal in terms of relative abundance to another target or signal, which is not quantified. In particular, in embodiments herein described detection of the reportable molecular component comprising a GV type is performed through contrast enhanced imaging techniques such as ultrasound and MRI (and light scattering).

The term "biochemical event" as used herein refers to an activating, inhibiting, binding or converting reaction between two or more molecular components within a prokaryotic cell.

Accordingly, in some embodiments, at least one genetic molecular component of the GVR genetic circuit comprises a GVB cassette and additional GVP cassettes of the GVES of the disclosure comprising genes gvpB gene gvpN, gvpF, gvpG, gvpL, gvpS, gvpK, gvpJ, and gvpU genes, in a gas vesicle (GV) gene cluster in which the GV genes are operatively connected to a promoter configured to be activated directly or indirectly by the biochemical event, and directly initiate expression of a GV type.

In some embodiments herein described, a genetic molecular component of the GVR genetic circuit comprises a gas vesicle (GV) gene cluster comprising the GVB cassette and additional GVP cassettes of the GVES of the disclosure in which genes gvpB gene gvpN, gvpF, gvpG, gvpL, gvpS, gvpK, gvpJ, and gvpU genes are configured to be activated directly or indirectly by the biochemical event, and directly initiate expression of a GV type through interactions with promoters as well as one or more enhancers and/or other regulatory DNA elements comprised within the GVB and/or additional GVP cassettes, which are identifiable by those skilled in the art. As would be understood by those skilled in the art, promoters are DNA regulatory elements that are typically located adjacent to the transcription start sites of genes, or a cluster of genes, on the same strand and upstream on a DNA sequence (towards the 5' region of the sense strand), and for transcription to occur, the enzyme that synthesizes RNA, known as RNA polymerase, attaches to the promoter. Promoters contain DNA sequences identifiable by those skilled in the art, such as those that provide binding sites for RNA polymerase and also for proteins that function as transcription regulatory factors that can either activate or repress gene transcription.

The term "transcription regulatory factor" or "transcription factor" as used herein refers to any type of factors that can function by acting on a regulatory DNA element such as a promoter or enhancer sequence. The transcription regulatory factors can be broadly classified into a transcription repression factor (also referred to as "repressor") and a transcription activation factor (also referred to as "activator"). The transcription repression factor acts on a regulatory DNA element to repress the transcription of a gene, thereby reducing the expression level of the gene. The transcription activation factor acts on a regulatory DNA element to promote the transcription of a gene, thereby increasing the expression level of the gene.

In particular, a transcription regulatory factor has typically at least one DNA-binding domain that can bind to a specific sequence of enhancer or promoter sequences. Some transcription factors bind to a DNA promoter sequence near the transcription start site and help form the transcription initiation complex. Other transcription factors bind to other regulatory sequences, such as enhancer sequences, and can either stimulate or repress transcription of the related gene.

Examples of specific transcription repression factors include KRAB, repressor domains of proteins Egr-1, Oct2A, Dr1, YY1, RE-1 silencing transcription factor (REST), Retinoblastoma protein, and MeCP2, mSin interaction domain, TALE repressors), and other identifiable by a skilled person, as well as homologues of known repression factors, that function in both prokarayotic and eukarayotic systems. Examples of transcription activation factors include (VP-16, VP-64, etc.) as well as homologues of known activation factors, that function in eukaryotic systems.

In some embodiments, one or more promoters operatively connected to one or more GVGC genes comprised within the GVB cassette and additional GVP cassettes of the GVES of the disclosure can be configured to be activated directly or indirectly by one or more biochemical events. In particular, in some embodiments, activation of expression of a GV genes introduced in a mammalian cell, can be linked to another molecular component in the GVR genetic circuit through activator or repressor transcription factors. In some embodiments, expression of the transcription factors can be regulated by a promoter of interest (see Examples section). In other embodiments, transcription factors can be regulated post-translationally through degradation or phosphorylation of the transcription factor.

Accordingly, the reportable genetic molecular component of the GVR genetic circuit comprising the GVB cassette and additional GVP cassettes of the GVES of the disclosure in which genes gvpB gene gvpN, gvpF, gvpG, gvpL, gvpS, gvpK, gvpJ, and gvpU genes are operatively connected to a promoter configured to be activated directly or indirectly by the biochemical event, and directly initiate expression of a GV type can in several embodiments comprise promoters and/or other DNA regulatory elements having one or more sequences identifiable to those skilled in the art that are configured to function as binding sites for any known transcription regulatory factor.

For example, in some embodiments GV genes expression in GVR circuit of the disclosure can be activated by promoters inducible by sugars (e.g., L-arabinose, L-rhamnose, xylose and sucrose), antibiotics (e.g., tetracycline), CRISPR-dCas9 (possibly in conjunction with conditionally active gRNAs), heat shock promoters, pH-dependent promoters, oxidation stress-dependent promoters, radiation-dependent promoters, metal-inducible promoters, inflammation factor-inducible promoters, signaling factor-inducible promoter and others identifiable by those skilled in the art. In other embodiments GV genes expression can be induced by activation of constitutive promoters of varying strengths that are suitable for regulating expression in mammalian cells described herein and identifiable by those skilled in the art.

In other embodiments, the GV gene or one or more of the regulatory elements of GVR circuit of the disclosure, is surrounded by recombination sites that are recognized by a recombinase, whose expression or activity is connected through the genetic circuit to a biochemical event in the bacterial cell. For example, a GV genes introduced in the mammalian cell in reverse (3'-5') orientation to its promoter (in 5'-3' orientation) can be flanked by recombination sites surrounding the GV genes, with the recombination sites configured to allow inversion of the hybrid GV gene cluster upon expression or activation of its respective recombinase, wherein upon recombination the hybrid GV gene is flipped into a 5'-3' orientation to allow initiation of expression by the promoter. Suitable recombination systems for use in mammalian cells are identifiable by those skilled in the art, such as the piggy-bac integrase system, phiC31 and Bxb1 integrases, and the FLP/FRT or Cre/lox recombination systems, and additional systems identifiable by a skilled person.

In embodiments described herein, a GV gene cluster introduced by the GVES of the disclosure comprised in one or more genetic molecular components of the GVR genetic circuits described herein is configured to function as a set of reporter genes, which together encode proteins required for the formation of a GV type, such that expression of the GV type functions as a genetically-encoded reporter of the biochemical event in the mammalian cell comprising a GVR genetic circuit. As described herein, the reportable characteristics of the GV are such that the genetically-encoded GV can be used as a contrast agent, which, when used together with one or more contrast-enhanced imaging techniques described herein, functions as a genetically-encoded reporter in prokaryotic cells that have been genetically engineered to comprise one or more of the GVR genetic circuits described herein.

In particular, in exemplary embodiments described herein, all the GV genes of the cluster (e.g. gvpF, gvpG, gvpJ, gvpL, gvpK, gvpS, and gvpU and gvpA) enable GV formation. Therefore, if expression any one of these genes is regulated according to the design of a GVR genetic circuit as described herein then the expression of the GV type will be regulated accordingly.

In some embodiments, the GVR genetic circuits described herein can comprise a plurality of genetic molecular components that function as Boolean logical operators in genetic circuit designs known to those skilled in the art, such as those described in [31, 32]. As would be understood by persons skilled in the art, Boolean logic is a branch of algebra in which the values of the variables are the truth values 'true' and 'false', usually denoted by the digital logic terms '1' and '0' respectively. In contrast with elementary algebra where the values of the variables are numbers, and the main operations are addition and multiplication, the main operations of Boolean logic are the conjunction 'AND', the disjunction 'OR', and the negation 'NOT'. As understood by those skilled in the art, it is thus a formalism for describing logical relations in the same way that ordinary algebra describes numeric relations.

Accordingly, the term "AND gate" refers to a digital logic gate that behaves according to the truth table shown in Table 3. A 'true' output (1) results only if both the inputs to the AND gate are 'true' (1). If neither or only one input to the AND gate is 'true' (1), a 'false' (0) output results. Therefore, the output is always 0 except when all the inputs are 1.

TABLE 3

'AND gate' truth table:

| Input | | Output |
|---|---|---|
| A | B | A AND B |
| 0 | 0 | 0 |
| 0 | 1 | 0 |
| 1 | 0 | 0 |
| 1 | 1 | 1 |

In particular, the term "AND gate" as used herein refers to the logical relation between two genetic molecular components in a GVR genetic circuit, wherein inputs 'A' and 'B' in Table 3 are two biochemical events, and the output 'A AND B' in Table 3 is the production of a certain GV type.

For example, in some embodiments of an "AND gate" comprised in a GVR genetic circuit described herein, the GVR genetic circuit comprises a plurality of genetic molecular components wherein at least a first genetic molecular component comprises a first subset of genes from the GV gene cluster, and at least a second genetic molecular component comprises a second subset of genes from the GV gene cluster, wherein together the GV proteins expressed from the first and second genetic molecular components are configured to form a GV type. In these embodiments, activation of both the first AND second genetic molecular component is required for the output of the GV type in the genetic circuit when the genetic circuit operates according to the design of the genetic circuit. For example, the first and second genetic molecular components can comprise promoters that are activated by two or more biochemical events in the mammalian cell comprising the GVR genetic circuit.

In exemplary embodiments, any of gvpN, gvpF, gvpG, gvpJ, gvpL, gvpK, gvpS, and gvpU and gvpA of a GV gene cluster formed by genes gvpB gene gvpN, gvpF, gvpG, gvpL, gvpS, gvpK, gvpJ, and gvpU genes within the GVB cassette and additional GVP cassettes of the GVES of the disclosure can be split into at least a first and second genetic molecular component comprising at least a first and a second subset of these genes to form an AND gate.

In other embodiments of an "AND gate" comprised in a GVGC genetic circuit, two or more regulatory elements operatively connected to a GV gene cluster comprised in a genetic molecular component of a GVGC genetic circuit that is activated by biochemical events A AND B would result in the output of the GV type in the GVGC genetic circuit. For example, the promoter requires binding of two transcriptional activators for activation of the promoter. In Examples described herein (see the Methods section of the Examples), GV gene clusters of exemplary ARG1 and ARG2 and A2C constructs is driven by the T7 promoter that has a lac operator downstream of the promoter. The T7 RNA Polymerase is regulated by the araBAD promoter (inducible by L-arabinose). The lac operator is repressed by LacI (IPTG derepresses). Therefore only under conditions wherein both IPTG AND L-ara are present are GVs expressed.

The term "OR gate" refers to a digital logic gate that behaves according to the truth table shown in Table 4. A 'true' output (1) results if either of the inputs to the OR gate are 'true' (1).

TABLE 4

'OR gate' truth table:

| Input | | Output |
|---|---|---|
| A | B | A OR B |
| 0 | 0 | 0 |
| 0 | 1 | 1 |
| 1 | 0 | 1 |
| 1 | 1 | 1 |

In particular, the term "OR gate" as used herein refers to the logical relation between two genetic molecular components in a GVGC genetic circuit, wherein inputs 'A' and 'B' in Table 3 are two biochemical events, and the output 'A OR B' in Table 3 is the production of a certain GV type.

For example, in some embodiments of an "OR gate" comprised in a GVGC genetic circuit described herein, a promoter operatively connected to a GV gene cluster comprised in a genetic molecular component of a GVGC genetic circuit that is activated by biochemical events A OR B would result in the output of the GV type in the GVGC genetic circuit. For example, the promoter is activated by binding of either of two different transcriptional activators.

In other embodiments, an OR gate can be achieved through the use of two consecutive promoters. In exemplary embodiments, both these promoters can be located directly upstream of the GV gene cluster or they can be independently located directly upstream of any one or more of gvpN, gvpF, gvpG, gvpJ, gvpL, gvpK, gvpS, or gvpU and gvpA genes.

In other embodiments, GV genes introduced in the mammalian cell with a GVES of the disclosure can be flanked by recombination sites that are recognized by a recombinase, whose expression or activity is, in turn, activated in response to a biochemical event in the mammalian cell. For example, in these embodiments, one input signal can activate the GV genes organized within a GV gene cluster while a constitutive promoter is positioned in the opposite direction of the gene cluster. The second input would drive a recombinase that flips the promoter so that GV genes can be expressed. Exemplary recombinase systems comprise the piggy-bac integrase system, phiC31 and Bxb1 integrases, and the FLP/FRT or Cre/lox recombination systems, and additional systems identifiable by a skilled person.

The term "Negated AND gate" or "NOT gate" refers to a digital logic gate that behaves according to the truth table shown in Table 5. A 'true' output (1) results if either of the inputs to the OR gate are 'true' (1).

TABLE 5

'Negated AND gate' or "NOT gate" truth table:

| Input | | Output |
|---|---|---|
| A | B | A NOT B |
| 0 | 0 | 0 |
| 0 | 1 | 0 |
| 1 | 0 | 1 |
| 1 | 1 | 0 |

In particular, the term "Negated AND gate" or "NOT gate" as used herein refers to the logical relation between two genetic molecular components in a GVGC genetic circuit, wherein inputs 'A' and 'B' in Table 5 are two biochemical events, and the output 'A OR B' in Table 5 is the production of a certain GV type.

For example, in some embodiments of an "Negated AND gate" or a "NOT gate" comprised in a GVR genetic circuit described herein, the GVGC genetic circuit comprises a plurality of genetic molecular components wherein at least a first genetic molecular component comprises a GV gene cluster, and at least a second genetic molecular component comprises an CRISPR/Cas9 complex configured to inhibit expression of a gyp gene comprised in the GV gene cluster, e.g. a gvpA. In these embodiments, activation of expression and the first genetic molecular component and absence of activation (or repression) of the second genetic molecular component are both required for the output of a GV type in the genetic circuit when the genetic circuit operates according to the design of the genetic circuit. For example, the first and second genetic molecular components can comprise promoters that are activated or repressed by one or more biochemical events in the mammalian cell comprising the GVGC genetic circuit.

In embodiments of the genetic circuits herein described wherein the input is a biochemical event and the output is an intracellular spatial translocation of the GV type, the GV type is a molecular component of the genetic circuit and intracellular spatial translocation of the GV type can occur through one or more converting and/or binding reactions involving the GV type as described herein.

In some embodiments, in the GVR genetic circuit herein described, an expression of the GV type or an intracellular spatial translocation of the GV type occurs when the hybrid GVR genetic circuit operates according to the circuit design in response to a trigger molecular component within the target mammalian cell.

In some embodiments, the trigger molecular component is a molecular component that is capable of being natively produced in the target host in its naturally occurring form. In particular, the natively produced molecular component can be a genetic molecular component or a cellular molecular component.

Examples of natively produced genetic molecular component can be one or more RNA or protein natively encoded in the genome of the naturally occurring form of the mammalian host and natively expressed by the target mammalian host. Examples of cellular molecular components natively produced by the target host comprise metabolites of enzymatic reactions produced by enzymes that are natively expressed by the target mammalian host in its naturally occurring form.

In these embodiments, the GVR genetic circuit comprises a GV type when the GVR genetic circuit operates according to a circuit design in response to the presence of the natively produced molecular component in the target mammalian cell.

In particular, in these embodiments, expression of the GVR in the mammalian host does not require the introduction into the host of any genetic molecular components in addition to the genetic molecular components comprising the GVGC. In these embodiments, the promoter operatively connected to a hybrid GV gene cluster in the GVGC genetic molecular component is configured to be activated in response to molecular components capable of being natively produced by the host in its naturally occurring form, such as natively expressed transcription factors. Genetic molecular components that can be activated by native molecular components include response elements (activating transcription factor 4 response element, activator protein 1 response element, antioxidant response element, cAMP response element, enhancer binding protein response element, hypoxia response element, metal response element, NFAT response element, p53 response element, serum response element, Smad binding element, Xenobiotic response element); additional are identifiable by those skilled in the art. Natively produced proteins or RNAs natively encoded in the genome of a particular mammalian cell hosts comprise transcription factors (SP-1, AP-1, C/EBP, EGR1, HSF, ATF/CREB, GLI1, HIF, c-Myc, Oct-1, p53, NF-1, STAT1) and lncRNAs (B2, roX1, roX2, Xist); additional are identifiable by those skilled in the art. Metabolites produced in biochemical reactions produced in the naturally occurring form of the mammalian host comprise cytokines such as chemokines, interferons (IFNy), interleukins (IL-2, IL-10), lymphokines (CSF1, CSF2, CSF3), and tumor necrosis factors (TNFa), as well as hormones (including endocrine, paracrine, autocrine, and intracrine hormones) and growth factors (BMP, EGF, ephrin, EPO, FGF); additional are identifiable by those skilled in the art.

Thus, in these embodiments, the target host mammalian cell is labeled with expression of a GV type, wherein expression of the GV type occurs in presence of the trigger molecular component that is capable of being natively produced in the target mammalian cell host in its naturally occurring form. In several embodiments described herein, one or more GVR genetic circuits can be introduced into one or more mammalian cell hosts according to genetic engineering methods described herein and known to those skilled in the art. Different cells expressing different GVs would be possible. The methods to introduce the GVES and related GVRMC are identifiable by a skilled person upon reading of the disclosure.

In other embodiments, the trigger molecular component is a heterologous molecular component that is not capable of being natively produced in the target mammalian host in its naturally occurring form. In these embodiments, the GVGC genetic molecular component is not configured to express the GV type in presence of a molecular component that is capable of being natively produced in the target mammalian host in its naturally occurring form, but is instead configured to express the GV type in presence of one or more heterologous (non-natively produced) trigger molecular components e.g. by using cell type specific promoters, described above, and/or viral transduction which would be cell type specific.

In these embodiments, the trigger molecular component can be one or more heterologous molecular components comprising a heterologous genetic molecular component and/or a heterologous cellular molecular component.

In some embodiments, the heterologous genetic molecular component can comprise one or more protein- and/or RNA-encoding genes and/or regulatory elements such as promoters and/or enhancer elements that are not native to the target mammalian genome. In some embodiments, the heterologous genetic molecular component can be introduced into the target prokaryotic host in addition to the one or more genetic molecular components comprising the GVGC. The additional heterologous genetic molecular component can be a constitutively expressed or an inducible genetic molecular component.

In some embodiments, the heterologous cellular molecular component can comprise a molecular component that is naturally present in the environment comprising the target prokaryotic cell, such as a metabolite produced by a mammalian host comprising the target prokaryotic host cell, or it can be a molecular component that is not naturally present in the environment comprising the target prokaryotic host cell, and introduced into the prokaryotic host cell, such as a drug configured to activate expression of the heterologous genetic component.

Accordingly, the GVR circuit of the disclosure comprise a first GVES reporting molecular component, which is a GVES genetic molecular component comprising the GVB cassette and at least one second GVES reporting molecular component which is a GVES genetic molecular component comprising the additional GVP cassettes of the GVES of the disclosure. In GVR circuit of the disclosure the first GVES reporting molecular component and the at least one second GVES reporting molecular component are activated to trigger expression of GV genes gvpB gene gvpN, gvpF, gvpG, gvpL, gvpS, gvpK, gvpJ, and gvpU to provide the gas vesicle in the mammalian cell.

In some embodiments, the GVES genetic molecular component of a GVR circuit in a mammalian host according to the present disclosure comprises promoter and/or enhancer elements that are configured to be activated in response to the presence of a heterologous molecular component. In exemplary embodiments, the promoter is a constitutive promoter such as CMV (e.g., see Example 12, Example 15, Example 24, Example 25). In other exemplary embodiments, the promoter is activated by a heterologous transcription factor that is encoded in a heterologous genetic molecular component introduced into the target mammalian host in addition to the GVGC genetic molecular component; in exemplary embodiments described herein, the GVGC genetic molecular component comprises a promoter controlled by heterologous transcription factors, for example, (tetracycline-dependent repressor fused to transactivation domain (VP16 domain) as illustrated in Example 13 and 18, similarly LacI and LexA fusions to transactivators (e.g. VP16) and repressor domains (KRAB), ET-dependent macrolide-responsive promoter, dead-Cas9 fusion to transactivators and repressors, zinc-finger proteins fused to transactivators and repressors, transcription activator-like effectors fused to transactivators and repressors).

In some embodiments, the GVGC genetic molecular component comprises recombination sites (e.g. piggy-bac recombination sites) surrounding one or more gyp genes comprised in the GV gene cluster or one or more regulatory elements (e.g. promoter) wherein the one or more gyp genes or regulatory elements are introduced into a mammalian host cell in an orientation that prevents expression of the encoded GV type, e.g., the promoter is in reverse orientation relative to the GV gene cluster; in these embodiments a heterologous genetic molecular component comprising the recombinase enzymes required for flipping the orientation of the elements flanked by the recombinase sites in the GVGC genetic molecular component is also introduced into the prokaryotic host cell and expression of the GV type occurs upon recombinase-mediated flipping of the flanked elements in the GVGC genetic molecular component into an orientation allowing initiation of expression of the GV type.

In these embodiments, the GVR genetic circuit comprises a GV type is when the GVR genetic circuit operates according to a circuit design in response to the presence of the one or more heterologous molecular components in the target mammalian cell.

Thus, in these embodiments, the target mammalian host is labeled with expression of a GV type, wherein expression of the GV type occurs in presence of the heterologous trigger molecular component introduced into the target mammalian host.

Accordingly, in some embodiments, a method to provide a genetically engineered mammalian cell comprising one or more GVR genetic circuits is described. The method comprises genetically engineering a mammalian cell by introducing into the cell one or more GVR genetic circuits described herein.

The mammalian cells described herein can be genetically engineered using methods known to those skilled in the art. For example, one or more genetic molecular components of a GVR genetic circuit comprised in vectors described herein can be introduced into mammalian cells using transformation techniques such as lenti-virus, adeno associated virus, adenovirus, baculovirus, nanoparticles that contain genome editing enzymes such as CRISPR, TALENs, ZFNs, transposase and others known to those skilled in the art and described herein. In some embodiments, the genetic molecular components of a GVR genetic circuit are introduced into the mammalian cell to persist as a plasmid or integrate into the genome, following methods known in the art and described herein.

In embodiments herein described, the GVES system and related genetic circuits, cells, vectors, genetically engineered prokaryotic cells, compositions, methods and systems, in several embodiments can be used together with contrast-enhanced imaging techniques to detect and report a biological event the location of and/or biochemical events in genetically engineered mammalian cells in an imaging target site.

The term "contrast enhanced imaging" or "imaging", as used herein indicates a visualization of a target site performed with the aid of a contrast agent present in the target site, wherein the contrast agent is configured to improve the visibility of structures or fluids by devices process and techniques suitable to provide a visual representation of a target site. Accordingly a contrast agent is a substance that enhances the contrast of structures or fluids within the target site, producing a higher contrast image for evaluation. In particular, as used herein, the term "contrast agent" refers to GVs expressed in prokaryotic cells comprised in the target site, the GVs comprised in GVGC genetic circuits in the mammalian cells when the GVGC genetic circuit operates according to a circuit design in response to a biochemical event, as described herein.

The term "target site" as used herein indicates an environment comprising one or more targets intended as a combination of structures and fluids to be contrasted, such as cells. In particular the term "target site" refers to biological environments such as cells, tissues, organs in vitro in vivo or ex vivo that contain at least one target. A target is a portion of the target site to be contrasted against the background (e.g. surrounding matter) of the target site. Accordingly, as used herein a target comprises one or more mammalian cells genetically engineered to comprise one or more GVGC genetic circuits as described herein within any suitable environment in vitro, in vivo or ex vivo as will be understood by a skilled person. Exemplary target sites include collections of microorganisms in vitro as well as cells grown in an in vitro culture, including, primary mammalian, cells, immortalized cell lines, tumor cells, stem cells, and the like. Additional exemplary target sites include tissues and organs in an ex vivo culture and tissue, organs, or organ systems in a subject, for example, lungs, brain, kidney, liver, heart, the central nervous system, the peripheral nervous system, the gastrointestinal system, the circulatory system, the immune system, the skeletal system, the sensory system, within a body of an individual and additional environments identifiable by a skilled person. The term "individual" or "subject" or "patient" as used herein in the context of imaging includes a single plant, fungus or animal and in particular higher plants or animals and in particular vertebrates such as mammals and more particularly human beings.

In some embodiments, imaging the target site comprising the mammalian host can be performed by applying ultrasound to obtain an ultrasound image of the target site.

The term "ultrasound imaging" or "ultrasound scanning" or "sonography" as used herein indicate imaging performed with techniques based on the application of ultrasound. Ultrasound refers to sound with frequencies higher than the audible limits of human beings, typically over 20 kHz. Ultrasound devices typically can range up to the gigahertz range of frequencies, with most medical ultrasound devices operating in the 1 to 18 MHz range. The amplitude of the waves relates to the intensity of the ultrasound, which in turn relates to the pressure created by the ultrasound waves. Applying ultrasound can be accomplished, for example, by sending strong, short electrical pulses to a piezoelectric transducer directed at the target. Ultrasound can be applied as a continuous wave, or as wave pulses as will be understood by a skilled person.

Accordingly, the wording "ultrasound imaging" as used herein refers in particular to the use of high frequency sound waves, typically broadband waves in the megahertz range, to image structures in the body. The image can be up to 3D with ultrasound. In particular, ultrasound imaging typically involves the use of a small transducer (probe) transmitting high-frequency sound waves to a target site and collecting the sounds that bounce back from the target site to provide the collected sound to a computer using sound waves to create an image of the target site. Ultrasound imaging allows detection of the function of moving structures in real-time. Ultrasound imaging works on the principle that different structures/fluids in the target site will attenuate and return sound differently depending on their composition. A contrast agent sometimes used with ultrasound imaging are microbubbles created by an agitated saline solution, which works due to the drop in density at the interface between the gas in the bubbles and the surrounding fluid, which creates a strong ultrasound reflection. Ultrasound imaging can be performed with conventional ultrasound techniques and devices displaying 2D images as well as three-dimensional (3-D) ultrasound that formats the sound wave data into 3-D images. In addition to 3D ultrasound imaging, ultrasound imaging also encompasses Doppler ultrasound imaging, which uses the Doppler Effect to measure and visualize movement, such as blood flow rates. Types of Doppler imaging includes continuous wave Doppler, where a continuous sinusoidal wave is used; pulsed wave Doppler, which uses pulsed waves transmitted at a constant repetition frequency, and color flow imaging, which uses the phase shift between pulses to determine velocity information which is given a false color (such as red=flow towards viewer and blue=flow away from viewer) superimposed on a grey-scale anatomical image. Ultrasound imaging can use linear or non-linear propagation depending on the signal level. Harmonic and harmonic transient ultrasound response imaging can be used for increased axial resolution, as harmonic waves are generated from non-linear distortions of the acoustic signal as the ultrasound waves insonate tissues in the body. Other ultrasound techniques and devices suitable to image a target site using ultrasound, such as non-linear ultrasound imaging such as AM, PI, AMPI, would be understood by a skilled person.

Types of ultrasound imaging of biological target sites include abdominal ultrasound, vascular ultrasound, obstetrical ultrasound, hysterosonography, pelvic ultrasound, renal ultrasound, thyroid ultrasound, testicular ultrasound, and pediatric ultrasound as well as additional ultrasound imaging as would be understood by a skilled person.

Applying ultrasound refers to sending ultrasound-range acoustic energy to a target. The sound energy produced by the piezoelectric transducer can be focused by beamforming, through transducer shape, lensing, or use of control pulses. The soundwave formed is transmitted to the body, then partially reflected or scattered by structures within a body; larger structures typically reflecting, and smaller structures typically scattering. The return sound energy reflected/scattered to the transducer vibrates the transducer and turns the return sound energy into electrical signals to be analyzed for imaging. The frequency and pressure of the input sound energy can be controlled and are selected based on the needs of the particular imaging task and, in some methods described herein, collapsing GVs. To create images, particularly 2D and 3D imaging, scanning techniques can be used where the ultrasound energy is applied in lines or slices which are composited into an image.

In some embodiments, the ultrasound imaging herein described can comprising collapsing a GV type expressed in the genetically engineered mammalian cell by applying collapsing ultrasound to the target site and/or imaging a GV type in the contrast agent by applying imaging ultrasound to the target site.

In some embodiments, a method is described to provide imaging of one or more biochemical events in a mammalian cell comprised in an imaging target site, the method comprising:

introducing into the mammalian cell a genetically engineered Gas Vesicle expression system (GVES) herein described in which the gyp genes encode for proteins of a Gas Vesicle (GV) type, wherein the GV type is a reportable molecular component of a gas vesicle reporting (GVR) genetic circuit, in which molecular components are connected one to another in accordance with a circuit design by activating, inhibiting, binding or converting reactions to form a fully connected network of interacting components, wherein in the GVR genetic circuit an expression of the GV type or an intracellular spatial translocation of the GV type occurs when the GVR genetic circuit operates according to the circuit design in response to the biochemical event the introducing performed for a time and under condition to allow expression of the gyp genes and production of the GV type in the mammalian cell when the GVR genetic circuit operates according to the circuit design; and imaging the target site comprising the mammalian host by applying an imaging ultrasound to the target site at a peak positive pressure below a collapse pressure of the GV type, increasing step-wise the peak positive pressure to above the collapse pressure of the GV type, taking image frames before, during, and after the step-wise increase, and performing signal separation on the image frames to image the GV type In some embodiments, a method is described to label a target mammalian host, the method comprising:

introducing into the target mammalian host a genetically engineered Gas Vesicle expression system (GVES) herein described in which the gyp genes encode for proteins of a Gas Vesicle (GV) type, the introducing performed for a time and under condition to allow expression of the gyp genes and production of the GV type in the mammalian cell, wherein the GV type is a reportable molecular component of a gas vesicle reporting (GVR) genetic circuit, in which molecular components are connected one to another in accordance with a circuit design by activating, inhibiting, binding or converting reactions to form a fully connected network of interacting components, wherein in the GVR genetic circuit an expression of the GV type or an intracellular spatial translocation of the GV type occurs when the GVR genetic circuit operates according to the circuit design in response to a trigger molecular component within the target prokaryotic host;

In the method, the introducing is performed under conditions resulting in presence of the trigger molecular component in the target mammalian host.

In some embodiments, the method can further comprise imaging the target site comprising the target mammalian host, by imaging the target site comprising the mammalian host by applying an imaging ultrasound to the target site at a peak positive pressure below a collapse pressure of the GV type, increasing step-wise the peak positive pressure to above the collapse pressure of the GV type, taking image frames before, during, and after the step-wise increase, and performing signal separation on the image frames to image the GV type.

The ability of GVs to act as a contrast agent for both ultrasound allows them to act as an acoustomagnetic reporter, thus creating possibilities for multimodal imaging. In some embodiments herein described, when collapsing ultrasound is used in combination with MRI imaging, acoustically collapsing a GV type expressed in a mammalian cell can remotely in situ erase the GV type to enable a background-free magnetic resonance imaging of a target site. The background-free magnetic resonance imaging removes background noise posed by background contrast from endogenous sources [33, 34] by allowing GV types to be identified specifically based on their acoustic responses.

Accordingly, in various embodiments herein described imaging of a biochemical event and/or labeling of a mammalian cell can be performed by multiplex imaging as will be understood by a skilled person upon reading of the present disclosure.

In methods herein described, administration of one or more genetically engineered mammalian cell types comprising one or more GVR genetic circuits to a target site to be imaged, can be performed in any way suitable to deliver the one or more mammalian cells comprising a GVR genetic circuit to the target site to be imaged.

In some embodiments, in which the target site is the body of an individual or a part thereof, the one or more genetically engineered mammalian cell types comprising a GVR genetic circuit can be administered to the target site locally or systemically.

The wording "local administration" or "topic administration" as used herein indicates any route of administration by which the one or more genetically engineered bacterial cell types comprising a GVR genetic circuit is brought in contact with the body of the individual, so that the resulting location of the one or more genetically engineered bacterial cell types comprising a GVR genetic circuit in the body is topic (limited to a specific tissue, organ or other body part where the imaging is desired). Exemplary local administration routes include injection into a particular tissue by a needle, gavage into the gastrointestinal tract, and spreading a solution containing the one or more genetically engineered bacterial cell types comprising a GVR genetic circuit on a skin surface.

The wording "systemic administration" as used herein indicates any route of administration by which the one or more genetically engineered bacterial cell types comprising a GVR genetic circuit is brought in contact with the body of the individual, so that the resulting location of the one or more genetically engineered bacterial cell types comprising a GVR genetic circuit in the body is systemic (not limited to a specific tissue, organ or other body part where the imaging is desired). Systemic administration includes enteral and parenteral administration. Enteral administration is a systemic route of administration where the substance is given via the digestive tract, and includes but is not limited to oral administration, administration by gastric feeding tube, administration by duodenal feeding tube, gastrostomy, enteral nutrition, and rectal administration. Parenteral administration is a systemic route of administration where the substance is given by route other than the digestive tract and includes but is not limited to intravenous administration, intra-arterial administration, intramuscular administration, subcutaneous administration, intradermal, administration, intraperitoneal administration, and intravesical infusion.

Accordingly, in some embodiments of methods herein described, administering the one or more genetically engineered mammalian cell types comprising a GVR genetic circuit can be performed topically or systemically by intradermal, intramuscular, intraperitoneal, intravenous, subcutaneous, intranasal, rectal, vaginal, and oral routes. In particular, the one or more genetically engineered mammalian cell types comprising a GVR genetic circuit can be administered by infusion or bolus injection, and can optionally be administered together with other biologically active agents. In some embodiments of methods herein described, administering the one or more genetically engineered mammalian cell types comprising a GVR genetic circuit can be performed by injecting the one or more genetically engineered mammalian cell types comprising a GVR genetic circuit such as in a body cavity or lumen. Upon expression of one or more GV types in one or more genetically engineered bacterial cell types comprised in the target site, the target site can be contrast imaged.

Accordingly, in some embodiments, a vector comprising one or more genetic molecular components of a GVR genetic circuit is described, wherein the vector is configured to introduce the one or more genetic molecular components comprised in a GVR genetic circuit into a mammalian cell.

The term "vector" indicates a molecule configured to be used as a vehicle to artificially carry foreign genetic material into a cell, where it can be replicated and/or expressed. An expression vector is configured to carry and express the material in a cell under appropriate conditions. In some embodiments, a suitable vector can comprise a recombinant plasmid, a recombinant non-viral vector, or a recombinant viral vector. Vectors described herein can comprise suitable promoters, enhancers, post-transcriptional and post-translational elements for expression in mammalian that are identifiable by those skilled in the art. Vectors suitable for transduction of mammalian cells, are known to those skilled in the art. Exemplary vectors for transformation of a mammalian cell with genetic molecular components comprising GV gene clusters are described herein in the Examples.

Accordingly, in some embodiments herein described, a genetically engineered mammalian cell and in particular a genetically engineered mammalian cell comprising one or more GVR genetic circuits is described.

In embodiments herein described, a composition is provided. The composition comprises one or more genetic molecular components of a GVR genetic circuit, vectors, or genetically engineered mammalian cells described herein together with a suitable vehicle.

The term "vehicle" as used herein indicates any of various media acting usually as solvents, carriers, binders or diluents for the one or more genetic molecular components, vectors, or prokaryotic cells herein described that are comprised in the composition as an active ingredient. In particular, the composition including the one or more genetic molecular components, vectors, or prokaryotic cells herein described can be used in one of the methods or systems herein described.

In some embodiments, the GVGC comprised in a genetic molecular component of a GVR genetic circuit can be engineered (e.g. by modifying the related gyp genes) to produce GV types with altered mechanical, acoustic, surface and targeting properties in order to achieve enhanced harmonic responses and multiplexed imaging to be better distinguished from background tissues. In particular, in some embodiments, a GV can be engineered to tune the related acoustic properties. In particular the engineering can be performed by genetically engineering a GV having an acoustic collapse pressure $aP_0$ performed to obtain a variant GV with a critical collapse pressure $aP_1$ lower than the $aP_0$.

In particular, in order to tune the acoustic collapse properties of the GV, one changes the structural proteins of the GV shell. For example, selecting proteins that make the GV shell longer, rounder, thicker, etc. or that add proteins to the shell that make it structurally stronger. Changes in the shape, size, and durability of the GV shell change its acoustic properties as will be understood by a skilled person.

Accordingly, in embodiments described herein, GVR genetic circuits comprising genetically-encoded GV types can be used together with contrast-enhanced imaging techniques such as ultrasound imaging and/or MRI to detect the location of and/or dynamic biochemical events in prokaryotic cells in an imaging target site, wherein the mammalian cells have been genetically engineered to comprise one or more GVR genetic circuits described herein. In some exemplary embodiments, this allows monitoring the activity of various natural and engineered signaling circuits in mammalian cells.

In some exemplary embodiments described herein, imaging of engineered mammalian cells expressing GV types in vivo allows imaging of engineered mammalian cells in target sites. However, conventional reporters based on fluorescent and luminescent proteins or radionuclide capture suffer from the poor penetration of light into tissue or the need to administer radioactive tracers [35-37]. In contrast to these techniques, ultrasound and MRI are widely available, inexpensive, radiation-free technologies capable of noninvasively imaging deep tissues [38]. For example, the spatial resolution of ultrasound is routinely on the order of 100 µm [39, 40] and can approach the single-micron level with recently developed super-resolution techniques [41]. With these performance characteristics and the ability to place signals within an anatomical context, ultrasound is an ideal technique for imaging microbes in vivo.

As described herein, GVESs and related polynucleotide constructs, GVR genetic circuits, vectors, genetically engineered mammalian cells, compositions, methods and systems can be used in several embodiments to detect biochemical events in mammalian cells In particular embodiments, the GVES and related genetic circuits, vectors, genetically engineered mammalian cells, compositions, methods and systems described herein enable cell imaging inside mammalian hosts.

In some embodiments described herein, GV type-expressing mammalian cells can be visualized in vivo in settings relevant to cell tracking such as immune cells, circulating tumor cells, stem cells, blood cells, or tracking of cellular parts around the body such as exosomes, differentiation of cells in stem cells and progenitor cells, genetic changes to cells, and additional settings identifiable by a skilled person. In exemplary embodiments described herein, expression of GV types can make mammalian cells visible to ultrasound at volumetric concentrations below 0.5%, allowing dynamic imaging of gene expression and other biochemical events, and allows the visualization in vivo, such as in tumor xenografts as shown in the Examples.

In some embodiments described herein, engineered gas vesicle gene clusters are used as reporter genes for ultrasound, giving this widely used noninvasive imaging modality the ability to visualize bacteria inside living animals with sub-100 µm resolution. In several embodiments described herein, transformation with GVES systems of the disclosure allow mammalian cells to be detected at concentrations above 3 mammalian cells per ultrasound voxel, making this technology relevant to a broad range of studies, demonstrating the ability of GVGC-expressing mammalian cells to be detected within living animals at relevant concentrations.

In some embodiments, the GVs and variants thereof comprised in GVR genetic circuits described herein can be used as a contrast agent in the contrast-enhanced imaging methods herein described.

In particular, a combination of different GV types and/or variants thereof comprised in GVR genetic circuits can be used as contrast agents, each expressed GV exhibiting a different acoustic collapse profile with progressively decreased midpoint collapse pressure values. In some cases, the percentage difference between the midpoint collapse pressure values of any given two expressed GVs types is at least twenty percent.

As mentioned above, the GV gene cluster and related GVR circuit, molecular component, polynucleotidic constructs, vectors, cells and compositions herein described can be provided as a part of systems to perform any of the above mentioned methods. The systems can be provided in the form of kits of parts. In a kit of parts, one or more the hybrid GV gene cluster and related GVR circuit, molecular component, polynucleotidic constructs, vectors, cells and other reagents to perform the methods herein described are comprised in the kit independently. The hybrid GV gene cluster and related GVR circuit, molecular component, polynucleotidic constructs, vectors, cells can be included in one or more compositions, and each the hybrid GV gene cluster and related GVR circuit, molecular component, polynucleotidic construct, vector and cell is in a composition together with a suitable vehicle.

In particular, the components of the kit can be provided, with suitable instructions and other necessary reagents, in order to perform the methods here disclosed. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (such as. wash buffers and the like).

The genetically engineered GVES, and related genetic circuits, vectors, genetically engineered mammalian cells, compositions, methods and systems herein described can be used in several embodiments to provide magnetic resonance imaging with enhanced contrast and molecular sensitivity at sub-nanomolar concentration.

The genetically engineered GVES, and related genetic circuits, vectors, genetically engineered mammalian cells, compositions, methods and systems herein described can be used in connection with various applications wherein contrast-enhanced imaging of a target site is desired. For example, the genetically engineered GVES, and related genetic circuits, vectors, genetically engineered mammalian cells, compositions, methods and systems herein described can be used for visualization of mammalian cells as part or introduced into a mammalian host, such as mammalian hosts, facilitating for example the study of the mammalian microbiome and the development of diagnostic and therapeutic prokaryotic cellular agents, among other advantages identifiable by a skilled person, in medical applications, as well diagnostics applications. Additional exemplary applications include uses of the genetically engineered GVES, and related genetic circuits, vectors, genetically engineered mammalian cells, compositions, methods and systems herein described in several fields including basic biology research, applied biology, bio-engineering, bio-energy, medical research, medical diagnostics, therapeutics, and in additional fields identifiable by a skilled person upon reading of the present disclosure.

Further details concerning the genetically engineered GVES, and related genetic circuits, engineered mammalian cells and methods of the present disclosure will become more apparent hereinafter from the following detailed disclosure of examples by way of illustration only with reference to an experimental section.

EXAMPLES

The polynucleotide constructs, and related genetic circuits, vectors, genetically engineered mammalian cells, compositions, methods and systems herein disclosed are further illustrated in the following examples, which are provided by way of illustration and are not intended to be limiting.

In particular, the following examples illustrate exemplary methods and protocols for providing and using polynucleotide constructs, and related genetic circuits, vectors, genetically engineered mammalian cells, compositions, methods and systems. A person skilled in the art will appreciate the applicability and the necessary modifications to adapt the features described in detail in the present section, to additional genetically engineered GVES, and related genetic circuits, vectors, genetically engineered mammalian cells, compositions, methods and systems according to embodiments of the present disclosure.

The following materials and method were used in the exemplary embodiments reported in this section.
Chemicals, Cell Lines and Synthesized DNA:

All chemicals were purchased form Sigma Aldrich unless otherwise noted. HEK293T and CHO-K1 cell lines were ordered from American Type Culture Collection (ATCC) and HEK293 tetON cells and CHO tetON cells were purchased form Clontech (Takara Bio). Synthetic DNA was ordered from Twist Bioscience.
Cloning Monocistronic plasmids used for transient transfection of HEK293T cells of gas vesicles genes used the pCMVSport backbone and codon optimized gas vesicle genes were assembled in each plasmid using Gibson assembly. To test the effect of N- and C-terminal p2A modification each *B. megaterium* gas vesicle gene on the pNL29 plasmid (addgene 91696) was individually cloned. To test the N-terminal modification, the CCT codon was mutagenized following the start codon. To test the C-terminal modification, linker-p2A sequence (GGAGCGCCAGGTTCCGGG-GC-TACTAACTTCAGCCTCCT-
TAAACAGGCCGGCGACGTGGAAGAGAATCCTGGC) (SEQ ID NO: 32) was mutagenized upstream of the stop codon for each gene.

The PiggyBac transposon system (System Biosciences) was used to genomically integrate the ARG cassettes. To clone the ARG cassettes to the PiggyBac transposon backbone, the plasmid was first restriction digested using SpeI/HpaI and the ARG cassettes were Gibson assembled to the backbone. For tetracycline inducible expression, the CMV promoter upstream of the GV genes was replaced with TRE3G promoter.
Cell Culture, Transient Transfection and TEM Analysis HEK 293T and CHO-K1 cells were cultured in DMEM with 10% FBS and penicillin/streptomycin and seeded in a 6-well plate for transfection experiments. When the cells reached 70-80%, 2 μg of total DNA (plasmids encoding gas vesicle genes) was transiently transfected into the culture using 2.58 μg polyethyleneimine per μg DNA for 12-18 hours. Cells were allowed to express the recombinant proteins for 72 hours.

Cells expressing gas vesicles in 6-well plates were lysed with 400 μL of Solulyse-M per well for one hour at 4° C. The lysate was then transferred to 2 mL tubes, diluted with 1.2 mL of 10 mM HEPES buffer at pH 8.0 and centrifugated overnight at 300 g at 8° C. Then, 60 μL of the supernatant transferred to a fresh tube to be analyzed using transmission electron microscopy (TEM).

From this top fraction, 2 μL of sample was added to Formvar/carbon 200 mesh grids (Ted Pella) that were rendered hydrophilic by glow discharging (Emitek K100X). The samples were then stained with 2% uranyl acetate. The samples were imaged on a FEI Tecnai T12 transmission electron microscope equipped with a Gatan Ultrascan CCD.
Genomic Integration and FACS (and 96 Well Plate Monoclonal)

HEK293 tetON and CHO tetON cells were used for genomic integration of the mammalian ARG. The cells were cultured in a 6-well plate containing 2 mL DMEM with 10% tetracycline-free FBS (Clonetech) and penicillin/streptomycin. Cells were transfected with the PiggyBac transposon backbone containing the ARG genes and the PiggyBac transposase plasmid at a transposon:transposase molar ration of 2.5:1. Transfection was conducted using parameters mentioned above and the cells were allowed to incubate for 72 hours. Cells were induced with 1 μg/mL of doxycycline 24 hours prior to FACS. To obtain a polyclonal ARG-expressing cell population, the top 10% brightest fluorescent positive cells were sorted. For monoclonal cell lines, 576 cells from the 10% brightest fluorescent positive cells population were sorted in individual wells of 96-well plate and the surviving 30 cells were analyzed.

Control mCherry-only cells were constructed similar to ARG-expressing cells. PiggyBac transposon plasmid containing TRE3G promoter driving mCherry were used to make a stable cell line. After genomic integration using PiggyBac, the top 10% brightest fluorescent positive ells were sort.
Gas Vesicle Yield Measurement, Size Distribution and Cell Sectioning with TEM TEM analysis of gas vesicle yield and size distribution analysis was conducted by seeding cells in 6-well plates and inducing gas vesicle expression using 1 μg/mL of doxycycline and 5 mM sodium butyrate for 72 hours. The cells were lysed using Solulyse-M and buoyancy enriched at 300 g at 8° C. overnight. The top fraction of the supernatant was fixed with 2M urea before being added to Formvar/carbon grids. The TEM grids were washed with water before staining with 2% uranyl acetate. To calculate gas vesicle yield per cell, the total number of gas vesicles per sub-grid on the TEM grid was manually counted. Gas vesicle side distribution was quantified using FIJI.

To visualize gas vesicles inside cells, ARG-expressing cells were seeded in 6-well plates and allowed to express gas vesicles for 72 hours. The cells were fixed with 4% paraformaldehyde. Cell sectioning and electron microscopy was conducted by Oak Crest Institute of Science.
In Vitro Toxicity Assays The viability of the ARG-expressing cells was determined using three different assays involving cellular metabolic activity (Resazurin reduction, MTT assay), quantification of cellular ATP content (CellTiter-Glo, Promega), and dye exclusion (Trypan Blue, Caisson Labs). The measurements were all quantified as percent viability compared with control cells that expressed mCherry only. For the MTT and CellTiter-Glo assays, cells were grown in 96-well plates and induced with 1 µg/mL doxycycline and 5 mM sodium butyrate for 72 hours. They were then treated with reagents according the manufacturers' protocols. Luminescence (CellTiter-Glo) and absorbance at 540 nM (MTT) was measured using a SpectraMax M5 spectrophotometer (Molecular Devices). For the Trypan Blue assay, the cells were first grown in 6-well plates and treated with 1 µg/mL doxycycline and 5 mM sodium butyrate for 72 hours. They were then trypsinized and resuspended in media before being stained 1:1 with Trypan Blue dye. Ten µL of the solution was loaded in a disposable hemocytometer (C-chip DHC 502, Incyto) and total cell count and blue-stained dead cells were quantified by bright field microscopy.

In Vitro Ultrasound Imaging

To create phantoms for in vitro ultrasound imaging, wells were casted with molten 1% w/v agarose in PBS using a custom 3D-printed template. ARG-expressing and mCherry-only control cells were allowed to express gas vesicles using the specified inducer concentrations and expression duration. They were then trypsinized and counted via disposable hemocytometers in bright field microscopy. Next, cells were mixed at a 1:1 ratio with 50° C. agarose and loaded into the wells before solidification. The volume of each well is 60 µl and contain 6×10$^6$ cells. The phantoms were submerged in PBS, and ultrasound images were acquired using a Verasonics Vantage programmable ultrasound scanning system and L22-14v 128-element linear array transducer with a 0.10-mm pitch, an 8-mm elevation focus, a 1.5-mm elevation aperture, and a center frequency of 18.5 MHz with 67% −6 dB bandwidth (Verasonics, Kirkland, WA). Each frame was formed from 89 focused beam ray lines, each with a 40-element aperture and 8 mm focus. A 3-half-cycle transmit waveform at 17.9 MHz was applied to each active array element.

For each ray line, the AM code is implemented using one transmit with all elements in the aperture active followed by 2 transmits in which the odd- and then even-numbered elements are silenced. Each image contains a circular cross-section of a well with a 4 mm diameter and center positioned at a depth of 8 mm. In AM mode, signal was acquired at 0.9 MPa (2V) for 10 frames and the acoustic pressure was increased to 4.3 MPa (12V) to collect 46 frames. There after the acoustic pressure was increased to 8.3 MPa (25V) to ensure complete collapse of gas vesicles. Gas vesicle-specific signal was determined by subtracting the area under the curve of the first sequence by the post-collapse imaging sequence.

Cytotoxicity Assay on Cells Exposed to Ultrasound

ARG-expressing and mCherry-only cells were cultured on custom made Mylar-bottom 24-well plates. Cells were cultured on fibronectin coated Mylar films until they reached 80% confluency and induced for gas vesicle expression for 3 days. The cells were then insonated from the bottom using a L22-14v 128-element linear array transducer (Verasonics). The transducer was mounted on a computer-controlled 3D translatable stage (Velmex). The bottom of the plates was acoustically coupled to the transducer with water and positioned 8 mm away from the transducer face. The cells were exposed to 8.3 MPa of pressure and the transducer was translated at a rate of 3.8 mm/s. The plates were returned to the incubator to allowed to rest for 24 hours. Cytotoxocity was assayed using Resazurin reduction (MTT) on cells exposed to ultrasound and compared to non-insonated negative control cells.

3D Cell Culture and In Vitro Acoustic Recovery after Collapse

ARG-expressing and mCherry-only cells were mixed in Matrigel (Corning) containing 1 µg/mL of Doxycycline and 5 mM sodium butyrate. The cell-laden hydrogels were placed in a 1% agarose base to prevent cell migration out of the hydrogel and separate the cells away from bottom of plates for imaging. Cells were cultured for total of 6 days and imaged every 3 days from the top using a L22-14v 128-element linear array transducer (Verasonics). The transducer was wiped with 70% ethanol and imaging is conducted in a tissue culture hood to preserve sterility. After imaging, all cells were exposed to 8.3 MPa ultrasound to ensure complete collapse of all gas vesicles in the cells at a rate of 1-2 mm/s. The culture media was changed daily and contained 1 µg/mL of Doxycycline and 5 mM sodium butyrate.

In Vivo Expression of Gas Vesicles and Ultrasound Imaging

All in vivo experiments were performed on NOD SCID mouse (NOD.CD17 Prkdc$^{scid}$/NCrCrl; Charles River), aged 10-15 weeks, under a protocol approved by the Institutional Animal Care and Use of Committee of the California Institute of Technology. The lower half of mice were shaved to allow for fluorescence imaging and ultrasound coupling. ARG-expressing and mCherry-only cells were cultured in tetracycline-free media in T225 flasks and 10-12 million cells were trypsinized and mixed with Matrigel (Corning) containing 5 mM sodium butyrate. The ARG-expressing cell and Matrigel mixture was injected subcutaneously in the left flank of mice and mCherry-only cell and Matrigel mixture was injected subcutaneously in the right flank of mice. Starting from the day of tumor inoculation, mice we interperitoneally injected with 200 µl of saline containing 75 µg of Doxycycline and 25 mg of sodium butyrate daily.

Example 1: Identification of Gvp Genes and Protein Sequences Through Alignment

Gyp genes and related protein can be identified through alignment of sequences in databases or identified through wet bench experiments with an approach and techniques identifiable by a skilled person.

Taking as gvpA/B as an example, the identification can be performed using consensus sequence: SSSLAEVL-DRILDKGXVIDAWARVSLVGIEILTIEARVVI-ASVDTYLR (SEQ ID NO: 3) wherein X can be any amino acid. LDRILD (SEQ ID NO: 4), RILDKGXVIDAWARVS (SEQ ID NO: 5) wherein X can be any amino acid, and/or DTYLR (SEQ ID NO: 6), and/or of exemplary gvpA and gvpB protein sequences already identified, as it will be understood by a skilled person.

FIG. 1 shows an exemplary Clustal omega alignment of amino acid sequences of selected exemplary gvpA and gvpB proteins.

The gvpA and gvpB proteins shown are from the following species: Sa_A2, *Serratia* sp. ATCC 39006 gvpA2; Sa_A3, *Serratia* sp. ATCC 39006 gvpA3; Sc_A2, *Streptomyces coelicolor* gvpA2; Sc_A1, *Streptomyces coelicolor* gvpA1; Fc_A, *Frankia* sp. gvpA; Bm_B1, *B. megaterium* gvpB1; Mb_A, *Methanosarcina barkeri* gvpA; Hv_A, *Halorubrum vacuolatum* gvpA; Hm_A, *Haloferax mediterranei* gvpA; Hs_A1, *Halobacterium* sp. NRC-1 gvpA1; Hs_A2, *Halobacterium* sp. NRC-1 gvpA2; Bm_A, *B. megaterium* gvpA; Bm_B2, *B. megaterium* gvpB2; Af_A, *A. flos-aquae* gvpA; Ma_A; Sa_A1, *Serratia* sp. ATCC 39006 gvpA1.

The bottom row of FIG. 1 indicated as "Consensus" shows an exemplary consensus sequence derived from alignment of the gvpA and gvpB amino acid sequences shown.

Homology-based searching (e.g., BLAST alignment) of sequences of proteins encoded in the genome of a prokaryotic organism compared to the exemplary consensus sequence shown in FIG. 1 can be used to identify gvpA and/or gvpB protein sequences in the prokaryotic organism.

Example 2: Identification gVp Genes and Protein Sequences Through Phylogenesis

Gyp genes and related protein can be identified based on phylogenetic relationships of sequences in databases or identified through wet bench experiments with an approach and techniques identifiable by a skilled person.

In particular, exemplary gvpA, gvpF and gvpN genes and proteins were identified phylogenetic relationships as shown below.

Figure 2:
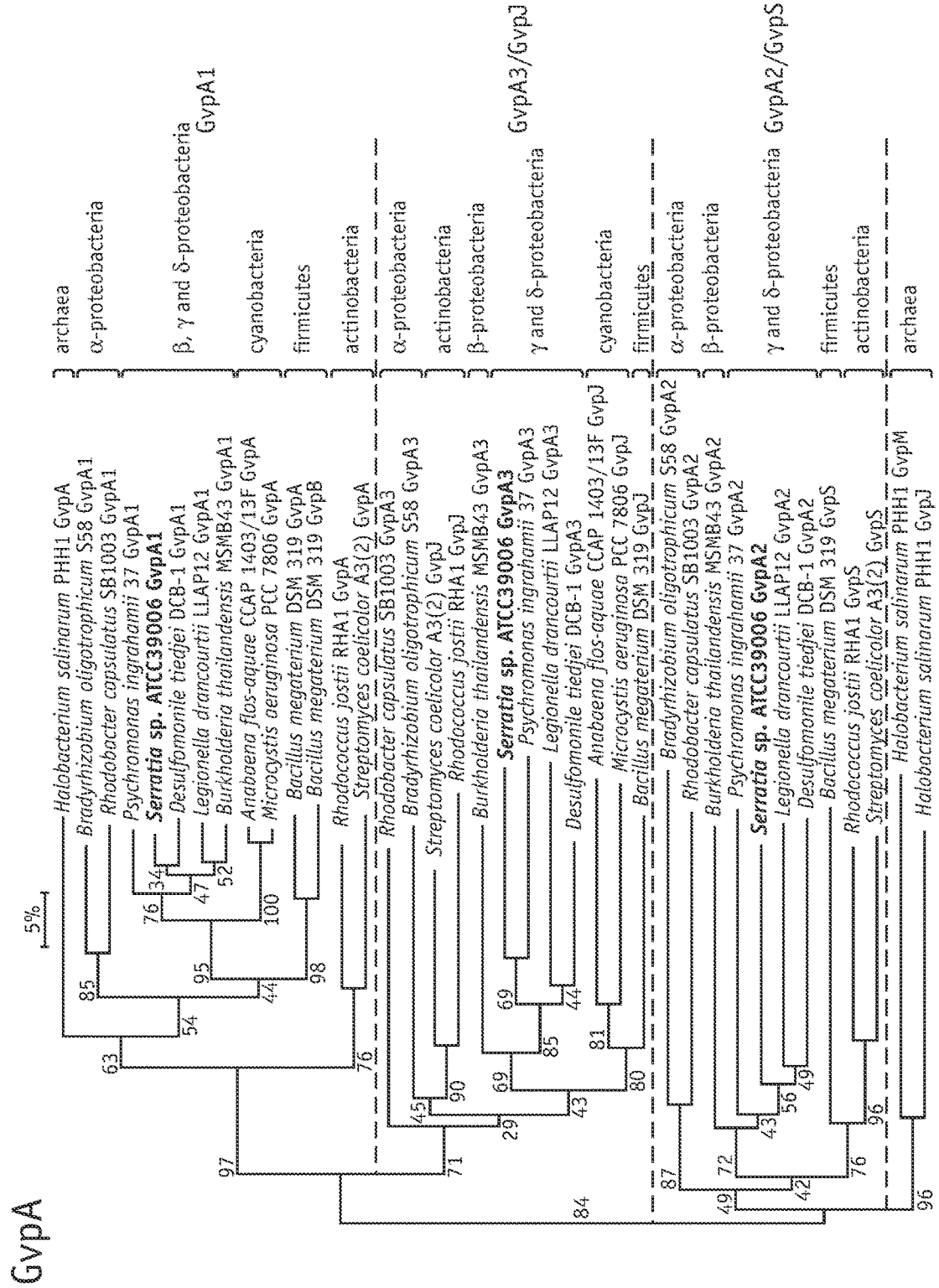
FIG. 2 shows exemplary phylogenetic relationships of the gvpA protein sequences from the indicated prokaryotic species. [1]

FIG. 2 shows exemplary phylogenetic relationships of the gvpA protein sequences from the indicated prokaryotic species [1]. Table 6 lists examples of GV protein sequences from a number of prokaryotic species.

Identification of a gvpA/B protein can be performed by comparing the sequence of an unknown protein in a prokaryotic cell with that of a known gvpA sequence from the closest phylogenetic relative of the prokaryotic species, such as those indicated in the exemplary phylogenetic tree diagram in FIG. 2. Alternatively, identification of gvpA/B can be done through protein alignment algorithms (e.g. BLAST) with the gvpA/B consensus sequence provided in this document, where the protein identity has 60% or higher to this sequence.

Figure 3:
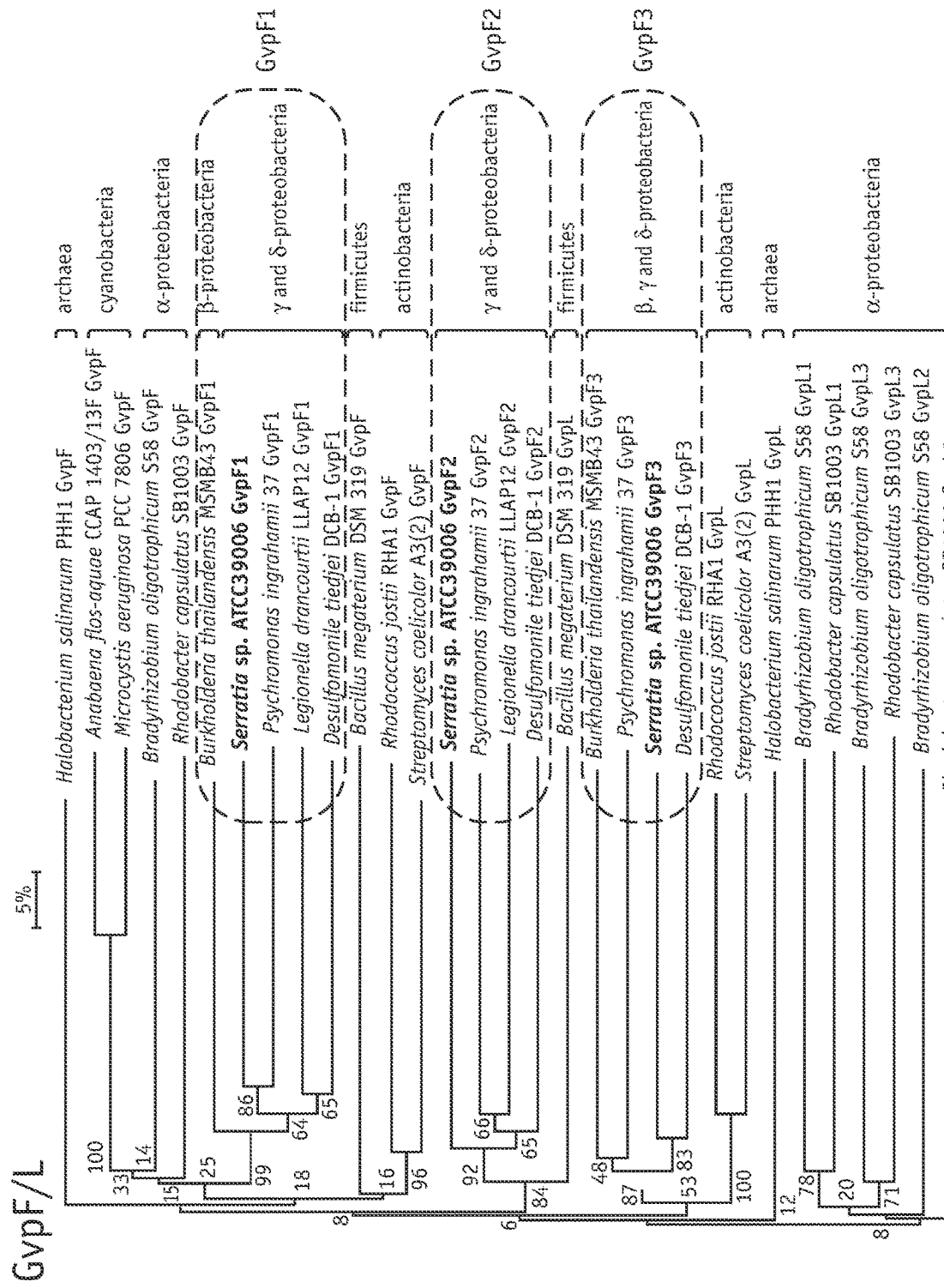
FIG. 3 shows exemplary phylogenetic relationships of the gvpF and gvpL protein sequences from the indicated prokaryotic species. [1]

FIG. 3 shows exemplary phylogenetic relationships of the gvpF and gvpL protein sequences from the indicated prokaryotic species [1]. In some embodiments described herein, the identification of a gvpF protein can be performed by comparing the sequence of an unknown protein in a prokaryotic cell with that of a known gvpF sequence from the closest phylogenetic relative of the prokaryotic species, such as those indicated in the exemplary phylogenetic tree diagram in FIG. 3.

Figure 4:
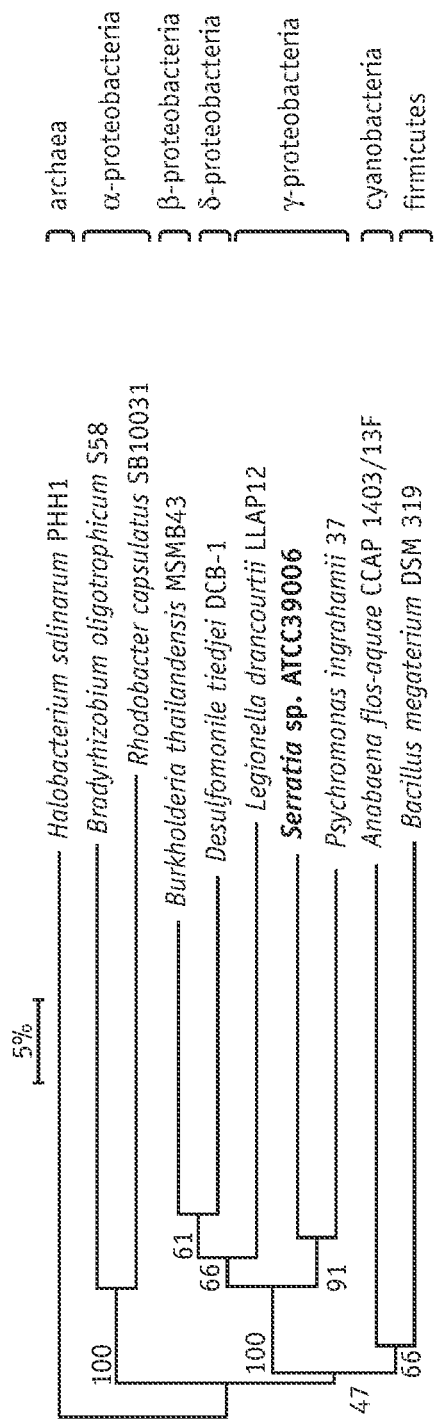
FIG. 4 shows exemplary phylogenetic relationships of the gvpN protein sequences from the indicated prokaryotic species. [1]

FIG. 4 shows exemplary phylogenetic relationships of the gvpN protein sequences from the indicated prokaryotic species [1]. In some embodiments described herein, the identification of a gvpN protein can be performed by comparing the sequence of an unknown protein in a prokaryotic cell with that of a known gvpN sequence from the closest phylogenetic relative of the prokaryotic species, such as those indicated in the exemplary phylogenetic tree diagram in FIG. 4.

The protein sequences provided in Table 6 can also be used with protein alignment algorithms to identify gvps. Where the using BLAST or other tools, if the top 100 based on protein identity or 100 lowest E-values are identified as "gas vesicle protein" or "gyp" or "gas vesicle structural protein", the protein can be designated as a gas vesicle protein.

Example 3: Identification of Gvp Genes and Proteins Through Analysis of Configuration Vesicle Gene Clusters in Prokaryotes Identification of gyp genes and proteins can be performed also GV cluster configuration of gas vesicle gene clusters in prokaryotes which can be used to identify the specific genes forming a GV cluster in a microorganism, in combination with use of consensus sequences, alignment and/or phylogenetic analysis of GV clusters.

FIG. 5 shows diagrams illustrating the organization of exemplary gas vesicle gene clusters. Gas vesicle gene clusters from the indicated organisms are shown, with genes shown as block-shaped arrows, and genes of predicted similar function indicated in the same shade of grey. The direction of the transcription of genes within a gene cluster is indicated by the direction of the block-shaped arrows, and genes grouped together having block arrows pointed in the same direction are typically organized in the same operon. The scale bar indicates 1 kb [1].

In addition, FIG. 6 shows diagrams illustrating organization of exemplary gyp gene clusters, wherein each letter indicates a gyp gene, and an arrow beneath a group of letters indicates an operon, with the direction of the arrow indicating the direction of transcription [2].

To identify gyp genes and gyp gene cluster, the following methodology can be used:

1. Using the 60+% gvpA/B and/or 50%+gvpN consensus sequences and/or gyp sequences provided in Table 6, identify gyp genes on the genome of the prokaryote.

2. For a gyp gene identified, test the next 10 protein coding sequences on both side of the gene to determine if it is gyp gene. Using BLAST or other tools, if the top 100 based on protein identity or 100 lowest E-values are identified as "gas vesicle protein" or "gyp" or "gas vesicle structural protein", the protein can be designated as a gas vesicle protein.

3. If the adjacent genes are labeled as gyp gene, continue testing the next 10 protein coding sequences on both sides of the protein, moving away from the labeled gyp genes. Use criterion 2 to continue identifying gyp genes. If the adjacent 10 genes are not marked as gyp genes continue to next part.

4. The genes at the extreme ends will mark the edge of the gene cluster and all the genes inside are part of the gene cluster than can be tested for heterologous expression gas vesicle in bacteria/mammalian cells. In some cases, there can be one or more gene clusters encoding gyp genes, therefore all the gene clusters are tested during heterologous expression.

In particular, the above methodology can be one way to identify gyp gene clusters in an unannotated or mis-annotated genome as will be understood by a skilled person.

Example 4: Amino Acid Sequences of Exemplary GV Proteins Including GVS and GVA Proteins Several gyp genes and related proteins have been identified and are available in accessible databases.

In particular, Tables 6-10 show amino acid sequences of exemplary GVS (gvpA/B or gvpC) and GVA proteins from several exemplary prokaryotic species. In particular, these exemplary amino acid sequences can be used as reference amino acid sequences in some embodiments for homology-based searches for related GVS and GVA proteins.

TABLE 6

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| gvpA/B | | |
| Ana-family-consensus_gvpA | MAVEKTNSSSSLAEVIDRILDKGIVIDAWVRVSLVGIELLAIEARXV IASVETYLKYAEAVGLTXSAAVPAX | 33 |
| Aphanizomenon-flos-aquae_gvpA | MAVEKTNSSSSLAEVIDRILDKGIVIDAWVRVSLVGIELLAIEARIVI ASVETYLKYAEAVGLTQSAAVPA* | 34 |
| Aphanothece-halophytica_gvpA | MAVEKTNSSSSLGEVVDRILDKGVVVDLWVRVSLVGIELLAVEAR VVVASVETYLKYAEAVGLTSSAAVPAE* | 35 |
| Anabaena-flos-aquae_gvpA | MAVEKTNSSSSLAEVIDRILDKGIVIDAWVRVSLVGIELLAIEARIVI ASVETYLKYAEAVGLTQSAAVPA* | 36 |
| Ancylobacter-aquaticus_gvpA | MAVEKINASSSLAEVVDRILDKGVVVDAWVRVSLVGIELLAVEAR VVVAGVDTYLKYAEAVGLTASAQAA* | 37 |
| Aquabacter-spiritensis_gvpA | MAVEKINASSSLAEVVDRILDKGVVVDAWVRVSLVGIELLAVEAR VVVAGVDTYLKYAEAVGLTAGAQAA* | 38 |
| Arthrospira-sp-PCC-8005_gvpA | MAVEKVNSSSSLAEVIDRILDKGIVIDAWVRVSLVGIELLSVEARV VIASVETYLKYAEAVGLTAQAAVPSV* | 39 |
| Calothrix-sp-strain-PCC-7601_gvpA | MAVEKTNSSSSLAEVIDRILDKGIVVDAWVRVSLVGIELLAIEARIV IASVETYLKYAEAVGLTQSAAVPA* | 40 |
| Dactylococcopsis-salina-PCC-8305_gvpA1 | MAVEKTNSSSSLGEVVDRILDKGVVVDLWVRVSLVGIELLAVEAR VVIASVETYLKYAEAVGLTSSAAVPAE* | 41 |
| Dolichospermum-circinale-AWQC131C_gvpA | MAVEKTNSSSSLAEVIDRILDKGIVIDAWVRVSLVGIELLAIEARIVI ASVETYLKYAEAVGLTQSAAVPA* | 42 |
| Dolichospermum-lemmermannii_gvpA | MAVEKTNSSSSLAEVIDRILDKGIVIDAWVRVSLVGIELLAIEARIVI ASVETYLKYAEAVGLTQSAAVPA | 43 |
| Enhydrobacter-aerosaccus_gvpA1 | MAVEKMNASSSLAEVVDRILDKGIVVDAWVRVSLVGIELLAVEAR VVVAGVDTYLKYAEAVGLTAGAEAA* | 44 |
| Lyngbya-confervoides-BDU141951_gvpA | MAVEKVNSSSSLAEVIDRILDKGIVVDAWVRVSLVGIELLAIEAR VVIASVETYLKYAEAVGLTAQAAVPAS* | 45 |
| Nostoc-punctiforme-PCC-73102_gvpA | MAVEKVNSSSSLAEVIDRILDKGIVIDAWVRVSLVGIELLSIEARIVI ASVETYLRYAEAVGLTSQAAVPSAA* | 46 |
| Nostoc-sp-PCC-7120_gvpA | MAVEKTNSSSSLAEVIDRILDKGIVVDAWVRVSLVGIELLAIEARIV IASVETYLKYAEAVGLTQSAAMPA* | 47 |
| Microchaete-diplosiphon_gvpA | MAVEKTNSSSSLAEVIDRILDKGIVVDAWVRVSLVGIELLAIEARIV IASVETYLKYAEAVGLTQSAAVPA* | 48 |
| Microcystis-aeruginosa-NIES-843_gvpA1 | MAVEKTNSSSSLAEVIDRILDKGIVIDAWARVSLVGIELLAIEARVV IASVETYLKYAEAVGLTQSAAVPA* | 49 |
| Microcystis-aeruginosa-NIES-843_gvpA2 | MAVEKTNSSSSLAEVIDRILDKGIVIDAWARVSLVGIELLAIEARVV IASVETYLKYAEAVGLTQSAAVPA* | 50 |
| Microcystis-aeruginosa-NIES-843_gvpA3 | MAVEKTNSSSSLAEVIDRILDKGIVIDAWARVSLVGIELLAIEARVV IASVETYLKYAEAVGLTQSAAVPA* | 51 |
| Microcystis-flos-aquae-TF09_gvpA | MAVEKTNSSSSLAEVIDRILDKGIVIDAWARVSLVGIELLAIEARVV IASVETYLKYAEAVGLTQSAAVPA* | 52 |
| Phormidium-tenue-NIES-30_gvpA | MAVEKVNSSSSLAEVVDRILDKGIVIDAWVRVSLVGIELLAIEARV VIASVDTYLKYAEAVGLTAQAAVPAA* | 53 |
| Planktothrix-agardhii_gvpA | MAVEKVNSSSSLAEVIDRILDKGIVIDAWVRVSLVGIELLSIEARIVI ASVETYLKYAEAVGLTAQAAVPSV | 54 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| Planktothrix-rubescens_gvpA | MAVEKVNSSSSLAEVIDRILDKGIVIDAWVRVSLVGIELLSIEARIVI ASVETYLKYAEAVGLTAQAAVPSV* | 55 |
| Pseudanabaena-galeata-PCC-6901_gvpA | MAVEKVNSSSSLAEVIDRILDKGIVIDAWVRVSLVGIELLSIEARVV IASVETYLKYAEAVGLTASAAVPAA | 56 |
| Stella-vacuolata_gvpA | MAVEKINASSSLAEVVDRILDKGVVVDAWVRVSLVGIELLAVEAR VVVAGVDTYLKYAEAVGLTAGAQTA* | 57 |
| Trichodesmium-erythraeum-IMS101_gvpA3 | MAVEKVNSSSSLAEVIDRILDKGVVVDAWIRLSLVGIELLTIEARIV VASVETYLKYAEAVGLTTLAAAPGEAAA* | 58 |
| Trichodesmium-erythraeum-IMS101_gvpA4 | MAVEKVNSSSSLAEVIDRILDKGVVVDAWVRLSLVGIELLTIEARI VIASVETYLKYAEAVGLTTLAAEPAA* | 59 |
| Tolypothrix-sp.-PCC-7601_gvpA1 | MAVEKTNSSSSLAEVIDRILDKGIVVDAWVRVSLVGIELLAIEARIV IASVETYLKYAEAVGLTQSAAVPA* | 60 |
| Tolypothrix-sp.-PCC-7601_gvpA2 | MAVEKTNSSSSLAEVIDRILDKGIVVDAWVRVSLVGIELLAIEARIV IASVETYLKYAEAVGLTQSAAVPA* | 61 |
| Halo-family-consensus_gvpA | MAQPDSSSLAEVLDRVLDKGVVVDVWARXSLVGIEILTVEARVV AASVDTFLHYAEEIAKIEQAELTAGAEA-XPAPEA | 62 |
| Halobacterium-salinarum_gvpA1 | MAQPDSSGLAEVLDRVLDKGVVVDVWARVSLVGIEILTVEARVV AASVDTFLHYAEEIAKIEQAELTAGAEAAPEA | 63 |
| Halobacterium-salinarum_gvpA2 | MAQPDSSSLAEVLDRVLDKGVVVDVWARISLVGIEILTVEARVVA ASVDTFLHYAEEIAKIEQAELTAGAEAPEPAPEA | 64 |
| Halobacterium-salinarum-NRC-1_gvpA1 | MAQPDSSGLAEVLDRVLDKGVVVDVWARVSLVGIEILTVEARVV AASVDTFLHYAEEIAKIEQAELTAGAEAAPEA* | 65 |
| Halobacterium-salinarum-NRC-1_gvpA2 | MAQPDSSSLAEVLDRVLDKGVVVDVWARISLVGIEILTVEARVVA ASVDTFLHYAEEIAKIEQAELTAGAEAPEPAPEA* | 66 |
| Haloferax-mediterranei-ATCC-33500_gvpA | MVQPDSSSLAEVLDRVLDKGVVVDVWARISLVGIEILTVEARVVA ASVDTFLHYAEEIAKIEQAELTAGAEAAPTPEA* | 67 |
| Halogeometricum-borinquense-DSM-11551_gvpA | MAQPDSSSLAEVLDRVLDKGVVVDVWARVSLVGIEILTVEARVV AASVDTFLHYAEEIAKIEQAELTATAEAAPTPEA* | 68 |
| Halopenitus-persicus-strain-DC30_gvpA | MAQPDSSGLAEVLDRVLDKGVVVDVWARVSLVGIEILTVEARVV AASVDTFLHYAEEIAKIEQAELTAGAEAAPEA | 69 |
| Haloquadratum-walsbyi-C23_gvpA | MAQPDSSSLAEVLDRVLDKGIVVDTFARISLVGIEILTVEARVVVA SVDTFLHYAEEIAKIEQAELTAGAEA* | 70 |
| Halorubrum-vacuolatum-strain-DSM-8800_gvpA | MAQPDSSSLAEVLDRVLDKGVVVDVYARLSLVGIEILTVEARVVA ASVDTFLHYAEEIAKIEQAELTAGAEAAPTPEA* | 71 |
| Halopiger-xanaduensis_gvpA1 | MAQPQRRPDSSSLAEVLDRILDKGVVIDVWARISVVGIELLTIEAR VVVASVDTFLHYAEEIAKIEQATAEGDLEELEELEVEPRPESSPQSA AE* | 72 |
| Natrialba-magadii-ATCC-43099_gvpA | MAQPQRRPDSSSLAEVLDRVLDKGVVIDIWARVSVVGIELLTVEA RVVVASVDTFLHYAEEIAKIEQATAEGDLEDLEELEVEPRPESSPKS ATE* | 73 |
| Natrinema-pellirubrum-DSM-15624_gvpA1 | MAQPQRRPDSSSLAEVLDRVLDKGVVIDVWARISVVGIELLTIEAR VVVASVDTFLHYAEEIAKIEQATAEGDLDELEELEVEPRPESSPKS AE* | 74 |
| Natronobacterium-gregoryi-SP2_gvpA1 | MAQPQRRPDSSSLAEVLDRILDKGVVIDVWARVSVVGIELLTIEAR VVVASVDTFLHYAEEIAKIEQATAEGDLEDLEELEVEPRPESSPQS ATE* | 75 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| Methanosaeta-thermophila_gvpA1 | MVTSTPDSSSLAEVLDRILDKGIVVDVWARVSLVGIEILTVEARVV VASVDTFLHYSEEMAKIEQAAIAAAPSA* | 76 |
| Methanosaeta-thermophila_gvpA2 | MVTSTPDSSSLAEVLDRILDKGIVVDVWARVSLVGIEILTVEARVV VASVDTFLHYSEEMAKIEQAAIAAAPGVPA* | 77 |
| Methanosarcina-barkeri-3_gvpA1 | MVSQSPDSSSLAEVLDRILDKGIVVDVWARVSLVGIEILAIEARVV VASVDTFLHYAEEITKIEIAAKEEKPAIAA* | 78 |
| Methanosarcina-vacuolata_gvpA1 | MVSQSPDSSSLAEVLDRILDKGIVVDTWARVSLVGIEILAIEARVV VASVDTFLHYAEEITKIEIAAREEKPVIAA* | 79 |
| Methanosarcina-vacuolata_gvpA2 | MVSQSPDCSSLAEVLDRILDKGIVVDTWARVSLVGIEILAIEARVV VASVDTFLHYAEEITKIEIAAREEKPVIAA* | 80 |
| Haladaptatus-paucihalophilus-DX253_gvpA | MVQAEPNSSSLADVLDRILDKGVVIDVWARISVVGIEVLTVEARV VVASVDTFLHYAKEMAKLERASSEDEIDFEQVEVASPEASTS* | 81 |
| Mega-family-consensus_gvpA | MSIQKSTXSSSLAEVIDRILDKGIVIDAFARVSXVGIEILTIEARVVIA SVDTWLRYAEAVGLL-D-VEE-GLP-RX- | 82 |
| Bacillus-megaterium_gvpA | MSIQKSTDSSSLAEVIDRILDKGIVIDAFARVSLVGIEILTIEARVVIA SVDTWLRYAEAVGLLTDKVEEEGLPGRTEERGAGLSF* | 83 |
| Bacillus-megaterium_gvpB | MSIQKSTNSSSLAEVIDRILDKGIVIDAFARVSVVGIEILTIEARVVIA SVDTWLRYAEAVGLLRDDVEENGLPERSNSSEGQPRFSI* | 84 |
| Serratia-family-consensus | MAKVQKSTDSSSLAEVVDRILDKGIVIDAWXKVSLVGIELLSIEAR VVIASVETYLKYAEAIGLTAXAAAPA* | 85 |
| Burkholderia-sp-Bp5365_gvpA1 | MAKVQKSTDSSSLAEVVDRILDKGIVIDVWAKVSLVGIELLSIEAR VVIASVETYLKYAEAIGLTATAAAPTA* | 86 |
| Desulfobacterium-vacuolatum-DSM-3385_gvpA | MAKVQKTTDSSSLAEVVDRILDKGIVVDAWAKISLVGIELISIEAR VVIASVETYLKYAEAIGLTAAAAAPA* | 87 |
| Desulfomonile-tiedjei-DSM-6799_gvpA1 | MAKIAKSTDSSSLAEVVDRILDKGIVIDAWAKVSLVGIELLSVEAR VVIASVETYLKYAEAIGLTASAAAPA* | 88 |
| Isosphaera-pallida-ATCC-43644_gvpA1 | MAKVTKSTDSSSLAEVVDRILDKGIVIDAFAKVSLVGIELLSVEAR VVIASVETYLKYAEAIGLTASAATPA* | 89 |
| Lamprocystis-purpurea-DSM-4197_gvpA1 | MAKVANSTDSSSLAEVVDRILDKGIVIDAWIKVSLVGIELLAIEARI VIASVETYLKYAEAIGLTAPAAAPA* | 90 |
| Lamprocystis-purpurea-DSM-4197_gvpA2 | MAKVANSTDSSSLAEVVDRILDKGIVIDAWLKVSLVGIELLAVEA RVVIASVETYLKYAEAIGLTAPAAAPA* | 91 |
| Legionella-drancourtii-LLAP12_gvpA1 | MAKVQKSTDSSSLAEVIDRILDKGIVIDVWAKVSLVGIELLSIEARV VIASVETYLKYAEAIGLTATASHPA* | 92 |
| Psychromonas-Ingrahamii_gvpA1 | MANVQKTTDSSGLAEVIDRILDKGIVIDAFVKVSLVGIELLSIEARV VIASVETYLKYAEAIGLTASAATPA* | 93 |
| Psychromonas-Ingrahamii_gvpA4 | MANVQKSTDSSGLAEVVDRILEKGIVIDAFVKVSLVGIELLSIEARV VIASVETYLKYAEAIGLTASAATPA* | 94 |
| Serratia-39006_gvpA1 | MAKVQKSTDSSSLAEVVDRILDKGIVIDAWVKVSLVGIELLSIEAR VVIASVETYLKYAEAIGLTASAATPA* | 95 |
| Thiocapsa-rosea-strain-DSM-235-Ga0242571-11_gvpA1 | MAKVANSTDSSSLAEVVDRILDKGIVIDAWVKVSLVGIELLAIEAR VVIASVETYLKYAEAIGLTAPAAAPA* | 96 |
| Other gvpAs | | |
| Bradyrhizobium-oligotrophicum-S58_gvpA1 | MAIEKATASSSLAEVIDRILDKGVVIDAFVRVSLVGIELLSIELRAV VASVETWLKYAEAIGLVAQPMPA* | 97 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| Desulfotomaculum-acetoxidans-DSM-771_gvpA1 | MAVKHSVASSSLVEVIDRILEKGIVIDAWARVSLVGIELLAIEARV VVASVDTFLKYAEAIGLTKFAAVPA* | 98 |
| Octadecabacter-antarcticus-307_gvpA1 | MAVNKMNSSSSLAEVVDRILDKGVVIDAWVRVSLVGIELIAVEAR VVIAGVDTYLKYAEAVGLTAEA* | 99 |
| Octadecabacter-arcticus-238_gvpA1 | MAVSKMNSSSSLAEVVDRILDKGVVIDAWVRVSLVGIELIAVEAR VVIAGVDTYLKYAEAVGLTAEA* | 100 |
| Pelodictyon-luteolum-DSM-273_gvpA1 | MAVEKTIGSSSLVEVIDRILDKGVVVDAWVRMSLVGIELLAIEARV VVASVETYLKYAEAIGLTAKAA* | 101 |
| Pelodictyon-luteolum-DSM-273_gvpA2 | MAVEKTIGSSSLVEVIDRILDKGVVVDAWVRVSLVGIELLAIEARV VVASVETYLKYAEAIGLTAKAA* | 102 |
| Pelodictyon-phaeoclathratiforme_gvpA1 | MSVEKTIGSSSLVEVIDRILDKGVVVDAWVRVSLVGIELLAIEARV VVASVETYLKYAEAIGLTAKAA* | 103 |
| Rhodobacter-capsulatus-SB-1003_gvpA1 | MAIEKSLASASIAEVIDRVLDKGIVVDAFVRISLVGIELLAIELRAV VASVETWLKYAEAIGLTVDPQTP* | 104 |
| Rhodobacter-sphaeroides_gvpA1 gvpF | MAIEKSVASASIAEVIDRILDKGVVIDAFVRVSLVGIELIAIEVRAVV ASIETWLKYAEAVGLTVDPATT* | 105 |
| Anabaena-flos-aquae_gvpF | MSIPLYLYGIFPNTIPETLELEGLDKQPVHSQVVDEFCFLYSEARQE KYLASRRNLLTHEKVLEQTMHAGFRVLLPLRFGLVVKDWETIMS QLINPHKDQLNQLFQKLAGKREVSIKIFWDAKAELQTMMESHQDL KQQRDNMEGKKLSMEEVIQIGQLIEINLLARKQAVIEVFSQELNPF AQEIVVSDPMTEEMIYNAAFLIPWESESEFSERVEVIDQKFGDRLRI RYNNFTAPYTFAQLDS* | 106 |
| Ancylobacter aquaticus strain UV5_gvpF | MSATLSAPGTANVAVEATAAADGKYLYGIIEAPAPATFDVPAIGG RGDVVHTIALGRLAAVVSNSPRIDYDNSRRNMLAHTKVLEAVMA RHTLLPVCFGTVGSDAEVIIEKILRERRDELAGLLGQMHGRMELGL KASWREEIIFEEVLAENPAIRKLRDALVGRSPDQSHYERIQLGERIG QALQRKRQDDEERILERVRPFVHKTRLNKLIGDRMVINAAFLVDA AVESRLDASIRAMDEEWGGRLAFKYVGPVPPYNFVTITIHW* | 107 |
| Aphanizomenon flos-aquae NIES-81_gvpF | MNTGLYLYGIFPDPIPETVDLQGLDKQSVHSQVVDGFSFLYSDAC QEKYLASRRNLLTHEKVLEQAMHEGFHVLLPLRFGLVVKDWETI QKQLIEPYKEQLNELFQKLAGQREVSIKILWDSKSELQAMMESNQ DLKQQRDNMEGKKLKMEEIIQIGQLIESNLAARKQTVIQEFFNNLH PLAKETIESEPMTEEMIYNAAFLIPWETESVFSERVEAIDRKFGDRL RIRYNNFTAPYTFAQLAS* | 108 |
| Aphanothece halophytica (strain PCC 7418)_gvpF | MAEGFYLYGIFPPPGPQTIAVQGLDKQPIFSHTVEGFTFLYSEAQQS RYLASRRNLITHTKVLEEAMEQGFRTLLPLQFGLVVPDWESVSQD LLQHQSETLQLLFQRLEGKREVSLKIYWETDAELNALLEENPDLK ARRDNLEGKNLSMDEVIQIGQALEQAMERRKQEVITRFEDALIPFA VETQENDVLTETMIYNTAFLIPWESEPEFGEAVETVDAEFAPRLKI RYNNFTPPYNFVELRE* | 109 |
| Aquabacter spiritensis strain DSM 9035_gvpF | MMQTDTLAPAETVAEGKYLYCLIDAPAPDTFASPGIGGRGDVVHT ITVGRLAAVVSDSPRIEYENSRRNMMAHTKVLEEVMARHTMLPV CFGTVATGPDPISGKILEGRRDELVGLLEQMRGRLELGLKATWRE DVIFAEILQENPAIAKLRDSLVGRSPEKSHFERIRLGEMIGQAMERK RRDDEERILERVRPFVHKTKLNKPIGDRMILNAAVLVEAAREAGL DQAVRQMDAEWGARLSFKYVGPVPPYNFVTITIHW* | 110 |
| Bacillus-megaterium_gvpF | MSETNETGIYIFSAIQTDKDEEFGAVEVEGTKAETFLIRYKDAAMV AAEVPMKIYHPNRQNLLMHQNAVAAIMDKNDTVIPISFGNVPKSK EDVKVLLENLYPQFEKLFPAIKGKIEVGLKVIGKKEWLEKKVNEN PELEKVSASVKGKSEAAGYYERIQLGGMAQKMFTSLGKEVKTDV FSPLEEAAEAAKANEPTGETMLLNASFLINREDEAKFDEKVNEAH ENWKDKADFHYSGPWPAYNFVNIRLKVEEK* | 111 |
| Bradyrhizobium oligotrophicum | MSNQPIYVYGLIRAEDHQPLAVRAVGDSEQPVNIIGSGNVAALVST IDLPEIMPTRRHMLAHTKVLEAAMANGPVLPMRFGIIVPNPATLLR | 112 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| S58_gvpF | VIGFRHQELRARLDEIDGRIEVALKASWDEQFMWRQLASEHPDLA VSGRTMMGRGEQQSYYDRIELGRAIGAALEERRTAARLQLLQTVT PFAVQVKELTPVDDAMFAHLALLVEKGAEPSLYQTVEALERSNDS GLKFRYVAPIPPYNFVAVTLDWEQHEQAPRR* | |
| Burkholderia thailandensis sp. Bp5365 strain MSMB43_gvpF | MNSRNGARYLYAVQHARDVPASLPAGIGGAAVRALTDGDVAAIV SDTGLAKVRPERRHLLAHHTVIQSLAAAGTVLPVAFGTIATSEVAL RRMLRKHRNALAGELARLVDHVEMSVRLNWDVTDLFRHLIDVRP DLKAARDAMLALGSAVTRDDKIELGSRFERVLNEERARHAALVD EALDACCKEIRRDPPRHETEILHLTCLVRHAELGRFESGVAAASRE LDDSLVLKYSGPCPPHHFVNLNMSL* | 113 |
| Chlorobium luteolum DSM 273_gvpF1 | MERDGKYIYCIIGADCECDFGPIGIGGRGDLVSTIGFEGISMVVSDH PLNRFVVDPDGILAHQRVIEAVMKEHESVIPVRFGTVAATPDEIRN LLDRRYGELSELLLRLRNKVEFNVTGRWHDMAAIYKEVERTHPEI KEQRARIESMRDGDGEALKQSLILDTGHQIEAALEVMKEEKFDAV ASLFRKTAMASKMNRTTSPDMFMNAAFLIDRGREVEFDGIMEILG QKDADRCDYRYSGPLAIFNFVDLRILPEKWEL* | 114 |
| Chlorobium luteolum DSM 273_gvpF2 | MAHEAAEQDGLYIYGIINNSGELDFGPIGIGGREERVYAVIHNDIA AVVSRTVVKEFEPRRANMIAHQKVLEAVMVSHAVLPVRFSTVSPG HDDMKVEKILEEDYLRLKKLLVKMEGKKEMGLKVMANEEKVYE SIITGYDNIRYLRDKLINLPPEKTHYQRVKIGELVAAALEKEVGTY KDAVLDALSPIAEEVKVNDSYGSMMVLNAAFLIRTAREEEFDRAV NALDDRYHDMMTFKYVGTLPPYNFVNISINIKGR* | 115 |
| Chlorobium luteolum DSM 273_gvpF3 | MNQSIYIYGIVNEPALAASFVETDPDIYAVASMGCSAIVENRPAIDL GELDRESLARMLLQHQQTLERLMESGMQLIPLKLGTFVSSAADAA CHIEDGYNLIERIFRETEDAHELEVVVKWSSFADLLQEVVSEGDVQ ELKREVEARQSSSTEDAIAVGRLIKEKIDRRNAALSASVLRQLGER ASQSKRHETMDDEMVLNAAFLVNRGDVDAFVATVEALDSQYLN ALHFRIVGPLPCYSFYTLEVTALFEEFIAEKRAVLGLDARSCEADV KKAYHAKAKVAHPDVHVPAGANNGADFTVLNEAYMTLHDYYS ALRNSASSRHGHEGQDSSSVVFSVKILN* | 116 |
| Dactylococcopsis salina PCC 8305_gvpF | MTEGFYLYGIFPPPGPKTIETQGLDKQPIFSHTVEGFTFLYSEAQQS RYLASRRNLITHTKVLEEAMENGSRTLLPLQFGLIVPDWETVVQD LLQHQAESLHFFLEKLEGKREVSLKIYWETNAELNALLEENPALK ARRDNLEGKQLSMDEVIQIGQALEQEMEGRKQDIISRFEEVLIPFAF EIKENDVLTETMIYNTAFLINWDAESDFGEQLEAIDAEFSPRLKIRY NNFTPPYNFVELRE* | 117 |
| Desulfobacterium vacuolatum_DSM 3385_gvpF | MSKKNLKRNGRYLYAIIEASEEKTFGSIGMDGSDVYLIVEDKTAA VVSDVPNKKIRPQRKNIAAHHAVLNKIMEEITPLPMAFGIIADGEQ AIRKILADNRDVFREQFATVSGKVEMGMRISYDVPNIFEYFISTDSE IRAARDQYFGGNREPSQEAKLELGRMFNRQLNANREEYTNQVIEI LDDYCDDIKENKCRNEQEVTSLACLINRSDQKRFEEGVFESARHFD NNFSFEYNGPWSPHNFVNILIEL* | 118 |
| Desulfomonile tiedjei DSM 6799_gvpF | MEKATIKTTGSNGRYLYAVVPGSQERVYGCLGINGGNVYTIAAKD VAAVVSDVPHQKIRPERRHFAAHQAVLKRVMLDGDLLPMSFGIIS QGPKAVRAILSRNNKSVQQQLKRISGKAEMGIKVTWDVPNIFEYFI DVNRELREARNKLVQPNYLPTQQEKIEIGRMFEEILNLERERHTKQ VERVMSKRCSEIKRSKCRTEIEVMNLSCLVDRTLLSDFEAGVLEAA SHFDDSFAFDFNGPWAPHNFVDLEIDV* | 119 |
| Desulfotomaculum acetoxidans_DSM 771_gvpF1 | MSTGRYVYCVINSIEPLTFMSGPVGNEPEGVFTVHYKELAAVVSQ SSEEKYNVCRENTIAHQKVLEEVLVSHPLLPVRFGTVAQNEEIVKK FLLQERYAELRSMLHNVTGKVQMGLKVLWTDMKTVYQEIVEENP QIKNLKKKLESKPAETIHYEMIDLGQMVNQALLRKKEKQKEMVL KPLQKIALETKESFLYGDQMFVNADFLISRSSLDDFNAKVNELGEF FNEQALFKYIGPLPPYNFVTLYVNF* | 120 |
| Desulfotomaculum acetoxidans_DSM 771_gvpF2 | MVKNHNTDHLKELYIYGLIGGTPFKDELEKISVIQENTPIYGVWHK NIGFAVSSAAPDYPLKDLSKESIIQLFVDHQQVLECLRQKFSLIPVKL GTVLESVTEAAAVLANNEEKFNDLLNYLKDKVELNLSVSWNDLN EVVAKIGEEDEVKKLKQSLLAQEQVSQEDLIKIGKIISFQMQQKKQ AAREYIISELRNLWEDYFINEVVDENSILNLTLLAITGKVDDVNKKI EYLNQIYRDSLDFSLTKSLLPQGFSTVSIKKITMDQLLLAKDILKLP DTASLQDINAARRALLHCYHPDKNDHAAVNKVQEINAAYKLLEE YCQENSSDFNVDLITDYYIMKVIKADKSNVNSMNME* | 121 |
| Dolichospermum circinale_gvpF | MNTDLAHKNFGLYLYGIFPDTIPETLEIKGLDGKSVHSQVVDGFTF LYSQACQEKYLASRRNLLAHERVLEQTMHEGFHVLLPLRFGLVV | 122 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| | KDWETIMSQLINPHKEQLHKLFEKLAGQREVSIKILWDAKAELQA MMESNHDLRQQRDNMEGKKLSMEEVIQIGQLIESNLQARKQAVIE VFTRELNPLAQEIVVSEPMTEEMIYNAAFLIPWDSEPLFSERVESID QKFGNRLRIRYNNFTAPYTFALLDS* | |
| *Enhydrobacter aerosaccus* strain ATCC 27094_gvpF | MNPPEAYIAGRTAAKSVEDRKARPQDLAEGKYVYAIIACDEPREF KNRGIGERGDKVHTINHRQMAAVVSDSPTIDYERSRRNMMAHTV VLEEVMKEFDLLPLRFGTVASSAESVERQLLVPRYGELSAMLEKM RGRSEFGLKAFWHEGVAFGEIVRENARVRKLRDALQGRSLEEESYY QRIQLGEEVEKALTAIRARDEELILSRLRPFMRDIRTNKIISDRMVL NAAFLVERGDVPALDEAIRQLDQEFSERLMFKYVGPVPPYNFVNI AINWER* | 123 |
| *Isosphaera pallida*_ATCC-43644_gvpF | MRNAPPTRPGSVTPASPGKPVIDGPARYLYAFTHDLPEGPLADLEG LPGARVVVVADGRVAAVVSPCPLGKVRPERQRVAGHHHVLRHL QDTLGKAILPASFGMVADSEEDLRALLRHHSAAIAEGLVRVQGKV EMTVKLRWAPDNVAQAVLGRDPELRQLRDQLYSNGQTPTRDQSL DLGRRFHHALERQRDHYAAYLRAALSPLLSELVEEDLRDERDLVH WACLIENQRRAGFEAALDRLAEELEDDLVLELTGPWPPHHFVDLD LDDDHDDDEEE* | 124 |
| *Legionella drancourtii* LLAP12_gvpF | MDSTSKKPAASNLYLYAIASVNENQEPISFHGIEEQPIDLVPYKDIM LVVSNLSKKKVRPERKNVAVHHAVLNHLMKHNTSMLPIRFGMIA DNRKEVQRLLTINYDMLHTKLKMMAGRVEMGVSLSWDVPNIFEY LLNRHSQLRETRDKLLANPAHEPSRDEKIEIGALFSQILDEERVYT DTILSLLSPVCCDVVKSTYRNDTEIMNIFCLISAARRDEFEEKIIEAS TILDDNFVIKYTGPWPPHNFSKLNLSLE* | 125 |
| *Lyngbya confervoides* BDU141951_gvpF | MPQLLYLYGIFPAPGPQDLEVQGLDQQPIHTHIIDEFVFLYSVAQQE RYLASRKNLLGHERVLEAAMKVGYRTLLPLQFGLIIETWDRVIKE LITPRGDALKRLFAKLEGRREVSVKLLWGPDAELNQLMEEDAGLR AERDRLEGQQLSMDQIVDIGQAIETAMTERKDDVINAFRQRLNAL AIEVLENDPLTDAMIYNTAYLIPWEDEVKFSQAIEELDEQFEDRLRI RYNNFTAPYNFAQLDQLS* | 126 |
| *Microcystis aeruginosa* NIES-843_gvpF | MTVGLYLYGIFPEPVPDGLVLQGIDNEPVHSEMIEGFSFLYSAAHK EKYLASRRYLICHEKVLETVMEAGFTTLLPLRFGLVIKTWESVTEQ LISPYKTQLKELFAKLSGQREVSIKIFWDNQWELAALESNPKLKQ ERDAMMGKNLNMEEIIHIGQLIEATVLQRKQDIIQVFRDQLNHRA QEVIESDPMTDDMIYNAAYLIPWEQEPEFSQNVEAIDQQFGDRLRI RYNNLTAPYTFAQLV* | 127 |
| *Nostoc punctiforme* ATCC 29133_gvpF | MSFYIYGILTLPAPQNLNLEGLDRQPVQIKILDDFAVIYSEAQQERY LASRRNLLSHEKVLEEIMQAGDRYLLPVQFGLLVSSWETVSSQLIR PHQEELTQLLAKLSGCREVSVKVFWDTEAEIQGLLAEHPNLKTER DKLVGQPLSMERVIQIGQVIEQGMSDRKQGIIDVFKGTLNSIAIEVV ENTPQVDTMIYNSAYLIPWEAESQFSEHVESLDRQFENRLRIRYNN FTAPYNFARLRLTTSN* | 128 |
| *Nostoc sp.* PCC 7120_gvpF | MSSGLYLYGIFPDPIPETVTLQGLDSQLVYSQIIDGFTFLYSEAKQE KYLASRRNLISHEKVLEQAMHAGFRTLLPLRFGLVVKNWETVVT QLLQPYKAQLRELFQKLAGRREVSVKIFWDSKAELQAMMDSHQD LKQKRDQMEGKALSMEEVIHIGQLIESNLLSRKESIIQVFFDELKPL ADEVIESDPMTEDMIYNAAFLIPWENESIFSQQVESIDHKFDERLRI RYNNFTAPYTFAQIS* | 129 |
| *Octadecabacter antarcticus* 307_gvpF1 | MKREVVRMTDENTINSKYLYAIIKCREQREFIARGIGERGDAVHTI AYKGLAAVVSDSPVMEYDQSRRNMMAHTAVLEELMEEFTLLPVR FNTVAPEAGAIEERLLVPRHEEFTQLLGQIDKRVELGIKAFWHDG MIFEEVLRENDSIRKMRDALEGKSVDGSYYERIQLGEKIEQAMIKK RVEDEEIILSRIRQHVHKSRSNKTIGDRMVLNGAFLVDANKESDFD KAVQLLDQDLGNRLMFKYVGPVPPYNFVNIVVNWGVV* | 130 |
| *Octadecabacter antarcticus* 307_gvpF2 | MTVVAEENMTGSVGLYVCAIVAEWESNSALIKCANEAQGEIQLIG QGGITAVVMVPPEDQPVSRDRQELVRQLLVHQQLVERFTEIAPVL PVKFGTLAPDRESVELGLERGREKFFTAFGGLSGKTQFEITVTWDV ADVFAKIAKLPAVVKLKVDLVATSESDRPINLDRVGRLVKETLDH QRAQTGKVLLDALLPLGVDSIVNPILNDSIVLNLALLVDTDQADAL DRCLDELDSTPHGALSFRCVGPMPPHSFATVEINYIEPTQVSHACC VLELDAAHNFEEIRSAYHRLARQTQQDIAPDVVVDNKSSSVGIAV LNDAYKTLLSFVDAGGPVVVSVQRQEDAYATDIPSSGG* | 131 |
| *Octadecabacter arcticus* 238_gvpF1 | MTDEKKVNSKYLYAIIQCREPRELKARGIGERGDVVHTVVHKGLA AVVSDSPVMEYDQSRRNMMAHTAVLEELMEEFTLLPVRFNTVAP | 132 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| | EAVAIEERLLVPRHDEFTQLLGQIDKRVELGLKAFWHDGMIFGEV LRENDSIRKMRDSLKGQSVDGSYYERIQLGEKIEKALTEKRLEDEE MILSRIRPHVHKSRSNKTIGDRMVLNGAFLVDAEKESKFDEAVQSL DQDLSDRLMFKYVGPVPPYNFVNIVVNWGES* | |
| Octadecabacter arcticus 238_gvpF2 | MRAQKVIPAAEENISGNVGLYVCAIVAERVSCSALIQCANDAPGEI QLIGHGDFTAVVMVPEKDQLVSPDRKELMQQLLVHQQLIEKFMEI APVLPVKFATLAPNRESVELGLEVGSEKFSAAFNSLSGKVQFEVIV TWDVAEVFAEIAKEPAVAKLKVDLAAMPESYGSVSLEQLGKLVK ETLELRRAETGKVLLDALVQVGVDNVVNSILDDSIILNLALLVEAK RADAFDRCLDELDSTYHGALTFRCVGPLPPHSFATVEITYLEPAKV TEACDILELDVARSTEEVRSAYHRLARKSHPDIVPDVAVGETASVS MAVLTDAYKTLLSFVGAGGSVVVSVQRQEASYAADIISSAG* | 133 |
| Pelodictyon phaeoclathratiforme_ gvpF1 | MDIETTKEGRYIYGIIRNSEFIDFGQIGIGKRNDRVYGVIYKDICAV VSSTPIIQYEARRANMIAHQKVLEEVMKRFNVLPVRFSTISPHDND DAIIKILITDYSRFDELLIKMKGKKELGLKVMADETRIYENIIQKYD NIRSLRDKLLNQPADKIHYQRVKIGEMVADALKKEIESYKQQILDI LSPIAEDIKITDNYGNLMILNAAFLIKEVKESEFDDSVNKLDEKYGN IMTFKYVGTLPPYNFVNLSINTKGV* | 134 |
| Pelodictyon phaeoclathratiforme_ gvpF2 | MEKDGKYVYCIIASTYECNFGAIGIGGRGDLVNTIGFQGLSMVVSD HPLNHFVLNPDNILAHQRVIEVVMSQFNSVIPVRFGTVAATPDEIR NLLDRRYGELSELLERFENKVEYNLKASWRCMIDIYKEIDKEHVE LKQLRREIEGLKDEEKRKLLIVEAGHIIENELQKKKEVEAYEIVTYL RKTVVAHKHNKTTGEAMFMNTAFLLNKGREVEFDNIMNDLGEQ YKDRSDYYYTGPLPIFNFIDLRILPEKWEL* | 135 |
| Pelodictyon phaeoclathratiforme_ gvpF3 | MDRQGIYIYGFIPNHYLTDIKTILIESGIYSIEYGSIAALVSDTMVDDI EYLNREDLAYLLVDHQKKIELIMSTGCSTIIPMQLGTIVNSGNDVIK IVKNGLRIINKTFDDIADIQEFDLVVMWNNFPDLIKKISDTPQIRIMK EEIANKGSYDQADSINIGKIIKKKIDEKNSKVNLDIMNSLSSLCICVK KHESMNDEMPLNSAFLIKKDKENSFIEMVNQLDIKYENLLRYKIV GPLPCYSFYTLESKLLNKKEIEKAEKILGIDAYKSESDIKKAYRAKA AHAHPDKNNTISAIDNDDFIEINKAYQILLEYSSVFKDSPDHKPDEP FYLVKIKK* | 136 |
| Phormidium tenue NIES-30_gvpF | MADRYYLYGIFPAPGPAELPLMGLDEQVVQAQQLGDFTFLYSLAC QKRYLSSRKNLLGHEKVLEAAMEQGHRTLLPLQFGLIVESWNQV QEDLVTPYAEDLTQLFGRLNGCREVSIKVQWEPSTELEMMMAEN ADLRAQRDQLEGTQLGMEQVIFIGQQIESALEERKQGIVDQFRQAL SPLAKDVLENAPQTDVMIYNAAFLIPWESEAEFSQAVDAIDSTFGD RLRIRYNNFTAPYNFAQLN* | 137 |
| Planktothrix agardhii str. 7805_gvpF | MGNGLYLYGILPTNRVRPLALHGLDKQPIQTHPVDEFSFLYSETQQ ERYLASRRNLLGHEDVLEKVMQHGYRSVLPLQFGLIVKDWDHVK AQLIIPYQDRLKELFHKLEGKREVGVKIFWEETEELDLLMTENQEL REKRDSLEGKRLSMDEIIGIGQEIERAMQDRQQGIIDKFQQILNPLA QEIVENDNLTSAMIYNAAYLIPWDIEPQFGDKIEELDHHFNNRLRIR YNNFTAPFNFAQLNP* | 138 |
| Psychromonas ingrahamii 37_gvpF | MAENKKKVRKSSSKVIAKPKVIYAITAGGLQDLGNLVGINKSDIYT IEKESISFVVSDLSPSSPRPRPDRRNIMAHNEILKQLMSKTSVLPVRF GTVATGERAVNRFCSQYNAQLLEQLDRVQDRVEMGIKVTWNVP NIYDYFVDNHSELREERDRVYDGNKNPRRDDRINLGHMYDALVT EARLSHQTDLEEIILPGCDEIHSIPPKDEKVVVNLACLVQRADLEVF EERVVEAGKTLDNTYDIELNGPWAPHNFVELDLKTMTGRR* | 139 |
| Serratia sp. ATCC 39006_gvpF | MMSIDKSRNHRAKVLYALCVSDDSTPNYKIRGLEAAPVYSIDQDG LRAVVSDTLSTRLRPERRNITAHQAVLHKLTEEGTVLPMRFGVIAR NAEAVKNLLVANQDTIREHFERLDGCVEMGLRVSWDVTNIYEYF VATYPVLSETRDEIWNGNSNANNHREEKIRLGNLYESLRSGDRKE STEKVKEVLLDYCEEIIENPVKKEKDVMNLACLVARERMDEFAKG VFEASKLFDNVYLFDYTGPWAPHNFVTLDLHAPTAKKKTLTRAG TLSD* | 140 |
| Stella vacuolata_ATCC-43931_gvpF | MQTEALAPAAVAAEGKYLYCIIDAPAPATFASPGIGGRGDVVHTL AVGRLAAVVSDTPRIEYENSRRNMMAHTKVLEEVMAHHTLLPVC FGTVGSGDDVIAEKILEGRREELSRLLEEMRGRVELGLKATWREE VIFAEVLDEDPAVRKLRDSLVGRSPEKSHFERIRLGELIGQALLRKR RDEEERILDRVRPFVRKTKLNKPIGDRMILNAAFLVETAREAALDQ SVREMDADWGARLSFKYVGPVPPYNFVTITIHW* | 141 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| *Thiocapsa rosea* strain DSM 235 Ga0242571_11_gvpF | MQQAKRQDVAAGRYIYAIIPDRGDHSLGRIGLDESEVYTIGDGRV AAVVSDLSGGRIRPQRRNMAAHQEVLKQVLREVSPLPAAFGLMA DDEAAIIRILKDNQDAFLNQLERVDGSLEMGLRMSWDVPNIFEYF VGAHPELQELRDDFFRDGSNLTQDQMITLGRSFERLLEQDREEYTE QVESVMRSCCREIKRNKCRTEKEVLHLACLVDRDAAGRFEQVVL QAARPFDNNYAFDFNGPWAPHNFVEMDIHV* | 142 |
| *Tolypothrix* sp. PCC 7601_gvpF | MDAGLYLYGIFSDPIPPTVSLKGLDSQPVYSQVIEGFTFLYSDAKQE KYLASRRNLISHEKVLEQAMQEGFRTLLPLRFGLVVKNWETVISQ LIQPCERQLRDLFQKLAGKREVSVKILWDTKAELQAMMQSNPDL KQKRDQMEGKNLSMEEVIEIGQLIESNLQQRKEAVIKTFFDELKPL AEEVVESEPMMEEMIYNAAFLIPWDQEALFSQRVEAIDKKFGDRL RIRYNNFTAPYTFAQIS* | 143 |
| *Trichodesmium erythraeum* IMS101_gvpF | MEFGFYVYGLIQEKGKMDESKDESKNGLKGSNESKDELKGLDKE DVKIQDVDEFAVLYSIAKKERYLASRRNLITHEKVLESAMEAGYR NLLPMQFGLVVSEWEKFSQDFTKPCEQQIHDLFTKLKNNREVGIKI YWEPDAELEKLLENDKDLKEERDSLKDKKLTMDQVIDIGQKIEQG MNERKQNIIEIFQETLNKMAIEVIENEVQTEKMIYNAAYLIPWDQE EDFGKEVETIDSKLCERGNFTIRYNSFTAPYNFARIRQQD* | 144 |
| gvpF/L | | |
| *Ancylobacter aquaticus* strain UV5_gvpFL1 | MTDLLVFAVVPADRFDPAILAEGDGLPPGLRAIAAGPLAAVVGAA PEGGLKGRERSALLPWLLASQKVMERLLANAPVLPVALGTVVED EGRVRHMLDAGAAILGEGFQAVGDGIEMNLSVLWHLDTVVARLL PGVAPELRQAAAGGDAIERQALGVVLAGLVSAERRRARARVIEAL QAVTRDFAIGEPTEPGGVVNLALLVDRAAEEALGAALEALDAEFD GALTFRLVGPLPPYSFASVQVHLSPAAAVCGARAALGVEPDASPE TVKAAYRRAARETHPDLVPMGGEDEEAPEATADETSRFVVLSDA YRVLEGEHAPVSLRRLDSVLTE* | 145 |
| *Ancylobacter aquaticus* strain UV5_gvpFL2 | MLYVYAITADYAAGANHLLPAKGIVPGVPVQRFGTGALGAVASP VPVTVFGKEALHALLDDADWTRARILAHQRVVSSLLPLATVLPLK FGTLVAGEASLAAALTSQHDALDATVARLRGAREWGVKLFFEAP TRTIRAEEPVGAGAGLAFFRRKKEEQETRAAAEAALDRCVAASHR RLASHARAAVANPLQPPELHGHPGTMGLNGAYLVAAENEAAWR VCFSELEQAYAALGARYVRTGPWAAYNFTGGGLV* | 146 |
| *Aquabacter spiritensis* strain DSM 9035_gvpFL1 | MSGLLVFAIVPADRIEPGLLAPAEGLPPGLETVVAAGFAAIVGTAP EGGLKGRDRGSLLPWLLASQKVIERLMARGPVLPAALGSVLEDES RVRHMLVCGQAALAAAFETLNGCWQTDLSVRWDLSRTVAHLMT ELPPGLRAAAETGDETARRSLGAALAGLVAGERRRIQSRIGAVLG AVARDLIVSDPVEPEGVVGVALLVDAPASAQVDAALDRLDGEFE GRLTFRLVGPLAPYSFATVQIHLGPAAGLAGAHAELGLEAGAPLE AVKAAYHRLIVGLHPDLVPHGSPGDDADDAASGKGGRAARFAAV TAAYRTLQAEHAPVSLRRQDGLSPG* | 147 |
| *Aquabacter spiritensis* strain DSM 9035_gvpFL2 | MLYVYAITADHPGPHDAGSLPGEGIVPGAPVRLLPFGDLAAAVSP VSAVDFGPEALPARLQDVDWTGQRVLAHQRVVDSLVDVATVLP MKFCTLFSGAAALRAALADNRAALEATVVRLRGAREWGVKLFW EAPPAEPAPVERGPGAGAAFFQRKRDAQRLRAEAEAALAHGVAE SHRRLAARARAAVANPVQPAAVHRRRGEMALNGAYLVPRADEA AWRESLAELERTYAGAGIRYELTGPWGPYNFTGGGLAGS* | 148 |
| *Bradyrhizobium oligotrophicum* S58_gvpFL1 | MTMNLVGITTPDVAGAIAAAGGRLADVETRAVEAGGLVALLALS KAPFWHVLRRSRTALRSMLTAQRILEAAAVYGPLLPARPGTLIRN DAEACMLLRSQCRHLAEGLRLHGTSRQYQITISWDPVAALAARRD HQDLVEAAAASADGAADKAASMIQRFMSDQQARFEAEAMRALA AVAEDVITLPVNQPDMLMNAVVLLAPGAEPELERVLEALDRGLR GKNLIRLIGPLPPVSFAAVSIERPGRQRIAAARRLLGIGEATRTCDLR RAYLDKAHAHHPDTGGHAADASIVGAAAEAFRLLARVAEARASA GQDDVILVDIRRQDQQRSLST* | 149 |
| *Bradyrhizobium oligotrophicum* S58_gvpFL2 | MSKANLGIGLVHGVVTAQSAALLPQIVDAFDATEIIVVNTEQQALL ISDIPQYLRGHVEADTLFSDPARISTLAMKHHRILQAAAVVTDVVP VRLGTLVRGPSGARDLLNREAVRFAGHLVTIHNALEFSVRILPTEQ PSRRVARPVPSSGRDYLRIRRDERCGQRPAVVDITLQELASRAVAI RERQSASRSGGRTPALAEAAFLVDRHALAAFDDCAGRIERQIAEN GLALDIFGPWPAYSFVDGARENLG* | 150 |
| *Bradyrhizobium oligotrophicum* S58_gvpFL3 | MSSPRLIGLLAADDVPADLADQIMSCGPVAAAIRFAPAAASSSESL DHHAAVVAWCRRAAFLPSRAGIPISPELLQSIARSAWYHRSTIEHIE GRVEISVELERRDGVRDGGIDGGGRAYLRATAHDLRACEVGVAT | 151 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| | AANLLAMYSERADADLIARTAPLPAIRLRASVLVRRAVAPRLARQ FDSMLSAISDRLVCRVTGPWPPYSFSTIREPS* | |
| Burkholderia thailandensis sp. Bp5365 strain MSMB43_gvpFL | MVWLTYAVLTPKRSITLPPGVAGARLEIVDGAHLRTIVSEHPRAPS ATIPSALDFGQTVAALFRHGAIVPMRFPTCLDSKQAVRDWLDDES DMYRDLLQRIDGCVEMGLRFRLPEAPRAQPRPQAGGPGHAYLAA RGAPNSVARSHGERIAAVLRNLYRDWRFDGLVEGFVSLSFLVRQT TLDDFVDRCRQAARETAFPLYMSGPWPPYSFATDERSSAPEPHRA LRLMRRPSTAVSISANVAAPEKKDSAR* | 152 |
| Desulfobacterium vacuolatum-DSM 3385_gvpFL | MTLHLLYCVFSSGEMEKTRKLVPPGIDGEPVHEICSNKISGVVSTL GKPPDTHVKSLLAYHGVIDSYHQNRTVIPMRFAAVFRTYAHMITA LNNNEKSYLLQLKRLHDCTEMCVRFISNSPCCVKKKEPAISPKKIS GTTFLQQRKAMYEQQNRLPPEIHEKTRDILQHFRGLYMEFKQESQ PLEKDCPSLSLQGAEKTDGNALLISLFFLISKKNISLFRSRFQNICGS SSGRHMMNGPWPPFNFINTESNLTDPS* | 153 |
| Desulfomonile tiedjei DSM 6799_gvpFL | MLGSLAAIQFLSISSYGADEMKFLMYCIFTENSIEPPHSLVGVNRSP VRIISCDGLAAAVSVITQKEIPRDPATGLDYHKVIQWFHERIGVIPL RLGTCLGHESDVVQLLHSHGARYKSLLKELDGCVEMGIRVIHDRP GPQELASKSPFISRFNGTESGTDYLMRRKVLFDADEFAISRNREIVE RYHSPFTGLYVSFKAQTSKFSPLGTDRNSVLTSLYFLIPRQSADSFR AIYGDLRSGLHERIMLSGPWPPYNFVLPEDCL* | 154 |
| Enhydrobacter aerosaccus strain ATCC 27094_gvpFL | MEGHRIYIYGIVRDAADGGPAPVPPVAGLDGGALRAIAGYGLAAI ASAVDLSKAGIPFEEQLKDPDRATALVLEHHRVLQQAIDAQTVLP MRFGALFQDDRGVTDALEKNRCGLMDALGRIDGAREWGVKIFCD RAVAARQLSATSAVVQAAEKELSGLAEGRAFFLRRRLERLRTEET DRAVAHEVDVSRQALCELARASAPLKLQPAAVHGRGEDMVWNG AFLVPRSGEERFLSRLEVVVQSRSDLGLHYEVTGPWPPFSFVDGQL EGGGDACPDGA* | 155 |
| Octadecabacter antarcticus 307_gvpFL | MRSATSIVYAYGVLTNCSDIALDMPRSDLAGLVKNGPLRILPFGNI AAVVCDFVLPNGSDLETLLEDSRSAERLILNHHQVLSYIVSQHTILP LRFGAAFTEDAGVIAALGGRCSELQKALGRIDGALEWGVKTFCDR KLLKQRVRGTGSEISDLESEIAKQGEGKAFFLRRRKERLILEEVEEI LEQCVVGTQEQLEPSVIEEALVKLQPPTVHGHEHDMLSNISYLIAR GTEDAFMQSLEDLRLAHAPYGLEYQMNGPWPAYSFSDQQLEGGV NDQ* | 156 |
| Octadecabacter arcticus 238_gvpFL | MSSATSIVYVYGVLTNCSDLVLDFPPGDLAGIVESGPLRILPFGDIG ALVCDFILPDGSDLKTILEDSRSAERMILNHHLVLADMVSRYTILPL RFGAVFAEDAGVIAALGGRYSTLQKELDRIDGAIEWGVKSFCNRK MFSECVAETVSEISVLEKEIADQGEGKAFFLRRRIQRLILDEVEKTL EQCLVGAQDQLKSRAIEETLVKLQPPTVHGHKHEMVSNRSYLIAR GAEDAFMQSLDDLRVVYAPFGFDYQINGPWPAYSFSDQQLGGGV NDK* | 157 |
| Rhodobacter capsulatus SB 1003_gvpFL1 | MGHYLYGLLAPPARGTLAQMQAAAAGVTSLGGPVALSAVEGML LVHCPCDLAEISQTRRNMLAHTRMLEALMPLATCLPVRFGVIAQD LAEVARMIHERRAELVGHAQRLLDPVEIGLRVRFPRDRALAQLMA ETPDFVAERDRLMGQGAGAHFARADFGRRLAEALDARRTRDQKR LLAALRPHVRDHVLRAPEEDVEVLRAEFLIPAAGVDAFSRIAHDLA AALGFAGAAEPELQVIGPAPPYHFLSLSLAFDNTSEAA* | 158 |
| Rhodobacter capsulatus SB 1003_gvpFL2 | MAHEIIAILPCEAAQLPSGLTGVVGRGATAVLAPAPGWAERLTGG PKQTAVRHHSRLEALMAMGSVLPFAAGIACTPEEAALLLRLDAPLI ARLAAEIGPRRHFQLALDWDESRVLAAFRDSPELAPLFSGAAVTPE ALRQAITALADRLSATALRLLDPVAEDPVEQPRAPGCLLNLVFLLR PEDEPRLDAALQAIDALWSEGLRLRLIGPSAPISHALVDIDRADVA ALAAAADLLKVAPEAGPEAVTEAAKAALRSPDLAANAAEQIRAA ARLLLRAGDIAALGLSGAATLPHLVHLRPGGRKSGLTSSGEAA* | 159 |
| Rhodobacter capsulatus SB 1003_gvpFL3 | MTGLALHGFVSPDGWSAAAAPPARCAVVLGGVAALVSEAGDAL DTPETAQAAALAHHALISAWHRRGPVLPVRLGTVFSSQAALQTAL APKAAQLRAALDALADKEEMVLTIVPAARPPDLPPPAATGADWL RARKAVRDRGQARQTDQQTLAGLQDALRAQGVASLAAPAPRE GGSRWHLLIARDDGAGLDRWLAAQADRFDAAGLDLTLDGPWPP YRFAAEILEALDG* | 160 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| Rhodobacter capsulatus SB 1003_gvpFL4 | MSEPRISGLAPWRADLPDVIGCHGGWVLMGAAADETPEARLRRQ VGWCRAAVDVLPLSPRLAPTRAEAERLVATRGPDLERAHRHIRGR LQVIVQLEMCRTDLGLVRREISGGRSWLQDRAERATREARANADF EAQVRRVVRALFPREGQVVTLAPSGTAGQLRLRRAVLVPRAGLQ AFAAALSADLDRDGRGGLWDVIAPLPPLAFAALEAGPGGAVT* | 161 |
| Rhodobacter sphaeroides 2.4.1_gvpFL1 | MIYLYGLLEEPASGHEVLAGMAGVTGPIALARLPGGILIYSSATEA DILPRRRLLLAHTRVLEAAAWFGNLLPMRFGMMASTLAEVAAML ASRLTELCAAFDRVRGRVELGLRLSFPREPALAATLATAPDLAAER ARLLALRRPDPMAQAEFGRRLAERLDARRGETQRLLFQSLRPLWV DHRLRVPDSDVQVIAVDVLVEDGAQDRLAAALVKAAADCSFAPT AEPSVRVIGPVPLFNFVDLVLSPRREEVA* | 162 |
| Rhodobacter sphaeroides 2.4.1_gvpFL2 | MRLREVVAVLEGHPPSVLPEGTEAICEAGLTAILGMPPGLLSGRRA LLEHAACRQAVLERLMAFGTVLPVLTGNCLTPAEAAAALAANSP RLRQELRRLAGRVQFQVLVQWHAALVPKRTDPDETAEDLRLRFT HRIADALARVAERHVNLPLREDMLANQALLLLQTRTDDLDRSLEQ IDALWTEGLRIRRIGPSPPVSFASLNFRRVSSAAIRRARHRFDLEGP VDPIRLRALRRDLLLRASEAERAEILAAAAVLDLLTRCAASGGDLH LVRIWSEGQAVPSDLEDAA* | 163 |
| Rhodobacter sphaeroides 2.4.1_gvpFL3 | MSGLLLLGVVSGLGISPAITSPHLRLDGDGYAAILLSLDRLPPDPAS PDWAVQAALAQNAILSAYAATEDVLPVALGAAFTGIAAVKRHLD AERATLDAGMERLAGRAEYVAQLIAEQVADGAAPAPASGSAFLK ARSARHEQRRHLARERTGFARATAEELASLSCSASARPLKPDGPLL DLSLLVARDRVPGLLEAAEASSRAGSRLALSVRLIGPCAPFSFLPET RGHD* | 164 |
| Rhodobacter sphaeroides 2.4.1_gvpFL4 | MAGDARSRVRLHLAAMRDCETFLPFPPAATIAVDEAIAWCGRRTN ALAEEIDRFSRQRQLTVSARLIAPLLPDAAASGAGWLRARRDASA HQARLRTVLMQIMSLLGEVRCIPGRLQDEVQVNLLVPAAETHPVL HELRERLRVGDALWSACTVTGPWPPYAFISWETA* | 165 |
| Rhodococcus hoagii 103S_gvpFL1 | MSEQESAPDGGGPVVYVYGLVPADVEVKEDATGIGSPPRPLKIVH HEDVAALVSEIDPDTPLGSSDDLRAHAAVLDSTATVAPVLPLRFG AVLTDTDAVVAELLEPYRDEFHEALEQLEGKVEFVVKGKYVEDAI LREILADDPEAARLRDVVREQPEDTTRDERLALGERISQALTAKRE QDTGRIVEALQPAATAVAPREPTDDEEAGSVAVLISADGVDELDK AVARLIDDWQGRVEVTVTGPLAAYDFVKTRAPGT* | 166 |
| Rhodococcus hoagii 103S_gvpFL2 | MTPDDGVWVYAVTGDGSFPGGISGIRGVAGEELRTVTDSGFTAVV GTVRLDTFGEEALRRNLEDLDWLADTARRHDAVVAAICAGGATV PLRLATVYFDDDRVRTMLRDNAEQLGEALQQIADRSEWGVRAYL ERPRSEPRDAREKTGRPSGTAYLMQRRAQVAAREQAESAAGRRA DEIFAELARWAVAGVRQPPSPPDLAGRRSQEILNTSFLVDNGRHRE FVTAVEELDARLSDVDLVLTGPWPPYSFTSVEASAR* | 167 |
| Serratia sp. ATCC 39006_gvpFL | MSLLLYGIVAEDTQLALEPDGSPHAGEEPMQLVKAATLAALVKPC EADVSREPAAALAFGQQIMHVHQQTTIIPIRYGCVLADEDAVTQH LLNHEAHYQTQLVELENCDEMGIRLSLASAEDNAVTTPQASGLDY LRSRKLAYAVPEHAERQAALLNNAFTGLYRRHCAEISMENGQRTY LLSYLVPRTGLQAFRDQFNTLANNMTDIGVISGPWPPYNFAS* | 168 |
| Stella vacuolata- ATCC-43931_gvpFL1 | MSGLLVFAIVPADGIEPGILAPREELPANLRAVAADGFAAVGAAP EGGLKGRDRSVLLPRLLASQKVIERLMARGPVLPVTLGTVLEDEA RVRHMLAAGAPMLEAAFGTLGDCWQMDLSVRWDLNQVVARLM GEVPGDVRAAAGSGDEAARRALGEALAGLAAGERRRVQSRLAA ALRDVARDLIVSEPVEPESVVDIAILVERPALAEVEAALDRLDAEF EGRLKFRLVGPLAPHSFATVQVHLAPEAALAGACAELGVERGAGL QDVKVAYHRALVRFHPDLAPHGDDGGPEDEHDGGEGRASRLLTV TAAYRALQAEHAPISLRRQDGIAVNQEQDASAAMGQQRGIVPGRE LQALRM* | 169 |
| Stella vacuolata- ATCC-43931_gvpFL2 | MLYVYAIAADHPDPDNAMFGGEGIVPDAPVRLLQLGDLAVAASL VSAADFAADALRAHLEDARWTALRVLAHQRVVDSLLPHATVLP MKFCTLFSGEAALKQALAHNRAALQATVERLRGAREWGVKLYW EAPRNPAPPSAGQGEAGAGAAFFQRKRDQQRQRAEAEAAVARCV AASHRRLADAARAAVANPVQPPAVHRQPGEMALNGAYLVARAA EPAWREVLAELERTHADGGIRYELTGPWGPYNFTGSGLVGS* | 170 |
| Thiocapsa rosea strain DSM 235 Ga0242571- 11_gvpFL | MSDRPRPMLHCILRSPPGSIARAEAGLRWIERDGLAALVADREPSE IAGASSVGLQRYADIVAEIHACAAVIPVRFGCLLAGDEAVGKLLHR SRDRLHGLLDQVGDCLEFGIRLLLPADAPAATDDDAAPRLHANAP SDPRADPDMGPGLSHLLAIRHRLDVEASLAARAREAREVIKGRVA | 171 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| | GRFREVREELGQIDGRSLLSLYFLVPREQGEHFVECLRQDASSLRG TGLLTGPWPPYNFVGAIDDDIRSLD* | |
| gvpG | | |
| Anabaena-flos-aquae_gvpG | MLTKLLLLPIMGPLNGVVWIAEQIQERTNTEFDAQENLHKQLLSL QLSFDIGEIGEEEFEIQEEEILLKIQALEEEARLELEAEQEEARLELEA EQEDFEYPPQFTAEVNKDQHLVLLP* | 172 |
| Bacillus-megaterium_gvpG | VLHKLVTAPINLVVKIGEKVQEEADKQLYDLPTIQQKLIQLQMMF ELGEIPEEAFQEKEDELLMRYEIAKRREIEQWEELTQKRNEES* | 173 |
| Ancylobacter aquaticus strain UV5_gvpG | MGMLTDVVFAPAVGPLKGVLWLARIIAEQAERTLYDEGVIRAALL DLEQQLEAGEIDEDAYETQETVLLERLKIARERMRSGL* | 174 |
| Aphanizomenon flos-aquae NIES-81_gvpG | MLTKLLLLPIMGPLNGLVWIGEQIQERTNTEFDAQENLHKQLLNL QLSFDIGEISEEDFEIQEEELLLKIQALEEEARLELELAEEEARLELEL EQEEEEDFVVKPQLTTEIDRDKDLVLLP* | 175 |
| Aphanothece halophytica (strain PCC 7418)_gvpG | MVFKLLLLPITGPIEGVTWLGEQILERANQELDEKENLNKRLLSLQ LSLDLGEISEEEYDEQEEEILLAMQAMEDEENNQAEEETD* | 176 |
| Aquabacter spiritensis strain DSM 9035_gvpG | MSLVTDVLFAPAVGPLKGVLWLARLIAEQAERTLYDEDVLRAAL LDLEQRFEAGEISEADYETEEDILLARLKIARERMRSGL* | 177 |
| Bradyrhizobium oligotrophicum S58_gvpG | MLFQILTSPVSGPFRMVSWIGGAIRDAVDTKMNDPAEIKRALAAL EQQLEAGSLSEQDYERMEMELIERLQSSLRHGSGNGG* | 178 |
| Burkholderia thailandensis sp. Bp5365 strain MSMB43_gvpG | MFILDNLLAAPIKGMFWIFEEIAQAAEEETIADIEMIKAALVELYRE LESGQIDETEFETRERALLDRLDSLETS* | 179 |
| Chlorobium luteolum DSM 273_gvpG | MFILDDILLAPLSGMVFLGRKINEIVQNEMSDEGAVKEQLMKLQF RFEMDELSEEEYDRLEDELLSTLAEIRAQKENR* | 180 |
| Dactylococcopsis salina PCC 8305_gvpG | MVFKLLLLPITGPIEGITWLGEQILERADQELDSKENLNKRLLSLQL SLDLGEISEEEYDEQEEEILLAMQAMEDEENEEEES* | 181 |
| Desulfobacterium vacuolatum_DSM 3385_gvpG | MFLVDDILFFPAKSLVWVFRELHNAVQQEKTNESDALTTELSELY MMLETGKITEEEFDEREEQILDRLDEIQERDQ* | 182 |
| Desulfomonile tiedjei DSM 6799_gvpG | MERYTMFLLDDILFLPMNGVLWICNEIHDAAEQELHNESDAITAQ LQKLYTLLEAGDIGESEFDVLEAELLDRLDAIQERGALLEA* | 183 |
| Desulfotomaculum acetoxidans_DSM 771_gvpG | MLGKLLLSPILGPVMGVKFIAEKIKQQADQELYDKSIKQDLMEL QIKLELEEITEEYYLQREEELLVRLDELASMETEEEEV* | 184 |
| Dolichospermum circinale_gvpG | MLTQLLLLPIMGPLNGVVWIAEQIQERTNTEFDAQENLHKQLLSL QLSFDIGEISEEEFEIQEEEILLKIQALEEEARLELEAEQEEARLELEA EQEQARLELEAEQEELENQPQLTPKIDTYRHLVKL* | 185 |
| Enhydrobacter aerosaccus strain ATCC 27094_gvpG | MGMLARLLTLPVSAPVGGVLWIARKIEEEANAERWDRNKITGALS ELELELDLGAIDVEEYDAREAVLLQKLKELQEVEND* | 186 |
| Isosphaera pallida_ATCC-43644_gvpG | MFLVDDILLAPAHSLMFLLREIHQAALEELRRDAQKVREELAECY RALETGALTDEEFASLETDLLDRLDALEELARFNSDEDDDPEDED WDVEDDDPAEAVW* | 187 |
| Legionella drancourtii LLAP12_gvpG | MLLLGSILMAPVHGLMAIFEKIKEAVDEEKQHDIERIKSELMALYT KLESGELSEADFEKQEKILLDKLDSLEDEDD* | 188 |
| Microcystis aeruginosa NIES-843_gvpG | MFLDLLFLPVTGPIGGLIWIGEKIQERADIEYDEAENLHKLLLSLQL SYDMGNISEEEFEIQEEELLLKIQALEEEEAENESESSL* | 189 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| Nostoc punctiforme ATCC 29133_gvpG | MVLRFLLLPITGPLMGVTWLGEKILEQASTEIDDKENLSKQLLALQ LAFDMGEIPEEEFEIQEEALLLAILEAEQEERDQTQEY* | 190 |
| Nostoc sp. PCC 7120_gvpG | MLGKILLLPVMGPINGLMWIGEQIQERTNTEFDAQENLHKQLLSL QLKFDMGEISEEEFDIQEEEILLKIQALEAEERLNAESEEDDDLDVQ PIFILASEENPVYQDQSRFSEEYEDKEDLVLSP* | 191 |
| Octadecabacter antarcticus 307_gvpG | MGIILNTLMSPLIGPMKGVFWVAEQIKDQTDAEIYDDSKILVELSE LELLLDLEKIELKDFEAKEDVLLKRLQEIRKAKKNDSV* | 192 |
| Octadecabacter arcticus 238_gvpG | MSIILNTLMGPLIGPMKGLLWVAEQIKDQADAELYDDSKILVALSE LELSFDLEQIELKEFEAQEDVLLQRLQAIRKAKQNDTD* | 193 |
| Pelodictyon phaeoclathratiforme_ gvpG | MFILDDILFAPLNGLIFIAKKINDVVEKETSDEGVVKERLMALQLRF ELDEIDEVEYDREEDELLQKLERIRLNKQNQ* | 194 |
| Phormidium tenue NIES-30_gvpG | MLFKLLFAPVLGPIEGISWVANKLLEQADVPTNDLESLQKQLLAL QLAFDMGEVAEADFEIQEEEILLAIQAIEDEEDEDE* | 195 |
| Planktothrix agardhii str. 7805_gvpG | MILRLLLSPITAPFEGVIWIGEQLLERAEAELDDKENLGKRLLALQL AFDMGDIPEEDFEVQEEELLLQIQALEDEANQENDEID* | 196 |
| Psychromonas ingrahamii 37_gvpG | MFILDDILLAPYSGIKWLFKEIQRQAQEELDGEADRITTDLTNLYR QFESNEITEQEFEERETVLLDRLDELQEESNLLDEEYDEEYEDDDE EYEDDDEEYEDDDEEYEDDDEEYEDDDKNDKDKNDDHDNDDDD ENKDENDKYNDEER* | 197 |
| Rhodobacter capsulatus SB 1003_gvpG | MGLLRKLLLAPVELPITGALWIVEKIAETAESELTDPGTVRRLLRG LEQQLEAGEITEEEYEFAEEIILLDRLKRGQAAEARSGGP* | 198 |
| Rhodobacter sphaeroides 2.4.1_gvpG | MGLLTSLLTLPFRGPFDGTLWIAARIGEAAEQSWNDPAALRAALV EAERQLLAGELSEETYDAIELDLLERLKGTAR* | 199 |
| Rhodococcus hoagii 103S_gvpG | MGLFSAIFGLPLAPVRGVVWIGEVVRRQVEEETTSPAAMRRDLEAI EEGRRSGEISEDEAAQAEDEILHRVTRRRDAGASGEE* | 200 |
| Serratia sp. ATCC 39006_gvpG | MLLIDDILFSPVKGVMWIFRQIHELAEDELAGEADRIRESLTDLYM LLETGQITEDEFEQQEAVLLDRLDALDEEDDMLGDEPGDDEDDEY EEDDDEEDDDEEDDDDEDDDDEDDDDEEDDDDDEDDDDEDEPE GTTK* | 201 |
| Stella vacuolata_ATCC-43931_gvpG | MGLVTNVAFAPVVGPLKGVLWLARLIADQAERTLYDEDLVRAAL LDLEQRLDAGQISEADYDAEEEILLARLKIARERMRSGL* | 202 |
| Thiocapsa rosea strain DSM 235 Ga0242571_11_gvpG | MLIVDDLLAAPFKGIIWVFEEIHKSATAEQRARRDEIMAALSALYR ALEQGEITDDTFDTREQALLDELDALDAREDANELGSDEDEDDLD GAGEDAS* | 203 |
| Tolypothrix sp. PCC 7601_gvpG | MEVMIMLGKILLFPVMGPISGLMWIGEQIQERTDTEFDAQENLHK QLLSLQLSFDIGEISEEDFEEQEEELLLKIQALEEEKARLEAESIEDE EDEVEPTYFIAEVEEDKVLAEAFRGNKKYEDNENLVLSP* | 204 |
| Trichodesmit erythraeum IMS101_gvpG | MLLRLLTLPISGPLEGVTWLGKKLQEQVDTEIDETENLSKKLLTLQ LAFDMGEISEEDFEDQEEELLLAIQALEEQKLKEEEEDA* | 205 |
| gvpJ | | |
| Anabaena-flos-aquae_gvpJ | MLPTRPQTNSSRTINTSTQGSTLADILERVLDKGIVIAGDISISIASTE LVHIRIRLLISSVDKAKEMGINWWESDPYLSTKAQRLVEENQQLQ HRLESLEAKLNSLTSSSVKEEIPLAADVKDDLYQTSAKIPSPVDTPI EVLDFQAQSSGGTPPYVNTSMEILDFQAQTSAESSSPVGSTVEILDF QAQTSEESSSPVVSTVEILDFQAQTSEESSSPVGSTVEILDFQAQTSE EIPSSVDPAIDV* | 206 |
| Bacillus-megaterium_gvpJ | MAVEHNMQSSTIVDVLEKILDKGVVIAGDITVGIADVELLTIKIRLI VASVDKAKEIGMDWWENDPYLSSKGANNKALEEENKMLHERLK TLEEKIETKR* | 207 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| Ancylobacter aquaticus strain UV5_gvpJ1 | MNEQRMEHSLQAVGLADILERVLDKGIVIAGDITISLVEVELLNIRL RLVVASVDRAMSMGINWWQSDPHLNSHARELAEENKLLRERLDR LEAAVVPSALPADAALEPSLAGEDARHGG* | 208 |
| Ancylobacter aquaticus strain UV5_gvpJ2 | MPSRHSGEIAVADLLDRALHKGLVVWGEATISVAGVDLVYLGLK LLLTSTDTVNRMREAANAPPDERHLHAD* | 209 |
| Aphanizomenon flos-aquae NIES-81_gvpJ | VTSTPILPTRPQTNSSRAINTSTQGSTLADILERVLDKGIVIAGDISISI ASTELIHIRIRLLIASVDKAKEMGINWWETDPYLSTKAQRLVEENQ QLQNRLENLESQINLLTSAKVQEQISLVETTEDNTHQTTEDNTHQT HEESIPLPIDSQLDV* | 210 |
| Aphanothece halophytica (strain PCC 7418)_gvpJ | MVNPNTNKPKSYQSKGITNSTQSSSLADILERVLDKGIVIAGDITVS VGSTELLSIRIRLLVSSVDKARELGINWWEGDPYLSSQANLLKEEN QALQNRLENMEAELRRLKGETNPEPSFLSESEDNS* | 211 |
| Aquabacter spiritensis strain DSM 9035_gvpJ1 | MSEQRMEHSLQAVGLADILERVLDKGIVIAGDISISLVEVDLLNIRL RLVVASVDRAMSMGINWWQSDPHLNSHARQLEEENRLLRERLDR LEAALAPPEGGMLRAEVEVAHGG* | 212 |
| Aquabacter spiritensis strain DSM 9035_gvpJ2 | MPDPEPIIPRTSGDVALADLLDRALHKGLVLWGEATISVAGVDLV YLGLKVLLASTDTANRMRDAAAASAAGSHLPGG* | 213 |
| Arthrospira platensis NIES-39_gvpJ | MTLQSRSSSPQRGVPMSTSGSSLADILERVLDKGIVIAGDISVSVGS TELLSIRIRLLIASVDKAKEIGINWWESDPYLSSQAQQLSQSNQQLL EEVKRLQEEVRSLKALTSQSSQPVTPPNSENDD* | 214 |
| Bradyrhizobium oligotrophicum S58_gvpJ1 | MTFTVHQPTGGDRLADILERVLDKGIVVAGDVTISLVGIELLNIKIR LIVATVDRALELGINWWEADPRLTTRASELSVENEELKKRLALLE ADAGRNQRPRKRRVRSIAATSGASHER* | 215 |
| Bradyrhizobium oligotrophicum S58_gvpJ2 | MTYRADLDYLEPAASSEGSLLELLDHLLDRGVLLWGELRISVADV ELIEVGLKLMLASARTADRWRQTTTQRASIAPGDCP* | 216 |
| Burkholderia thailandensis sp. Bp5365 strain MSMB43_gvpJ1 | MRSADGEPVSAELAQRLSLCESLDRILNKGAVISAQVVVSVADVD LLYLHLRLLLTSVETALVGRAMPREEASR* | 217 |
| Burkholderia thailandensis sp. Bp5365 strain MSMB43_gvpJ2 | MADLLERVLDKGVVITGDIRINLVDVELLTIRIRLLVCSVDKAKEL GIDWWNADTFFLGPDRGQSALPGRASAVDVAAGSAVHADAAHR* | 218 |
| Chlorobium luteolum DSM 273_gvpJ1 | MPELKHAVNATGLADILERVLDKGIVIAGDIKIQIADIDLLTIKIRL MVASVDKAIEMGINWWQEDPYLSTGAKTSEQTRLLGEINQRIEKL ESINR* | 219 |
| Chlorobium luteolum DSM 273_gvpJ2 | MQEDLYTANRQVTLLDILDRVLNKGVVISGDIIISVAGIDLVYVGL RVLLSSVETMERLDAARAEGLQQ* | 220 |
| Chlorobium luteolum DSM 273_gvpJ3 | MAVEKTIGSSSLVEVIDRILDKGVVVDAWVRVSLVGIELLAIEARV VVASVETYLKYAEAIGLTAKAA* | 221 |
| Chlorobium luteolum DSM 273_gvpJ4 | MAVEKTIGSSSLVEVIDRILDKGVVVDAWVRVSLVGIELLAIEARV VVASVETYLKYAEAIGLTAKAA* | 222 |
| Dactylococcopsis salina PCC 8305_gvpJ | MVNSNTNQPKSYQSKGITNSTQSSSLADILERVLDKGIVIAGDISVS VGSTELLTIRIRLLISSVDRAREIGINWWESDPYLSSQAHLMKEENQ ALQSRLENMEAELRRLKGETNLDQSSLGESDQRSLQ* | 223 |
| Desulfobacterium vacuolatum_DSM 3385_gvpJ1 | MAYIDIDNDASKQISICEALDRVLNKGAVITGELTISVADIDLIYLSL QAVLTSVETARHMFDSQINDAVKEVK* | 224 |
| Desulfobacterium vacuolatum_DSM 3385_gvpJ2 | MPIQRTAQHSIESTNIADLLERVLDKGIVIAGDIKISLVDIELLSIQLR LVICSVDKAKEMGMDWWVNNPVFMPNKGTQNDEIADTLTKINSR LEHLEKATISGS* | 225 |
| Desulfomonile tiedjei DSM 6799_gvpJ1 | MMDEEEHVSLCEALDRVLNKGAVIAGEVTISVANVDLIYLGLQVV LASVDTIRGKRNELLRHDVGLHLTADNA* | 226 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| *Desulfomonile tiedjei* DSM 6799_gvpJ2 | MSIQASTRHSIQSTNLADLLERVLDKGVVIAGDIKIKLVDVELLTIQ IRLVVCSVDKAKEMGMDWWTNNPAFQPALAQISE* | 227 |
| *Desulfotomaculum acetoxidans*_DSM 771_gvpJ1 | MGPQMGPIKSTGNLSLLDVIDRILDKGLVINADISVSIVGVELLGIKI KAAVASFETAAKYGLQPPTGTEINEKVSEAAKQLKEICPECGKKSG RDELLHEGCPWCGWISARALRLETEHSQR* | 228 |
| *Desulfotomaculum acetoxidans*_DSM 771_gvpJ2 | MLPIREERATLTDLLDRVLDKGLLLNADILISVAGVPLIGITLKAAI AGMETMKKYGLLIDWDQESRLAERRLRSSRH* | 229 |
| *Enhydrobacter aerosaccus* strain ATCC 27094_gvpJ1 | MAVTNGRMEHSIQGSSLADILDRILDKGIVIAGDVTISLVGVELLNI RLRLLVASVDKAIEMGINWWEADPYLTSQTKASSEQTELLQQRLE RIEGLLAGQATKEQPL* | 230 |
| *Enhydrobacter aerosaccus* strain ATCC 27094_gvpJ2 | MPVQTAHDGELALADLLDRALNKGVVLWGDATISLAGVELVYV GLRVLVASCSTMEKYRSSPRKGSMPIARGES* | 231 |
| *Isosphaera pallida*_ATCC-43644_gvpJ1 | MIVCSSSTPERIGPPMNLPPPHHAPWCYDSPDLETLPLDPAERIALC EVLDRVLNKGVVIHGEITISVAGVDLVYLGLNLLLTSVETAQSWK FRGMIE* | 232 |
| *Isosphaera pallida*_ATCC-43644_gvpJ2 | MAITRSSRPDVTHSTSGATLADVLERVLDKGLVIAGDIKIKLVDVE LLTIQIRLVVASVDKAREMGLDWWTRSPELSSLAATTCPALTPPKQ EATPPATRIQAPTESAQTTPDQSHPSDPSASNIDEVAELRRHIELMQ LRDEARQRAHREELAALRAQLTRLTELLDSPR* | 233 |
| *Legionella drancourtii* LLAP12_gvpJ1 | MIIEDKPVSLCETLDRVLNKGVVVAGTVTISVADVDLLYLDLHCL LSSMKGMNLIGSERER* | 234 |
| *Legionella drancourtii* LLAP12_gvpJ2 | MELQKSPTHSIGSTTIADLLERILDKGIVIAGDIKVNLVQVELLTIQI RLLICSVDKAKEIGMDWWTHQNDVQSKNGSMPIQEYVTQMEERL KNLENTLASSKNAI* | 235 |
| *Lyngbya confervoides* BDU141951_gvpJ | MTGQSLSRSSSANRQMATATQGSTLVDVLERVLDKGIVIAGDISVS VGSTELLTIRIRLLVASVDKAREMGINWWENDPYLSARSQELLTA NEQLQSRIESLEQELKSLRSQED* | 236 |
| *Microcystis aeruginosa* NIES-843_gvpJ | MTSSTFAGSLRNQSNNSLKTATQGSSLADILERVLDKGIVIAGDISV SIASTELINIRIRLLIASVDKAREMGINWWEGDPYLHSQSQALLAEN RELSLRLQTLETELETLKSLTQLSAMESHDTSPNDEAHSSDA* | 237 |
| *Nostoc punctiforme* ATCC 29133_gvpJ | MSTNTNRGAITTSTQGSTLADILERVLDKGIVIAGDISISVGSTELLN IRIRLLISSVDKAKEIGINWWESDPYLNSQTRTLLATNQQLQERLAS LETELQSLKALNPINHQNAGD* | 238 |
| *Nostoc* sp. PCC 7120_gvpJ | MTTTPIHPTRPQTNSNRVIPTSTQGSTLADILERVLDKGIVIAGDISIS IASTELIHIRIRLLISSVDKAREMGINWWENDPYLSSKSQRLVEENQ QLQQRLESLETQLRLLTSAAKEETTLANNPEDLQPMYEVNSQEG DNSQLEA* | 239 |
| *Octadecabacter antarcticus* 307_gvpJ1 | MNDGKMEHSLNATNLADILERVLDKGIVIAGDVTISLVGVELLNIK LRLLIASVDKAMEMGINWWAHDPFLTAGAQAPAVADPAMLERM DRLEAALATALASNQTTPMKGHK* | 240 |
| *Octadecabacter antarcticus* 307_gvpJ2 | MTNKAQGGQDLALADLLDRALSTGVVIWGEATISLAGVDLVYVG LKVLVASVDAAERMKAASLVDRPTDRGQQI* | 241 |
| *Octadecabacter arcticus* 238_gvpJ1 | MNNGKMEHSLDATNLADILERVLDKGIVIAGDVTISLVGVELLNIK LRLLIASVDKAMEMGINWWAHDPYLTAGAQAPVGVDPAMLERM DRLEAALAKALASNQTTPAEGqSS* | 242 |
| *Octadecabacter arcticus* 238_gvpJ2 | MTNETQGGQDLALADLLDRALSTGVVIWGEATISLAGVDLVYVG LKVLVASVDAAQRMKDASLVDRPTDGGQ* | 243 |
| *Pelodictyon phaeoclathratiforme*_gvpJ1 | MPELKHAVNATGLADILERVLDKGIVIAGDIKIQIADIDLLTIKIRLL IASVDKAMEMGINWQEDTYLSTKAKDKEQQLLRDDLQQRIEKL EALTKIT* | 244 |
| *Pelodictyon phaeoclathratiforme*_gvpJ2 | MQDEFYSKNKEITILDVLDRVLTKGVVITGDIVISVADIDLVYVGL RLLLSSVETMEKNKQNSIKM* | 245 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| Phormidium tenue NIES-30_gvpJ | MATATQGSSLVDVIERVLDKGIVIAGDISVSVGSTELLSIRIRLIISSV DKAREIGINWWESDPYLSSRTNELLEANQQLQSRLETLEAELKALR SAEPVS* | 246 |
| Planktothrix agardhii str. 7805_gvpJ | MNSQQLPSNIQRGVPTSTQGSSLADILERVLDKGIVIAGDISVSVGS TELLNIRIRLLIASVDKAREIGINWWESDPYLSSQTKVLTESNQQLL EQVKFLQEEVKALKALLPQENQPNPISDPHK* | 247 |
| Planktothrix rubescens_gvpJ | MNSQQRPSNIQRGVPTSTQGSSLADILERVLDKGIVIAGDISVSVGS TELLNIRIRLLIASVDKAREIGINWWESDPYLSSQTKVLTESNQELL EQVKLLQEEVKALKALLPQENQPKEME* | 248 |
| Psychromonas ingrahamii 37_gvpJ1 | MANVQKSTDSSGLAEVVDRILEKGIVIDAFVKVSLVGIELLSIEARV VIASVETYLKYAEAIGLTASAATPA* | 249 |
| Psychromonas ingrahamii 37_gvpJ2 | MPMANVSINPELTAQECEKISLCDALDRIINKGVVIHGEITISVANV DLISLGVRLILSNVETREQSNTPKEEV* | 250 |
| Psychromonas ingrahamii 37_gvpJ3 | MATGKPQSMTHSVKSTTVADLLERILDKGIVVTGDIKIKLVDVELL TVELRLVICSVDKAVEMGMDWWNNNPAFAPQAPAQEGELSSIEK RLEKIEKALVK* | 251 |
| Rhodobacter capsulatus SB 1003_gvpJ1 | MGYRSASQPEGLADVLERILDKGIVIAGDVSVSLVGIELLTIRLRLL IATVDKAREMGIDWWSHDPYLNGRLRPGEPAPETETETAALRDRL AQLEAQLSALGAQVGAAPALAEPALRGLAAAGSSALCAAPEASSA DVVQPVFRRYKEAP* | 252 |
| Rhodobacter capsulatus SB 1003_gvpJ2 | MDDRFSLRLFGPEEVFDAPSGGLADLLDGLLGHGIVLHGDLWLTV ADVELVYVGLSAVLASPEALRSHE* | 253 |
| Rhodobacter sphaeroides 2.4.1_gvpJ1 | MSFQMQSPLQQDSLADVLERILDKGIVIAGDISISLVGIELLTIRLRL LVATVDKAREMGINWWESDPRLCITQAPASDGSAALLDRLERIET QIGQLAAAREG* | 254 |
| Rhodobacter sphaeroides 2.4.1_gvpJ2 | MTDSAPTLQFATAEEALQSSETRLVDVVDALLSQGIAIRGELWLTI ADVDLVFLGLDLLLANPDRLQCRVPDAA* | 255 |
| Rhodococcus hoagii 103S_gvpJ | MTRSGSGANYPQQYSQGLGGAGHEPANLGDILERVLDKGIVIAGD IRVNLLDIELLTIKLRLVIASLETAREVGIDWWEHDPWLSGNNRDL ELENERLRARIEALESGERRVADVTDPHRAVQPAESPAAEVRDDD A* | 256 |
| Serratia sp. ATCC 39006_gvpJ1 | MPVNKQYQDEQQQVSLCEALDRVLNKGVVIVADITISVANIDLIYL SLQALVSSVEAKNRLPGRE* | 257 |
| Serratia sp. ATCC 39006_gvpJ2 | MSGNKKLTHSTDSTTVADLLERLLDKGVVISGDIRIRLVEVELLTL EIRLLICSVDKAVEMGLDWWSGNPAFDSRARVSSSAPAPELEERL QRLEARLEAAPSVIEETHL | 258 |
| Stella vacuolata_ATCC-43931_gvpJ1 | MSGQRMEHSVQAVGLADILERVLDKGIVIAGDISISLVEVELLTIRL RLVVASVDRAMSMGINWWQSDPNLNSHARQLEEDNRLLRERLDR LEAALALPEMAGERLADAGQGGGAEQGVTHGR* | 259 |
| Stella vacuolata ATCC-43931_gvpJ2 | MSDPEPIIPRTSGDIALADLLDRALHKGLVLWGEATISVAGVDLVY LGLKVLVASTETADRMRAAAASQSADPKVRAG* | 260 |
| Thiocapsa rosea strain DSM 235 Ga0242571_11_gvpJ1 | MMLAIGEHPDCPEEIQRVSLCEALDRILNKGAVVSGELTIAVANVD LLYLSLQLVITSVETAKREMLYVRH* | 261 |
| Thiocapsa rosea strain DSM 235 Ga0242571_11_gvpJ2 | MSVQRSTLTHSTNSTSVADLLERVLDKGIVIAGDIRIKLVDIELLTIQ LRLVICSVDKAREMGIDWWSDNAMFKGLSSQASAASLPGTAAAS GIEDRLARLESLLVKQSAAAETVL* | 262 |
| Tolypothrix sp. PCC 7601_gvpJ | MADILERVLDKGIVIAGDISVSIASTELLHIRIRLLISSVDKAKELGIN WWENDPYLSSKSQRLVEENQQLQQRLESLEAQLRSLTAAKINNPE LFPVNAEDNGQSDEENVPLPMNYQPND* | 263 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| Trichodesmium erythraeum IMS101_gvpJ1 | MFIRVDFLLDKGVIVDAWVRLSLVVIELLTIEAKIVIASVEAYLKYS EAFCFNY* | 264 |
| Trichodesmium erythraeum IMS101_gvpJ2 | MAVEKVNSSSSLAEVIDRILDKGVVVDAWIRLSLVGIELLTIEARIV VASVETYLKYAEAVGLTTLAAAPGEAAA* | 265 |
| Trichodesmium erythraeum IMS101_gvpJ3 | MAVEKVNSSSSLAEVIDRILDKGVVVDAWVRLSLVGIELLTIEARI VIASVETYLKYAEAVGLTTLAAEPAA* | 266 |
| Trichodesmium erythraeum IMS101_gvpJ4 | MKTSANIATSASGNGLADVLERVLDKGVVIAGDISVSIASTELLNI KIRLLISSVERAKEIGINWWESDPYFSSQNNSLVQANEKLLERVASL ESEIKALRSN* | 267 |
| Trichodesmium erythraeum IMS101_gvpJ5 gvpK | MKTSANIAKSAGGDSLADVLERVLDKGIVIAGDISVSIASTELLNIK IRLLISSVERAKEIGINWWESDPSLSSQNNSLVQVNQKLLERVASLE SEIEALKYSQ* | 268 |
| Anabaena-flos-aquae_gvpK | MVCTPAENFNNSLTIASKPKNEAGLAPLLLTVLELVRQLMEAQVIR RMEEDLLSEPDLERAADSLQKLEEQILHLCEMFEVDPADLNINLGE IGTLLPSSGSYYPGQPSSRPSVLELLDRLLNTGIVVDGEIDLGIAQID LIHAKLRLVLTSKPI* | 269 |
| Bacillus-megaterium_gvpK | MQPVSQANGRIHLDPDQAEQGLAQLVMTVIELLRQIVERHAMRR VEGGTLTDEQIENLGIALMNLEEKMDELKEVFGLDAEDLNIDLGPL GSLL* | 270 |
| Ancylobacter aquaticus strain UV5_gvpK | MTAPCTAETLENALRGRIDIDPEKVEQGLVKLVLMLVETVRQVVE RQAIRRVEGGTLTEEETERLGLALMRLEEKMAELRLHFGLEDGDL DLKLQLPLGEL* | 271 |
| Aphanizomenon flos-aquae NIES-81_gvpK | MVYSPVENSNDFLNVIPVENSNEFLNTSPKKKSNSETGLAPLLLTV LELIRQLMEAQIIRRMEEDLLSESDLERTAESLQKLEEQILNLCQIFD IDPADLNINLGDFGSLLPASGSYYPGETGNRPSILELLDRLLNTGIV VDGEIDIGVAQLDLIHAKLRLVLTSKPI* | 272 |
| Aphanothece halophytica (strain PCC 7418)_gvpK | MSADESNLSQVNLNPATSNSDAGLAPLLLTVTELIRQLMEAQVIRR MDGGLLNEEEELDRAGDSLQRLEAEIIRLCEIFEIDPKDLNVDLGELG TLMPKNGGYYPGESSDDPSILELLDRILHKGVVIDGNLDLGIAQLS LIQARLHLVLTSQPINGK* | 273 |
| Aquabacter spiritensis strain DSM 9035_gvpK | MTGFAGGPAVTETLESVLQGRVDIDPERVEQGLVKLVLMVVETLR QVIERQAIRRVEAGALTDEEIERLGLTLLRLEEKMAELRVQFNLSE ADLSLKLRLPLGEL* | 274 |
| Bradyrhizobium oligotrophicum S58_gvpK | MSASSHSEAPGLRLQLGDLDTALAAVFTDAAPNGSINLDPDKIEHD LARLVLTLIEFLRRLLELQAIRRMEANELSEDEEERVGLALMRAAA QVSRLARELGVDPRELNLQLGPLGRLL* | 275 |
| Burkholderia thailandensis sp. Bp5365 strain MSMB43_gvpK | MNAPHAAAVSDAAALAAALEQALAQQQAPPPRATQRFDVATAS AGNGLAKLVLALMKLLHELLERQALRRIEAGSLNDDEIERLGLAL MRQAEEIERLAAQFGFTDADLNLDLGPLGRLF* | 276 |
| Chlorobium luteolum DSM 273_gvpK | MHEDKVQFQASSVEEALRQLEGMKQGKESRIEANPDNVESGLAR LVLTLIELLRKLMEKQAMRRIDGGSLDEAQIDELGETLMKLEMKM DELKKTFNLTDSDLNLNLGPLGDLM* | 277 |
| Dactylococcopsis salina PCC 8305_gvpK | MSEEESNLSRVDLNPASSNSDAGLAPLLLTVTELIRQLMEAQVIRR MDAELLTEAELDRAGESLQRLEEEIIRLCEIFDVDPADLNVHLGEL GTLLPKEGGYYPGETSDQPSILELLDRVLHTGVVIDGNLDLGIAQL NLIQAKLHLVLTSQPINN* | 278 |
| Desulfobacterium vacuolatum_DSM 3385_gvpK | MIKDPEAKDFKIESDSIDAFARVMHADTSSCSSSSVTAGQRQQRLK IDEENIKNGLAQLVMTLIKLLHELLERQAIRRIESGSLDDDQIERLG LTLMQQCEEIDRLRKLFDLEEEDLNLDLGPLGKLL* | 279 |
| Desulfomonile tiedjei DSM 6799_gvpK | MNPMNIAKVESDSLGDFAEIMQTDWISSLHSDKEEKRLNLNQDSV KNGLGQLVLTLVKLLHDLLERQAIRRMEAGTLTDTEIDRLGTTLM MQAQEIERLRSEFGLEEEDLNLDLGPLGKLL* | 280 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| *Desulfotomaculum acetoxidans* DSM 771_gvpK | MYIDISEGSLKQGVLGLLLALVEIIKDALKIQALKRIEGDSLTEDEIE RLGNALHELEEALVEIEMEHNLQNVVQNIREGLDNVVNEVVDTFN PERWIAENEFN* | 281 |
| *Dolichospermum circinale*_gvpK | MLSTPADNFDESLTTVSKSKNEAGLAPLLLTVLELLRQLMEAQVIR RMEDNLLSESELERAADSIQKLEEQILHLCETFEVDPAELNINLGDF GTLLPQSGSYYPGETGSRPSVLELLDRLLNTGVVLDGEIDLGLAQL DLIHAKLRLVLTSKPI* | 282 |
| *Enhydrobacter aerosaccus* strain ATCC 27094_gvpK | MTKLLEAKTVDPDKAGDDLVKLVLALVETLRQLVERQAIRRVDS GVLNDDEVERLGLALLRLEEKMSELKAHFGFGDEELTLKLGSLGE LARDV* | 283 |
| *Isosphaera pallida*_ATCC-43644_gvpK | MSDSLFEVRSPSAAPPSPVNPGVADEWTAVLKDWDTLTAQLRQA TAPPNAENSARSHATTGRIDLDPEQVGDGLAKLVLTLLELIRQLLE RQAIRRLDAGSLDHEQTERLGLTLMRLAQRMEELKTHFGLQGEDL NLDLGPLGKLL* | 284 |
| *Legionella drancourtii* LLAP12_gvpK | MNDKREEDNALPQRINLQPDDVKNGLGKLVLILIQLIHELLERQAI GRIEAGDLSDEQIDRLGITLMKQAEEIDKLREVFGLTQEDLNLDLG PLGKLL* | 285 |
| *Microcystis aeruginosa* NIES-843_gvpK | MTLACTPYDSDNQALLTRPESNSQAGLAPLLLTVVELVRQLLEAQI IRRMEKGVLSESDLDRAAESIQKLQEQILYLCEIFEVEPEELNVHLG EFGTLLPEAGSYYPGEEGIKPSVLELVDRLLNTGVVVEGNVDLGL AQLDLIHLKLRLVLTSQPV* | 286 |
| *Nostoc punctiforme* ATCC 29133_gvpK | MQAISKSKGSDSGLAPLLLTVVELIRQLMEAQVIRRMDAGTLNDS ELDRAAESLQKLEQQVVQLCEIFDIDPADLNINLGEMGNLLPQSGG YYPGETSSQPSILELLDRLLNTGVVVEGDLDLGLAQLSLVHAKLRL VLTSKPL* | 287 |
| *Nostoc* sp. PCC 7120_gvpK | MVCTPVEKSPNLLPTTSKANSKAGLAPLLLTVVELIRQLMEAQVIR RMEQDCLSESELEQASESLQKLEEQVLNLCHIFEIEPADLNINLGDV GTLLPSPGSYYPGEIGNKPSVLELLDRLLNTGIVVDGEIDLGLAQLN LIHAKLRLVLTSRPL* | 288 |
| *Octadecabacter antarcticus* 307_gvpK | MKTTSDSQFDSMKKILTDSSKEDSASCDPTDLLPNKSLPPSLSTSPE TAADDLVKLVLAVIDTVRQVMEKQAIRRVESGALAEAEIERLGLT LMRLEARMVELKSHFGLSNEDLNLHFGTVQDLKDILNDEE* | 289 |
| *Octadecabacter arcticus* 238_gvpK | MKTQNDTQFDSMKKILTDSGGGDPNPNGSPDQTQHASLPSNLSTD PETAADDLVKLVLAVIDTVRQVMERQAIRRVDSGALADEEIERLG LTLMRLEERMADLKSHFGLSNEDLNLNFGTVQDLKDILNDEE* | 290 |
| *Pelodictyon phaeoclathratiforme*_gvpK | MDSDKILYYAGSADEIIEELEKLKPGIQGRINATPDNVESGLAKLVL TLIELIRKLIEKQAMRRIDGNSLSESQIEELGETLMKLEKKMEELKG IFNLTDKDLNLNLGPLGDLM* | 291 |
| *Phormidium tenue* NIES-30_gvpK | MTSENAEPDLSTTLALQPPAKTDAGLAPLLLTVIELVRQLMEAQVI RRMESGDLDDNDLERAADSLRKLEEQVVSMCEIFDVDPADLNIDL GEIGTLLPKEGNYYPGQKNQNPTILELLDRLLDTGVVVEGDVDLG MAQLNLIHAKLRLVLTSKPI* | 292 |
| *Planktothrix agardhii* str. 7805_gvpK | MSSSEPSIETIITPKSSRKDAGLAPLVLTLVELIRQLMEAQVIRRMEG NTLSEEELDRAAQSLQQLEIQVLKLCEIFEIDPTDLNIELSEFGTLLP KSGSYYPGENTQNPSILELLDRLMNTGIVVEGSVDLGLAQLNLIHA KLRLVLTSKPL* | 293 |
| *Psychromonas ingrahamii* 37_gvpK | MPFEHFKSNNQADVNSDTKPAASVGGLNLESDDLKNGLGRLVLT LVKLLHELLERQALRRMDAGSLQDDEIERLGLAFMKQAEEIDRLR KEFGLEVEDLNLDLGPLGRLL* | 294 |
| *Rhodobacter capsulatus* SB 1003_gvpK | MSAAMHLELGDVDAVLSQAARSLAAGGRLTLDPERVEQDLARLV LGIVELLRKLMELQAIRRMEAGSLTPEQEETLGLTLMRAEAALHE VAAKFGLQPADLILDLGPLGRSV* | 295 |
| *Rhodobacter sphaeroides* 2.4.1_gvpK | MTYPFPPLLLRDDRLPPTEAPVTAPRIALDPDRLEHDLARILLGLME MLRQIMELQAIRRMEAGSLSESQQEQLGTTLMRAEAAIHEMAARF GLTPADLSLDLGPLGRTI* | 296 |
| *Rhodococcus hoagii* 103S_gvpK | MRRRIDSDPESVERGLVALVLTLVELLRQLMERQALRRVDAGDLS DDQIERIGTTLMLLEEKMEELREHFGLEPEDLNIDLGPLGPLLAED* | 297 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| Serratia sp. ATCC 39006_gvpK | MTTNQLSHHSPVFGPTSPAIQRPITEANRHKIDIDGERVRDGLAQL VLTLVKLLHELLERQAIRRMDSGSLSDEEVERLGLALMRQAEELT HLCDVFGFKDDDLNLDLGPLGRLL* | 298 |
| Stella vacuolata_ATCC-43931_gvpK | MTGFLNGPADVETLETALRGRVDIDPERVEQGLVKLVLMVVETLR QVIERQAIRRVESGSLTDDEVERLGLTLMRLEEKMDQLRRQFDLG EEDLSMRLRLPLQEL* | 299 |
| Thiocapsa rosea strain DSM 235 Ga0242571_11_gvpK | MSDTRTGTAPSSAASAAPDTSTLQRANLLADLLETKVAAAGRRIDI DPERVQRGLGQLVLTVVKLLHVLLERQAIRRVDGGDLDEDEIEQL GLALMRQSEEIERLRRLLGLEEQDLNLDLGPLGKLF* | 300 |
| Tolypothrix sp. PCC 7601_gvpK | MAMVCTPSENSNDLLATNSKANNQAGLVPLLLTVVELIRQLMEA QVIRRMEEECLSESDLERAAESLQKLEEQVLNLCQIFEIDPADLNIH LGELGSLLPAAGSYYPGETGNTPSVLELLDRLLNTGVVVDGELDL GVAQLNLIHAKLRLVLTSKPLNTK* | 301 |
| Trichodesmium erythraeum IMS101_gvpK | MSLENSPEESLIVPIDKSKSNPEAGLAPLLLTVIELLRELMQAQVIR RMDAGILSDEQLERAAEGLRQLEEQVIKLCKVFDIPTEDLNLDLGE IGTLLLPKSGEYYPGEKSENPSVLELLDRILNTGVVLDGTVDLGLAE LDLIHARLRLVLTA* | 302 | gvpL

| Ancylobacter aquaticus strain UV5_gvpL | MLYLYAILESPPPQKPLPPGIGGAAPLFVESHALVCAASEAADAAI AREPSQIWRHQEVVAALMEGRPVLPLRFGTVVEDSAACLRLLARH HAELSAQLDRVRHCVEFALRVAGLSELADPGLDPNATPAGLGPGA SHLRTLVRRERGWPVSSAAFPHDTLTAHAASRLLWARSPSQPDLR ASFLVQRRSASAFLDDVNALQRLRPDLGITVTGPWPPYSFSDPDLS GGRE* | 303 |
| Aphanothece halophytica (strain PCC 7418)_gvpL | MLYTYCFLFSPEKTLSLPQGFKGDLQMIEKGAIAAVVEPNLPKAEL EEDDQKLVQAVVHHDWVICELFRGLTVLPLRFGTYFRGEADLRSH LAAYEESYQQKLTALTGKVEVTLKLTPIPFSEEGSSSTAKGKAYLQ AKKQRYQQQSNYQTQQQEALEKLQEEIKKTYPQLIHDEPKENTER FYLLIDSHSFSVFGEKMEQWKQFLSSWSIEISDPLPPYHFL* | 304 |
| Aquabacter spiritensis strain DSM 9035_gvpL | MLYLYAVLEAPPPARSLPPGIGGGAPHFIEAFELVCAASETPNRSV APEPAEVWRHQQVVEALIDRAPALPLRFGTLVEDASACRRLLTRH RDALGAQLGRVRHCVEFALRVSGLPEEVAPDPGIGGGPGTSLRT LARREAGWPPSTAVFPHDGLAAHAAERLLWARSTSQPDLRASFLV RKPNVAAFLADVSALQRVRPDLGITCTGPWPPYSFSDPDLSGVSP* | 305 |
| Bacillus-megaterium_gvpL | MGELLYLYGLIPTKEAAAIEPFPSYKGFDGEHSLYPIAFDQVTAVV SKLDADTYSEKVIQEKMEQDMSWLQEKAFHHHETVAALYEEFTII PLKFCTIYKGEESLQAAIEINKEKIENSLTLLQGNEEWNVKIYCDDT ELKKGISETNESVKAKKQEISHLSPGRQFFEKKKIDQLIEKELELHK NKVCEEIHDKLKELSLYDSVKKNWSKDVTGAAEQMAWNSVFLLP SLQITKFVNEIEELQQRLENKGWKFEVTGPWPPYHFSSFA* | 306 |
| Burkholderia thailandensis sp. Bp5365 strain MSMB43_gvpL | MNDALYLFCFARAEPLAPAWAKRAPGEPRLQLLHEGNLAAVLCD VSRSEFAGADAERRLADPAWIAGRVAVHAAAIEWTMRYSPVIPAQ FGTLFSGAGRVIALMESCHAHIGRVLDHVEGKTEWAVKGWLDRQ AAADSQAALLRADEPESAARTAGARYLREROLQARAGQNLRDW LEQSVPPISARLQRHAVEMCSRPCRASDSEHEIVANWAFLVRNRD VPAFRRQAEAIDAEFATWGLHFDFSGPWPPYSFCAPLTEETTWSG* | 307 |
| Chlorobium luteolum DSM 273_gvpL | MPCRLTVTWKSLRTAGLLPTAKGIQGRTERMAQNILYVYCIVRQL PGADIVARYPDLVFIEAGSAYVAAKYVSPLEYSDASMKLKLADEE WLDRNAREHLSVNVMIMAQQTIIPFNFGTIFKSRESLSGFLGDYGR KLDESFDALEGREEWAVKAYCNESFLLKNLHLESPAIAAIEQEIQA ASPGKAYLLKKKEAMSASALEGVHQGHAKAVWGELAALSKEH VLNRLIPEDVSGVDGRMIVNGVFLIANTDVGAFIRTTEDLGERYRD AGVFLDVTGPWPPYDFVDIPY* | 308 |
| Dactylococcopsis salina PCC 8305_gvpL | MLYTYCLIASSPSALSLPSGFRGELQLIKQGAIAAIVEAELPLEELEE NDQKLIQAVIHHDAVICEIFQQIPLLPLRFGTYFPTEKDLLEHLDFK AEKYQKKLQEIQDKVELTLKLTPLPFSTENASPMEKQGKNYLKAK KQRYQEQTNYQSQQQAELNQLQTQINQDYPQFIHGEPKENIERFY LLIKERDRSVFSEQLEQWKKDFPTWTIEVSDPLPPYHFIE* | 309 |
| Desulfobacterium vacuolatum-DSM 3385_gvpL | MEKKKAVYLYCVTRANKFNAPGITGIDANTPVCFEHLENFVAVY NIIPLNTFVGTSAEENMKNIDWIGPRAMRHENVIERMMQESSVYPA RFATLFSSMENLRETLHLKSGILISRFLNQTQHKCEYSLKGFINRKQ | 310 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| | LLEFLIKTKFKQEKKQLDGLSPGKKYFAQHQFNKKVETGINQWIK RRCGIFLDHLTKRNPEVSPRELFTEKTEKNNLEMMFNLAFLIHNDS KSAFLQEISQAEKEFSQTGISLVVSGPWAPYSFCKTTRGEGL* | |
| Desulfomonile tiedjei DSM 6799_gvpL | MSNVLYLFCLARTGLVDHIEGTGITGTEDLILKNFSGVTAVTCEVP EDDFSGESAEIKLQDLAWVGPRAVRHDRIIEEIMQYSPVFPAPFGSL FSSEKRLGTLIESNIDAIREFLDHTADKQEWSVKGLVCKSKAVDEIF TGKLKILSETLSSSPAGMRYFKERQMRSEAEKELSGKVKAACTVV GEKLLACSNNFRQRKNISFGKAEGDKQLVVNWAFLVDHSRISYFL DQVEHANSNYQAGGLAFECSGPWPPYSFCPSLHMEPTR* | 311 |
| Desulfotomaculum acetoxidans-DSM 771_gvpL | MNLIDDCKAKYIYCIGENPGNWPSEVMGVEGSLVYHVVYRDIAA VVHDCAEQPYNSDDNNKVIDWVLGHQLVVDKACSCYSSVLPFTF NSIVKGKEDLSSHEILVNWLEDNYDNFKLKLGKIKGKKEYSVQLF LDKQVSLSLLQSESDILELQVELLGSAKGKAYFVQEKINKKIGELM ANRADSYCRQFYHEISSVVSECKLCKLKQAGRNEIMIINLVCLAGD NEVEVLGDVLEKIKSNDIAIKIKFSGPWPAYSFV* | 312 |
| Enhydrobacter aerosaccus strain ATCC 27094_gvpL | MLYVYGIADNAFEVLRGAGLLNSDVFAVPAGCLAAAASKLAQGG IETTPQGVWRHEQVLRQLMQDHAVLPLRFGTICRDRETLTDRLME ASDDLVRGLGRVRGKVEIALRIVDEREHEAHPVPSETPTVDAIGGG RGTAYLRARRRHHAAEMGREARAERVGKMLSAYIDVGAEDLVC SVAPEGDHAVSVSCLLGRDQLATLQAALERFQSDHPAIGLSWTGP WTPYSFVAPSLFGVGLP* | 313 |
| Legionella drancourtii LLAP12_gvpL | MNKALYLFCLTPASDLPMMEGELLPNFSPLFIHPFQTFNAILSWVP AKEYQEQSTDSNLINTEEFMQRVFFHELVVEKIMRDEAVFPIGFGT LFSSIASLEEQILTHQTLISSCLANLNQKDEYAVRVYLNQDKALESL LSVMLQERESSWASSSPGVQYLKKQQLHNEIQRNLNQHLGGMLD EVLSMFQRHATDFKSRENTAQSSDIHGTSILHWAFLIPRVVSSIFKE QVDLMNAKYNPFGLHFVLTGPWPAYSFCTLQSVEAP* | 314 |
| Lyngbya confervoides BDU141951_gvpL | MRWHRSEAVISYCDLSMIYLYALCPNSTETNNLPEGIGTAQVEVLT VGTLGAVIERDVDIAQIQKDDAQLMAAVLAHDRILSHLFTYSPLLP LRFGTQFSNSEAVTTFLKTQGETYRQKLSHLQDRAEYLVKLIPQPL DLPAIASDLKGREYFLAKKQRLQDHTAALNQQADELQTFLTDLAT QDIPLVRSAPQDHEERLHVLLSRDTDTTEQVIMTWQEQLPNWQVV CSEPLPPYHFAA* | 315 |
| Octadecabacter antarcticus 307_gvpL | MKRLYVYGIVGATSFDDPLPNGHDEASVFALVSGDIAVAVSFVER SAVEASAANVWLHDNVLSALMTRYAVLPMRFGTIAVGATQLLEG IVKRQKQLMKDLMRLNENVEIALHISGKNWEKVNQKVTKKNTDQ AITQGTAYLLGRQQSLYGSDKTQLLVQNVRRAIRSGLDPLMKDVI WPIDKPQALPFKASCLINRNDVASFVQIVNDIAAQNLDARVTCTGP WAPYSFVGKSGVEGET* | 316 |
| Octadecabacter arcticus 238_gvpL | MTKLYVYGIVGATHFDVKLPNGHDEAPVFAIVSGDLAVAVSSLER SAVEASAANVWLHENVLSALMEGHAVLPMRFGTIATGAAQLLGD IVKRRGQLMKDLTRLDGKVEIALRISGKNREKVEQRIAGQIVDTNV TQGVAYLQEKQQNLYGSFYTQSSVQCARRAIRSQLDPFIVEAIWPT DEPQMLPFRASCLIKKGDIARFVQTVDDVVVKVSDIRVTCTGPWA PYSFVGQSGSEAET* | 317 |
| Pelodictyon phaeoclathratiforme_ gvpL1 | MVAIQERLIYIFCVTSEPPLLQQYQLQKGICVVDVDGLFVTTMDVT DNDFAENQLQSNLSDVVWLDTKVREHLDVITSIMQHVKSLIPFNF GTLYKSESSLMQFIIKYAEEFKKNLVYLEEKEEWAVKLYCNKNKI VENITHLSKKVSDINALIQNSSIGKAYILGKKKNEIIENEIINIYNTYS KKIFTKFSILSEEFRFNPIPNNETLEKEDDMILNVVLLLNKANVESFI ETSDQLIIQHQNIGLNIEITGPWPCYSFINISH* | 318 |
| Pelodictyon phaeoclathratiforme_ gvpL2 | MPLIIYAIFDSINYIDSFSSYVDAISLKSKIKLEIISTSTLSAIVSRTTDE KKQACQNDVMIYATIIGDIAAKYSILPMRYGSIVSSPFDVTELLKN HNETFVTIIKKITDKEEYSLRILYSHQDKEKNNIEDLFDLPQNVPDIL HGNTDSKKYLLNKYIKHLSEEKRLQYIDKIQSIVACNLQKITDLIVY NKQTTTGFIVDAVFMIERSKKSELLDLVIQMTLFSEHNVVLSGPW PPYNFSNINIG* | 319 |
| Psychromonas ingrahamii 37_gvpL1 | MKNSNHSGLDPNQALYLYCFVHADSIQSVTSQAIEKDSPVFIYQW QDIAAVLSHVPTSYFTGYDDEEPEQTIARILPRTQLHEQVIEEVMRQ SPVFPAQFGTLFSSQESLEQEISQQYLAITHTLKEVSGSVEWAVKG VLDRGVAEKALYSQQLTEQQNSLSSSPGMRHLQEQRLRRETQSKL NSWLHQLYTDIATPLSELSGDFFQRKIPSSIEEGKEVILNWAFLVPE SAGDDFHAQIDKLNQRLNSFGLVIQCSGPWPPYSFCNQSS* | 320 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| Psychromonas ingrahamii 37_gvpL2 | MKNSNHSGLDPNQALYLYCFVHADSIQSVTSQAIEKDSPVFIYQW QDIAAVLSHVPTSYFTGYDDEEPEQTIARILPRTQLHEQVIEEVMRQ SPVFPAQFGTLFSSQESLEQEISQQYLAITHTLKEVSGSVEWAVKG VLDRGVAEKALYSQQLTEQQNSLSSSPGMRHLQEQRLRRETQSKL NSWLHQLYTDIATPLSELSGDFFQRKIPSSIEEGKEVILNWAFLVPE SAGDDFHAQIDKLNQRLNSFGLVIQCSGPWPPYSFCNQSS* | 321 |
| Serratia sp. ATCC 39006_gvpL | MTMNTEAQTEQAIYLYGLTLPDLAAPPILGVDNQHPINTHQCAGL NAVISPVALSDFTGEKGEDNVQNVTWLTPRICRHAQIIDSLMAQGP VYPLPFGTLFSSQNALEQEMKSRATDVFVSLRRITGCQEWALEATL DRKQAVDVLFTEGLDSGRFCLPEAIGRRHLEEQKLRRRLTTELSD WLAHALTAMQNELHPLVRDFRSRRLLDDKILHWAYLLPVEDVAA FQQQVADIVERYEAYGFSFRVTGPWAAYSFCQPDES* | 322 |
| Stella vacuolata- ATCC-43931_gvpL | MLYLYAVLEALPAARTLPAGIGGGELLFVEAFELVCAASETPERAI APEPTQVWRHQQVVEALIDCAAALPLRFGTLVEDAVACRRLLTRH REALCAQLDRVRHCVEFALRVSGLREEVGSDHVIGGGPGVSYMR ALARREASWPPSTGTFPHDGLAAHAADRLLWSRSASQPDLRASFL VLKPNVAAFLADVSALQRMRPDLGITCTGPWPPYSFSDPDLSGMS P* | 323 |
| Thiocapsa rosea strain DSM 235 Ga0242571- 11_gvpL | MDAFYCFCFAPACLASDLRFDDCGWEDPIEIRRLAGLDVILSRVPL GRFAGAEAEQRLADLEWLVPRAQAHDRVITRTMERSTVFPLTFAT LFSSLPALALEVAARRRALLDFFERMAGREEWAVKVSMDRERVIA TRMQSLYPEGGDVPAGGRGYLLKQRRRGEAEQAIGPWLKGQIGC LDEALRPSCETLLIRPLRDEMVASRACLVARDLGPSLSEAIERSREA FADQGLDLHCSGPWPLYSFCGTP* | 324 |
| Trichodesmium erythraeum IMS101_gvpL | MSYVVYGFLYLPESCLALPKGMEKEVELVPYQNIAAVVEANVSIE AIQETEEKLLEAILAHDRVVREIFQQVSMLPLRFGNAFALRENIIND LQNNQQQYLNILTKLQQQAEYTITFTPVSYPSTLEVSKVRGKAYLL AKKQQFEQQQAFQTKQRQQWENIRQLIFKNYPKAVFRDSTESKIK QVHLLANRDARVITTEELSTWQTECSYWQITLSEQLPPYHFV* | 325 |
| gvpN | | |
| Anabaena-flos- aquae_gvpN | MTTTKVNHKRAVLRLRPGQFVVTPAIERVAIRALRYLKSGFPVHL RGPAGTGKTTLAMHLANCLDRPVMLLFGDDQFKSSDLIGSESGYT HKKVLDNYIHSVVKLEDEFKQNWVDSRLTLACREGFTLVYDEFN RSRPEVNNVLLSALEEKILSLPPSSNQPEYLSVNPQFRVIFTSNPEEY AGVHSTQDALMDRLVTISMPEPDEITQTEILIQKTNIDRESANFIVR LVKSFRLATGAEKTSGLRSCLMIAKVCADNNIPVTTESLDFPDIAID ILFNRSHLSMSESTNIFLELLDKFSAEELEILNNRVTGDNDFLIDNSQ FVSQQLAGQPN* | 326 |
| Ancylobacter aquaticus strain UV5_gvpN | MTSEAASKDPISLLSGFGAGAASSGPKAGGRSTPSALTPRPRTGFV EAEQVRDLTRRGLGFLNAGYPLHFRGPAGTGKTTLALHVAAQLG RPVIIITGDNELGTADLVGSQRGYHYRKVVDQFIHNVTKLEETANQ HWTDHRLTTACREGFTLVYDEFTRSRPETHNVLLGVFEERMLFLP AQAREECYIKVHPEFRAIFTSNPQEYAGVHASQDALADRLATIDVD YPDRAMELAVASARTGMPEASAARIIDLVRAFRASGDYQQTPTMR AGLMIARVAAQEGFEVSVDDPRFVQLCSDALESRIFSGQRAEEVA REQRRAALHALIDTHCPSAAKPRARRAGGAVRASIEGAQS* | 327 |
| Aphanizomenon flos- aquae NIES-81_gvpN | MTKTNHKRAVLRVRPGQFVVTPAIEQVAIRALLYLKSGFPIHLRGP AGTGKTTLALHLAHCLDRPVMLLFGDDEFKQNWVDSRLTLACRE GFTLVYDEFNRSRP EVNNVLLSALEEKILSLPPSSNQPEYLSVSPQFRAIFTSNPEEYCGV HSTQDALMDRLVTINMPEPDEITQTEILIQKTNIQKESAHLIVRLVK SFRIATGAEKTSGLRSCLMIAKVCADNNLVAEPENSFFQEIAMEILS NRTHLSVNESTDIFLDVISQFSNKEIEILNDAELGSLPTMDTLANTD LGNDVPLEKEASDYVIQQKNNEFKGFQKPSTKVLN* | 328 |
| Aphanothece halophytica (strain PCC 7418)_gvpN | MTTVLHARPKGFVSTPTIDRISRRAWRYLQSGFSIHLRGPAGTGKT TLAMHLADLLNRPIMLLYGDDEFKSTDLIGSNTGYTRKKVVDNYI HSVVKEEDELRQQWVDSRLTMACREGFTLVYDEFNRSPPEVNNV LLSALEEKLLVLPPDSHRSEYVRVSPNFRAIFTSNPEEYWGVHGTQ DALLDRVVTINVPEPDLETQREIIVQKVGINADDGDMIVNFVRNFR DRAEMENSSGLRSCLMIAQVCHQHEIPVQTSNEDFQDICYDILTSR CPLSTQESISLLEQLFREYELELVVEDEDEDVPSVIVEGETEDLSSDE KPHLRLSHPFGNTEND* | 329 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| Aquabacter spiritensis strain DSM 9035_gvpN | MSTEPAPLVSPSQDVETTPQRPARPEPAEALAVGYRLSARPASPAT LTPRPRADFVETDQVKDLTRRGLGFLRAGYPLHFRGPAGTGKTTL ALHVAAQLGRPVIVITGDNELGTADLVGSQRGYHYRKVVDQFIHN VTKLEETANQRWTDHRLTTACREGYTLVYDEFTRSRPETHNVLLG VFEEKILFLPAQAREECYIRVHPDFRAIFTSNPQEYAGVHASQDAL ADRLATIDVDYPDRGMELAVASARTGLGETEAARIIDLVRAFRAS GDYQQTPTMRASLMIARVAAQEGLRVSIDDPGFVQLCMDALESR MFSGARLEAATRETSRAALLALLAVHCPSEAPIVRVTAARRAKKA DAS* | 330 |
| Arthrospira platensis NIES-39_gvpN | MTTVLRAVPKGFVNTPAIERITVRALRYLQSGFSVHLRGPAGTGKT TLALHLADLLNRPIMLIFGDDELKSSDMIGNQTGYTRKKVVDNFIH SVVKLEDSLKQNWIDSRLTLACREGFTLVYDEFNRSRPEVNNVLL SALEEKLLVLPPNNSRSEYIRVNPHFRAIFTSNPEEYCGVYSTQDAL LDRLITMNMPEPDEATQQEILIQKVAVTPEEAQTIVTLVQQFREAT HAIAPSKIQTVARQQTNADKASGLRPSLMLARICQEHNIPIVPIDPD FQEVCRDILLSRAIGDITELESRLHQIFDHLSGLENDQIIALPPREELT TSSVPNNLSDTEQKIYTYIKDSDGARVSEIEIALGLNRVQTTDALRS LLRKSYLTQQDNRLFVVYEGD* | 331 |
| Bacillus-megaterium_gvpN | MTVLTDKRKKGSGAFIQDDETKEVLSRALSYLKSGYSIHFTGPAG GGKTSLARALAKKRKRPVMLMHGNHELNNKDLIGDFTGYTSKKV IDQYVRSVYKKDEQVSENWQDGRLLEAVKNGYTLIYDEFTSKPA TNNIFLSILEEGVLPLYGVKMTDPFVRVHPDFRVIFTSNPAEYAGV YDTQDALLDRLITMFIDYKDIDRETAILTEKTDVEEDEARTIVTLVA NVRNRSGDENSSGLSLRASLMIATLATQQDIPIDGSDEDFQTLCIDI LHHPLTKCLDEENAKSKAEKIILEECKNIDTEEK* | 332 |
| Bradyrhizobium oligotrophicum S58_gvpN | MLRSDRAAIAGGQRGSRAQGDAVARNDAAAGSRAAIAQISPRPD ADNAALSPAPRTDLFENPQLASMAARALTYLNAGIPVHLRGPAGT GKTTMAMQLAARLGRPVVLLTGDDGLTAAHLVGREIGTKSRQVV DRYVHSVRRVETETSSMWCDAVLAQAVVEGLTFVYDEFTRSPPQ ANNPLLSVVEERILIFPAGSRKERLVHAHPEFRAILTSNPEEYAGVS RPQDALLDRLITFDLDDYDRETEIGIVSNRTGLAYAEAGVIVDLVR GVRRWPKAHHPPSMRSAIMIARIVARELITPSVDDPRFVRLCLDVL AAKAKPTDRDDRDRFAATLLRLMNNHCPAGAIDGG* | 333 |
| Burkholderia thailandensis sp. Bp5365 strain MSMB43_gvpN | MEASAEFVQTPAVRNLTERALTYLGAGYGVHLAGPSGTGKTTLA FHIAAQLGRQVVLMHGDDELGSADLVGRGAGYRRSRVVDNFIHS VVKTEEEMTTTWIDNRLTTACQHGLTLIYDEFNRSRPEANNALLP VLSEGILNLPNRMTGAGYLTVHPGFRAIFTSNPEEYVGVHKTQNA LMGRLITIQVGHYDRETEVEIVRARSGIARADAERIVDLTRRLRDA DDNGHHPSIRAAIALARALSYCGGEATPDNAGYVWACRDILGVDL EQDARTRSQAGRRTKARR* | 334 |
| Chlorobium luteolum DSM 273_gvpN | MRAAVNDNEMNTVLAPRPMANFVETEYIRDITERGLTYLKAGFPV HFRGPSGTGKTTVAMHLAGKIGRPVVVIHGDSEYKTSDLIGSEQG YKFRRLNDNFIHSVHKYEEDMSKQWVNNRLSIAIKKGFTLVHDEF TRSRPEANNILLPILQEKMLSTSASNEEDYYMKVHPEFRAIFTSNPE EYAGVNRTQDALRDRMVTMDLDYFDYETELRVTHAKSELTLEDS EKIVQVVRGLRESGKTEFDPTVRGSIMIARTLHIMQVRPEKTNDAV RKVFQDILTSETSRVGSKTNQEKVRAIVNDLIEAYL* | 335 |
| Dactylococcopsis salina PCC 8305_gvpN | MTTVLHARPKGFVSTPTIDRISGRAWRYLQSGFSIHLRGPAGTGKT TLAMHLADLLNRPIMLLYGDDEFKSTDLIGSNTGYTRKKVVDNYI HSVVKEEDELRQQWVDSRLTMACREGFTLVYDEFNRSPPEVNNV LLSALEEKLLVLPPDSNRSEYRVSPNFRAIFTSNPEEYWGVHGTQ DALLDRVVTINVPEPDLETQQEIITQKVGINANDGEKIVNFVRQFR DRAAVKNSSGLRSCLMIAQVCHQHEIPVQTSDEGFRDICYDILSSR | 336 |
| Desulfobacterium vacuolatum_DSM 3385_gvpN | MSASMSSMKETRQRMSAPEQDNVVPEAGSDFVETPYVKDITDRA LAYLHVGYPVHFSGPAGTGKTTLAFHVAAKLKRTVMLIHGDDEF GSSDLIGKDSGYRKAKVVDNYIHSVVKTEESMNTVWADNRLTIAC QQGCTLVYDEFTRSRPEANNAFLSVLEEKILNIPSLRDIDQGYLQV HPEFRAIFTSNPEEYAGVHKTQDAMMDRLITITLDHFDRDTEVQVT MSKSDLPQKDAEKIVDIVRKLRKTGVNNHRPTIRACIAIGKILKHM GGGASKDNFVFKQICRDVLNVDTTKVTRDGEPLLPRKIDELINSL* | 337 |
| Desulfomonile tiedjei DSM 6799_gvpN | MNGAELRIASIETEVITANNENIVPEAGDRFVNTPHVEELTARAMA YLEVGYSVHFSGVAGTGKTTLAFHAAAKLGRPVILVHGDHEFGSS DLIGRDAGYKKSRLVDNFIHSVVKTEEEMRSLWDNRLTTACRD GYTLIYDEFTRSRPEANNVLLSILEEKILNLPSLRRTGEGYLEVHPSF RAIFTSNPEEYAGVHKTQDALMDRIITINVDHYDRETEIEITRAKSG VCKQDATVIVDIIRELRLLGVNNHRPTIRAAIAIARVLAHTGEHAD | 338 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| | QHNSVFQWLCKDVLSTDTVKVSRGGSPLMAKKVEEVIRKVCGRT GGKRSGKPVGSKEETSE* | |
| Desulfotomaculum acetoxidans_DSM 771_gvpN | MQLNGLDKNSIINPVVLSDFVVTDYISNVVDRALAYIKAGFAIHLR GRSGTGKTSIAMYISSKLNRPTLVIHGDEEFRTSDLIGGRYGYRIRK TIDNFVQSVVKVEEDLVERWVDSRLTTACKNGYTLVYDEFTRSRP EANNILLSVLQERLLDISVARGAEEGYVKVHPDFTAIFTSNPEDYA GVYGSQDALRDRMVTLDLDNYDKETEISIIKSKSKLSREDSERVVN ILRDLRELGDCEYGPTIRGGIMIAKTLQVLGAPVDKNNEMFRQICE EVLASETSRAGNLQALRKVRKVINELFNKYA* | 339 |
| Dolichospermum circinale_gvpN | MSITKVNHKRAVLRLRPGQFVVTPAIERVVIRALRYLRSGFPIHLR GPAGTGKTTLGMHLANCLDRPVMLLFGDDQFKSSDLIGSESGYTH KKLLDNYIHSVVKVEDEFKQNWVDSRLTLACREGFTLVYDEFNRS RPEVNNVLLSALEEKILSLPPSSNQPEYLSVNPQFRVIFTSNPEEYCG VHSTQDALMDRLVTINMPEPDEITQTEILIQKTNIGRESANLIVRLV KSFRLATGAEKTSGLRSCLMIAKICADHDIPASTEDLDFREIAIDILF NRAQLSISESTDIFMGLLEQFSAEEIKVLNDTHFPTDELLINNSQFIT QELVTQPNTELATDIPQELRKTEQN* | 340 |
| Enhydrobacter aerosaccus strain ATCC 27094_gvpN | MSMDQAEEIGVVTTIEPRPRADFVRTQSVEATARRALGYLNAGFS VHFRGPAGTGKTTLALHLAALLGRPMVMITGDEEMLTSTLVGTQ HGYHFRRVVDRFIHTVTKTEETADKRWADHRLTTACREGYTLVY EFTRSRPEANNVLLSVLEEGLLVLPAQNQNEPYIKVHPNFRVIFTSN PQEYAGVHDAQDALGDRIVTIDMGHADRELELAIAAARSGLPPTQ VAPIVDMVREFRETGEYDQTPTLRTSIMICRMMSQERLAPTIEDQQ FVQICMDILGGKSLPGGKGDNKRAQQQKMLLSLIEHHCPARSFTS VGEV* | 341 |
| Isosphaera pallida_ATCC-43644_gvpN | MDYESTALQLKPRPDFVATPWVRELADRALGYLTAGYPVHFSGP AGTGKTTLAMHLAALVNRPVVLLHGDDEFGSSDLVGDHLGFRST KVVDNFIHSVVKTEQSVSKTWVDHRLTTACRHGFTLIYDEFNRSR PEANNILLTILEERLLELPPIAGGRDGSGPLRVHPEFRAIFTSNPEEY AGVHKTQDALLDRMITISMGGHDEATETEITAAKSGLSRDEAARI VELARAVRALKPLRHPPTIRSCLMIAKVAALRKVPIDPNDALFLAI CRDVLRIDALPVDDPEATFAELIRRVFAPTPAVAPPRVPTTGFAAN RVVPIPRRPLAASASPPPGANGHAHLR* | 342 |
| Legionella drancourtii LLAP12_gvpN | MMTQENNGSLTDSKNNDKLIRFVNNRSDNILLEASEEFTETPHIRGI SERALAYLDIGYPIHLLGPAGTGKTTVALHIAAQLGRPVILIHGDDE FTGADLVGRGTGYHHSKLVDNFIHSVLKTEEEMTTMWTDNRLTT ACEQGYTLIYDEFNRSRAEANNALLSVLSEGILNLPGRRERDGIGY VDVHSNFRAIFTSNSEEYVGIHKTQNALADRLIAIKMDYPDQQSEI QHIEKKSTLPRKDIEIIVNLARELRLKSEKRPSIRGCIAIARVLAYHNR HAHADDPIFQAVCQDIFGISKEFLKQLLHPMDSGLQKRSEKNQESI KKYKTKNQKL* | 343 |
| Lyngbya confervoides BDU141951_gvpN | MSTVLQARPRNFVSTPAVERIARRALRYLQSGYSVHLRGPAGTGK TTLALHLADLLSRPIMLVFGDDEFKTSDLIGNQSGYTRKKVVDNYI HSVVKVEDELRHNWVDSRLTLACREGFTLVYDEFNRSRPEVNNV LLSALEEKLLVLPPSGHRPEYLRVNPHFRAIFTSNPEEYAGVHGTQ DALLDRLITIHMPEPDELTQQQILIQKVGIEPADALMIVRLVKAFKS QMGNHSATSLRPSLMIANICHEHGVAMMTEDADFRDVCSDVLLS RVTNELSPATHTLWDLFNELTASADVLGPESNSTDVSPQPEADKP VETKGSKGKSTTKSKAKESAKASEEADEAGDDSASAPELDEIESSI LTFLTARESASLSEIESELSLTRFKAVDALRSLVEAGYLQKQNGAG KPAIYGLVPEES* | 344 |
| Microcystis aeruginosa NIES-843_gvpN | MTVTETQTRRAVLSLRPGQFVVTPSIDQIATRALRYLNSGFSIHLCG PAGTGKTTLAMHLANCLARPVMLIFGDDDFTSSDLIGSQSGYTHK KLMDNYIHSVLKVEDELKHNWVDSRLTMACREGFTLVYDEFNRS RPEVNNVLLSALEEKILTLPPTSHQPDYLQVNSQFRAIFTSNPEEYC GVHATQDALMDRLVTINMPEPDQLTQTEILAQKTGIGREDALFIVN LVKTFRVKTATEKTSGLRSCLMIAKVCASHDIAANSADSDFRDICA DVLLSRTNLSVDKSRAILWEILEDNPLESLSFLEEEEPSDAQVSTSE PSTGNQSLKAIQSLLRGNLPQRKD* | 345 |
| Nostoc punctiforme ATCC 29133_gvpN | MTTVLNASPQRFVNTPAVQRIAQRALRYLQSGFSIHLRGAAGVGK TTLAMHLADLLNQPIILLFGDDEFKTSDLIGNQLGYTRKKVVDNFI HSVIKVEDEVRQHWVDARLTLACKEGFTLVYDEFNRSHPEVNNV LLSVLEERLLVLPTNQHRAEYIRVHPQFRAILTSNPQEYCGVHATQ DALMDRVITIDMPTPDELSQQEIVVHKTGIDSEKAEVIVRIVRTFWS RSGSGQGGGLRSCLMIAKICHEHEISVNPGDPSFQDICADILLSRTN QPLIEATRLLEEVLSEFYHRINTQSQPSEIIPNNQNQIVLEQRVPYEH | 346 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| | EVYNYLCNSPGRRFSELAVELGIDRSQIVAALKSLREQGVLVQMQ GNAESPSISQTVAFDSGHLINK* | |
| Nostoc sp. PCC 7120_gvpN | MTLTANNKKRAVLRVRPGQFVVTPAIEQVAIRALRYLTSGFAIHLR GPAGTGKTTLAMHLANCLDRPIMLIFGDDEFKSSDLIGSESGYTHK KLLDNYIHSVLKVEDEFKQNWVDSRLTLACREGFTLVYDEFNRSR PEVNNVLLSALEEKILTLPPSSNQPEYLHVNPQFRAIFTSNPEEYCG VHSTQDALMDRLVTINMPEPDELTQTEILAQKTALNRADALLIVRL VKAFRSRTGGEKTSGLRSCLMIAKVCAEHNILVSPQSSDFREICAD VLFNRTNWSASEAATIFLELLNHLDLQQIEEFKNSIIPEDTDAIAEG GFPTIIDSHFGTLDSEVLEQPGVEDSIPFEQEIYLYLQQYKSAALAL VQQEFELSRTVATNALNSLEQKGLVSKNNHVYTIEEPNQS* | 347 |
| Octadecabacter antarcticus 307_gvpN | MNSNLRATNSGGPDISKTMMPEAREDFVQTESVKSISRRALAYINA GYSVHFRGPAGTGKTTMAMHTAALLGRPVVLITGDEEMITSNLVG AESGYNYRKVTDNYIHTVSKIEESSDRSWNDHRLTTACREGYTLIY DEFTRSRAEANNVLLSVLEEGILVLPAQNRGEPFIKVHPNFRVIFTS NPQEYAGVHEAQDALSDRIVTIDIGEADRELEVSIASSRSGLEVAK TEPIVDMVRAFRDTGEYDQTPTLRACIVICRMVANEKLNTTIDDPF FVQICLDVLGSKSTFGGKEHDKRTQQRKLLLDNLKHYCPSKVSTK PSAKDDESKSTLIQVSSRGSL* | 348 |
| Octadecabacter arcticus 238_gvpN | MMPEARKDFVQTDSVKSVSRRALAYINAGYSVHFRGPAGTGKTT MAMHTAALLGRPVVMITGDEEMVTSNLVGAESGYNYRKVTDNYI HTVSKVEESSDRSWNDHRLTTACREGYTLIYDEFTRSRAEANNVL LSVLEEGILVLPAQNRGEPFIKVHPDFRVIFTSNPQEYAGVHDAQD ALSDRIVTIDIGAADRELEVSIASSRSGLEVAKTAPIVDMVRAFRDT GEYDQTPTLRACIMICRMVANEKLNPTIDDSYFVQICLDVLGSKSM FGAKEQGKRTQQEKLLLDNLSHHCPSPPPSKPSAKEAEAKPRSIQA TSRGPA* | 349 |
| Pelodictyon phaeoclathratiforme_ gvpN | MRRQGCDSEMNTVLEPKPMPNFVETDYIRDITSRGLTYMKAGFPV HFRGPSGTGKTTVALHLASKIGRPVVIIHGDSEYKTSDLIGSEQGYK YRRLDDNFIHSVHKYEEDMTKQWVNNRLTIAIKKGFTLVYDEFTR SRPEANNILLPILQEKMMSTSSSNEEEYYMKVHPEFRAIFTSNPEEY AGVNRTQDALRDRMVTMDLDYFDYETELMITHAKSGMSLDDAE KIVKIVRGLRESGKTEFDPTIRGSIMIAKTLNVLNARPDKTNELFKK VCQDILTSETSRVGSKTNQERVRGIVNELIDLHS* | 350 |
| Phormidium tenue NIES-30_gvpN | MNTVLQARPRNFVSTPTLERTSIRALRYLQSGYSIHLKGPAGTGKT TLALHLADLLARPIMLLFGDDEFKTSDLIGNQSGYTRKKVVDNYIH SVVKVEDELRHNWTDSRLTLACREGFTMVYDEFNRSRPEVNNVL LSALEEKLLVLPPSNNRAEYIRVSPHFRAILTSNPEEYCGVHGTQD ALQDRLITINMPEPDELAQQQILVQKVGIDSSAALQIVQLVKAFQS AVAPDMVSSLRPSLMIATICHDHDILPLAENADFRDVCSDILLARS KEPAPDATRHLWNLFNRFVVSQAALVNDLSLKPEAHPTARFHGEE EDDAPLQPLEALVESDIDDVAVEDQPVIGPQDLQGETLPEAVIPEP QGETVVETPAEAEALPEEIARVQVSPDDIETRIFDYLDATGTASLV NIEAALDLNRFQAVNAVKSMLDQGLIEKQETDGQLQGYQLSSN* | 351 |
| Planktothrix agardhii str. 7805_gvpN | MTTVLQARPKGFVNTPTIEQLTIRALRYLQSGFSLHLRGPAGTGKT TLAMHLADLLNRPIVLIFGDDELKSSDLIGNQLGYTRKKVVDNFIH SVVKLEDELRQNWIDSRLTLACKEGFTLVYDEFNRSRPEVNNVLL SALEEKLLVLPPNNSREYIRVNPHFRAIFTSNPEEYCGVYGTQDAL LDRLITIDMPEPDDETQQEILIQKIGISPEDAKNIIEIVKIYLEITTQKK EIKPVQNGKAARPHIDKASGLRPGLIIAKICHEHDISIQENNQDFIKV CADILLSRTNLSLTEAQNKLEKVIKTVLTDGDTSNNSFLPPSETQLT ENNSLEIEEQVYQYLQKTTSARVSEIEVALGLNRVQTTNVLRSLLK QGHLKQQDNRFFAVNKQGELIQP* | 352 |
| Planktothrix rubescens_gvpN | MTTVLQARPKGFVNTPTIEQLTIRALRYLQSGFSLHLRGPAGTGKT TLAMHLADLLNRPIVLIFGDDELKSSDLIGNQLGYTRKKVIDNFIHS VVKLEDELRQNWIDSRLTLACKEGFTLVYDEFNRSRPEVNNVLLS ALEEKLLVLPPNNSRSEYIRVNPHFRAIFTSNPEEYCGVYGTQDAL LDRLITIDMPEPDDETQQEILIQKIGISPEDAKNIIEIVKIYLEITTQKK EIKPVQNGKAARPHIDKASGLRPGLIIAKICHEHDISIQENNQDFIKV CADILLSRTNLSLTEAQNKLEKVIKTVLTDGDTSNSFLPLSETQLT ENNSLEIEEQVYQYLQKTTSARVSEIEVALGLNRVQTTNVLRSLLK QGHLKQQDNRFFAVNKQGELIQP* | 353 |
| Psychromonas ingrahamii 37_gvpN1 | MSIENLNNVSEIKIEQSDDDHIYPEASEDFVETPYIKEVTERAMLYL DAGYPVHFAGPAGTGKTTLAFHIAALRQRPVTLIHGNHEFGTSDLI GKESGYRRHRVVDNYVHSVVKEEEELQSLWSDNRLTTCCRNGDT LVYDEFNRSTPEANNVLLSILEEGILNLPSSRSDGYLEVHPQFRAIFT | 354 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| | SNPQEYAGTHATQDALVDRMITIMLHYPDRHTEVRVAIAKSGINS DEAGSIVDIVNEFRELCGSKIVSSGPKTMPTVRASIAIARVLVQKGE HAFRDNTFFHRICRDVLCMYTQQVSFSNRSVLDKQLEDLIMKFCP ATYKSSGSKIRA* | |
| Psychromonas ingrahamii 37_gvpN2 | MSINNLNISTIKIEQPENDNIYPEASAEFVQTPYIQEVTERALLYLDA GYPVHFAGPAGTGKTTLAFHIAALRKRPVTLIHGNHEFGSSDLIGK ESGYRRHRLVDNYVHSVMKEEEELKSLWVDNRLTTCCRNGDTLV YDEFNRSTPEANNVLLSILEEGILNLPSLRSMGDGYLEVHPSFRAIF TSNPQEYAGTHATQDALVDRMITIMLNYPDRDTEVRVAVAKSGIS NEEAGFIVDIVNEFRELSNHKSLSSGQKSMPTVRASIAISRVLIQKG EHAFRDNVFFHRVCHDVLCMYIQKISPSNRSFLDKQLEVLIGKFCP AAKSALVPKVVK* | 355 |
| Rhodobacter capsulatus SB 1003_gvpN | MTIPRDLPWGDARTPLFEDEELRSLLDRAEIYLREGIAIHFRGPAGV GKTTLALHLAQRFARPVTFFVGNDWLGRADIFGRDLGETVSTVQD HYISSVRRAERKSRIDWQEAPLARAMRDGHVLVYDEFSRSRPEAN AALLSVIEEGVLPLSDPAAGRSHIVAHPDFRVILTSNPRDYVGVQA VPDALLDRMITFSLDGMSFETEVGIVATAARTDPADARAICALIHL LRAEKPGTMEISMRSGIMIARLARAAGVAPDPADPVFVQICADVL GTRMRGSDIDDVMALLLRPDPAPAACAGGAR* | 356 |
| Rhodobacter sphaeroides 2.4.1_gvpN | MTVLSPSLPHAAGIDAALVENPWLGLRRSGRYFQNAETEALFARA LGYARAGVCVHLAGPAGLGKTTLALRIAQALGRPVAFMTGNEWL GSRDFIGGEIGQTVTSVVDRYIQSVRRTEQSARIDWKESILGQAMR CGQTFIYDEFTRASPEANAALLSVLEEGVLVSTDGASRHQYIEAHP DFRVLLTSNPHEYQGVKAAPDALIDRMVTLRLEEPSAPTLAGIVAL RSGLDPATARRIVDLILSVQRSGEMQAPPSMRTAILVARLAAPLRL AGRLSDAALAEIAADVLRGRGLEADAAAFEAKLAAPTPGETAR* | 357 |
| Serratia sp. ATCC 39006_gvpN | MIKQNTVSQYTVDDDLVVPEASEHFVATSYVNDIIERALVYLRAG YPVHFAGPSGIGKTTLAFHLAALWGRPVTMLQGNEEFVSSDLTGK DIGYRKSSLVDNYIHSVLKTEEQMNRMWVDNRLTTACRNGDMLI YDEFNRSKAETNNVLLSVLSEGILNLPGLRGVGEGYLDVHPEFRAI FTSNPEEYAGTHKTQDALMDRMITINIGLVDRDTELQILHARSELE LKEAAYIVDIIRELRGNEHETKHGLRAGIAIAHILHQQGIKPRYGDK LFHAICYDVLSMDAAKIQHAGRSIYREMVDGVIRKICPPIGSDTVK ASTQKIKAVE* | 358 |
| Stella vacuolata_ATCC-43931_gvpN | MSTEPAPVMPPSTDIEFGSQRPARPKPAEALAVGYRLSARPAAPST LTLRPRADFVETDQVKDLTRRGLGFLRAGYPLHFRGPAGTGKTTL ALHVAAQLGRPVIVITGDNELGTADLVGSQRGYHYRKVVDQFIHN VTKLEETANQRWTDHRLTTACREGYTLVYDEFTRSRPETHNVLLG VFEEKILFLPAEAREECYIRVHPDFRAIFTSNPQEYAGVHASQDALA DRLATIDVDYPNRAMELAVASARTGLAEAEAARIIDLVRAFRASG DYQQTPTMRASLMIARVAAQEGLRISVDDPGFVQLCMDALESRIF SGARQEADARARHRVALLGLLATHCPSEAPVARVATVARAKRKS AS* | 359 |
| Thiocapsa rosea strain DSM 235 Ga0242571_11_gvpN | MSAKPLQDASEVSALNNDNVQPEASDTFVCTPSVEALAERASAYL QAGYPVHLAGPAGTGKTTLAFHAAAKRGRPVKLIHGNDELGLAD MVGQDNGYRRNTLVDNYIHSVVKTQEEVRTFWIDNRVTTACLNG ETLIYDEFNRSRPEVNNIFLSILGEGILNLPNRRHQGAGYLEVHPEF RVIFTSNPEEYAGTHKTQDALMDRMITMKIGHYDRETEIRVTRAK SGLPPSEVAIVVDIVRELRGQSVNHHRPTLRACIAIARIMADRRISA RSNNSFFRDICRDILDMDSAKVRRDGNALGESPVDDVVASISARAR RPKIVEPKGLHKEI* | 360 |
| Tolypothrix sp. PCC 7601_gvpN | MTNTENHKKRAVLRVRPGQFVVTPAIEKVAIRALRYLTSGFAIHLR GPAGTGKTTLAMHLANCLDRPIMLIFGDDEFKSSDLIGSESGYTHK KLLDNYIHNVLKVEDELKQNWVDSRLTLACREGLTLVYDEFNRS RPEVNNVLLSALEEKILTLPPSSNQPEYLHVHPKFRAIFTSNPEEYC GVHSTQDALMDRLVTINMPEPDEQTQIEILTHKTGIHHEYAQLIAR LVKAFRSATGAEKTSGLRSCLMVAKVCAEHDILVTPENTDFREICA DVLFNRTNLSASDATTLFLELLNHVQVKPVEPVDDSDPYDVAEAE IVGAAEPQTDAIAEPVTLDESLLSDQPN* | 361 |
| Trichodesmium erythraeum IMS101_gvpN1 | MTTVLNVSPDRFVSTPGVERVTQRASRYLESGYSVHLRGPAGVGK TTLALHLAHLRQQPIPFLMIGDDEFKTSDLIGNKSGYTRKKLVDNYI HTVLKVEDELRDNWIDSRLTLACKEGFTLIYDEFNRSRPEVNNVLL SVLEEKMLVLPPSQNQSEYIQVHPQFRVILTSNSEEWTGVHATQDA LLDRVVTIGMEQPDISTEQNIVIQKTGINPLKAEVIIKLVRSVRQRV DKEDLGSLRSALMISKVCHDHDIPLDGKDSSFSDLCADILISRPNLP RQEALQQLDEVLEEFFPADQPSSSDVGLEKEGSL* | 362 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| Trichodesmium erythraeum IMS101_gvpN2 | MTTVLNVSPDRFVSTPSVERVTQRASRYLESGYSVHLRGPAGVGK TTLALHLAHLRQQPIFLMIGDDEFKTSDLIGNKSGYTRKKLVDNYI HTVLKVEDELKHNWIDSRLTLACKEGFTLIYDEFNRSRPEVNNVLL SVLEEKMLVLPPSQNQSEYIQVHPQFRVILTSNSEEWTGVHATQDA LLDRVVTIGMGQPDISTEQNIIIQKTGINPLKAEVIIKLVRSVRERLE TEDLGSLRSALMISKVCHDHDIPLGGKDSNFSDLCADILISRANLPR QEALKQLDEVLEELFPADQLSISDIGLKKEGSL* | 363 | gvpV

| Anabaena-flos-aquae_gvpV | MIKNIQVFFMKTISNRSISRAKISTMPRPKSDASSQLDLYKMVTEK QRIQRDMYSIKERMGLLQQRLDILNQQIEATEKTIHKLRQPHSNTA QNIVRSNIFVESNNYQTFEVEY* | 364 |
| Aphanizomenon flos-aquae NIES-81_gvpV | MKSFRHRSIIRAKISTMPRHISEASSQLELYKMVAEKQRISRELSSIK ERMATLQKRLDSLNNEIDNTEKTIHKLRQPHSSTAQNIVRSKNVVE SNNYQTFEIEY* | 365 |
| Arthrospira platensis NIES-39_gvpV | MRYKYHRQIQPKLSAIPRQKSQANLYRNSYLLAVEKKRLTEELEV LQSRSHIIEQRLALIEDQLGELEKDVTQLSVPPSPKPQNNLPVNNPE PPPQSNPTNSSHINTFMVDY* | 473 |
| Burkholderia thailandensis sp. Bp5365 strain MSMB43_gvpV | MPIPKKGLHDIRFRHAPGATPLPVHSMYMRISCIEMEKSRRTIERRA AQRRIAAVDSRVADLEREKARLYAAIDNEAPQAGDIRGSFRIRY* | 366 |
| Desulfobacterium vacuolatum_DSM 3385_gvpV | MLKNRNRSIKGVQNIKTHAGKVDHVSHPHMAYMRISCLEMEKAR KNKEKSGAQKRIDMINQRLMEIEKEKAHIQRILGDTSIALESSNVD HDSEIKGGFKIKY* | 367 |
| Desulfomonile tiedjei DSM 6799_gvpV | MNIRMKGNSRGLRDIRTHSGKVDRVGLPYMAYMSISCLEMEKAR REKERLSALTRIKNIEQRIREIEAEKDLLLKGVGERTRTDLQKASTP RDQSAQCKGGFKIRY* | 368 |
| Legionella drancourtii LLAP12_gvpV | MMPALVKGLRNIKTMSNRLDKVQSPHEAFISAAALHREKQRHLQ ELAILRNRLDEINLRLEQINEQQNQVAEAFDISPPRAVKSALRTGIQ SKTGSTSHGFKIKY* | 369 |
| Microcystis aeruginosa NIES-843_gvpV | MTTTRPPRPIRSKISTMPRKQSEADHQLELYKLITEKQRIQEKLEM MERQIQQLKNRLTFVTEQIETTEQSIQNLRTANPPSVAKKPDSPKT VAHSSNNSSNFQTFYLEY* | 370 |
| Nostoc punctiforme ATCC 29133_gvpV | MHRTPNRRQIQAKLSTMPPQRSQATVYLNAYKMMLEKERLEEEL EKLEARRHQIQQRLAILNSQTIPEENMTHQQANTDLENNTPKFNTL TLEY* | 371 |
| Nostoc sp. PCC 7120_gvpV | MLSIIQVFPMTKVRNRGIIRPKITTMPRNKSEASSQLELYKLVTEQQ RIKQELAFIEQRTVLLKQRLSTLKTQIEGTERSINHLRHSELKYSRIA LPKIFSETNNYQAFDIEY* | 372 |
| Planktothrix agardhii str. 7805_gvpV | MRPFRSQPPILPKISTMPRQKTEATLYRSLYQLAVEKKRLQEELESL GQRFETVTQRLQQIETQIQGLETDVKQIAPPKPPETKPNQPSTPTPT KAEPGSVSTFTLDY* | 373 |
| Psychromonas ingrahamii 37_gvpV1 | MTAAKRKTLRGLADIRTISSCGTSGQEAYQMYLKRGVLEMEKLR RQKEKNSALERVTNINRRLMAIDTDIDFLCQSLKVIEKRTNQENSIV EKSVSRGFKLRY* | 374 |
| Psychromonas ingrahamii 37_gvpV2 | MIFSKKKNALRGLADIRTLSGCGTSGQEAYQMYLKRGVLEMEKL RRQKEKNSALERVRNINYRLMAIDADIDFLCQSLKVIEERTNKENS ISNESVTYKKGFKLRY* | 375 |
| Serratia sp. ATCC 39006_gvp V | MAISTRPLRTLSDIKTHSGRVSGEHQTYRDYFQIGALELERWRRTR EREAASSRIASIDERIADIDKEKAALLADATAASAVAENNDKSEAA EKKKKSSGLRIKY* | 376 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| Thiocapsa rosea strain DSM 235 Ga0242571_11_gvpV | MSKFTQPSRSVRDIKTLAGMADDVRAPHKMYMRLFALETERHRR LQERASAMLRVDNIDARCAEIAEEMEQLLQILGVEAVAPGGPPAN ARPGSGRVPTQPHRGRGKGTGAGRQTTSGETSVGEAVKIRY* | 377 |
| gvpW | | |
| Anabaena-flos-aquae_gvpW | MELENLYTYAFLEIPSSPLILPQGAANQVVLINGTELAAIVEPGIFLE SFQNNDEKIIQMALSHDRVICELFQQITVLPLRFGTYFTSTNNLLNH LKSHEKEYQNKLEKINGKNEFTLKLIPRMIEEIVPSEGGGKDYFLA KKQRYQNQNNFSIAQAAEKQNLIDLITKVNQLPVVVQEQEEQIQIY LLVSCQDKTLLLEQFLTWQKACPRWDLLLGDCLPPYHFI* | 378 |
| Aphanizomenon flos-aquae NIES-81_gvpW | MELENLYTYAFLKTPSFSLHLPQGSTTSVIQIDGNGLSAIVEPGISLD SFQDDDEKIVQMAIEHDRVICDIFRQITVLPLRFGTYFANTDNLLTH LESYGQEYLDKLEKINCKTEFILKLIPRMITEESPVLESGRHYFLAK KQHYQRQKNFILAQASEKEILINFISKINQIPVIIQEQEEEVRIYLLVN YQDKTLLLEQFLTWQQTCPRWDLFLGEGIPPYHFI* | 379 |
| Arthrospira platensis NIES-39_gvpW | MYVYAFIKSQSISWKSVQGIYEPVVLLEAGALAAVVEPNLQAENL SADNEEELMRAVLTHDRIVCQIFEETTVLPVRFGTCFDSEARLCEH LTTEGDRYFRQLEKLTGRAEYLLEAIPQPFNQEKPSSDTTAPPTKG RDYFLQKKRLHQQRLNFEQQQEQQWQDFINAIASKYPIVQGKATE DAERIYLLIPRSQEVALVEWVAQQQQNIDLWEFSLGNAVPAYHFL* | 380 |
| Dolichospermum circinale_gvpW | MKLENFYTYAFLEIPRFPLVLPQGAASQVILINGSGMSAIVEPGISLE SFQNNDEKIIQMALSHDRVICELFQQVTVLPLRFGTCFTSTNNLLN YLELHRQEYQEKLEKINGKIEFTLKLIPQTMEEPAPLERGGRDYFL AKKQRYQDQNNFRIAQAAEKQNLIDSISKVNQLPFVIQEKEEEVNI YLLVKSEDKTLLLEQFLNWQKACPRWDLLLGEPLPPYHFI | 381 |
| Microcystis aeruginosa NIES-843_gvpW | MKLYNLYTYAFLKTPIESLKLPVGMANPLLLITGGELSAVVEPEVG LDTLQNDDERLIQSVLCHDRVICQLFQQTTILPLRFGTSFLEAENLL THLCSHGQEYQEKIEELEGKGEYLLKCIPRKPEEPVLFSESKGRQYF LAKKQLYEAQQDFYTLQGSEWQNLVNLITQSYPSTRIITAPGTESRI YLLVNLQEEPLLIEQVLHWQKACPRWELQLGQVSPPYHFT* | 382 |
| Nostoc punctiforme ATCC 29133_gvpW | MSIYAYALLVPTASPLVLPLGMERNTELVYSSGLAALVEPEISLEAI QATDERLLQAVLNHDHVIRELFQQTPLLPLRFGRGFTSVEKLLNHL ENHQEQYLETLTQLADKVEYSVKVTACSLLDDSDTIDARGKAYLL AKKQRYQTQQAFQAQQCEQWELLNELILKTYTNVICETRQSDVR QIHFLAQRNDSTLSTQLFSLWQVQCSHWQLALSEPLPPYHFLKNTL T* | 383 |
| Nostoc sp. PCC 7120_gvpW | MRSPNFYTYAFLNTPDIPLRLPSGNLGQLLLIHGHKLSAVVEPGISL ESSQNNDEEVIKMVLAHDRVICELSQQTTVLPLRFGTYFNSEETLL NHIESHAQEYQKKLDHIQGKTEYTLKLIPRKFEELAKVSGGNGRD YFLAKKLHYEHQKNFIGDQNREKNHLINLIMDVYRSSAIIQDYVEE VRLHLLVDRHDKTLLFKQVLTLQEKCPHWNLILGEPLPPYHFV* | 384 |
| gvpR | | |
| Bacillus-megaterium_gvpR | MEIKKIMQAVNDFFGEHVAPPHKITSVEATEDEGWRVIVEVIEERE YMKKYAKDEMLGTYECFVNKEKEVISFKRLDVRYRSAIGIEA* | 385 |
| gvpS | | |
| Bacillus-megaterium_gvpS | MSLKQSMENKDIALIDILDVILDKGVAIKGDLIISIAGVDLVYLDLR VLISSVETLVQAKEGNHKPITSEQFDKQKEELMDATGQPSKWTNP LGS* | 386 |
| Rhodococcus hoagii 103S_gvpS | MSATPDRRIALVDLLDRVLGGGVVVAGEITLSIADVDMVHISLRTL VSSVSALTRPPDEKPENDG* | 387 |
| gvpT | | |
| Bacillus-megaterium_gvpT | MATETKLDNTQAENKENKNAENGSKEKNGSKASKTTSSGPIKRA VAGGIIGATIGYVSTPENRKSLLDRIDTDELKSKASDLGTKVKEKS KSSVASLKTSAGSLFKKDKDKSKDDEENVNSSSSETEDDNVQEYD ELKEENQTLQDRLSQLEEKMNMLVELSLNKNQDEEAEDTDSDEEE NDENDENDENEQDDENEEETSKPRKKDKKEAEEEESESDEDSEEE EEDSRSNKKNKKVKTEEEDEDESEEEKKEAKPKKSTAKKSKNTKA KKNTDEEDDEATSLSSEDDTTA* | 388 |

TABLE 6-continued

Amino acid sequences of exemplary gvpA/B, gvpF, gvpF/L, gvpG, gvpJ, gvpK, gvpL, gvpN, gvpV, gvpW, gvpR, gvpS, gvpT, and gvpU proteins

| Species, protein; | Amino acid sequence | SEQ ID NO.: |
|---|---|---|
| gvpU | | |
| Bacillus-megaterium_gvpU | MSTGPSFSTKDNTLEYFVKASNKHGFSLDISLNVNGAVISGTMISA KEYFDYLSETFEEGSEVAQALSEQFSLASEASESNGEAEAHFIHLK NTKIYCGDSKSTPSKGKIFWRGKIAEVDGFFLGKISDAKSTSKKSS* | 389 |

TABLE 7

Protein sequences of gvpC from exemplary species:

| Species | UniProt ID No. | Amino acid Sequence | SEQ ID NO: |
|---|---|---|---|
| Anabaena flos-aquae | P09413 | MISLMAKIRQEHQSIAEKVAELSLETREFLSVTTAKRQEQAEK QAQELQAFYKDLQETSQQFLSETAQARIAQAEKQAQELLAFH KELQETSQQFLSATAQARIAQAEKQAQELLAFYQEVRETSQQ FLSATAQARIAQAEKQAQELLAFHKELQETSQQFLSATADAR TAQAKEQKESLLKFRQDLFVSIFG | 390 |
| Halobacterium salinarum | P24574 | MSVTDKRDEMSTARDKFAESQQEFESYADEFAADITAKQDD VSDLVDAITDFQAEMTNTTDAFHTYGDEFAAEVDHLRADID AQRDVIREMQDAFEAYADIFATDIADKQDIGNLLAAIEALRTE MNSTHGAFEAYADDFAADVAALRDISDLVAAIDDFQEEFIAV QDAFDNYAGDFDAEIDQLHAAIADQHDSFDATADAFAEYRD EFYRIEVEALLEAINDFQQDIGDFRAEFETTEDAFVAFARDFY GHEITAEEGAAEAEAEPVEADADVEAEAEVSPDEAGGESAGT EEEETEPAEVETAAPEVEGSPADTADEAEDTEAEEETEEEAPE DMVQCRVCGEYYQAITEPHLQTHDMTIQEYRDEYGEDVPLR PDDKT | 391 |
| Halobacterium mediterranei | Q02228 | MSVKDKREKMTATREEFAEVQQAFAAYADEFAADVDDKRD VSELVDGIDTLRTEMNSTNDAFRAYSEEFAADVEHFHTSVAD RRDAFDAYADIFATDVAEMQDVSDLLAAIDDLRAEMDETHE AFDAYADAFVTDVATLRDVSDLLTAISELQSEFVSVQGEFNG YASEFGADIDQFHAVVAEKRDGHKDVADAFLQYREEFHGVE VQSLLDNIAAFQREMGDYRKAFETTEEAFASFARDFYGQGA APMATPLNNAAETAVTGTETEVDIPPIEDSVEPDGEDEDSKAD DVEAEAEVETVEMEFGAEMDTEADEDVQSESVREDDQFLDD ETPEDMVQCLVCGEYYQAITEPHLQTHDMTIKKYREEYGED VPLRPDDKA | 392 |
| Microchaete diplosiphon | P08041 | MTPLMIRIRQEHRGIAEEVTQLFKDTQEFLSVTTAQRQAQAK EQAENLHQFHKDLEKDTEEFLTDTAKERMAKAKQQAEDLFQ FHKEMAENTQEFLSETAKERMAQAQEQARQLREFHQNLEQT TNEFLADTAKERMAQAQEQKQQLHQFRQDLFASIFGTF | 393 |
| Nostoc sp. | Q8YUS9 | MTALMVRIRQEHRSIAEEVTQLFRETHEFLSATTAHRQEQAK QQAQQLHQFHQNLEQTTHEFLTETTTQRVAQAEAQANFLHK FHQNLEQTTQEFLAETAKNRTEQAKAQSQYLQQFRKDLFASI FGTF | 394 |

TABLE 8

Amino acid sequences of exemplary GVS and GVA proteins from B. megaterium.

| GVA Protein | Amino acid sequence | SEQ ID NO.: |
|---|---|---|
| gvpB | MSIQKSTNSSSLAEVIDRILDKGIVIDAFARVSVVGIEILTIEARVVIASVDTWLRYAEAVGLL RDDVEENGLPERSNSSEGQPRFSI | 395 |
| gvpR | MEIKKIMQAVNDFFGEHVAPPHKITSVEATEDEGWRVIVEVIEEREYMKKYAKD EMLGTYECFVNKEKEVISFKRLDVRYRSAIGIEA | 396 |

TABLE 8-continued

Amino acid sequences of exemplary GVS and GVA proteins from *B. megaterium*.

| GVA Protein | Amino acid sequence | SEQ ID NO.: |
|---|---|---|
| gvpN | MTVLTDKRKKGSGAFIQDDETKEVLSRALSYLKSGYSIHFTGPAGGGKTSLARA LAKKRKRPVMLMHGNHELNNKDLIGDFTGYTSKKVIDQYVRSVYKKDEQVSE NWQDGRLLEAVKNGYTLIYDEFTRSKPATNNIFLSILEEGVLPLYGVKMTDPFVR VHPDFRVIFTSNPAEYAGVYDTQDALLDRLITMFIDYKDIDRETAILTEKTDVEE DEARTIVTLVANVRNSGDENSSGLSLRASLMIATLATQQDIPIDGSDEDFQTLCI DILHHPLTKCLDEENAKSKAEKIILEECKNIDTEEK | 397 |
| gvpF | MSETNETGIYIFSAIQTDKDEEFGAVEVEGTKAETFLIRYKDAAMVAAEVPMKIY HPNRQNLLMHQNAVAAIMDKNDTVIPISFGNVFKSKEDVKVLLENLYPQFEKLF PAIKGKIEVGLKVIGKKEWLEKKVNENPELEKVSASVKGKSEAAGYYERIQLGG MAQKMFTSLQKEVKTDVFSPLEEAAEAAKANEPTGETMLLNASFLINREDEAKF DEKVNEAHENWKDKADFHYSGPWPAYNFVNIRLKVEEK | 398 |
| gvpG | MLHKLVTAPINLVVKIGEKVQEEADKQLYDLPTIQQKLIQLQMMFELGEIPEEAF QEKEDELLMRYEIAKRREIEQWEELTQKRNEES | 399 |
| gvpL | MGELLYLYGLIPTKEAAAIEPFPSYKGFDGEHSLYPIAFDQVTAVVSKLDADTYS EKVIQEKMEQDMSWLQEKAFHHHETVAALYEEFTIIPLKFCTIYKGEESLQAAIEI NKEKIENSLTLLQGNEEWNVKIYCDDTELKKGISETNESVKAKKQEISHLSPGRQ FFEKKKIDQLIEKELELHKNKVCEEIHDKLKELSLYDSVKKNWSKDVTGAAEQM AWNSVFLLPSLQITKFVNEIEELQQRLENKGWKFEVTGPWPPYHFSSFA | 400 |
| gvpS | MSLKQSMENKDIALIDILDVILDKGVAIKGDLIISIAGVDLVYLDLRVLISSVETLV QAKEGNHKPITSEQFDKQKEELMDATGQPSKWTNPLGS | 401 |
| gvpK | MQPVSQANGRIHLDPDQAEQGLAQLVMTVIELLRQIVERHAMRRVEGGTLTDE QIENLGIALMNLEEKMDELKEVFGLDAEDLNIDLGPLGSLL | 402 |
| gvpJ | MAVEHNMQSSTIVDVLEKILDKGVVIAGDITVGIADVELLTIKIRLIVASVDKAKE IGMDWWENDPYLSSKGANNKALEEENKMLHERLKTLEEKIETKR | 403 |
| gvpT | MATETKLDNTQAENKENKNAENGSKEKNGSKASKTTSSGPIKRAVAGGIIGATI GYVSTPENRKSLLDRIDTDELKSKASDLGTKVKEKSKSSVASLKTSAGSLFKKDK DKSKDDEENVNSSSSETEDDNVQEYDELKEENQTLQDRLSQLEEKMNMLVELS LNKNQDEEAEDTDSDEEENDENDENDENEQDDENEEETSKPRKKDKKEAEEEE SESDEDSEEEEEDSRSNKKNKKVKTEEEDEDESEEEKKEAKPKKSTAKKSKNTK AKKNTDEEDDEATSLSSEDDTTA | 404 |
| gvpU | MSTGPSFSTKDNTLEYFVKASNKHGFSLDISLNVNGAVISGTMISAKEYFDYLSE TFEEGSEVAQALSEQFSLASEASESNGEAEAHFIHLKNTKIYCGDSKSTPSKGKIF WRGKIAEVDGFFLGKISDAKSTSKKSS | 405 |

TABLE 9

Amino acid sequences of exemplary GVS and GVA proteins from *Serratia* sp.

| GVA Protein | Amino acid sequence | SEQ ID NO.: |
|---|---|---|
| gvpA1 | MAKVQKSTDSSSLAEVVDRILDKGIVIDAWVKVSLVGIELLSIEARVVIASVETY LKYAEAIGLTASAATPA | 406 |
| gvpA2 | MPVNKQYQDEQQQVSLCEALDRVLNKGVVIVADITISVANIDLIYLSLQALVSSV EAKNRLPGRE | 407 |
| gvpA3 | MPVNKQYQDEQQQVSLCEALDRVLNKGVVIVADITISVANIDLIYLSLQALVSSV EAKNRLPGRE | 408 |
| gvpc | MGCLTDGMAQLRKNIDDSHESRIAQQNARVSSVSAQIAGFSTTRARNAAQDAR ARATFVADNVRGVNRMLSDFCHTREVMSRQQSEERATFVTDMSKKTLALLDGF NAERKSMAERCAKERADFIANVANDVAAFLSASEKDRMAAHAVFFGMTLAKK KTSLAV | 409 |
| gvpN | MIKQNTVSQYTVDDDLVVPEASEHFVATSYVNDIIERALVYLRAGYPVHFAGPS GIGKTTLAFHLAALWGRPVTMLQGNEEFVSSDLTGKDIGYRKSSLVDNYIHSVL KTEEQMNRMWVDNRLTTACRNGDMLIYDEFNRSKAETNNVLLSVLSEGILNLP GLRGVGEGYLDVHPEFRAIFTSNPEEYAGTHKTQDALMDRMITINIGLVDRDTEL QILHARSELELKEAAYIVDIIRELRGNEHETKHGLRAGIAIAHILHQQGIKPRYGD KLFHAICYDVLSMDAAKIQHAGRSIYREMVDGVIRKICPPIGSDTVKASTQKIKA VE | 410 |

TABLE 9-continued

Amino acid sequences of exemplary GVS and GVA proteins from Serratia sp..

| GVA Protein | Amino acid sequence | SEQ ID NO.: |
|---|---|---|
| gvpV | MAISTRPLRTLSDIKTHSGRVSGEHQTYRDYFQIGALELERWRRTREREAASSRI ASIDERIADIDKEKAALLADATAASAVAENNDKSEAAEKKKKSSGLRIKY | 411 |
| gvpF1 | MMSIDKSRNHRAKVLYALCVSDDSTPNYKIRGLEAAPVYSIDQDGLRAVVSDTL STRLRPERRNITAHQAVLHKLTEEGTVLPMRFGVIARNAEAVKNLLVANQDTIR EHFERLDGCVEMGLRVSWDVTNIYEYFVATYPVLSETRDEIWNGNSNANNHRE EKIRLGNLYESLRSGDRKESTEKVKEVLLDYCEEIIENPVKKEKDVMNLACLVA RERMDEFAKGVFEASKLFDNVYLFDYTGPWAPHNFVTLDLHAPTAKKKTLTRA GTLSD | 412 |
| gvpF2 | MTMNTEAQTEQAIYLYGLTLPDLAAPPILGVDNQHPINTHQCAGLNAVISPVALS DFTGEKGEDNVQNVTWLTPRICRHAQIIDSLMAQGPVYPLPFGTLFSSQNALEQE MKSRATDVFVSLRRITGCQEWALEATLDRKQAVDVLFTEGLDSGRFCLPEAIGR RHLEEQKLRRRLTTELSDWLAHALTAMQNELHPLVRDFRSRRLLDDKILHWAY LLPVEDVAAFQQQVADIVERYEAYGFSFRVTGPWAAYSFCQPDES | 413 |
| gvpF3 | MSLLLYGIVAEDTQLALEPDGSPHAGEEPMQLVKAATLAALVKPCEADVSREPA AALAFGQQIMHVHQQTTIIPIRYGCVLADEDAVTQHLLNHEAHYQTQLVELENC DEMGIRLSLASAEDNAVTTPQASGLDYLRSRKLAYAVPEHAERQAALLNNAFT GLYRRHCAEISMENGQRTYLLSYLVPRTGLQAFRDQFNTLANNMTDIGVISGPW PPYNFAS | 414 |
| gvpG | MLLIDDILFSPVKGVMWIFRQIHELAEDELAGEADRIRESLTDLYMLLETGQITED EFEQQEAVLLDRLDALDEEDDMLGDEPGDDEDDEYEEDDDEEDDDEEDDDDE DDDDEDDDDEEDDDDDEDDDDEDEPEGTTK | 415 |
| gvpW | MKPAIYPKFLLESPLKLVFFGGKGGVGKSTCATSTALRLAQEQPQHHFLLVSTDP AHSLQNILSDLVLPKNLDVRELNAAASLHEFKSQHEGVLKEIAYRGTVLDQNDV QGLMDTALPGMDELAAYLEIAEWIQKDTYYRIIIDTAPTGHTLRLLEMPDLIYRW LTALDTLLAKQRYIRKRFAGDNRLDHLDHFLLDMNDSLKAMHELVTDSTRCCF VLVMLAEAMSVEESIDLAGALNQQRVFLSDLVVNRLFPENDCPTCCVERNRQM LALQNGYQRLPGHVFWTLPLLAIEPRGALLHEFWSGVRLLDENEVMATTCHHQ LPLRVESSISLPASTFRLLIFAGKGGVGKTTLACATALRLNSEYPELRILLFSADPA HSLSDCLGVTLQQQPISVLVNIDAQEINAQADFDKIRQGYRAELEAFLLDTLPNL DITFDREVLEHLLDLAPPGLDEIMALTAIMDHLDSGRYDMVIVDGAPSGHLLRLL ELPELIRDWLKQFFSLLLKYRKVMRFPHLSERLVQLSRELKNLRALLQDTKQTG LYAVTVPTHLALEKTYEMTCALQRLGLTANALFINQITPPSDCTLCQAITSRESLE LKCADEMFPSQPHAQIFRQTEPTGLSKLKTLGSALFL | 416 |
| gvpK | MTTNQLSHHSPVFGPTSPAIQRPITEANRHKIDIDGERVRDGLAQLVLTLVKLLH ELLERQAIRRMDSGSLSDEEVERLGLALMRQAEEELTHLCDVFGFKDDDLNLDLG PLGRLL | 417 |
| gvpX | MVNTTNDINAATRGLLLRMGNAWFEQDELRQAVDIYLKIIEQYPDSKESKTAQT ALLTISQRYERDGLFRLSLDILERVGEITPTSI | 418 |
| gvpY | MRALIHFPIIHSPKDLGTLSEAASHLRTETQTRAYLAAVEGFWTMITTTIEGLDLD YTHLKLYQDGLPVCGKENEIVTDVANAGSQNYKLLLTLQHKGAILMGTESPELL LQERDLMTQLLQSTEQTEASLETAKTLLNRRDDYIAQRIDETLQDGEMAILFLGL MHNIEAKLPADIVFIQPLGKPPGGESI | 419 |
| gvpH | MTGNVEGILRGLGDLVEKLVETGEQIKRSGAFDIDTNDGKNAKAVYGFSIKMGL DGNQENRVEPFGNIRRDEQTGEATVQEVSEPLVDVIEESDHVLVLAEMPGVADE DVQVELNGDILTLHSERGSKKYHKEIVLPCSFDDKAMERSCRNGILEVKLGK | 420 |
| gvpZ | MSEELKLKVAEALPKDAGRGYARLDPADMARLNLAVGDIVQLTSKKGTGIAKL MPTYPDMRNKGIVQLDGLTRRNTSLSLDEKVQIEPASCKHATQIVLIPTTITPNQR DLDYIGSLLDGLPVQKGDLLRAHLFGSRSADFKVESTIPDGAVLIDPTTTLVIGKS NAVGNSSHSTQRLSYEDVGGLKNQVRRIREMIELPLRYPEVFERLGIDAPKGVLL SGPPPGCGKTLIARIIAQETDAQFFTISGPEIVHKFYGESEAHLRKIFEEAGRKGPSII FLDEIDSIAPHRDKVVGDVEKRIVAQLLALMDGLKNRGKVIVIAATNLPNAIDPA LRRPGRFDREISIPIPDREGRREIIEIHSTGMPLNADVDLNVLADITHGFVGADLEA LCREAAMSALRRLLPEIDFSSAELPYDRLAELTVMMDDFRAALCEVSPSAIRELF VDIPDVRWEDVGGLDDVRRRLIESVEWPIKYPELYEQAGVKPPKGLLLAGPPGV GKTLIAKAVANESGVNVISVKGPALMSRYVGDSEKGVRELFLKARQAAPCIIFLD EVDSVIPARNEGAIDSHVAERVLSQFLSEMDGLEELKGVFVMGATNRADLIDPA MLRPGRFDEIIELGLPDEDARRQILAVHLRNKPLGDNIHADDLAERCDGASGAEL AAVCNRAALAALRRAIQQSEEAVLSPSTVGETPVALTVRIEQHDFAEVIAEMFG DDA | 421 |

TABLE 10

Amino Acid Sequences of GV proteins from *Anabaena flos-aquae*

| gvp gene | Sequence | SEQ ID NO: |
|---|---|---|
| gvpA | MAVEKTNSSSSLAEVIDRILDKGIVIDAWVRVSLVGIELLAIEARIVIASVETYLK YAEAVGLTQSAAVPA | 422 |
| gvpC | MISLMAKIRQEHQSIAEKVAELSLETREFLSVTTAKRQEQAEKQAQELQAFYKD LQETSQQFLSETAQARIAQAEKQAQELLAFHKELQETSQQFLSATAQARIAQAEK QAQELLAFYQEVRETSQQFLSATAQARIAQAEKQAQELLAFHKELQETSQQFLS ATADARTAQAKEQKESLLKFRQDLFVSIFG | 423 |
| gvpN | MTTTKVNHKRAVLRLRPGQFVVTPAIERVAIRALRYLKSGFPVHLRGPAGTGKT TLAMHLANCLDRPVMLLFGDDQFKSSDLIGSESGYTHKKVLDNYIHSVVKLEDE FKQNWVDSRLTLACREGFTLVYDEFNRSRPEVNNVLLSALEEKILSLPPSSNQPE YLSVNPQFRVIFTSNPEEYAGVHSTQDALMDRLVTISMPEPDEITQTEILIQKTNID RESANFIVRLVKSFRLATGAEKTSGLRSCLMIAKVCADNNIPVTTESLDFPDIAIDI LFNRSHLSMSESTNIFLELLDKFSAEELEILNNRVTGDNDFLIDNSQFVSQQLAGQ PN | 424 |
| gvpJ | MLPTRPQTNSSRTINTSTQGSTLADILERVLDKGIVIAGDISISIASTELVHIRIRLLI SSVDKAKEMGINWWESDPYLSTKAQRLVEENQQLQHRLESLEAKLNSLTSSSVK EEIPLAADVKDDLYQTSAKIPSPVDTPIEVLDFQAQSSGGTPPYVNTSMEILDFQA QTSAESSSPVGSTVEILDFQAQTSEESSSPVVSTVEILDFQAQTSEESSSPVGSTVEI LDFQAQTSEEIPSSVDPAIDV | 425 |
| gvpK | MVCTPAENFNNSLTIASKPKNEAGLAPLLLTVLELVRQLMEAQVIRRMEEDLLS EPDLERAADSLQKLEEQILHLCEMFEVDPADLNINLGEIGTLLPSSGSYYPGQPSS RPSVLELLDRLLNTGIVVDGEIDLGIAQIDLIHAKLRLVLTSKPI | 426 |
| gvpF | MSIPLYLYGIFPNTIPETLELEGLDKQPVHSQVVDEFCFLYSEARQEKYLASRRNL LTHEKVLEQTMHAGFRVLLPLRFGLVVKDWETIMSQLINPHKDQLNQLFQKLA GKREVSIKIFWDAKAELQTMMESHQDLKQQRDNMEGKKLSMEEVIQIGQLIEIN LLARKQAVIEVFSQELNPFAQEIVVSDPMTEEMIYNAAFLIPWESESEFSERVEVI DQKFGDRLRIRYNNFTAPYTFAQLDS | 427 |
| gvpG | MLTKLLLLPIMGPLNGVVWIAEQIQERTNTEFDAQENLHKQLLSLQLSFDIGEIGE EEFEIQEEEILLKIQALEEEARLELEAEQEEARLELEAEQEDFEYPPQFTAEVNKD QHLVLLP | 428 |
| gvpV | MIKNIQVFFMKTISNRSISRAKISTMPRPKSDASSQLDLYKMVTEKQRIQRDMYSI KERMGLLQQRLDILNQQIEATEKTIHKLRQPHSNTAQNIVRSNIFVESNNYQTFE VEY | 429 |
| gvpW | MELENLYTYAFLEIPSSPLILPQGAANQVVLINGTELAAIVEPGIFLESFQNNDEKII QMALSHDRVICELFQQITVLPLRFGTYFTSTNNLLNHLKSHEKEYQNKLEKINGK NEFTLKLIPRMIEEIVPSEGGGKDYFLAKKQRYQNQNNFSIAQAAEKQNLIDLITK VNQLPVVVQEQEEQIQIYLLVSCQDKTLLLEQFLTWQKACPKWDLLLGDCLPPY HFI | 430 |

Example 5: Identification of Alternative *B. megaterium* Gene Cluster Detectable by TEM in *E. coli*

The Gas Vesicle gene cluster of Table 8 above was tested to identify possible alternative clusters detectable by TEM.

Figure 7:
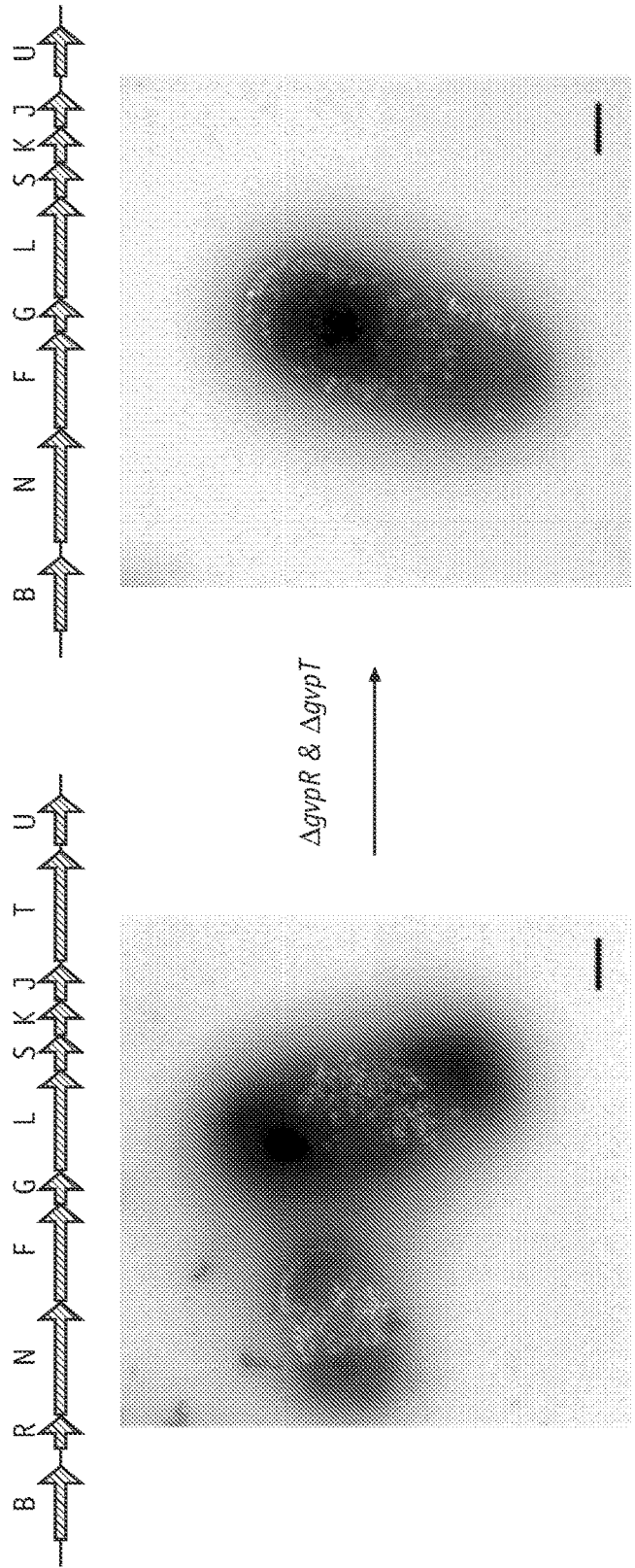
FIG. 7 illustrates the expression of an exemplary *B. megaterium* gene cluster for gas vesicle formation. In particular, FIG. 7 top panel shows a schematic representation of bacterial gas vesicle gene clusters used for heterologous expression of gas vesicles in *E. coli*.

In particular, the *B. megaterium* gene cluster can be expressed in *E. coli* Rosetta 2(DE3)pLysS cells using the two construct schematically illustrated in FIG. 7 top panel.

The formation of gas vesicles was detected through Transmission Electronic Microscopy (TEM) after expression of gas vesicles genes for 22 hours.

The results shown in FIG. 7 bottom panel indicate that gvpR and gvpT genes in the *B. megaterium* gene cluster are not necessary for gas vesicle formation.

Therefore, the following alternative GV cluster including 9 gyp gene sequences of *B. megaterium* genes shown in the following Table 11 and FIG. 12B was identified as detectable by TEM and ultrasound in mammalian cells (HEK293 and CHO-Ki).

| Gene | Sequence | Seq ID NO: |
|---|---|---|
| gvpB | ATGAGCATCCAGAAGTCCACCAACAGCAGCAGCCTGGCCGAAGTGAT CGACCGGATCCTGGACAAGGGCATCGTGATCGACGCCTTCGCCAGAG TGTCCGTCGTGGGCATCGAGATCCTGACCATCGAGGCCAGAGTCGTG ATCGCCAGCGTGGACACCTGGCTGAGATATGCCGAAGCCGTGGGCCT GCTGCGGGACGACGTGGAAGAAAATGGCCTGCCCGAGCGGAGCAAC AGCTCTGAGGGACAGCCCCGGTTCAGCATCTGA | 431 |

-continued

| Gene | Sequence | Seq ID NO: |
|---|---|---|
| gvpN | ATGACCGTGCTGACCGACAAGCGGAAGAAGGGCAGCGGCGCCTTCAT CCAGGACGACGAGACAAAAGAGGTGCTGAGCAGAGCCCTGAGCTAC CTGAAGTCCGGCTACAGCATCCACTTCACCGGACCTGCCGGCGGAGG CAAGACATCTCTGGCTAGAGCCCTGGCCAAGAAACGGAAGCGGCCCG TGATGCTGATGCACGGCAACCACGAGCTGAACAACAAGGACCTGATC GGCGATTTCACCGGCTACACCAGCAAGAAAGTGATCGACCAGTACGT GCGGAGCGTGTACAAGAAAGACGAACAGGTGTCCGAGAACTGGCAG GACGGCAGACTGCTGGAAGCCGTGAAGAATGGCTACACCCTGATCTA CGACGAGTTCACCAGAAGCAAGCCCGCTACCAACAACATCTTCCTGA GCATCCTGGAAGAGGGCGTGCTGCCCCTGTACGGCGTGAAGATGACC GACCCTTTCGTGCGCGTGCACCCCGACTTCAGAGTGATCTTCACCAGC AACCCCGCCGAGTATGCCGGCGTGTACGATACCCAGGACGCCCTGCT GGACCGGCTGATCACCATGTTCATCGACTACAAGGACATCGACCGGG AAACCGCCATCCTGACCGAGAAAACCGACGTGGAAGAGGACGAGGC CCGGACCATCGTGACCCTGGTGGCCAACGTGCGGAACAGAAGCGGCG ACGAGAATAGCAGCGGCCTGAGCCTGAGAGCCAGCCTGATGATTGCC ACCCTGGCCACCCAGCAGGACATCCCTATCGATGGCAGCGACGAGGA CTTCCAGACCCTGTGCATCGACATCCTGCACCACCCCCTGACCAAGTG CCTGGACGAGAAAACGCCAAGAGCAAGGCCGAGAAGATCATTCTG GAAGAGTGCAAGAACATCGACACCGAGGAAAAGTGA | 432 |
| gvpF | ATGAGCGAGACAAACGAGACAGGCATCTACATCTTCAGCGCCATCCA GACCGACAAGGACGAGGAATTCGGCGCCGTGGAAGTGGAAGGGACC AAGGCCGAGACATTCCTGATCCGGTACAAGGACGCCGCCATGGTGGC CGCCGAAGTGCCCATGAAGATCTACCACCCCAACCGGCAGAACCTGC TGATGCACCAGAATGCCGTGGCCGCCATCATGGACAAGAACGACACC GTGATCCCCATCCAGCTTCGGCAACGTGTTCAAGAGCAAAGAGGACGT GAAGGTGCTGCTGGAAAACCTGTACCCCCAGTTCGAGAAGCTGTTCC CCGCCATCAAGGGAAAGATCGAAGTGGGCCTGAAAGTGATCGGCAA GAAAGAGTGGCTGGAAAAGAAAGTGAACGAGAACCCCGAGCTGGAA AAAGTGTCCGCCAGCGTGAAGGGCAAGAGCGAGGCCGCTGGCTACT ACGAGAGAATCCAGCTGGGCGGCATGGCCCAGAAGATGTTCACCAGC CTGCAGAAAGAAGTGAAAACCGACGTGTTCAGCCCCCTGGAAGAAG CCGCCGAGGCCGCCAAAGCCAATGAGCCTACAGGCGAGACAATGCT GCTGAACGCCAGCTTCCTGATCAACAGAGAGGACGAGGCCAAGTTCG ACGAAAAAGTGAATGAGGCCCACGAACTGGAAGGATAAGGCCGA CTTCCACTACAGCGGCCCCTGGCCCGCCTACAACTTCGTGAACATCCG GCTGAAGGTGGAAGAGAAGTGA | 433 |
| gvpG | ATGCTGCACAAGCTCGTGACCGCCCCCATCAACCTGGTCGTGAAGAT CGGCGAGAAGGTGCAGGAAGAGGCCGACAAGCAGCTGTACGACCTG CCCACCATCCAGCAGAAGCTGATCCAGCTGCAGATGATGTTCGAGCT GGGCGAGATCCCCGAGGAAGCCTTCCAGGAAAAAGAGGACGAGCTG CTGATGAGATACGAGATCGCCAAGCGGCGCGAGATCGAGCAGTGGG AGGAACTGACCCAGAAGCGGAACGAGGAAAGCTGA | 434 |
| gvpL | ATGGGCGAGCTGCTGTACCTGTACGGCCTGATCCCCACCAAAGAGGC CGCTGCCATCGAGCCCCTTCCCATTCTACAAGGGCTTCGACGGCGAGC ACAGCCTGTACCCTATCGCCTTCGACCAAGTGACCGCCGTGGTGTTCA AGCTGGACGCCGACACCTACAGCGAGAAAGTGATCCAGGAAAAGAT GGAACAGGACATGAGCTGGCTGCAGGAAAAGGCCTTCCACCACCAC GAGACAGTGGCCGCCCTGTACGAGGAATTCACCATCATCCCCCTGAA GTTCTGCACCATCTATAAGGGCGAGGAATCCCTGCAGGCCGCCATCG AGATCAACAAAGAAGATCGAGAACTCCCTGACCCTGCTGCAGGGC AACGAGGAATGGAACGTGAAGATCTACTGCGACGACACCGAGCTGA AGAAGGGCATCAGCGAGACAAACGAGAGCGTGAAGGCCAAGAAGCA GGAAATCAGCCACCTGAGCCCCGGCAGACAGTTCTTCGAGAAGAAGA AGATTGACCAGCTGATCGAGAAAGAGCTGGAACTGCACAAGAACAA AGTGTGCGAGGAAATCCACGACAAGCTGATTGAGCTGAGCCTGTACG ACTCCGTGAAGAAGAACTGGTCCAAGGACGTGACCGGCGCTGCCGAA CAGATGGCCTGGAACAGCGTGTTCCTGCTGCCCAGCCTGCAGATCAC CAAGTTCGTGAACGAGATCGAGGAACTGCAGCAGCGGCTGGAAAAC AAGGGCTGGAAGTTCGAAGTGACCGGCCCCTGGCCTCCCTACCACTT CAGCAGCTTTGCCTGA | 435 |
| gvpS | ATGAGCCTGAAGCAGAGCATGGAAAACAAGGATATCGCCCTGATCG ACATCCTGGACGTGATCCTGGACAAGGGCGTGGCCATCAAGGGCGAC CTGATCATCTCTATCGCCGGCGTGGACCTGGTGTACCTGGACCTGAGA GTGCTGATCTCCAGCTGGAAACCCTGGTGCAGGCCAAAGAGGGCAA CCACAAGCCCATCACCAGCGAGCAGTTCGACAAGCAGAAAGAGGAA CTGATGGACGCCACCGGCCAGCCCAGCAAGTGGACAAATCCTCTGGG CAGC | 436 |
| gvpK | ATGCAGCCCGTGTCCCAGGCCAACGGCAGAATCCACCTGGATCCCGA TCAGGCCGAACAGGGACTGGCCCAGCTCGTGATGACCGTGATCGAGC TGCTGCGGCAGATCGTGGAACGGCACGCCATGAGAAGAGTGGAAGG | 437 |

| Gene | Sequence | Seq ID NO: |
|---|---|---|
| | CGGCACCCTGACCGACGAGCAGATCGAGAATCTGGGAATCGCCCTGA<br>TGAACCTGGAAGAGAAGATGGACGAGCTGAAAGAGGTGTTCGGACT<br>GGACGCCGAGGACCTGAACATCGACCTGGGCCCTCTGGGCAGCCTGC<br>TGTGA | |
| gvpJ | ATGGCCGTGGAACACAACATGCAGAGCAGCACCATCGTGGACGTGCT<br>GGAAAAGATCCTGGACAAGGGCGTCGTGATCGCCGGGGACATCACA<br>GTGGGAATCGCCGACGTGGAACTGCTGACCATCAAGATCCGGCTGAT<br>CGTGGCCAGCGTGGACAAGGCCAAAGAAATCGGCATGGATTGGTGG<br>GAGAACGACCCCTACCTGAGCAGCAAGGGCGCCAACAACAAGGCCC<br>TGGAAGAGGAAAACAAGATGCTGCACGAGCGGCTGAAAACACTGGA<br>AGAGAAGATCGAGACAAAGCGCTGA | 438 |
| gvpU | ATGAGCACCGGCCCCAGCTTCAGCACCAAGGACAACACCCTGGAATA<br>CTTCGTGAAGGCCAGCAACAAGCACGGCTTCAGCCTGGACATCAGCC<br>TGAACGTGAACGGGGCCGTGATCAGCGGCACCATGATCAGCGCCAAA<br>GAGTACTTCGACTACCTGAGCGAGACATTCGAAGAGGGCAGCGAGGT<br>GGCCCAGGCCCTGTCTGAGCAGTTTAGCCTGGCCAGCGAGGCCTCCG<br>AGTCTAATGGCGAAGCCGAGGCCCACTTCATCCACCTGAAGAACACC<br>AAGATCTACTGCGGCGACAGCAAGAGCACCCCCAGCAAGGGCAAGA<br>TCTTCTGGCGCGGCAAGATCGCCGAGGTGGACGGATTCTTCCTGGGA<br>AAGATCAGCGACGCCAAGTCCACCAGCAAGAAGTCCAGCTGA | 439 |

Each gene is cloned in pCMVSport plasmid which contains CMV promoter upstream of each gene and SV40 polyadenylation tail downstream of each gene, as illustrated in FIG. 12B. The gene cassettes elements of the pCMVSport plasmid are reported in Table 11a below.

TABLE 11a

Additional elements of the GVP cassettes

| Element | Sequence | SEQ ID NO: |
|---|---|---|
| CMV enhancer/ CMV promoter | CGTTACATAACTTACGGTAAATGGCCCGCCTGGCTGACCGCCCAACGAC<br>CCCCGCCCATTGACGTCAATAATGACGTATGTTCCCATAGTAACGCCAA<br>TAGGGACTTTCCATTGACGTCAATGGGTGGAGTATTTACGGTAAACTGC<br>CCACTTGGCAGTACATCAAGTGTATCATATGCCAAGTACGCCCCCTATT<br>GACGTCAATGACGGTAAATGGCCCGCCTGGCATTATGCCCAGTACATGA<br>CCTTATGGGACTTTCCTACTTGGCAGTACATCTACGTATTAGTCATCGCT<br>ATTACCATGGTGATGCGGTTTTGGCAGTACATCAATGGGCGTGGATAGC<br>GGTTTGACTCACGGGGATTTCCAAGTCTCCACCCCATTGACGTCAATGG<br>GAGTTTGTTTTGGCACCAAAATCAACGGGACTTTCCAAAATGTCGTAAC<br>AACTCCGCCCCATTGACGCAAATGGGCGGTAGGCGTGTACGGTGGGAG<br>GTCTATATAAGCAGAGCT | 440 |
| SV40 poly- adenylation tail | AACTTGTTTATTGCAGCTTATAATGGTTACAAATAAAGCAATAGCATCAC<br>AAATTTCACAAATAAAGCATTTTTTTCACTGCATTCTAGTTGTGGTTTGTC<br>CAAACTCATCAATGTATCTTATCATGTCTGGATC | 441 |

Example 6 Construction of a GVES Configured for Expression in Mammalian Cells Using the genes of the exemplary *B. megaterium* cluster reported in Table 11 above, the development of a synthetic mammalian operon with the minimum number of genes required to produce gas vesicles was investigated.

For this, the Applicant turned to viral elements that have evolved to exploit the eukaryotic genetic machinery to allow for the expression of multiple genes from a single promoter (polycistronic gene expression).

The most common elements used the internal ribosomal entry sequence (IRES) and the 2A self-cleavage peptide [42]. Briefly, when placed between two genes the IRES region of the transcribed mRNA form a secondary structure that enables cap-independent ribosomal entry leading to co-translation of the downstream gene.

Alternatively, by placing the 2A self-cleavage peptide element between two genes, the resultant mRNA sequence causes a 'ribosomal skip' that releases the first protein and proceeds to translate the second protein. The 2A element has a smaller genetic footprint and higher co-expression efficiency for the downstream gene compared with IRES, however, its use results in n- and c-terminal modifications to the proteins.

To test if the gas vesicle genes could tolerate modifications due to the addition of element 2A, additional experiments were performed reported in the following Example 7.

Example 7: Identification of Tolerability *B. megaterium* Gene Cluster Detectable by TEM To test if the gas vesicle genes could tolerate the N- and C-terminal 2A modifications, the genes of the exemplary *B. megaterium* gene cluster of Example 5 and Table 11 were modified.

Figure 8:
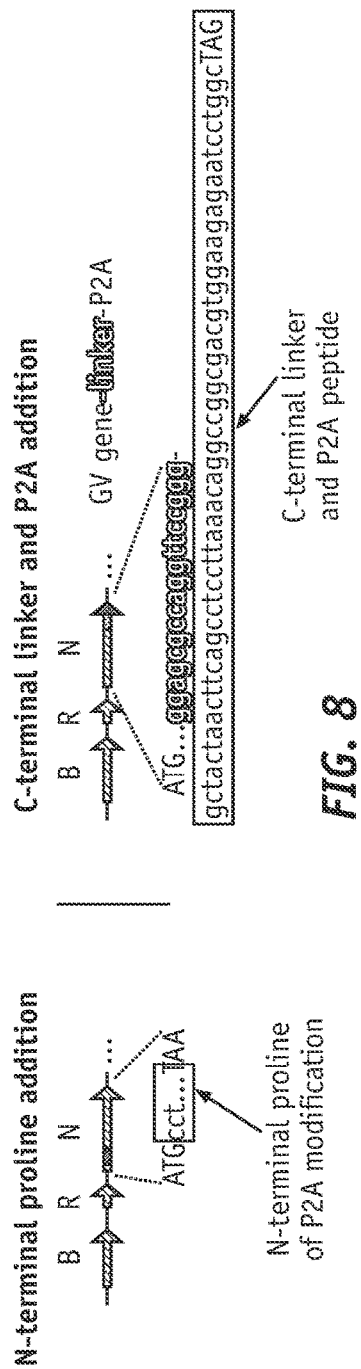
FIG. 8 shows a schematic illustration of an assay for tolerability of P2A peptide additions. In particular, FIG. 8 provides a schematic illustration of gas vesicle gene cluster with N-terminal modifications (left) or C-terminal modifications (right) of each gene (SEQ ID NO: 479 and 480) to test tolerability of P2A peptides, in a one-by-one settings in *E. coli*.

In particular, the n-terminal proline and c-terminal 24 amino acid (GAPGSGATNFSLLKQAG-DVEENPG) (SEQ ID NO: 442) modification were tested in *Escherichia coli* using the bacterial gas vesicle gene cluster, according to the approach schematically illustrated in FIG. 8.

All genes except for the structural protein gas vesicle protein B tolerated the n- and c-terminal 2A modifications) as shown by the results summarized in the following Table 12.

TABLE 12

| Gene | GVs after N-term addition? | GVs after C-term addition? |
| --- | --- | --- |
| gvpB | — | No |
| gvpR | Yes | Yes |
| gvpN | Yes | Yes |
| gvpF | Yes | Yes |
| gvpG | Yes | Yes |
| gvpL | Yes | Yes |
| gvpS | Yes | Yes |
| gvpK | Yes | Yes |
| gvpJ | Yes | Yes |
| gvpT | Yes | Yes |
| gvpU | Yes | Yes |

In particular, the results of Table 12 above indicate tolerability of P2A peptide additions to *B. megaterium* gas vesicle genes. Each gene of the *B. megaterium* gene cluster was modified with an N-terminal proline after the start codon or with a linker and P2A peptide at the C-terminus, resulting in a total of 21 unique GV gene clusters as illustrated in FIG. 8, *E. coli* were transformed with each plasmid and gas vesicles were induced for expression for a total of 22 hours and assayed for the presence of gas vesicles using TEM. The table indicates whether gas vesicles were observed by TEM. Expression and TEM imaging performed as in [43].

Example 8: Engineering of a GVPC Construct

An exemplary polynucleotide construct was provided including all the genes of the GV gene cluster of *B. megaterium* reported in Table 11. A GVPC construct was therefore provided using the related GVA genes separated by a separation elements encoding peptide 2A.

The sequence of this exemplary GVPC construct in which the gyp genes are included in a pCMVSport backbone is reported in Table 13 below, gyp N, F, G, L, S, K, J, U and EmGFP are separated by GAPGSG-p2A sequence.

TABLE 13

Exemplary GVPC construct

| Construct | Sequence | SEQ ID NO: |
| --- | --- | --- |
| CMV:gvp NFGLSKJU- EmGFP: polyA | CGTTACATAACTTACGGTAAATGGCCCGCCTGGCTGACCGCCCAACGACCC<br>CCGCCCATTGACGTCAATAATGACGTATGTTCCCATAGTAACGCCAATAGG<br>GACTTTCCATTGACGTCAATGGGTGGAGTATTTACGGTAAACTGCCCACTTG<br>GCAGTACATCAAGTGTATCATATGCCAAGTACGCCCCCTATTGACGTCAATG<br>ACGGTAAATGGCCCGCCTGGCATTATGCCCAGTACATGACCTTATGGGACTT<br>TCCTACTTGGCAGTACATCTACGTATTAGTCATCGCTATTACCATGGTGATG<br>CGGTTTTGGCAGTACATCAATGGGCGTGGATAGCGGTTTGACTCACGGGGA<br>TTTCCAAGTCTCCACCCCATTGACGTCAATGGGAGTTTGTTTTGGCACCAAA<br>ATCAACGGGACTTTCCAAAATGTCGTAACAACTCCGCCCCATTGACGCAAA<br>TGGGCGGTAGGCGTGTACGGTGGGAGGTCTATATAAGCAGAGCTCGTTTAG<br>TGAACCGTCAGATCGCCTGGAGACGCCATCCACGCTGTTTTGACCTCCATAG<br>AAGACACCGGGACCGATCCAGCCTCCGGACTCTAGCCTAGGCTTTTGCAAA<br>AAGCTATTTAGGTGACACTATAGAAGGTACGCCTGCAGGTACCGAGCTCGG<br>ATCCAGTACCCTTCACCATGACCGTGCTGACCGACAAGCGGAAGAAGGGCA<br>GCGGCGCCTTCATCCAGGACGACGAGACAAAAGAGGTGCTGAGCAGAGCC<br>CTGAGCTACCTGAAGTCCGGCTACAGCATCCACTTCACCGGACCTGCCGGC<br>GGAGGCAAGACATCTCTGGCTAGAGCCCTGGCCAAGAAACGGAAGCGGCC<br>CGTGATGCTGATGCACGGCAACCACGAGCTGAACAACAAGGACCTGATCGG<br>CGATTTCACCGGCTACACCAGCAAAAAGGTGATCGACCAGTACGTGCGGAG<br>CGTGTACAAGAAAGACGAACAGGTGTCCGAGAACTGGCAGGACGGCAGAC<br>TGCTGGAAGCCGTGAAGAATGGCTACACCCTGATCTACGACGAGTTCACCA | 443 |

TABLE 13-continued

Exemplary GVPC construct

| Construct | Sequence | SEQ ID NO: |
|---|---|---|
| | GAAGCAAGCCCGCTACCAACAACATCTTCCTGAGCATCCTTGAGGAGGGCG<br>TGCTGCCCCTGTACGGCGTGAAGATGACCGACCCTTTCGTGCGCGTGCACCC<br>CGACTTCAGAGTGATCTTTACCAGCAACCCCGCCGAGTATGCCGGCGTGTA<br>CGATACCCAGGACGCCCTGCTGGACCGGCTGATCACCATGTTCATCGACTA<br>CAAGGACATCGACCGGGAAACCGCTATCCTGACCGAGAAAACTGACGTGG<br>AAGAAGACGAGGCCCGGACCCATCGTGACCCTGGTGGCCAACGTGCGGAAC<br>AGAAGCGGCGACGAGAATAGCAGCGGCCTGAGCCTGAGAGCCAGCCTGAT<br>GATTGCCACCCTGGCCACCCAGCAGGACATCCCTATCGATGGCAGCGACGA<br>GGACTTCCAGACCCTGTGCATCGACATCCTGCACCACCCCTGACCAAGTGC<br>CTGGACGAAGAGAACGCCAAGAGCAAGGCCGAGAAGATCATTCTCGAAGA<br>GTGCAAGAACATCGACACCGAGGAGAAGGGTGCCCCGGGATCTGGCGCAA<br>CAAATTTTAGTCTTTTAAAGCAGGCAGGAGACGTCGAGGAAAACCCTGGAC<br>CCGTGAGCGAGACAAACGAGACAGGCATCTACATCTTCAGCGCCATCCAGA<br>CAGACAAGGATGAGGAATTCGGCGCCGTGGAAGTGGAAGGGACCAAGGCT<br>GAGACATTCCTGATCCGGTATAAGGACGCCGCCATGGTGGCCGCCGAAGTG<br>CCCATGAAGATCTACCACCCCAACCGGCAGAACCTGCTGATGCACCAGAAT<br>GCCGTGGCCGCCATCATGGACAAGAACGACACCGTGATCCCCATCAGCTTC<br>GGCAACGTGTTCAAGAGCAAAGAGGACGTGAAGGTGCTCCTGGAAAACCT<br>GTACCCCCAGTTCGAGAAGCTGTTCCCCGCCATCAAGGGAAAGATCGAAGT<br>GGGCCTGAAGGTGATCGGCAAGAAAGAGTGGCTCGAAAAGAAAGTGAACG<br>AGAACCCCGAGCTGGAAAAAGTGTCCGCCAGCGTGAAGGGCAAGAGCGAG<br>GCCGCTGGCTACTACGAGAGAATCCAGCTGGGCGGCATGGCCCAGAAGATG<br>TTCACAAGCCTGCAGAAAGAAGTGAAAACCGACGTGTTCAGCCCCCTGGAA<br>GAAGCCGCCGAGGCCGCCAAAGCCAATGAGCCTACAGGCGAAACAATGCT<br>GCTGAACGCCAGCTTCCTGATCAACAGAGAGGATGAGGCCAAGTTCGACGA<br>GAAAGTCAATGAGGCCCACGAGAACTGGAAGGATAAGGCCGACTTCCACT<br>ACAGCGGCCCCTGGCCCGCCTACAACTTCGTGAACATCCGGCTGAAGGTGG<br>AAGAGAAGGGGGCACCTGGCTCGGGAGCGACCAACTTCTCATTACTCAAAC<br>AAGCCGGAGACGTTGAGGAGAATCCAGGCCCTGTGCTGCACAAGCTCGTGA<br>CCGCCCCCATCAACCTGGTCGTGAAGATCGGCGAGAAGGTGCAGGAAGAG<br>GCCGACAAGCAGCTGTACGACCTGCCCACCATCCAGCAGAAGCTGATCCAG<br>CTGCAGATGATGTTCGAGCTGGGCGAGATCCCCGAGGAAGCCTTCCAGGAA<br>AAAGAGGACGAACTGCTGATGAGATACGAGATCGCCAAGCGGCGCGAGAT<br>TGAGCAGTGGGAAGAACTGACCCAGAAGCGGAATGAGGAAAGCGGTGCCC<br>CGGGATCTGGCGCAACAAATTTTAGTCTTTTAAAGCAGGCAGGAGACGTCG<br>AGGAAAACCCTGGACCCGTGGGCGAGCTGCTGTACCTCTACGGCCTGATCC<br>CCACCAAAGAGGCCGCTGCTATCGAGCCCTTCCCATTCTACAAGGGCTTCG<br>ACGGCGAGCACAGCCTGTACCCTATCGCCTTCGACCAAGTGACCGCCGTGG<br>TGTTCAAGCTGGACGCCGACACCTACAGCGAGAAAGTGATCCAGGAAAAG<br>ATGGAACAGGACATGAGCTGGCTGCAGGAAAAGGCCTTCCACCACCACGA<br>GACAGTGGCCGCCCTGTATGAGGAATTCACCATCATCCCCCTGAAGTTCTGC<br>ACCATCTATAAGGGAGAGGAATCCCTGCAGGCCGCCATCGAGATCAACAAA<br>GAGAAGATCGAAAACTCCCTGACCCTGCTGCAGGGCAACGAGGAATGGAA<br>CGTGAAGATCTACTGCGACGACACCGAGCTGAAGAAGGGCATCAGCGAGA<br>CAAACGAGAGCGTGAAGGCCAAGAAGCAGGAAATCAGCCACCTGAGCCCC<br>GGCAGACAGTTCTTCGAGAAGAAGAAGATTGACCAGCTCATCGAGAAAGA<br>GCTGGAACTGCACAAGAACAAAGTGTGCGAGGAAATCCACGACAAGCTGA<br>TTGAGCTGAGCCTCTACGACTCCGTGAAGAAGAACTGGTCCAAGGACGTGA<br>CAGGCGCTGCCGAACAGATGGCCTGGAACAGCGTGTTCCTGCTGCCCAGCC<br>TGCAGATCACCAAGTTCGTGAACGAGATCGAGGAACTCCAGCAGCGGCTGG<br>AGAACAAGGGATGGAAGTTCGAAGTGACCGGCCCCTGGCCTCCCTACCACT<br>TCAGCAGCTTTGCCGGGGCACCTGGCTCGGGAGCGACCAACTTCTCATTACT<br>CAAACAAGCCGGAGACGTTGAGGAGAATCCAGGCCCTGTGAGCCTGAAGC<br>AGAGCATGGAGAATAAGGATATCGCCCTGATCGACATCCTCGACGTGATCC<br>TGGACAAGGGAGTGGCCATCAAGGGCGACCTGATCATCTCTATCGCCGGCG<br>TGGACCTGGTGTACCTGGATCTGAGAGTGCTGATCTCCAGCGTGGAAACCC<br>TGGTGCAGGCCAAAGAGGGCAACCACAAGCCCATCACCAGCGAGCAGTTC<br>GACAAGCAGAAAGAGGAGCTGATGGACGCCACCGGCCAGCCCAGCAAGTG<br>GACAAATCCTCTGGGCAGCGGCGCTCCCGGGTCAGGTGCCACGAATTTTTC<br>GTTGTTGAAGCAAGCTGGGGATGTTGAAGAAACCCAGGGCCTGTGCAGCC<br>CGTGTCCCAGGCCAACGGCAGAATCCACCTGGATCCCGATCAGGCCGAACA<br>GGGACTGGCCCAGCTCGTGATGACCGTGATCGAGCTGCTGCGGCAGATCGT<br>GGAACGGCACGCCATGAGAAGAGTGGAAGGCGGCACCCTGACCGACGAGC<br>AGATCGAGAATCTGGGAATCGCTCTGATGAACCTGGAGGAGAAGATGGAC<br>GAGCTGAAAGAGGTGTTCGGACTGGACGCTGAGGATCTGAACATCGACCTG<br>GGCCCTCTGGGCAGCCTGCTGGGTGCCCCGGGATCTGGCGCAACAAATTTT<br>AGTCTTTTAAAGCAGGCAGGAGACGTCGAGGAAAACCCTGGACCCGTGGCC<br>GTGGAACACAACATGCAGAGCAGCACCATCGTGGACGTGCTGGAAAAGAT<br>CCTGGACAAGGGCGTCGTGATCGCCGGGGACATCACAGTGGGAATCGCCGA<br>CGTGGAACTGCTGACCATCAAGATCCGGCTGATCGTGGCCAGCGTGGACAA<br>GGCCAAAGAAATCGGCATGATTGGTGGGAGAACGACCCCTACCTGAGCA<br>GCAAGGGCGCCAACAACAAGGCTCTGGAAGAGGAAAACAAGATGCTGCAC<br>GAGCGGCTGAAAACACTGGAAGAGAAGATCGAGACAAAGCGCGGGGCACC<br>TGGCTCGGGAGCGACCAACTTCTCATTACTCAAACAAGCCGGAGACGTTGA | |

TABLE 13-continued

Exemplary GVPC construct

| Construct | Sequence | SEQ ID NO: |
|---|---|---|
| | GGAGAATCCAGGCCCTGTGAGCACCGGCCCCAGCTTCAGCACCAAGGACAA<br>CACCCTGGAATACTTCGTGAAGGCCAGCAACAAGCACGGCTTTAGCCTCGA<br>CATCAGCCTGAACGTGAATGGGGCCGTGATTAGCGGCACCATGATCAGCGC<br>CAAAGAGTACTTCGACTACCTGAGCGAGACATTCGAAGAGGGCAGCGAAGT<br>GGCCCAGGCCCTGTCTGAGCAGTTTAGCCTGGCTAGCGAGGCCTCCGAGTC<br>TAATGGCGAAGCCGAGGCCCACTTCATCCACCTGAAGAACACCAAGATCTA<br>CTGCGGCGACAGCAAGAGCACCCCCAGCAAGGGCAAGATCTTCTGGCGCGG<br>CAAGATCGCCGAGGTGGACGGATTCTTCCTGGGAAAAATCAGCGACGCCAA<br>GTCCACCAGCAAGAAGTCCAGCGGCGCTCCCGGGTCAGGTGCCACGAATTT<br>TTCGTTGTTGAAGCAAGCTGGGGATGTTGAAGAGAACCCAGGGCCTGTGGT<br>GTCCAAGGGCGAGGAACTGTTCACCGGCGTGGTGCCCATCCTGGTGGAACT<br>GGATGGCGACGTGAACGGCCACAAGTTCAGCGTGTCCGGCGAGGGCGAAG<br>GCGACGCCACATACGGAAAGCTGACCCTGAAGTTCATCTGCACCACCGGCA<br>AGCTGCCCGTGCCTTGGCCTACCCTCGTGACCACACTGACCTACGGCGTGCA<br>GTGCTTCGCCAGATACCCCGACCACATGAAGCAGCACGATTTCTTCAAGAG<br>CGCCATGCCCGAGGGCTACGTGCAGGAACGGACCATCTTCTTCAAGGACGA<br>CGGCAACTACAAGACAAGAGCCGAAGTGAAGTTCGAGGGCGACACCCTCG<br>TGAACCGGATCGAGCTGAAGGGCATCGACTTCAAAGAGGATGGCAACATCC<br>TGGGCCACAAGCTGGAGTACAACTACAACAGCCACAAGGTGTACATCACCG<br>CCGACAAGCAGAAAAACGGCATCAAAGTGAACTTCAAGACCCGGCACAAC<br>ATCGAGGACGGCAGCGTGCAGCTGGCCGACCACTACCAGCAGAACACCCCC<br>ATCGGAGATGGCCCCGTGCTGCTGCCCGACAACCACTACCTGAGCACACAA<br>AGCGCCCTGAGCAAGGACCCCAACGAGAAGCGGGACCACATGGTGCTGCT<br>GGAATTTGTGACCGCCGCTGGCATCACCCTGGGCATGGACGAGCTGTACAA<br>GTGACTCGAGTCTAGAGGGCCCCGTGGCTGTAATCTAGAGGATCCCTCGAG<br>GGGCCCAAGCTTACGCGTGCATGCGACGTCATAGCTCTCTCCCTATAGTGAG<br>TCGTATTATAAGCTAGCTTGGGATCTTTGTGAAGGAACCTTACTTCTGTGGT<br>GTGACATAATTGGACAAACTACCTACAGAGATTTAAAGCTCTAAGGTAAAT<br>ATAAAATTTTTAAGTGTATAATGTGTTAAACTAGCTGCATATGCTTGCTGCT<br>TGAGAGTTTTGCTTACTGAGTATGATTTATGAAAATATTATACACAGGAGCT<br>AGTGATTCTAATTGTTTGTGTATTTTAGATTCACAGTCCCAAGGCTCATTTCA<br>GGCCCCTCAGTCCTCACAGTCTGTTCATGATCATAATCAGCCATACCACATT<br>TGTAGAGGTTTTACTTGCTTTAAAAAACCTCCCACACCTCCCCCTGAACCTG<br>AAACATAAAATGAATGCAATTGTTGTTGTTAACTTGTTTATTGCAGCTTATA<br>ATGGTTACAAATAAAGCAATAGCATCACAAATTTCACAAATAAAGCATTTT<br>TTTCACTGCATTCTAGTTGTGGTTTGTCCAAACTCATCAATGTATCTTATCAT<br>GTCTGGATC | |

The DNA sequence for the CMV enhancer/CMV promoter used is) and the DNA sequence for SV40 polyadenylation tail used are the same reported in Table 11a above.

Example 9: Identification of Detectable Gene Clusters in Mammalian Cells

To identify a set of genes capable of assembling gas vesicles in the mammalian cell, an exemplary GVES was constructed using the exemplary GV gene cluster from *B. megaterium* reported in Table 11 above, which can be used as a Gas Vesicle Reporting Component as will be understood by a skilled person upon review of the instant disclosure.

A transient transfection screening assay was performed to allow the testing of different gas vesicle gene clusters without the need to optimize their stoichiometry and expression levels individually; although from the previous work these are expected to be important parameters.

In particular, a cell culture, transient transfection of HEK 293T and CHO-K1 cells and TEM analysis were performed as described in the material and method with various genes cluster.

An exemplary GV cluster the gyp genes of nine *B. megaterium* of Table 11 above was shown to be detectable by TEM and BURST ultrasound.

In particular, a monocistronic GVES with the nine *B. megaterium* of Table 11 was used in the experiments illustrated in FIGS. 9A-9C and 12A-12E.

Example 10: Identification of Bottleneck Genes in Mammalian Cells to Enable Robust GV Formation in Mammalian Cells Genes having a lower expression rate in GV constructs herein described (herein also indicated as bottleneck genes) were identified in exemplary mammalian cells HEK293T cells using an experimental approach illustrated in FIGS. 9A-9C.

Figure 9A:
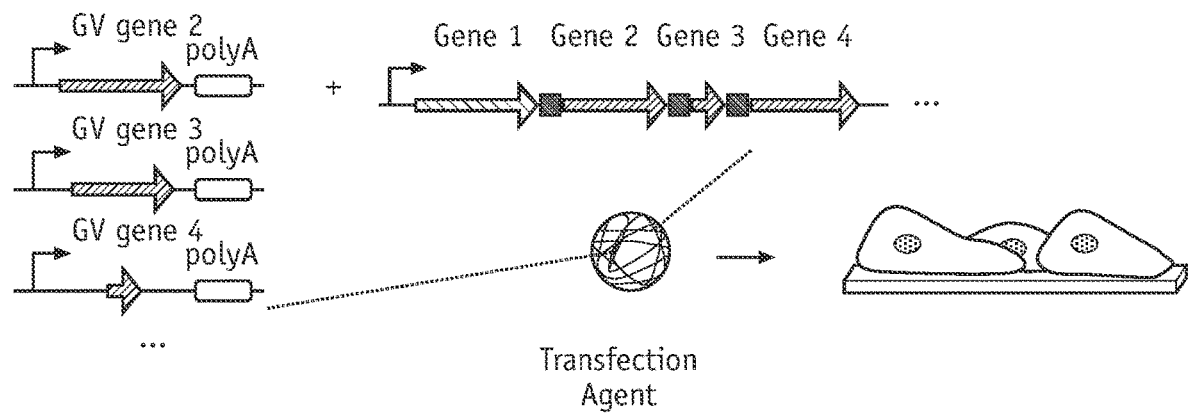
FIGS. 9A-9C illustrate an exemplary identification of bottleneck genes on an exemplary polycistronic gas vesicle gene plasmid.

In particular, test the efficiency with which gas vesicles could be formed when a given gene was supplied only on the polycistronic plasmid, and thereby identify "bottleneck" genes, the HEK293T cells were co-transfected with a monocistronic plasmid containing gvpB, 7 other monocistronic plasmids including all but the gene being assayed, and the polycistronic plasmid (for example Table 13) according to the approach schematically illustrated in FIG. 9A.

Figure 9B:
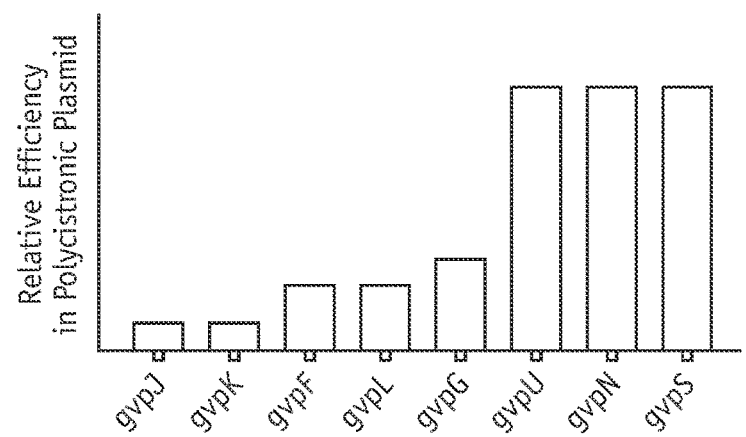
Figure 9C:
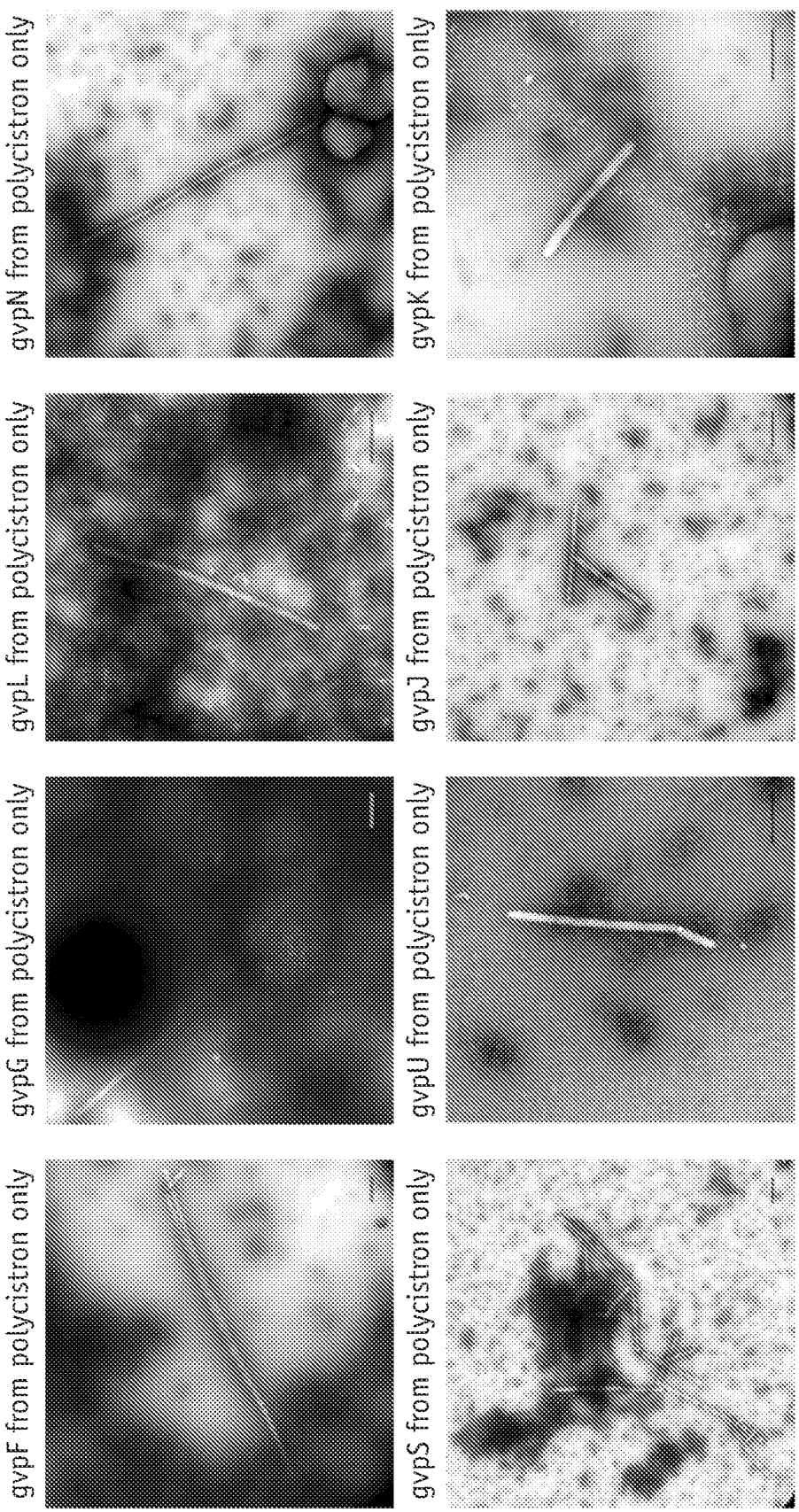

A qualitative estimate of the relative number of gas vesicles produced when each indicated gene was supplied solely by the polycistronic plasmid is reported in FIG. 9B, and representative TEM images of gas vesicles in the lysate of HEK293T cells for all 8 assays are shown in FIG. 9C.

These results suggest that gvpN, gvpS and gvpU supplied in either monocistronic or polycistronic form supported abundant gas vesicle assembly. However, the production of gas vesicles was significantly reduced when gvpJ, gvpF, gvpG, gvpL or gvpK was supplied from the polycistronic vector. Therefore, these results supported the conclusion that these genes represented a bottleneck in gas vesicle formation for the tested GV cluster.

Example 11; Optimization of Gene Stoichiometry Through Booster Construct

In order to address the stoichiometry issues raised by bottleneck genes in the exemplary *B. megatherium* cluster identified in Example 12 a booster plasmid comprising duplicate cassettes for the bottleneck genes was provided.

In particular, a booster plasmid containing gyp genes J, F, G, L and K connected with p2A elements was constructed to elevate the expression of these genes in in a pCMVSport backbone.

The related sequence is reported in Table 14 below. gvpJ, F, G, L, K are separated by GAPGSG-p2A sequence.

TABLE 14

Exemplary GPVC booster construct

| Construct | Sequence | SEQ ID NO |
|---|---|---|
| CMV:gvp JFGLK: polyA | CGTTACATAACTTACGGTAAATGGCCCGCCTGGCTGACCGCCCAACGACCC CCGCCCATTGACGTCAATAATGACGTATGTTCCCATAGTAACGCCAATAGG GACTTTCCATTGACGTCAATGGGTGGAGTATTTACGGTAAACTGCCCACTT GGCAGTACATCAAGTGTATCATATGCCAAGTACGCCCCCTATTGACGTCAA TGACGGTAAATGGCCCGCCTGGCATTATGCCCAGTACATGACCTTATGGGA CTTTCCTACTTGGCAGTACATCTACGTATTAGTCATCGCTATTACCATGGTG ATGCGGTTTTGGCAGTACATCAATGGGCGTGGATAGCGGTTTGACTCACGG GGATTTCCAAGTCTCCACCCCATTGACGTCAATGGGAGTTTGTTTTGGCACC AAAATCAACGGGACTTTCCAAAATGTCGTAACAACTCCGCCCCATTGACGC AAATGGGCGGTAGGCGTGTACGGTGGGAGGTCTATATAAGCAGAGCTCGT TTAGTGAACCGTCAGATCGCCTGGAGACGCCATCCACGCTGTTTTGACCTC CATAGAAGACACCGGGACCGATCCAGCCTCCGGACTCTAGCCTAGGCTTTT GCAAAAAGCTATTTAGGTGACACTATAGAAGGTACGCCTGCAGGTACCGA GCTCGGATCCAGTACCCTTCACCATGGCCGTGGAACACAACATGCAGAGCA GCACCATCGTGGACGTGCTGGAAAAGATCCTGGACAAGGGCGTCGTGATC GCCGGGGACATCACAGTGGGAATCGCCGACGTGGAACTGCTGACCATCAA GATCCGGCTGATCGTGGCCAGCGTGGACAAGGCCAAAGAAATCGGCATGG ATTGGTGGGAGAACGACCCCTACCTGAGCAGCAAGGGCGCCAACAACAAG GCCCTGGAAGAGGAAAACAAGATGCTGCACGAGCGGCTGAAAACACTGGA AGAGAAGATCGAGACAAAGCGCGGTGCCCCGGGATCTGGCGCAACAAATT TTAGTCTTTTAAAGCAGGCAGGAGACGTCGAGGAAAACCCTGGACCCGTG AGCGAGACAAACGAGACAGGCATCTACATCTTCAGCGCCATCCAGACAGA CAAGGATGAGGAATTCGGCGCCGTGGAAGTGGAAGGGACCAAGGCTGAGA CATTCCTGATCCGGTATAAGGACGCCGCCATGGTGGCCGCCGAAGTGCCCA TGAAGATCTACCACCCCAACCGGCAGAACCTGCTGATGCACCAGAATGCC GTGGCCGCCATCATGGACAAGAACGACACCGTGATCCCCATCAGCTTCGGC AACGTGTTCAAGAGCAAAGAGGACGTGAAGGTGCTCCTGGAAAACCTGTA CCCCCAGTTCGAGAAGCTGTTCCCCGCCATCAAGGGAAAGATCGAAGTGG GCCTGAAGGTGATCGGCAAGAAAGAGTGGCTCGAAAAGAAAGTGAACGA GAACCCCGAGCTGGAAAAAGTGTCCGCCAGCGTGAAGGGCAAGAGCGAGG CCGCTGGCTACTACGAGAGAATCCAGCTGGGCGGCATGCCCAGAAGATG TTCACAAGCCTGCAGAAAGAAGTGAAAACCGACGTGTTCAGCCCCCTGGA AGAAGCCGCCGAGGCCGCCAAAGCCAATGAGCCTACAGGCGAAACAATGC TGCTGAACGCCAGCTTCCTGATCAACAGAGAGGATGAGGCCAAGTTCGAC GAGAAAGTCAATGAGGCCCACGAGAACTGGAAGGATAAGGCCGACTTCCA CTACAGCGGCCCCTGGCCCGCCTACAACTTCGTGAACATCCGGCTGAAGGT GGAAGAGAAGGGGGCACCTGGCTCGGGAGCGACCAACTTCTCATTACTCA AACAAGCCGGAGACGTTGAGGAGAATCCAGGCCCTGTGCTGCACAAGCTC GTGACCGCCCCCATCAACCTGGTCGTGAAGATCGGCGAGAAGGTGCAGGA AGAGGCCGACAAGCAGCTGTACGACCTGCCCACCATCCAGCAGAAGCTGA TCCAGCTGCAGATGATGTTCGAGCTGGGCGAGATCCCCGAGGAAGCCTTCC AGGAAAAAGAGGACGAACTGCTGATGAGATACGAGATCGCCAAGCGGCGC GAGATTGAGCAGTGGGAAGAACTGACCCAGAAGCGGAATGAGGAAAGCG GTGCCCCGGGATCTGGCGCAACAAATTTTAGTCTTTTAAAGCAGGCAGGAG ACGTCGAGGAAAACCCTGGACCCGTGGGCGAGCTGCTGTACCTCTACGGCC TGATCCCCACCAAAGAGGCCGCTGCTATCGAGCCCTTCCCATTCTACAAGG GCTTCGACGGCGAGCACAGCCTGTACCCTATCGCCTTCGACCAAGTGACCG CCGTGGTGTTCAAGCTGGACGCCGACACCTACAGCGAGAAAGTGATCCAG GAAAAGATGGAACAGGACATGAGCTGGCTGCAGGAAAAGGCCTTCCACCA CCACGAGACAGTGGCCGCCCTGTATGAGGAATTCACCATCATCCCCCTGAA GTTCTGCACCATCTATAAGGGAGAGGAATCCCTGCAGGCCGCCATCGAGAT CAACAAAGAGAAGATCGAAAACTCCCTGACCCTGCTGCAGGGCAACGAGG AATGGAACGTGAAGATCTACTGCGACGACACCGAGCTGAAGAAGGGCATC AGCGAGACAAACGAGAGCGTGAAGGCCAAGAAGCAGGAAATCAGCCACC TGAGCCCCGGCAGACAGTTCTTCGAGAAGAAGAAGATTGACCAGCTCATC GAGAAAGAGCTGGAACTGCACAAGAACAAAGTGTGCGAGGAAATCCACG ACAAGCTGATTGAGCTGAGCCTCTACGACTCCGTGAAGAAGAACTGGTCCA AGGACGTGACAGGCGCTGCCGAACAGATGGCCTGGAACAGCGTGTTCCTG CTGCCCAGCCTGCAGATCACCAAGTTCGTGAACGAGATCGAGGAACTCCA GCAGCGGCTGGAGAACAAGGGATGGAAGTTCGAAGTGACCGGCCCCTGGC CTCCCTACCACTTCAGCAGCTTTGCCGGGGCACCTGGCTCGGGAGCGACCA ACTTCTCATTACTCAAACAAGCCGGAGACGTTGAGGAGAATCCAGGCCCTG TGCAGCCCGTGTCCCAGGCCAACGGCAGAATCCACCTGGATCCCGATCAGG | 444 |

TABLE 14-continued

Exemplary GPVC booster construct

| Construct | Sequence | SEQ ID NO |
|---|---|---|
| | CCGAACAGGGACTGGCCCAGCTCGTGATGACCGTGATCGAGCTGCTGCGG<br>CAGATCGTGGAACGGCACGCCATGAGAAGAGTGGAAGGCGGCACCCTGAC<br>CGACGAGCAGATCGAGAATCTGGGAATCGCCCTGATGAACCTGGAAGAGA<br>AGATGGACGAGCTGAAAGAGGTGTTCGGACTGGACGCCGAGGACCTGAAC<br>ATCGACCTGGGCCCTCTGGGCAGCCTGCTGTGATAATCTAGAGGATCCCTC<br>GAGGGGCCCAAGCTTACGCGTGCATGCGACGTCATAGCTCTCTCCCTATAG<br>TGAGTCGTATTATAAGCTAGCTTGGGATCTTTGTGAAGGAACCTTACTTCTG<br>TGGTGTGACATAATTGGACAAACTACCTACAGAGATTTAAAGCTCTAAGGT<br>AAATATAAAATTTTTAAGTGTATAATGTGTTAAACTAGCTGCATATGCTTG<br>CTGCTTGAGAGTTTTGCTTACTGAGTATGATTTATGAAAATATTATACACAG<br>GAGCTAGTGATTCTAATTGTTTGTGTATTTTAGATTCACAGTCCCAAGGCTC<br>ATTTCAGGCCCCTCAGTCCTCACAGTCTGTTCATGATCATAATCAGCCATAC<br>CACATTTGTAGAGGTTTTACTTGCTTTAAAAAACCTCCCACACCTCCCCCTG<br>AACCTGAAACATAAAATGAATGCAATTGTTGTTGTTAACTTGTTTATTGCA<br>GCTTATAATGGTTACAAATAAAGCAATAGCATCACAAATTTCACAAATAAA<br>GCATTTTTTTCACTGCATTCTAGTTGTGGTTTGTCCAAACTCATCAATGTAT<br>CTTATCATGTCTGGATC | |

The DNA sequence for the CMV enhancer/CMV promoter used and the DNA sequence for SV40 polyadenylation tail used are the same reported in Table 11a above.

Example 12: Gas Vesicle Expression System

The GVES that includes GVPB gene expression cassette of Table 11 with the GVPC construct of Table 13 and the GVP booster plasmid of Table 14, illustrated in FIG. 121D, is able to robustly express GVs in mammalian cells as detected by TEM and BURST ultrasound. The sequences of the corresponding exemplary GVES herein are also indicated as mARG.

The GVES of this example provide a polycistronic GVES which was used in the experiments illustrated in FIGS. 9A-9C and 12A-12E have been collected using GVES described in Example 9 for monocistronic cassettes and Example 12A for polycistronic cassettes.

Example 13: Gas Vesicle Expression System

The mARG GVES can be cloned within the piggyBac backbone are reported in Tables 15, 16 and 17 below, as illustrated in FIG. 13A, for integration in the genome of mammalian cells.

TABLE 15

Construct comprising the GVPB cassette

| Construct | SEQUENCE | SEQ ID NO: |
|---|---|---|
| Piggybac transposon containing gvpB | CCCTAGAAAGATAATCATATTGTGACGTACGTTAAAGATAAT<br>CATGTGTAAAATTGACGCATGTGTTTTATCGGTCTGTATATCG<br>AGGTTTATTTATTAATTTGAATAGATATTAAGTTTTATTATATT<br>TACACTTACATACTAATAATAAATTCAACAAACAATTTATTTA<br>TGTTTATTTATTTATTAAAAAAAACAAAAACTCAAAATTTCTT<br>CTATAAAGTAACAAAACTTTTATGAGGGACAGCCCCCCCCCA<br>AAGCCCCCAGGGATGTAATTACGTCCCTCCCCCGCTAGGGGG<br>CAGCAGCGAGCCGCCCGGGGCTCCGCTCCGGTCCGGCGCTCC<br>CCCCGCATCCCCGAGCCGGCAGCGTGCGGGGACAGCCCGGGC<br>ACGGGGAAGGTGGCACGGGATCGCTTTCCTCTGAACGCTTCT<br>CGCTGCTCTTTGAGCCTGCAGACACCTGGGGGGATACGGGGA<br>AAAGGCCTCCACGGCCACTAGTTTCACTCGAGTTTACTCCCTA<br>TCAGTGATAGAGAACGTATGAAGAGTTTACTCCCTATCAGTG<br>ATAGAGAACGTATGCAGACTTTACTCCCTATCAGTGATAGAG<br>AACGTATAAGGAGTTTACTCCCTATCAGTGATAGAGAACGTA<br>TGACCAGTTTACTCCCTATCAGTGATAGAGAACGTATCTACA<br>GTTTACTCCCTATCAGTGATAGAGAACGTATATCCAGTTTACT<br>CCCTATCAGTGATAGAGAACGTATGTCGAGGTAGGCGTGTAC<br>GGTGGGCGCCTATAAAAGCAGAGCTCGTTTAGTGAACCGTCA<br>GATCGCCTGGAGCAATTCCACAACACTTTTGTCTTATACTTGG<br>TACCTATGCATGCCACCATGAGCATCCAGAAGTCCACCAACA<br>GCAGCAGCCTGGCCGAAGTGATCGACCGGATCCTGGACAAGG<br>GCATCGTGATCGACGCCTTCGCCAGAGTGTCCGTCGTGGGCA<br>TCGAGATCCTGACCATCGAGGCCAGAGTCGTGATCGCCAGCG<br>TGGACACCTGGCTGAGATATGCCGAAGCCGTGGGCCTGCTGC<br>GGGACGACGTGGAAGAAAATGGCCTGCCCGAGCGGAGCAAC<br>AGCTCTGAGGGACAGCCCCGGTTCAGCATCTGAACTAAATCG<br>CACTGTCGGCGTCCCCCCCTAACGTTACTGGCCGAAGCCGCTT<br>GGAATAAGGCCGGTGTGCGTTTGTCTATATGTTATTTTCCACC<br>ATATTGCCGTCTTTTGGCAATGTGAGGGCCCGGAAACCTGGC<br>CCTGTCTTCTTGACGAGCATTCCTAGGGGTCTTTCCCCTCTCG<br>CCAAAGGAATGCAAGGTCTGTTGAATGTCGTGAAGGAAGCAG | 445 |

TABLE 15-continued

Construct comprising the GVPB cassette

| Construct | SEQUENCE | SEQ ID NO: |
|---|---|---|
| | TTCCTCTGGAAGCTTCTTGAAGACAAACAACGTCTGTAGCGA<br>CCCTTTGCAGGCAGCGGAACCCCCCACCTGGCGACAGGTGCC<br>TCTGCGGCCAAAAGCCACGTGTATAAGATACACCTGCAAAGG<br>CGGCACAACCCCAGTGCCACGTTGTGAGTTGGATAGTTGTGG<br>AAAGAGTCAAATGGCTCTCCTCAAGCGTATTCAACAAGGGGC<br>TGAAGGATGCCCAGAAGGTACCCCATTGTATGGGATCTGATC<br>TGGGGCCTCGGTGCACATGCTTTACATGTGTTTAGTCGAGGTT<br>AAAAAACGTCTAGGCCCCCCGAACCACGGGGACGTGGTTTTC<br>CTTTGAAAAACACGATGATAATATGGCCACAACCATGGTGAG<br>CAAGGGCGAGGAGGATAACATGGCCATCATCAAGGAGTTCAT<br>GCGCTTCAAGGTGCACATGGAGGGCTCCGTGAACGGCCACGA<br>GTTCGAGATCGAGGGCGAGGGCGAGGGCCGCCCCTACGAGG<br>GCACCCAGACCGCCAAGCTGAAGGTGACCAAGGGCGGCCCC<br>CTGCCCTTCGCCTGGGACATCCTGTCCCCTCAGTTCATGTACG<br>GCTCCAAGGCCTACGTGAAGCACCCCGCCGACATCCCCGACT<br>ACTTGAAGCTGTCCTTCCCCGAGGGCTTCAAGTGGGAGCGCG<br>TGATGAACTTCGAGGACGGCGGCGTGGTGACCGTGACCCAGG<br>ACTCCTCCCTGCAGGACGGCGAGTTCATCTACAAGGTGAAGC<br>TGCGCGGCACCAACTTCCCCTCCGACGGCCCCGTAATGCAGA<br>AGAAGACCATGGGCTGGGAGGCCTCCTCCGAGCGGATGTACC<br>CCGAGGACGGCGCCCTGAAGGGCGAGATCAAGCAGAGGCTG<br>AAGCTGAAGGACGGCGGCCACTACGACGCTGAGGTCAAGAC<br>CACCTACAAGGCCAAGAAGCCCGTGCAGCTGCCCGGCGCCTA<br>CAACGTCAACATCAAGTTGGACATCACCTCCCACAACGAGGA<br>CTACACCATCGTGGAACAGTACGAACGCGCCGAGGGCCGCCA<br>CTCCACCGGCGGCATGGACGAGCTGTACAAGTGAACTAGTTC<br>GTTAACTAAACTTGTTTATTGCAGCTTATAATGGTTACAAATA<br>AAGCAATAGCATCACAAATTTCACAAATAAAGCATTTTTTTC<br>ACTGCATTCTAGTTGTGGTTTGTCCAAACTCATCAATGTATCT<br>TATCATGTCTGGAATTGACTCAAATGATGTCAATTAGTCTATC<br>AGAAGCTCATCTGGTCTCCCTTCCGGGGGACAAGACATCCCT<br>GTTTAATATTTAAACAGCAGTGTTCCCAAACTGGGTTCTTATA<br>TCCCTTGCTCTGGTCAACCAGGTTGCAGGGTTTCCTGTCCTCA<br>CAGGAACGAAGTCCCTAAAGAAACAGTGGCAGCCAGGTTTA<br>GCCCCGGAATTGACTGGATTCCTTTTTTAGGGCCCATTGGTAT<br>GGCTTTTTCCCCGTATCCCCCCAGGTGTCTGCAGGCTCAAAGA<br>GCAGCGAGAAGCGTTCAGAGGAAAGCGATCCCGTGCCACCTT<br>CCCCGTGCCCGGGCTGTCCCCGCACGCTGCCGGCTCGGGGAT<br>GCGGGGGAGCGCCGGACCGGAGCGGAGCCCCGGGCGGCTC<br>GCTGCTGCCCCCTAGCGGGGGAGGGACGTAATTACATCCCTG<br>GGGGCTTTGGGGGGGGGCTGTCCCTGATATCTATAACAAGAA<br>AATATATATATAATAAGTTATCACGTAAGTAGAACATGAAAT<br>AACAATATAATTATCGTATGAGTTAAATCTTAAAAGTCACGT<br>AAAAGATAATCATGCGTCATTTTGACTCACGCGGTCGTTATA<br>GTTCAAAATCAGTGACACTTACCGCATTGACAAGCACGCCTC<br>ACGGGAGCTCCAAGCGGCGACTGAGATGTCCTAAATGCACAG<br>CGACGGATTCGCGCTATTTAGAAAGAGAGAGCAATATTCAA<br>GAATGCATGCGTCAATTTTACGCAGACTATCTTTCTAGGG | |

| Construct | SEQUENCE | SEQ ID NO: |
|---|---|---|
| PiggyBac<br>transposon<br>containing<br>gvpNFGLSKJU-<br>EmGFP | CCCTAGAAAGATAATCATATTGTGACGTACGTTAAAGATAAT<br>CATGTGTAAAATTGACGCATGTGTTTTATCGGTCTGTATATCG<br>AGGTTTATTTATTAATTTGAATAGATATTAAGTTTTATTATATT<br>TACACTTACATACTAATAATAAATTCAACAAACAATTTATTTA<br>TGTTTATTTATTTATTAAAAAAAACAAAAACTCAAAATTTCTT<br>CTATAAAGTAACAAAACTTTTATGAGGGACAGCCCCCCCCCA<br>AAGCCCCCAGGGATGTAATTACGTCCCTCCCCCGCTAGGGGG<br>CAGCAGCGAGCCGCCCGGGGCTCCGCTCCGGTCCGGCGCTCC<br>CCCCGCATCCCCGAGCCGGCAGCGTGCGGGGACAGCCCGGGC<br>ACGGGGAAGGTGGCACGGGATCGCTTTCCTCTGAACGCTTCT<br>CGCTGCTCTTTGAGCCTGCAGACACCTGGGGGATACGGGGA<br>AAAGGCCTCCACGGCCACTAGTTTCACTCGAGTTTACTCCCTA<br>TCAGTGATAGAGAACGTATGAAGAGTTTACTCCCTATCAGTG<br>ATAGAGAACGTATGCAGACTTTACTCCCTATCAGTGATAGAG<br>AACGTATAAGGAGTTTACTCCCTATCAGTGATAGAGAACGTA<br>TGACCAGTTTACTCCCTATCAGTGATAGAGAACGTATCTACA<br>GTTTACTCCCTATCAGTGATAGAGAACGTATATCCAGTTTACT<br>CCCTATCAGTGATAGAGAACGTATGTCGAGGTAGGCGTGTAC<br>GGTGGGCGCCTATAAAAGCAGAGCTCGTTTAGTGAACCGTCA<br>GATCGCCTGGAGCAATTCCACAACACTTTTGTCTTATACTTGG<br>TACCTATGCATGCCACCATGACCGTGCTGACCGACAAGCGGA | 446 |

-continued

| Construct | SEQUENCE | SEQ ID NO: |
|---|---|---|
| | AGAAGGGCAGCGGCGCCTTCATCCAGGACGACGAGACAAAA | |
| | GAGGTGCTGAGCAGAGCCCTGAGCTACCTGAAGTCCGGCTAC | |
| | AGCATCCACTTCACCGGACCTGCCGGCGGAGGCAAGACATCT | |
| | CTGGCTAGAGCCCTGGCCAAGAAACGGAAGCGGCCCGTGATG | |
| | CTGATGCACGGCAACCACGAGCTGAACAACAAGGACCTGATC | |
| | GGCGATTTCACCGGCTACACCAGCAAAAAGGTGATCGACCAG | |
| | TACGTGCGGAGCGTGTACAAGAAAGACGAACAGGTGTCCGA | |
| | GAACTGGCAGGACGGCAGACTGCTGGAAGCCGTGAAGAATG | |
| | GCTACACCCTGATCTACGACGAGTTCACCAGAAGCAAGCCCG | |
| | CTACCAACAACATCTTCCTGAGCATCCTTGAGGAGGGCGTGC | |
| | TGCCCCTGTACGGCGTGAAGATGACCGACCCTTTCGTGCGCG | |
| | TGCACCCCGACTTCAGAGTGATCTTTACCAGCAACCCCGCCG | |
| | AGTATGCCGGCGTGTACGATACCCAGGACGCCCTGCTGGACC | |
| | GGCTGATCACCATGTTCATCGACTACAAGGACATCGACCGGG | |
| | AAACCGCTATCCTGACCGAGAAAACTGACGTGGAAGAAGAC | |
| | GAGGCCCGGACCATCGTGACCCTGGTGGCCAACGTGCGGAAC | |
| | AGAAGCGGCGACGAGAATAGCAGCGGCCTGAGCCTGAGAGC | |
| | CAGCCTGATGATTGCCACCCTGGCCACCCAGCAGGACATCCC | |
| | TATCGATGGCAGCGACGAGGACTTCCAGACCCTGTGCATCGA | |
| | CATCCTGCACCACCCCTGACCAAGTGCCTGGACGAAGAGAA | |
| | CGCCAAGAGCAAGGCCGAGAAGATCATTCTCGAAGAGTGCA | |
| | AGAACATCGACACCGAGGAGAAGGGTGCCCCGGGATCTGGC | |
| | GCAACAAATTTTAGTCTTTTAAAGCAGGCAGGAGACGTCGAG | |
| | GAAAACCCTGGACCCGTGAGCGAGACAAACGAGACAGGCAT | |
| | CTACATCTTCAGCGCCATCCAGACAGACAAGGATGAGGAATT | |
| | CGGCGCCGTGGAAGTGGAAGGGACCAAGGCTGAGACATTCCT | |
| | GATCCGGTATAAGGACGCCGCCATGGTGGCCGCCGAAGTGCC | |
| | CATGAAGATCTACCACCCCAACCGGCAGAACCTGCTGATGCA | |
| | CCAGAATGCCGTGGCCGCCATCATGGACAAGAACGACACCGT | |
| | GATCCCCATCAGCTTCGGCAACGTGTTCAAGAGCAAAGAGGA | |
| | CGTGAAGGTGCTCCTGGAAAACCTGTACCCCCAGTTCGAGAA | |
| | GCTGTTCCCCGCCATCAAGGGAAAGATCGAAGTGGGCCTGAA | |
| | GGTGATCGGCAAGAAAGAGTGGCTCGAAAAGAAAGTGAACG | |
| | AGAACCCCGAGCTGGAAAAAGTGTCCGCCAGCGTGAAGGGC | |
| | AAGAGCGAGGCCGCTGGCTACTACGAGAGAATCCAGCTGGG | |
| | CGGCATGGCCCAGAAGATGTTCACAAGCCTGCAGAAAGAAGT | |
| | GAAAACCGACGTGTTCAGCCCCCTGGAAGAAGCCGCCGAGGC | |
| | CGCCAAAGCCAATGAGCCTACAGGCGAAACAATGCTGCTGAA | |
| | CGCCAGCTTCCTGATCAACAGAGAGGATGAGGCCAAGTTCGA | |
| | CGAGAAAGTCAATGAGGCCCACGAGAACTGGAAGGATAAGG | |
| | CCGACTTCCACTACAGCGGCCCCTGGCCCGCCTACAACTTCGT | |
| | GAACATCCGGCTGAAGGTGGAAGAGAAGGGGGCACCTGGCT | |
| | CGGGAGCGACCAACTTCTCATTACTCAAACAAGCCGGAGACG | |
| | TTGAGGAGAATCCAGGCCCTGTGCTGCACAAGCTCGTGACCG | |
| | CCCCCATCAACCTGGTCGTGAAGATCGGCGAGAAGGTGCAGG | |
| | AAGAGGCCGACAAGCAGCTGTACGACCTGCCCACCATCCAGC | |
| | AGAAGCTGATCCAGCTGCAGATGATGTTCGAGCTGGGCGAGA | |
| | TCCCCGAGGAAGCCTTCCAGGAAAAAGAGGACGAACTGCTG | |
| | ATGAGATACGAGATCGCCAAGCGGCGCGAGATTGAGCAGTG | |
| | GGAAGAACTGACCCAGAAGCGGAATGAGGAAAGCGGTGCCC | |
| | CGGGATCTGGCGCAACAAATTTTAGTCTTTTAAAGCAGGCAG | |
| | GAGACGTCGAGGAAAACCCTGGACCCGTGGGCGAGCTGCTGT | |
| | ACCTCTACGGCCTGATCCCCACCAAAGAGGCCGCTGCTATCG | |
| | AGCCCTTCCCATTCTACAAGGGCTTCGACGGCGAGCACAGCC | |
| | TGTACCCTATCGCCTTCGACCAAGTGACCGCCGTGGTGTTCAA | |
| | GCTGGACGCCGACACCTACAGCGAGAAAGTGATCCAGGAAA | |
| | AGATGGAACAGGACATGAGCTGGCTGCAGGAAAAGGCCTTC | |
| | CACCACCACGAGACAGTGGCCGCCCTGTATGAGGAATTCACC | |
| | ATCATCCCCCTGAAGTTCTGCACCATCTATAAGGGAGAGGAA | |
| | TCCCTGCAGGCCGCCATCGAGATCAACAAAGAGAAGATCGAA | |
| | AACTCCCTGACCCTGCTGCAGGGCAACGAGGAATGGAACGTG | |
| | AAGATCTACTGCGACGACACCGAGCTGAAGAAGGGCATCAG | |
| | CGAGACAAACGAGAGCGTGAAGGCCAAGAAGCAGGAAATCA | |
| | GCCACCTGAGCCCCGGCAGACAGTTCTTCGAGAAGAAGAAGA | |
| | TTGACCAGCTCATCGAGAAAGAGCTGGAACTGCACAAGAACA | |
| | AAGTGTGCGAGGAAATCCACGACAAGCTGATTGAGCTGAGCC | |
| | TCTACGACTCCGTGAAGAAGAACTGGTCCAAGGACGTGACAG | |
| | GCGCTGCCGAACAGATGGCCTGGAACAGCGTGTTCCTGCTGC | |
| | CCAGCCTGCAGATCACCAAGTTCGTGAACGAGATCGAGGAAC | |
| | TCCAGCAGCGGCTGGAGAACAAGGGATGGAAGTTCGAAGTG | |
| | ACCGGCCCCTGGCCTCCCTACCACTTCAGCAGCTTTGCCGGGG | |
| | CACCTGGCTCGGGAGCGACCAACTTCTCATTACTCAAACAAG | |
| | CCGGAGACGTTGAGGAGAATCCAGGCCCTGTGAGCCTGAAGC | |
| | AGAGCATGGAGAATAAGGATATCGCCCTGATCGACATCCTCG | |
| | ACGTGATCCTGGACAAGGGAGTGGCCATCAAGGGCGACCTGA | |
| | TCATCTCTATCGCCGGCGTGGACCTGGTGTACCTGGATCTGAG | |
| | AGTGCTGATCTCCAGCGTGGAAACCCTGGTGCAGGCCAAAGA | |

| Construct | SEQUENCE | SEQ ID NO: |
|---|---|---|
| | GGGCAACCACAAGCCCATCACCAGCGAGCAGTTCGACAAGC<br>AGAAAGAGGAGCTGATGGACGCCACCGGCCAGCCCAGCAAG<br>TGGACAAATCCTCTGGGCAGCGGCGCTCCCGGGTCAGGTGCC<br>ACGAATTTTTCGTTGTTGAAGCAAGCTGGGGATGTTGAAGAG<br>AACCCAGGGCCTGTGCAGCCCGTGTCCCAGGCCAACGGCAGA<br>ATCCACCTGGATCCCGATCAGGCCGAACAGGGACTGGCCCAG<br>CTCGTGATGACCGTGATCGAGCTGCTGCGGCAGATCGTGGAA<br>CGGCACGCCATGAGAAGAGTGGAAGGCGGCACCCTGACCGA<br>CGAGCAGATCGAGAATCTGGGAATCGCTCTGATGAACCTGGA<br>GGAGAAGATGGACGAGCTGAAAGAGGTGTTCGGACTGGACG<br>CTGAGGATCTGAACATCGACCTGGGCCCTCTGGGCAGCCTGC<br>TGGGTGCCCCGGGATCTGGCGCAACAAATTTTAGTCTTTTAAA<br>GCAGGCAGGAGACGTCGAGGAAAACCCTGGACCCGTGGCCG<br>TGGAACACAACATGCAGAGCAGCACCATCGTGGACGTGCTGG<br>AAAAGATCCTGGACAAGGGCGTCGTGATCGCCGGGGACATCA<br>CAGTGGGAATCGCCGACGTGGAACTGCTGACCATCAAGATCC<br>GGCTGATCGTGGCCAGCGTGGACAAGGCCAAAGAAATCGGC<br>ATGGATTGGTGGGAGAACGACCCCTACCTGAGCAGCAAGGGC<br>GCCAACAACAAGGCTCTGGAAGAGGAAAACAAGATGCTGCA<br>CGAGCGGCTGAAAACACTGGAAGAGAAGATCGAGACAAAGC<br>GCGGGGCACCTGGCTCGGGAGCGACCAACTTCTCATTACTCA<br>AACAAGCCGGAGACGTTGAGGAGAATCCAGGCCCTGTGAGC<br>ACCGGCCCCAGCTTCAGCACCAAGGACAACACCCTGGAATAC<br>TTCGTGAAGGCCAGCAACAAGCACGGCTTTAGCCTCGACATC<br>AGCCTGAACGTGAATGGGGCCGTGATTAGCGGCACCATGATC<br>AGCGCCAAAGAGTACTTCGACTACCTGAGCGAGACATTCGAA<br>GAGGGCAGCGAAGTGGCCCAGGCCCTGTCTGAGCAGTTTAGC<br>CTGGCTAGCGAGGCCTCCGAGTCTAATGGCGAAGCCGAGGCC<br>CACTTCATCCACCTGAAGAACACCAAGATCTACTGCGGCGAC<br>AGCAAGAGCACCCCCAGCAAGGGCAAGATCTTCTGGCGCGGC<br>AAGATCGCCGAGGTGGACGGATTCTTCCTGGGAAAAATCAGC<br>GACGCCAAGTCCACCAGCAAGAAGTCCAGCGGCGCTCCCGGG<br>TCAGGTGCCACGAATTTTTCGTTGTTGAAGCAAGCTGGGGAT<br>GTTGAAGAGAACCCAGGGCCTGTGGTGTCCAAGGGCGAGGA<br>ACTGTTCACCGGCGTGGTGCCCATCCTGGTGGAACTGGATGG<br>CGACGTGAACGGCCACAAGTTCAGCGTGTCCGGCGAGGGCGA<br>AGGCGACGCCACATACGGAAAGCTGACCCTGAAGTTCATCTG<br>CACCACCGGCAAGCTGCCCGTGCCTTGGCCTACCCTCGTGAC<br>CACACTGACCTACGGCGTGCAGTGCTTCGCCAGATACCCCGA<br>CCACATGAAGCAGCACGATTTCTTCAAGAGCGCCATGCCCGA<br>GGGCTACGTGCAGGAACGGACCATCTTCTTCAAGGACGACGG<br>CAACTACAAGACAAGAGCCGAAGTGAAGTTCGAGGGCGACA<br>CCCTCGTGAACCGGATCGAGCTGAAGGGCATCGACTTCAAAG<br>AGGATGGCAACATCCTGGGCCACAAGCTGGAGTACAACTACA<br>ACAGCCACAAGGTGTACATCACCGCCGACAAGCAGAAAAAC<br>GGCATCAAAGTGAACTTCAAGACCCGGCACAACATCGAGGAC<br>GGCAGCGTGCAGCTGGCCGACCACTACCAGCAGAACACCCCC<br>ATCGGAGATGGCCCCGTGCTGCTGCCCGACAACCACTACCTG<br>AGCACACAAAGCGCCCTGAGCAAGGACCCCAACGAGAAGCG<br>GGACCACATGGTGCTGCTGGAATTTGTGACCGCCGCTGGCAT<br>CACCCTGGGCATGGACGAGCTGTACAAGTGAACTAGTTCGTT<br>AACTAAACTTGTTTATTGCAGCTTATAATGGTTACAAATAAAG<br>CAATAGCATCACAAATTTCACAAATAAAGCATTTTTTTCACTG<br>CATTCTAGTTGTGGTTTGTCCAAACTCATCAATGTATCTTATC<br>ATGTCTGGAATTGACTCAAATGATGTCAATTAGTCTATCAGA<br>AGCTCATCTGGTCTCCCTTCCGGGGGACAAGACATCCCTGTTT<br>AATATTTAAACAGCAGTGTTCCCAAACTGGGTTCTTATATCCC<br>TTGCTCTGGTCAACCAGGTTGCAGGGTTTCCTGTCCTCACAGG<br>AACGAAGTCCCTAAAGAAACAGTGGCAGCCAGGTTTAGCCCC<br>GGAATTGACTGGATTCCTTTTTTAGGGCCCATTGGTATGGCTT<br>TTTCCCCGTATCCCCCCAGGTGTCTGCAGGCTCAAAGAGCAG<br>CGAGAAGCGTTCAGAGGAAAGCGATCCCGTGCCACCTTCCCC<br>GTGCCCGGGCTGTCCCCGCACGCTGCCGGCTCGGGGATGCGG<br>GGGGAGCGCCGGACCGGAGCGGAGCCCCGGGCGGCTCGCTG<br>CTGCCCCCTAGCGGGGAGGGACGTAATTACATCCCTGGGGG<br>CTTTGGGGGGGGCTGTCCCTGATATCTATAACAAGAAAATA<br>TATATATAATAAGTTATCACGTAAGTAGAACATGAAATAACA<br>ATATAATTATCGTATGAGTTAAATCTTAAAAGTCACGTAAAA<br>GATAATCATGCGTCATTTTGACTCACGCGGTCGTTATAGTTCA<br>AAATCAGTGACACTTACCGCATTGACAAGCACGCCTCACGGG<br>AGCTCCAAGCGGCGACTGAGATGTCCTAAATGCACAGCGACG<br>GATTCGCGCTATTTAGAAAGAGAGAGCAATATTCAAGAATG<br>CATGCGTCAATTTTACGCAGACTATCTTTCTAGGG | |

TABLE 17

Exemplary Booster Construct

| Construct | SEQUENCE | SEQ ID NO: |
|---|---|---|
| PiggyBac transposon containing gvpJFGLK | CCCTAGAAAGATAATCATATTGTGACGTACGTTAAAGATAAT<br>CATGTGTAAAATTGACGCATGTGTTTATCGGTCTGTATATCG<br>AGGTTTATTTATTAATTTGAATAGATATTAAGTTTTATTATATT<br>TACACTTACATACTAATAATAAATTCAACAAACAATTTATTTA<br>TGTTTATTTATTTATTAAAAAAAACAAAAACTCAAAATTTCTT<br>CTATAAAGTAACAAAACTTTTATGAGGGACAGCCCCCCCCCA<br>AAGCCCCCAGGGATGTAATTACGTCCCTCCCCCGCTAGGGGG<br>CAGCAGCGAGCCGCCCGGGGCTCCGCTCCGGTCCGGCGCTCC<br>CCCCGCATCCCCGAGCCGGCAGCGTGCGGGGACAGCCCGGGC<br>ACGGGGAAGGTGGCACGGGATCGCTTTCCTCTGAACGCTTCT<br>CGCTGCTCTTTGAGCCTGCAGACACCTGGGGGATACGGGGA<br>AAAGGCCTCCACGGCCACTAGTTTTCCCCGAAAAGTGCCACC<br>TGACGTCGGCAGTGAAAAAAATGCTTTATTTGTGAAATTTGT<br>GATGCTATTGCTTTATTTGTAACCATTATAAGCTGCAATAAAC<br>AAGTTAACAACAACAATTGCATTCATTTTATGTTTCAGGTTCA<br>GGGGGAGGTGTGGGAGGTTTTTTAAAGCAAGTAAAACCTCTA<br>CAAATGTGGTATGGCTGATTATGATCCTCTAGACATATGCTAC<br>AGTCACTTGTACAGCTCATCCATGCCCAGGGTGATGCCAGCG<br>GCGGTCCGAAATTCCAGCAGCACCATGTGGTCCCGCTTCTCGT<br>TGGGGTCCTTGCTCAGCACGCTCTGGGTGCTCAGGTAGTGGCT<br>ATCAGGCAGCAGCACGGGGCCATCTCCGATGGGGGTGTTCTG<br>CTGGTAGTGGTCGGCCAGCTGCACGCTGCCATCTTCCACGTTG<br>TGCCGGATCTTGAAGTTCACTTTGATGCCGTTTTTCTGCTTCA<br>CGGCCATGATGTAGATGTTGTGGCTGTTGAAGTTGTACTCCAG<br>CTTGTGGCCCAGGATGTTGCCGTCCTCTTTGAAGTCCACGCCC<br>TTCAGCTCGATCCGGTTCACGAGGGTGTCGCCCTCGAACTTCA<br>CTTCGGCTCTGGTCTTGTAGGTGCCGTCGTCCTTGAAGAAGAT<br>GGTCCGTTCCTGCACGTAGCCCTCGGGCATGGCGCTCTTGAA<br>GAAATCGTGCTGCTTCATGTGGTCGGGGTATCTGGCGAAGCA<br>CTGCACGCCGTGAGACAGTGTGGTCACGAGGGTAGGCCAAGG<br>CACGGGCAGCTTGCCGGTGGTGCAGATGAACTTCAGGGTCAG<br>CTTGCCATTTGTGGCGTCGCCTTCGCCCTCTCCCCGCACAGAG<br>AACTTGTGGCCGTTCACGTCGCCATCCAGTTCCACCAGGATG<br>GGCACCACGCCGGTGAACAGTTCCTCGCCCTTGGACACCATG<br>GTGAAGGGTACTGGATCCGAGCTCGGTACCTGCAGGCGTACC<br>TTCTATAGTGTCACCTAAATGCGATCTGACGGTTCACTAAACG<br>AGCTCTGCTTATATAGGCCTCCCACCGTACACGCCACCTCGAC<br>ATACTCGAGTTTACTCCCTATCAGTGATAGAGAACGTATGAA<br>GAGTTTACTCCCTATCAGTGATAGAGAACGTATGCAGACTTT<br>ACTCCCTATCAGTGATAGAGAACGTATAAGGAGTTTACTCCC<br>TATCAGTGATAGAGAACGTATGACCAGTTTACTCCCTATCAGT<br>GATAGAGAACGTATCTACAGTTTACTCCCTATCAGTGATAGA<br>GAACGTATATCCAGTTTACTCCCTATCAGTGATAGAGAACGT<br>ATGTCGAGGTAGGCGTGTACGGTGGGCGCCTATAAAAGCAGA<br>GCTCGTTTAGTGAACCGTCAGATCGCCTGGAGCAATTCCACA<br>ACACTTTTGTCTTATACTTGGTACCTATGCATGCCACCATGGC<br>CGTGGAACACAACATGCAGAGCAGCACCATCGTGGACGTGCT<br>GGAAAAGATCCTGGACAAGGGCGTCGTGATCGCCGGGGACA<br>TCACAGTGGGAATCGCCGACGTGGAACTGCTGACCATCAAGA<br>TCCGGCTGATCGTGGCCAGCGTGGACAAGGCCAAAGAAATCG<br>GCATGGATTGGTGGGAGAACGACCCCTACCTGAGCAGCAAGG<br>GCGCCAACAACAAGGCCCTGGAAGAGGAAAACAAGATGCTG<br>CACGAGCGGCTGAAAACACTGGAAGAGAAGATCGAGACAAA<br>GCGCGGTGCCCCGGGATCTGGCGCAACAAATTTTAGTCTTTTA<br>AAGCAGGCAGGAGACGTCGAGGAAAACCCTGGACCCGTGAG<br>CGAGACAAACGAGACAGGCATCTACATCTTCAGCGCCATCCA<br>GACAGACAAGGATGAGGAATTCGGCGCCGTGGAAGTGGAAG<br>GGACCAAGGCTGAGACATTCCTGATCCGGTATAAGGACGCCG<br>CCATGGTGGCCGCCGAAGTGCCCATGAAGATCTACCACCCCA<br>ACCGGCAGAACCTGCTGATGCACCAGAATGCCGTGGCCGCCA<br>TCATGGACAAGAACGACACCGTGATCCCCATCAGCTTCGGCA<br>ACGTGTTCAAGAGCAAAGAGGACGTGAAGGTGCTCCTGGAA<br>AACCTGTACCCCCAGTTCGAGAAGCTGTTCCCCGCCATCAAG<br>GGAAAGATCGAAGTGGGCCTGAAGGTGATCGGCAAGAAAGA<br>GTGGCTCGAAAAGAAAGTGAACGAGAACCCCGAGCTGGAAA<br>AAGTGTCCGCCAGCGTGAAGGGCAAGAGCGAGGCCGCTGGC<br>TACTACGAGAGAATCCAGCTGGGCGGCATGGCCCAGAAGATG<br>TTCACAAGCCTGCAGAAAGAAGTGAAAACCGACGTGTTCAGC<br>CCCCTGGAAGAAGCCGCCGAGGCCGCCAAAGCCAATGAGCCT<br>ACAGGCGAAACAATGCTGCTGAACGCCAGCTTCCTGATCAAC<br>AGAGAGGATGAGGCCAAGTTCGACGAGAAAGTCAATGAGGC<br>CCACGAGAACTGGAAGGATAAGGCCGACTTCCACTACAGCGG<br>CCCCTGGCCCGCCTACAACTTCGTGAACATCCGGCTGAAGGT<br>GGAAGAGAAGGGGGCACCTGGCTCGGGAGCGACCAACTTCT<br>CATTACTCAAACAAGCCGGAGACGTTGAGGAGAATCCAGGCC<br>CTGTGCTGCACAAGCTCGTGACCGCCCCCATCAACCTGGTCGT | 447 |

TABLE 17-continued

Exemplary Booster Construct

| Construct | SEQUENCE | SEQ ID NO: |
|---|---|---|
| | GAAGATCGGCGAGAAGGTGCAGGAAGAGGCCGACAAGCAGC<br>TGTACGACCTGCCCACCATCCAGCAGAAGCTGATCCAGCTGC<br>AGATGATGTTCGAGCTGGGCGAGATCCCCGAGGAAGCCTTCC<br>AGGAAAAAGAGGACGAACTGCTGATGAGATACGAGATCGCC<br>AAGCGGCGCGAGATTGAGCAGTGGGAAGAACTGACCCAGAA<br>GCGGAATGAGGAAAGCGGTGCCCCGGGATCTGGCGCAACAA<br>ATTTTAGTCTTTTAAAGCAGGCAGGAGACGTCGAGGAAAACC<br>CTGGACCCGTGGGCGAGCTGCTGTACCTCTACGGCCTGATCC<br>CCACCAAAGAGGCCGCTGCTATCGAGCCCTTCCCATTCTACA<br>AGGGCTTCGACGGCGAGCACAGCCTGTACCCTATCGCCTTCG<br>ACCAAGTGACCGCCGTGGTGTTCAAGCTGGACGCCGACACCT<br>ACAGCGAGAAAGTGATCCAGGAAAAGATGGAACAGGACATG<br>AGCTGGCTGCAGGAAAAGGCCTTCCACCACCACGAGACAGTG<br>GCCGCCCTGTATGAGGAATTCACCATCATCCCCCTGAAGTTCT<br>GCACCATCTATAAGGGAGAGGAATCCCTGCAGGCCGCCATCG<br>AGATCAACAAAGAGAAGATCGAAAACTCCCTGACCCTGCTGC<br>AGGGCAACGAGGAATGGAACGTGAAGATCTACTGCGACGAC<br>ACCGAGCTGAAGAAGGGCATCAGCGAGACAAACGAGAGCGT<br>GAAGGCCAAGAAGCAGGAAATCAGCCACCTGAGCCCCGGCA<br>GACAGTTCTTCGAGAAGAAGAAGATTGACCAGCTCATCGAGA<br>AAGAGCTGGAACTGCACAAGAACAAAGTGTGCGAGGAAATC<br>CACGACAAGCTGATTGAGCTGAGCCTCTACGACTCCGTGAAG<br>AAGAACTGGTCCAAGGACGTGACAGGCGCTGCCGAACAGAT<br>GGCCTGGAACAGCGTGTTCCTGCTGCCCAGCCTGCAGATCAC<br>CAAGTTCGTGAACGAGATCGAGGAACTCCAGCAGCGGCTGGA<br>GAACAAGGGATGGAAGTTCGAAGTGACCGGCCCCTGGCCTCC<br>CTACCACTTCAGCAGCTTTGCCGGGGCACCTGGCTCGGGAGC<br>GACCAACTTCTCATTACTCAAACAAGCCGGAGACGTTGAGGA<br>GAATCCAGGCCCTGTGCAGCCCGTGTCCCAGGCCAACGGCAG<br>AATCCACCTGGATCCCGATCAGGCCGAACAGGGACTGGCCCA<br>GCTCGTGATGACCGTGATCGAGCTGCTGCGGCAGATCGTGGA<br>ACGGCACGCCATGAGAAGAGTGGAAGGCGGCACCCTGACCG<br>ACGAGCAGATCGAGAATCTGGGAATCGCCCTGATGAACCTGG<br>AAGAGAAGATGGACGAGCTGAAAGAGGTGTTCGGACTGGAC<br>GCCGAGGACCTGAACATCGACCTGGGCCCTCTGGGCAGCCTG<br>CTGTGAACTAGTTCGATACCGTCGACCGTTAACTAAACTTGTT<br>TATTGCAGCTTATAATGGTTACAAATAAAGCAATAGCATCAC<br>AAATTTCACAAATAAAGCATTTTTTTCACTGCATTCTAGTTGT<br>GGTTTGTCCAAACTCATCAATGTATCTTATCATGTCTGGAATT<br>GACTCAAATGATGTCAATTAGTCTATCAGAAGCTCATCTGGTC<br>TCCCTTCCGGGGACAAGACATCCCTGTTTAATATTTAAACAG<br>CAGTGTTCCCAAACTGGGTTCTTATATCCCTTGCTCTGGTCAA<br>CCAGGTTGCAGGGTTTCCTGTCCTCACAGGAACGAAGTCCCT<br>AAAGAAACAGTGGCAGCCAGGTTTAGCCCCGGAATTGACTGG<br>ATTCCTTTTTTAGGGCCCATTGGTATGGCTTTTTCCCCGTATCC<br>CCCCAGGTGTCTGCAGGCTCAAAGAGCAGCGAGAAGCGTTCA<br>GAGGAAAGCGATCCCGTGCCACCTTCCCCGTGCCCGGGCTGT<br>CCCCGCACGCTGCCGGCTCGGGGATGCGGGGGGAGCGCCGG<br>ACCGGAGCGGAGCCCCGGGCGGCTCGCTGCTGCCCCCTAGCG<br>GGGGAGGGACGTAATTACATCCCTGGGGGCTTTGGGGGGGGG<br>CTGTCCCTGATATCTATAACAAGAAAATATATATATAATAAG<br>TTATCACGTAAGTAGAACATGAAATAACAATATAATTATCGT<br>ATGAGTTAAATCTTAAAAGTCACGTAAAAGATAATCATGCGT<br>CATTTTGACTCACGCGGTCGTTATAGTTCAAAATCAGTGACAC<br>TTACCGCATTGACAAGCACGCCTCACGGGAGCTCCAAGCGGC<br>GACTGAGATGTCCTAAATGCACAGCGACGGATTCGCGCTATT<br>TAGAAAGAGAGAGCAATATTCAAGAATGCATGCGTCAATTT<br>TACGCAGACTATCTTTCTAGGG | |

The DNA sequence for the additional regulatory regions of the cassettes are reported in Table 18 below.

TABLE 18

Additional elements of GV gene expression cassettes

| Element | Sequence | SEQ ID NO |
|---|---|---|
| 5'ITR | CCCTAGAAAGATAATCATATTGTGACGTACGTTAAAGATAAT<br>CATGTGTAAAATTGACGCATGTGTTTTATCGGTCTGTATATC<br>GAGGTTTATTTATTAATTTGAATAGATATTAAGTTTTATTATA | 448 |

TABLE 18-continued

Additional elements of GV gene expression cassettes

| Element | Sequence | SEQ ID NO |
|---|---|---|
| | TTTACACTTACATACTAATAATAAATTCAACAAACAATTTAT<br>TTATGTTTATTTATTTATTAAAAAAAACAAAAACTCAAAATT<br>TCTTCTATAAAGTAACAAAACTTTTA | |
| 5'<br>insulator<br>element | GAGGGACAGCCCCCCCCAAAGCCCCCAGGGATGTAATTACGTC<br>CCTCCCCCGCTAGGGGGCAGCAGCGAGCCGCCCGGGGCTCCGCT<br>CCGGTCCGGCGCTCCCCCCGCATCCCCGAGCCGGCAGCGTGCGGG<br>GACAGCCCGGGCACGGGGAAGGTGGCACGGGATCGCTTTCCTCT<br>GAACGCTTCTCGCTGCTCTTTGAGCCTGCAGACACCTGGGGGGAT<br>ACGGGGAAAA | 449 |
| TRE3G<br>promoter | GAGTTTACTCCCTATCAGTGATAGAGAACGTATGAAGAGTTTACT<br>CCCTATCAGTGATAGAGAACGTATGCAGACTTTACTCCCTATCAG<br>TGATAGAGAACGTATAAGGAGTTTACTCCCTATCAGTGATAGAGA<br>ACGTATGACCAGTTTACTCCCTATCAGTGATAGAGAACGTATCTA<br>CAGTTTACTCCCTATCAGTGATAGAGAACGTATATCCAGTTTACT<br>CCCTATCAGTGATAGAGAACGTATGTCGAGGTAGGCGTGTACGGT<br>GGGCGCCTATAAAAGCAGAGCTCGTTTAGTGAACCGTCAGATCG<br>CCTGGAGCAATTCCACAACACTTTTGTCTTATACTT | 450 |
| SV40<br>poly-<br>adenylation<br>tail | AACTTGTTTATTGCAGCTTATAATGGTTACAAATAAAGCAATAGC<br>ATCACAAATTTCACAAATAAAGCATTTTTTTCACTGCATTCTAGTT<br>GTGGTTTGTCCAAACTCATCAATGTATCTTA | 451 |
| 3'<br>insulator<br>element | TTTTCCCCGTATCCCCCCAGGTGTCTGCAGGCTCAAAGAGCAGCG<br>AGAAGCGTTCAGAGGAAAGCGATCCCGTGCCACCTTCCCCGTGCC<br>CGGGCTGTCCCCGCACGCTGCCGGCTCGGGGATGCGGGGGGAGC<br>GCCGGACCGGAGCGGAGCCCCGGGCGGCTCGCTGCTGCCCCCTA<br>GCGGGGGAGGGACGTAATTACATCCCTGGGGGCTTTGGGGGGGG<br>GCTGTCCCT | 452 |
| 3' IRT | GATATCTATAACAAGAAAATATATATATAATAAGTTATCACGTAA<br>GTAGAACATGAAATAACAATATAATTATCGTATGAGTTAAATCTT<br>AAAAGTCACGTAAAAGATAATCATGCGTCATTTTGACTCACGCGG<br>TCGTTATAGTTCAAAATCAGTGACACTTACCGCATTGACAAGCAC<br>GCCTCACGGGAGCTCCAAGCGGCGACTGAGATGTCCTAAATGCA<br>CAGCGACGGATTCGCGCTATTTAGAAAGAGAGAGCAATATTTCA<br>AGAATGCATGCGTCAATTTTACGCAGACTATCTTTCTAGGG | 453 |

The GVES exemplified here has been used in the experiments illustrated in FIGS. 11A-11G, and 13A-24D.

Example 14: Identification of Cassettes Resulting in Expression of GV in Mammalian Cells Experiments were performed that can be used to identify the elements of a cassette for the expression of GV genes in mammalian cells inclusive of regulatory genes and gene configuration with the GVES and regulatory regions reported in Example 13 above.

A first set of experiments was performed to identify the features of an exemplary genetic construct to be used to express exemplary GV genes in a mammalian cell.

In particular a genetic construct was provided configured to obtain stable genomic integration of mCherry in HEK-293 cells. The construct schematically shown in FIG. 10A contained a 5'ITR for piggyBac transposase, chicken beta-globin insulator, TRE3G promoter upstream of the mCherry sequence and SV40 polyadenylation element downstream, followed by a chicken beta-globin insulator and 3'ITR for piggyBac transposase.

Figure 10A:
FIGS. 10A-10B illustrate testing of regulatory genes in a genetic construct and sorting of resulting cell line.

HEK-293 cells were transfected with the construct of FIG. 10A and plasmid encoding the piggyBac transposase, and subjected to FACS. And the genomic integration of the construct was detected as reported in FIG. 10B.

Figure 10B:
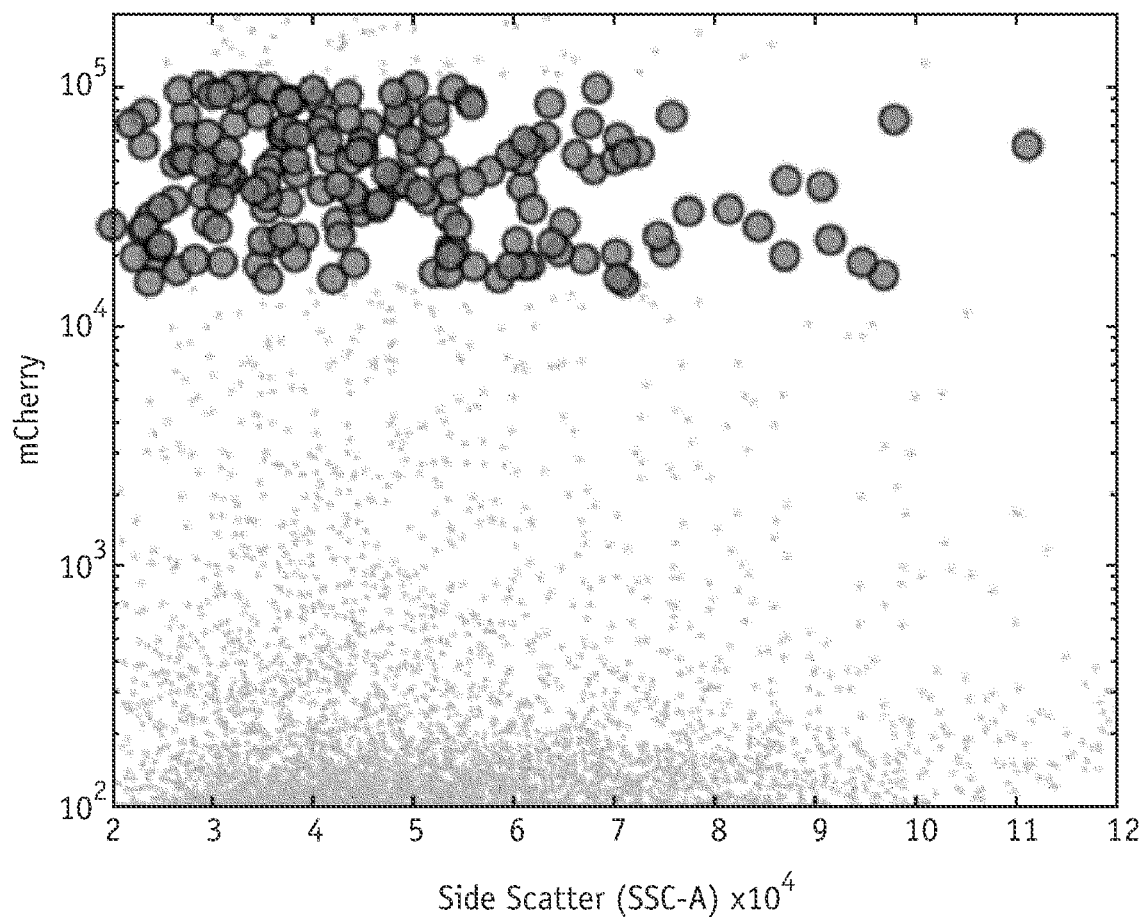

The regulatory regions of the above construct were therefore used to express the exemplary GVES of Example 13 herein also indicated as mARG, and in particular the three constructs were provided using the regulatory sequences tested in FIGS. 10A-10B, one including a GVPB cassette and one including a GPC construct as shown in FIG. 11A.

The constructs of FIG. 11A were used to generate polyclonal cell in HEK293-tetON cells and the fluorescence activated cell sorting of the HEK293-tetON cells transfected with integrating mARG constructs of FIG. 11A.

FACS results of mARG-expressing HEK293-tetON cells. Cells were binned in different relative expression levels, subtypes 1-4 illustrated FIGS. 11B-11C, showed that while all subtypes produced GVs but some subtypes expressed different amounts of average gas vesicles per cell (FIG. 11D).

Similar experiments were performed in CHO-tetON which were further transfected with the constructs of FIG. 11A to generate polyclonal cell in the CHO-tetON.

The FACS of mARG-expressing CHO-tetON cells are reported in FIG. 11E, representative TEM image of buoyancy-enriched lysate from CHO-tetON cells sorted are reported in FIG. 11G and the approximate gas vesicle yield for the sorted mARG-expressing CHO-tetON cells. is reported in FIG. 11G. Result illustrates that mARG-expression in different mammalian cells, for example HEK293 and CHO-K1, is possible.

Example 15: Transfection and Expression of an Exemplary GV Gene Cluster with GVES Codon-optimized gas vesicle genes from Table 8 were cloned from different microbial species into unique monocistronic plasmids and mammalian cells were transiently transfected using polyethylenimine nanoparticles (FIG. 12A).

This assay uses the combination of two stochastic events to sample a broad range of gene stoichiometries and expression levels. First, the heterogeneous loading of plasmids in each nanoparticle and second, the variable delivery of each nanoparticle to the nucleus results in a combinatorial distribution of plasmid copy numbers during each transfection experiment.

Upon transfection, the cells were allowed to express the gas vesicle proteins for 72 hours and then gently lysed. The lysate was centrifuged to buoyancy-enrich any fully formed gas vesicles. Finally, the top fraction of the lysate was analyzed under transmission electron microscopy for presence and phenotype of gas vesicles.

Transfection of the gas vesicle genes from *Halobacteria salinarum* and *Anabaena flos-aquae* did not lead to the formation of detectable gas vesicles in mammalian cells with transmission electron microscopy (see Example 25), however, the genes from *Bacillus megaterium* reported in Example 12 were able to produce gas vesicles in mammalian cells detectable with the transmission microscopy detection method (FIG. 12B).

The co-transfection of these three plasmids (see Example 12) was sufficient for robust expression of gas vesicles in cells, herein referred to as mammalian acoustic reporter gene (mammalian ARG) (FIG. 12C).

The first plasmid encodes gas vesicle protein B, the second encodes all assembly factors and the third encodes the proteins requiring a boost in expression (FIG. 12D).

Accordingly, a polycistronic plasmid was constructed containing eight gas vesicle genes connected with the porcine teschovirus-1 2A self-cleavage (p2A) element as schematically shown in FIG. 12D.

In particular, the schematic illustration of FIG. 12D (middle and bottom) shows an exemplary polycistronic configuration according to the disclosure.

The construct in the middle of FIG. 12D comprises gvpN, F, G, L, S, K, J and U with two adjacent genes separated by a 2A self-cleaving element which is further exemplified in Example 12 and Table 16 above. The construct at the bottom of FIG. 12D comprises gvpJ, F, G, L, and K with two adjacent genes separated by a self-cleaving element, exemplified in Table 17.

However, the gene stoichiometry of the one-to-one architecture of the illustration of FIG. 12D (middle, Table 16) was not optimal since the co-transfection of this plasmid together with a plasmid that encoded for gas vesicle protein B and did not lead to detectable gas vesicles expression in mammalian cells. By assaying for the relative efficiency of gas vesicle protein expression from each gene in this plasmid it became apparent that three gas vesicle genes (N, S and U) could be expressed to lower levels compared with gas vesicle genes J, F, G, L and K.

A booster plasmid was therefore provided to further express vesicle genes J, F, G, L and K which is further described in Example 12 and Table 17 above.

Example 16: Mammalian ARG can be Genomically Integrated

To test the generalizability of the mammalian ARG, the mARG formed in Example 13 was genomically integrated in human embryonic kidney (HEK) cells as well as Chinese hamster ovary cells, allowing them to express gas vesicles, as exemplified in FIGS. 11A-11G, using the construct illustrated in FIG. 11A and FIG. 13A.

Mammalian ARGs behaved similarly in both cell lines and using transmission electron microscopy. An average yield of one gas vesicle for every four cells was estimated (FIGS. 11D, and 11G for HEK-tetON and CHO-tetON, respectively). This indicated that a subpopulation of cells was optimally producing gas vesicles. FIG. 13B illustrates a representative image of gas vesicles in the cytosol of HEK cells.

To select for this subpopulation, FIGS. 13C and 13D, the Applicant screened 30 monoclonal HEK cells and 20% of the cell lines produced on average greater than one gas vesicle per cell.

The cell line yielding the highest expression of gas vesicles produced on average 45 gas vesicles per cell (FIG. 13E) when induced with 1 µg/mL of doxycycline and 5 mM sodium butyrate for 72 hours, and the Applicant focused on this cell line for the remainder of this work. Importantly, the expression of gas vesicles was not toxic to cells as determined using five different assays. These included observing that the shape of cells expressing mARGs did not change as a result of mARG-expression, FIG. 13I, including membrane integrity with trypan blue, relative number of metabolically active cells with CellTiter-Glo®, and metabolic activity using Resazurin reduction (FIG. 13J), as well as including a 6-day co-culture of mARG-HEK cells showed only a minor growth disadvantage compared with mCherry-HEK cells (FIG. 13K. In addition, a co-culture of mARG-HEK and HEK293T was compared with mCherry-HEK and HEK293T cells over 6-days was assayed for fraction of co-culture (FIG. 16). This showed that the expression of reporter genes (here mARG and mCherry) led to decrease in the fraction of reporter gene-expressing cells relative to HEK293T cells.

Using transmission electron microscopy, as exemplified in FIG. 13G, the average gas vesicles produced in this cell line were measured to be 64±12 nm (standard deviation) wide and 276±212 nm (standard deviation) long with some reaching aspect ratios greater than 30 (lengths larger than 1 micron) (FIG. 13H). This corresponds to an average gas vesicles volume of 0.605 attoliters (ranging from 0.008-10 attoliters), assuming a tapered cylindrical shape as will be understood by a skilled person. Representative TEM image of a 60-nm section through an mARG-HEK cell showing an angled slice through two bundles of gas vesicles in the cytosol in FIG. 13F.

Example 17: Ultrasound Imaging of Mammalian ARG-Expressing Cells

From previous studies, it was anticipated that gas vesicles encoded by the *B. megaterium* gene cluster will linearly scatter ultrasound signal (scattering the same ultrasound frequency that was insonated). Due to the strong linear scattering of ultrasound by mammalian cells this can lead to a challenge for detecting any added echogenicity from the expressed gas vesicles.

To address this, the Applicant turned to the unique physical property of gas vesicles in order to extract a unique acoustic signature from the expressed gas vesicles. In particular Applicant surprisingly found that acoustic fields with pressures beyond the collapsing threshold of gas vesicles will cause a rapid change in volume, which will transiently distort the insonated acoustic field (FIG. 14A) (see U.S.

application Ser. No. 16/736,581 entitled "BURST Ultrasound Reconstruction with Signal Templates and related Methods and Systems" filed on Jan. 7, 2020 herein incorporated by reference in its entirety).

This can be used to sensitively detect gas vesicles-specific nonlinear signals at the moment of collapse. To image this, serial amplitude modulation images were acquired during and after the collapse of gas vesicles. This allows for the discrimination of the steady-state background signal from the delta function-like signal obtained from the collapse of gas vesicles (FIGS. 14B and 14C). During the serial acquisition, each amplitude modulation sequence extracts nonlinear ultrasound echoes by sending two half-amplitude echoes that are digitally subtracted from a third full amplitude echo. Using this imaging paradigm, any cytotoxicity from the collapse of gas vesicles was not observed (FIG. 14D).

Using this new ultrasound imaging paradigm, the Applicant is interested in measuring the different characteristics of mammalian ARGs in vitro. To measure the effect of expression length on the ultrasound intensity, cells where allowed to express gas vesicles for the specified number of days and $6\times10^6$ cells were loaded into acoustically transparent agarose phantoms. After two days, cells expressing gas vesicles produced robust ultrasound contrast which increased with respect to expression duration (FIG. 14F). Similar results are obtained by measuring fluorescence from the mCherry reporter expressed by the same cells expressed under the same conditions (FIG. 17A).

Example 18: Using Mammalian ARGs to Monitor Circuit-Driven Gene Expression

It is often desirable to obtain a readout of the dynamic cellular function of cells the body, for example, to investigate the activation of immune cells at the site of disease or the dynamics of a genetic pathway.

To test if mammalian ARGs can faithfully monitor circuit-driven gene expression, the Applicant measured the ultrasound response of the exemplary mammalian ARGs of Example 13 under the control of the tetracycline-inducible promoter (using reverse tetracycline-controlled transactivator). FIG. 14E illustrates mARGs controlled by a conditional promoter (e.g. tetracycline-inducible promoter). The ultrasound contrast produced by cells followed the expected transfer function of the promoter, as measured by fluorescence (FIG. 17B), confirming the ability of mARGs to follow the dynamics of cells using ultrasound (FIG. 14G).

Next, the Applicant sought to identify the sensitivity of detecting mARG-expressing cells in a mixed cell population. For this, control cells that only expressing mCherry together with gas vesicle-expressing cells were combined at varying ratios. The Applicant was able to sensitively detect cells down a 2.5% of total cells, corresponding to 0.5% volumetric densities or approximately 4 cells per voxel (FIG. 14H). This sensitivity is expected to be sufficient for in vivo scenarios.

An alternative method to monitor the dynamics of gene expression or the movement of cells is to erase the signal of a region and monitoring the return of that signal. This is a method called acoustic recovery after collapse (ARC), analogous to fluorescence recovery after photobleaching (FRAP). In addition, in many imaging experiments, the output of a gene circuit is read out only once. However, in some cases, it may be desirable to track gene expression over time. To test the above descriptions, the Applicant tested whether mARG-expressing cells in which the gas vesicles have been collapsed during imaging could re-express these reporters to allow additional imaging. mARG-HEK cells cultured in a nutrient-supported hydrogel produced clear ultrasound contrast 3 days after induction and were able to re-express their acoustic reporters over three additional days (FIGS. 14I and 14J).

Example 19: Mammalian ARGs Enable Ultrasound Imaging of Gene Expression In Vivo

Having characterized the core capabilities of mammalian ARGs for monitoring cellular location and function in vitro, the Applicant set out in this example to test if this new tool can be used for in vivo studies.

Figure 22A:
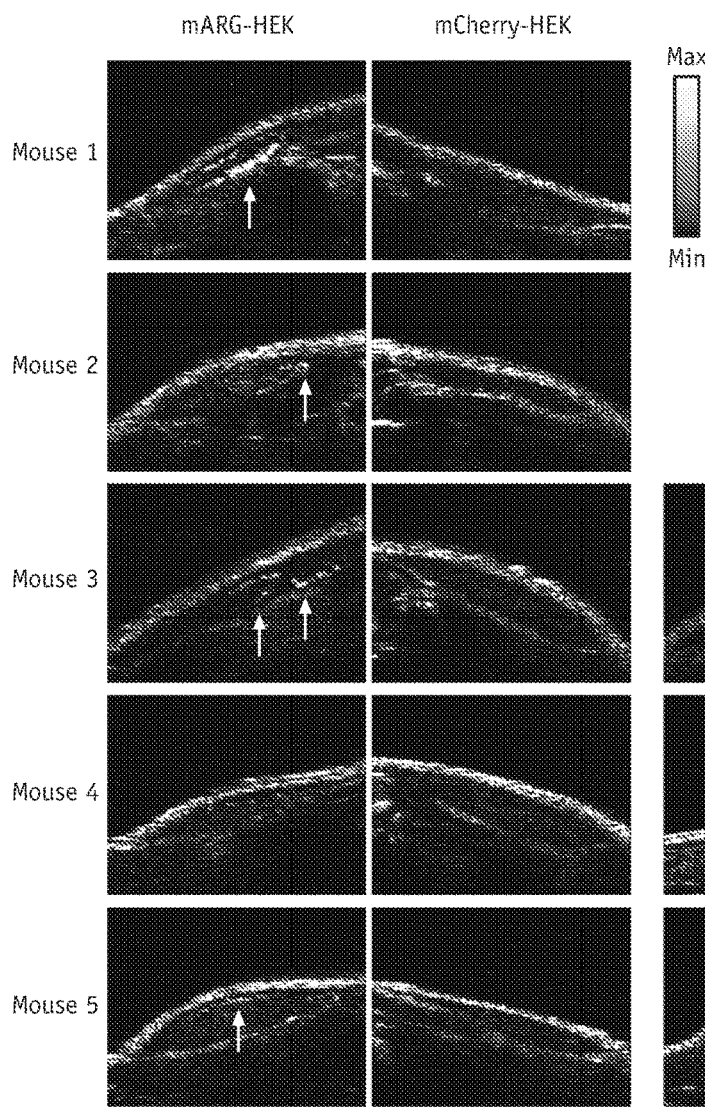
FIGS. 22A-22B show biological replicates of in vivo ultrasound imaging of gene expression. In particular, in FIG. 22A, the left column shows ultrasound images of tumors containing mARG-HEK cells after 4 days of doxycycline administration. The right column shows ultrasound images of tumors containing mCherry-HEK cells after 4 days of doxycycline administration. After imaging the tumors were insonated with 3.2 MPa of ultrasound to collapse the expressed gas vesicles.

ARG-expressing mammalian cells were introduced subcutaneously in the left flank of mice while loading mCherry-only control cells in their right flank (FIG. 15A). The reporter genes in both cells were under the control of the tetracycline-inducible protomer, as a result the mice were intraperitoneally injected with 75 µg doxycycline and 25 mg sodium butyrate on a daily basis (FIG. 15B). After the cells were allowed to express their respective reporter genes, fluorescence and ultrasound contrast of the cells was collected. The Applicant was able to for the first time monitor gene expression in vivo with great spatial resolution using BURST ultrasound (FIG. 15C and FIG. 22A). Ultrasound imaging of control tumor expressing mCherry did not produce BURST ultrasound signal (FIG. 15D and FIG. 22A).

Figure 20:
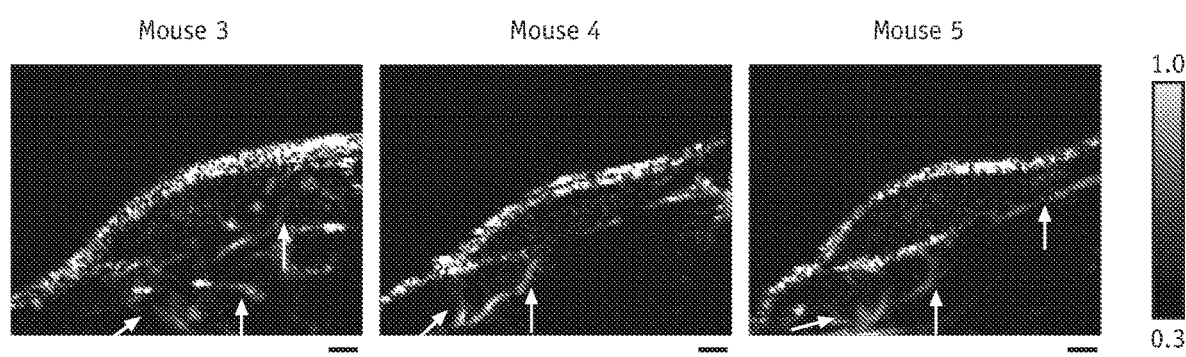
FIG. 20 shows representative Doppler ultrasound images of tumors containing mARG-HEK cells. Doppler ultrasound images were acquired using 250 frames of ultrafast plane-waves at 25V and used to reconstruct vascular maps plotted as normalized power doppler signal overlaid on anatomical images in grayscale. White arrows indicate location of vasculature around the tumor and not in the core of the tumor as seen by Doppler ultrasound. Scale bars represent 1 mm.
Figure 21:
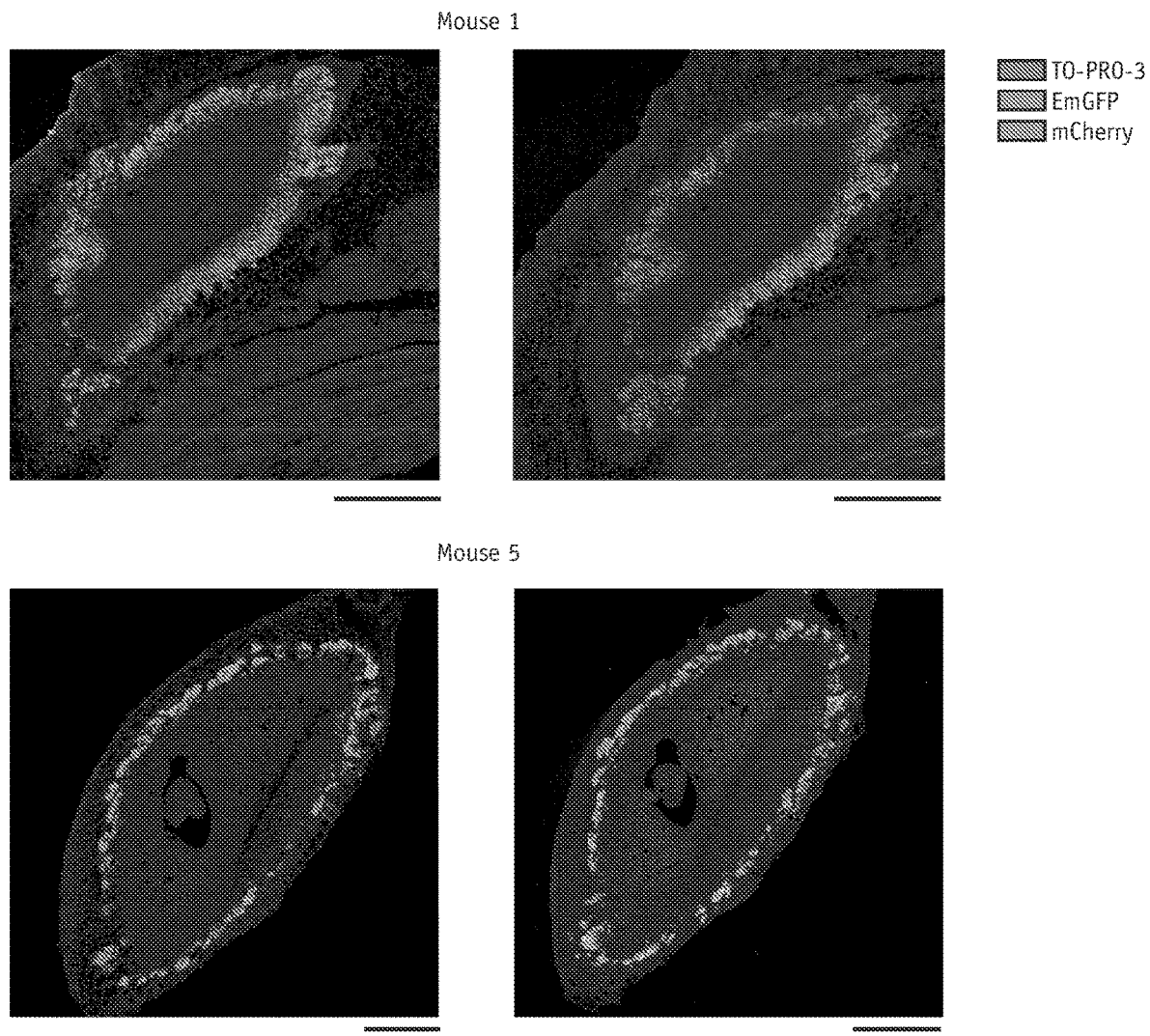
FIG. 21 shows representative histology sections of tumors containing mARG-HEK cells. For each mouse, two neighboring sections are presented. The light gray color shows the GFP and mCherry fluorescence around the periphery of the tumor.

Interestingly, fluorescence imaging indicated that both tumors were receiving the inducer doxycycline (FIG. 15G) but it appears as though the entire tumor was equally expressing the reporter genes. However, using ultrasound only a 'zone' of gas vesicles-specific contrast was observed. Using doppler ultrasound, a technique used to visualize the vasculature, it was observed that inside the tumor was avascular as expected from the short period post inoculation (FIG. 20).

Figure 19:
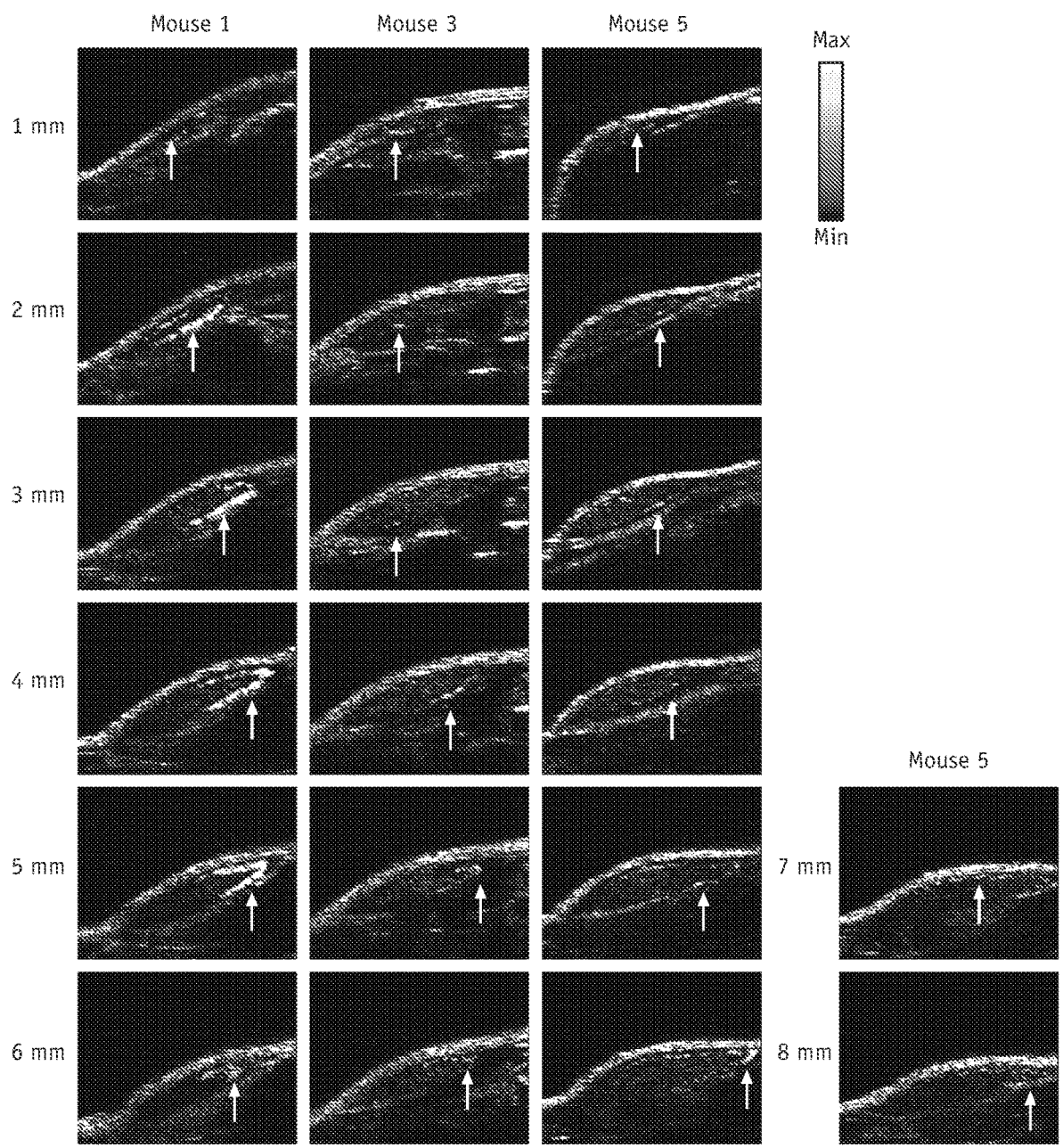
FIG. 19 shows exemplary in vivo ultrasound images of adjacent planes in mARG-HEK tumors acquired at 1 mm intervals. For each imaging slice the difference heatmap of nonlinear signal between frame 1 and frame 4 is overlaid on grayscale anatomical scale. Minimum and maximum values of color bar are 4000 and 40000, respectively. White arrows indicate location of mARG-specific BURST ultrasound signal. Scale bars are 1 mm.
Figure 22B:
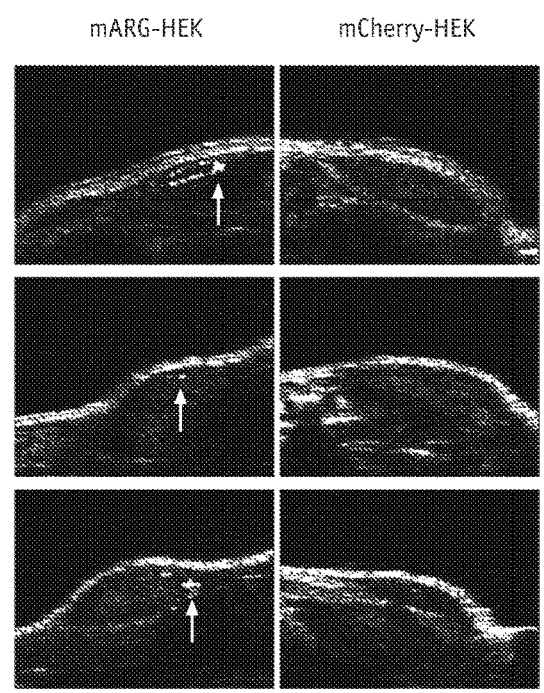

After the tumors were sectioned and imaged using fluorescent histology (FIG. 15F and FIG. 21), it became evident that the diffusion of inducer to the tumor cells painted a band of gene expression. This pattern of gene expression was non-invasively visualized with ultrasound using mARGs, whereas fluorescent imaging could not reveal this expression pattern due to the limited penetration of light in tissue. BURST ultrasound imaging of adjacent planes could be collected to non-invasively image gene expression across the tumor (FIG. 15E and FIG. 19). Furthermore, similar to the in vitro experiments, mARG-expressing cells can repeatedly express gas vesicles, imaged and re-express gas vesicles to enable repeated monitoring cellular location and function (FIG. 22B).

Example 20: Ultrasound Contrast in View of GV Concentration in Mammalian Cells In Vitro A further set of experiments was performed to test the dependence of ultrasound contrast on gas vesicle density in mammalian cell culture. In particular, a monoculture of mARG-HEK cells was induced with different concentrations of doxycycline, or after fully-induced mARG-HEK cells were mixed with mCherry-HEK cells at different ratios. All cells were cultured with 5 mM sodium butyrate during expression. After that relative ultrasound contrast produced by mARG-HEK cells was tested in hydrogel as a function of the estimated average number of gas vesicles (GV) per nanoliter present. The number of gas vesicles was quantified after 72 hours of induced expression, as counted in lysates using TEM. Ultrasound contrast was normalized to the maximum in each type of titration.

Figure 18:
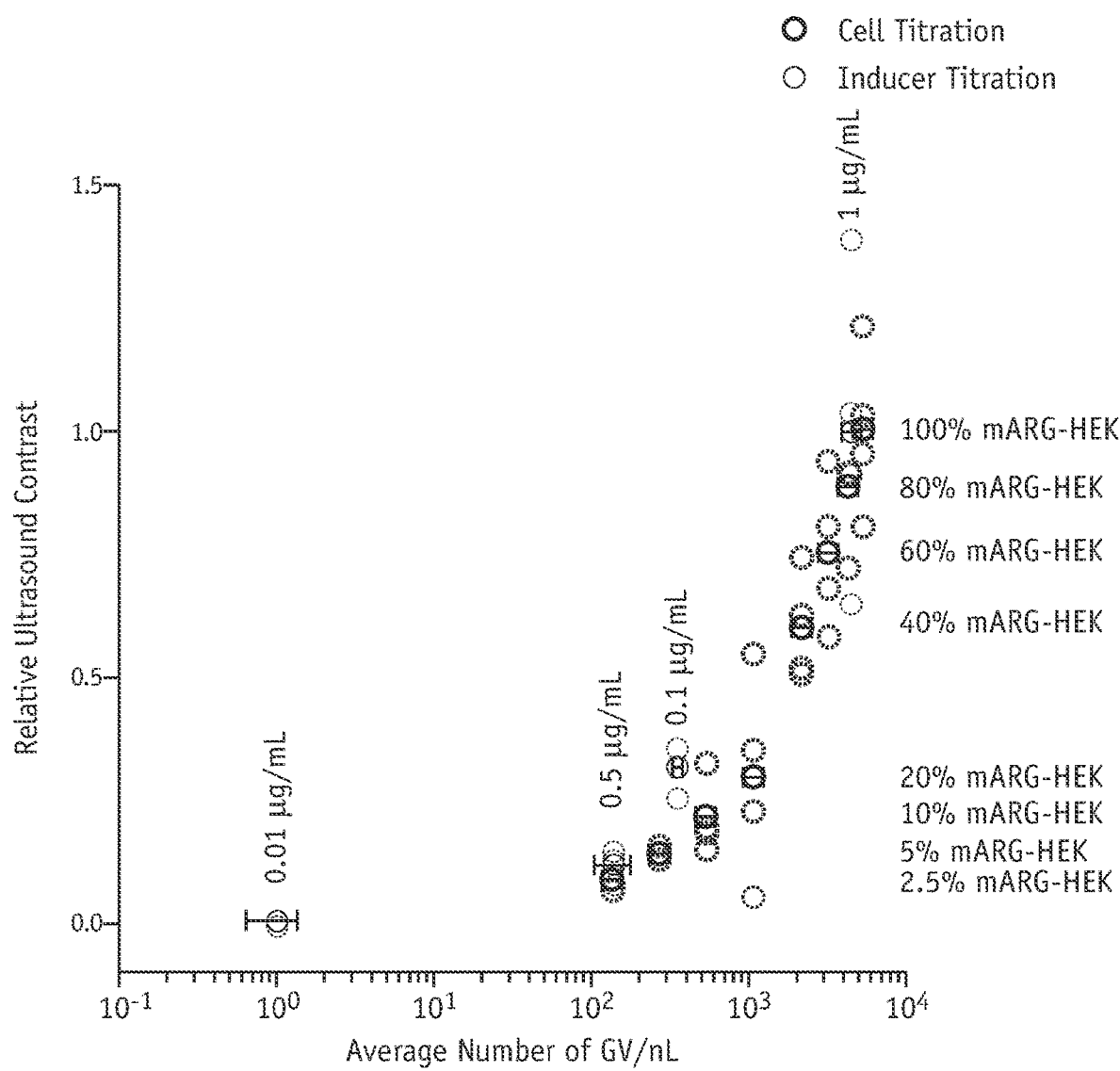
FIG. 18 shows a chart illustrating a relative ultrasound contrast produced by mARG-HEK cells in hydrogel as a function of the estimated average number of gas vesicles (GV) per nanoliter gray circle symbols represent results from mARG-HEK cells induced with 1 µg/mL doxycycline for 3 days (producing on average 45 gas vesicles per cell) mixed with mCherry-HEK cells (expressing no gas vesicles) in varying proportions, as presented in FIG. 14H. Square Gray symbols represent results from mARG-HEK cells induced with 0.01, 0.05, 0.1 and 1 µg/mL doxycycline for 3 days; expressing on average 0.01±0.004, 1.4±0.4, 3.5±0.3, 45±5.1 (mean±SEM) gas vesicles per cell, respectively, as quantified by TEM . . . Dark symbols show the mean of ultrasound contrast for 4 replicates. Error bars represent SEM of 4 biological replicates for 0.01, 0.05, 0.1 µg/mL induction and n=3 biological replicates (each from two technical replicates) for 1 µg/mL samples.

In particular the ultrasound contrast mARG-HEK cells induced with 1 µg/mL doxycycline for 3 days (producing on average 45 gas vesicles per cell) mixed with mCherry-HEK cells (expressing no gas vesicles) in varying proportions is reported in FIG. 18 with light gray symbols.

The ultrasound contrast of mARG-HEK cells induced with 0.01, 0.05, 0.1 and 1 µg/mL doxycycline for 3 days; expressing on average 0.01±0.004, 1.4±0.4, 3.5±0.3, 45±5.1 (mean±SEM) gas vesicles per cell, respectively, as quantified by TEM is reported in FIG. 18 with dark gray symbols.

From this study, illustrated in FIG. 18, the applicants can conclude to detect the presence of mARG-expressing cells in these mixtures down to 2.5% of total cells, corresponding to <0.5% volumetric density, or about three cells or 135 gas vesicles per voxel with dimensions of 100 mm. A similar voxel-averaged concentration of gas vesicles was detectable in a monoculture of mARG-HEK cells induced to express 1.4±0.6 gas vesicles per cell.

Example 21: Selection Funnel for GVES Transfected n Mammalian Cells In Vitro

GVES can be integrated in the genome of mammalian cells, e.g. Example 13. Genomic integration methods described above and known by a skilled person will produce a heterogeneous polyclonal population of cells. In this heterogeneous population of cells, there will be a range of GVES expression levels from high expression down to no detectable expression.

The polyclonal population of mammalian cells will produce gas vesicles as illustrated in FIGS. 11A-11G. Using cell sorting methods such as FACS and/or magnetic assisted cell sorting (MACS), the cells can be binned into groups of cells with similar expression profiles, as exemplified in (FIG. 11B) or monoclonal cells can be selected (FIGS. 12C and 12D). Monoclonal cells are a colony of cells that have been expanded from a single parent cell.

The applicant selected 575 monoclonal cells using FACS from polyclonal HEK-tetON cells that using the piggyBac transposase system, had Example 13 GVES integrated in their genome. From these cells, the best performing monoclonal cells were assayed by measuring cellular viability, fluorescence intensity, and gas vesicle expression as measured by TEM for each cell after expression for 72 hours (upon induction with 1 µg/mL of doxycycline and 5 mM sodium butyrate (Table 19).

TABLE 19 selection funnel for mARG-HEK cells

| Collected from FACS | Formed colonies | Triple positive fluorescence | Formed GVs (TEM) | >1 GVs/cell |
|---|---|---|---|---|
| 576 | 30 | 21 | 12 | 6 |

The numbers indicate the number of cells or cell lines selected at each stage. From this experiment, the best performing cells produced on average 45 gas vesicles per cell (FIG. 13E).

Example 22: Exemplary GVGC Polynucleotide Construct to Allow Expression of Two Different GV Cassettes Experiments were performed to identify elements that can be used to create configurations of a construct designed to allow expression of two different GV cassettes.

Figure 23:
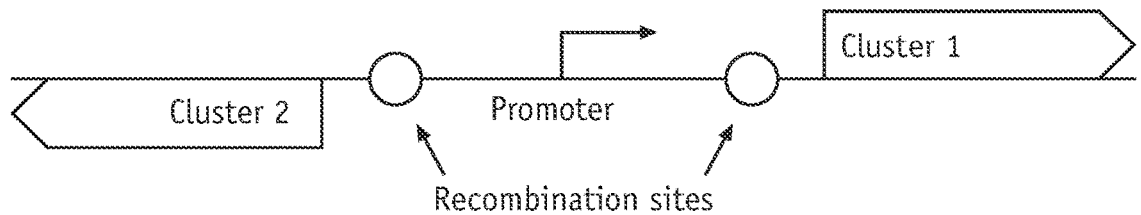
FIG. 23 shows an exemplary configuration of a construct designed to allow expression of two different GV types in one prokaryotic cell.

An element that can be used in constructs of the present disclosure is exemplified in the exemplary construct in FIG. 23 designed to provide alternating expression of two GV types in a prokaryotic cell and/or mammalian cell, the first GV type encoded by Cluster 1, and the second GV type encoded by Cluster 2, shown as block-shaped arrows facing in opposite orientations of a DNA strand (shown as a straight line), with a promoter between the two clusters. The promoter is flanked by recombination sites (e.g. flippase recognition target, FRT sites) shown as circles. For example, initially, the promoter can be oriented in a direction operatively linked to Cluster 1, initiating expression of gyp genes for the formation of GV type 1.

In presence of a cognate recombinase (e.g. flippase, Flp, CRE/Lox), expressed from another genetic construct in the mammalian cell, the orientation of the promoter is reversed upon recombination at the FRT sites, and thereafter is oriented in the opposite direction, operatively linked to Cluster 2, initiating expression of gyp genes for the formation of GV type 2.

The use of recombination sites can alternatively control the conditional expression of a transactivating or repressing protein element that control the activity of GVES promoter(s). The recombination site, flanking a promoter that controls the expression of the transcription regulatory factor (e.g. TET) can be switched in an orientation that can express the transactivating or repressing protein element, or can switch to the opposite direction so that transcription regulatory factor is no longer expressed. As a result, the activity of the GVES promoter can be tuned.

Example 23: Construction of Consolidated Optimized GVES System

Experiments were performed to verify whether the architecture of the mARG of Example 13 can be further consolidated by connecting the gas vesicle protein B gene to the polycistronic construct using IRES. When this architecture is co-transfected to cells with the booster plasmid, it robustly produces gas vesicles. This strategy is being further pursued to consolidate the mammalian ARG to a single genetic cassette.

In particular, a consolidated mARG construct comprising 2 gene cassettes enabling mammalian gas vesicle expression has been identified following the Experiments reporting in FIGS. 24A-24D.

The construct encoding gvpB from *B. megaterium* of Table 15 was combined with the construct in Table 16 using an IRES sequence. A schematic illustrates this in FIG. 24A (top) and Table 20 indicates the gene sequence.

Figure 24A:
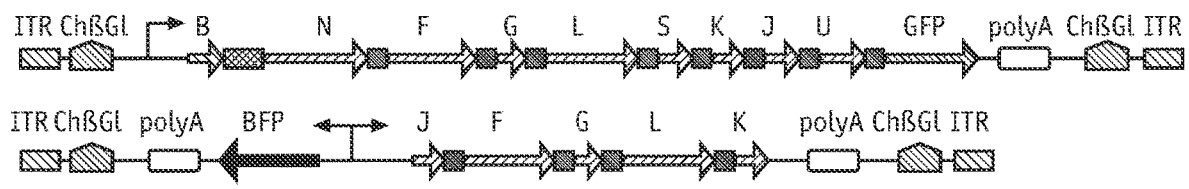
FIGS. 24A-24D illustrate an consolidated mARG construct comprising 2 gene cassettes enabling mammalian gas vesicle expression.
Figure 24B:
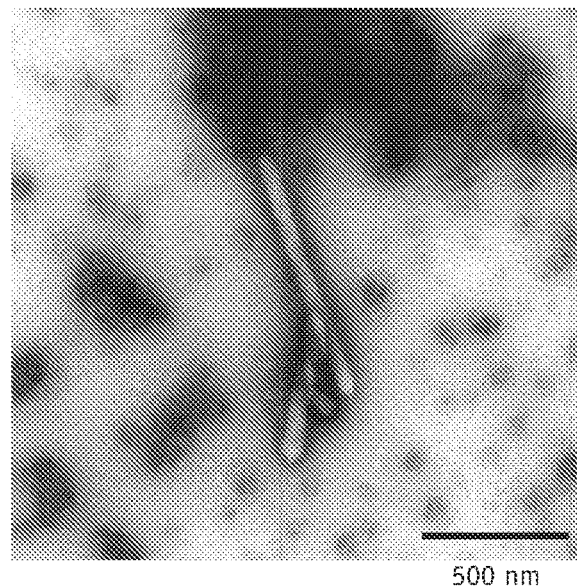
Figure 24C:
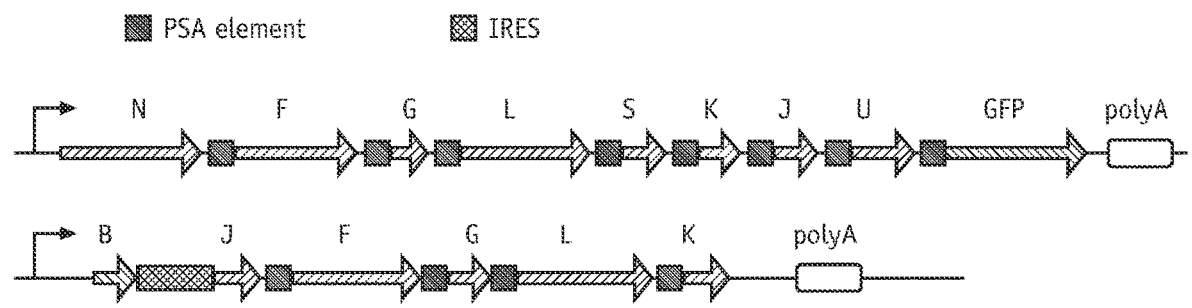
Figure 24D:
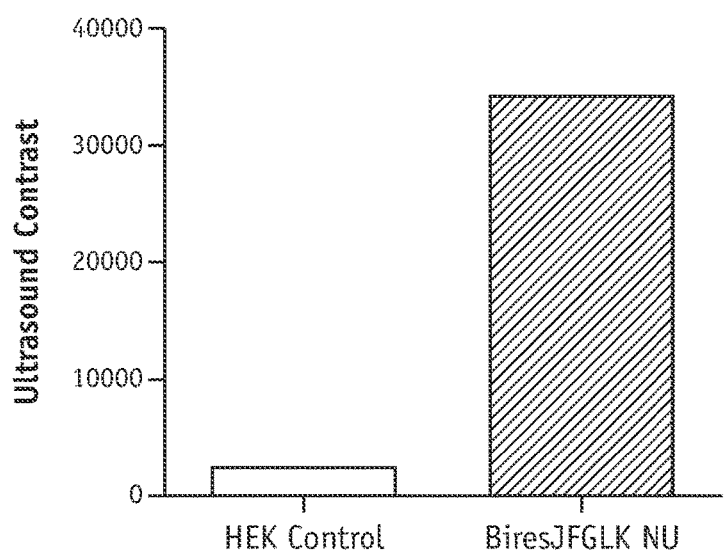

The cassette from Table 20 and table 17 were integrated to the genome of HEK293-tetON cells as reported the material and methods. GV expression in these cells was detectable using TEM of the cell lysate after 72 hours of expression with 1 µg/mL doxycycline (FIG. 24B).

Similarly, the construct encoding gvpB from *B. megaterium* of Table 11 was combined with the construct in Table 14 using an IRES sequence. A schematic illustrates this in FIG. 24C (top) and Table 21 indicates the gene sequence. The cassette from Table 21 and table 12 were transiently transfected to the genome of HEK293T cells as reported the material and methods. GV expression in these cells was detectable using BURST ultrasound imaging of the cells after 72 hours of expression (FIG. 24D), HEK control refers to wild types HEK293T cells and BiresJFGLK NU refers to HEK293T cells that have been transfected with constructs in Table 21 and Table 12.

TABLE 20

Exemplary consolidated polynucleotide cassette for polycistronic expression of gvpB with GVA proteins.

| Construct | Sequence | seq id no: |
|---|---|---|
| CMV:gvpB<br>:IRES:<br>gvpNFGLSKJU-<br>EmGFP:<br>polyA | CGTTACATAACTTACGGTAAATGGCCCGCCTGGCTGACCGCCCAACGACC<br>CCCGCCCATTGACGTCAATAATGACGTATGTTCCCATAGTAACGCCAATA<br>GGGACTTTCCATTGACGTCAATGGGTGGAGTATTTACGGTAAACTGCCCA<br>CTTGGCAGTACATCAAGTGTATCATATGCCAAGTACGCCCCCTATTGACG<br>TCAATGACGGTAAATGGCCCGCCTGGCATTATGCCCAGTACATGACCTTA<br>TGGGACTTTCCTACTTGGCAGTACATCTACGTATTAGTCATCGCTATTACC<br>ATGGTGATGCGGTTTTGGCAGTACATCAATGGGCGTGGATAGCGGTTTGA<br>CTCACGGGGATTTCCAAGTCTCCACCCCATTGACGTCAATGGGAGTTTGTT<br>TTGGCACCAAAATCAACGGGACTTTCCAAAATGTCGTAACAACTCCGCCC<br>CATTGACGCAAATGGGCGGTAGGCGTGTACGGTGGGAGGTCTATATAAGC<br>AGAGCTCGTTTAGTGAACCGTCAGATCGCCTGGAGACGCCATCCACGCTG<br>TTTTGACCTCCATAGAAGACACCGGGACCGATCCAGCCTCCGGACTCTAG<br>CCTAGGCTTTTGCAAAAAGCTATTTAGGTGACACTATAGAAGGTACGCCT<br>GCAGGTACCGAGCTCGGATCCAGTACCCTTCACCATGAGCATCCAGAAGT<br>CCACCAACAGCAGCAGCCTGGCCGAAGTGATCGACCGGATCCTGGACAA<br>GGGCATCGTGATCGACGCCTTCGCCAGAGTGTCCGTCGTGGGCATCGAGA<br>TCCTGACCATCGAGGCCAGAGTCGTGATCGCCAGCGTGGACACCTGGCTG<br>AGATATGCCGAAGCCGTGGGCCTGCTGCGGGACGACGTGGAAGAAAATG<br>GCCTGCCCGAGCGGAGCAACAGCTCTGAGGGACAGCCCCGGTTCAGCATC<br>TGAACTAAATCGCACTGTCGGCGTCCCCCCCTAACGTTACTGGCCGAAGC<br>CGCTTGGAATAAGGCCGGTGTGCGTTTGTCTATATGTTATTTTCCACCATA<br>TTGCCGTCTTTTGGCAATGTGAGGGCCCGGAAACCTGGCCCTGTCTTCTTG<br>ACGAGCATTCCTAGGGGTCTTTCCCCTCTCGCCAAAGGAATGCAAGGTCT<br>GTTGAATGTCGTGAAGGAAGCAGTTCCTCTGGAAGCTTCTTGAAGACAAA<br>CAACGTCTGTAGCGACCCTTTGCAGGCAGCGGAACCCCCCACCTGGCGAC<br>AGGTGCCTCTGCGGCCAAAAGCCACGTGTATAAGATACACCTGCAAAGGC<br>GGCACAACCCCAGTGCCACGTTGTGAGTTGGATAGTTGTGGAAAGAGTCA<br>AATGGCTCTCCTCAAGCGTATTCAACAAGGGGCTGAAGGATGCCCAGAAG<br>GTACCCCATTGTATGGGATCTGATCTGGGGCCTCGGTGCACATGCTTTACA<br>TGTGTTTAGTCGAGGTTAAAAAACGTCTAGGCCCCCCGAACCACGGGGAC<br>GTGGTTTTCCTTTGAAAAACACGATGATAATATGGCCACAACCGTGACCG<br>TGCTGACCGACAAGCGGAAGAAGGGCAGCGGCGCCTTCATCCAGGACGA<br>CGAGACAAAAGAGGTGCTGAGCAGAGCCCTGAGCTACCTGAAGTCCGGC<br>TACAGCATCCACTTCACCGGACCTGCCGGCGGAGGCAAGACATCTCTGGC<br>TAGAGCCCTGGCCAAGAAACGGAAGCGGCCCGTGATGCTGATGCACGGC<br>AACCACGAGCTGAACAACAAGGACCTGATCGGCGATTTCACCGGCTACAC<br>CAGCAAAAAGGTGATCGACCAGTACGTGCGGAGCGTGTACAAGAAAGAC<br>GAACAGGTGTCCGAGAACTGGCAGGACGGCAGACTGCTGGAAGCCGTGA<br>AGAATGGCTACACCCTGATCTACGACGAGTTCACCAGAAGCAAGCCCGCT<br>ACCAACAACATCTTCCTGAGCATCCTTGAGGAGGGCGTGCTGCCCCTGTA<br>CGGCGTGAAGATGACCGACCCTTTCGTGCGCGTGCACCCCGACTTCAGAG<br>TGATCTTTACCAGCAACCCCGCCGAGTATGCCGGCGTGTACGATACCCAG<br>GACGCCCTGCTGGACCGGCTGATCACCATGTTCATCGACTACAAGGACAT<br>CGACCGGGGAAACCGCTATCCTGACCGAGAAAACTGACGTGGAAGAAGAC<br>GAGGCCCGGACCATCGTGACCCTGGTGGCCAACGTGCGGAACAGAAGCG<br>GCGACGAGAATAGCAGCGGCCTGAGCCTGAGAGCCAGCCTGATGATTGC<br>CACCCTGGCCACCCAGCAGGACATCCCTATCGATGGCAGCGACGAGGACT<br>TCCAGACCCTGTGCATCGACATCCTGCACCACCCCCTGACCAAGTGCCTG<br>GACGAAGAGAACGCCAAGAGCAAGGCCGAGAAGATCATTCTCGAAGAGT<br>GCAAGAACATCGACACCGAGGAGAAGGGTGCCCCGGGATCTGGCGCAAC<br>AAATTTTAGTCTTTTAAAGCAGGCAGGAGACGTCGAGGAAAACCCTGGAC<br>CCGTGAGCGAGACAAACGAGACAGGCATCTACATCTTCAGCGCCATCCAG<br>ACAGACAAGGATGAGGAATTCGGCGCCGTGGAAGTGGAAGGGACCAAGG<br>CTGAGACATTCCTGATCCGGTATAAGGACGCCGCCATGGTGGCCGCCGAA<br>GTGCCCATGAAGATCTACCACCCCAACCGGCAGAACCTGCTGATGCACCA<br>GAATGCCGTGGCCGCCATCATGGACAAGAACGACACCGTGATCCCCATCA<br>GCTTCGGCAACGTGTTCAAGAGCAAAGAGGACGTGAAGGTGCTCCTGGA<br>AAACCTGTACCCCCAGTTCGAGAAGCTGTTCCCCGCCATCAAGGGAAAGA<br>TCGAAGTGGGCCTGAAGGTGATCGGCAAGAAAGAGTGGCTCGAAAAGAA<br>AGTGAACGAGAACCCCGAGCTGGAAAAAGTGTCCGCCAGCGTGAAGGGC<br>AAGAGCGAGGCCGCTGGCTACTACGAGAATCCAGCTGGGCGGCATGG<br>CCCAGAAGATGTTCACAAGCCTGCAGAAAGAAGTGAAAACCGACGTGTT<br>CAGCCCCCTGGAAGAAGCCGCCGAGGCCGCCAAAGCCAATGAGCCTACA<br>GGCGAAACAATGCTGCTGAACGCCAGCTTCCTGATCAACAGAGAGGATG<br>AGGCCAAGTTCGACGAGAAAGTCAATGAGGCCCACGAGAACTGGAAGGA<br>TAAGGCCGACTTCCACTACAGCGGCCCCTGGCCCGCCTACAACTTCGTGA<br>ACATCCGGCTGAAGGTGGAAGAGAAGGGGGCACCTGGCTCGGGAGCGAC<br>CAACTTCTCATTACTCAAACAAGCCGGAGACGTTGAGGAGAATCCAGGCC<br>CTGTGCTGCACAAGCTCGTGACCGCCCCCATCAACCTGGTCGTGAAGATC<br>GGCGAGAAGGTGCAGGAAGAGGCCGACAAGCAGCTGTACGACCTGCCCA<br>CCATCCAGCAGAAGCTGATCCAGCTGCAGATGATGTTCGAGCTGGGCGAG<br>ATCCCCGAGGAAGCCTTCCAGGAAAAAGAGGACGAACTGCTGATGAGAT<br>ACGAGATCGCCAAGCGGCGCGAGATTGAGCAGTGGGAAGAACTGACCCA<br>GAAGCGGAATGAGGAAAGCGGTGCCCCGGGATCTGGCGCAACAAATTTT | 454 |

TABLE 20-continued

Exemplary consolidated polynucleotide cassette for polycistronic expression of gvpB with GVA proteins.

| Construct | Sequence | seq id no: |
|---|---|---|
| | AGTCTTTTAAAGCAGGCAGGAGACGTCGAGGAAAACCCTGGACCCGTGG<br>GCGAGCTGCTGTACCTCTACGGCCTGATCCCCACCAAAGAGGCCGCTGCT<br>ATCGAGCCCTTCCCATTCTACAAGGGCTTCGACGGCGAGCACAGCCTGTA<br>CCCTATCGCCTTCGACCAAGTGACCGCCGTGGTGTTCAAGCTGGACGCCG<br>ACACCTACAGCGAGAAAGTGATCCAGGAAAAGATGGAACAGGACATGAG<br>CTGGCTGCAGGAAAAGGCCTTCCACCACCACGAGACAGTGGCCGCCCTGT<br>ATGAGGAATTCACCATCATCCCCCTGAAGTTCTGCACCATCTATAAGGGA<br>GAGGAATCCCTGCAGGCCGCCATCGAGATCAACAAAGAGAAGATCGAAA<br>ACTCCCTGACCCTGCTGCAGGGCAACGAGGAATGGAACGTGAAGATCTAC<br>TGCGACGACACCGAGCTGAAGAAGGGCATCAGCGAGACAAACGAGAGCG<br>TGAAGGCCAAGAAGCAGGAAATCAGCCACCTGAGCCCCGGCACAGTT<br>CTTCGAGAAGAAGAAGATTGACCAGCTCATCGAGAAAGAGCTGGAACTG<br>CACAAGAACAAAGTGTGCGAGGAAATCCACGACAAGCTGATTGAGCTGA<br>GCCTCTACGACTCCGTGAAGAAGAACTGGTCCAAGGACGTGACAGGCGCT<br>GCCGAACAGATGGCCTGGAACAGCGTGTTCCTGCTGCCCAGCCTGCAGAT<br>CACCAAGTTCGTGAACGAGATCGAGGAACTCCAGCAGCGGCTGGAGAAC<br>AAGGGATGGAAGTTCGAAGTGACCGGCCCCTGGCCTCCCTACCACTTCAG<br>CAGCTTTGCCGGGGCACCTGGCTCGGGAGCGACCAACTTCTCATTACTCA<br>AACAAGCCGGAGACGTTGAGGAGAATCCAGGCCCTGTGAGCCTGAAGCA<br>GAGCATGGAGAATAAGGATATCGCCCTGATCGACATCCTCGACGTGATCC<br>TGGACAAGGGAGTGGCCATCAAGGGCGACCTGATCATCTCTATCGCCGGC<br>GTGGACCTGGTGTACCTGGATCTGAGAGTGCTGATCTCCAGCGTGGAAAC<br>CCTGGTGCAGGCCAAAGAGGGCAACCACAAGCCCATCACCAGCGAGCAG<br>TTCGACAAGCAGAAAGAGGAGCTGATGGACGCCACCGGCCAGCCCAGCA<br>AGTGGACAAATCCTCTGGGCAGCGGCGCTCCCGGGTCAGGTGCCACGAAT<br>TTTTCGTTGTTGAAGCAAGCTGGGGATGTTGAAGAGAACCCAGGGCCTGT<br>GCAGCCCGTGTCCCAGGCCAACGGCAGAATCCACCTGGATCCCGATCAGG<br>CCGAACAGGGACTGGCCCAGCTCGTGATGACCGTGATCGAGCTGCTGCGG<br>CAGATCGTGGAACGGCACGCCATGAGAAGAGTGGAAGGCGGCACCCTGA<br>CCGACGAGCAGATCGAGAATCTGGGAATCGCTCTGATGAACCTGGAGGA<br>GAAGATGGACGAGCTGAAAGAGGTGTTCGGACTGGACGCTGAGGATCTG<br>AACATCGACCTGGGCCCTCTGGGCAGCCTGCTGGGTGCCCCGGGATCTGG<br>CGCAACAAATTTTAGTCTTTTAAAGCAGGCAGGAGACGTCGAGGAAAACC<br>CTGGACCCGTGGCCGTGGAACACAACATGCAGAGCAGCACCATCGTGGA<br>CGTGCTGGAAAAGATCCTGGACAAGGGCGTCGTGATCGCCGGGGACATC<br>ACAGTGGGAATCGCCGACGTGGAACTGCTGACCATCAAGATCCGGCTGAT<br>CGTGGCCAGCGTGGACAAGGCCAAAGAAATCGGCATGGATTGGTGGGAG<br>AACGACCCCTACCTGAGCAGCAAGGGCGCCAACAACAAGGCTCTGGAAG<br>AGGAAAACAAGATGCTGCACGAGCGGCTGAAAACACTGGAAGAGAAGAT<br>CGAGACAAAGCGCGGGCACCTGGCTCGGGAGCGACCAACTTCTCATTAC<br>TCAAACAAGCCGGAGACGTTGAGGAGAATCCAGGCCCTGTGAGCACCGG<br>CCCCAGCTTCAGCACCAAGGACAACACCCTGGAATACTTCGTGAAGGCCA<br>GCAACAAGCACGGCTTTAGCCTCGACATCAGCCTGAACGTGAATGGGGCC<br>GTGATTAGCGGCACCATGATCAGCGCCAAAGAGTACTTCGACTACCTGAG<br>CGAGACATTCGAAGAGGGCAGCGAAGTGGCCCAGGCCCTGTCTGAGCAG<br>TTTAGCCTGGCTAGCGAGGCCTCCGAGTCTAATGGCGAAGCCGAGGCCCA<br>CTTCATCCACCTGAAGAACACCAAGATCTACTGCGGCGACAGCAAGAGCA<br>CCCCCAGCAAGGGCAAGATCTTCTGGCGCGGCAAGATCGCCGAGGTGGA<br>CGGATTCTTCCTGGGAAAAATCAGCGACGCCAAGTCCACCAGCAAGAAGT<br>CCAGCGGCGCTCCCGGGTCAGGTGCCACGAATTTTTCGTTGTTGAAGCAA<br>GCTGGGGATGTTGAAGAGAACCCAGGGCCTGTGGTGTCCAAGGGCGAGG<br>AACTGTTCACCGGCGTGGTGCCCATCCTGGTGGAACTGGATGGCGACGTG<br>AACGGCCACAAGTTCAGCGTGTCCGGCGAGGGCGAAGGCGACGCCACAT<br>ACGGAAAGCTGACCCTGAAGTTCATCTGCACCACCGGCAAGCTGCCCGTG<br>CCTTGGCCTACCCTCGTGACCACACTGACCTACGGCGTGCAGTGCTTCGCC<br>AGATACCCCGACCACATGAAGCAGCACGATTTCTTCAAGAGCGCCATGCC<br>CGAGGGCTACGTGCAGGAACGGACCATCTTCTTCAAGGACGACGGCAACT<br>ACAAGACAAGAGCCGAAGTGAAGTTCGAGGGCGACACCCTCGTGAACCG<br>GATCGAGCTGAAGGGCATCGACTTCAAAGAGGATGGCAACATCCTGGGC<br>CACAAGCTGGAGTACAACTACAACAGCCACAAGGTGTACATCACCGCCG<br>ACAAGCAGAAAAACGGCATCAAAGTGAACTTCAAGACCCGGCACAACAT<br>CGAGGACGGCAGCGTGCAGCTGGCCGACCACTACCAGCAGAACACCCCC<br>ATCGGAGATGGCCCCGTGCTGCTGCCCGACAACCACTACCTGAGCACACA<br>AAGCGCCCTGAGCAAGGACCCCAACGAGAAGCGGGACCACATGGTGCTG<br>CTGGAATTTGTGACCGCCGCTGGCATCACCCTGGGCATGGACGAGCTGTA<br>CAAGTGACTCGAGTCTAGAGGGCCCCGTGGCTGTAATCTAGAGGATCCCT<br>CGAGGGGCCCAAGCTTACGCGTGCATGCGACGTCATAGCTCTCTCCCTAT<br>AGTGAGTCGTATTATAAGCTAGCTTGGGATCTTTGTGAAGGAACCTTACTT<br>CTGTGGTGTGACATAATTGGACAAACTACCTACAGAGATTTAAAGCTCTA<br>AGGTAAATATAAAATTTTTAAGTGTATAATGTGTTAAACTAGCTGCATAT<br>GCTTGCTGCTTGAGAGTTTTGCTTACTGAGTATGATTTATGAAAATATTAT<br>ACACAGGAGCTAGTGATTCTAATTGTTTGTGTATTTTAGATTCACAGTCCC<br>AAGGCTCATTTCAGGCCCCTCAGTCCTCACAGTCTGTTCATGATCATAATC<br>AGCCATACCACATTTGTAGAGGTTTTACTTGCTTTAAAAAACCTCCCACAC | |

TABLE 20-continued

Exemplary consolidated polynucleotide cassette for polycistronic expression of gvpB with GVA proteins.

| Construct | Sequence | seq id no: |
|---|---|---|
| | CTCCCCCTGAACCTGAAACATAAAATGAATGCAATTGTTGTTGTTAACTTG<br>TTTATTGCAGCTTATAATGGTTACAAATAAAGCAATAGCATCACAAATTT<br>CACAAATAAAGCATTTTTTTCACTGCATTCTAGTTGTGGTTTGTCCAAACT<br>CATCAATGTATCTTATCATGTCTGGATC | |

TABLE 21

Alternative exemplary consolidated polynucleotide cassette for polycistronic

| Construct | Sequence | seq id no: |
|---|---|---|
| CMV:gvpB<br>:IRES:<br>gvpJFGLK:<br>polyA | CGTTACATAACTTACGGTAAATGGCCCGCCTGGCTGACCGCCCAACGACC<br>CCCGCCCATTGACGTCAATAATGACGTATGTTCCCATAGTAACGCCAATA<br>GGGACTTTCCATTGACGTCAATGGGTGGAGTATTTACGGTAAACTGCCCA<br>CTTGGCAGTACATCAAGTGTATCATATGCCAAGTACGCCCCCTATTGACG<br>TCAATGACGGTAAATGGCCCGCCTGGCATTATGCCCAGTACATGACCTTA<br>TGGGACTTTCCTACTTGGCAGTACATCTACGTATTAGTCATCGCTATTACC<br>ATGGTGATGCGGTTTTGGCAGTACATCAATGGGCGTGGATAGCGGTTTGA<br>CTCACGGGGATTTCCAAGTCTCCACCCCATTGACGTCAATGGGAGTTTGTT<br>TTGGCACCAAAATCAACGGGACTTTCCAAAATGTCGTAACAACTCCGCCC<br>CATTGACGCAAATGGGCGGTAGGCGTGTACGGTGGGAGGTCTATATAAGC<br>AGAGCTCGTTTAGTGAACCGTCAGATCGCCTGGAGACGCCATCCACGCTG<br>TTTTGACCTCCATAGAAGACACCGGGACCGATCCAGCCTCCGGACTCTAG<br>CCTAGGCTTTTGCAAAAAGCTATTTAGGTGACACTATAGAAGGTACGCCT<br>GCAGGTACCGAGCTCGGATCCAGTACCCTTCACCATGAGCATCCAGAAGT<br>CCACCAACAGCAGCAGCCTGGCCGAAGTGATCGACCGGATCCTGGACAA<br>GGGCATCGTGATCGACGCCTTCGCCAGAGTGTCCGTCGTGGGCATCGAGA<br>TCCTGACCATCGAGGCCAGAGTCGTGATCGCCAGCGTGGACACCTGGCTG<br>AGATATGCCGAAGCCGTGGGCCTGCTGCGGGACGACGTGGAAGAAAATG<br>GCCTGCCCGAGCGGAGCAACAGCTCTGAGGGACAGCCCCGGTTCAGCATC<br>TGAACTAAATCGCACTGTCGGCGTCCCCCCCTAACGTTACTGGCCGAAGC<br>CGCTTGGAATAAGGCCGGTGTGCGTTTGTCTATATGTTATTTTCCACCATA<br>TTGCCGTCTTTTGGCAATGTGAGGGCCCGGAAACCTGGCCCTGTCTTCTTG<br>ACGAGCATTCCTAGGGGTCTTTCCCCTCTCGCCAAAGGAATGCAAGGTCT<br>GTTGAATGTCGTGAAGGAAGCAGTTCCTCTGGAAGCTTCTTGAAGACAAA<br>CAACGTCTGTAGCGACCCTTTGCAGGCAGCGGAACCCCCCACCTGGCGAC<br>AGGTGCCTCTGCGGCCAAAAGCCACGTGTATAAGATACACCTGCAAAGGC<br>GGCACAACCCCAGTGCCACGTTGTGAGTTGGATAGTTGTGGAAAGAGTCA<br>AATGGCTCTCCTCAAGCGTATTCAACAAGGGGCTGAAGGATGCCCAGAAG<br>GTACCCCATTGTATGGGATCTGATCTGGGGCCTCGGTGCACATGCTTTACA<br>TGTGTTTAGTCGAGGTTAAAAAAACGTCTAGGCCCCCCGAACCACGGGGAC<br>GTGGTTTTCCTTTGAAAAACACGATGATAATATGGCCACAACCGTGGCCG<br>TGGAACACAACATGCAGAGCAGCACCATCGTGGACGTGCTGGAAAAGAT<br>CCTGGACAAGGGCGTCGTGATCGCCGGGGACATCACAGTGGGAATCGCC<br>GACGTGGAACTGCTGACCATCAAGATCCGGCTGATCGTGGCCAGCGTGGA<br>CAAGGCCAAAGAAATCGGCATGGATTGGTGGGAGAACGACCCCTACCTG<br>AGCAGCAAGGGCGCCAACAACAAGGCCCTGGAAGAGGAAACAAGATG<br>CTGCACGAGCGGCTGAAACACTGGAAGAGAAGATCGAGACAAAGCGCG<br>GTGCCCCGGGATCTGGCGCAACAAATTTTAGTCTTTTAAAGCAGGCAGGA<br>GACGTCGAGGAAAACCCTGGACCCGTGAGCGAGACAAACGAGACAGGCA<br>TCTACATCTTCAGCGCCATCCAGACAGACAAGGATGAGGAATTCGGCGCC<br>GTGGAAGTGGAAGGGACCAAGGCTGAGACATTCCTGATCCGGTATAAGG<br>ACGCCGCCATGGTGGCCGCCGAAGTGCCCATGAAGATCTACCACCCCAAC<br>CGGCAGAACCTGCTGATGCACCAGAATGCCGTGGCCGCCATCATGGACAA<br>GAACGACACCGTGATCCCCATCAGCTTCGGCAACGTGTTCAAGAGCAAAG<br>AGGACGTGAAGGTGCTCCTGGAAAACCTGTACCCCCAGTTCGAGAAGCTG<br>TTCCCCGCCATCAAGGGAAAGATCGAAGTGGGCCTGAAGGTGATCGGCA<br>AGAAAGAGTGGCTCGAAAAGAAAGTGAACGAGAACCCCGAGCTGGAAA<br>AAGTGTCCGCCAGCGTGAAGGGCAAGAGCGAGGCCGCTGGCTACTACGA<br>GAGAATCCAGCTGGGCGGCATGGCCCAGAAGATGTTCACAAGCCTGCAG<br>AAAGAAGTGAAAACCGACGTGTTCAGCCCCCTGGAAGAAGCCGCGAGG<br>CCGCCAAAGCCAATGAGCCTACAGGCGAAACAATGCTGCTGAACGCCAG<br>CTTCCTGATCAACAGAGAGGATGAGGCCAAGTTCGACGAGAAAGTCAAT<br>GAGGCCCACGAGAACTGGAAGGATAAGGCCGACTTCCACTACAGCGGCC<br>CCTGGCCCGCCTACAACTTCGTGAACATCCGGCTGAAGGTGGAAGAGAAG<br>GGGGCACCTGGCTCGGGAGCGACCAACTTCTCATTACTCAAACAAGCCGG<br>AGACGTTGAGGAGAATCCAGGCCCTGTGCTGCACAAGCTCGTGACCGCCC<br>CCATCAACCTGGTCGTGAAGATCGGCGAGAAGGTGCAGGAAGAGGCCGA<br>CAAGCAGCTGTACGACCTGCCCACCATCCAGCAGAAGCTGATCCAGCTGC<br>AGATGATGTTCGAGCTGGGCGAGATCCCCGAGGAAGCCTTCCAGGAAAA | 455 |

TABLE 21-continued

Alternative exemplary consolidated polynucleotide cassette for polycistronic

| Construct | Sequence | seq id no: |
|---|---|---|
| | AGAGGACGAACTGCTGATGAGATACGAGATCGCCAAGCGGCGCGAGATT | |
| | GAGCAGTGGGAAGAACTGACCCAGAAGCGGAATGAGGAAAGCGGTGCCC | |
| | CGGGATCTGGCGCAACAAATTTTAGTCTTTTAAAGCAGGCAGGAGACGTC | |
| | GAGGAAAACCCTGGACCCGTGGGCGAGCTGCTGTACCTCTACGGCCTGAT | |
| | CCCCACCAAAGAGGCCGCTGCTATCGAGCCCTTCCCATTCTACAAGGGCT | |
| | TCGACGGCGAGCACAGCCTGTACCCTATCGCCTTCGACCAAGTGACCGCC | |
| | GTGGTGTTCAAGCTGGACGCCGACACCTACAGCGAGAAAGTGATCCAGG | |
| | AAAAGATGGAACAGGACATGAGCTGGCTGCAGGAAAAGGCCTTCCACCA | |
| | CCACGAGACAGTGGCCGCCCTGTATGAGGAATTCACCATCATCCCCCTGA | |
| | AGTTCTGCACCATCTATAAGGGAGAGGAATCCCTGCAGGCCGCCATCGAG | |
| | ATCAACAAAGAGAAGATCGAAAACTCCCTGACCCTGCTGCAGGGCAACG | |
| | AGGAATGGAACGTGAAGATCTACTGCGACGACACCGAGCTGAAGAAGGG | |
| | CATCAGCGAGACAAACGAGAGCGTGAAGGCCAAGAAGCAGGAAATCAGC | |
| | CACCTGAGCCCCGGCAGACAGTTCTTCGAGAAGAAGAAGATTGACCAGCT | |
| | CATCGAGAAAGAGCTGGAACTGCACAAGAACAAAGTGTGCGAGGAAATC | |
| | CACGACAAGCTGATTGAGCTGAGCCTCTACGACTCCGTGAAGAAGAACTG | |
| | GTCCAAGGACGTGACAGGCGCTGCCGAACAGATGGCCTGGAACAGCGTG | |
| | TTCCTGCTGCCCAGCCTGCAGATCACCAAGTTCGTGAACGAGATCGAGGA | |
| | ACTCCAGCAGCGGCTGGAGAACAAGGGATGGAAGTTCGAAGTGACCGGC | |
| | CCCTGGCCTCCCTACCACTTCAGCAGCTTTGCCGGGGCACCTGGCTCGGG | |
| | AGCGACCAACTTCTCATTACTCAAACAAGCCGGAGACGTTGAGGAGAATC | |
| | CAGGCCCTGTGCAGCCCGTGTCCCAGGCCAACGGCAGAATCCACCTGGAT | |
| | CCCGATCAGGCCGAACAGGGACTGGCCCAGCTCGTGATGACCGTGATCGA | |
| | GCTGCTGCGGCAGATCGTGGAACGGCACGCCATGAGAAGAGTGGAAGGC | |
| | GGCACCCTGACCGACGAGCAGATCGAGAATCTGGGAATCGCCCTGATGA | |
| | ACCTGGAAGAGAAGATGGACGAGCTGAAAGAGGTGTTCGGACTGGACGC | |
| | CGAGGACCTGAACATCGACCTGGGCCCTCTGGGCAGCCTGCTGTGATCGA | |
| | GTCTAGAGGGCCCCGTGGCTGTAATCTAGAGGATCCCTCGAGGGGCCCAA | |
| | GCTTACGCGTGCATGCGACGTCATAGCTCTCTCCCTATAGTGAGTCGTATT | |
| | ATAAGCTAGCTTGGGATCTTTGTGAAGGAACCTTACTTCTGTGGTGTGAC | |
| | ATAATTGGACAAACTACCTACAGAGATTTAAAGCTCTAAGGTAAATATAA | |
| | AATTTTTAAGTGTATAATGTGTTAAACTAGCTGCATATGCTTGCTGCTTGA | |
| | GAGTTTTGCTTACTGAGTATGATTTATGAAAATATTATACACAGGAGCTA | |
| | GTGATTCTAATTGTTTGTGTATTTTAGATTCACAGTCCCAAGGCTCATTTC | |
| | AGGCCCCTCAGTCCTCACAGTCTGTTCATGATCATAATCAGCCATACCAC | |
| | ATTTGTAGAGGTTTTACTTGCTTTAAAAAACCTCCCACACCTCCCCCTGAA | |
| | CCTGAAACATAAAATGAATGCAATTGTTGTTGTTAACTTGTTTATTGCAGC | |
| | TTATAATGGTTACAAATAAAGCAATAGCATCACAAATTTCACAAATAAAG | |
| | CATTTTTTTCACTGCATTCTAGTTGTGGTTTGTCCAAACTCATCAATGTATC | |
| | TTATCATGTCTGGATC | |

Example 24—Hybrid GVES Constructs can Produce Gas Vesicles in Mammalian Cells Gvps from different organisms have been combined together to produce hybrid gas vesicles reporting constructs.

Figure 25A:
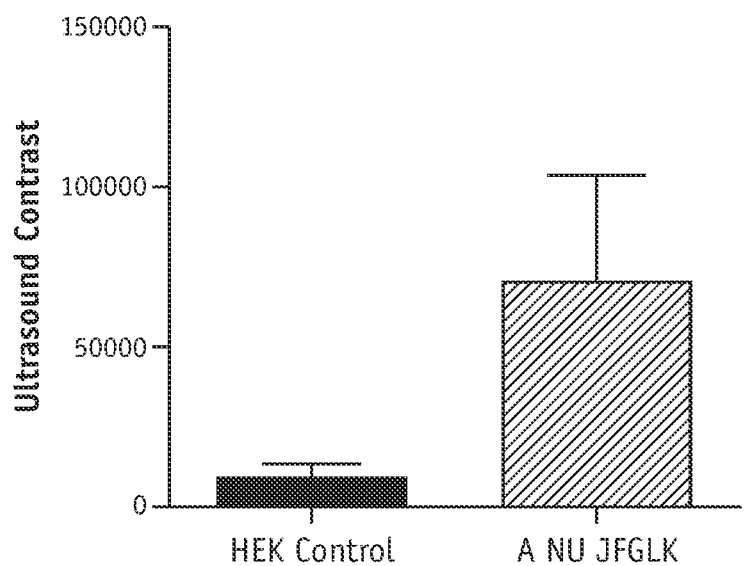
FIG. 25A shows HEK293T cells transfected with Ana-gpvA and the constructs in table 13 and table 14. After 72 hours of expression representative BURST ultrasound signal is quantified. HEK293T control without GV genes do not produce BURST ultrasound signal.

The applicants have combined Ana-gvpA, Table 10, with polynucleotide plasmids from *B. megaterium* of Table 13 and Table 14 to make a hybrid GV. The GVAs are from *Anabaena flos-aquae* and the GVS are from *B. megaterium*. HEK293T cells expressing constructs Ana-gvpA from Table 10, and constructs from Table 13 and Table 14 were able to produce gas vesicles as detectable by BURST ultrasound imaging (FIG. 25A). The skilled person will recognize that a hybrid construct with the above gene cassettes in addition to Ana-gvpC will also produce gas vesicles in mammalian cells as detectable by the methods described in this application.

Figure 25B:
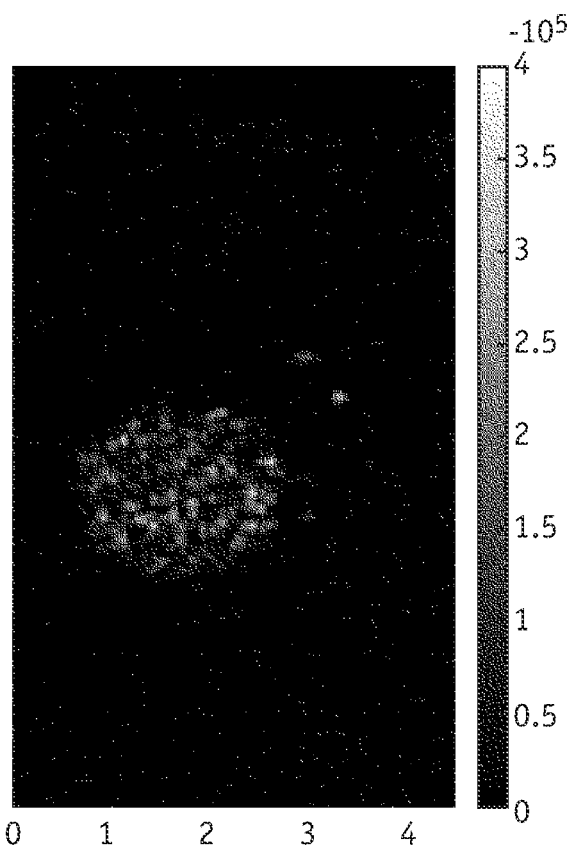
FIG. 25B shows Ana-gvpA, Ana-gvpC, Ana-gvpN from Table 10 together with B. megaterium GVS genes from Table 8. HEK293T cells expressing these hybrid genes were able to produce gas vesicles as detectable by BURST ultrasound imaging.

Similarly, the applicants have combined Ana-gvpA, Ana-gvpC, Ana-gvpN from Table 10, together with *B. megaterium* GVS genes from Table 8. HEK293T cells expressing these hybrid genes were able to produce gas vesicles as detectable by BURST ultrasound imaging (FIG. 25B).

Example 25: GVES Constructs Using *Anabaena flos-Aquae* Genes can Produce Gas Vesicles in Mammalian Cells Using gvps from Table 10, the applicants have expressed gas vesicles as detectable by TEM and ultrasound imaging in mammalian cells (e.g. HEK293T). HEK293T cells were transfected with the following constructs and were detectable by both TEM imaging (FIGS. 26A-D).

Figure 26A:
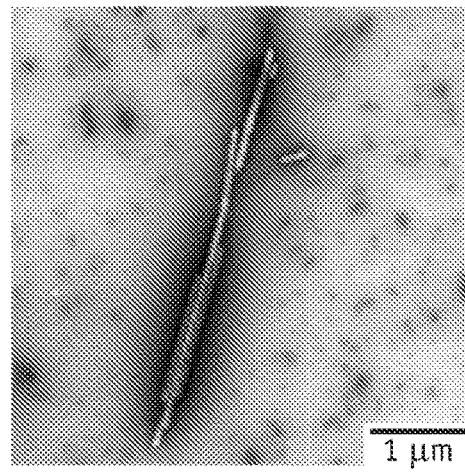
FIG. 26A shows HEK293T cells that have been transfected with Ana-gvpA, Ana-gvpC, Ana-gvpN, Ana-gpvJ, Ana-gvpK, Ana-gvpF, Ana-gvpG, Ana-gvpV, Ana-gvpW, and after 72 hours imaged with BURST ultrasound imaging.

The applicants have transfected HEK293T cells using gvps originating from *Anabaena flos-aquae* as catalogues in the NCBI database, with all genes have the same sequences as shown in Table 10 except for gvpG, which has the following sequence (MGSLTKLLLLPIMGPLNGVVWI-AEQIQERTNTEFDAQENLHKQLLSLQLSFDIGEIGEEE FEIQEEEILLKIQALEEEARLELEAEQEEARLELE-AEQEDFEYHLNSQQKLIKINISSCYLSI DGRK, SEQ ID NO: 456). Gas vesicles from this construct produces gas vesicles as detectable by BURST ultrasound imaging (FIG. 26E) but not TEM, since BURT ultrasound imaging is a more sensitive technique at detecting gas vesicle expression compared with TEM. The applicants sequenced gvpG gene from native *Anabaena flos-aquae* cells that natively express gas vesicles and found the gvpG sequence in table 10. HEK293T cells transfected with constructs from Table 10 produce gas vesicles as detectable by a higher BURST ultrasound signal (FIG. 26E) and TEM (FIG. 26A).

Figure 26B:
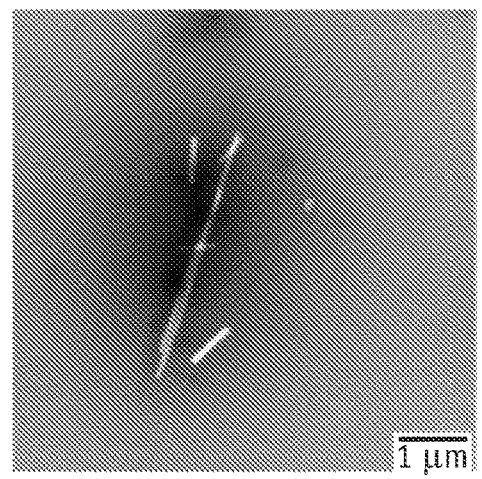
FIG. 26B shows HEK293T cells that have been transfected with Ana-gvpA, Ana-gvpN, Ana-gpvJ, Ana-gvpK, Ana-gvpF, Ana-gvpG, Ana-gvpV, Ana-gvpW, and after 72 hours cell lysate imaged with TEM.
Figure 26C:
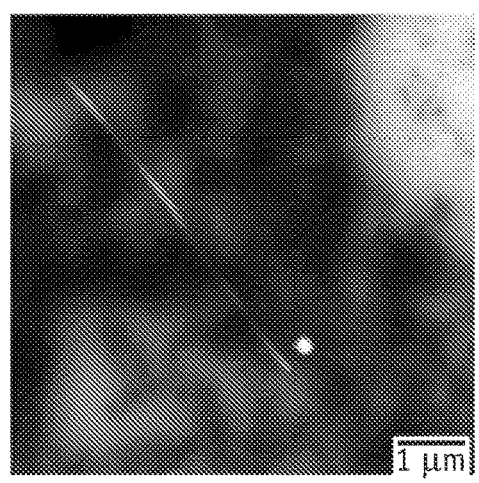
FIG. 26C shows HEK293T cells that have been transfected with Ana-gvpA, Ana-gvpN, Ana-gpvJ, Ana-gvpK, Ana-gvpF, Ana-gvpG, Ana-gvpW, and after 72 hours cell lysate imaged with TEM.
Figure 26D:
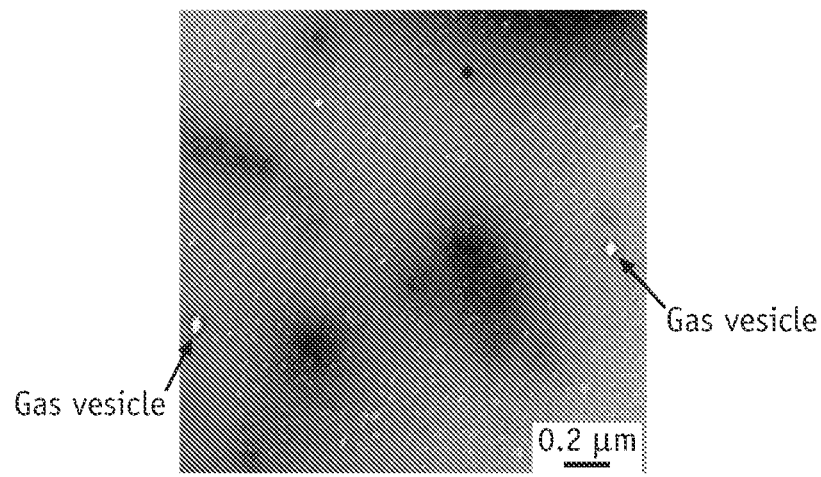
FIG. 26D shows HEK293T cells that have been transfected with Ana-gvpA, Ana-gpvJ, Ana-gvpK, Ana-gvpF, Ana-gvpG, Ana-gvpW, and after 72 hours cell lysate imaged with TEM. White arrows indicate small gas vesicle particles.
Figure 26E:
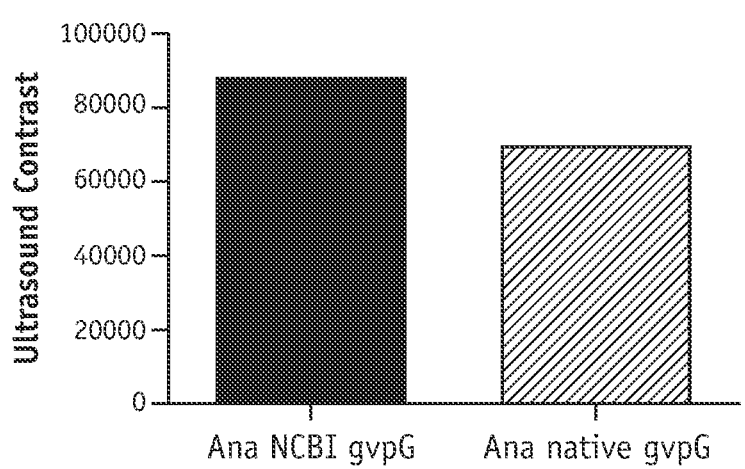
FIG. 26E shows HEK293T cells transfected with Ana GV genes with gene sequences acquired from the NCBI database (denoted ans Ana NCBI gvpG) and GV genes with gene sequences sequenced directly from native GV-expressing *Anabaena flos-aquae* cells. Representative BURST ultrasound images were quantified.
Figure 27A:
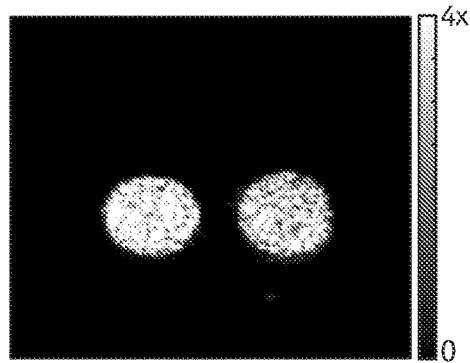
FIGS. 27A-27B show HEK293T cells transfected with Ana GV genes from Table 10. Cells transfected with the constructs expressed GV proteins for 72 hours before ultrasound imaging.
Figure 27B:
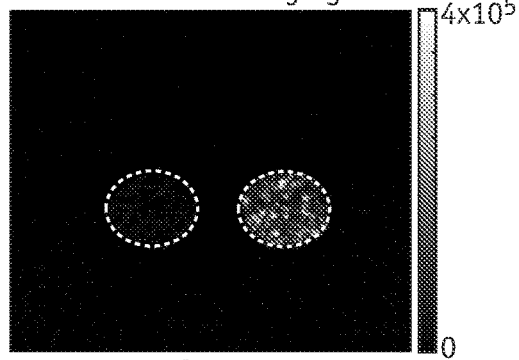

Gas vesicles with the structural properties of *Anabaena flos-aquae* genes can be tuned to have different non-linear properties using the structural protein gvpC [44] [45]. The applicants have demonstrated that HEK293T cells expressing the Ana genetic construct in FIG. 26A produces BURST ultrasound image (FIG. 27A, left) but do not produce nonlinear ultrasound images using amplitude modulation (AM) ultrasound method (FIG. 27B, left). However, HEK293T cells expressing Ana genetic construct in FIG. 26B are able to produce both BURST ultrasound image (FIG. 27A, right) and nonlinear ultrasound images using AM ultrasound method (FIG. 27B, right).

These different variants can be used for multiplexed imaging as their signature ultrasound properties can be distinguished. Importantly, GV constructs that can produce nonlinear ultrasound signal as detectable by amplitude modulation, pulse inversion, amplitude modulation pulse inversion, and other nonlinear ultrasound imaging methods known to the skilled person will be useful for detecting and imaging gas vesicles in complex biological environments (for example imaging inside the animal).

In summary, provided herein are genetically engineered gas vesicle expression systems (GVES) that are configured to express gas vesicles (GVs) in a mammalian cell, related gas vesicle polynucleotide constructs, gas vesicle reporting genetic circuits, vectors, genetically engineered mammalian cells, non-human mammalian hosts, compositions, methods and systems, which in several embodiments can be used together with contrast-enhanced imaging techniques to detect and report biological events in an imaging target site comprising a mammalian cell and/or organism.

The examples set forth above are provided to give those of ordinary skill in the art a complete disclosure and description of how to make and use the embodiments of the of the GVES system, polynucleotide constructs for expression of a gas vesicle in mammalian cells, and related GVR genetic circuits, vectors, genetically engineered mammalian cells, compositions, methods and systems of the disclosure, and are not intended to limit the scope of what the inventors regard as their disclosure. Those skilled in the art will recognize how to adapt the features of the exemplified polynucleotide GV constructs, and related genetic circuits, vectors, genetically engineered prokaryotic cells, compositions, methods and systems herein disclosed to additional polynucleotide GV constructs, and related genetic circuits, vectors, genetically engineered mammalian cells, compositions, methods and systems according to various embodiments and scope of the claims.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible sub-combinations of the group are intended to be individually included in the disclosure. Every combination of components or materials described or exemplified herein can be used to practice the disclosure, unless otherwise stated. One of ordinary skill in the art will appreciate that methods, system elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the genetic circuits, genetic molecular components, and methods steps set forth in the present description. As will be obvious to one of skill in the art, methods and systems useful for the present methods and systems may include a large number of optional composition and processing elements and steps.

In particular, it will be understood that various modifications may be made without departing from the spirit and scope of the present disclosure. Accordingly, other embodiments are within the scope of the following claims.

REFERENCES

1. Tashiro, Y., et al., *Molecular genetic and physical analysis of gas vesicles in buoyant enterobacteria*. Environmental microbiology, 2016. 18(4): p. 1264-1276.
2. Van Keulen, G., et al., *Gas vesicles in actinomycetes: old buoys in novel habitats?* Trends in microbiology, 2005. 13(8): p. 350-354.

3. Walsby, A. E., *Gas vesicles*. Microbiol. Rev., 1994. 58(1): p. 94-144.
4. Walsby, A. E., *Gas-vacuolate bacteria (apart from cyanobacteria)*, in *The Prokaryotes*. 1981, Springer. p. 441-447.
5. Walsby, A. E., *Cyanobacteria: planktonic gas-vacuolate forms*. The Prokaryotes, a Handbook on Habitats, Isolation, and Identification of Bacteria, 2013. 1: p. 224-235.
6. Woese, C. R., *Bacterial evolution*. Microbiological reviews, 1987. 51(2): p. 221.
7. Walsby, A. E., *Gas vesicles*. Microbiol Rev, 1994. 58(1): p. 94-144.
8. Pfeifer, F., *Distribution, formation and regulation of gas vesicles*. Nat. Rev. Microbiol., 2012. 10(10): p. 705-15.
9. Yi, G., S.-H. Sze, and M. R. Thon, *Identifying clusters of functionally related genes in genomes*. Bioinformatics, 2007. 23(9): p. 1053-1060.
10. Bourdeau, R. W., et al., *Acoustic reporter genes for noninvasive imaging of microorganisms in mammalian hosts*. Nature, 2018. 553(7686): p. 86-90.
11. Lakshmanan, A., et al., *Preparation of biogenic gas vesicle nanostructures for use as contrast agents for ultrasound and MRI*. Nat Protoc, 2017. 12(10): p. 2050-2080.
12. Hayes, P. and R. Powell, *The gvpA/C cluster of Anabaena flos-aquae has multiple copies of a gene encoding GvpA*. Archives of microbiology, 1995. 164(1): p. 50-57.
13. Kinsman, R. and P. Hayes, *Genes encoding proteins homologous to halobacterial Gvps N, J, K, F & L are located downstream of gvpC in the cyanobacterium Anabaena flos-aquae*. DNA Sequence, 1997. 7(2): p. 97-106.
14. Myers, E. W. and W. Miller, *Optimal alignments in linear space*. Computer applications in the biosciences: CABIOS, 1988. 4(1): p. 11-17.
15. Smith, T. F. and M. S. Waterman, *Comparison of biosequences*. Advances in applied mathematics, 1981. 2(4): p. 482-489.
16. Needleman, S. B. and C. D. Wunsch, *A general method applicable to the search for similarities in the amino acid sequence of two proteins*. Journal of molecular biology, 1970. 48(3): p. 443-453.
17. Pearson, W. R. and D. J. Lipman, *Improved tools for biological sequence comparison*. Proceedings of the National Academy of Sciences, 1988. 85(8): p. 2444-2448.
18. Karlin, S. and S. F. Altschul, *Methods for assessing the statistical significance of molecular sequence features by using general scoring schemes*. Proceedings of the National Academy of Sciences, 1990. 87(6): p. 2264-2268.
19. Karlin, S. and S. F. Altschul, *Applications and statistics for multiple high-scoring segments in molecular sequences*. Proceedings of the National Academy of Sciences, 1993. 90(12): p. 5873-5877.
20. Lu, G. J., et al., *Acoustically modulated magnetic resonance imaging of gas-filled protein nanostructures*. Nat Mater, 2018. 17(5): p. 456-463.
21. Pfeifer, F., *Distribution, formation and regulation of gas vesicles*. Nat Rev Microbiol, 2012. 10(10): p. 705-15.
22. Li, N. and M. C. Cannon, *Gas vesicle genes identified in Bacillus megaterium and functional expression in Escherichia coli*. J Bacteriol, 1998. 180(9): p. 2450-8.
23. Tashiro, Y., et al., *Molecular genetic and physical analysis of gas vesicles in buoyant enterobacteria*. Environ Microbiol, 2016. 18(4): p. 1264-76.
24. Ramsay, J. P., et al., *A quorum-sensing molecule acts as a morphogen controlling gas vesicle organelle biogenesis and adaptive flotation in an enterobacterium*. Proc Natl Acad Sci USA, 2011. 108(36): p. 14932-7.
25. Schechter, I. and A. Berger, *On the size of the active site in proteases. L Papain*. Biochem Biophys Res Commun., 1967. 27(2): p. 157-162.
26. Schechter, I. and A. Berger, *On the active site of proteases. 3. Mapping the active site of papain; specific peptide inhibitors of papain*. Biochem Biophys Res Commun., 1968 32(5): p. 898-902.
27. Calvo, S. E., D. J. Pagliarini, and V. K. Mootha, *Upstream open reading frames cause widespread reduction of protein expression and are polymorphic among humans*. Proc Natl Acad Sci USA, 2009. 106(18): p. 7507-12.
28. Rose, A. B., *Intron-mediated regulation of gene expression*. Curr Top Microbiol Immunol, 2008. 326: p. 277-90.
29. Reddy A. S. N., G. M., *Nuclear pre-mRNA Processing in Plants*. Current Topics in Microbiology and Immunology. 326: p. 14.
30. Purnick, P. E. and R. Weiss, *The second wave of synthetic biology: from modules to systems*. Nat Rev Mol Cell Biol, 2009. 10(6): p. 410-22.
31. Buchler, N. E., U. Gerland, and T. Hwa, *On schemes of combinatorial transcription logic*. Proceedings of the National Academy of Sciences, 2003. 100(9): p. 5136-5141.
32. Silva-Rocha, R. and V. de Lorenzo, *Mining logic gates in prokaryotic transcriptional regulation networks*. FEBS letters, 2008. 582(8): p. 1237-1244.
33. Terreno, E., et al., *Challenges for Molecular Magnetic Resonance Imaging*. Chemical Reviews, 2010. 110(5): p. 3019-3042.
34. Cunningham, C. H., et al., *Positive contrast magnetic resonance imaging of cells labeled with magnetic nanoparticles*. Magnetic Resonance in Medicine, 2005. 53(5): p. 999-1005.
35. Foucault, M.-L., et al., *In vivo bioluminescence imaging for the study of intestinal colonization by Escherichia coli in mice*. Applied and environmental microbiology, 2010. 76(1): p. 264-274.
36. Daniel, C., et al., *Bioluminescence imaging study of spatial and temporal persistence of Lactobacillus plantarum and Lactococcus lactis in living mice*. Applied and environmental microbiology, 2013. 79(4): p. 1086-1094.
37. Chu, J., et al., *A bright cyan-excitable orange fluorescent protein facilitates dual-emission microscopy and enhances bioluminescence imaging in vivo*. Nat Biotech, 2016. 34(7): p. 760-767.
38. Smith-Bindman, R., et al., *Use of diagnostic imaging studies and associated radiation exposure for patients enrolled in large integrated health care systems, 1996-2010*. JAMA, 2012. 307(22): p. 2400-9.
39. Foster, F. S., et al., *Advances in ultrasound biomicroscopy*. Ultrasound in medicine & biology, 2000. 26(1): p. 1-27.
40. Foster, F. S., et al., *Principles and applications of ultrasound backscatter microscopy*. Ultrasonics, Ferroelectrics and Frequency Control, IEEE Transactions on, 1993. 40(5): p. 608-617.

41. Errico, C., et al., *Ultrafast ultrasound localization microscopy for deep super-resolution vascular imaging.* Nature, 2015. 527(7579): p. 499-502.
42. Szymczak, A. L. and D. A. A. Vignali, *Development of 2A peptide-based strategies in the design of multicistronic vectors.* Expert Opinion on Biological Therapy, 2005. 5(5): p. 627-638.
43. Farhadi, A., et al., *Recombinantly Expressed Gas Vesicles as Nanoscale Contrast Agents for Ultrasound and Hyperpolarized MRI.* AIChE J, 2018. 64(8): p. 2927-2933.
44. Lakshmanan, A., et al., *Molecular Engineering of Acoustic Protein Nanostructures.* ACS Nano, 2016. 10(8): p. 7314-22.
45. Maresca, D., et al., *Nonlinear ultrasound imaging of nanoscale acoustic biomolecules.* Appl Phys Lett, 2017. 110(7): p. 073704.

The invention claimed is:

1. A method of ultrasound imaging to be used on a target site comprising a mammalian cell, the method comprising:
introducing into the mammalian cell a Gas Vesicle Expression System (GVES) configured of one or more gene clusters of gvp genes (GVGC) encoding GV proteins capable of forming a GV type having an acoustic collapse pressure threshold, the Gas Vesicle Expression System comprising:
a GVPA/B gene expression cassette comprising a gvpA or a gvpB gene under control of a mammalian promoter and additional mammalian regulatory regions in a configuration allowing expression of the gvpA or gvpB protein in the mammalian cell; and
one or more additional gvp gene expression cassettes comprising the gvp genes of the GV gene cluster other than the gvpA and gvpB, under control of a mammalian promoter and additional regulatory regions in a configuration allowing expression of the GV proteins other than the gvpA and gvpB in the mammalian cell,
wherein each of the one or more additional gvp gene expression cassettes, when comprising two or more gvp genes, further comprises a separation element between the two or more gvp genes configured to provide a separate expression of the corresponding GV protein;
wherein the GVPA/B gene expression cassette and the one or more additional gvp gene expression cassettes are operably linked by regulatory sequences allowing co-expression of the GV proteins and formation of the GV type in the mammalian cell, and
wherein the one or more gas vesicle gene clusters comprise at least one of
a GVGC having gvpB, gvpN, gvpF, gvpG, gvpL, gvpS, gvpK, gvpJ, and gvpU from *B. megaterium*;
a GVGC having gvpA, gvpC, gvpN, gvpJ, gvpK, gvpF, gvpG, gvpV, and gvpW from *Anabaena flos-aquae*;
a GVGC having gvpR, gvpN, gvpF, gvpG, gvpL, gvpS, gvpK, gvpJ, gvpT and gvpU from *B. megaterium* and gvpA gene from *Anabaena flos-aquae*;
a GVGC having gvpA, and gvpC from *Anabaena flos-aquae*, and gvpN, gvpF, gvpG, gvpL, gvpS, gvpK, gvpJ, and gvpU from *B. megaterium*; and
a GVGC having gvpA, gvpC and gvpN from *Anabaena flos-aquae*, gvpF, gvpG, gvpL, gvpS, gvpK, gvpJ, and gvpU from *B. megaterium*,
the introducing being performed for a time and under conditions to allow expression of the GV proteins and the production of one or more GV types, having the acoustic collapse pressure threshold, in the mammalian cell;

the method further comprising:
applying ultrasound to the target site at a peak positive pressure less than the acoustic collapse pressure threshold;
increasing peak positive pressure (PPP) to above the selective acoustic collapse pressure value threshold as a step function;
imaging the target site in successive frames during the increasing;
extracting a time-series vector for each of at least one pixel of the successive frames; and
detecting from the time-series vectors a transient signal from, due to the increasing PPP, fluid displacement from collapsing of the GVs or cavitating bubbles released from the GVs, the detecting being in a time domain of the successive frames, the transient signal providing an increase in contrast signal in the ultrasound imaging.

2. The method of claim 1, wherein the expression of the GV proteins and production of the GV type occurs in response to a biochemical event and/or following the expression of the GV proteins and the production of the GV type, an intracellular spatial translocation of the produced GV type occurs in response to a biochemical event.

3. The method of claim 2, wherein the biological event is one or more of a gene expression, proteolysis, and biochemical reactions.

4. The method of claim 3, wherein the biochemical reactions comprise production of signaling molecule and ion concentration changes, and cell location on a target site.

5. The method of claim 1, wherein the mammalian regulatory regions comprise a gas vesicle reporting (GVR) target region configured to be activated and/or inhibited by a molecular component of a genetic circuit; and
wherein the gvp genes and mammalian regulatory regions are in a configuration allowing expression of the gvp genes through activation and/or inhibition of the gas vesicle reporting (GVR) target region when the genetic circuit operates according to the circuit design in the mammalian cell.

6. The method of claim 5, wherein the GVR genetic circuit operates according to the circuit design in response to a trigger molecular component.

7. The method of claim 6, wherein, the introducing is also performed under conditions resulting in presence of the trigger molecular component in the target mammalian host.

8. The method of claim 6, wherein the trigger molecular component is a cell type specific promoter, and/or a heterologous cell type specific molecular component introduced by viral transduction.

9. The method of claim 1, further comprising performing a signal separation algorithm separating a signal due to the GVs from other signals on the time-series vectors and estimating at least one template vector by averaging pixel time series from regions of interest containing known samples.

10. The method of claim 9, wherein the signal separation algorithm includes template projection.

11. The method of claim 9, wherein the signal separation algorithm includes template unmixing.

12. The method of claim 11, wherein the at least one template vector is based on data from linear scatterers, noise, gas vesicles, or a combination thereof.

13. The method of claim 1, wherein the successive frames comprise a frame prior to GVs collapse, a frame during GVs collapse, and a frame after GVs collapse.

14. The method of claim 1, wherein the detecting is performed by one or more of:
detecting the spatial location of the ultrasound contrast produced by the mammalian cell in an image;
tracking the spatial changes of that contrast over time; and
measuring movement of cells inside a tissue.

15. The method of claim 1, wherein the mammalian cell is a mammalian tumor cell, a mammalian immune cell, mammalian red blood cell, and/or a mammalian stem cell.

16. The method of claim 15, wherein the detecting is performed to label the mammalian cells, and/or the track the mammalian cell movement.

17. The method of claim 1, wherein the increasing includes increasing the PPP to a hiBURST regime.

18. The method of claim 17, wherein the PPP in hiBURST regime is 4.3 MPa or higher.

19. The method of claim 1, wherein the increasing includes increasing the PPP to a loBURST regime.

20. The method of claim 19, wherein the PPP in loBURST regime is no higher than 3.7 MPa.

21. A system for imaging a target site contrasted with gas vesicles (GVs) having an acoustic collapse pressure threshold, the system comprising:
a Gas Vesicle Expression System (GVES) configured for expression, in a mammalian cell at the target site, of one or more gene clusters of gvp genes (GVGC) encoding GV proteins capable of forming a GV type of the GVs, the Gas Vesicle Expression System comprising:
a GVPA/B gene expression cassette comprising a gvpA or a gvpB gene under control of a mammalian promoter and additional mammalian regulatory regions in a configuration allowing expression of the gvpA or gvpB protein in the mammalian cell; and
one or more additional gvp gene expression cassettes comprising the gvp genes of the GV gene cluster other than the gvpA and gvpB, under control of a mammalian promoter and additional regulatory regions in a configuration allowing expression of the GV proteins other than the gvpA and gvpB in the mammalian cell,
wherein each of the one or more additional gvp gene expression cassette, when comprising two or more gvp genes, further comprises a separation element between the two or more gvp genes configured to provide a separate expression of the corresponding GV protein;
wherein the GVPA/B gene expression cassette and the one or more additional gvp gene expression cassettes are operably linked by regulatory sequences allowing co-expression of the GV proteins and formation of the GV type in the mammalian cell, and
wherein the one or more gas vesicle gene clusters comprise at least one of a GVGC having gvpB, gvpN, gvpF, gvpG, gvpL, gvpS, gvpK, gvpJ, and gvpU from *B. megaterium*;
a GVGC having gvpA, gvpC, gvpN, gvpJ, gvpK, gvpF, gvpG, gvpV, and gvpW from *Anabaena flos-aquae;*
a GVGC having gvpR, gvpN, gvpF, gvpG, gvpL, gvpS, gvpK, gvpJ, gvpT and gvpU from *B. megaterium* and gvpA gene from *Anabaena flos-aquae;*
a GVGC having gvpA, and gvpC from *Anabaena flos-aquae*, and gvpN, gvpF, gvpG, gvpL, gvpS, gvpK, gvpJ, and gvpU from *B. megaterium*; and
a GVGC having gvpA, gvpC and gvpN from *Anabaena flos-aquae*, gvpF, gvpG, gvpL, gvpS, gvpK, gvpJ, and gvpU from *B. megaterium*, the system further comprising an ultrasound source capable of producing peak positive pressure both below and above the acoustic collapse pressure threshold;

an ultrasound imager configured to capture successive frames from the target site; and a processor configured to:

calculate a time-series vector for each of at least one pixel of the successive frames and detect from the time-series vectors a transient signal from, due to the increasing PPP, fluid displacement from collapsing of the GVs or cavitating bubbles released from the GVs, the detecting being in a time domain of the successive frames, and the transient signal providing an increase in contrast signal in the imaging.

22. The system of claim 21, wherein and the one or more additional gvp expression cassettes is a single additional gvp gene expression cassette comprising the gvp genes of the GV gene cluster other than the gvpA and gvpB.

23. The system of claim 21, wherein the GVPA/B gene expression cassette and one or more additional gvp gene expression cassettes are within a same polynucleotide construct.

24. The system of claim 21, wherein the GVPA/B gene expression cassette and one or more additional gvp gene expression cassettes are on at least two separate polynucleotide constructs.

25. The system of claim 24, wherein in the GVES the one or more additional gvp gene expression cassette is a single additional gvp gene expression cassette on a Gas Vesicle Polynucleotide Construct (GVPC).

26. The system of claim 21, wherein the one or more gene clusters of gvp genes (GVGCs) comprise a naturally occurring gas vesicle gene cluster, or an engineered gas vesicle gene cluster.

27. The system of claim 21, wherein the processor is further configured to perform a signal separation algorithm separating a signal due to the GVs from other signals on the time-series vectors using at least one template vector estimated by averaging pixel time series from regions of interest containing known samples.

28. The system of claim 27, wherein the signal separation algorithm includes template projection.

29. The system of claim 27, wherein the signal separation algorithm includes template unmixing.

30. The system of claim 29, wherein the at least one template vector is based on data from linear scatterers, noise, gas vesicles, or a combination thereof.

31. The system of claim 21, wherein the successive frames comprise a frame prior to GVs collapse, a frame during GVs collapse, and a frame after GVs collapse.

32. The system of claim 21 further comprising molecular component, polynucleotide constructs, vectors, cells and other reagents for introducing the GVES into the mammalian cell.

* * * * *

```
                            SEQUENCE LISTING

Sequence total quantity: 481
SEQ ID NO: 1            moltype = AA  length = 125
FEATURE                 Location/Qualifiers
VARIANT                 4
                        note = X can be any amino acid
source                  1..125
                        mol_type = protein
                        organism = synthetic construct
VARIANT                 11
                        note = X can be any amino acid
VARIANT                 14
                        note = X can be any amino acid
VARIANT                 31
                        note = X can be any amino acid
VARIANT                 32
                        note = X can be any amino acid
VARIANT                 34
                        note = X can be any amino acid
VARIANT                 41
                        note = X can be any amino acid
VARIANT                 47
                        note = X can be any amino acid
VARIANT                 59
                        note = X can be any amino acid
VARIANT                 60
                        note = X can be any amino acid
VARIANT                 60
                        note = X can be any amino acid
VARIANT                 89
                        note = X can be any amino acid
VARIANT                 123
                        note = X can be any amino acid
SEQUENCE: 1
RALXYLQAGY XVHXRGPAGT GKTTLAMHLA XXLXRPVMLI XGDDEFXTSD LIGSESGYXX   60
KKVVDNYIHS VVKVEDELRQ NWVDNRLTXA CREGFTLVYD EFNRSRPEXN NVLLSVLEEK  120
ILXLP                                                              125

SEQ ID NO: 2            moltype = AA  length = 5
FEATURE                 Location/Qualifiers
REGION                  1..5
                        note = synthetic polypeptide
source                  1..5
                        mol_type = protein
                        organism = synthetic construct
SEQUENCE: 2
GSGSG                                                               5

SEQ ID NO: 3            moltype = AA  length = 48
FEATURE                 Location/Qualifiers
REGION                  1..48
                        note = synthetic polypeptide
source                  1..48
                        mol_type = protein
                        organism = synthetic construct
VARIANT                 16
                        note = X can be any amino acid
SEQUENCE: 3
SSSLAEVLDR ILDKGXVIDA WARVSLVGIE ILTIEARVVI ASVDTYLR                48

SEQ ID NO: 4            moltype = AA  length = 6
FEATURE                 Location/Qualifiers
REGION                  1..6
                        note = synthetic polypeptide
source                  1..6
                        mol_type = protein
                        organism = synthetic construct
```

```
SEQUENCE: 4
LDRILD                                                                          6

SEQ ID NO: 5              moltype = AA   length = 16
FEATURE                   Location/Qualifiers
REGION                    1..16
                          note = synthetic polypeptide
source                    1..16
                          mol_type = protein
                          organism = synthetic construct
VARIANT                   7
                          note = X can be any amino acid
SEQUENCE: 5
RILDKGXVID AWARVS                                                              16

SEQ ID NO: 6              moltype = AA   length = 5
FEATURE                   Location/Qualifiers
REGION                    1..5
                          note = synthetic polypeptide
source                    1..5
                          mol_type = protein
                          organism = synthetic construct
SEQUENCE: 6
DTYLR                                                                           5

SEQ ID NO: 7              moltype = AA   length = 6
FEATURE                   Location/Qualifiers
REGION                    1..6
                          note = synthetic polypeptide
source                    1..6
                          mol_type = protein
                          organism = synthetic construct
SEQUENCE: 7
VVNMSV                                                                          6

SEQ ID NO: 8              moltype = AA   length = 19
FEATURE                   Location/Qualifiers
REGION                    1..19
                          note = synthetic polypeptide
source                    1..19
                          mol_type = protein
                          organism = synthetic construct
SEQUENCE: 8
KSPDSSSLAE VLDRILDKG                                                           19

SEQ ID NO: 9              moltype = AA   length = 36
FEATURE                   Location/Qualifiers
REGION                    1..36
                          note = synthetic polypeptide
source                    1..36
                          mol_type = protein
                          organism = synthetic construct
SEQUENCE: 9
VIDAWARVSL VGIEILTIEA RVVIASVDTY LRYAEA                                        36

SEQ ID NO: 10             moltype = AA   length = 6
FEATURE                   Location/Qualifiers
REGION                    1..6
                          note = synthetic polypeptide
source                    1..6
                          mol_type = protein
                          organism = synthetic construct
SEQUENCE: 10
NRLDLE                                                                          6

SEQ ID NO: 11             moltype = AA   length = 308
FEATURE                   Location/Qualifiers
REGION                    1..308
                          note = synthetic polypeptide
source                    1..308
                          mol_type = protein
                          organism = synthetic construct
SEQUENCE: 11
MTVLTDKRKK GSGAFIQDDE TKEVLSRALS YLKSGYSIHF TGPAGGGKTS LARALAKKRK               60
RPVMLMHGNH ELNNKDLIGD FTGYTSKKVI DQYVRSVYKK DEQVSENWQD GRLLEAVKNG              120
YTLIYDEFTR SKPATNNIFL SILEEGVLPL YGVKMTDPFV RVHPDFRVIF TSNPAEYAGV              180
YDTQDALLDR LITMFIDYKD IDRETAILTE KTDVEEDEAR TIVTLVANVR NRSGDENSSG              240
LSLRASLMIA TLATQQDIPI DGSDEDFQTL CIDILHHPLT KCLDEENAKS KAEKIILEEC              300
KNIDTEEK                                                                      308
```

```
SEQ ID NO: 12              moltype = AA   length = 255
FEATURE                    Location/Qualifiers
REGION                     1..255
                           note = synthetic polypeptide
source                     1..255
                           mol_type = protein
                           organism = synthetic construct
SEQUENCE: 12
MSETNETGIY IFSAIQTDKD EEFGAVEVEG TKAETFLIRY KDAAMVAAEV PMKIYHPNRQ    60
NLLMHQNAVA AIMDKNDTVI PISFGNVFKS KEDVKVLLEN LYPQFEKLFP AIKGKIEVGL   120
KVIGKKEWLE KKVNENPELE KVSASVKGKS EAAGYYERIQ LGGMAQKMFT SLQKEVKTDV   180
FSPLEEAAEA AKANEPTGET MLLNASFLIN REDEAKFDEK VNEAHENWKD KADFHYSGPW   240
PAYNFVNIRL KVEEK                                                   255

SEQ ID NO: 13              moltype =    length =
SEQUENCE: 13
000

SEQ ID NO: 14              moltype =    length =
SEQUENCE: 14
000

SEQ ID NO: 15              moltype = AA   length = 19
FEATURE                    Location/Qualifiers
REGION                     1..19
                           note = synthetic polypeptide
source                     1..19
                           mol_type = protein
                           organism = synthetic construct
SEQUENCE: 15
ATNFSLLKQA GDVEENPGP                                                19

SEQ ID NO: 16              moltype = AA   length = 18
FEATURE                    Location/Qualifiers
REGION                     1..18
                           note = synthetic polypeptide
source                     1..18
                           mol_type = protein
                           organism = synthetic construct
SEQUENCE: 16
EGRGSLLTCG DVEENPGP                                                 18

SEQ ID NO: 17              moltype = AA   length = 20
FEATURE                    Location/Qualifiers
REGION                     1..20
                           note = synthetic polypeptide
source                     1..20
                           mol_type = protein
                           organism = synthetic construct
SEQUENCE: 17
QCTNYALLKL AGDVESNPGP                                               20

SEQ ID NO: 18              moltype = AA   length = 22
FEATURE                    Location/Qualifiers
REGION                     1..22
                           note = synthetic polypeptide
source                     1..22
                           mol_type = protein
                           organism = synthetic construct
SEQUENCE: 18
VKQTLNFDLL KLAGDVESNP GP                                            22

SEQ ID NO: 19              moltype = AA   length = 22
FEATURE                    Location/Qualifiers
REGION                     1..22
                           note = synthetic polypeptide
source                     1..22
                           mol_type = protein
                           organism = synthetic construct
SEQUENCE: 19
DVFRSNYDLL KLCGDIESNP GP                                            22

SEQ ID NO: 20              moltype = AA   length = 22
FEATURE                    Location/Qualifiers
REGION                     1..22
                           note = synthetic polypeptide
source                     1..22
                           mol_type = protein
```

```
                         -continued
                         organism = synthetic construct
SEQUENCE: 20
TLTRAKIEDE LIRAGIESNP GP                                      22

SEQ ID NO: 21            moltype = AA  length = 6
FEATURE                  Location/Qualifiers
REGION                   1..6
                         note = synthetic polypeptide
source                   1..6
                         mol_type = protein
                         organism = synthetic construct
SEQUENCE: 21
GAPGSG                                                         6

SEQ ID NO: 22            moltype = AA  length = 8
FEATURE                  Location/Qualifiers
REGION                   1..8
                         note = synthetic polypeptide
source                   1..8
                         mol_type = protein
                         organism = synthetic construct
SEQUENCE: 22
LEVLFQGP                                                       8

SEQ ID NO: 23            moltype = AA  length = 5
FEATURE                  Location/Qualifiers
REGION                   1..5
                         note = synthetic polypeptide
source                   1..5
                         mol_type = protein
                         organism = synthetic construct
SEQUENCE: 23
DDDDK                                                          5

SEQ ID NO: 24            moltype = AA  length = 4
FEATURE                  Location/Qualifiers
REGION                   1..4
                         note = synthetic polypeptide
source                   1..4
                         mol_type = protein
                         organism = synthetic construct
SEQUENCE: 24
IEGR                                                           4

SEQ ID NO: 25            moltype = AA  length = 7
FEATURE                  Location/Qualifiers
REGION                   1..7
                         note = synthetic polypeptide
source                   1..7
                         mol_type = protein
                         organism = synthetic construct
SEQUENCE: 25
ENLYFQG                                                        7

SEQ ID NO: 26            moltype = AA  length = 6
FEATURE                  Location/Qualifiers
REGION                   1..6
                         note = synthetic polypeptide
source                   1..6
                         mol_type = protein
                         organism = synthetic construct
SEQUENCE: 26
LVPRGS                                                         6

SEQ ID NO: 27            moltype = AA  length = 10
FEATURE                  Location/Qualifiers
REGION                   1..10
                         note = synthetic polypeptide
source                   1..10
                         mol_type = protein
                         organism = synthetic construct
SEQUENCE: 27
DLEVVTSTWV                                                    10

SEQ ID NO: 28            moltype = AA  length = 10
FEATURE                  Location/Qualifiers
REGION                   1..10
                         note = synthetic polypeptide
source                   1..10
```

```
                        mol_type = protein
                        organism = synthetic construct
SEQUENCE: 28
DEMEECASHL                                                               10

SEQ ID NO: 29           moltype = AA   length = 10
FEATURE                 Location/Qualifiers
REGION                  1..10
                        note = synthetic polypeptide
source                  1..10
                        mol_type = protein
                        organism = synthetic construct
SEQUENCE: 29
DCSTPCSGSW                                                               10

SEQ ID NO: 30           moltype = AA   length = 10
FEATURE                 Location/Qualifiers
REGION                  1..10
                        note = synthetic polypeptide
source                  1..10
                        mol_type = protein
                        organism = synthetic construct
SEQUENCE: 30
EDVVCCSMSY                                                               10

SEQ ID NO: 31           moltype = AA   length = 9
FEATURE                 Location/Qualifiers
REGION                  1..9
                        note = synthetic polypeptide
source                  1..9
                        mol_type = protein
                        organism = synthetic construct
SEQUENCE: 31
DEMEECSQH                                                                 9

SEQ ID NO: 32           moltype = DNA  length = 72
FEATURE                 Location/Qualifiers
misc_feature            1..72
                        note = synthetic polynucleotide
source                  1..72
                        mol_type = other DNA
                        organism = synthetic construct
SEQUENCE: 32
ggagcgccag gttccggggc tactaacttc agcctcctta acaggccgg cgacgtggaa         60
gagaatcctg gc                                                            72

SEQ ID NO: 33           moltype = AA   length = 72
FEATURE                 Location/Qualifiers
REGION                  1..72
                        note = synthetic polypeptide
VARIANT                 46
                        note = X can be any naturally occurring amino acid
VARIANT                 65
                        note = X can be any naturally occuring amino acid
VARIANT                 72
                        note = X can be any naturally occurring amino acid
source                  1..72
                        mol_type = protein
                        organism = synthetic construct
SEQUENCE: 33
MAVEKTNSSS SLAEVIDRIL DKGIVIDAWV RVSLVGIELL AIEARXVIAS VETYLKYAEA         60
VGLTXSAAVP AX                                                            72

SEQ ID NO: 34           moltype = AA   length = 71
FEATURE                 Location/Qualifiers
source                  1..71
                        mol_type = protein
                        organism = Aphanizomenon flos-aquae
SEQUENCE: 34
MAVEKTNSSS SLAEVIDRIL DKGIVIDAWV RVSLVGIELL AIEARIVIAS VETYLKYAEA         60
VGLTQSAAVP A                                                             71

SEQ ID NO: 35           moltype = AA   length = 72
FEATURE                 Location/Qualifiers
source                  1..72
                        mol_type = protein
                        organism = Aphanothece halophytica
SEQUENCE: 35
MAVEKTNSSS SLGEVVDRIL DKGVVVDLWV RVSLVGIELL AVEARVVVAS VETYLKYAEA         60
```

```
VGLTSSAAVP AE                                                           72

SEQ ID NO: 36              moltype = AA   length = 71
FEATURE                    Location/Qualifiers
source                     1..71
                           mol_type = protein
                           organism = Anabaena flos-aquae
SEQUENCE: 36
MAVEKTNSSS SLAEVIDRIL DKGIVIDAWV RVSLVGIELL AIEARIVIAS VETYLKYAEA        60
VGLTQSAAVP A                                                            71

SEQ ID NO: 37              moltype = AA   length = 70
FEATURE                    Location/Qualifiers
source                     1..70
                           mol_type = protein
                           organism = Ancylobacter aquaticus
SEQUENCE: 37
MAVEKINASS SLAEVVDRIL DKGVVVDAWV RVSLVGIELL AVEARVVVAG VDTYLKYAEA        60
VGLTASAQAA                                                              70

SEQ ID NO: 38              moltype = AA   length = 70
FEATURE                    Location/Qualifiers
source                     1..70
                           mol_type = protein
                           organism = Aquabacter spiritensis
SEQUENCE: 38
MAVEKINASS SLAEVVDRIL DKGVVVDAWV RVSLVGIELL AVEARVVVAG VDTYLKYAEA        60
VGLTAGAQAA                                                              70

SEQ ID NO: 39              moltype = AA   length = 72
FEATURE                    Location/Qualifiers
source                     1..72
                           mol_type = protein
                           note = PCC-8005
                           organism = Arthrospira sp.
SEQUENCE: 39
MAVEKVNSSS SLAEVIDRIL DKGIVIDAWV RVSLVGIELL SVEARVVIAS VETYLKYAEA        60
VGLTAQAAVP SV                                                           72

SEQ ID NO: 40              moltype = AA   length = 71
FEATURE                    Location/Qualifiers
source                     1..71
                           mol_type = protein
                           note = Strain PCC-7601
                           organism = Calothrix sp.
SEQUENCE: 40
MAVEKTNSSS SLAEVIDRIL DKGIVVDAWV RVSLVGIELL AIEARIVIAS VETYLKYAEA        60
VGLTQSAAVP A                                                            71

SEQ ID NO: 41              moltype = AA   length = 72
FEATURE                    Location/Qualifiers
source                     1..72
                           mol_type = protein
                           note = PCC-8305
                           organism = Dactylococcopsis salina
SEQUENCE: 41
MAVEKTNSSS SLGEVVDRIL DKGVVVDLWV RVSLVGIELL AVEARVVIAS VETYLKYAEA        60
VGLTSSAAVP AE                                                           72

SEQ ID NO: 42              moltype = AA   length = 71
FEATURE                    Location/Qualifiers
source                     1..71
                           mol_type = protein
                           note = AWQC131C
                           organism = Dolichospermum circinale
SEQUENCE: 42
MAVEKTNSSS SLAEVIDRIL DKGIVIDAWV RVSLVGIELL AIEARIVIAS VETYLKYAEA        60
VGLTQSAAVP A                                                            71

SEQ ID NO: 43              moltype = AA   length = 71
FEATURE                    Location/Qualifiers
source                     1..71
                           mol_type = protein
                           organism = Dolichospermum lemmermannii
SEQUENCE: 43
MAVEKTNSSS SLAEVIDRIL DKGIVIDAWV RVSLVGIELL AIEARIVIAS VETYLKYAEA        60
VGLTQSAAVP A                                                            71

SEQ ID NO: 44              moltype = AA   length = 70
```

```
FEATURE                 Location/Qualifiers
source                  1..70
                        mol_type = protein
                        organism = Enhydrobacter aerosaccus
SEQUENCE: 44
MAVEKMNASS SLAEVVDRIL DKGIVIDAWV RVSLVGIELL AVEARVVVAG VDTYLKYAEA   60
VGLTAGAEAA                                                         70

SEQ ID NO: 45           moltype = AA  length = 72
FEATURE                 Location/Qualifiers
source                  1..72
                        mol_type = protein
                        note = BDU141951
                        organism = Lyngbya confervoides
SEQUENCE: 45
MAVEKVNSSS SLAEVVDRIL DKGIVVDAWV RVSLVGIELL AIEARVVIAS VETYLKYAEA   60
VGLTAQAAVP AS                                                      72

SEQ ID NO: 46           moltype = AA  length = 73
FEATURE                 Location/Qualifiers
source                  1..73
                        mol_type = protein
                        note = PCC-73102
                        organism = Nostoc punctiforme
SEQUENCE: 46
MAVEKVNSSS SLAEVIDRIL DKGIVIDAWV RVSLVGIELL SIEARIVIAS VETYLRYAEA   60
VGLTSQAAVP SAA                                                     73

SEQ ID NO: 47           moltype = AA  length = 71
FEATURE                 Location/Qualifiers
source                  1..71
                        mol_type = protein
                        note = PCC-7120
                        organism = Nostoc sp.
SEQUENCE: 47
MAVEKTNSSS SLAEVIDRIL DKGIVVDAWV RVSLVGIELL AIEARIVIAS VETYLKYAEA   60
VGLTQSAAMP A                                                       71

SEQ ID NO: 48           moltype = AA  length = 71
FEATURE                 Location/Qualifiers
source                  1..71
                        mol_type = protein
                        organism = Microchaete diplosiphon
SEQUENCE: 48
MAVEKTNSSS SLAEVIDRIL DKGIVVDAWV RVSLVGIELL AIEARIVIAS VETYLKYAEA   60
VGLTQSAAVP A                                                       71

SEQ ID NO: 49           moltype = AA  length = 71
FEATURE                 Location/Qualifiers
source                  1..71
                        mol_type = protein
                        note = NIES-843
                        organism = Microcystis aeruginosa
SEQUENCE: 49
MAVEKTNSSS SLAEVIDRIL DKGIVIDAWA RVSLVGIELL AIEARVVIAS VETYLKYAEA   60
VGLTQSAAVP A                                                       71

SEQ ID NO: 50           moltype = AA  length = 71
FEATURE                 Location/Qualifiers
source                  1..71
                        mol_type = protein
                        note = NIES-843
                        organism = Microcystis aeruginosa
SEQUENCE: 50
MAVEKTNSSS SLAEVIDRIL DKGIVIDAWA RVSLVGIELL AIEARVVIAS VETYLKYAEA   60
VGLTQSAAVP A                                                       71

SEQ ID NO: 51           moltype = AA  length = 71
FEATURE                 Location/Qualifiers
source                  1..71
                        mol_type = protein
                        note = NIES-843
                        organism = Microcystis aeruginosa
SEQUENCE: 51
MAVEKTNSSS SLAEVIDRIL DKGIVIDAWA RVSLVGIELL AIEARVVIAS VETYLKYAEA   60
VGLTQSAAVP A                                                       71

SEQ ID NO: 52           moltype = AA  length = 71
FEATURE                 Location/Qualifiers
```

```
source          1..71
                mol_type = protein
                note = TF09
                organism = Microcystis flos-aquae
SEQUENCE: 52
MAVEKTNSSS SLAEVIDRIL DKGIVIDAWA RVSLVGIELL AIEARVVIAS VETYLKYAEA    60
VGLTQSAAVP A                                                        71

SEQ ID NO: 53           moltype = AA  length = 72
FEATURE                 Location/Qualifiers
source                  1..72
                        mol_type = protein
                        note = NIES-30
                        organism = Phormidium tenue
SEQUENCE: 53
MAVEKVNSSS SLAEVVDRIL DKGIVIDAWV RVSLVGIELL AIEARVVIAS VDTYLKYAEA    60
VGLTAQAAVP AA                                                       72

SEQ ID NO: 54           moltype = AA  length = 72
FEATURE                 Location/Qualifiers
source                  1..72
                        mol_type = protein
                        organism = Planktothrix agardhii
SEQUENCE: 54
MAVEKVNSSS SLAEVIDRIL DKGIVIDAWV RVSLVGIELL SIEARIVIAS VETYLKYAEA    60
VGLTAQAAVP SV                                                       72

SEQ ID NO: 55           moltype = AA  length = 72
FEATURE                 Location/Qualifiers
source                  1..72
                        mol_type = protein
                        organism = Planktothrix rubescens
SEQUENCE: 55
MAVEKVNSSS SLAEVIDRIL DKGIVIDAWV RVSLVGIELL SIEARIVIAS VETYLKYAEA    60
VGLTAQAAVP SV                                                       72

SEQ ID NO: 56           moltype = AA  length = 72
FEATURE                 Location/Qualifiers
source                  1..72
                        mol_type = protein
                        note = PCC-6901
                        organism = Pseudanabaena galeata
SEQUENCE: 56
MAVEKVNSSS SLAEVIDRIL DKGIVIDAWV RVSLVGIELL SIEARVVIAS VETYLKYAEA    60
VGLTASAAVP AA                                                       72

SEQ ID NO: 57           moltype = AA  length = 70
FEATURE                 Location/Qualifiers
source                  1..70
                        mol_type = protein
                        organism = Stella vacuolata
SEQUENCE: 57
MAVEKINASS SLAEVVDRIL DKGVVVDAWV RVSLVGIELL AVEARVVVAG VDTYLKYAEA    60
VGLTAGAQTA                                                          70

SEQ ID NO: 58           moltype = AA  length = 75
FEATURE                 Location/Qualifiers
source                  1..75
                        mol_type = protein
                        note = IMS101
                        organism = Trichodesmium erythraeum
SEQUENCE: 58
MAVEKVNSSS SLAEVIDRIL DKGVVVDAWI RLSLVGIELL TIEARIVVAS VETYLKYAEA    60
VGLTTLAAAP GEAAA                                                    75

SEQ ID NO: 59           moltype = AA  length = 72
FEATURE                 Location/Qualifiers
source                  1..72
                        mol_type = protein
                        note = IMS101
                        organism = Trichodesmium erythraeum
SEQUENCE: 59
MAVEKVNSSS SLAEVIDRIL DKGVVVDAWV RLSLVGIELL TIEARIVIAS VETYLKYAEA    60
VGLTTLAAEP AA                                                       72

SEQ ID NO: 60           moltype = AA  length = 71
FEATURE                 Location/Qualifiers
source                  1..71
                        mol_type = protein
```

```
                              note = PCC-7601
                              organism = Tolypothrix sp.
SEQUENCE: 60
MAVEKTNSSS SLAEVIDRIL DKGIVVDAWV RVSLVGIELL AIEARIVIAS VETYLKYAEA    60
VGLTQSAAVP A                                                        71

SEQ ID NO: 61             moltype = AA  length = 71
FEATURE                   Location/Qualifiers
source                    1..71
                          mol_type = protein
                          note = PCC-7601
                          organism = Tolypothrix sp.
SEQUENCE: 61
MAVEKTNSSS SLAEVIDRIL DKGIVVDAWV RVSLVGIELL AIEARIVIAS VETYLKYAEA    60
VGLTQSAAVP A                                                        71

SEQ ID NO: 62             moltype = AA  length = 78
FEATURE                   Location/Qualifiers
REGION                    1..78
                          note = synthetic polypeptide
VARIANT                   29
                          note = X can be any naturally occurring amino acid
VARIANT                   73
                          note = X can be any naturally occurring amino acid
source                    1..78
                          mol_type = protein
                          organism = synthetic construct
SEQUENCE: 62
MAQPDSSSLA EVLDRVLDKG VVVDVWARXS LVGIEILTVE ARVVAASVDT FLHYAEEIAK    60
IEQAELTAGA EAXPAPEA                                                 78

SEQ ID NO: 63             moltype = AA  length = 76
FEATURE                   Location/Qualifiers
source                    1..76
                          mol_type = protein
                          organism = Halobacterium salinarum
SEQUENCE: 63
MAQPDSSGLA EVLDRVLDKG VVVDVWARVS LVGIEILTVE ARVVAASVDT FLHYAEEIAK    60
IEQAELTAGA EAAPEA                                                   76

SEQ ID NO: 64             moltype = AA  length = 79
FEATURE                   Location/Qualifiers
source                    1..79
                          mol_type = protein
                          organism = Halobacterium salinarum
SEQUENCE: 64
MAQPDSSSLA EVLDRVLDKG VVVDVWARIS LVGIEILTVE ARVVAASVDT FLHYAEEIAK    60
IEQAELTAGA EAPEPAPEA                                                79

SEQ ID NO: 65             moltype = AA  length = 76
FEATURE                   Location/Qualifiers
source                    1..76
                          mol_type = protein
                          note = NRC-1
                          organism = Halobacterium salinarum
SEQUENCE: 65
MAQPDSSGLA EVLDRVLDKG VVVDVWARVS LVGIEILTVE ARVVAASVDT FLHYAEEIAK    60
IEQAELTAGA EAAPEA                                                   76

SEQ ID NO: 66             moltype = AA  length = 79
FEATURE                   Location/Qualifiers
source                    1..79
                          mol_type = protein
                          note = NRC-1
                          organism = Halobacterium salinarum
SEQUENCE: 66
MAQPDSSSLA EVLDRVLDKG VVVDVWARIS LVGIEILTVE ARVVAASVDT FLHYAEEIAK    60
IEQAELTAGA EAPEPAPEA                                                79

SEQ ID NO: 67             moltype = AA  length = 78
FEATURE                   Location/Qualifiers
source                    1..78
                          mol_type = protein
                          note = ATCC-33500
                          organism = Haloferax mediterranei
SEQUENCE: 67
MVQPDSSSLA EVLDRVLDKG VVVDVWARIS LVGIEILTVE ARVVAASVDT FLHYAEEIAK    60
IEQAELTAGA EAAPTPEA                                                 78
```

```
SEQ ID NO: 68            moltype = AA  length = 78
FEATURE                  Location/Qualifiers
source                   1..78
                         mol_type = protein
                         note = DSM-11551
                         organism = Halogeometricum borinquense
SEQUENCE: 68
MAQPDSSSLA EVLDRVLDKG VVVDVWARVS LVGIEILTVE ARVVAASVDT FLHYAEEIAK    60
IEQAELTATA EAAPTPEA                                                 78

SEQ ID NO: 69            moltype = AA  length = 76
FEATURE                  Location/Qualifiers
source                   1..76
                         mol_type = protein
                         note = strain DC30
                         organism = Halopenitus persicus
SEQUENCE: 69
MAQPDSSGLA EVLDRVLDKG VVVDVWARVS LVGIEILTVE ARVVAASVDT FLHYAEEIAK    60
IEQAELTAGA EAAPEA                                                   76

SEQ ID NO: 70            moltype = AA  length = 72
FEATURE                  Location/Qualifiers
source                   1..72
                         mol_type = protein
                         note = C23
                         organism = Haloquadratum walsbyi
SEQUENCE: 70
MAQPDSSSLA EVLDRVLDKG IVVDTFARIS LVGIEILTVE ARVVVASVDT FLHYAEEIAK    60
IEQAELTAGA EA                                                       72

SEQ ID NO: 71            moltype = AA  length = 78
FEATURE                  Location/Qualifiers
source                   1..78
                         mol_type = protein
                         note = strain DSM-8800
                         organism = Halorubrum vacuolatum
SEQUENCE: 71
MAQPDSSSLA EVLDRVLDKG VVVDVYARLS LVGIEILTVE ARVVAASVDT FLHYAEEIAK    60
IEQAELTAGA EAAPTPEA                                                 78

SEQ ID NO: 72            moltype = AA  length = 95
FEATURE                  Location/Qualifiers
source                   1..95
                         mol_type = protein
                         organism = Halopiger xanaduensis
SEQUENCE: 72
MAQPQRRPDS SSLAEVLDRI LDKGVVIDVW ARISVVGIEL LTIEARVVVA SVDTFLHYAE    60
EIAKIEQATA EGDLEELEEL EVEPRPESSP QSAAE                              95

SEQ ID NO: 73            moltype = AA  length = 95
FEATURE                  Location/Qualifiers
source                   1..95
                         mol_type = protein
                         note = ATCC-43099
                         organism = Natrialba magadii
SEQUENCE: 73
MAQPQRRPDS SSLAEVLDRV LDKGVVIDIW ARSVVGIEL LTVEARVVVA SVDTFLHYAE     60
EIAKIEQATA EGDLEDLEEL EVEPRPESSP KSATE                              95

SEQ ID NO: 74            moltype = AA  length = 94
FEATURE                  Location/Qualifiers
source                   1..94
                         mol_type = protein
                         note = DSM-15624
                         organism = Natrinema pellirubrum
SEQUENCE: 74
MAQPQRRPDS SSLAEVLDRV LDKGVVIDVW ARISVVGIEL LTIEARVVVA SVDTFLHYAE    60
EIAKIEQATA EGDLDELEEL EVEPRPESSP KSAE                               94

SEQ ID NO: 75            moltype = AA  length = 95
FEATURE                  Location/Qualifiers
source                   1..95
                         mol_type = protein
                         note = SP2
                         organism = Natronobacterium gregoryi
SEQUENCE: 75
MAQPQRRPDS SSLAEVLDRI LDKGVVIDVW ARSVVGIEL LTIEARVVVA SVDTFLHYAE     60
EIAKIEQATA EGDLEDLEEL EVEPRPESSP QSATE                              95
```

```
SEQ ID NO: 76            moltype = AA   length = 74
FEATURE                  Location/Qualifiers
source                   1..74
                         mol_type = protein
                         organism = Methanosaeta thermophila
SEQUENCE: 76
MVTSTPDSSS LAEVLDRILD KGIVVDVWAR VSLVGIEILT VEARVVVASV DTFLHYSEEM    60
AKIEQAAIAA APSA                                                     74

SEQ ID NO: 77            moltype = AA   length = 76
FEATURE                  Location/Qualifiers
source                   1..76
                         mol_type = protein
                         organism = Methanosaeta thermophila
SEQUENCE: 77
MVTSTPDSSS LAEVLDRILD KGIVVDVWAR VSLVGIEILT VEARVVVASV DTFLHYSEEM    60
AKIEQAAIAA APGVPA                                                   76

SEQ ID NO: 78            moltype = AA   length = 76
FEATURE                  Location/Qualifiers
source                   1..76
                         mol_type = protein
                         organism = Methanosarcina barkeri-3
SEQUENCE: 78
MVSQSPDSSS LAEVLDRILD KGIVVDVWAR VSLVGIEILA IEARVVVASV DTFLHYAEEI    60
TKIEIAAKEE KPAIAA                                                   76

SEQ ID NO: 79            moltype = AA   length = 76
FEATURE                  Location/Qualifiers
source                   1..76
                         mol_type = protein
                         organism = Methanosarcina vacuolata
SEQUENCE: 79
MVSQSPDSSS LAEVLDRILD KGIVVDTWAR VSLVGIEILA IEARVVVASV DTFLHYAEEI    60
TKIEIAAREE KPVIAA                                                   76

SEQ ID NO: 80            moltype = AA   length = 76
FEATURE                  Location/Qualifiers
source                   1..76
                         mol_type = protein
                         organism = Methanosarcina vacuolata
SEQUENCE: 80
MVSQSPDCSS LAEVLDRILD KGIVVDTWAR VSLVGIEILA IEARVVVASV DTFLHYAEEI    60
TKIEIAAREE KPVIAA                                                   76

SEQ ID NO: 81            moltype = AA   length = 87
FEATURE                  Location/Qualifiers
source                   1..87
                         mol_type = protein
                         note = DX253
                         organism = Haladaptatus paucihalophilus
SEQUENCE: 81
MVQAEPNSSS LADVLDRILD KGVVIDVWAR ISVVGIEVLT VEARVVVASV DTFLHYAKEM    60
AKLERASSED EIDFEQVEVA SPEASTS                                       87

SEQ ID NO: 82            moltype = AA   length = 73
FEATURE                  Location/Qualifiers
REGION                   1..73
                         note = synthetic polypeptide
VARIANT                  8
                         note = X can be any naturally occurring amino acid
VARIANT                  34
                         note = X can be any naturally occurring amino acid
VARIANT                  73
                         note = X can be any naturally occurring amino acid
source                   1..73
                         mol_type = protein
                         organism = synthetic construct
SEQUENCE: 82
MSIQKSTXSS SLAEVIDRIL DKGIVIDAFA RVSXVGIEIL TIEARVVIAS VDTWLRYAEA    60
VGLLDVEEGL PRX                                                      73

SEQ ID NO: 83            moltype = AA   length = 86
FEATURE                  Location/Qualifiers
source                   1..86
                         mol_type = protein
                         organism = Bacillus megaterium
SEQUENCE: 83
MSIQKSTDSS SLAEVIDRIL DKGIVIDAFA RVSLVGIEIL TIEARVVIAS VDTWLRYAEA    60
```

```
VGLLTDKVEE EGLPGRTEER GAGLSF                                           86

SEQ ID NO: 84           moltype = AA  length = 88
FEATURE                 Location/Qualifiers
source                  1..88
                        mol_type = protein
                        organism = Bacillus megaterium
SEQUENCE: 84
MSIQKSTNSS SLAEVIDRIL DKGIVIDAFA RVSVVGIEIL TIEARVVIAS VDTWLRYAEA      60
VGLLRDDVEE NGLPERSNSS EGQPRFSI                                         88

SEQ ID NO: 85           moltype = AA  length = 72
FEATURE                 Location/Qualifiers
REGION                  1..72
                        note = synthetic polypeptide
VARIANT                 31
                        note = X can be any naturally occurring amino acid
VARIANT                 67
                        note = X can be any naturally occurring amino acid
source                  1..72
                        mol_type = protein
                        organism = synthetic construct
SEQUENCE: 85
MAKVQKSTDS SSLAEVVDRI LDKGIVIDAW XKVSLVGIEL LSIEARVVIA SVETYLKYAE      60
AIGLTAXAAA PA                                                          72

SEQ ID NO: 86           moltype = AA  length = 73
FEATURE                 Location/Qualifiers
source                  1..73
                        mol_type = protein
                        note = Bp5365
                        organism = Burkholderia sp.
SEQUENCE: 86
MAKVQKSTDS SSLAEVVDRI LDKGIVIDVW AKVSLVGIEL LSIEARVVIA SVETYLKYAE      60
AIGLTATAAA PTA                                                         73

SEQ ID NO: 87           moltype = AA  length = 72
FEATURE                 Location/Qualifiers
source                  1..72
                        mol_type = protein
                        note = DSM-3385
                        organism = Desulfobacterium vacuolatum
SEQUENCE: 87
MAKVQKTTDS SSLAEVVDRI LDKGIVVDAW AKISLVGIEL ISIEARVVIA SVETYLKYAE      60
AIGLTAAAAA PA                                                          72

SEQ ID NO: 88           moltype = AA  length = 72
FEATURE                 Location/Qualifiers
source                  1..72
                        mol_type = protein
                        note = DSM-6799
                        organism = Desulfomonile tiedjei
SEQUENCE: 88
MAKIAKSTDS SSLAEVVDRI LDKGIVIDAW AKVSLVGIEL LSVEARVVIA SVETYLKYAE      60
AIGLTASAAA PA                                                          72

SEQ ID NO: 89           moltype = AA  length = 72
FEATURE                 Location/Qualifiers
source                  1..72
                        mol_type = protein
                        note = ATCC-43644
                        organism = Isosphaera pallida
SEQUENCE: 89
MAKVTKSTDS SSLAEVVDRI LDKGIVIDAF AKVSLVGIEL LSVEARVVIA SVETYLKYAE      60
AIGLTASAAT PA                                                          72

SEQ ID NO: 90           moltype = AA  length = 72
FEATURE                 Location/Qualifiers
source                  1..72
                        mol_type = protein
                        note = DSM-4197
                        organism = Lamprocystis purpurea
SEQUENCE: 90
MAKVANSTDS SSLAEVVDRI LDKGIVIDAW IKVSLVGIEL LAIEARIVIA SVETYLKYAE      60
AIGLTAPAAA PA                                                          72

SEQ ID NO: 91           moltype = AA  length = 72
FEATURE                 Location/Qualifiers
source                  1..72
```

```
                              mol_type = protein
                              note = DSM-4197
                              organism = Lamprocystis purpurea
SEQUENCE: 91
MAKVANSTDS SSLAEVVDRI LDKGIVIDAW LKVSLVGIEL LAVEARVVIA SVETYLKYAE    60
AIGLTAPAAA PA                                                       72

SEQ ID NO: 92                 moltype = AA  length = 72
FEATURE                       Location/Qualifiers
source                        1..72
                              mol_type = protein
                              note = LLAP12
                              organism = Legionella drancourtii
SEQUENCE: 92
MAKVQKSTDS SSLAEVIDRI LDKGIVIDVW AKVSLVGIEL LSIEARVVIA SVETYLKYAE    60
AIGLTATASH PA                                                       72

SEQ ID NO: 93                 moltype = AA  length = 72
FEATURE                       Location/Qualifiers
source                        1..72
                              mol_type = protein
                              organism = Psychromonas Ingrahamii
SEQUENCE: 93
MANVQKTTDS SGLAEVIDRI LDKGIVIDAF VKVSLVGIEL LSIEARVVIA SVETYLKYAE    60
AIGLTASAAT PA                                                       72

SEQ ID NO: 94                 moltype = AA  length = 72
FEATURE                       Location/Qualifiers
source                        1..72
                              mol_type = protein
                              organism = Psychromonas Ingrahamii
SEQUENCE: 94
MANVQKSTDS SGLAEVVDRI LEKGIVIDAF VKVSLVGIEL LSIEARVVIA SVETYLKYAE    60
AIGLTASAAT PA                                                       72

SEQ ID NO: 95                 moltype = AA  length = 72
FEATURE                       Location/Qualifiers
source                        1..72
                              mol_type = protein
                              note = 39006
                              organism = Serratia
SEQUENCE: 95
MAKVQKSTDS SSLAEVVDRI LDKGIVIDAW VKVSLVGIEL LSIEARVVIA SVETYLKYAE    60
AIGLTASAAT PA                                                       72

SEQ ID NO: 96                 moltype = AA  length = 72
FEATURE                       Location/Qualifiers
source                        1..72
                              mol_type = protein
                              note = strain DSM-235-Ga0242571-11
                              organism = Thiocapsa rosea
SEQUENCE: 96
MAKVANSTDS SSLAEVVDRI LDKGIVIDAW VKVSLVGIEL LAIEARVVIA SVETYLKYAE    60
AIGLTAPAAA PA                                                       72

SEQ ID NO: 97                 moltype = AA  length = 70
FEATURE                       Location/Qualifiers
source                        1..70
                              mol_type = protein
                              note = S58
                              organism = Bradyrhizobium oligotrophicum
SEQUENCE: 97
MAIEKATASS SLAEVIDRIL DKGVVIDAFV RVSLVGIELL SIELRAVVAS VETWLKYAEA    60
IGLVAQPMPA                                                          70

SEQ ID NO: 98                 moltype = AA  length = 71
FEATURE                       Location/Qualifiers
source                        1..71
                              mol_type = protein
                              note = DSM-771
                              organism = Desulfotomaculum acetoxidans
SEQUENCE: 98
MAVKHSVASS SLVEVIDRIL EKGIVIDAWA RVSLVGIELL AIEARVVVAS VDTFLKYAEA    60
IGLTKFAAVP A                                                        71

SEQ ID NO: 99                 moltype = AA  length = 67
FEATURE                       Location/Qualifiers
source                        1..67
                              mol_type = protein
```

```
                              note = 307
                              organism = Octadecabacter antarcticus
SEQUENCE: 99
MAVNKMNSSS SLAEVVDRIL DKGVVIDAWV RVSLVGIELI AVEARVVIAG VDTYLKYAEA    60
VGLTAEA                                                              67

SEQ ID NO: 100                moltype = AA  length = 67
FEATURE                       Location/Qualifiers
source                        1..67
                              mol_type = protein
                              note = 238
                              organism = Octadecabacter arcticus
SEQUENCE: 100
MAVSKMNSSS SLAEVVDRIL DKGVVIDAWV RVSLVGIELI AVEARVVIAG VDTYLKYAEA    60
VGLTAEA                                                              67

SEQ ID NO: 101                moltype = AA  length = 68
FEATURE                       Location/Qualifiers
source                        1..68
                              mol_type = protein
                              note = DSM-273
                              organism = Pelodictyon luteolum
SEQUENCE: 101
MAVEKTIGSS SLVEVIDRIL DKGVVVDAWV RMSLVGIELL AIEARVVVAS VETYLKYAEA    60
IGLTAKAA                                                             68

SEQ ID NO: 102                moltype = AA  length = 68
FEATURE                       Location/Qualifiers
source                        1..68
                              mol_type = protein
                              note = DSM-273
                              organism = Pelodictyon luteolum
SEQUENCE: 102
MAVEKTIGSS SLVEVIDRIL DKGVVVDAWV RVSLVGIELL AIEARVVVAS VETYLKYAEA    60
IGLTAKAA                                                             68

SEQ ID NO: 103                moltype = AA  length = 68
FEATURE                       Location/Qualifiers
source                        1..68
                              mol_type = protein
                              organism = Pelodictyon phaeoclathratiforme
SEQUENCE: 103
MSVEKTIGSS SLVEVIDRIL DKGVVVDAWV RVSLVGIELL AIEARVVVAS VETYLKYAEA    60
IGLTAKAA                                                             68

SEQ ID NO: 104                moltype = AA  length = 70
FEATURE                       Location/Qualifiers
source                        1..70
                              mol_type = protein
                              note = SB-1003
                              organism = Rhodobacter capsulatus
SEQUENCE: 104
MAIEKSLASA SIAEVIDRVL DKGIVVDAFV RISLVGIELL AIELRAVVAS VETWLKYAEA    60
IGLTVDPQTP                                                           70

SEQ ID NO: 105                moltype = AA  length = 70
FEATURE                       Location/Qualifiers
source                        1..70
                              mol_type = protein
                              organism = Rhodobacter sphaeroides
SEQUENCE: 105
MAIEKSVASA SIAEVIDRIL DKGVVIDAFV RVSLVGIELI AIEVRAVVAS IETWLKYAEA    60
VGLTVDPATT                                                           70

SEQ ID NO: 106                moltype = AA  length = 245
FEATURE                       Location/Qualifiers
source                        1..245
                              mol_type = protein
                              organism = Anabaena flos-aquae
SEQUENCE: 106
MSIPLYLYGI FPNTIPETLE LEGLDKQPVH SQVVDEFCFL YSEARQEKYL ASRRNLLTHE    60
KVLEQTMHAG FRVLLPLRFG LVVKDWETIM SQLINPHKDQ LNQLFQKLAG KREVSIKIFW   120
DAKAELQTMM ESHQDLKQQR DNMEGKKLSM EEVIQIGQLI EINLLARKQA VIEVFSQELN   180
PFAQEIVVSD PMTEEMIYNA AFLIPWESES EFSERVEVID QKFGDRLRIR YNNFTAPYTF   240
AQLDS                                                               245

SEQ ID NO: 107                moltype = AA  length = 268
FEATURE                       Location/Qualifiers
source                        1..268
```

```
                        mol_type = protein
                        note = strain UV5
                        organism = Ancylobacter aquaticus
SEQUENCE: 107
MSATLSAPGT ANVAVEATAA ADGKYLYGII EAPAPATFDV PAIGGRGDVV HTIALGRLAA    60
VVSNSPRIDY DNSRRNMLAH TKVLEAVMAR HTLLPVCFGT VGSDAEVIIE KILRERRDEL   120
AGLLGQMHGR MELGLKASWR EEIIFEEVLA ENPAIRKLRD ALVGRSPDQS HYERIQLGER   180
IGQALQRKRQ DDEERILERV RPFVHKTRLN KLIGDRMVIN AAFLVDAAVE SRLDASIRAM   240
DEEWGGRLAF KYVGPVPPYN FVTITIHW                                     268

SEQ ID NO: 108          moltype = AA  length = 245
FEATURE                 Location/Qualifiers
source                  1..245
                        mol_type = protein
                        note = NIES-81
                        organism = Aphanizomenon flos-aquae
SEQUENCE: 108
MNTGLYLYGI FPDPIPETVD LQGLDKQSVH SQVVDGFSFL YSDACQEKYL ASRRNLLTHE    60
KVLEQAMHEG FHVLLPLRFG LVVKDWETIQ KQLIEPYKEQ LNELFQKLAG QREVSIKILW   120
DSKSELQAMM ESNQDLKQQR DNMEGKKLKM EEIIQIGQLI ESNLAARKQT VIQEFFNNLH   180
PLAKEIIESE PMTEEMIYNA AFLIPWETES VFSERVEAID RKFGDRLRIR YNNFTAPYTF   240
AQLAS                                                              245

SEQ ID NO: 109          moltype = AA  length = 245
FEATURE                 Location/Qualifiers
source                  1..245
                        mol_type = protein
                        note = strain PCC 7418
                        organism = Aphanothece halophytica
SEQUENCE: 109
MAEGFYLYGI FPPPGPQTIA VQGLDKQPIF SHTVEGFTFL YSEAQQSRYL ASRRNLITHT    60
KVLEEAMEQG FRTLLPLPQFG LVVPDWESVS QDLLQHQSET LQLLFQRLEG KREVSLKIYW  120
ETDAELNALL EENPDLKARR DNLEGKNLSM DEVIQIGQAL EQAMERRKQE VITRFEDALI   180
PPFAVETQEND VLTETMIYNT AFLIPWESEP EFGEAVETVD AEFAPRLKIR YNNFTPPYNF  240
VELRE                                                              245

SEQ ID NO: 110          moltype = AA  length = 261
FEATURE                 Location/Qualifiers
source                  1..261
                        mol_type = protein
                        note = strain DSM 9035
                        organism = Aquabacter spiritensis
SEQUENCE: 110
MMQTDTLAPA ETVAEGKYLY CLIDAPAPDT FASPGIGGRG DVVHTITVGR LAAVVSDSPR    60
IEYENSRRNM MAHTKVLEEV MARHTMLPVC FGTVATGPDP ISGKILEGRR DELVGLLEQM   120
RGRLELGLKA TWREDVIFAE ILQENPAIAK LRDSLVGRSP EKSHFERIRL GEMIGQAMER   180
KRRDDEERIL ERVRPFVHKT KLNKPIGDRM ILNAAVLVEA AREAGLDQAV RQMDAEWGAR   240
LSFKYVGPVP PYNFVTITIH W                                            261

SEQ ID NO: 111          moltype = AA  length = 255
FEATURE                 Location/Qualifiers
source                  1..255
                        mol_type = protein
                        organism = Bacillus-megaterium
SEQUENCE: 111
MSETNETGIY IFSAIQTDKD EEFGAVEVEG TKAETFLIRY KDAAMVAAEV PMKIYHPNRQ    60
NLLMHQNAVA AIMDKNDTVI PISFGNVFKS KEDVKVLLEN LYPQFEKLFP AIKGKIEVGL   120
KVIGKKEWLE KKVNENPELE KVSASVKGKS EAAGYYERIQ LGGMAQKMFT SLQKEVKTDV   180
FSPLEEAAEA AKANEPTGET MLLNASFLIN REDEAKFDEK VNEAHENWKD KADFHYSGPW   240
PAYNFVNIRL KVEEK                                                   255

SEQ ID NO: 112          moltype = AA  length = 258
FEATURE                 Location/Qualifiers
source                  1..258
                        mol_type = protein
                        note = S58
                        organism = Bradyrhizobium oligotrophicum
SEQUENCE: 112
MSNQPIYVYG LIRAEDHQPL AVRAVGDSEQ PVNIIGSGNV AALVSTIDLP EIMPTRRHML    60
AHTKVLEAAM ANGPVLPMRF GIIVPNPATL LRVIGFRHQE LRARLDEIDG RIEVALKASW   120
DEQFMWRQLA SEHPDLAVSG RTMMGRGEQQ SYYDRIELGR AIGAALEERR TAARLQLLQT   180
VTPFAVQVKE LTPVDDAMFA HLALLVEKGA EPSLYQTVEA LERSNDSGLK FRYVAPIPPY   240
NFVAVTLDWE QHEQAPRR                                                258

SEQ ID NO: 113          moltype = AA  length = 249
FEATURE                 Location/Qualifiers
source                  1..249
                        mol_type = protein
                        note = sp. Bp5365 strain MSMB43
```

```
                        organism = Burkholderia thailandensis
SEQUENCE: 113
MNSRNGARYL YAVQHARDVP ASLPAGIGGA AVRALTDGDV AAIVSDTGLA KVRPERRHLL   60
AHHTVIQSLA AAGTVLPVAF GTIATSEVAL RRMLRKHRNA LAGELARLVD HVEMSVRLNW  120
DVTDLFRHLI DVRPDLKAAR DAMLALGSAV TRDDKIELGS RFERVLNEER ARHAALVDEA  180
LDACCKEIRR DPPRHETEIL HLTCLVRHAE LGRFESGVAA ASRELDDSLV LKYSGPCPPH  240
HFVNLNMSL                                                         249

SEQ ID NO: 114          moltype = AA   length = 260
FEATURE                 Location/Qualifiers
source                  1..260
                        mol_type = protein
                        note = DSM 273
                        organism = Chlorobium luteolum
SEQUENCE: 114
MERDGKYIYC IIGADCECDF GPIGIGGRGD LVSTIGFEGI SMVVSDHPLN RFVVDPDGIL   60
AHQRVIEAVM KEHESVIPVR FGTVAATPDE IRNLLDRRYG ELSELLLRLR NKVEFNVTGR  120
WHDMAAIYKE VERTHPEIKE QRARIESMRD GDGEALKQSL ILDTGHQIEA ALEVMKEEKF  180
DAVASLFRKT AMASKMNRTT SPDMFMNAAF LIDRGREVEF DGIMEILGQK DADRCDYRYS  240
GPLAIFNFVD LRILPEKWEL                                             260

SEQ ID NO: 115          moltype = AA   length = 259
FEATURE                 Location/Qualifiers
source                  1..259
                        mol_type = protein
                        note = DSM 273
                        organism = Chlorobium luteolum
SEQUENCE: 115
MAHEAAEQDG LYIYGIINNS GELDFGPIGI GGREERVYAV IHNDIAAVVS RTVVKEFEPR   60
RANMIAHQKV LEAVMVSHAV LPVRFSTVSP GHDDMKVEKI LEEDYLRLKK LLVKMEGKKE  120
MGLKVMANEE KVYESIITGY DNIRYLRDKL INLPPEKTHY QRVKIGELVA AALEKEVGTY  180
KDAVLDALSP IAEEVKVNDS YGSMMVLNAA FLIRTAREEE FDRAVNALDD RYHDMMTFKY  240
VGTLPPYNFV NISINIKGR                                              259

SEQ ID NO: 116          moltype = AA   length = 343
FEATURE                 Location/Qualifiers
source                  1..343
                        mol_type = protein
                        note = DSM 273
                        organism = Chlorobium luteolum
SEQUENCE: 116
MNQSIYIYGI VNEPALAASF VETDPDIYAV ASMGCSAIVE NRPAIDLGEL DRESLARMLL   60
QHQQTLERLM ESGMQLIPLK LGTFVSSAAD AACIIEDGYN LIERIFRETE DAHELEVVVK  120
WSSFADLLQE VVSEGDVQEL KREVEARQSS STEDAIAVGR LIKEKIDRRN AALSASVLRQ  180
LGERASQSKR HETMDDEMVL NAAFLVNRGD VDAFVATVEA LDSQYLNALH FRIVGPLPCY  240
SFYTLEVTAL FEEFIAEKRA VLGLDARSCE ADVKKAYHAK AKVAHPDVHV PAGANNGADF  300
TVLNEAYMTL HDYYSALRNS ASSRHGHEGQ DSSSVVFSVK ILN                   343

SEQ ID NO: 117          moltype = AA   length = 245
FEATURE                 Location/Qualifiers
source                  1..245
                        mol_type = protein
                        note = PCC 8305
                        organism = Dactylococcopsis salina
SEQUENCE: 117
MTEGFYLYGI FPPPGPKTIE TQGLDKQPIF SHTVEGFTFL YSEAQQSRYL ASRRNLITHT   60
KVLEEAMENG SRTLLPLQFG LIVPDWETVV QDLLQHQAES LHFFLEKLEG KREVSLKIYW  120
ETNAELNALL EENPALKARR DNLEGKQLSM DEVIQIGQAL EQEMEGRKQD IISRFEEVLI  180
PPAFEIKEND VLTETMIYNT AFLINWDAES DFGEQLEAID AEFSPRLKIR YNNFTPPYNF  240
VELRE                                                             245

SEQ ID NO: 118          moltype = AA   length = 252
FEATURE                 Location/Qualifiers
source                  1..252
                        mol_type = protein
                        note = DSM 3385
                        organism = Desulfobacterium vacuolatum
SEQUENCE: 118
MSKKNLKRNG RYLYAIIEAS EEKTFGSIGM DGSDVYLIVE DKTAAVVSDV PNKKIRPQRK   60
NIAAHHAVLN KIMEEITPLP MAFGIIADGE QAIRKILADN RDVFREQFAT VSGKVEMGMR  120
ISYDVPNIFE YFISTDSEIR AARDQYFGGN REPSQEAKLE LGRMFNRQLN ANREEYTNQV  180
IEILDDYCDD IKENKCRNEQ EVTSLACLIN RSDQKRFEEG VFESARHFDN NFSFEYNGPW  240
SPHNFVNILI EL                                                     252

SEQ ID NO: 119          moltype = AA   length = 255
FEATURE                 Location/Qualifiers
source                  1..255
                        mol_type = protein
                        note = DSM 6799
```

```
                        organism = Desulfomonile tiedjei
SEQUENCE: 119
MEKATIKTTG SNGRYLYAVV PGSQERVYGC LGINGGNVYT IAAKDVAAVV SDVPHQKIRP    60
ERRHFAAHQA VLKRVMLDGD LLPMSFGIIS QGPKAVRAIL SRNNKSVQQQ LKRISGKAEM   120
GIKVTWDVPN IFEYFIDVNR ELREARNKLV QPNYLPTQQE KIEIGRMFEE ILNLERERHT   180
KQVERVMSKR CSEIKRSKCR TEIEVMNLSC LVDRTLLSDF EAGVLEAASH FDDSFAFDFN   240
GPWAPHNFVD LEIDV                                                   255

SEQ ID NO: 120          moltype = AA  length = 250
FEATURE                 Location/Qualifiers
source                  1..250
                        mol_type = protein
                        note = DSM 771
                        organism = Desulfotomaculum acetoxidans
SEQUENCE: 120
MSTGRYVYCV INSIEPLTFM SGPVGNEPEG VFTVHYKELA AVVSQSSEEK YNVCRENTIA    60
HQKVLEEVLV SHPLLPVRFG TVAQNEEIVK KFLLQERYAE LRSMLHNVTG KVQMGLKVLW   120
TDMKTVYQEI VEENPQIKNL KKKLESKPAE TIHYEMIDLG QMVNQALLRK KEKQKEMVLK   180
PLQKIALETK ESFLYGDQMF VNADFLISRS SLDDFNAKVN ELGEFFNEQA LFKYIGPLPP   240
YNFVTLYVNF                                                         250

SEQ ID NO: 121          moltype = AA  length = 357
FEATURE                 Location/Qualifiers
source                  1..357
                        mol_type = protein
                        note = DSM 771
                        organism = Desulfotomaculum acetoxidans
SEQUENCE: 121
MVKNHNTDHL KELYIYGLIG GTPFKDELEK ISVIQENTPI YGVWHKNIGF AVSAAPDYPL    60
KDLSKESIIQ LFVDHQQVLE CLRQKFSLIP VKLGTVLESV TEAAAVLANN EEKFNDLLNY   120
LKDKVELNLS VSWNDLNEVV AKIGEEDEVK KLKQSLLAQE QVSQEDLIKI GKIISFQMQQ   180
KKQAAREYII SELRNLWEDY FINEVVDENS ILNLTLLAIT GKVDDVNKKI EYLNQIYRDS   240
LDFSLTKSLL PQGFSTVSIK KITMDQLLLA KDILKLPDTA SLQDINAARR ALLHCYHPDK   300
NDHAAVNKVQ EINAAYKLLE EYCQENSSDF NVDLITDYYI MKVIKADKSN VNSMNME     357

SEQ ID NO: 122          moltype = AA  length = 252
FEATURE                 Location/Qualifiers
source                  1..252
                        mol_type = protein
                        organism = Dolichospermum circinale
SEQUENCE: 122
MNTDLAHKNF GLYLYGIFPD TIPETLEIKG LDGKSVHSQV VDGFTFLYSQ ACQEKYLASR    60
RNLLAHERVL EQTMHEGFHV LLPLRFGLVV KDWETIMSQL INPHKEQLHK LFEKLAGQRE   120
VSIKILWDAK AELQAMMESN HDLRQQRDNM EGKKLSMEEV IQIGQLIESN LQARKQAVIE   180
VFTRELNPLA QEIVVSEPMT EEMIYNAAFL IPWDSEPLFS ERVESIDQKF GNRLRIRYNN   240
FTAPYTFALL DS                                                      252

SEQ ID NO: 123          moltype = AA  length = 277
FEATURE                 Location/Qualifiers
source                  1..277
                        mol_type = protein
                        note = strain ATCC 27094
                        organism = Enhydrobacter aerosaccus
SEQUENCE: 123
MNPPEAYIAG RTAAKSVEDR KARPQDLAEG KYVYAIIACD EPREFKNRGI GERGDKVHTI    60
NHRQMAAVVS DSPTIDYERS RRNMMAHTVV LEEVMKEFDL LPLRFGTVAS SAESVERQLL   120
VPRYGELSAM LEKMRGRSEF GLKAFWHEGV AFGEIVRENA RVRKLRDALQ GRSLEESYYQ   180
RIQLGEEVEK ALTAIRARDE ELILSRLRPF MRDIRTNKII SDRMVLNAAF LVERGDVPAL   240
DEAIRQLDQE FSERLMFKYV GPVPPYNFVN IAINWER                           277

SEQ ID NO: 124          moltype = AA  length = 279
FEATURE                 Location/Qualifiers
source                  1..279
                        mol_type = protein
                        note = ATCC-43644
                        organism = Isosphaera pallida
SEQUENCE: 124
MRNAPPTRPG SVTPASPGKP VIDGPARYLY AFTHDLPEGP LADLEGLPGA RVVVVADGRV    60
AAVVSPCPLG KVRPERQRVA GHHHVLKHLQ DTLGKAILPA SFGMVADSEE DLRALLRHHS   120
AAIAEGLVRV QGKVEMTVKL RWAPDNVAQA VLGRDPELRQ LRDQLYSNGQ TPTRDQSLDL   180
GRRFHHALER QRDHYAAYLR AALSPLLSEL VEEDLRDERD LVHWACLIEN QRRAGFEAAL   240
DRLAEELEDD LVLELTGPWP PHHFVDLDLD DDHDDDEEE                          279

SEQ ID NO: 125          moltype = AA  length = 258
FEATURE                 Location/Qualifiers
source                  1..258
                        mol_type = protein
                        note = LLAP12
                        organism = Legionella drancourtii
```

```
SEQUENCE: 125
MDSTSKKPAA SNLYLYAIAS VNENQEPISF HGIEEQPIDL VPYKDIMLVV SNLSKKKVRP    60
ERKNVAVHHA VLNHLMKHNT SMLPIRFGMI ADNRKEVQRL LTINYDMLHT KLKMMAGRVE   120
MGVSLSWDVP NIFEYLLNRH SQLRETRDKL LANPAHEPSR DEKIEIGALF SQILDEEREV   180
YTDTILSLLS PVCCDVVKST YRNDTEIMNI FCLISAARRD EFEEKIIEAS TILDDNFVIK   240
YTGPWPPHNF SKLNLSLE                                                 258

SEQ ID NO: 126          moltype = AA  length = 247
FEATURE                 Location/Qualifiers
source                  1..247
                        mol_type = protein
                        note = BDU141951
                        organism = Lyngbya confervoides
SEQUENCE: 126
MPQLLYLYGI FPAPGPQDLE VQGLDQQPIH THIIDEFVFL YSVAQQERYL ASRKNLLGHE    60
RVLEAAMKVG YRTLLPLQFG LIIETWDRVI KELITPRGDA LKRLFAKLEG RREVSVKLLW   120
GPDAELNQLM EEDAGLRAER DRLEGQQLSM DQIVDIGQAI ETAMTERKDD VINAFRQRLN   180
ALAIEVLEND PLTDAMIYNT AYLIPWEDEV KFSQAIEELD EQFEDRLRIR YNNFTAPYNF   240
AQLDQLS                                                             247

SEQ ID NO: 127          moltype = AA  length = 244
FEATURE                 Location/Qualifiers
source                  1..244
                        mol_type = protein
                        note = NIES-843
                        organism = Microcystis aeruginosa
SEQUENCE: 127
MTVGLYLYGI FPEPVPDGLV LQGIDNEPVH SEMIEGFSFL YSAAHKEKYL ASRRYLICHE    60
KVLETVMEAG FTTLLPLRFG LVIKTWESVT EQLISPYKTQ LKELFAKLSG QREVSIKIFW   120
DNQWELQAAL ESNPKLKQER DAMMGKNLNM EEIIHIGQLI EATVLQRKQD IIQVFRDQLN   180
HRAQEVIESD PMTDDMIYNA AYLIPWEQEP EFSQNVEAID QQFGDRLRIR YNNLTAPYTF   240
AQLV                                                                244

SEQ ID NO: 128          moltype = AA  length = 247
FEATURE                 Location/Qualifiers
source                  1..247
                        mol_type = protein
                        note = ATCC 29133
                        organism = Nostoc punctiforme
SEQUENCE: 128
MSFYIYGILT LPAPQNLNLE GLDRQPVQIK ILDDFAVIYS EAQQERYLAS RRNLLSHEKV    60
LEEIMQAGDR YLLPVQFGLL VSSWETVSQQ LIRPHQEELT QLLAKLSGCR EVSVKVFWDT   120
EAEIQGLLAE HPNLKTERDK LVGQPLSMER VIQIGQVIEQ GMSDRKQGII DVFKGTLNSI   180
AIEVVENTPQ VDTMIYNSAY LIPWEAESQF SEHVESLDRQ FENRLRIRYN NFTAPYNFAR   240
LRLTTSN                                                             247

SEQ ID NO: 129          moltype = AA  length = 244
FEATURE                 Location/Qualifiers
source                  1..244
                        mol_type = protein
                        note = PCC 7120
                        organism = Nostoc sp.
SEQUENCE: 129
MSSGLYLYGI FPDPIPETVT LQGLDSQLVY SQIIDGFTFL YSEAKQEKYL ASRRNLISHE    60
KVLEQAMHAG FRTLLPLRFG LVVKNWETVV TQLLQPYKAQ LRELFQKLAG RREVSVKIFW   120
DSKAELQAMM DSHQDLKQKR DQMEGKALSM EEVIHIGQLI ESNLLSRKES IIQVFFDELK   180
PLADEVIESD PMTEDMIYNA AFLIPWENES IFSQQVESID HKFDERLRIR YNNFTAPYTF   240
AQIS                                                                244

SEQ ID NO: 130          moltype = AA  length = 264
FEATURE                 Location/Qualifiers
source                  1..264
                        mol_type = protein
                        note = 307
                        organism = Octadecabacter antarcticus
SEQUENCE: 130
MKREVVRMTD ENTINSKYLY AIIKCREQRE FIARGIGERG DAVHTIAYKG LAAVVSDSPV    60
MEYDQSRRNM MAHTAVLEEL MEEFTLLPVR FNTVAPEAGA IEERLLVPRH EEFTQLLGQI   120
DKRVELGIKA FWHDGMIFEE VLRENDSIRK MRDALEGKSV DGSYYERIQL GEKIEQAMIK   180
KRVEDEEIIL SRIRQHVHKS RSNKTIGDRM VLNGAFLVDA NKESDFDKAV QLLDQDLGNR   240
LMFKYVGPVP PYNFVNIVVN WGVV                                          264

SEQ ID NO: 131          moltype = AA  length = 356
FEATURE                 Location/Qualifiers
source                  1..356
                        mol_type = protein
                        note = 307
                        organism = Octadecabacter antarcticus
SEQUENCE: 131
```

```
MTVVAEENMT GSVGLYVCAI VAEWESNSAL IKCANEAQGE IQLIGQGGIT AVVMVPPEDQ    60
PVSRDRQELV RQLLVHQQLV ERFTEIAPVL PVKFGTLAPD RESVELGLER GREKFFTAFG   120
GLSGKTQFEI TVTWDVADVF AKIAKLPAVV KLKVDLVATS ESDRPINLDR VGRLVKETLD   180
HQRAQTGKVL LDALLPLGVD SIVNPILNDS IVLNLALLVD TDQADALDRC LDELDSTFHG   240
ALSFRCVGPM PPHSFATVEI NYIEPTQVSH ACCVLEDAA HNFEEIRSAY HRLARQTQQD   300
IAPDVVVDNK SSSVGIAVLN DAYKTLLSFV DAGGPVVVSV QRQEDAYATD IPSSGG       356

SEQ ID NO: 132            moltype = AA  length = 257
FEATURE                   Location/Qualifiers
source                    1..257
                          mol_type = protein
                          note = 238
                          organism = Octadecabacter arcticus
SEQUENCE: 132
MTDEKKVNSK YLYAIIQCRE PRELKARGIG ERGDVVHTVV HKGLAAVVSD SPVMEYDQSR    60
RNMMAHTAVL EELMEEFTLL PVRFNTVAPE AVAIEERLLV PRHDEFTQLL GQIDKRVELG   120
LKAFWHDGMI FGEVLRENDS IRKMRDSLKG QSVDGSYYER IQLGEKIEKA LTEKRLEDEE   180
MILSRIRPHV HKSRSNKTIG DRMVLNGAFL VDAEKESKFD EAVQSLDQDL SDRLMFKYVG   240
PVPPYNFVNI VVNWGES                                                  257

SEQ ID NO: 133            moltype = AA  length = 360
FEATURE                   Location/Qualifiers
source                    1..360
                          mol_type = protein
                          note = 238
                          organism = Octadecabacter arcticus
SEQUENCE: 133
MRAQKVIPAA EENISGNVGL YVCAIVAERV SCSALIQCAN DAPGEIQLIG HGDFTAVVMV    60
PEKDQLVSPD RKELMQQLLV HQQLIEKFME IAPVLPVKFA TLAPNRESVE LGLEVGSEKF   120
SAAFNSLSGK VQFEVIVTWD VAEVFAEIAK EPAVAKLKVD LAAMPESYGS VSLEQLGKLV   180
KETLELRRAE TGKVLLDALV QVGVDNVVNS ILDDSIILNL ALLVEAKRAD AFDRCLDELD   240
STYHGALTFR CVGPLPPHSF ATVEITYLEP AKVTEACDIL ELDVARSTEE VRSAYHRLAR   300
KSHPDIVPDV AVGETASVSM AVLTDAYKTL LSFVGAGGSV VVSQRQEAS YAADIISSAG    360

SEQ ID NO: 134            moltype = AA  length = 258
FEATURE                   Location/Qualifiers
source                    1..258
                          mol_type = protein
                          organism = Pelodictyon phaeoclathratiforme
SEQUENCE: 134
MDIETTKEGR YIYGIIRNSE FIDFGQIGIG KRNDRVYGVI YKDICAVVSS TPIIQYEARR    60
ANMIAHQKVL EEVMKRFNVL PVRFSTISPH DNDDAIIKIL ITDYSRFDEL LIKMKGKKEL   120
GLKVMADETR IYENIIQKYD NIRSLRDKLL NQPADKIHYQ RVKIGEMVAD ALKKEIESYK   180
QQILDILSPI AEDIKITDNY GNLMILNAAF LIKEVKESEF DDSVNKLDEK YGNIMTFKYV   240
GTLPPYNFVN LSINTKGV                                                 258

SEQ ID NO: 135            moltype = AA  length = 257
FEATURE                   Location/Qualifiers
source                    1..257
                          mol_type = protein
                          organism = Pelodictyon phaeoclathratiforme
SEQUENCE: 135
MEKDGKYVYC IIASTYECNF GAIGIGGRGD LVNTIGFQGL SMVVSDHPLN HFVLNPDNIL    60
AHQRVIEVVM SQFNSVIPVR FGTVAATPDE IRNLLDRRYG ELSELLERFE NKVEYNLKAS   120
WRCMIDIYKE IDKEHVELKQ LRREIEGLKD EEKRKLLIVE AGHIIENELQ KKKEVEAYEI   180
VTYLRKTVVA HKHNKTTGEA MFMNTAFLLN KGREVEFDNI MNDLGEQYKD RSDYYYTGPL   240
PIFNFIDLRI LPEKWEL                                                  257

SEQ ID NO: 136            moltype = AA  length = 339
FEATURE                   Location/Qualifiers
source                    1..339
                          mol_type = protein
                          organism = Pelodictyon phaeoclathratiforme
SEQUENCE: 136
MDRQGIYIYG FIPNHYLTDI KTILIESGIY SIEYGSIAAL VSDTMVDDIE YLNREDLAYL    60
LVDHQKKIEL IMSTGCSTII PMQLGTIVNS GNDVIKIVKN GLRIINKTFD DIADIQEFDL   120
VVMWNNFPDL IKKISDTPQI RIMKEEIANK GSYDQADSIN IGKIIKKKID EKNSKVNLDI   180
MNSLSSLCIC VKKHESMNDE MPLNSAFLIK KDKENSFIKM VNQLDIKYEN LLRYKIVGPL   240
PCYSFYTLES KLLNKKEIEK AEKILGIDAY KSESDIKKAY RAKAAHAHPD KNNTISAIDN   300
DDFIEINKAY QILLEYSSVF KDSPDHKPDE PFYLVKIKK                          339

SEQ ID NO: 137            moltype = AA  length = 244
FEATURE                   Location/Qualifiers
source                    1..244
                          mol_type = protein
                          note = NIES-30
                          organism = Phormidium tenue
SEQUENCE: 137
MADRYYLYGI FPAPGPAELP LMGLDEQVVQ AQQLGDFTFL YSLACQKRYL SSRKNLLGHE    60
```

```
KVLEAAMEQG HRTLLPLQFG LIVESWNQVQ EDLVTPYAED LTQLFGRLNG CREVSIKVQW    120
EPSTELEMMM AENADLRAQR DQLEGTQLGM EQVIFIGQQI ESALEERKQG IVDQFRQALS    180
PLAKDVLENA PQTDVMIYNA AFLIPWESEA EFSQAVDAID STFGDRLRIR YNNFTAPYNF    240
AQLN                                                                244

SEQ ID NO: 138            moltype = AA   length = 245
FEATURE                   Location/Qualifiers
source                    1..245
                          mol_type = protein
                          note = str. 7805
                          organism = Planktothrix agardhii
SEQUENCE: 138
MGNGLYLYGI LPTNRVRPLA LHGLDKQPIQ THPVDEFSFL YSETQQERYL ASRRNLLGHE    60
DVLEKVMQHG YRSVLPLQFG LIVKDWDHVK AQLIIPYQDR LKELFHKLEG KREVGVKIFW    120
EETEEELDLLM TENQELREKR DSLEGKRLSM DEIIGIGQEI ERAMQDRQQG IIDKFQQILN    180
PLAQEIVEND NLTSAMIYNA AYLIPWDIEP QFGDKIEELD HHFNNRLRIR YNNFTAPFNF    240
AQLNP                                                               245

SEQ ID NO: 139            moltype = AA   length = 268
FEATURE                   Location/Qualifiers
source                    1..268
                          mol_type = protein
                          note = 37
                          organism = Psychromonas ingrahamii
SEQUENCE: 139
MAENKKKVRK SSSKVIAKPK VIYAITAGGL QDLGNLVGIN KSDIYTIEKE SISFVVSDLS    60
PSSPRPRPDR RNIMAHNEIL KQLMSKTSVL PVRFGTVATG ERAVNRFCSQ YNAQLLEQLD    120
RVQDRVEMGI KVTWNVPNIY DYFVDNHSEL REERDRVYDG NKNPRRDDRI NLGHMYDALV    180
TEARLSHQTD LEEIILPGCD EIHSIPPKDE KVVVNLACLV QRADLEVFEE RVVEAGKTLD    240
NTYDIELNGP WAPHNFVELD LKTMTGRR                                      268

SEQ ID NO: 140            moltype = AA   length = 273
FEATURE                   Location/Qualifiers
source                    1..273
                          mol_type = protein
                          note = ATCC 39006
                          organism = Serratia sp.
SEQUENCE: 140
MMSIDKSRNH RAKVLYALCV SDDSTPNYKI RGLEAAPVYS IDQDGLRAVV SDTLSTRLRP    60
ERRNITAHQA VLHKLTEEGT VLPMRFGVIA RNAEAVKNLL VANQDTIREH FERLDGCVEM    120
GLRVSWDVTN IYEYFVATYP VLSETRDEIW NGNSNANNHR EEKIRLGNLY ESLRSGDRKE    180
STEKVKEVLL DYCEEIIENP VKKEKDVMNL ACLVARERMD EFAKGVFEAS KLFDNVYLFD    240
YTGPWAPHNF VTLDLHAPTA KKKTLTRAGT LSD                                273

SEQ ID NO: 141            moltype = AA   length = 260
FEATURE                   Location/Qualifiers
source                    1..260
                          mol_type = protein
                          note = ATCC-43931
                          organism = Stella vacuolate
SEQUENCE: 141
MQTEALAPAA VAAEGKYLYC IIDAPAPATF ASPGIGGRGD VVHTLAVGRL AAVVSDTPRI    60
EYENSRRNMM AHTKVLEEVM AHHTLLPVCF GTVGSGDDVI AEKILEGRRE ELSRLLEEMR    120
GRVELGLKAT WREEVIFAEV LDEDPAVRKL RDSLVGRSPE KSHFERIRLG ELIGQALLRK    180
RRDEEERILD RVRPFVRKTK LNKPIGDRMI LNAAFLVETA REAALDQSVR EMDADWGARL    240
SFKYVGPVPP YNFVTITIHW                                               260

SEQ ID NO: 142            moltype = AA   length = 254
FEATURE                   Location/Qualifiers
source                    1..254
                          mol_type = protein
                          note = strain DSM 235
                          organism = Thiocapsa rosea
SEQUENCE: 142
MQQAKRQDVA AGRYIYAIIP DRGDHSLGRI GLDESEVYTI GDRVAAVVS DLSGGRIRPQ     60
RRNMAAHQEV LKQVLREVSP LPAAFGLMAD DEAAIIRILK DNQDAFLNQL ERVDGSLEMG    120
LRMSWDVPNI FEYFVGAHPE LQELRDDFFR DGSNLTQDQM ITLGRSFERL LEQDREEYTE    180
QVESVMRSCC REIKRNKCRT EKEVLHLACL VDRDAAGRFE QVVLQAARPF DNNYAFDFNG    240
PWAPHNFVEM DIHV                                                     254

SEQ ID NO: 143            moltype = AA   length = 244
FEATURE                   Location/Qualifiers
source                    1..244
                          mol_type = protein
                          note = PCC 7601
                          organism = Tolypothrix sp.
SEQUENCE: 143
MDAGLYLYGI FSDPIPPTVS LKGLDSQPVY SQVIEGFTFL YSDAKQEKYL ASRRNLISHE    60
KVLEQAMQEG FRTLLPLRFG LVVKNWETVI SQLIQPCERQ LRDLFQKLAG KREVSVKILW    120
```

```
DTKAELQAMM QSNPDLKQKR DQMEGKNLSM EEVIEIGQLI ESNLQQRKEA VIKTFFDELK    180
PLAEEVVESE PMMEEMIYNA AFLIPWDQEA LFSQRVEAID KKFGDRLRIR YNNFTAPYTF    240
AQIS                                                                244

SEQ ID NO: 144          moltype = AA   length = 266
FEATURE                 Location/Qualifiers
source                  1..266
                        mol_type = protein
                        note = IMS101
                        organism = Trichodesmium erythraeum
SEQUENCE: 144
MEFGFYVYGL IQEKGKMDES KDESKNGLKG SNESKDELKG LDKEDVKIQD VDEFAVLYSI     60
AKKERYLASR RNLITHEKVL ESAMEAGYRN LLPMQFGLVV SEWEKFSQDF TKPCEQQIHD    120
LFTKLKNNRE VGIKIYWEPD AELEKLLEND KDLKEERDSL KDKKLTMDQV IDIGQKIEQG    180
MNERKQNIIE IFQETLNKMA IEVIENEVQT EKMIYNAAYL IPWDQEEDFG EKVETIDSKL    240
CERGNFTIRY NSFTAPYNFA RIRQQD                                        266

SEQ ID NO: 145          moltype = AA   length = 334
FEATURE                 Location/Qualifiers
source                  1..334
                        mol_type = protein
                        note = strain UV5
                        organism = Ancylobacter aquaticus
SEQUENCE: 145
MTDLLVFAVV PADRFDPAIL AEGDGLPPGL RAIAAGPLAA VVGAAPEGGL KGRERSALLP     60
WLLASQKVME RLLANAPVLP VALGTVVEDE GRVRHMLDAG AAILGEGFQA VGDGIEMNLS    120
VLWHLDTVVA RLLPGVAPEL RQAAAGGDAI ERQALGVVLA GLVSAERRRA RARVIEALQA    180
VTRDFAIGEP TEPGGVVNLA LLVDRAAEEA LGAALEALDA EFDGALTFRL VGPLPPYSFA    240
SVQVHLSPAA AVCGARAALG VEPDASPETV KAAYRRAARE THPDLVPMGG EDEEAPEATA    300
DETSRFVVLS DAYRVLEGEH APVSLRRLDS VLTE                               334

SEQ ID NO: 146          moltype = AA   length = 255
FEATURE                 Location/Qualifiers
source                  1..255
                        mol_type = protein
                        note = strain UV5
                        organism = Ancylobacter aquaticus
SEQUENCE: 146
MLYVYAITAD YAAGANHLLP AKGIVPGVPV QRFGTGALGA VASPVPVTVF GKEALHALLD     60
DADWTRARIL AHQRVVSSLL PLATVLPLKF GTLVAGEASL AAALTSQHDA LDATVARLRG    120
AREWGVKLFF EAPTRTIRAE EPVGAGAGLA FFRRKKEEQE TRAAAEAALD RCVAASHRRL    180
ASHARAAVAN PLQPPELHGH PGTMGLNGAY LVAAENEAAW RVCFSELEQA YAALGARYVR    240
TGPWAAYNFT GGGLV                                                    255

SEQ ID NO: 147          moltype = AA   length = 337
FEATURE                 Location/Qualifiers
source                  1..337
                        mol_type = protein
                        note = strain DSM 9035
                        organism = Aquabacter spiritensis
SEQUENCE: 147
MSGLLVFAIV PADRIEPGLL APAEGLPPGL ETVVAAGFAA IVGTAPEGGL KGRDRGSLLP     60
WLLASQKVIE RLMARGPVLP AALGSVLEDE SRVRHMLVCG QAALAAAFET LNGCWQTDLS    120
VRWDLSRTVA HLMTELPPGL RAAAETGDET ARRSLGAALA GLVAGERRRI QSRIGAVLGA    180
VARDLIVSDP VEPEGVVGVA LLVDAPASAQ VDAALDRLDG EFEGRLTFRL VGPLAPYSFA    240
TVQIHLGPAA GLAGAHAELG LEAGAPLEAV KAAYHRLIVG LHPDLVPHGS PGDDADDAAS    300
GKGGRAARFA AVTAAYRTLQ AEHAPVSLRR QDGLSPG                            337

SEQ ID NO: 148          moltype = AA   length = 257
FEATURE                 Location/Qualifiers
source                  1..257
                        mol_type = protein
                        note = strain DSM 9035
                        organism = Aquabacter spiritensis
SEQUENCE: 148
MLYVYAITAD HPGPHDAGSL PGEGIVPGAP VRLLPFGDLA AVSPVSAVD FGPEALPARL      60
QDVDWTGQRV LAHQRVVDSL VDVATVLPMK FCTLFSGAAA LRAALADNRA ALEATVVRLR    120
GAREWGVKLF WEAPPAEPAP VERGPGAGAA FFQRKRDAQR LRAEAEAALA HGVAESHRRL    180
AARARAAVAN PVQPPAAVHRR RGEMALNGAY LVPRADEAAW RESLAELERT YAGAGIRYEL   240
TGPWGPYNFT GGGLAGS                                                  257

SEQ ID NO: 149          moltype = AA   length = 334
FEATURE                 Location/Qualifiers
source                  1..334
                        mol_type = protein
                        note = S58
                        organism = Bradyrhizobium oligotrophicum
SEQUENCE: 149
MTMNLVGITT PDVAGAIAAA GGRLADVETR AVEAGGLVAL LALSKAPFWH VLRRSRTALR     60
```

```
SMLTAQRILE AAAVYGPLLP ARPGTLIRND AEACMLLRSQ CRHLAEGLRL HGTSRQYQIT      120
ISWDPVAALA ARRDHQDLVE AAAASADGAA DKAASMIQRF MSDQQARFEA EAMRALAAVA      180
EDVITLPVNQ PDMLMNAVVL LAPGAEPELE RVLEALDRGL RGKNLIRLIG PLPPVSFAAV      240
SIERPGRQRI AAARRLLGIG EATRTCDLRR AYLDKAHAHH PDTGGHAADA SIVGAAAEAF      300
RLLARVAEAR ASAGQDDVIL VDIRRQDQQR SLST                                 334

SEQ ID NO: 150           moltype = AA  length = 253
FEATURE                  Location/Qualifiers
source                   1..253
                         mol_type = protein
                         note = S58
                         organism = Bradyrhizobium oligotrophicum
SEQUENCE: 150
MSKANLGIGL VHGVVTAQSA ALLPQIVDAF DATEIIVVNT EQQALLISDI PQYLRGHVEA      60
DTLFSDPARI STLAMKHHRI LQAAAVVTDV VPVRLGTLVR GPSGARDLLN REAVRFAGHL     120
VTIHNALEFS VRILPTEQPS RRVARPVPSS GRDYLRIRRD ERCGQRPAVV DITLQELASR     180
AVAIRERQSA SRSGGRTPAL AEAAFLVDRH ALAAFDDCAG RIERQIAENG LALDIFGPWP     240
AYSFVDGARE NLG                                                        253

SEQ ID NO: 151           moltype = AA  length = 214
FEATURE                  Location/Qualifiers
source                   1..214
                         mol_type = protein
                         note = S58
                         organism = Bradyrhizobium oligotrophicum
SEQUENCE: 151
MSSPRLIGLL AADDVPADLA DQIMSCGPVA AAIRFAPAAA SSSESLDHHA AVVAWCRRAA      60
FLPSRAGIPI SPELLQSIAR SAWYHRSTIE HIEGRVEISV ELERRDGVRD GGIDGGGRAY    120
LRATAHDLRA CEVGVATAAN LLAMYSERAD ADLIARTAPL PAIRLRASVL VRRAVAPRLA    180
RQFDSMLSAI SDRLVCRVTG PWPPYSFSTI REPS                                 214

SEQ ID NO: 152           moltype = AA  length = 252
FEATURE                  Location/Qualifiers
source                   1..252
                         mol_type = protein
                         note = sp. Bp5365 strain MSMB43
                         organism = Burkholderia thailandensis
SEQUENCE: 152
MVWLTYAVLT PKRSITLPPG VAGARLEIVD GAHLRTIVSE HPRAPSATIP SALDFGQTVA      60
ALFRHGAIVP MRFPTCLDSK QAVRDWLDDE SDMYRDLLQR IDGCVEMGLR FRLPEAPRAQ    120
PRPQAGGPGH AYLAARGAPN SVARSHGERI AAVLRNLYRD WRFDGLVEGF VSLSFLVRQT    180
TLDDFVDRCR QAARETAFPL YMSGPWPPYS FATDERSSAP EPHRALRLMR RPSTAVSISA    240
NVAAPEKKDS AR                                                         252

SEQ ID NO: 153           moltype = AA  length = 257
FEATURE                  Location/Qualifiers
source                   1..257
                         mol_type = protein
                         note = DSM 3385
                         organism = Desulfobacterium vacuolatum
SEQUENCE: 153
MTLHLLYCVF SSGEMEKTRK LVPPGIDGEP VHEICSNKIS GVVSTLGKPP DTHVKSLLAY      60
HGVIDSYHQN RTVIPMRFAA VFRTYAHMIT ALNNNEKSYL LQLKRLHDCT EMCVRFISNS    120
PCCVKKKEPA ISPKKISGTT FLQQRKAMYE QQNRLPPEIH EKTRDILQHF RGLYMEFKQE    180
SQPLEKDCPS LSLQGAEKTD GNALLISLFF LISKKNISLF RSRFQNICGS SSGRHMMNGP    240
WPPFNFINTE SNLTDPS                                                    257

SEQ ID NO: 154           moltype = AA  length = 265
FEATURE                  Location/Qualifiers
source                   1..265
                         mol_type = protein
                         note = DSM 6799
                         organism = Desulfomonile tiedjei
SEQUENCE: 154
MLGSLAAIQF LSISSYGADE MKFLMYCIFT ENSIEPPHSL VGVNRSPVRI ISCDGLAAAV      60
SVITQKEIPR DPATGLDYHK VIQWFHERIG VIPLRLGTCL GHESDVVQLL HSHGARYKSL    120
LKELDGCVEM GIRVIHDRPG PQELASKSPF ISRFNGTESG TDYLMRRKVL FDADEFAISR    180
NREIVERYHS PFTGLYVSFK AQTSKFSPLG TDRNSVLTSL YFLIPRQSAD SFRAIYGDLR    240
SGLHERIMLS GPWPPYNFVL PEDCL                                           265

SEQ ID NO: 155           moltype = AA  length = 279
FEATURE                  Location/Qualifiers
source                   1..279
                         mol_type = protein
                         note = strain ATCC 27094
                         organism = Enhydrobacter aerosaccus
SEQUENCE: 155
MEGHRIYIYG IVRDAADGGP APVPPVAGLD GGALRAIAGY GLAAIASAVD LSKAGIPFEE      60
QLKDPDRATA LVLEHHRVLQ QAIDAQTVLP MRFGALFQDD RGVTDALEKN RCGLMDALGR    120
```

```
IDGAREWGVK IFCDRAVAAR QLSATSAVVQ AAEKELSGLA EGRAFFLRRR LERLRTEETD    180
RAVAHEVDVS RQALCELARA SAPLKLQPAA VHGRGEDMVW NGAFLVPRSG EERFLSRLEV    240
VVQSRSDLGL HYEVTGPWPP FSFVDGQLEG GGDACPDGA                           279

SEQ ID NO: 156          moltype = AA   length = 278
FEATURE                 Location/Qualifiers
source                  1..278
                        mol_type = protein
                        note = 307
                        organism = Octadecabacter antarcticus
SEQUENCE: 156
MRSATSIVYA YGVLTNCSDI ALDMPRSDLA GLVKNGPLRI LPFGNIAAVV CDFVLPNGSD    60
LETLLEDSRS AERLILNHHQ VLSYIVSQHT ILPLRFGAAF TEDAGVIAAL GGRCSELQKA    120
LGRIDGALEW GVKTFCDRKL LKQRVRGTGS EISDLESEIA KQGEGKAFFL RRRKERLILE    180
EVEEILEQCV VGTQEQLEPS VIEEALVKLQ PPTVHGHEHD MLSNISYLIA RGTEDAFMQS    240
LEDLRLAHAP YGLEYQMNGP WPAYSFSDQQ LEGGVNDQ                            278

SEQ ID NO: 157          moltype = AA   length = 278
FEATURE                 Location/Qualifiers
source                  1..278
                        mol_type = protein
                        note = 238
                        organism = Octadecabacter arcticus
SEQUENCE: 157
MSSATSIVYV YGVLTNCSDL VLDFPPGDLA GIVESGPLRI LPFGDIGALV CDFILPDGSD    60
LKTILEDSRS AERMILNHHL VLADMVSRYT ILPLRFGAVF EDAGVIAAL GGRYSTLQKE     120
LDRIDGAIEW GVKSFCNRKM FSECVAETVS EISVLEKEIA DQGEGKAFFL RRRIQRLILD    180
EVEKTLEQCL VGAQDQLKSR AIEETLVKLQ PPTVHGHKHE MVSNRSYLIA RGAEDAFMQS    240
LDDLRVVYAP FGFDYQINGP WPAYSFSDQQ LGGGVNDK                            278

SEQ ID NO: 158          moltype = AA   length = 261
FEATURE                 Location/Qualifiers
source                  1..261
                        mol_type = protein
                        note = SB 1003
                        organism = Rhodobacter capsulatus
SEQUENCE: 158
MGHYLYGLLA PPARGTLAQM QAAAAGVTSL GGPVALSAVE GMLLVHCPCD LAEISQTRRN    60
MLAHTRMLEA LMPLATCLPV RFGVIAQDLA EVARMIHERR AELVGHAQRL LDPVEIGLRV    120
RFPRDRALAQ LMAETPDFVA ERDRLMGQGA GAHFARADFG RRLAEALDAR RTRDQKRLLA    180
ALRPHVRDHV LRAPEEDVEV LRAEFLIPAA GVDAFSRIAH DLAAALGFAG AAEPELQVIG    240
PAPPYHFLSL SLAFDNTSEA A                                              261

SEQ ID NO: 159          moltype = AA   length = 316
FEATURE                 Location/Qualifiers
source                  1..316
                        mol_type = protein
                        note = SB 1003
                        organism = Rhodobacter capsulatus
SEQUENCE: 159
MAHEIIAILP CEAAQLPSGL TGVVGRGATA VLAPAPGWAE RLTGGPKQTA VRHHSRLEAL    60
MAMGSVLPFA AGIACTPEEA ALLLRLDAPL IARLAAEIGP RRHFQLALDW DESRVLAAFR    120
DSPELAPLFS GAAVTPEALR QAITALADRL SATALRLLDP VAEDPVEQPR APGCLLNLVF    180
LLRPEDEPRL DAALQAIDAL WSEGLRLRLI GPSAPISHAL VDIDRADVAA LAAAADLLKV    240
APEAGPEAVT EAAKAALRSP DLAANAAEQI RAAARLLLRA GDIAALGLSG AATLPHLVHL    300
RPGGRKSGLT SSGEAA                                                    316

SEQ ID NO: 160          moltype = AA   length = 231
FEATURE                 Location/Qualifiers
source                  1..231
                        mol_type = protein
                        note = SB 1003
                        organism = Rhodobacter capsulatus
SEQUENCE: 160
MTGLALHGFV SPDGWSAAAA PPARCAVVLG GVAALVSEAG DALDTPETAQ AAALAHHALI    60
SAWHRRGPVL PVRLGTVFSS QAALQTALAP KAAQLRAALD ALADKEEMVL TIVPAARPPD    120
LPPPAATGAD WLRARKAVRD RGQARQTDRQ QTLAGLQDAL RAQGVASLAA PAPREGGSRW    180
HLLIARDDGA GLDRWLAAQA DRFDAAGLDL TLDGPWPPYR FAAEILEALD G             231

SEQ ID NO: 161          moltype = AA   length = 220
FEATURE                 Location/Qualifiers
source                  1..220
                        mol_type = protein
                        note = SB 1003
                        organism = Rhodobacter capsulatus
SEQUENCE: 161
MSEPRISGLA PWRADLPDVI GCHGGWVLMG AAADETPEAR LRRQVGWCRA AVDVLPLSPR    60
LAPTRAEAER LVATRGPDLE RAHRHIRGRL QVIVQLEMCR TDLGLVRREI SGGRSWLQDR    120
AERATREARA NADFEAQVRR VVRALFPREG QVVTLAPSGT AGQLRLRRAV LVPRAGLQAF    180
```

```
AAALSADLDR DGRGGLWDVI APLPPLAFAA LEAGPGGAVT                           220

SEQ ID NO: 162           moltype = AA  length = 254
FEATURE                  Location/Qualifiers
source                   1..254
                         mol_type = protein
                         note = 2.4.1
                         organism = Rhodobacter sphaeroides
SEQUENCE: 162
MIYLYGLLEE PASGHEVLAG MAGVTGPIAL ARLPGGILIY SSATEADILP RRRLLLAHTR     60
VLEAAAWFGN LLPMRFGMMA STLAEVAAML ASRLTELCAA FDRVRGRVEL GLRLSFPREP    120
ALAATLATAP DLAAERARLL ALRRPDPMAQ AEFGRRLAER LDARRGETQR LLFQSLRPLW    180
VDHRLRVPDS DVQVIAVDVL VEDGAQDRLA AALVKAAADC SFAPTAEPSV RVIGPVPLFN    240
FVDLVLSPRR EEVA                                                     254

SEQ ID NO: 163           moltype = AA  length = 291
FEATURE                  Location/Qualifiers
source                   1..291
                         mol_type = protein
                         note = 2.4.1
                         organism = Rhodobacter sphaeroides
SEQUENCE: 163
MRLREVVAVL EGHPPSVLPE GTEAICEAGL TAILGMPPGL LSGRRALLEH AACRQAVLER     60
LMAFGTVLPV LTGNCLTPAE AAAALAANSP RLRQELRRLA GRVQFQVLVQ WHAALVPKRT    120
DPDETAEDLR LRFTHRIADA LARVAERHVN LPLREDMLAN QALLLLQTRT DDLDRSLEQI    180
DALWTEGLRI RRIGPSPPVS FASLNFRRVS SAAIRRARHR FDLEGPVDPI RLRALRRDLL    240
LRASEAERAE ILAAAAVLDL LTRCAASGGD LHLVRIWSEG QAVPSDLEDA A             291

SEQ ID NO: 164           moltype = AA  length = 232
FEATURE                  Location/Qualifiers
source                   1..232
                         mol_type = protein
                         note = 2.4.1
                         organism = Rhodobacter sphaeroides
SEQUENCE: 164
MSGLLLLGVV SGLGISPAIT SPHLRLDGDG YAAILLSLDR LPPDPASPDW AVQAALAQNA     60
ILSAYAATED VLPVALGAAF TGIAAVKRHL DAERATLDAG MERLAGRAEY VAQLIAEQVA    120
DGAAPAPASG SAFLKARSAR HEQRRHLARE RTGFARATAE ELASLSCSAS ARPLKPDGPL    180
LDLSLLVARD RVPGLLEAAE ASSRAGSRLA LSVRLIGPCA PFSFLPETRG HD            232

SEQ ID NO: 165           moltype = AA  length = 169
FEATURE                  Location/Qualifiers
source                   1..169
                         mol_type = protein
                         note = 2.4.1
                         organism = Rhodobacter sphaeroides
SEQUENCE: 165
MAGDARSRVR LHLAAMRDCE TFLPFPPAAT IAVDEAIAWC GRRTNALAEE IDRFSRQRQL     60
TVSARLIAPL LPDAAASGAG WLRARRDASA HQARLRTVLM QIMSLLGEVR CIPGRLQDEV    120
QVNLLVPAAE THPVLHELRE RLRVGDALWS ACTVTGPWPP YAFISWETA                169

SEQ ID NO: 166           moltype = AA  length = 260
FEATURE                  Location/Qualifiers
source                   1..260
                         mol_type = protein
                         note = 103S
                         organism = Rhodococcus hoagie
SEQUENCE: 166
MSEQESAPDG GGPVVYVYGL VPADVEVKED ATGIGSPPRP LKIVHHEDVA ALVSEIDPDT     60
PLGSSDDLRA HAAVLDSTAT VAPVLPLRFG AVLTDTDAVV AELLEPYRDE FHEALEQLEG    120
KVEFVVKGKY VEDAILREIL ADDPEAARLR DVVREQPEDT TRDERLALGE RISQALTAKR    180
EQDTGRIVEA LQPAATAVAP REPTDDEEAG SVAVLISADG VDELDKAVAR LIDDWQGRVE    240
VTVTGPLAAY DFVKTRAPGT                                                260

SEQ ID NO: 167           moltype = AA  length = 259
FEATURE                  Location/Qualifiers
source                   1..259
                         mol_type = protein
                         note = 103S
                         organism = Rhodococcus hoagie
SEQUENCE: 167
MTPDDGVWVY AVTGDGSFPG GISGIRGVAG EELRTVTDSG FTAVVGTVRL DTFGEEALRR     60
NLEDLDWLAD TARRHDAVVA AICAGGATVP LRLATVYFDD DRVRTMLRDN AEQLGEALQQ    120
IADRSEWGVR AYLERPRSEP RDAREKTGRP SGTAYLMQRR AQVAAREQAE SAAGRRADEI    180
FAELARWAVA GVRQPPSPPD LAGRRSQEIL NTSFLVDNGR HREFVTAVEE LDARLSDVDL    240
VLTGPWPPYS FTSVEASAR                                                 259

SEQ ID NO: 168           moltype = AA  length = 222
FEATURE                  Location/Qualifiers
```

```
source                          1..222
                                mol_type = protein
                                note = ATCC 39006
                                organism = Serratia sp
SEQUENCE: 168
MSLLLYGIVA EDTQLALEPD GSPHAGEEPM QLVKAATLAA LVKPCEADVS REPAAALAFG         60
QQIMHVQQT  TIIPIRYGCV LADEDAVTQH LLNHEAHYQT QLVELENCDE MGIRLSLASA        120
EDNAVTTPQA SGLDYLRSRK LAYAVPEHAE RQAALLNNAF TGLYRRHCAE ISMFNGQRTY        180
LLSYLVPRTG LQAFRDQFNT LANNMTDIGV ISGPWPPYNF AS                          222

SEQ ID NO: 169                  moltype = AA   length = 362
FEATURE                         Location/Qualifiers
source                          1..362
                                mol_type = protein
                                note = ATCC-43931
                                organism = Stella vacuolate
SEQUENCE: 169
MSGLLVFAIV PADGIEPGIL APREELPANL RAVAADGFAA VVGAAPEGGL KGRDRSVLLP         60
RLLASQKVIE RLMARGPVLP VTLGTVLEDE ARVRHMLAAG APMLEAAFGT LGDCWQMDLS        120
VRWDLNQVVA RLMGEVPGDV RAAAGSGDEA ARRALGEALA GLAAGERRRV QSRLAAALRD        180
VARDLIVSEP VEPESVVDIA ILVERPALAE VEAALDRLDA EFEGRLKFRL VGPLAPHSFA        240
TVQVHLAPEA ALAGACAELG VERGAGLQDV KVAYHRALVR FHPDLAPHGD DGGPEDEHDG        300
GEGRASRLLT VTAAYRALQA EHAPISLRRQ DGIAVNQEQD ASAAMGQQRG IVPGRELQAL        360
RM                                                                     362

SEQ ID NO: 170                  moltype = AA   length = 258
FEATURE                         Location/Qualifiers
source                          1..258
                                mol_type = protein
                                note = ATCC-43931
                                organism = Stella vacuolate
SEQUENCE: 170
MLYVYAIAAD HPDPDNAMFG GEGIVPDAPV RLLQLGDLAV AASLVSAADF AADALRAHLE         60
DARWTALRVL AHQRVVDSLL PHATVLPMKF CTLFSGEARL KQALAHNRAA LQATVERLRG        120
AREWGVKLYW EAPRNPAPPS AGQGEAGAGA AFFQRKRDQQ RQRAEAEAAV ARCVAASHRR        180
LADAARAAVA NPVQPPAVHR QPGEMALNGA YLVARAAEPA WREVLAELER THADGGIRYE        240
LTGPWGPYNF TGSGLVGS                                                    258

SEQ ID NO: 171                  moltype = AA   length = 253
FEATURE                         Location/Qualifiers
source                          1..253
                                mol_type = protein
                                note = strain DSM 235
                                organism = Thiocapsa rosea
SEQUENCE: 171
MSDRPRPMLH CILRSPPGSI ARAEAGLRWI ERDGLAALVA DREPSEIAGA SSVGLQRYAD         60
IVAEIHACAA VIPVRFGCLL AGDEAVGKLL HRSRDRLHGL LDQVGDCLEF GIRLLLPADA        120
PAATDDDAAP RLHANAPSDP RADPDMGPGL SHLLAIRHRL DVEASLAARA REAREVIKGR        180
VAGRFREVRE ELGQIDGRSL LSLYFLVPRE QGEHFVECLR QDASSLRGTG LLTGPWPPYN        240
FVGAIDDDIR SLD                                                         253

SEQ ID NO: 172                  moltype = AA   length = 119
FEATURE                         Location/Qualifiers
source                          1..119
                                mol_type = protein
                                organism = Anabaena-flos-aquae
SEQUENCE: 172
MLTKLLLLPI MGPLNGVVWI AEQIQERTNT EFDAQENLHK QLLSLQLSFD IGEIGEEEFE         60
IQEEEILLKI QALEEEARLE LEAEQEEARL ELEAEQEDFE YPPQFTAEVN KDQHLVLLP        119

SEQ ID NO: 173                  moltype = AA   length = 88
FEATURE                         Location/Qualifiers
source                          1..88
                                mol_type = protein
                                organism = Bacillus-megaterium
SEQUENCE: 173
VLHKLVTAPI NLVVKIGEKV QEEADKQLYD LPTIQQKLIQ LQMMFELGEI PEEAFQEKED         60
ELLMRYEIAK RREIEQWEEL TQKRNEES                                          88

SEQ ID NO: 174                  moltype = AA   length = 83
FEATURE                         Location/Qualifiers
source                          1..83
                                mol_type = protein
                                note = strain UV5
                                organism = Ancylobacter aquaticus
SEQUENCE: 174
MGMLTDVVFA PAVGPLKGVL WLARIIAEQA ERTLYDEGVI RAALLDLEQQ LEAGEIDEDA         60
YETQETVLLE RLKIARERMR SGL                                               83
```

```
SEQ ID NO: 175            moltype = AA  length = 122
FEATURE                   Location/Qualifiers
source                    1..122
                          mol_type = protein
                          note = NIES-81
                          organism = Aphanizomenon flos-aquae
SEQUENCE: 175
MLTKLLLLPI MGPLNGLVWI GEQIQERTNT EFDAQENLHK QLLNLQLSFD IGEISEEDFE    60
IQEEELLLKI QALEEEARLE LELAEEEARL ELELEQEEEE DFVVKPQLTT EIDRDKDLVL   120
LP                                                                  122

SEQ ID NO: 176            moltype = AA  length = 86
FEATURE                   Location/Qualifiers
source                    1..86
                          mol_type = protein
                          note = strain PCC 7418
                          organism = Aphanothece halophytica
SEQUENCE: 176
MVFKLLLLPI TGPIEGVTWL GEQILERANQ ELDEKENLNK RLLSLQLSLD LGEISEEEYD    60
EQEEEILLAM QAMEDEENNQ AEEETD                                        86

SEQ ID NO: 177            moltype = AA  length = 83
FEATURE                   Location/Qualifiers
source                    1..83
                          mol_type = protein
                          note = strain DSM 9035
                          organism = Aquabacter spiritensis
SEQUENCE: 177
MSLVTDVLFA PAVGPLKGVL WLARLIAEQA ERTLYDEDVL RAALLDLEQR FEAGEISEAD    60
YETEEDILLA RLKIARERMR SGL                                           83

SEQ ID NO: 178            moltype = AA  length = 82
FEATURE                   Location/Qualifiers
source                    1..82
                          mol_type = protein
                          note = S58
                          organism = Bradyrhizobium oligotrophicum
SEQUENCE: 178
MLFQILTSPV SGPFRMVSWI GGAIRDAVDT KMNDPAEIKR ALAALEQQLE AGSLSEQDYE    60
RMEMELIERL QSSLRHGSGN GG                                            82

SEQ ID NO: 179            moltype = AA  length = 75
FEATURE                   Location/Qualifiers
source                    1..75
                          mol_type = protein
                          note = sp. Bp5365 strain MSMB43
                          organism = Burkholderia thailandensis
SEQUENCE: 179
MFILDNLLAA PIKGMFWIFE EIAQAAEEET IADIEMIKAA LVELYRELES GQIDETEFET    60
RERALLDRLD SLETS                                                    75

SEQ ID NO: 180            moltype = AA  length = 78
FEATURE                   Location/Qualifiers
source                    1..78
                          mol_type = protein
                          note = DSM 273
                          organism = Chlorobium luteolum
SEQUENCE: 180
MFILDDILLA PLSGMVFLGR KINEIVQNEM SDEGAVKEQL MKLQFRFEMD ELSEEEYDRL    60
EDELLSTLAE IRAQKENR                                                 78

SEQ ID NO: 181            moltype = AA  length = 83
FEATURE                   Location/Qualifiers
source                    1..83
                          mol_type = protein
                          note = PCC 8305
                          organism = Dactylococcopsis salina
SEQUENCE: 181
MVFKLLLLPI TGPIEGITWL GEQILERADQ ELDSKENLNK RLLSLQLSLD LGEISEEEYD    60
EQEEEILLAM QAMEDEENEE EES                                           83

SEQ ID NO: 182            moltype = AA  length = 77
FEATURE                   Location/Qualifiers
source                    1..77
                          mol_type = protein
                          note = DSM 3385
                          organism = Desulfobacterium vacuolatum
SEQUENCE: 182
MFLVDDILFF PAKSLVWVFR ELHNAVQQEK TNESDALTTE LSELYMMLET GKITEEEFDE    60
```

```
REEQILDRLD EIQERDQ                                                          77

SEQ ID NO: 183           moltype = AA   length = 86
FEATURE                  Location/Qualifiers
source                   1..86
                         mol_type = protein
                         note = DSM 6799
                         organism = Desulfomonile tiedjei
SEQUENCE: 183
MERYTMFLLD DILFLPMNGV LWICNEIHDA AEQELHNESD AITAQLQKLY TLLEAGDIGE            60
SEFDVLEAEL LDRLDAIQER GALLEA                                                86

SEQ ID NO: 184           moltype = AA   length = 83
FEATURE                  Location/Qualifiers
source                   1..83
                         mol_type = protein
                         note = DSM 771
                         organism = Desulfotomaculum acetoxidans
SEQUENCE: 184
MLGKLLLSPI LGPVMGVKFI AEKIKQQADQ ELYDKSKIKQ DLMELQIKLE LEEITEEYYL            60
QREEELLVRL DELASMETEE EEV                                                   83

SEQ ID NO: 185           moltype = AA   length = 129
FEATURE                  Location/Qualifiers
source                   1..129
                         mol_type = protein
                         organism = Dolichospermum circinale
SEQUENCE: 185
MLTQLLLLPI MGPLNGVVWI AEQIQERTNT EFDAQENLHK QLLSLQLSFD IGEISEEEFE            60
IQEEEILLKI QALEEEARLE LEAEQEEARL ELEAEQEQAR LELEAEQEEL ENQPQLTPKI           120
DTYRHLVKL                                                                  129

SEQ ID NO: 186           moltype = AA   length = 81
FEATURE                  Location/Qualifiers
source                   1..81
                         mol_type = protein
                         note = strain ATCC 27094
                         organism = Enhydrobacter aerosaccus
SEQUENCE: 186
MGMLARLLTL PVSAPVGGVL WIARKIEEEA NAERWDRNKI TGALSELELE LDLGAIDVEE            60
YDAREAVLLQ KLKELQEVEN D                                                     81

SEQ ID NO: 187           moltype = AA   length = 103
FEATURE                  Location/Qualifiers
source                   1..103
                         mol_type = protein
                         note = ATCC-43644
                         organism = Isosphaera pallida
SEQUENCE: 187
MFLVDDILLA PAHSLMFLLR EIHQAALEEL RRDAQKVREE LAECYRALET GALTDEEFAS            60
LETDLLLRLD ALEELARFNS DEDDDPEDED WDVEDDDPAE AVW                            103

SEQ ID NO: 188           moltype = AA   length = 77
FEATURE                  Location/Qualifiers
source                   1..77
                         mol_type = protein
                         note = LLAP12
                         organism = Legionella drancourtii
SEQUENCE: 188
MLLLGSILMA PVHGLMAIFE KIKEAVDEEK QHDIERIKSE LMALYTKLES GELSEADFEK            60
QEKILLDKLD SLEDEDD                                                          77

SEQ ID NO: 189           moltype = AA   length = 86
FEATURE                  Location/Qualifiers
source                   1..86
                         mol_type = protein
                         note = NIES-843
                         organism = Microcystis aeruginosa
SEQUENCE: 189
MFLDLLFLPV TGPIGGLIWI GEKIQERADI EYDEAENLHK LLLSLQLSYD MGNISEEEFE            60
IQEEELLLKI QALEEEEAEN ESESSL                                                86

SEQ ID NO: 190           moltype = AA   length = 84
FEATURE                  Location/Qualifiers
source                   1..84
                         mol_type = protein
                         note = ATCC 29133
                         organism = Nostoc punctiforme
SEQUENCE: 190
```

```
MVLRFLLLPI TGPLMGVTWL GEKILEQAST EIDDKENLSK QLLALQLAFD MGEIPEEEFE    60
IQEEALLLAI LEAEQEERDQ TQEY                                         84

SEQ ID NO: 191           moltype = AA  length = 125
FEATURE                  Location/Qualifiers
source                   1..125
                         mol_type = protein
                         note = PCC 7120
                         organism = Nostoc sp
SEQUENCE: 191
MLGKILLLPV MGPINGLMWI GEQIQERTNT EFDAQENLHK QLLSLQLKFD MGEISEEEFD   60
IQEEEILLKI QALEAEERLN AESEEDDDLD VQPIFILASE ENPVYQDQSR FSEEYEDKED  120
LVLSP                                                             125

SEQ ID NO: 192           moltype = AA  length = 84
FEATURE                  Location/Qualifiers
source                   1..84
                         mol_type = protein
                         note = 307
                         organism = Octadecabacter antarcticus
SEQUENCE: 192
MGIILNTLMS PLIGPMKGVF WVAEQIKDQT DAEIYDDSKI LVELSELELL LDLEKIELKD    60
FEAKEDVLLK RLQEIRKAKK NDSV                                          84

SEQ ID NO: 193           moltype = AA  length = 84
FEATURE                  Location/Qualifiers
source                   1..84
                         mol_type = protein
                         note = 238
                         organism = Octadecabacter arcticus
SEQUENCE: 193
MSIILNTLMG PLIGPMKGLL WVAEQIKDQA DAELYDDSKI LVALSELELS FDLEQIELKE    60
FEAQEDVLLQ RLQAIRKAKQ NDTD                                          84

SEQ ID NO: 194           moltype = AA  length = 78
FEATURE                  Location/Qualifiers
source                   1..78
                         mol_type = protein
                         organism = Pelodictyon phaeoclathratiforme
SEQUENCE: 194
MFILDDILFA PLNGLIFIAK KINDVVEKET SDEGVVKERL MALQLRFELD EIDEVEYDRE    60
EDELLQKLER IRLNKQNQ                                                 78

SEQ ID NO: 195           moltype = AA  length = 81
FEATURE                  Location/Qualifiers
source                   1..81
                         mol_type = protein
                         note = NIES-30
                         organism = Phormidium tenue
SEQUENCE: 195
MLFKLLFAPV LGPIEGISWV ANKLLEQADV PTNDLESLQK QLLALQLAFD MGEVAEADFE    60
IQEEEILLAI QAIEDEEDED E                                             81

SEQ ID NO: 196           moltype = AA  length = 85
FEATURE                  Location/Qualifiers
source                   1..85
                         mol_type = protein
                         note = str. 7805
                         organism = Planktothrix agardhii
SEQUENCE: 196
MILRLLLSPI TAPFEGVIWI GEQLLERAEA ELDDKENLGK RLLALQLAFD MGDIPEEDFE    60
VQEEELLLQI QALEDEANQE NDEID                                         85

SEQ ID NO: 197           moltype = AA  length = 149
FEATURE                  Location/Qualifiers
source                   1..149
                         mol_type = protein
                         note = 37
                         organism = Psychromonas ingrahamii
SEQUENCE: 197
MFILDDILLA PYSGIKWLFK EIQRQAQEEL DGEADRITTD LTNLYRQFES NEITEQEFEE    60
RETVLLDRLD ELQEESNLLD EEYDEEYEDD DEEYEDDDEE YEDDDEEYED DDEEYEDDDK  120
NDKDKNDDHD NDDDDENKDE NDKYNDEER                                   149

SEQ ID NO: 198           moltype = AA  length = 85
FEATURE                  Location/Qualifiers
source                   1..85
                         mol_type = protein
                         note = SB 1003
```

```
                        organism = Rhodobacter capsulatus
SEQUENCE: 198
MGLLRKLLLA PVELPITGAL WIVEKIAETA ESELTDPGTV RRLLRGLEQQ LEAGEITEEE    60
YEFAEEILLD RLKRGQAAEA RSGGP                                          85

SEQ ID NO: 199          moltype = AA  length = 77
FEATURE                 Location/Qualifiers
source                  1..77
                        mol_type = protein
                        note = 2.4.1
                        organism = Rhodobacter sphaeroides
SEQUENCE: 199
MGLLTSLLTL PFRGPFDGTL WIAARIGEAA EQSWNDPAAL RAALVEAERQ LLAGELSEET    60
YDAIELDLLE RLKGTAR                                                   77

SEQ ID NO: 200          moltype = AA  length = 83
FEATURE                 Location/Qualifiers
source                  1..83
                        mol_type = protein
                        note = 103S
                        organism = Rhodococcus hoagie
SEQUENCE: 200
MGLFSAIFGL PLAPVRGVVW IGEVVRRQVE EETTSPAAMR RDLEAIEEGR RSGEISEDEA    60
AQAEDEILHR VTRRRDAGAS GEE                                            83

SEQ ID NO: 201          moltype = AA  length = 138
FEATURE                 Location/Qualifiers
source                  1..138
                        mol_type = protein
                        note = ATCC 39006
                        organism = Serratia sp
SEQUENCE: 201
MLLIDDILFS PVKGVMWIFR QIHELAEDEL AGEADRIRES LTDLYMLLET GQITEDEFEQ    60
QEAVLLDRLD ALDEEDDMLG DEPGDDEDDE YEEDDDDEEDD DEEDDDDEED             120
DDDDEDDDDE DEPEGTTK                                                 138

SEQ ID NO: 202          moltype = AA  length = 83
FEATURE                 Location/Qualifiers
source                  1..83
                        mol_type = protein
                        note = ATCC-43931
                        organism = Stella vacuolate
SEQUENCE: 202
MGLVTNVAFA PVVGPLKGVL WLARLIADQA ERTLYDEDLV RAALLDLEQR LDAGQISEAD    60
YDAEEEILLA RLKIARERMR SGL                                            83

SEQ ID NO: 203          moltype = AA  length = 98
FEATURE                 Location/Qualifiers
source                  1..98
                        mol_type = protein
                        note = strain DSM 235
                        organism = Thiocapsa rosea
SEQUENCE: 203
MLIVDDLLAA PFKGIIWVFE EIHKSATAEQ RARRDEIMAA LSALYRALEQ GEITDDTFDT    60
REQALLDELD ALDAREDANE LGSDEDEDDL DGAGEDAS                            98

SEQ ID NO: 204          moltype = AA  length = 132
FEATURE                 Location/Qualifiers
source                  1..132
                        mol_type = protein
                        note = PCC 7601
                        organism = Tolypothrix sp
SEQUENCE: 204
MEVMIMLGKI LLFPVMGPIS GLMWIGEQIQ ERTDTEFDAQ ENLHKQLLSL QLSFDIGEIS    60
EEDFEEQEEE LLLKIQALEE EKARLEAESI EDEEDEVEPT YFIAEVEEDK VLAEAFRGNK   120
KYEDNENLVL SP                                                       132

SEQ ID NO: 205          moltype = AA  length = 85
FEATURE                 Location/Qualifiers
source                  1..85
                        mol_type = protein
                        note = IMS101
                        organism = Trichodesmium erythraeum
SEQUENCE: 205
MLLRLLTLPI SGPLEGVTWL GKKLQEQVDT EIDETENLSK KLLTLQLAFD MGEISEEDFE    60
DQEEELLLAI QALEEQKLKE EEEDA                                          85

SEQ ID NO: 206          moltype = AA  length = 248
FEATURE                 Location/Qualifiers
```

```
source                     1..248
                           mol_type = protein
                           organism = Anabaena-flos-aquae
SEQUENCE: 206
MLPTRPQTNS SRTINTSTQG STLADILERV LDKGIVIAGD ISISIASTEL VHIRIRLLIS      60
SVDKAKEMGI NWWESDPYLS TKAQRLVEEN QQLQHRLESL EAKLNSLTSS SVKEEIPLAA     120
DVKDDLYQTS AKIPSPVDTP IEVLDFQAQS SGGTPPYVNT SMEILDFQAQ TSAESSSPVG     180
STVEILDFQA QTSEESSSPV VSTVEILDFQ AQTSEESSSP VGSTVEILDF QAQTSEEIPS     240
SVDPAIDV                                                             248

SEQ ID NO: 207             moltype = AA  length = 100
FEATURE                    Location/Qualifiers
source                     1..100
                           mol_type = protein
                           organism = Bacillus-megaterium
SEQUENCE: 207
MAVEHNMQSS TIVDVLEKIL DKGVVIAGDI TVGIADVELL TIKIRLIVAS VDKAKEIGMD      60
WWENDPYLSS KGANNKALEE ENKMLHERLK TLEEKIETKR                           100

SEQ ID NO: 208             moltype = AA  length = 120
FEATURE                    Location/Qualifiers
source                     1..120
                           mol_type = protein
                           note = strain UV5
                           organism = Ancylobacter aquaticus
SEQUENCE: 208
MNEQRMEHSL QAVGLADILE RVLDKGIVIA GDITISLVEV ELLNIRLRLV VASVDRAMSM      60
GINWWQSDPH LNSHARELAE ENKLLRERLD RLEAAVVPSA LPADAALEPS LAGEDARHGG     120

SEQ ID NO: 209             moltype = AA  length = 72
FEATURE                    Location/Qualifiers
source                     1..72
                           mol_type = protein
                           note = strain UV5
                           organism = Ancylobacter aquaticus
SEQUENCE: 209
MPSRHSGEIA VADLLDRALH KGLVVWGEAT ISVAGVDLVY LGLKLLLLTST DTVNRMREAA     60
NAPPDERHLH AD                                                         72

SEQ ID NO: 210             moltype = AA  length = 157
FEATURE                    Location/Qualifiers
source                     1..157
                           mol_type = protein
                           note = NIES-81
                           organism = Aphanizomenon flos-aquae
SEQUENCE: 210
VTSTPILPTR PQTNSSRAIN TSTQGSTLAD ILERVLDKGI VIAGDISISI ASTELIHIRI      60
RLLIASVDKA KEMGINWWET DPYLSTKAQR LVEENQQLQN RLENLESQIN LLTSAKVQEQ     120
ISLVETTEDN THQTTEDNTH QTHEESIPLP IDSQLDV                              157

SEQ ID NO: 211             moltype = AA  length = 128
FEATURE                    Location/Qualifiers
source                     1..128
                           mol_type = protein
                           note = strain PCC 7418
                           organism = Aphanothece halophytica
SEQUENCE: 211
MVNPNTNKPK SYQSKGITNS TQSSSLADIL ERVLDKGIVI AGDITSVGS TELLSIRIRL       60
LVSSVDKARE LGINWWEGDP YLSSQANLLK EENQALQNRL ENMEAELRRL KGETNPEPSF    120
LSESEDNS                                                             128

SEQ ID NO: 212             moltype = AA  length = 114
FEATURE                    Location/Qualifiers
source                     1..114
                           mol_type = protein
                           note = strain DSM 9035
                           organism = Aquabacter spiritensis
SEQUENCE: 212
MSEQRMEHSL QAVGLADILE RVLDKGIVIA GDISISLVEV DLLNIRLRLV VASVDRAMSM      60
GINWWQSDPH LNSHARQLEE ENRLLRERLD RLEAALAPPE GGMLRAEVEV AHGG           114

SEQ ID NO: 213             moltype = AA  length = 78
FEATURE                    Location/Qualifiers
source                     1..78
                           mol_type = protein
                           note = strain DSM 9035
                           organism = Aquabacter spiritensis
SEQUENCE: 213
MPDPEPIIPR TSGDVALADL LDRALHKGLV LWGEATISVA GVDLVYLGLK VLLASTDTAN      60
```

```
RMRDAAAASA AGSHLPGG                                                     78

SEQ ID NO: 214          moltype = AA  length = 127
FEATURE                 Location/Qualifiers
source                  1..127
                        mol_type = protein
                        note = NIES-39
                        organism = Arthrospira platensis
SEQUENCE: 214
MTLQSRSSSP QRGVPMSTSG SSLADILERV LDKGIVIAGD ISVSVGSTEL LSIRIRLLIA        60
SVDKAKEIGI NWWESDPYLS SQAQQLSQSN QQLLEEVKRL QEEVRSLKAL TSQSSQPVTP       120
PNSENDD                                                                127

SEQ ID NO: 215          moltype = AA  length = 119
FEATURE                 Location/Qualifiers
source                  1..119
                        mol_type = protein
                        note = S58
                        organism = Bradyrhizobium oligotrophicum
SEQUENCE: 215
MTFTVHQPTG GDRLADILER VLDKGIVVAG DVTISLVGIE LLNIKIRLIV ATVDRALELG        60
INWWEADPRL TTRASELSVE NEELKKRLAL LEADAGRNQR PRKRRVRSIA ATSGASHER       119

SEQ ID NO: 216          moltype = AA  length = 81
FEATURE                 Location/Qualifiers
source                  1..81
                        mol_type = protein
                        note = S58
                        organism = Bradyrhizobium oligotrophicum
SEQUENCE: 216
MTYRADLDYL EPAASSEGSL LELLDHLLDR GVLLWGELRI SVADVELIEV GLKLMLASAR        60
TADRWRQTTT QRASIAPGDC P                                                 81

SEQ ID NO: 217          moltype = AA  length = 74
FEATURE                 Location/Qualifiers
source                  1..74
                        mol_type = protein
                        note = sp. Bp5365 strain MSMB43
                        organism = Burkholderia thailandensis
SEQUENCE: 217
MRSADGEPVS AELAQRLSLC ESLDRILNKG AVISAQVVVS VADVDLLYLH LRLLLTSVET        60
ALVGRAMPRE EASR                                                         74

SEQ ID NO: 218          moltype = AA  length = 89
FEATURE                 Location/Qualifiers
source                  1..89
                        mol_type = protein
                        note = sp. Bp5365 strain MSMB43
                        organism = Burkholderia thailandensis
SEQUENCE: 218
MADLLERVLD KGVVITGDIR INLVDVELLT IRIRLLVCSV DKAKELGIDW WNADTFFLGP        60
DRGQSALPGR ASAVDVAAGS AVHADAAHR                                         89

SEQ ID NO: 219          moltype = AA  length = 97
FEATURE                 Location/Qualifiers
source                  1..97
                        mol_type = protein
                        note = DSM 273
                        organism = Chlorobium luteolum
SEQUENCE: 219
MPELKHAVNA TGLADILERV LDKGIVIAGD IKIQIADIDL LTIKIRLMVA SVDKAIEMGI        60
NWWQEDPYLS TGAKTSEQTR LLGEINQRIE KLESINR                                97

SEQ ID NO: 220          moltype = AA  length = 69
FEATURE                 Location/Qualifiers
source                  1..69
                        mol_type = protein
                        note = DSM 273
                        organism = Chlorobium luteolum
SEQUENCE: 220
MQEDLYTANR QVTLLDILDR VLNKGVVISG DIIISVAGID LVYVGLRVLL SSVETMERLD        60
AARAEGLQQ                                                               69

SEQ ID NO: 221          moltype = AA  length = 68
FEATURE                 Location/Qualifiers
source                  1..68
                        mol_type = protein
                        organism = Chlorobium luteolum
```

```
SEQUENCE: 221
MAVEKTIGSS SLVEVIDRIL DKGVVVDAWV RVSLVGIELL AIEARVVVAS VETYLKYAEA   60
IGLTAKAA                                                            68

SEQ ID NO: 222          moltype = AA  length = 68
FEATURE                 Location/Qualifiers
source                  1..68
                        mol_type = protein
                        note = DSM 273
                        organism = Chlorobium luteolum
SEQUENCE: 222
MAVEKTIGSS SLVEVIDRIL DKGVVVDAWV RVSLVGIELL AIEARVVVAS VETYLKYAEA   60
IGLTAKAA                                                            68

SEQ ID NO: 223          moltype = AA  length = 130
FEATURE                 Location/Qualifiers
source                  1..130
                        mol_type = protein
                        note = PCC 8305
                        organism = Dactylococcopsis salina
SEQUENCE: 223
MVNSNTNQPK SYQSKGITNS TQSSSLADIL ERVLDKGIVI AGDISVSVGS TELLTIRIRL   60
LISSVDRARE IGINWWESDP YLSSQAHLMK EENQALQSRL ENMEAELRRL KGETNLDQSS  120
LGESDQRSLQ                                                         130

SEQ ID NO: 224          moltype = AA  length = 74
FEATURE                 Location/Qualifiers
source                  1..74
                        mol_type = protein
                        note = DSM 3385
                        organism = Desulfobacterium vacuolatum
SEQUENCE: 224
MAYIDIDNDA SKQISICEAL DRVLNKGAVI TGELTISVAD IDLIYLSLQA VLTSVETARH   60
MFDSQINDAV KEVK                                                     74

SEQ ID NO: 225          moltype = AA  length = 105
FEATURE                 Location/Qualifiers
source                  1..105
                        mol_type = protein
                        note = DSM 3385
                        organism = Desulfobacterium vacuolatum
SEQUENCE: 225
MPIQRTAQHS IESTNIADLL ERVLDKGIVI AGDIKISLVD IELLSIQLRL VICSVDKAKE   60
MGMDWWVNNP VFMPNKGTQN DEIADTLTKI NSRLEHLEKA TISGS                  105

SEQ ID NO: 226          moltype = AA  length = 73
FEATURE                 Location/Qualifiers
source                  1..73
                        mol_type = protein
                        note = DSM 6799
                        organism = Desulfomonile tiedjei
SEQUENCE: 226
MMDEEEHVSL CEALDRVLNK GAVIAGEVTI SVANVDLIYL GLQVVLASVD TIRGKRNELL   60
RHDVGLHLTA DNA                                                      73

SEQ ID NO: 227          moltype = AA  length = 81
FEATURE                 Location/Qualifiers
source                  1..81
                        mol_type = protein
                        note = DSM 6799
                        organism = Desulfomonile tiedjei
SEQUENCE: 227
MSIQASTRHS IQSTNLADLL ERVLDKGVVI AGDIKIKLVD VELLTIQIRL VVCSVDKAKE   60
MGMDWWTNNP AFQPALAQIS E                                             81

SEQ ID NO: 228          moltype = AA  length = 123
FEATURE                 Location/Qualifiers
source                  1..123
                        mol_type = protein
                        note = DSM 771
                        organism = Desulfotomaculum acetoxidans
SEQUENCE: 228
MGPQMGPIKS TGNLSLLDVI DRILDKGLVI NADISVSIVG VELLGIKIKA AVASFETAAK   60
YGLQFPTGTE INEKVSEAAK QLKEICPECG KKSGRDELLH EGCPWCGWIS ARALRLETEH  120
SQR                                                                123

SEQ ID NO: 229          moltype = AA  length = 78
FEATURE                 Location/Qualifiers
source                  1..78
```

```
                                    mol_type = protein
                                    note = DSM 771
                                    organism = Desulfotomaculum acetoxidans
SEQUENCE: 229
MLPIREERAT LTDLLDRVLD KGLLLNADIL ISVAGVPLIG ITLKAAIAGM ETMKKYGLLI    60
DWDQESRLAE RRLRSSRH                                                  78

SEQ ID NO: 230                      moltype = AA  length = 108
FEATURE                             Location/Qualifiers
source                              1..108
                                    mol_type = protein
                                    note = strain ATCC 27094
                                    organism = Enhydrobacter aerosaccus
SEQUENCE: 230
MAVTNGRMEH SIQGSSLADI LDRILDKGIV IAGDVTISLV GVELLNIRLR LLVASVDKAI    60
EMGINWWEAD PYLTSQTKAS SEQTELLQQR LERIEGLLAG QATKEQPL                108

SEQ ID NO: 231                      moltype = AA  length = 74
FEATURE                             Location/Qualifiers
source                              1..74
                                    mol_type = protein
                                    note = strain ATCC 27094
                                    organism = Enhydrobacter aerosaccus
SEQUENCE: 231
MPVQTAHDGE LALADLLDRA LNKGVVLWGD ATISLAGVEL VYVGLRVLVA SCSTMEKYRS    60
SPRKGSMPIA RGES                                                      74

SEQ ID NO: 232                      moltype = AA  length = 98
FEATURE                             Location/Qualifiers
source                              1..98
                                    mol_type = protein
                                    note = ATCC-43644
                                    organism = Isosphaera pallida
SEQUENCE: 232
MIVCSSSTPE RIGPPMNLPP PHHAPWCYDS PDLETLPLDP AERIALCEVL DRVLNKGVVI    60
HGEITISVAG VDLVYLGLNL LLTSVETAQS WKFRGMIE                            98

SEQ ID NO: 233                      moltype = AA  length = 171
FEATURE                             Location/Qualifiers
source                              1..171
                                    mol_type = protein
                                    note = ATCC-43644
                                    organism = Isosphaera pallida
SEQUENCE: 233
MAITRSSRPD VTHSTSGATL ADVLERVLDK GLVIAGDIKI KLVDVELLTI QIRLVVASVD    60
KAREMGLDWW TRSPELSSLA ATTCPALTPP KQEATPPATR IQAPTESAQT TPDQSHPSDP   120
SASNIDEVAE LRRHIELMQL RDEARQRAHR EELAALRAQL TRLTELLDSP R            171

SEQ ID NO: 234                      moltype = AA  length = 61
FEATURE                             Location/Qualifiers
source                              1..61
                                    mol_type = protein
                                    note = LLAP12
                                    organism = Legionella drancourtii
SEQUENCE: 234
MIIEDKPVSL CETLDRVLNK GVVVAGTVTI SVADVDLLYL DLHCLLSSMK GMNLIGSERE    60
R                                                                    61

SEQ ID NO: 235                      moltype = AA  length = 106
FEATURE                             Location/Qualifiers
source                              1..106
                                    mol_type = protein
                                    note = LLAP12
                                    organism = Legionella drancourtii
SEQUENCE: 235
MELQKSPTHS IGSTTIADLL ERILDKGIVI AGDIKVNLVQ VELLTIQIRL LICSVDKAKE    60
IGMDWWTHQN DVQSKNGSMP IQEYVTQMEE RLKNLENTLA SSKNAI                  106

SEQ ID NO: 236                      moltype = AA  length = 114
FEATURE                             Location/Qualifiers
source                              1..114
                                    mol_type = protein
                                    note = BDU141951
                                    organism = Lyngbya confervoides
SEQUENCE: 236
MTGQSLSRSS SANRQMATAT QGSTLVDVLE RVLDKGIVIA GDISVSVGST ELLTIRIRLL    60
VASVDKAREM GINWWENDPY LSARSQELLT ANEQLQSRIE SLEQELKSLR SQED         114

SEQ ID NO: 237                      moltype = AA  length = 136
```

```
FEATURE                Location/Qualifiers
source                 1..136
                       mol_type = protein
                       note = NIES-843
                       organism = Microcystis aeruginosa
SEQUENCE: 237
MTSSTPAGSL RNQSNNSLKT ATQGSSLADI LERVLDKGIV IAGDISVSIA STELINIRIR      60
LLIASVDKAR EMGINWWEGD PYLHSQSQAL LAENRELSLR LQTLETELET LKSLTQLSAM     120
ESHDTSPNDE AHSSDA                                                    136

SEQ ID NO: 238         moltype = AA   length = 116
FEATURE                Location/Qualifiers
source                 1..116
                       mol_type = protein
                       note = ATCC 29133
                       organism = Nostoc punctiforme
SEQUENCE: 238
MSTNTNRGAI TTSTQGSTLA DILERVLDKG IVIAGDISIS VGSTELLNIR IRLLISSVDK      60
AKEIGINWWE SDPYLNSQTR TLLATNQQLQ ERLASLETEL QSLKALNPIN HQNAGD        116

SEQ ID NO: 239         moltype = AA   length = 148
FEATURE                Location/Qualifiers
source                 1..148
                       mol_type = protein
                       note = PCC 7120
                       organism = Nostoc sp
SEQUENCE: 239
MTTTPIHPTR PQTNSNRVIP TSTQGSTLAD ILERVLDKGI VIAGDISISI ASTELIHIRI      60
RLLISSVDKA REMGINWWEN DPYLSSKSQR LVEENQQLQQ RLESLETQLR LLTSAAKEET    120
TLTANNPEDL QPMYEVNSQE GDNSQLEA                                       148

SEQ ID NO: 240         moltype = AA   length = 112
FEATURE                Location/Qualifiers
source                 1..112
                       mol_type = protein
                       note = 307
                       organism = Octadecabacter antarcticus
SEQUENCE: 240
MNDGKMEHSL NATNLADILE RVLDKGIVIA GDVTISLVGV ELLNIKLRLL IASVDKAMEM      60
GINWWAHDPF LTAGAQAPAV ADPAMLERMD RLEAALATAL ASNQTTPMKG HK            112

SEQ ID NO: 241         moltype = AA   length = 74
FEATURE                Location/Qualifiers
source                 1..74
                       mol_type = protein
                       note = 307
                       organism = Octadecabacter antarcticus
SEQUENCE: 241
MTNKAQGGQD LALADLLDRA LSTGVVIWGE ATISLAGVDL VYVGLKVLVA SVDAAERMKA      60
ASLVDRPTDR GQQI                                                       74

SEQ ID NO: 242         moltype = AA   length = 113
FEATURE                Location/Qualifiers
source                 1..113
                       mol_type = protein
                       note = 238
                       organism = Octadecabacter arcticus
SEQUENCE: 242
MNNGKMEHSL DATNLADILE RVLDKGIVIA GDVTISLVGV ELLNIKLRLL IASVDKAMEM      60
GINWWAHDPY LTAGAQAPVG VDPAMLERMD RLEAALAKAL ASNQTTPAEG QSS           113

SEQ ID NO: 243         moltype = AA   length = 72
FEATURE                Location/Qualifiers
source                 1..72
                       mol_type = protein
                       note = 238
                       organism = Octadecabacter arcticus
SEQUENCE: 243
MTNETQGGQD LALADLLDRA LSTGVVIWGE ATISLAGVDL VYVGLKVLVA SVDAAQRMKD      60
ASLVDRPTDG GQ                                                         72

SEQ ID NO: 244         moltype = AA   length = 99
FEATURE                Location/Qualifiers
source                 1..99
                       mol_type = protein
                       organism = Pelodictyon phaeoclathratiforme
SEQUENCE: 244
MPELKHAVNA TGLADILERV LDKGIVIAGD IKIQIADIDL LTIKIRLLIA SVDKAMEMGI      60
NWWQEDTYLS TKAKDKEQQL LRDDLQQRIE KLEALTKIT                            99
```

```
SEQ ID NO: 245          moltype = AA   length = 66
FEATURE                 Location/Qualifiers
source                  1..66
                        mol_type = protein
                        organism = Pelodictyon phaeoclathratiforme
SEQUENCE: 245
MQDEFYSKNK EITILDVLDR VLTKGVVITG DIVISVADID LVYVGLRLLL SSVETMEKNK    60
QNSIKM                                                              66

SEQ ID NO: 246          moltype = AA   length = 101
FEATURE                 Location/Qualifiers
source                  1..101
                        mol_type = protein
                        note = NIES-30
                        organism = Phormidium tenue
SEQUENCE: 246
MATATQGSSL VDVIERVLDK GIVIAGDISV SVGSTELLSI RIRLIISSVD KAREIGINWW    60
ESDPYLSSRT NELLEANQQL QSRLETLEAE LKALRSAEPV S                       101

SEQ ID NO: 247          moltype = AA   length = 125
FEATURE                 Location/Qualifiers
source                  1..125
                        mol_type = protein
                        note = str. 7805
                        organism = Planktothrix agardhii
SEQUENCE: 247
MNSQQLPSNI QRGVPTSTQG SSLADILERV LDKGIVIAGD ISVSVGSTEL LNIRIRLLIA    60
SVDKAREIGI NWWESDPYLS SQTKVLTESN QQLLEQVKFL QEEVKALKAL LPQENQPNPI    120
SDPHK                                                               125

SEQ ID NO: 248          moltype = AA   length = 121
FEATURE                 Location/Qualifiers
source                  1..121
                        mol_type = protein
                        organism = Planktothrix rubescens
SEQUENCE: 248
MNSQQRPSNI QRGVPTSTQG SSLADILERV LDKGIVIAGD ISVSVGSTEL LNIRIRLLIA    60
SVDKAREIGI NWWESDPYLS SQTKVLTESN QELLEQVKLL QEEVKALKAL LPQENQPKEM    120
E                                                                   121

SEQ ID NO: 249          moltype = AA   length = 72
FEATURE                 Location/Qualifiers
source                  1..72
                        mol_type = protein
                        note = 37
                        organism = Psychromonas ingrahamii
SEQUENCE: 249
MANVQKSTDS SGLAEVVDRI LEKGIVIDAF VKVSLVGIEL LSIEARVVIA SVETYLKYAE    60
AIGLTASAAT PA                                                       72

SEQ ID NO: 250          moltype = AA   length = 74
FEATURE                 Location/Qualifiers
source                  1..74
                        mol_type = protein
                        note = 37
                        organism = Psychromonas ingrahamii
SEQUENCE: 250
MPMANVSINP ELTAQECEKI SLCDALDRII NKGVVIHGEI TISVANVDLI SLGVRLILSN    60
VETREQSNTP KEEV                                                     74

SEQ ID NO: 251          moltype = AA   length = 101
FEATURE                 Location/Qualifiers
source                  1..101
                        mol_type = protein
                        note = 37
                        organism = Psychromonas ingrahamii
SEQUENCE: 251
MATGKPQSMT HSVKSTTVAD LLERILDKGI VVTGDIKIKL VDVELLTVEL RLVICSVDKA    60
VEMGMDWWNN NPAFAPQAPA QEGELSSIEK RLEKIEKALV K                       101

SEQ ID NO: 252          moltype = AA   length = 151
FEATURE                 Location/Qualifiers
source                  1..151
                        mol_type = protein
                        note = SB 1003
                        organism = Rhodobacter capsulatus
SEQUENCE: 252
MGYRSASQPE GLADVLERIL DKGIVIAGDV SVSLVGIELL TIRLRLLIAT VDKAREMGID    60
```

```
WWSHDPYLNG RLRPGEPAPE TETETAALRD RLAQLEAQLS ALGAQVGAAP ALAEPALRGL    120
AAAGSSALCA APEASSADVV QPVFRRYKEA P                                  151

SEQ ID NO: 253           moltype = AA  length = 69
FEATURE                  Location/Qualifiers
source                   1..69
                         mol_type = protein
                         note = SB 1003
                         organism = Rhodobacter capsulatus
SEQUENCE: 253
MDDRFSLRLF GPEEVFDAPS GGLADLLDGL LGHGIVLHGD LWLTVADVEL VYVGLSAVLA    60
SPEALRSHE                                                           69

SEQ ID NO: 254           moltype = AA  length = 104
FEATURE                  Location/Qualifiers
source                   1..104
                         mol_type = protein
                         note = 2.4.1
                         organism = Rhodobacter sphaeroides
SEQUENCE: 254
MSFQMQSPLQ QDSLADVLER ILDKGIVIAG DISISLVGIE LLTIRLRLLV ATVDKAREMG    60
INWWESDPRL CITQAPASDG SAALLDRLER IETQIGQLAA AREG                    104

SEQ ID NO: 255           moltype = AA  length = 74
FEATURE                  Location/Qualifiers
source                   1..74
                         mol_type = protein
                         note = 2.4.1
                         organism = Rhodobacter sphaeroides
SEQUENCE: 255
MTDSAPTLQF ATAEEALQSS ETRLVDVVDA LLSQGIAIRG ELWLTIADVD LVFLGLDLLL    60
ANPDRLQCRV PDAA                                                     74

SEQ ID NO: 256           moltype = AA  length = 137
FEATURE                  Location/Qualifiers
source                   1..137
                         mol_type = protein
                         note = 103S
                         organism = Rhodococcus hoagie
SEQUENCE: 256
MTRSGSGANY PQQYSQGLGG AGHEPANLGD ILERVLDKGI VIAGDIRVNL LDIELLTIKL    60
RLVIASLETA REVGIDWWEH DPWLSGNNRD LELENERLRA RIEALESGER RVADVTDPHR    120
AVQPAESPAA EVRDDDA                                                  137

SEQ ID NO: 257           moltype = AA  length = 65
FEATURE                  Location/Qualifiers
source                   1..65
                         mol_type = protein
                         note = ATCC 39006
                         organism = Serratia sp
SEQUENCE: 257
MPVNKQYQDE QQQVSLCEAL DRVLNKGVVI VADITISVAN IDLIYLSLQA LVSSVEAKNR    60
LPGRE                                                               65

SEQ ID NO: 258           moltype = AA  length = 110
FEATURE                  Location/Qualifiers
source                   1..110
                         mol_type = protein
                         note = ATCC 39006
                         organism = Serratia sp
SEQUENCE: 258
MSGNKKLTHS TDSTTVADLL ERLLDKGVVI SGDIRIRLVE VELLTLEIRL LICSVDKAVE    60
MGLDWWSGNP AFDSRARVSS SAPAPELEER LQRLEARLEA APSVIEETHL              110

SEQ ID NO: 259           moltype = AA  length = 123
FEATURE                  Location/Qualifiers
source                   1..123
                         mol_type = protein
                         note = ATCC-43931
                         organism = Stella vacuolate
SEQUENCE: 259
MSGQRMEHSV QAVGLADILE RVLDKGIVIA GDISISLVEV ELLTIRLRLV VASVDRAMSM    60
GINWWQSDPN LNSHARQLEE DNRLLRERLD RLEAALALPE MAGERLADAG QGGGAEQGVT    120
HGR                                                                 123

SEQ ID NO: 260           moltype = AA  length = 78
FEATURE                  Location/Qualifiers
source                   1..78
                         mol_type = protein
```

```
                        note = ATCC-43931
                        organism = Stella vacuolate
SEQUENCE: 260
MSDPEPIIPR TSGDIALADL LDRALHKGLV LWGEATISVA GVDLVYLGLK VLVASTETAD    60
RMRAAAASQS ADPKVRAG                                                  78

SEQ ID NO: 261          moltype = AA  length = 71
FEATURE                 Location/Qualifiers
source                  1..71
                        mol_type = protein
                        note = strain DSM 235
                        organism = Thiocapsa rosea
SEQUENCE: 261
MMLAIGEHPD CPEEIQRVSL CEALDRILNK GAVVSGELTI AVANVDLLYL SLQLVITSVE    60
TAKREMLYVR H                                                         71

SEQ ID NO: 262          moltype = AA  length = 116
FEATURE                 Location/Qualifiers
source                  1..116
                        mol_type = protein
                        note = strain DSM 235
                        organism = Thiocapsa rosea
SEQUENCE: 262
MSVQRSTLTH STNSTSVADL LERVLDKGIV IAGDIRIKLV DIELLTIQLR LVICSVDKAR    60
EMGIDWWSDN AMFKGLSSQA SAASLPGTAA ASGIEDRLAR LESLLVKQSA AAETVL       116

SEQ ID NO: 263          moltype = AA  length = 121
FEATURE                 Location/Qualifiers
source                  1..121
                        mol_type = protein
                        note = PCC 7601
                        organism = Tolypothrix sp
SEQUENCE: 263
MADILERVLD KGIVIAGDIS VSIASTELLH IRIRLLISSV DKAKELGINW WENDPYLSSK    60
SQRLVEENQQ LQQRLESLEA QLRSLTAAKI NNPELFPVNA EDNGQSDEEN VPLPMNYQPN   120
D                                                                   121

SEQ ID NO: 264          moltype = AA  length = 54
FEATURE                 Location/Qualifiers
source                  1..54
                        mol_type = protein
                        note = IMS101
                        organism = Trichodesmium erythraeum
SEQUENCE: 264
MFIRVDFLLD KGVIVDAWVR LSLVVIELLT IEAKIVIASV EAYLKYSEAF CFNY           54

SEQ ID NO: 265          moltype = AA  length = 75
FEATURE                 Location/Qualifiers
source                  1..75
                        mol_type = protein
                        note = IMS101
                        organism = Trichodesmium erythraeum
SEQUENCE: 265
MAVEKVNSSS SLAEVIDRIL DKGVVVDAWI RLSLVGIELL TIEARIVVAS VETYLKYAEA    60
VGLTTLAAAP GEAAA                                                     75

SEQ ID NO: 266          moltype = AA  length = 72
FEATURE                 Location/Qualifiers
source                  1..72
                        mol_type = protein
                        note = IMS101
                        organism = Trichodesmium erythraeum
SEQUENCE: 266
MAVEKVNSSS SLAEVIDRIL DKGVVVDAWV RLSLVGIELL TIEARIVIAS VETYLKYAEA    60
VGLTTLAAEP AA                                                        72

SEQ ID NO: 267          moltype = AA  length = 103
FEATURE                 Location/Qualifiers
source                  1..103
                        mol_type = protein
                        note = IMS101
                        organism = Trichodesmium erythraeum
SEQUENCE: 267
MKTSANIATS ASGNGLADVL ERVLDKGVVI AGDISVSIAS TELLNIKIRL LISSVERAKE    60
IGINWWESDP YFSSQNNSLV QANEKLLERV ASLESEIKAL RSN                     103

SEQ ID NO: 268          moltype = AA  length = 104
FEATURE                 Location/Qualifiers
source                  1..104
```

```
                          mol_type = protein
                          note = MS101
                          organism = Trichodesmium erythraeum
SEQUENCE: 268
MKTSANIAKS AGGDSLADVL ERVLDKGIVI AGDISVSIAS TELLNIKIRL LISSVERAKE    60
IGINWWESDP SLSSQNNSLV QVNQKLLERV ASLESEIEAL KYSQ                    104

SEQ ID NO: 269            moltype = AA   length = 155
FEATURE                   Location/Qualifiers
source                    1..155
                          mol_type = protein
                          organism = Anabaena-flos-aquae
SEQUENCE: 269
MVCTPAENFN NSLTIASKPK NEAGLAPLLL TVLELVRQLM EAQVIRRMEE DLLSEPDLER    60
AADSLQKLEE QILHLCEMFE VDPADLNINL GEIGTLLPSS GSYYPGQPSS RPSVLELLDR   120
LLNTGIVVDG EIDLGIAQID LIHAKLRLVL TSKPI                              155

SEQ ID NO: 270            moltype = AA   length = 94
FEATURE                   Location/Qualifiers
source                    1..94
                          mol_type = protein
                          organism = Bacillus-megaterium
SEQUENCE: 270
MQPVSQANGR IHLDPDQAEQ GLAQLVMTVI ELLRQIVERH AMRRVEGGTL TDEQIENLGI    60
ALMNLEEKMD ELKEVFGLDA EDLNIDLGPL GSLL                                94

SEQ ID NO: 271            moltype = AA   length = 101
FEATURE                   Location/Qualifiers
source                    1..101
                          mol_type = protein
                          note = strain UV5
                          organism = Ancylobacter aquaticus
SEQUENCE: 271
MTAPCTAETL ENALRGRIDI DPEKVEQGLV KLVLMLVETV RQVVERQAIR RVEGGTLTEE    60
ETERLGLALM RLEEKMAELR LHFGLEDGDL DLKLQLPLGE L                       101

SEQ ID NO: 272            moltype = AA   length = 169
FEATURE                   Location/Qualifiers
source                    1..169
                          mol_type = protein
                          note = NIES-81
                          organism = Aphanizomenon flos-aquae
SEQUENCE: 272
MVYSPVENSN DFLNVIPVEN SNEFLNTSPK KKSNSETGLA PLLLTVLELI RQLMEAQIIR    60
RMEEDLLSES DLERTAESLQ KLEEQILNLC QIFDIDPADL NINLGDFGSL LPASGSYYPG   120
ETGNRPSILE LLDRLLNTGI VVDGEIDIGV AQLDLIHAKL RLVLTSKPI               169

SEQ ID NO: 273            moltype = AA   length = 157
FEATURE                   Location/Qualifiers
source                    1..157
                          mol_type = protein
                          note = strain PCC 7418
                          organism = Aphanothece halophytica
SEQUENCE: 273
MSADESNLSQ VNLNPATSNS DAGLAPLLLT VTELIRQLME AQVIRRMDGG LLNEEELDRA    60
GDSLQRLEAE IIRLCEIFEI DPKDLNVDLG ELGTLMPKNG GYYPGESSDD PSILELLDRI   120
LHKGVVIDGN LDLGIAQLSL IQARLHLVLT SQPINGK                            157

SEQ ID NO: 274            moltype = AA   length = 105
FEATURE                   Location/Qualifiers
source                    1..105
                          mol_type = protein
                          note = strain DSM 9035
                          organism = Aquabacter spiritensis
SEQUENCE: 274
MTGFAGGPAV TETLESVLQG RVDIDPERVE QGLVKLVLMV VETLRQVIER QAIRRVEAGA    60
LTDEEIERLG LTLLRLEEKM AELRVQFNLS EADLSLKLRL PLGEL                   105

SEQ ID NO: 275            moltype = AA   length = 119
FEATURE                   Location/Qualifiers
source                    1..119
                          mol_type = protein
                          note = S58
                          organism = Bradyrhizobium oligotrophicum
SEQUENCE: 275
MSASSHSEAP GLRLQLGDLD TALAAVFTDA APNGSINLDP DKIEHDLARL VLTLIEFLRR    60
LLELQAIRRM EANELSEDEE ERVGLALMRA AQVSRLARE LGVDPRELNL QLGPLGRLL    119

SEQ ID NO: 276            moltype = AA   length = 120
```

| FEATURE | Location/Qualifiers |
|---|---|
| source | 1..120 |
| | mol_type = protein |
| | note = sp. Bp5365 strain MSMB43 |
| | organism = Burkholderia thailandensis |

SEQUENCE: 276
```
MNAPHAAAVS DAAALAAALE QALAQQQAPP PRATQRFDVA TASAGNGLAK LVLALMKLLH    60
ELLERQALRR IEAGSLNDDE IERLGLALMR QAEEIERLAA QFGFTDADLN LDLGPLGRLF   120
```

| SEQ ID NO: 277 | moltype = AA   length = 114 |
|---|---|
| FEATURE | Location/Qualifiers |
| source | 1..114 |
| | mol_type = protein |
| | note = DSM 273 |
| | organism = Chlorobium luteolum |

SEQUENCE: 277
```
MHEDKVQFQA SSVEEALRQL EGMKQGKESR IEANPDNVES GLARLVLTLI ELLRKLMEKQ    60
AMRRIDGGSL DEAQIDELGE TLMKLEMKMD ELKKTFNLTD SDLNLNLGPL GDLM         114
```

| SEQ ID NO: 278 | moltype = AA   length = 156 |
|---|---|
| FEATURE | Location/Qualifiers |
| source | 1..156 |
| | mol_type = protein |
| | note = PCC 8305 |
| | organism = Dactylococcopsis salina |

SEQUENCE: 278
```
MSEEESNLSR VDLNPASSNS DAGLAPLLLT VTELIRQLME AQVIRRMDAE LLTEAELDRA    60
GESLQRLEEE ILRLCEIFDV DPADLNVHLG ELGTLLPKEG GYYPGETSDQ PSILELLDRV   120
LHTGVVIDGN LDLGIAQLNL IQAKLHLVLT SQPINN                             156
```

| SEQ ID NO: 279 | moltype = AA   length = 128 |
|---|---|
| FEATURE | Location/Qualifiers |
| source | 1..128 |
| | mol_type = protein |
| | note = DSM 3385 |
| | organism = Desulfobacterium vacuolatum |

SEQUENCE: 279
```
MIKDPEAKDF KIESDSIDAF ARVMHADTSS CSSSSVTAGQ RQQRLKIDEE NIKNGLAQLV    60
MTLIKLLHEL LERQAIRRIE SGSLDDDQIE RLGLTLMQQC EEIDRLRKLF DLEEEDLNLD   120
LGPLGKLL                                                            128
```

| SEQ ID NO: 280 | moltype = AA   length = 121 |
|---|---|
| FEATURE | Location/Qualifiers |
| source | 1..121 |
| | mol_type = protein |
| | note = DSM 6799 |
| | organism = Desulfomonile tiedjei |

SEQUENCE: 280
```
MNPMNIAKVE SDSLGDFAEI MQTDWISSLH SDKEEKRLNL NQDSVKNGLG QLVLTLVKLL    60
HDLLERQAIR RMEAGTLTDT EIDRLGTTLM MQAQEIERLR SEFGLEEEDL NLDLGPLGKL   120
L                                                                  121
```

| SEQ ID NO: 281 | moltype = AA   length = 104 |
|---|---|
| FEATURE | Location/Qualifiers |
| source | 1..104 |
| | mol_type = protein |
| | note = DSM 771 |
| | organism = Desulfotomaculum acetoxidans |

SEQUENCE: 281
```
MYIDISEGSL KQGVLGLLLA LVEIIKDALK IQALKRIEGD SLTEDEIERL GNALHELEEA    60
LVEIEMEHNL QNVVQNIREG LDNVVNEVVD TFNPERWIAE NEFN                    104
```

| SEQ ID NO: 282 | moltype = AA   length = 155 |
|---|---|
| FEATURE | Location/Qualifiers |
| source | 1..155 |
| | mol_type = protein |
| | organism = Dolichospermum circinale |

SEQUENCE: 282
```
MLSTPADNFD ESLTTVSKSK NEAGLAPLLL TVLELLRQLM EAQVIRRMED NLLSESELER    60
AADSIQKLEE QILHLCETFE VDPAELNINL GDFGTLLPQS GSYYPGETGS RPSVLELLDR   120
LLNTGVVLDG EIDLGLAQLD LIHAKLRLVL TSKPI                              155
```

| SEQ ID NO: 283 | moltype = AA   length = 94 |
|---|---|
| FEATURE | Location/Qualifiers |
| source | 1..94 |
| | mol_type = protein |
| | note = strain ATCC 27094 |
| | organism = Enhydrobacter aerosaccus |

SEQUENCE: 283

```
MTKLLEAKTV DPDKAGDDLV KLVLALVETL RQLVERQAIR RVDSGVLNDD EVERLGLALL    60
RLEEKMSELK AHFGFGDEEL TLKLGSLGEL ARDV                                94

SEQ ID NO: 284          moltype = AA  length = 146
FEATURE                 Location/Qualifiers
source                  1..146
                        mol_type = protein
                        note = ATCC-43644
                        organism = Isosphaera pallida
SEQUENCE: 284
MSDSLFEVRS PSAAPPSPVN PGVADEWTAV LKDWDTLTAQ LRQATAPPNA ENSARSHATT    60
GRIDLDPEQV GDGLAKLVLT LLELIRQLLE RQAIRRLDAG SLDHEQTERL GLTLMRLAQR   120
MEELKTHFGL QGEDLNLDLG PLGKLL                                        146

SEQ ID NO: 285          moltype = AA  length = 98
FEATURE                 Location/Qualifiers
source                  1..98
                        mol_type = protein
                        note = LLAP12
                        organism = Legionella drancourtii
SEQUENCE: 285
MNDKREEDNA LPQRINLQPD DVKNGLGKLV LILIQLIHEL LERQAIGRIE AGDLSDEQID    60
RLGITLMKQA EEIDKLREVF GLTQEDLNLD LGPLGKLL                            98

SEQ ID NO: 286          moltype = AA  length = 157
FEATURE                 Location/Qualifiers
source                  1..157
                        mol_type = protein
                        note = NIES-843
                        organism = Microcystis aeruginosa
SEQUENCE: 286
MTLACTPYDS DNQALLTRPE SNSQAGLAPL LLTVVELVRQ LLEAQIIRRM EKGVLSESDL    60
DRAAESIQKL QEQILYLCEI FEVEPEELNV HLGEFGTLLP EAGSYYPGEE GIKPSVLELV   120
DRLLNTGVVV EGNVDLGLAQ LDLIHLKLRL VLTSQPV                            157

SEQ ID NO: 287          moltype = AA  length = 144
FEATURE                 Location/Qualifiers
source                  1..144
                        mol_type = protein
                        note = ATCC 29133
                        organism = Nostoc punctiforme
SEQUENCE: 287
MQAISKSKGS DSGLAPLLLT VVELIRQLME AQVIRRMDAG TLNDSELDRA AESLQKLEQQ    60
VVQLCEIFDI DPADLNINLG EMGNLLPQSG GYYPGETSSQ PSILELLDRL LNTGVVVEGD   120
LDLGLAQLSL VHAKLRLVLT SKPL                                          144

SEQ ID NO: 288          moltype = AA  length = 155
FEATURE                 Location/Qualifiers
source                  1..155
                        mol_type = protein
                        note = PCC 7120
                        organism = Nostoc sp
SEQUENCE: 288
MVCTPVEKSP NLLPTTSKAN SKAGLAPLLL TVVELIRQLM EAQVIRRMEQ DCLSESELEQ    60
ASESLQKLEE QVLNLCHIFE IEPADLNINL GDVGTLLPSP GSYYPGEIGN KPSVLELLDR   120
LLNTGIVVDG EIDLGLAQLN LIHAKLRLVL TSRPL                              155

SEQ ID NO: 289          moltype = AA  length = 132
FEATURE                 Location/Qualifiers
source                  1..132
                        mol_type = protein
                        note = 307
                        organism = Octadecabacter antarcticus
SEQUENCE: 289
MKTTSDSQFD SMKKILTDSS KEDSASCDPT DLLPNKSLPP SLSTSPETAA DDLVKLVLAV    60
IDTVRQVMEK QAIRRVESGA LAEAEIERLG LTLMRLEARM VELKSHFGLS NEDLNLHFGT   120
VQDLKDILND EE                                                       132

SEQ ID NO: 290          moltype = AA  length = 132
FEATURE                 Location/Qualifiers
source                  1..132
                        mol_type = protein
                        note = 238
                        organism = Octadecabacter arcticus
SEQUENCE: 290
MKTQNDTQFD SMKKILTDSG GGDPNPNGSP DQTQHASLPS NLSTDPETAA DDLVKLVLAV    60
IDTVRQVMER QAIRRVDSGA LADEEIERLG LTLMRLEERM ADLKSHFGLS NEDLNLNFGT   120
VQDLKDILND EE                                                       132
```

```
SEQ ID NO: 291            moltype = AA  length = 114
FEATURE                   Location/Qualifiers
source                    1..114
                          mol_type = protein
                          organism = Pelodictyon phaeoclathratiforme
SEQUENCE: 291
MDSDKILYYA GSADEIIEEL EKLKPGIQGR INATPDNVES GLAKLVLTLI ELIRKLIEKQ  60
AMRRIDGNSL SESQIEELGE TLMKLEKKME ELKGIFNLTD KDLNLNLGPL GDLM        114

SEQ ID NO: 292            moltype = AA  length = 156
FEATURE                   Location/Qualifiers
source                    1..156
                          mol_type = protein
                          note = NIES-30
                          organism = Phormidium tenue
SEQUENCE: 292
MTSENAEPDL STTLALQPPA KTDAGLAPLL LTVIELVRQL MEAQVIRRME SGDLDDNDLE  60
RAADSLRKLE EQVVSMCEIF DVDPADLNID LGEIGTLLPK EGNYYPGQKN QNPTILELLD  120
RLLDTGVVVE GDVDLGMAQL NLIHAKLRLV LTSKPI                           156

SEQ ID NO: 293            moltype = AA  length = 153
FEATURE                   Location/Qualifiers
source                    1..153
                          mol_type = protein
                          note = str. 7805
                          organism = Planktothrix agardhii
SEQUENCE: 293
MSSSEPSIET IITPKSSRKD AGLAPLVLTL VELIRQLMEA QVIRRMEGNT LSEEELDRAA  60
QSLQQLEIQV LKLCEIFEID PTDLNIELSE FGTLLPKSGS YYPGENTQNP SILELLDRLM  120
NTGIVVEGSV DLGLAQLNLI HAKLRLVLTS KPL                              153

SEQ ID NO: 294            moltype = AA  length = 110
FEATURE                   Location/Qualifiers
source                    1..110
                          mol_type = protein
                          note = 37
                          organism = Psychromonas ingrahamii
SEQUENCE: 294
MPFEHFKSNN QADVNSDTKP AASVGGLNLE SDDLKNGLGR LVLTLVKLLH ELLERQALRR  60
MDAGSLQDDE IERLGLAFMK QAEEIDRLRK EFGLEVEDLN LDLGPLGRLL            110

SEQ ID NO: 295            moltype = AA  length = 112
FEATURE                   Location/Qualifiers
source                    1..112
                          mol_type = protein
                          note = SB 1003
                          organism = Rhodobacter capsulatus
SEQUENCE: 295
MSAAMHLELG DVDAVLSQAA RSLAAGGRLT LDPERVEQDL ARLVLGIVEL LRKLMELQAI  60
RRMEAGSLTP EQEETLGLTL MRAEAALHEV AAKFGLQPAD LILDLGPLGR SV         112

SEQ ID NO: 296            moltype = AA  length = 110
FEATURE                   Location/Qualifiers
source                    1..110
                          mol_type = protein
                          note = 2.4.1
                          organism = Rhodobacter sphaeroides
SEQUENCE: 296
MTYPFPPLLL RDDRLPPTEA PVTAPRIALD PDRLEHDLAR ILLGLMEMLR QIMELQAIRR  60
MEAGSLSESQ QEQLGTTLMR AEAAIHEMAA RFGLTPADLS LDLGPLGRTI            110

SEQ ID NO: 297            moltype = AA  length = 91
FEATURE                   Location/Qualifiers
source                    1..91
                          mol_type = protein
                          note = 103S
                          organism = Rhodococcus hoagie
SEQUENCE: 297
MRRRIDSDPE SVERGLVALV LTLVELLRQL MERQALRRVD AGDLSDDQIE RIGTTLMLLE  60
EKMEELREHF GLEPEDLNID LGPLGPLLAE D                                91

SEQ ID NO: 298            moltype = AA  length = 115
FEATURE                   Location/Qualifiers
source                    1..115
                          mol_type = protein
                          note = ATCC 39006
                          organism = Serratia sp.
SEQUENCE: 298
MTTNQLSHHS PVFGPTSPAI QRPITEANRH KIDIDGERVR DGLAQLVLTL VKLLHELLER  60
```

```
QAIRRMDSGS LSDEEVERLG LALMRQAEEL THLCDVFGFK DDDLNLDLGP LGRLL         115

SEQ ID NO: 299          moltype = AA   length = 105
FEATURE                 Location/Qualifiers
source                  1..105
                        mol_type = protein
                        note = ATCC-43931
                        organism = Stella vacuolate
SEQUENCE: 299
MTGFLNGPAD VETLETALRG RVDIDPERVE QGLVKLVLMV VETLRQVIER QAIRRVESGS   60
LTDDEVERLG LTLMRLEEKM DQLRRQFDLG EEDLSMRLRL PLQEL                  105

SEQ ID NO: 300          moltype = AA   length = 127
FEATURE                 Location/Qualifiers
source                  1..127
                        mol_type = protein
                        note = strain DSM 235
                        organism = Thiocapsa rosea
SEQUENCE: 300
MSDTRTGTAP SSAASAAPDT STLQRANLLA DLLETKVAAA GRRIDIDPER VQRGLGQLVL   60
TVVKLLHVLL ERQAIRRVDG GDLDEDEIEQ LGLALMRQSE EIERLRRLLG LEEQDLNLDL  120
GPLGKLF                                                            127

SEQ ID NO: 301          moltype = AA   length = 160
FEATURE                 Location/Qualifiers
source                  1..160
                        mol_type = protein
                        note = PCC 7601
                        organism = Tolypothrix sp.
SEQUENCE: 301
MAMVCTPSEN SNDLLATNSK ANNQAGLVPL LLTVVELIRQ LMEAQVIRRM EEECLSESDL   60
ERAAESLQKL EEQVLNLCQI FEIDPADLNI HLGELGSLLP AAGSYYPGET GNTPSVLELL  120
DRLLNTGVVV DGELDLGVAQ LNLIHAKLRL VLTSKPLNTK                        160

SEQ ID NO: 302          moltype = AA   length = 153
FEATURE                 Location/Qualifiers
source                  1..153
                        mol_type = protein
                        note = IMS101
                        organism = Trichodesmium erythraeum
SEQUENCE: 302
MSLENSPEES LIVPIDKSKS NPEAGLAPLL LTVIELLREL MQAQVIRRMD AGILSDEQLE   60
RAAEGLRQLE EQVIKLCKVF DIPTEDLNLD LGEIGTLLPK SGEYYPGEKS ENPSVLELLD  120
RILNTGVVLD GTVDLGLAEL DLIHARLRLV LTA                               153

SEQ ID NO: 303          moltype = AA   length = 231
FEATURE                 Location/Qualifiers
source                  1..231
                        mol_type = protein
                        note = strain UV5
                        organism = Ancylobacter aquaticus
SEQUENCE: 303
MLYLYAILES PPPQKPLPPG IGGAAPLFVE SHALVCAASE AADAAIAREP SQIWRHQEVV   60
AALMEGRPVL PLRFGTVVED SAACLRLLAR HHAELSAQLD RVRHCVEFAL RVAGLSELAD  120
PGLDPNATPA GLGPGASHLR TLVRRERGWP VSSAAFPHDT LTAHAASRLL WARSPSQPDL  180
RASFLVQRRS ASAFLDDVNA LQRLRPDLGI TVTGPWPPYS FSDPDLSGGR E           231

SEQ ID NO: 304          moltype = AA   length = 223
FEATURE                 Location/Qualifiers
source                  1..223
                        mol_type = protein
                        note = strain PCC 7418
                        organism = Aphanothece halophytica
SEQUENCE: 304
MLYTYCFLFS PEKTLSLPQG FKGDLQMIEK GAIAAVVEPN LPKAELEEDD QKLVQAVVHH   60
DWVICELFRG LTVLPLRFGT YFRGEADLRS HLAAYEESYQ QKLTALTGKV EVTLKLTPIP  120
FSEEGSSSTA KGKAYLQAKK QRYQQQSNYQ TQQQEALEKL QEEIKKTYPQ LIHDEPKENT  180
ERFYLLIDSH SFSVFGEKME QWKQFLSSWS IEISDPLPPY HFL                    223

SEQ ID NO: 305          moltype = AA   length = 226
FEATURE                 Location/Qualifiers
source                  1..226
                        mol_type = protein
                        note = strain DSM 9035
                        organism = Aquabacter spiritensis
SEQUENCE: 305
MLYLYAVLEA PPPARSLPPG IGGGAPHFIE AFELVCAASE TPNRSVAPEP AEVWRHQQVV   60
EALIDRAPAL PLRFGTLVED ASACRRLLTR HRDALGAQLG RVRHCVEFAL RVSGLPEEVA  120
PDPGIGGGPG TSYLRTLARR EAGWPPSTAV FPHDGLAAHA AERLLWARST SQPDLRASFL  180
```

```
VRKPNVAAFL ADVSALQRVR PDLGITCTGP WPPYSFSDPD LSGVSP            226

SEQ ID NO: 306           moltype = AA  length = 269
FEATURE                  Location/Qualifiers
source                   1..269
                         mol_type = protein
                         organism = Bacillus-megaterium
SEQUENCE: 306
MGELLYLYGL IPTKEAAAIE PFPSYKGFDG EHSLYPIAFD QVTAVVSKLD ADTYSEKVIQ  60
EKMEQDMSWL QEKAFHHHET VAALYEEFTI IPLKFCTIYK GEESLQAAIE INKEKIENSL 120
TLLQGNEEWN VKIYCDDTEL KKGISETNES VKAKKQEISH LSPGRQFFEK KKIDQLIEKE 180
LELHKNKVCE EIHDKLKELS LYDSVKKNWS KDVTGAAEQM AWNSVFLLPS LQITKFVNEI 240
EELQQRLENK GWKFEVTGPW PPYHFSSFA                                 269

SEQ ID NO: 307           moltype = AA  length = 266
FEATURE                  Location/Qualifiers
source                   1..266
                         mol_type = protein
                         note = sp. Bp5365 strain MSMB43
                         organism = Burkholderia thailandensis
SEQUENCE: 307
MNDALYLFCF ARAEPLAPAW AKRAPGEPRL QLLHEGNLAA VLCDVSRSEF AGADAERRLA  60
DPAWIAGRVA VHAAAIEWTM RYSPVIPAQF GTLFSGAGRV IALMESCHAH IGRVLDHVEG 120
KTEWAVKGWL DRQAAADSQA ALLRADEPES AARTAGARYL RERQLQARAG QNLRDWLEQS 180
VPPISARLQR HAVEMCSRPC RASDSEHEIV ANWAFLVRNR DVPAFRRQAE AIDAEFATWG 240
LHFDFSGPWP PYSFCAPLTE ETTWSG                                    266

SEQ ID NO: 308           moltype = AA  length = 292
FEATURE                  Location/Qualifiers
source                   1..292
                         mol_type = protein
                         note = DSM 273
                         organism = Chlorobium luteolum
SEQUENCE: 308
MPCRLTVTWK SLRTAGLLPT AKGIQGRTER MAQNILYVYC IVRQLPGADI VARYPDLVFI  60
EAGSAYVAAK YVSPLEYSDA SMKLKLADEE WLDRNAREHL SVNVMIMAQQ TIIPFNFGTI 120
FKSRESLSGF LGDYGRKLDE SFDALEGREE WAVKAYCNES FLLKNLHLES PAIAAIEQEI 180
QAASPGKAYL LKKKKEAMSA SALEGVHQGH AKAVWGELAA LSKEHVLNRL IPEDVSGVDG 240
RMIVNGVFLI ANTDVGAFIR TTEDLGERYR DAGVFLDVTG PWPPYDFVDI PY        292

SEQ ID NO: 309           moltype = AA  length = 225
FEATURE                  Location/Qualifiers
source                   1..225
                         mol_type = protein
                         note = PCC 8305
                         organism = Dactylococcopsis salina
SEQUENCE: 309
MLYTYCLIAS SPSALSLPSG FRGELQLIKQ GAIAAIVEAE LPLEELEEND QKLIQAVIHH  60
DAVICEIFQQ IPLLPLRFGT YFPTEKDLLE HLDFKAEKYQ KKLQEIQDKV ELTLKLTPLP 120
FSTENASPME KQGKNYLKAK KQRYQEQTNY QSQQQAELNQ LQTQINQDYP QFIHGEPKEN 180
IERFYLLIKE RDRSVFSEQL EQWKKDFPTW TIEVSDPLPP YHFIE               225

SEQ ID NO: 310           moltype = AA  length = 269
FEATURE                  Location/Qualifiers
source                   1..269
                         mol_type = protein
                         note = DSM 3385
                         organism = Desulfobacterium vacuolatum
SEQUENCE: 310
MEKKKAVYLY CVTRANKFNA PGITGIDANT PVCFEHLENF VAVYNIIPLN TFVGTSAEEN  60
MKNIDWIGPR AMRHENVIER MMQESSVYPA RFATLFSSME NLRETLHLKS GLISRFLNQT 120
QHKCEYSLKG FINRKQLLEF LIKTKFKQEK KQLDGLSPGK KYFAQHQFNK KVETGINQWI 180
KRRCGIFLDH LTKRNPEVSP RELFTEKTEK NNLEMMFNLA FLIHNDSKSA FLQEISQAEK 240
EFSQTGISLV VSGPWAPYSF CKTTRGEGL                                 269

SEQ ID NO: 311           moltype = AA  length = 268
FEATURE                  Location/Qualifiers
source                   1..268
                         mol_type = protein
                         note = DSM 6799
                         organism = Desulfomonile tiedjei
SEQUENCE: 311
MSNVLYLFCL ARTGLVDHIE GTGITGTEDL ILKNFSGVTA VTCEVPEDDF SGESAEIKLQ  60
DLAWVGPRAV RHDRIIEEIM QYSPVFPAPF GSLFSEKRL GTLIESNIDA IREFLDHTAD 120
KQEWSVKGLV CKSKAVDEIF TGKLKILSET LSSSPAGMRY FKERQMRSEA EKELSGKVKA 180
ACTVVGEKLL ACSNNFRQRK NISFGKAEGD KQLVVNWAFL VDHSRISYFL DQVEHANSNY 240
QAGGLAFECS GPWPPYSFCP SLHMEPTR                                  268

SEQ ID NO: 312           moltype = AA  length = 259
```

```
FEATURE                 Location/Qualifiers
source                  1..259
                        mol_type = protein
                        note = DSM 771
                        organism = Desulfotomaculum acetoxidans
SEQUENCE: 312
MNLIDDCKAK YIYCIGENPG NWPSEVMGVE GSLVYHVVYR DIAAVVHDCA EQPYNSDDNN    60
KVIDWVLGHQ LVVDKACSCY SSVLPFTFNS IVKGKEDLSS HEILVNWLED NYDNFKLKLG   120
KIKGKKEYSV QLFLDKQVSL SLLQSESDIL ELQVELLGSA KGKAYFVQEK INKKIGELMA   180
NRADSYCRQF YHEISSVVSE CKLCKLKQAG RNEIMIIINLV CLAGDNEVEV LGDVLEKIKS   240
NDIAIKIKFS GPWPAYSFV                                                259

SEQ ID NO: 313          moltype = AA  length = 240
FEATURE                 Location/Qualifiers
source                  1..240
                        mol_type = protein
                        note = strain ATCC 27094
                        organism = Enhydrobacter aerosaccus
SEQUENCE: 313
MLYVYGIADN AFEVLRGAGL LNSDVFAVPA GCLAAAASKL AQGGIETTPQ GVWRHEQVLR    60
QLMQDHAVLP LRFGTICRDR ETLTDRLMEA SDDLVRGLGR VRGKVEIALR IVDEREHEAH   120
PVPSETPTVD AIGGGRGTAY LRARRRHHAA EMGREARAER VGKMLSAYID VGAEDLVCSV   180
APEGDHAVSV SCLLGRDQLA TLQAALERFQ SDHPAIGLSW TGPWTPYSFV APSLFGVGLP   240

SEQ ID NO: 314          moltype = AA  length = 266
FEATURE                 Location/Qualifiers
source                  1..266
                        mol_type = protein
                        note = LLAP12
                        organism = Legionella drancourtii
SEQUENCE: 314
MNKALYLFCL TPASDLPMME GELLPNFSPL FIHPFQTFNA ILSWVPAKEY QEQSTDSNLI    60
NTEEFMQRVF FHELVVEKIM RDEAVFPIGF GTLFSSIASL EEQILTHQTL ISSCLANLNQ   120
KDEYAVRVYL NQDKALESLL SVMLQERESS WASSSPGVQY LKKQQLHNEI QRNLNQHLGG   180
MLDEVLSMFQ RHATDFKSRE NTAQSSDIHG TSILHWAFLI PRVVSSIFKE QVDLMNAKYN   240
PFGLHFVLTG PWPAYSFCTL QSVEAP                                        266

SEQ ID NO: 315          moltype = AA  length = 240
FEATURE                 Location/Qualifiers
source                  1..240
                        mol_type = protein
                        note = BDU141951
                        organism = Lyngbya confervoides
SEQUENCE: 315
MRWHRSEAVI SYCDLSMIYL YALCPNSTET NNLPEGIGTA QVEVLTVGTL GAVIERDVDI    60
AQIQKDDAQL MAAVLAHDRI LSHLFTYSPL LPLRFGTQFS NSEAVTTFLK TQGETYRQKL   120
SHLQDRAEYL VKLIPQPLDL PAIASDLKGR EYFLAKKQRL QDHTAALNQQ ADELQTFLTD   180
LATQDIPLVR SAPQDHEERL HVLLSRDTDT TEQVIMTWQE QLPNWQVVCS EPLPPYHFAA   240

SEQ ID NO: 316          moltype = AA  length = 240
FEATURE                 Location/Qualifiers
source                  1..240
                        mol_type = protein
                        note = 307
                        organism = Octadecabacter antarcticus
SEQUENCE: 316
MKRLYVYGIV GATSFDDPLP NGHDEASVFA LVSGDIAVAV SFVERSAVEA SAANVWLHDN    60
VLSALMTRYA VLPMRFGTIA VGATQLLEGI VKRQKQLMKD LMRLNENVEI ALHISGKNWE   120
KVNQKVTKKN TDQAITQGTA YLLGRQQSLY GSDKTQLLVQ NVRRAIRSGL DPLMKDVIWP   180
IDKPQALPFK ASCLINRNDV ASFVQIVNDI AAQNLDARVT CTGPWAPYSF VGKSGVEGET   240

SEQ ID NO: 317          moltype = AA  length = 240
FEATURE                 Location/Qualifiers
source                  1..240
                        mol_type = protein
                        note = 238
                        organism = Octadecabacter arcticus
SEQUENCE: 317
MTKLYVYGIV GATHFDVKLP NGHDEAPVFA IVSGDLAVAV SSLERSAVEA SAANVWLHEN    60
VLSALMEGHA VLPMRFGTIA TGAAQLLGDI VKRRGQLMKD LTRLDGKVEI ALRISGKNRE   120
KVEQRIAGQI VDTNVTQGVA YLQEKQQNLY GSFYTQSSVQ CARRAIRSQL DPFIVEAIWP   180
TDEPQMLPFR ASCLIKKGDI ARFVQTVDDV VVKVSDIRVT CTGPWAPYSF VGQSGSEAET   240

SEQ ID NO: 318          moltype = AA  length = 266
FEATURE                 Location/Qualifiers
source                  1..266
                        mol_type = protein
                        organism = Pelodictyon phaeoclathratiforme
SEQUENCE: 318
```

```
MVAIQERLIY IFCVTSEPPL LQQYQLQKGI CVVDVDGLFV TTMDVTDNDF AENQLQSNLS    60
DVVWLDTKVR EHLDVITSIM QHVKSLIPFN FGTLYKSESS LMQFIIKYAE EFKKNLVYLE   120
EKEEWAVKLY CNKNKIVENI THLSKKVSDI NALIQNSSIG KAYILGKKKN EIIENEIINI   180
YNTYSKKIFT KFSILSEEFR FNPIPNNETL EKEDDMILNV VLLLNKANVE SFIETSDQLI   240
IQHQNIGLNI EITGPWPCYS FINISH                                      266

SEQ ID NO: 319         moltype = AA   length = 249
FEATURE                Location/Qualifiers
source                 1..249
                       mol_type = protein
                       organism = Pelodictyon phaeoclathratiforme
SEQUENCE: 319
MPLIIYAIFD SINYIDSFSS YVDAISLKSK IKLEIISTST LSAIVSRTTD EKKQACQNDV    60
MIYATIIGDI AAKYSILPMR YGSIVSSPFD VTELLKNHNE TFVTIIKKIT DKEEYSLRIL   120
YSHQDKEKNN IEDLFDLPQN VPDILHGNTD SKKYLLNKYI KHLSEEKRLQ YIDKIQSIVA   180
CNLQKITDLI VYNKQTTTGF IVDAVFMIER SKKSELLDLV IQMQTLFSEH NVVLSGPWPP   240
YNFSNINIG                                                         249

SEQ ID NO: 320         moltype = AA   length = 270
FEATURE                Location/Qualifiers
source                 1..270
                       mol_type = protein
                       note = 37
                       organism = Psychromonas ingrahamii
SEQUENCE: 320
MKNSNHSGLD PNQALYLYCF VHADSIQSVT SQAIEKDSPV FIYQWQDIAA VLSHVPTSYF    60
TGYDDEEPEQ TIARILPRTQ LHEQVIEEVM RQSPVFPAQF GTLFSSQESL EQEISQQYLA   120
ITHTLKEVSG SVEWAVKGVL DRGVAEKALY SQQLTEQQNS LSSSPGMRHL QEQRLRRETQ   180
SKLNSWLHQL YTDIATPLSE LSGDFFQRKI PSSIEEGKEV ILNWAFLVPE SAGDDFHAQI   240
DKLNQRLNSF GLVIQCSGPW PPYSFCNQSS                                  270

SEQ ID NO: 321         moltype = AA   length = 270
FEATURE                Location/Qualifiers
source                 1..270
                       mol_type = protein
                       note = 37
                       organism = Psychromonas ingrahamii
SEQUENCE: 321
MKNSNHSGLD PNQALYLYCF VHADSIQSVT SQAIEKDSPV FIYQWQDIAA VLSHVPTSYF    60
TGYDDEEPEQ TIARILPRTQ LHEQVIEEVM RQSPVFPAQF GTLFSSQESL EQEISQQYLA   120
ITHTLKEVSG SVEWAVKGVL DRGVAEKALY SQQLTEQQNS LSSSPGMRHL QEQRLRRETQ   180
SKLNSWLHQL YTDIATPLSE LSGDFFQRKI PSSIEEGKEV ILNWAFLVPE SAGDDFHAQI   240
DKLNQRLNSF GLVIQCSGPW PPYSFCNQSS                                  270

SEQ ID NO: 322         moltype = AA   length = 262
FEATURE                Location/Qualifiers
source                 1..262
                       mol_type = protein
                       note = ATCC 39006
                       organism = Serratia sp
SEQUENCE: 322
MTMNTEAQTE QAIYLYGLTL PDLAAPPILG VDNQHPINTH QCAGLNAVIS PVALSDFTGE    60
KGEDNVQNVT WLTPRICRHA QIIDSLMAQG PVYPLPFGTL FSSQNALEQE MKSRATDVFV   120
SLRRITGCQE WALEATLDRK QAVDVLFTEG LDSGRFCLPE AIGRRHLEEQ KLRRRLTTEL   180
SDWLAHALTA MQNELHPLVR DFRSRRLLDD KILHWAYLLP VEDVAAFQQQ VADIVERYEA   240
YGFSFRVTGP WAAYSFCQPD ES                                          262

SEQ ID NO: 323         moltype = AA   length = 226
FEATURE                Location/Qualifiers
source                 1..226
                       mol_type = protein
                       note = ATCC-43931
                       organism = Stella vacuolate
SEQUENCE: 323
MLYLYAVLEA LPAARTLPAG IGGGELLFVE AFELVCAASE TPERAIAPEP TQVWRHQQVV    60
EALIDCAAAL PLRFGTLVED AVACRRLLTR HREALCAQLD RVRHCVEFAL RVSGLREEVG   120
SDHVIGGGPG VSYMRALARR EASWPPSTGT FPHDGLAAHA ADRLLWSRSA SQPDLRASFL   180
VLKPNVAAFL ADVSALQRMR PDLGITCTGP WPPYSFSDPD LSGMSP                226

SEQ ID NO: 324         moltype = AA   length = 250
FEATURE                Location/Qualifiers
source                 1..250
                       mol_type = protein
                       note = strain DSM 235
                       organism = Thiocapsa rosea
SEQUENCE: 324
MDAFYCFCFA PACLASDLRF DDCGWEDPIE IRRLAGLDVI LSRVPLGRFA GAEAEQRLAD    60
LEWLVPRAQA HDRVITRTME RSTVFPPLTFA TLFSSLPALA LEVAARRRAL LDFFERMAGR   120
EEWAVKVSMD RERVIATRMQ SLYPEGGDVP AGGRGYLLKQ RRRGEAEQAI GPWLKGGQIGC  180
```

```
LDEALRPSCE TLLIRPLRDE MVASRACLVA RDLGPSLSEA IERSREAFAD QGLDLHCSGP    240
WPLYSFCGTP                                                          250

SEQ ID NO: 325          moltype = AA  length = 225
FEATURE                 Location/Qualifiers
source                  1..225
                        mol_type = protein
                        note = IMS101
                        organism = Trichodesmium erythraeum
SEQUENCE: 325
MSYYVYGFLY LPESCLALPK GMEKEVELVP YQNIAAVVEA NVSIEAIQET EEKLLEAILA    60
HDRVVREIFQ QVSMLPLRFG NAFALRENII NDLQNNQQQY LNILTKLQQQ AEYTITFTPV    120
SYPSTLEVSK VRGKAYLLAK KQQFEQQQAF QTKQRQQWEN IRQLIFKNYP KAVFRDSTES    180
KIKQVHLLAN RDARVITTEE LSTWQTECSY WQITLSEQLP PYHFV                    225

SEQ ID NO: 326          moltype = AA  length = 335
FEATURE                 Location/Qualifiers
source                  1..335
                        mol_type = protein
                        organism = Anabaena flos-aquae
SEQUENCE: 326
MTTTKVNHKR AVLRLRPGQF VVTPAIERVA IRALRYLKSG FPVHLRGPAG TGKTTLAMHL    60
ANCLDRPVML LFGDDQFKSS DLIGSESGYT HKKVLDNYIH SVVKLEDEFK QNWVDSRLTL    120
ACREGFTLVY DEFNRSRPEV NNVLLSALEE KILSLPPSSN QPEYLSVNPQ FRVIFTSNPE    180
EYAGVHSTQD ALMDRLVTIS MPEPDEITQT EILIQKTNID RESANFIVRL VKSFRLATGA    240
EKTSGLRSCL MIAKVCADNN IPVTTESLDF PDIAIDILFN RSHLSMSEST NIFLELLDKF    300
SAEELEILNN RVTGDNDFLI DNSQFVSQQL AGQPN                               335

SEQ ID NO: 327          moltype = AA  length = 357
FEATURE                 Location/Qualifiers
source                  1..357
                        mol_type = protein
                        note = strain UV5
                        organism = Ancylobacter aquaticus
SEQUENCE: 327
MTSEAASKDP ISLLSGFGAG AASSGPKAGG RSTPSALTPR PRTGFVEAEQ VRDLTRRGLG    60
FLNAGYPLHF RGPAGTGKTT LALHVAAQLG RPVIIITGDN ELGTADLVGS QRGYHYRKVV    120
DQFIHNVTKL EETANQHWTD HRLTTACREG FTLVYDEFTR SRPETHNVLL GVFEERMLFL    180
PAQAREECYI KVHPEFRAIF TSNPQEYAGV HASQDALADR LATIDVDYPD RAMELAVASA    240
RTGMPEASAA RIIDLVRAFR ASGDYQQTPT MRAGLMIARV AAQEGFEVSV DDPRFVQLCS    300
DALESRIFSG QRAEEVAREQ RRAALHALID THCPSAAKPR ARRAGGAVRA SIEGAQS      357

SEQ ID NO: 328          moltype = AA  length = 359
FEATURE                 Location/Qualifiers
source                  1..359
                        mol_type = protein
                        note = NIES-81
                        organism = Aphanizomenon flos-aquae
SEQUENCE: 328
MTKTNHKRAV LRVRPGQFVV TPAIEQVAIR ALLYLKSGFP IHLRGPAGTG KTTLALHLAH    60
CLDRPVMLLF GDDEFKSSDL IGSESGYTHK KLLDNYIHSV VKVEDEFKQN WVDSRLTLAC    120
REGFTLVYDE FNRSRPEVNN VLLSALEEKI LSLPPSSNQP EYLSVSPQFR AIFTSNPEEY    180
CGVHSTQDAL MDRLVTINMP EPDEITQTEI LIQKTNIQKE SAHLIVRLVK SFRIATGAEK    240
TSGLRSCLMI AKVCADNNLV AEPENSFFQE IAMEILSNRT HLSVNESTDI FLDVISQFSN    300
KEIEIEILNDAE LGSLPTMDTL ANTDLGNDVP LEKEASDYVI QQKNNEFKGF QKPSTKVLN   359

SEQ ID NO: 329          moltype = AA  length = 337
FEATURE                 Location/Qualifiers
source                  1..337
                        mol_type = protein
                        note = strain PCC 7418
                        organism = Aphanothece halophytica
SEQUENCE: 329
MTTVLHARPK GFVSTPTIDR ISRRAWRYLQ SGFSIHLRGP AGTGKTTLAM HLADLLNRPI    60
MLLYGDDEFK STDLIGSNTG YTRKKVVDNY IHSVVKEEDE LRQQWVDSRL TMACREGFTL    120
VYDEFNRSPP EVNNVLLSAL EEKLLVLPPD SHRSEYVRVS PNFRAIFTSN PEEYWGVHGT    180
QDALLDRVVT INVPEPDLET QREIIVQKVG INADDGDMIV NFVRNFRDRA EMENSSGLRS    240
CLMIAQVCHQ HEIPVQTSNE DFQDICYDIL TSRCPLSTQE SISLLEQLFR EYELELVVED    300
EDEDVPSVIV EGETEDLSSD EKPHLRLSHP FGNTEND                             337

SEQ ID NO: 330          moltype = AA  length = 364
FEATURE                 Location/Qualifiers
source                  1..364
                        mol_type = protein
                        note = strain DSM 9035
                        organism = Aquabacter spiritensis
SEQUENCE: 330
MSTEPAPLVS PSQDVETTPQ RPARPEPAEA LAVGYRLSAR PASPATLTPR PRADFVETDQ    60
VKDLTRRGLG FLRAGYPLHF RGPAGTGKTT LALHVAAQLG RPVIVITGDN ELGTADLVGS    120
```

```
QRGYHYRKVV DQFIHNVTKL EETANQRWTD HRLTTACREG YTLVYDEFTR SRPETHNVLL    180
GVFEEKILFL PAQAREECYI RVHPDFRAIF TSNPQEYAGV HASQDALADR LATIDVDYPD    240
RGMELAVASA RTGLGETEAA RIIDLVRAFR ASGDYQQTPT MRASLMIARV AAQEGLRVSI    300
DDDPGFVQLCM DALESRMFSG ARLEAATRET SRAALLALLA VHCPSEAPIV RVTAARRAKK   360
ADAS                                                                364

SEQ ID NO: 331          moltype = AA  length = 394
FEATURE                 Location/Qualifiers
source                  1..394
                        mol_type = protein
                        note = NIES-39
                        organism = Arthrospira platensis
SEQUENCE: 331
MTTVLRAVPK GFVNTPAIER ITVRALRYLQ SGFSVHLRGP AGTGKTTLAL HLADLLNRPI    60
MLIFGDDELK SSDMIGNQTG YTRKKVVDNF IHSVVKLEDS LKQNWIDSRL TLACREGFTL    120
VYDEFNRSRP EVNNVLLSAL EEKLLVLPPN NSRSEYIRVN PHFRAIFTSN PEEYCGVYST    180
QDALLDRLIT MNMPEPDEAT QQEILIQKVA VTPEEAQTIV TLVQQFREAT HAIAPSKIQT    240
VARQQTNADK ASGLRPSLML ARICQEHNIP IVPIDPDFQE VCRDILLSRA IGDITELESR    300
LHQIFDHLSG LENDQIIALP PREELTTSSV PNNLSDTEQK IYTYIKDSDG ARVSEIEIAL    360
GLNRVQTTDA LRSLLRKSYL TQQDNRLFVV YEGD                               394

SEQ ID NO: 332          moltype = AA  length = 308
FEATURE                 Location/Qualifiers
source                  1..308
                        mol_type = protein
                        organism = Bacillus-megaterium
SEQUENCE: 332
MTVLTDKRKK GSGAFIQDDE TKEVLSRALS YLKSGYSIHF TGPAGGGKTS LARALAKKRK    60
RPVMLMHGNH ELNNKDLIGD FTGYTSKKVI DQYVRSVYKK DEQVSENWQD GRLLEAVKNG    120
YTLIYDEFTR SKPATNNIFL SILEEGVLPL YGVKMTDPFV RVHPDFRVIF TSNPAEYAGV    180
YDTQDALLDR LITMFIDYKD IDRETAILTE KTDVEEDEAR TIVTLVANVR NRSGDENSSG    240
LSLRASLMIA TLATQQDIPI DGSDEDFQTL CIDILHHPLT KCLDEENAKS KAEKIILEEC    300
KNIDTEEK                                                            308

SEQ ID NO: 333          moltype = AA  length = 351
FEATURE                 Location/Qualifiers
source                  1..351
                        mol_type = protein
                        note = S58
                        organism = Bradyrhizobium oligotrophicum
SEQUENCE: 333
MLRSDRAAIA GGQRGSRAQG DAVARNDAAA GSRAAIAQIS PRPDADNAAL SPAPRTDLFE    60
NPQLASMAAR ALTYLNAGIP VHLRGPAGTG KTTMAMQLAA RLGRPVVLLT GDDGLTAAHL    120
VGREIGTKSR QVVDRYVHSV RRVETETSSM WCDAVLAQAV VEGLTFVYDE FTRSPPQANN    180
PLLSVVEERI LIFPAGSRKE RLVHAHPEFR AILTSNPEEY AGVSRPQDAL LDRLITFDLD    240
DYDRETEIGI VSNRTGLAYA EAGVIVDLVR GVRRWPKAHH PPSMRSAIMI ARIVARELIT    300
PSVDDPRFVR LCLDVLAAKA KPTDRDDRDR FAATLLRLMN NHCPAGAIDG G            351

SEQ ID NO: 334          moltype = AA  length = 287
FEATURE                 Location/Qualifiers
source                  1..287
                        mol_type = protein
                        note = sp. Bp5365 strain MSMB43
                        organism = Burkholderia thailandensis
SEQUENCE: 334
MEASAEFVQT PAVRNLTERA LTYLGAGYGV HLAGPSGTGK TTLAFHIAAQ LGRQVVLMHG    60
DDELGSADLV GRGAGYRRSR VVDNFIHSVV KTEEEMTTTW IDNRLTTACQ HGLTLIYDEF    120
NRSRPEANNA LLPVLSEGIL NLPNRMTGAG YLTVHPGFRA IFTSNPEEYV GVHKTQNALM    180
GRLITIQVGH YDRETEVEIV RARSGIARAD AERIVDLTRR LRDADDNGHH PSIRAAIALA    240
RALSYCGGEA TPDNAGYVWA CRDILGVDLE QDARTRSQAG RRTKARR                 287

SEQ ID NO: 335          moltype = AA  length = 308
FEATURE                 Location/Qualifiers
source                  1..308
                        mol_type = protein
                        note = DSM 273
                        organism = Chlorobium luteolum
SEQUENCE: 335
MRAAVNDNEM NTVLAPRPMA NFVETEYIRD ITERGLTYLK AGFPVHFRGP SGTGKTTVAM    60
HLAGKIGRPV VVIHGDSEYK TSDLIGSEQG YKFRRLNDNF IHSVHKYEED MSKQWVNNRL    120
SIAIKKGFTL VYDEFTRSRP EANNILLPIL QEKMLSTSAS NEEDYYMKVH PEFRAIFTSN    180
PEEYAGVNRT QDALRDRMVT MDLDYFDYET ERVTHAKSE LTLVEDSEKIV QVVRGLRESG    240
KTEFDPTVRG SIMIARTLHI MQVRPEKTND AVRKVFQDIL TSETSRVGSK TNQEKVRAIV   300
NDLIEAYL                                                            308

SEQ ID NO: 336          moltype = AA  length = 273
FEATURE                 Location/Qualifiers
source                  1..273
                        mol_type = protein
```

```
                    note = PCC 8305
                    organism = Dactylococcopsis salina
SEQUENCE: 336
MTTVLHARPK GFVSTPTIDR ISGRAWRYLQ SGFSIHLRGP AGTGKTTLAM HLADLLNRPI  60
MLLYGDDEFK STDLIGSNTG YTRKKVVDNY IHSVVKEEDE LRQQWVDSRL TMACREGFTL 120
VYDEFNRSPP EVNNVLLSAL EEKLLVLPPD SNRSEYVRVS PNFRAIFTSN PEEYWGVHGT 180
QDALLDRVVT INVPEPDLET QQEIITQKVG INANDGEKIV NFVRQFRDRA AVKNSSGLRS 240
CLMIAQVCHQ HEIPVQTSDE GFRDICYDIL SSR                             273

SEQ ID NO: 337          moltype = AA  length = 316
FEATURE                 Location/Qualifiers
source                  1..316
                        mol_type = protein
                        note = DSM 3385
                        organism = Desulfobacterium vacuolatum
SEQUENCE: 337
MSASMSSMKE TRQRMSAPEQ DNVVPEAGSD FVETPYVKDI TDRALAYLHV GYPVHFSGPA  60
GTGKTTLAFH VAAKLKRTVM LIHGDDEFGS SDLIGKDSGY RKAKVVDNYI HSVVKTEESM 120
NTVWADNRLT IACQQGCTLV YDEFTRSRPE ANNAFLSVLE EKILNIPSLR DIDQGYLQVH 180
PEFRAIFTSN PEEYAGVHKT QDAMMDRLIT ITLDHFDRDT EVQVTMSKSD LPQKDAEKIV 240
DIVRKLRKTG VNNHRPTIRA CIAIGKILKH MGGGASKDNF VFKQICRDVL NVDTTKVTRD 300
GEPLLPRKID ELINSL                                                316

SEQ ID NO: 338          moltype = AA  length = 337
FEATURE                 Location/Qualifiers
source                  1..337
                        mol_type = protein
                        note = DSM 6799
                        organism = Desulfomonile tiedjei
SEQUENCE: 338
MNGAELRIAS IETEVITANN ENIVPEAGDR FVNTPHVEEL TARAMAYLEV GYSVHFSGVA  60
GTGKTTLAFH AAAKLGRPVI LVHGDHEFGS SDLIGRDAGY KKSRLVDNFI HSVVKTEEEM 120
RSLWVDNRLT TACRDGYTLI YDEFTRSRPE ANNVLLSILE EKILNLPSLR RTGEGYLEVH 180
PSFRAIFTSN PEEYAGVHKT QDALMDRIIT INVDHYDRET EIEITRAKSG VCKQDATVIV 240
DIIRELRLLG VNNHRPTIRA AIAIARVLAH TGEHADQHNS VFQWLCKDVL STDTVKVSRG 300
GSPLMAKKVE EVIRKVCGRT GGKRSGKPVG SKEETSE                         337

SEQ ID NO: 339          moltype = AA  length = 307
FEATURE                 Location/Qualifiers
source                  1..307
                        mol_type = protein
                        note = DSM 771
                        organism = Desulfotomaculum acetoxidans
SEQUENCE: 339
MQLNGLDKNS IINPVVLSDF VVTDYISNVV DRALAYIKAG FAIHLRGRSG TGKTSIAMYI  60
SSKLNRPTLV IHGDEEFRTS DLIGGRYGYR IRKTIDNFVQ SVVKVEEDLV ERWVDSRLTT 120
ACKNGYTLVY DEFTRSRPEA NNILLSVLQE RLLDISVARG AEEGYVKVHP DFTAIFTSNP 180
EDYAGVYGSQ DALRDMVTL DLDNYDKETE ISIIKSKSKL SREDSERVVN ILRDLRELGD 240
CEYGPTIRGG IMIAKTLQVL GAPVDKNNEM FRQICEEVLA SETSRAGNLQ ALRKVRKVIN 300
ELFNKYA                                                          307

SEQ ID NO: 340          moltype = AA  length = 352
FEATURE                 Location/Qualifiers
source                  1..352
                        mol_type = protein
                        organism = Dolichospermum circinale
SEQUENCE: 340
MSITKVNHKR AVLRLRPGQF VVTPAIERVV IRALRYLRSG FPIHLRGPAG TGKTTLGMHL  60
ANCLDRPVML LFGDDQFKSS DLIGSESGYT HKKLLDNYIH SVVKVEDEFK QNWVDSRLTL 120
ACREGFTLVY DEFNRSRPEV NNVLLSALEE KILSLPPSSN QPEYLSVNPQ FRVIFTSNPE 180
EYCGVHSTQD ALMDRLVTIN MPEPDEITQT EILIQKTNIG RESANLIVRL VKSFRLATGA 240
EKTSGLRSCL MIAKICADHD IPASTEDLDF REIAIDILFN RAQLSISEST DIFMGLLEQF 300
SAEEIKVLND THFPTDELLI NNSQFITQEL VTQPNTELAT DIPQELRKTE QN         352

SEQ ID NO: 341          moltype = AA  length = 321
FEATURE                 Location/Qualifiers
source                  1..321
                        mol_type = protein
                        note = strain ATCC 27094
                        organism = Enhydrobacter aerosaccus
SEQUENCE: 341
MSMDQAEEIG VVTTIEPRPR ADFVRTQSVE ATARRALGYL NAGFSVHFRG PAGTGKTTLA  60
LHLAALLGRP MVMITGDEEM LTSTLVGTQH GYHFRRVVDR FIHTVTKTEE TADKRWADHR 120
LTTACREGYT LIYDEFTRSR PEANNVLLSV LEEGLLVLPA QNQNEPYIKV HPNFRVIFTS 180
NPQEYAGVHD AQDALGDRIV TIDMGHADRE LELAIAAARS GLPPTQVAPI VDMVREFRET 240
GEYDQTPTLR TSIMICRMMS QERLAPTIED QQFVQICMDI LGGKSLPGGK GDNKRAQQQK 300
MLLSLIEHHC PARSFTSVGE V                                          321

SEQ ID NO: 342          moltype = AA  length = 345
```

| FEATURE | Location/Qualifiers |
|---|---|
| source | 1..345 |
| | mol_type = protein |
| | note = ATCC-43644 |
| | organism = Isosphaera pallida |

SEQUENCE: 342

```
MDYESTALQL KPRPDFVATP WVRELADRAL GYLTAGYPVH FSGPAGTGKT TLAMHLAALV   60
NRPVVLLHGD DEFGSSDLVG DHLGFRSTKV VDNFIHSVVK TEQSVSKTWV DHRLTTACRH  120
GFTLIYDEFN RSRPEANNIL LTILEERLLE LPPIAGGRDG SGPLRVHPEF RAIFTSNPEE  180
YAGVHKTQDA LLDRMITISM GGHDEATETE ITAAKSGLSR DEAARIVELA RAVRALKPLR  240
HPPTIRSCLM IAKVAALRKV PIDPNDALFL AICRDVLRID ALPVDDPEAT FAELIRRVFA  300
PTPAVAPPRV PTTGFAANRV VPIPRRPLAA SASPPPGANG HAHLR                 345
```

| SEQ ID NO: 343 | moltype = AA length = 335 |
|---|---|
| FEATURE | Location/Qualifiers |
| source | 1..335 |
| | mol_type = protein |
| | note = LLAP12 |
| | organism = Legionella drancourtii |

SEQUENCE: 343

```
MMTQENNGSL TDSKNNDKLI RFVNNRSDNI LLEASEEFTE TPHIRGISER ALAYLDIGYP   60
IHLLGPAGTG KTTVALHIAA QLGRPVILIH GDDEFTGADL VGRGTGYHHS KLVDNFIHSV  120
LKTEEEMTTM WTDNRLTTAC EQGYTLIYDE FNRSRAEANN ALLSVLSEGI LNLPGRRERD  180
GIGIYVDVHSN FRAIFTSNSE EYVGIHKTQN ALADRLIAIK MDYPDQQSEI QIIEKKSTLP  240
RKDIEIIVNL ARELRLKSEK RPSIRGCIAI ARVLAYHNRH AHADDPIFQA VCQDIFGISK  300
EFLKQLLHPM DSGLQKRSEK NQESIKKYKT KNQKL                             335
```

| SEQ ID NO: 344 | moltype = AA length = 421 |
|---|---|
| FEATURE | Location/Qualifiers |
| source | 1..421 |
| | mol_type = protein |
| | note = BDU141951 |
| | organism = Lyngbya confervoides |

SEQUENCE: 344

```
MSTVLQARPR NFVSTPAVER IARRALRYLQ SGYSVHLRGP AGTGKTTLAL HLADLLSRPI   60
MLVFGDDEFK TSDLIGNQSG YTRKKVVDNY IHSVVKVEDE LRHNWVDSRL TLACREGFTL  120
VYDEFNRSRP EVNNVLLSAL EEKLLVLPPS GHRPEYLRVN PHFRAIFTSN PEEYAGVHGT  180
QDALLDRLIT IHMPEPDELT QQQILIQKVG IEPADALMIV RLVKAFKSQM GNHSATSLRP  240
SLMIANICHE HGVAMMTEDA DFRDVCSDVL LSRVTNELSP ATHTLWDLFN ELTASADVLG  300
PESNSTDVSP QPEADKPVET KGSKGKSTTK SKAKESAKAS EEADEAGDDS ASAPELDEIE  360
SSILTFLTAR ESASLSEIES ELSLTRFKAV DALRSLVEAG YLQKQNGAGK PAIYGLVPEE  420
S                                                                421
```

| SEQ ID NO: 345 | moltype = AA length = 346 |
|---|---|
| FEATURE | Location/Qualifiers |
| source | 1..346 |
| | mol_type = protein |
| | note = NIES-843 |
| | organism = Microcystis aeruginosa |

SEQUENCE: 345

```
MTVTETQTRR AVLSLRPGQF VVTPSIDQIA TRALRYLNSG FSIHLCGPAG TGKTTLAMHL   60
ANCLARPVML IFGDDDFTSS DLIGSQSGYT HKKLMDNYIH SVLKVEDELK HNWVDSRLTM  120
ACREGFTLVY DEFNRSRPEV NNVLLSALEE KILTLPPTSH QPDYLQVNSQ FRAIFTSNPE  180
EYCGVHATQO ALMDRLVTIN MPEPDQLTQT EILAQKTGIG REDALFIVNL VKTFRVKTAT  240
EKTSGLRSCL MIAKVCASHD IAANSADSDF RDICADVLLS RTNLSVDKSR AILWEILEDN  300
PLESLSFLEE EEPSDAQVST SEPSTGNQSL KAIQSLLRGN LPQRKD                 346
```

| SEQ ID NO: 346 | moltype = AA length = 390 |
|---|---|
| FEATURE | Location/Qualifiers |
| source | 1..390 |
| | mol_type = protein |
| | note = ATCC 29133 |
| | organism = Nostoc punctiforme |

SEQUENCE: 346

```
MTTVLNASPQ RFVNTPAVQR IAQRALRYLQ SGFSIHLRGA AGVGKTTLAM HLADLLNQPI   60
ILLFGDDEFK TSDLIGNQLG YTRKKVVDNF IHSVIKVEDE VRQHWVDARL TLACKEGFTL  120
VYDEFNRSHP EVNNVLLSVL EERLLVLPTN QHRAEYIRVH PQFRAILTSN PQEYCGVHAT  180
QDALMDRVIT IDMPTPDELS QQEIVVHKTG IDSEKAEVIV RIVRTFWSRS GSGQGGGLRS  240
CLMIAKICHE HEISVNPGDP SFQDICADIL LSRTNQPLIE ATRLLEEVLS EFYHRINTQS  300
QPSEIIPNNQ NQIVLEQRVP YEHEVYNYLC NSPGRRFSEL AVELGIDRSQ IVAALKSLRE  360
QGVLVQMQGN AESPSISQTV AFDSGHLINK                                   390
```

| SEQ ID NO: 347 | moltype = AA length = 410 |
|---|---|
| FEATURE | Location/Qualifiers |
| source | 1..410 |
| | mol_type = protein |
| | note = PCC 7120 |
| | organism = Nostoc sp |

SEQUENCE: 347

```
MTLTANNKKR AVLRVRPGQF VVTPAIEQVA IRALRYLTSG FAIHLRGPAG TGKTTLAMHL    60
ANCLDRPIML IFGDDEFKSS DLIGSESGYT HKKLLDNYIH SVLKVEDEFK QNWVDSRLTL   120
ACREGFTLVY DEFNRSRPEV NNVLLSALEE KILTLPPSSN QPEYLHVNPQ FRAIFTSNPE   180
EYCGVHSTQD ALMDRLVTIN MPEPDELTQT EILAQKTALN RADALLIVRL VKAFRSRTGG   240
EKTSGLRSCL MIAKVCAEHN ILVSPQSSDF REICADVLFN RTNWSASEAA TIFLELLNHL   300
DLQQIEEFKN SIIPEDTDAI AEGGFPTIID SHFGTLDSEV LEQPGVEDSI PFEQEIYLYL   360
QQYKSAALAL VQQEFELSRT VATNALNSLE QKGLVSKNNH VYTIEEPNQS              410

SEQ ID NO: 348          moltype = AA   length = 342
FEATURE                 Location/Qualifiers
source                  1..342
                        mol_type = protein
                        note = 307
                        organism = Octadecabacter antarcticus
SEQUENCE: 348
MNSNLRATNS GGPDISKTMM PEAREDFVQT ESVKSISRRA LAYINAGYSV HFRGPAGTGK    60
TTMAMHTAAL LGRPVVLITG DEEMITSNLV GAESGYNYRK VTDNYIHTVS KIEESSDRSW   120
NDHRLTTACR EGYTLIYDEF TRSRAEANNV LLSVLEEGIL VLPAQNRGEP FIKVHPNFRV   180
IFTSNPQEYA GVHEAQDALS DRIVTIDIGE ADRELEVSIA SSRSGLEVAK TEPIVDMVRA   240
FRDTGEYDQT PTLRACIVIC RMVANEKLNT TIDDPFFVQI CLDVLGSKST FGGKEHDKRT   300
QQRKLLLDNL KHYCPSKVST KPSAKDDESK STLIQVSSRG SL                     342

SEQ ID NO: 349          moltype = AA   length = 324
FEATURE                 Location/Qualifiers
source                  1..324
                        mol_type = protein
                        note = 238
                        organism = Octadecabacter arcticus
SEQUENCE: 349
MMPEARKDFV QTDSVKSVSR RALAYINAGY SVHFRGPAGT GKTTMAMHTA ALLGRPVVMI    60
TGDEEMVTSN LVGAESGYNY RKVTDNYIHT VSKVEESSDR SWNDHRLTTA CREGYTLIYD   120
EFTRSRAEAN NVLLSVLEEG ILVLPAQNRG EPPIKVHPDF RVIFTSNPQE YAGVHDAQDA   180
LSDRIVTIDI GAADRELEVS IASSRSGLEV AKTAPIVDMV RAFRDTGEYD QTPTLRACIM   240
ICRMVANEKL NPTIDDSYFV QICLDVLGSK SMFGAKEQGK RTQQEKLLLD NLSHHCPSPP   300
PSKPSAKEAE AKPRSIQATS RGPA                                         324

SEQ ID NO: 350          moltype = AA   length = 308
FEATURE                 Location/Qualifiers
source                  1..308
                        mol_type = protein
                        organism = Pelodictyon phaeoclathratiforme
SEQUENCE: 350
MRRQGCDSEM NTVLEPKPMP NFVETDYIRD ITSRGLTYMK AGFPVHFRGP SGTGKTTVAL    60
HLASKIGRPV VIIHGDSEYK TSDLIGSEQG YKYRRLDDNF IHSVHKYEED MTKQWVNNRL   120
TIAIKKGFTL VYDEFTRSRP EANNILLPIL QEKMMSTSSS NEEEYYMKVH PEFRAIFTSN   180
PEEYAGVNRT QDALRDRMVT MDLDYFDYET ELMITHAKSG MSLDDAEKIV KIVRGLRESG   240
KTEFDPTIRG SIMIAKTLNV LNARPDKTNE LFKKVCQDIL TSETSRVGSK TNQERVRGIV   300
NELIDLHS                                                           308

SEQ ID NO: 351          moltype = AA   length = 454
FEATURE                 Location/Qualifiers
source                  1..454
                        mol_type = protein
                        note = NIES-30
                        organism = Phormidium tenue
SEQUENCE: 351
MNTVLQARPR NFVSTPTLER TSIRALRYLQ SGYSIHLKGP AGTGKTTLAL HLADLLARPI    60
MLLFGDDEFK TSDLIGNQSG YTRKKVVDNY IHSVVKVEDE LRHNWTDSRL TLACREGFTM   120
VYDEFNRSRP EVNNVLLSAL EEKLLVLPPS NNRAEYIRVS PHFRAILTSN PEEYCGVHGT   180
QDALQDRLIT INMPEPDELA QQQILVQKVG IDSSAALQIV QLVKAFQSAV APDMVSSLRP   240
SLMIATICHD HDILPLAENA DFRDVCSDIL LARSKEPAPD ATRHLWNLFN RFVVSQAALV   300
NDLSLKPEAH PTARFHGEEE DDAPLQPLEA LVESDIDDVA VEDQPVIGPQ DLQGETLPEA   360
VIPEPQGETV VETPAEAEAL PEEIARVQVS PDDIETRIFD YLDATGTASL VNIEAALDLN   420
RFQAVNAVKS MLDQGLIEKQ ETDGQLQGYQ LSSN                              454

SEQ ID NO: 352          moltype = AA   length = 398
FEATURE                 Location/Qualifiers
source                  1..398
                        mol_type = protein
                        note = str. 7805
                        organism = Planktothrix agardhii
SEQUENCE: 352
MTTVLQARPK GFVNTPTIEQ LTIRALRYLQ SGFSLHLRGP AGTGKTTLAM HLADLLNRPI    60
VLIFGDDELK SSDLIGNQLG YTRKKVVDNF IHSVVKLEDE LRQNWIDSRL TLACKEGFTL   120
VYDEFNRSRP EVNNVLLSAL EEKLVLPPN NSRSEYIRVN PHFRAIFTSN PEEYCGVYGT    180
QDALLDRLIT IDMPEPDDET QQEILIQKIG ISPEDAKNII EIVKIYLEIT TQKKEIKPVQ   240
NGKAARPHID KASGLRPGLI IAKICHEHDI SIQENNQDFI KVCADILLSR TNLSLTEAQN   300
KLEKVIKTVL TDGDTSNNSF LPPSETQLTE NNSLEIEEQV YQYLKTTSA RVSEIEVALG    360
LNRVQTTNVL RSLLKQGHLK QQDNRFFAVN KQGELIQP                          398
```

```
SEQ ID NO: 353          moltype = AA   length = 398
FEATURE                 Location/Qualifiers
source                  1..398
                        mol_type = protein
                        organism = Planktothrix rubescens
SEQUENCE: 353
MTTVLQARPK GFVNTPTIEQ LTIRALRYLQ SGFSLHLRGP AGTGKTTLAM HLADLLNRPI    60
VLIFGDDELK SSDLIGNQLG YTRKKVIDNF IHSVVKLEDE LRQNWIDSRL TLACKEGFTL   120
VYDEFNRSRP EVNNVLLSAL EEKLLVLPPN NSRSEYIRVN PHFRAIFTSN PEEYCGVYGT   180
QDALLDRLIT IDMPEPDDET QQEILIQKIG ISPEDAKNII EIVKIYLEIT TQKKEIKPVQ   240
NGKAARPHID KASGLRPGLI IAKICHEHDI SIQENNQDFI KVCADILLSR TNLSLTEAQN   300
KLEKVIKTVL TDGDTSTNSF LPLSETQLTE NNSLEIEEQV YQYLQKTTSA RVSEIEVALG   360
LNRVQTTNVL RSLLKQGHLK QQDNRFFAVN KQGELIQP                          398

SEQ ID NO: 354          moltype = AA   length = 334
FEATURE                 Location/Qualifiers
source                  1..334
                        mol_type = protein
                        note = 37
                        organism = Psychromonas ingrahamii
SEQUENCE: 354
MSIENLNNVS EIKIEQSDDD HIYPEASEDF VETPYIKEVT ERAMLYLDAG YPVHFAGPAG    60
TGKTTLAFHI AALRQRPVTL IHGNHEFGTS DLIGKESGYR RHRVVDNYVH SVVKEEEELQ   120
SLWSDNRLTT CCRNGDTLVY DEFNRSTPEA NNVLLSILEE GILNLPSSRS DGYLEVHPQF   180
RAIFTSNPQE YAGTHATQDA LVDRMITIML HYPDRHTEVR VAIAKSGINS DEAGSIVDIV   240
NEFRELCGSK IVSSGPKTMP TVRASIAIAR VLVQKGEHAF RDNTFFHRIC RDVLCMYTQQ   300
VSFSNRSVLD KQLEDLIMKF CPATYKSSGS KIRA                              334

SEQ ID NO: 355          moltype = AA   length = 335
FEATURE                 Location/Qualifiers
source                  1..335
                        mol_type = protein
                        note = 37
                        organism = Psychromonas ingrahamii
SEQUENCE: 355
MSINNLNIST IKIEQPENDN IYPEASAEFV QTPYIQEVTE RALLYLDAGY PVHFAGPAGT    60
GKTTLAFHIA ALRKRPVTLI HGNHEFGSSD LIGKESGYRR HRLVDNYVHS VMKEEEELKS   120
LWVDNRLTTC CRNGDTLVYD EFNRSTPEAN NVLLSILEEG ILNLPSLRSM GDGYLEVHPS   180
FRAIFTSNPQ EYAGTHATQD ALVDRMITIM LNYPDRDTEV RVAVAKSGIS NEEAGFIVDI   240
VNEFRELSNH KSLSSGQKSM PTVRASIAIS RVLIQKGEHA FRDNVFFHRV CHDVLCMYIQ   300
KISPSNRSFL DKQLEVLIGK FCPAAKSALV PKVVK                             335

SEQ ID NO: 356          moltype = AA   length = 305
FEATURE                 Location/Qualifiers
source                  1..305
                        mol_type = protein
                        note = SB 1003
                        organism = Rhodobacter capsulatus
SEQUENCE: 356
MTIPRDLPWG DARTPLFEDE ELRSLLDRAE IYLREGIAIH FRGPAGVGKT TLALHLAQRF    60
ARPVTFFVGN DWLGRADIFG RDLGETVSTV QDHYISSVRR AERKSRIDWQ EAPLARAMRD   120
GHVLVYDEFS RSRPEANAAL LSVIEEGVLP LSDPAAGRSH IVAHPDFRVI LTSNPRDYVG   180
VQAVPDALLD RMITFSLDGM SFETEVGIVA TAARTDPADA RAICALIHLL RAEKPGTMEI   240
SMRSGIMIAR LARAAGVAPD PADPVFVQIC ADVLGTRMRG SDIDDVMALL LRPDPAPAAC   300
AGGAR                                                              305

SEQ ID NO: 357          moltype = AA   length = 316
FEATURE                 Location/Qualifiers
source                  1..316
                        mol_type = protein
                        note = 2.4.1
                        organism = Rhodobacter sphaeroides
SEQUENCE: 357
MTVLSPSLPH AAGIDAALVE NPWLGLRRSG RYFQNAETEA LFARALGYAR AGVCVHLAGP    60
AGLGKTTLAL RIAQALGRPV AFMTGNEWLG SRDPIGGEIG QTVTSVVDRY IQSVRRTEQS   120
ARIDWKESIL GQAMRCGQTF IYDEFTRASP EANAALLSVL EEGVLSTDG ASRHQYIEAH    180
PDFRVLLTSN PHEYQGVKAA PDALIDRMVT LRLEEPSAPT LAGIVALRSG LDPATARRIV   240
DLILSVQRSG EMQAPPSMRT AILVARLAAP LRLAGRLSDA ALAEIAADVL RGRGLEADAA   300
AFEAKLAAPT PGETAR                                                  316

SEQ ID NO: 358          moltype = AA   length = 329
FEATURE                 Location/Qualifiers
source                  1..329
                        mol_type = protein
                        note = ATCC 39006
                        organism = Serratia sp
SEQUENCE: 358
MIKQNTVSQY TVDDDLVVPE ASEHFVATSY VNDIIERALV YLRAGYPVHF AGPSGIGKTT    60
```

```
LAFHLAALWG RPVTMLQGNE EFVSSDLTGK DIGYRKSSLV DNYIHSVLKT EEQMNRMWVD    120
NRLTTACRNG DMLIYDEFNR SKAETNNVLL SVLSEGILNL PGLRGVGEGY LDVHPEFRAI    180
FTSNPEEYAG THKTQDALMD RMITINIGLV DRDTELQILH ARSELELKEA AYIVDIIREL    240
RGNEHETKHG LRAGIAIAHI LHQQGIKPRY GDKLFHAICY DVLSMDAAKI QHAGRSIYRE    300
MVDGVIRKIC PPIGSDTVKA STQKIKAVE                                     329

SEQ ID NO: 359             moltype = AA  length = 364
FEATURE                    Location/Qualifiers
source                     1..364
                           mol_type = protein
                           note = ATCC-43931
                           organism = Stella vacuolate
SEQUENCE: 359
MSTEPAPVMP PSTDIEFGSQ RPARPKPAEA LAVGYRLSAR PAAPSTLTLR PRADFVETDQ     60
VKDLTRRGLG FLRAGYPLHF RGPAGTGKTT LALHVAAQLG RPVIVITGDN ELGTADLVGS    120
QRGYHYRKVV DQFIHNVTKL EETANQRWTD HRLTTACREG YTLVYDEFTR SRPETHNVLL    180
GVFEEKILFL PAEAREECYI RVHPDFRAIF TSNPQEYAGV HASQDALADR LATIDVDYPN    240
RAMELAVASA RTGLAEAEAA RIIDLVRAFR ASGDYQQTPT MRASLMIARV AAQEGLRISV    300
DDPGFVQLCM DALESRIFSG ARQEADARAR HRVALLGLLA THCPSEAPVA RVATVARAKR    360
KSAS                                                                364

SEQ ID NO: 360             moltype = AA  length = 332
FEATURE                    Location/Qualifiers
source                     1..332
                           mol_type = protein
                           note = strain DSM 235
                           organism = Thiocapsa rosea
SEQUENCE: 360
MSAKPLQDAS EVSALNNDNV QPEASDTFVC TPSVEALAER ASAYLQAGYP VHLAGPAGTG     60
KTTLAPHAAA KRGRPVKLIH GNDELGLADM VGQDNGYRRN TLVDNYIHSV VKTQEEVRTF    120
WIDNRVTTAC LNGETLIYDE FNRSRPEVNN IFLSILGEGI LNLPNRRHQG AGYLEVHPEF    180
RVIFTSNPEE YAGTHKTQDA LMDRMITMKI GHYDRETEIR VTRAKSGLPP SEVAIVVDIV    240
RELRGQSVNH HRPTLRACIA IARIMADRRI SARSNNSFFR DICRDILDMD SAKVRRDGNA    300
LGESPVDDVV ASISARARRP KIVEPKGLHK EI                                 332

SEQ ID NO: 361             moltype = AA  length = 348
FEATURE                    Location/Qualifiers
source                     1..348
                           mol_type = protein
                           note = PCC 7601
                           organism = Tolypothrix sp
SEQUENCE: 361
MTNTENHKKR AVLRVRPGQF VVTPAIEKVA IRALRYLTSG FAIHLRGPAG TGKTTLAMHL     60
ANCLDRPIML IFGDDEFKSS DLIGSESGYT HKKLLDNYIH NVLKVEDELK QNWVDSRLTL    120
ACREGLTLVY DEFNRSRPEV NNVLLSALEE KILTLPPSSN QPEYLHVHPK FRAIFTSNPE    180
EYCGVHSTQD ALMDRLVTIN MPEPDEQTQI EILTHKTGIH HEYAQLIARL VKAFRSATGA    240
EKTSGLRSCL MVAKVCAEHD ILVTPENTDF REICADVLFN RTNLSASDAT TLFLELLNHV    300
QVKPVEPVDD SDPYDVAEAE IVGAAEPQTD AIAEPVTLDE SLLSDQPN                348

SEQ ID NO: 362             moltype = AA  length = 311
FEATURE                    Location/Qualifiers
source                     1..311
                           mol_type = protein
                           note = IMS101
                           organism = Trichodesmium erythraeum
SEQUENCE: 362
MTTVLNVSPD RFVSTPGVER VTQRASRYLE SGYSVHLRGP AGVGKTTLAL HLAHLRQQPI     60
FLMIGDDEFK TSDLIGNKSG YTRKKLVDNY IHTVLKVEDE LRDNWIDSRL TLACKEGFTL    120
IYDEFNRSRP EVNNVLLSVL EEKMLVLPPS QNQSEYIQVH PQFRVILTSN SEEWTGVHAT    180
QDALLDRVVT IGMEQPDIST EQNIVIQKTG INPLKAEVII KLVRSVRQRV DKEDLGSLRS    240
ALMISKVCHD HDIPLDGKDS SFSDLCADIL ISRPNLPRQE ALQQLDEVLE EFFPADQPSS    300
SDVGLEKEGS L                                                        311

SEQ ID NO: 363             moltype = AA  length = 311
FEATURE                    Location/Qualifiers
source                     1..311
                           mol_type = protein
                           note = IMS101
                           organism = Trichodesmium erythraeum
SEQUENCE: 363
MTTVLNVSPD RFVSTPSVER VTQRASRYLE SGYSVHLRGP AGVGKTTLAL HLAHLRQQPI     60
FLMIGDDEFK TSDLIGNKSG YTRKKLVDNY IHTVLKVEDE LKHNWIDSRL TLACKEGFTL    120
IYDEFNRSRP EVNNVLLSVL EEKMLVLPPS QNQSEYIQVH PQFRVILTSN SEEWTGVHAT    180
QDALLDRVVT IGMGQPDIST EQNIIIQKTG INPLKAEVII KLVRSVRERL ETEDLGSLRS    240
ALMISKVCHD HDIPLGGKDS NFSDLCADIL ISRANLPRQE ALKQLDEVLE ELFPADQLSI    300
SDIGLKKEGS L                                                        311

SEQ ID NO: 364             moltype = AA  length = 114
FEATURE                    Location/Qualifiers
```

```
source                  1..114
                        mol_type = protein
                        organism = Anabaena-flos-aquae
SEQUENCE: 364
MIKNIQVFFM KTISNRSISR AKISTMPRPK SDASSQLDLY KMVTEKQRIQ RDMYSIKERM    60
GLLQQRLDIL NQQIEATEKT IHKLRQPHSN TAQNIVRSNI FVESNNYQTF EVEY         114

SEQ ID NO: 365          moltype = AA  length = 105
FEATURE                 Location/Qualifiers
source                  1..105
                        mol_type = protein
                        note = NIES-81
                        organism = Aphanizomenon flos-aquae
SEQUENCE: 365
MKSFRHRSII RAKISTMPRH ISEASSQLEL YKMVAEKQRI SRELSSIKER MATLQKRLDS    60
LNNEIDNTEK TIHKLRQPHS STAQNIVRSK NVVESNNYQT FEIEY                   105

SEQ ID NO: 366          moltype = AA  length = 91
FEATURE                 Location/Qualifiers
source                  1..91
                        mol_type = protein
                        note = sp. Bp5365 strain MSMB43
                        organism = Burkholderia thailandensis
SEQUENCE: 366
MPIPKKGLHD IRFRHAPGAT PLPVHSMYMR ISCIEMEKSR RTIERRAAQR RIAAVDSRVA    60
DLEREKARLY AAIDNEAPQA GDIRGSFRIR Y                                   91

SEQ ID NO: 367          moltype = AA  length = 103
FEATURE                 Location/Qualifiers
source                  1..103
                        mol_type = protein
                        note = DSM 3385
                        organism = Desulfobacterium vacuolatum
SEQUENCE: 367
MLKNRNRSIK GVQNIKTHAG KVDHVSHPHM AYMRISCLEM EKARKNKEKS GAQKRIDMIN    60
QRLMEIEKEK AHIQRILGDT SIALESSNVD HDSEIKGGFK IKY                     103

SEQ ID NO: 368          moltype = AA  length = 106
FEATURE                 Location/Qualifiers
source                  1..106
                        mol_type = protein
                        note = DSM 6799
                        organism = Desulfomonile tiedjei
SEQUENCE: 368
MNIRMKGNSR GLRDIRTHSG KVDRVGLPYM AYMSISCLEM EKARREKERL SALTRIKNIE    60
QRIREIEAEK DLLLKGVGER TRTDLQKAST PRDQSAQCKG GFKIRY                  106

SEQ ID NO: 369          moltype = AA  length = 105
FEATURE                 Location/Qualifiers
source                  1..105
                        mol_type = protein
                        note = LLAP12
                        organism = Legionella drancourtii
SEQUENCE: 369
MMPALVKGLR NIKTMSNRLD KVQSPHEAFI SAAALHREKQ RHLQELAILR NRLDEINLRL    60
EQINEQQNQV AEAFDISPPR AVKSALRTGI QSKTGSTSHG FKIKY                   105

SEQ ID NO: 370          moltype = AA  length = 110
FEATURE                 Location/Qualifiers
source                  1..110
                        mol_type = protein
                        note = NIES-843
                        organism = Microcystis aeruginosa
SEQUENCE: 370
MTTTRPPRPI RSKISTMPRK QSEADHQLEL YKLITEKQRI QEKLEMMERQ IQQLKNRLTF    60
VTEQIETTEQ SIQNLRTANP PSVAKKPDSP KTVAHSSNNS SNFQTFYLEY             110

SEQ ID NO: 371          moltype = AA  length = 94
FEATURE                 Location/Qualifiers
source                  1..94
                        mol_type = protein
                        note = ATCC 29133
                        organism = Nostoc punctiforme
SEQUENCE: 371
MHRTPNRRQI QAKLSTMPPQ RSQATVYLNA YKMMLEKERL EEELEKLEAR RHQIQQRLAI    60
LNSQTIPEEN MTHQQANTDL ENNTPKFNTL TLEY                                94

SEQ ID NO: 372          moltype = AA  length = 113
FEATURE                 Location/Qualifiers
```

```
source                  1..113
                        mol_type = protein
                        note = PCC 7120
                        organism = Nostoc sp
SEQUENCE: 372
MLSIIQVFPM TKVRNRGIIR PKITTMPRNK SEASSQLELY KLVTEQQRIK QELAFIEQRT    60
VLLKQRLSTL KTQIEGTERS INHLRHSELK YSRIALPKIF SETNNYQAFD IEY          113

SEQ ID NO: 373          moltype = AA  length = 108
FEATURE                 Location/Qualifiers
source                  1..108
                        mol_type = protein
                        note = str. 7805
                        organism = Planktothrix agardhii
SEQUENCE: 373
MRPFRSQPPI LPKISTMPRQ KTEATLYRSL YQLAVEKKRL QEELSLGQR FETVTQRLQQ     60
IETQIQGLET DVKQIAPPKP PETKPNQPST PTPTKAEPGS VSTFTLDY                108

SEQ ID NO: 374          moltype = AA  length = 103
FEATURE                 Location/Qualifiers
source                  1..103
                        mol_type = protein
                        note = 37
                        organism = Psychromonas ingrahamii
SEQUENCE: 374
MTAAKRKTLR GLADIRTISS CGTSGQEAYQ MYLKRGVLEM EKLRRQKEKN SALERVTNIN    60
RRLMAIDTDI DFLCQSLKVI EKRTNQENSI VEKSVSRGFK LRY                    103

SEQ ID NO: 375          moltype = AA  length = 106
FEATURE                 Location/Qualifiers
source                  1..106
                        mol_type = protein
                        note = 37
                        organism = Psychromonas ingrahamii
SEQUENCE: 375
MIFSKKKNAL RGLADIRTLS GCGTSGQEAY QMYLKRGVLE MEKLRRQKEK NSALERVRNI    60
NYRLMAIDAD IDFLCQSLKV IEERTNKENS ISNESVTYKK GFKLRY                 106

SEQ ID NO: 376          moltype = AA  length = 105
FEATURE                 Location/Qualifiers
source                  1..105
                        mol_type = protein
                        note = ATCC 39006
                        organism = Serratia sp
SEQUENCE: 376
MAISTRPLRT LSDIKTHSGR VSGEHQTYRD YFQIGALELE RWRRTREREA ASSRIASIDE    60
RIADIDKEKA ALLADATAAS AVAENNDKSE AAEKKKKSSG LRIKY                  105

SEQ ID NO: 377          moltype = AA  length = 130
FEATURE                 Location/Qualifiers
source                  1..130
                        mol_type = protein
                        note = strain DSM 235
                        organism = Thiocapsa rosea
SEQUENCE: 377
MSKFTQPSRS VRDIKTLAGM ADDVRAPHKM YMRLFALETE RHRRLQERAS AMLRVDNIDA    60
RCAEIAEEME QLLQILGVEA VAPGGPPANA RPGSGRVPTQ PHRGRGKGTG AGRQTTSGET   120
SVGEAVKIRY                                                         130

SEQ ID NO: 378          moltype = AA  length = 226
FEATURE                 Location/Qualifiers
source                  1..226
                        mol_type = protein
                        organism = Anabaena-flos-aquae
SEQUENCE: 378
MELENLYTYA FLEIPSSPLI LPQGAANQVV LINGTELAAI VEPGIFLESF QNNDEKIIQM    60
ALSHDRVICE LFQQITVLPL RFGTYFTSTN NLLNHLKSHE KEYQNKLEKI NGKNEFTLKL   120
IPRMIEEIVP SEGGGKDYFL AKKQRYQNQN NFSIAQAAEK QNLIDLITKV NQLPVVVQEQ   180
EEQIQIYLLV SCQDKTLLLE QFLTWQKACP RWDLLLGDCL PPYHFI                 226

SEQ ID NO: 379          moltype = AA  length = 226
FEATURE                 Location/Qualifiers
source                  1..226
                        mol_type = protein
                        note = NIES-81
                        organism = Aphanizomenon flos-aquae
SEQUENCE: 379
MELENLYTYA FLKTPSFSLH LPQGSTTSVI QIDGNGLSAI VEPGISLDSF QDDDEKIVQM    60
AIEHDRVICD IFRQITVLPL RFGTYFANTD NLLTHLESYG QEYLDKLEKI NCKTEFILKL   120
```

```
IPRMITEESP VLESGRHYFL AKKQHYQRQK NFILAQASEK EILINFISKI NQIPVIIQEQ    180
EEEVRIYLLV NYQDKTLLLE QFLTWQQTCP RWDLFLGEGI PPYHFI                   226

SEQ ID NO: 380          moltype = AA  length = 227
FEATURE                 Location/Qualifiers
source                  1..227
                        mol_type = protein
                        note = NIES-39
                        organism = Arthrospira platensis
SEQUENCE: 380
MYVYAFIKSQ SISWKSVQGI YEPVVLLEAG ALAAVVEPNL QAENLSADNE EELMRAVLTH     60
DRIVCQIFEE TTVLPVRFGT CFDSEARLCE HLTTEGDRYF RQLEKLTGRA EYLLEAIPQP    120
FNQEKPSSDT TAPPTKGRDY FLQKKRLHQQ RLNFEQQQEQ QWQDFINAIA SKYPIVQGKA    180
TEDAERIYLL IPRSQEVALV EWVAQQQQNI DLWEFSLGNA VPAYHFL                  227

SEQ ID NO: 381          moltype = AA  length = 226
FEATURE                 Location/Qualifiers
source                  1..226
                        mol_type = protein
                        organism = Dolichospermum circinale
SEQUENCE: 381
MKLENFYTYA FLEIPRFPLV LPQGAASQVI LINGSGMSAI VEPGISLESF QNNDEKIIQM     60
ALSHDRVICE LFQQVTVLPL RFGTCFTSTN NLLNYLELHR QEYQEKLEKI NGKIEFTLKL    120
IPQTMEEPAP LERGGRDYFL AKKQRYQDQN NFRIAQAAEK QNLIDSISKV NQLPFVIQEK    180
EEEVNIYLLV KSEDKTLLLE QFLNWQKACP RWDLLLGEPL PPYHFI                   226

SEQ ID NO: 382          moltype = AA  length = 227
FEATURE                 Location/Qualifiers
source                  1..227
                        mol_type = protein
                        note = NIES-843
                        organism = Microcystis aeruginosa
SEQUENCE: 382
MKLYNLYTYA FLKTPIESLK LPVGMANPLL LITGGELSAV VEPEVGLDTL QNDDERLIQS     60
VLCHDRVICQ LFQQTTILPL RFGTSFLEAE NLLTHLCSHG QEYQEKIEEL EGKGEYLLKC    120
IPRKPEEPVL FSESKGRQYF LAKKQLYEAQ QDFYTLQGSE WQNLVNLITQ SYPSTRIITA    180
PGTESRIYLL VNLQEEPLLI EQVLHWQKAC PRWELQLGQV SPPYHFT                  227

SEQ ID NO: 383          moltype = AA  length = 229
FEATURE                 Location/Qualifiers
source                  1..229
                        mol_type = protein
                        note = ATCC 29133
                        organism = Nostoc punctiforme
SEQUENCE: 383
MSIYAYALLV PTASPLVLPL GMERNTELVY SSGLAALVEP EISLEAIQAT DERLLQAVLN     60
HDHVIRELFQ QTPLLRFG RGFTSVEKLL NHLENHGRVY LETLTQLADK VEYSVKVTAC    120
SLLDDSDTID ARGKAYLLAK KQRYQTQQAF QAQQCEQWEL LNELILKTYT NVICETRQSD    180
VRQIHFLAQR NDSTLSTQLF SLWQVQCSHW QLALSEPLPP YHFLKNTLI                229

SEQ ID NO: 384          moltype = AA  length = 227
FEATURE                 Location/Qualifiers
source                  1..227
                        mol_type = protein
                        note = PCC 7120
                        organism = Nostoc sp
SEQUENCE: 384
MRSPNFYTYA FLNTPDIPLR LPSGNLGQLL LIHGHKLSAV VEPGISLESS QNNDEEVIKM     60
VLAHDRVICE LSQQTTVLPL RFGTYFNSEE TLLNHIESAS QYQKKLDHI QGKTEYTLKL    120
IPRKFEELAK VSGGNGRDYF LAKKLHYEHQ KNFIGDQNRE KNHLINLIMD VYRSSAIIQD    180
YVEEVRLHLL VDRHDKTLLF KQVLTLQEKC PHWNLILGEP LPPYHFV                  227

SEQ ID NO: 385          moltype = AA  length = 88
FEATURE                 Location/Qualifiers
source                  1..88
                        mol_type = protein
                        organism = Bacillus-megaterium
SEQUENCE: 385
MEIKKIMQAV NDFFGEHVAP PHKITSVEAT EDEGWRVIVE VIEEREYMKK YAKDEMLGTY     60
ECFVNKEKEV ISFKRLDVRY RSAIGIEA                                       88

SEQ ID NO: 386          moltype = AA  length = 95
FEATURE                 Location/Qualifiers
source                  1..95
                        mol_type = protein
                        organism = Bacillus-megaterium
SEQUENCE: 386
MSLKQSMENK DIALIDILDV ILDKGVAIKG DLIISIAGVD LVYLDLRVLI SSVETLVQAK     60
EGNHKPITSE QFDKQKEELM DATGQPSKWT NPLGS                                95
```

```
SEQ ID NO: 387          moltype = AA   length = 65
FEATURE                 Location/Qualifiers
source                  1..65
                        mol_type = protein
                        note = 103S
                        organism = Rhodococcus hoagie
SEQUENCE: 387
MSATPDRRIA LVDLLDRVLG GGVVVAGEIT LSIADVDMVH ISLRTLVSSV SALTRPPDEK  60
PENDG                                                             65

SEQ ID NO: 388          moltype = AA   length = 292
FEATURE                 Location/Qualifiers
source                  1..292
                        mol_type = protein
                        organism = Bacillus-megaterium
SEQUENCE: 388
MATETKLDNT QAENKENKNA ENGSKEKNGS KASKTTSSGP IKRAVAGGII GATIGYVSTP  60
ENRKSLLDRI DTDELKSKAS DLGTKVKEKS KSSVASLKTS AGSLFKKDKD KSKDDEENVN 120
SSSSETEDDN VQEYDELKEE NQTLQDRLSQ LEEKMNMLVE LSLNKNQDEE AEDTDSDEEE 180
NDENDENDEN EQDDENEEET SKPRKKDKKE AEEEESESDE DSEEEEEDSR SNKKNKKVKT 240
EEEDEDESEE EKKEAKPKKS TAKKSKNTKA KKNTDEEDDE ATSLSSEDDT TA         292

SEQ ID NO: 389          moltype = AA   length = 138
FEATURE                 Location/Qualifiers
source                  1..138
                        mol_type = protein
                        organism = Bacillus-megaterium
SEQUENCE: 389
MSTGPSFSTK DNTLEYFVKA SNKHGFSLDI SLNVNGAVIS GTMISAKEYF DYLSETFEEG  60
SEVAQALSEQ FSLASEASES NGEAEAHFIH LKNTKIYCGD SKSTPSKGKI FWRGKIAEVD 120
GFFLGKISDA KSTSKKSS                                              138

SEQ ID NO: 390          moltype = AA   length = 193
FEATURE                 Location/Qualifiers
source                  1..193
                        mol_type = protein
                        organism = Anabaena flos-aquae
SEQUENCE: 390
MISLMAKIRQ EHQSIAEKVA ELSLETREFL SVTTAKRQEQ AEKQAQELQA FYKDLQETSQ  60
QFLSETAQAR IAQAEKQAQE LLAFHKELQE TSQQFLSATA QARIAQAEKQ AQELLAFYQE 120
VRETSQQFLS ATAQARIAQA EKQAQELLAF HKELQETSQQ FLSATADART AQAKEQKESL 180
LKFRQDLFVS IFG                                                   193

SEQ ID NO: 391          moltype = AA   length = 382
FEATURE                 Location/Qualifiers
source                  1..382
                        mol_type = protein
                        organism = Halobacterium salinarum
SEQUENCE: 391
MSVTDKRDEM STARDKFAES QQEFESYADE FAADITAKQD DVSDLVDAIT DFQAEMTNTT  60
DAFHTYGDEF AAEVDHLRAD IDAQRDVIRE MQDAFEAYAD IFATDIADKQ DIGNLLAAIE 120
ALRTEMNSTH GAFEAYADDF AADVAALRDI SDLVAAIDDF QEEFIAVQDA FDNYAGDFDA 180
EIDQLHAAIA DQHDSFDATA DAFAEYRDEF YRIEVEALLE AINDFQQDIG DFRAEFETTE 240
DAFVAFARDF YGHEITAEEG AAEAEAEPVE ADADVEAEAE VSPDEAGGES AGTEEEETEP 300
AEVETAAPEV EGSPADTADE AEDTEAEEET EEEAPEDMVQ CRVCGEYYQA ITEPHLQTHD 360
MTIQEYRDEY GEDVPLRPDD KT                                         382

SEQ ID NO: 392          moltype = AA   length = 381
FEATURE                 Location/Qualifiers
source                  1..381
                        mol_type = protein
                        organism = Halobacterium mediterranei
SEQUENCE: 392
MSVKDKREKM TATREEFAEV QQAFAAYADE FAADVDDKRD VSELVDGIDT LRTEMNSTND  60
APFRAYSEEFA ADVEHFHTSV ADRRDAFDAY ADIFATDVAE MQDVSDLLAA IDDLRAEMDE 120
THEAFDAYAD AFVTDVATLR DVSDLLTAIS ELQSEFVSVQ GEFNGYASEF GADIDQFHAV 180
VAEKRDGHKD VADAFLQYRE EFHGVEVQSL LDNIAAFQRE MGDYRKAPFET TEEAFASFAR 240
DFYGQGAAPM ATPLNNAAET AVTGTETEVD IPPIEDSVEP DGEDEDSKAD DVEAEAEVET 300
VEMEFGAEMD TEADEDVQSE SVREDDQFLD DETPEDMVQC LVCGEYYQAI TEPHLQTHDM 360
TIKKYREEYG EDVPLRPDDK A                                          381

SEQ ID NO: 393          moltype = AA   length = 162
FEATURE                 Location/Qualifiers
source                  1..162
                        mol_type = protein
                        organism = Microchaete diplosiphon
SEQUENCE: 393
MTPLMIRIRQ EHRGIAEEVT QLFKDTQEFL SVTTAQRQAQ AKEQAENLHQ FHKDLEKDTE  60
```

```
EFLTDTAKER MAKAKQQAED LFQFHKEMAE NTQEFLSETA KERMAQAQEQ ARQLREFHQN    120
LEQTTNEFLA DTAKERMAQA QEQKQQLHQF RQDLFASIFG TF                       162

SEQ ID NO: 394           moltype = AA  length = 129
FEATURE                  Location/Qualifiers
source                   1..129
                         mol_type = protein
                         organism = Nostoc sp
SEQUENCE: 394
MTALMVRIRQ EHRSIAEEVT QLFRETHEFL SATTAHRQEQ AKQQAQQLHQ FHQNLEQTTH    60
EFLTETTTQR VAQAEAQANF LHKFHQNLEQ TTQEFLAETA KNRTEQAKAQ SQYLQQFRKD   120
LFASIFGTF                                                            129

SEQ ID NO: 395           moltype = AA  length = 88
FEATURE                  Location/Qualifiers
source                   1..88
                         mol_type = protein
                         organism = Bacillus megaterium
SEQUENCE: 395
MSIQKSTNSS SLAEVIDRIL DKGIVIDAFA RVSVVGIEIL TIEARVVIAS VDTWLRYAEA    60
VGLLRDDVEE NGLPERSNSS EGQPRFSI                                       88

SEQ ID NO: 396           moltype = AA  length = 88
FEATURE                  Location/Qualifiers
source                   1..88
                         mol_type = protein
                         organism = Bacillus megaterium
SEQUENCE: 396
MEIKKIMQAV NDFFGEHVAP PHKITSVEAT EDEGWRVIVE VIEEREYMKK YAKDEMLGTY    60
ECFVNKEKEV ISFKRLDVRY RSAIGIEA                                       88

SEQ ID NO: 397           moltype = AA  length = 308
FEATURE                  Location/Qualifiers
source                   1..308
                         mol_type = protein
                         organism = Bacillus megaterium
SEQUENCE: 397
MTVLTDKRKK GSGAFIQDDE TKEVLSRALS YLKSGYSIHF TGPAGGGKTS LARALAKKRK    60
RPVMLMHGNH ELNNKDLIGD FTGYTSKKVI DQYVRSVYKK DEQVSENWQD GRLLEAVKNG   120
YTLIYDEFTR SKPATNNIFL SILEEGVLPL YGVKMTDPFV RVHPDFRVIF TSNPAEYAGV   180
YDTQDALLDR LITMFIDYKD IDRETAILTE KTDVEEDEAR TIVTLVANVR NRSGDENSSG   240
LSLRASLMIA TLATQQDIPI DGSDEDFQTL CIDILHHPLT KCLDEENAKS KAEKIILEEC   300
KNIDTEEK                                                             308

SEQ ID NO: 398           moltype = AA  length = 255
FEATURE                  Location/Qualifiers
source                   1..255
                         mol_type = protein
                         organism = Bacillus megaterium
SEQUENCE: 398
MSETNETGIY IFSAIQTDKD EEFGAVEVEG TKAETFLIRY KDAAMVAAEV PMKIYHPNRQ    60
NLLMHQNAVA AIMDKNDTVI PISFGNVFKS KEDVKVLLEN LYPQFEKLFP AIKGKIEVGL   120
KVIGKKEWLE KKVNENPELE KVSASVKGKS EAAGYYERIQ LGGMAQKMFT SLQKEVKTDV   180
FSPLEEAAEA AKANEPTGET MLLNASFLIN REDEAKFDEK VNEAHENWKD KADFHYSGPW   240
PAYNFVNIRL KVEEK                                                     255

SEQ ID NO: 399           moltype = AA  length = 88
FEATURE                  Location/Qualifiers
source                   1..88
                         mol_type = protein
                         organism = Bacillus megaterium
SEQUENCE: 399
MLHKLVTAPI NLVVKIGEKV QEEADKQLYD LPTIQQKLIQ LQMMFELGEI PEEAFQEKED    60
ELLMRYEIAK RREIEQWEEL TQKRNEES                                       88

SEQ ID NO: 400           moltype = AA  length = 269
FEATURE                  Location/Qualifiers
source                   1..269
                         mol_type = protein
                         organism = Bacillus megaterium
SEQUENCE: 400
MGELLYLYGL IPTKEAAAIE PFPSYKGFDG EHSLYPIAFD QVTAVVSKLD ADTYSEKVIQ    60
EKMEQDMSWL QEKAPHHHET VAALYEEFTI IPLKFCTIYK GEESLQAAIE INKEKIENSL   120
TLLQGNEEWN VKIYCDDTEL KKGISETNES VKAKKQEISH LSPGRQFFEK KKIDQLIEKE   180
LELHKNKVCE EIHDKLKELS LYDSVKKNWS KDVTGAAEQM AWNSVFLLPS LQITKFVNEI   240
EELQQRLENK GWKFEVTGPW PPYHFSSFA                                      269

SEQ ID NO: 401           moltype = AA  length = 95
FEATURE                  Location/Qualifiers
```

```
source                  1..95
                        mol_type = protein
                        organism = Bacillus megaterium
SEQUENCE: 401
MSLKQSMENK DIALIDILDV ILDKGVAIKG DLIISIAGVD LVYLDLRVLI SSVETLVQAK    60
EGNHKPITSE QFDKQKEELM DATGQPSKWT NPLGS                              95

SEQ ID NO: 402          moltype = AA   length = 94
FEATURE                 Location/Qualifiers
source                  1..94
                        mol_type = protein
                        organism = Bacillus megaterium
SEQUENCE: 402
MQPVSQANGR IHLDPDQAEQ GLAQLVMTVI ELLRQIVERH AMRRVEGGTL TDEQIENLGI    60
ALMNLEEKMD ELKEVFGLDA EDLNIDLGPL GSLL                               94

SEQ ID NO: 403          moltype = AA   length = 100
FEATURE                 Location/Qualifiers
source                  1..100
                        mol_type = protein
                        organism = Bacillus megaterium
SEQUENCE: 403
MAVEHNMQSS TIVDVLEKIL DKGVVIAGDI TVGIADVELL TIKIRLIVAS VDKAKEIGMD    60
WWENDPYLSS KGANNKALEE ENKMLHERLK TLEEKIETKR                         100

SEQ ID NO: 404          moltype = AA   length = 292
FEATURE                 Location/Qualifiers
source                  1..292
                        mol_type = protein
                        organism = Bacillus megaterium
SEQUENCE: 404
MATETKLDNT QAENKENKNA ENGSKEKNGS KASKTTSSGP IKRAVAGGII GATIGYVSTP    60
ENRKSLLDRI DTDELKSKAS DLGTKVKEKS KSSVASLKTS AGSLFKKDKD KSKDDEENVN   120
SSSSETEDDN VQEYDELKEE NQTLQDRLSQ LEEKMNMLVE LSLNKNQDEE AEDTDSDEEE   180
NDENDENDEN EQDDENEEET SKPRKKDKKE AEEEESESDE DSEEEEEDSR SNKKNKKVKT   240
EEEDEDESEE EKKEAKPKKS TAKKSKNTKA KKNTDEEDDE ATSLSSEDDT TA           292

SEQ ID NO: 405          moltype = AA   length = 138
FEATURE                 Location/Qualifiers
source                  1..138
                        mol_type = protein
                        organism = Bacillus megaterium
SEQUENCE: 405
MSTGPSFSTK DNTLEYFVKA SNKHGFSLDI SLNVNGAVIS GTMISAKEYF DYLSETFEEG    60
SEVAQALSEQ FSLASEASES NGEAEAHFIH LKNTKIYCGD SKSTPSKGKI FWRGKIAEVD   120
GFFLGKISDA KSTSKKSS                                                138

SEQ ID NO: 406          moltype = AA   length = 72
FEATURE                 Location/Qualifiers
source                  1..72
                        mol_type = protein
                        organism = Serratia sp.
SEQUENCE: 406
MAKVQKSTDS SSLAEVVDRI LDKGIVIDAW VKVSLVGIEL LSIEARVVIA SVETYLKYAE    60
AIGLTASAAT PA                                                       72

SEQ ID NO: 407          moltype = AA   length = 65
FEATURE                 Location/Qualifiers
source                  1..65
                        mol_type = protein
                        organism = Serratia sp.
SEQUENCE: 407
MPVNKQYQDE QQQVSLCEAL DRVLNKGVVI VADITISVAN IDLIYLSLQA LVSSVEAKNR    60
LPGRE                                                               65

SEQ ID NO: 408          moltype = AA   length = 65
FEATURE                 Location/Qualifiers
source                  1..65
                        mol_type = protein
                        organism = Serratia
SEQUENCE: 408
MPVNKQYQDE QQQVSLCEAL DRVLNKGVVI VADITISVAN IDLIYLSLQA LVSSVEAKNR    60
LPGRE                                                               65

SEQ ID NO: 409          moltype = AA   length = 164
FEATURE                 Location/Qualifiers
source                  1..164
                        mol_type = protein
                        organism = Serratia sp.
```

```
SEQUENCE: 409
MGCLTDGMAQ LRKNIDDSHE SRIAQQNARV SSVSAQIAGF STTRARNAAQ DARARATFVA    60
DNVRGVNRML SDFCHTREVM SRQQSEERAT FVTDMSKKTL ALLDGFNAER KSMAERCAKE   120
RADFIANVAN DVAAFLSASE KDRMAAHAVF FGMTLAKKKT SLAV                   164

SEQ ID NO: 410              moltype = AA   length = 329
FEATURE                     Location/Qualifiers
source                      1..329
                            mol_type = protein
                            organism = Serratia sp.
SEQUENCE: 410
MIKQNTVSQY TVDDDLVVPE ASEHFVATSY VNDIIERALV YLRAGYPVHF AGPSGIGKTT    60
LAFHLAALWG RPVTMLQGNE EFVSSDLTGK DIGYRKSSLV DNYIHSVLKT EEQMNRMWVD   120
NRLTTACRNG DMLIYDEFNR SKAETNNVLL SVLSEGILNL PGLRGVGEGY LDVHPEFRAI   180
FTSNPEEYAG THKTQDALMD RMITINIGLV DRDTELQILH ARSELELKEA AYIVDIIREL   240
RGNEHETKHG LRAGIAIAHI LHQQGIKPRY GDKLFHAICY DVLSMDAAKI QHAGRSIYRE   300
MVDGVIRKIC PPIGSDTVKA STQKIKAVE                                    329

SEQ ID NO: 411              moltype = AA   length = 105
FEATURE                     Location/Qualifiers
source                      1..105
                            mol_type = protein
                            organism = Serratia sp.
SEQUENCE: 411
MAISTRPLRT LSDIKTHSGR VSGEHQTYRD YFQIGALELE RWRRTREREA ASSRIASIDE    60
RIADIDKEKA ALLADATAAS AVAENNDKSE AAEKKKKSSG LRIKY                  105

SEQ ID NO: 412              moltype = AA   length = 273
FEATURE                     Location/Qualifiers
source                      1..273
                            mol_type = protein
                            organism = Serratia sp.
SEQUENCE: 412
MMSIDKSRNH RAKVLYALCV SDDSTPNYKI RGLEAAPVYS IDQDGLRAVV SDTLSTRLRP    60
ERRNITAHQA VLHKLTEEGT VLPMRFGVIA RNAEAVKNLL VANQDTIREH FERLDGCVEM   120
GLRVSWDVTN IYEYFVATYP VLSETRDEIW NGNSNANNHR EEKIRLGNLY ESLRSGDRKE   180
STEKVKEVLL DYCEEIIENP VKKEKDVMNL ACLVARERMD EFAKGVFEAS KLFDNVYLFD   240
YTGPWAPHNF VTLDLHAPTA KKKTLTRAGT LSD                                273

SEQ ID NO: 413              moltype = AA   length = 262
FEATURE                     Location/Qualifiers
source                      1..262
                            mol_type = protein
                            organism = Serratia sp.
SEQUENCE: 413
MTMNTEAQTE QAIYLYGLTL PDLAAPPILG VDNQHPINTH QCAGLNAVIS PVALSDFTGE    60
KGEDNVQNVT WLTPRICRHA QIIDSLMAQG PVYPLPFGTL FSSQNALEQE MKSRATDVFV   120
SLRRITGCQE WALEATLDRK QAVDVLFTEG LDSGRFCLPE AIGRRHLEEQ KLRRRLTTEL   180
SDWLAHALTA MQNELHPLVR DFRSRRLLDD KILHWAYLLP VEDVAAFQQQ VADIVERYEA   240
YGFSFRVTGP WAAYSFCQPD ES                                          262

SEQ ID NO: 414              moltype = AA   length = 222
FEATURE                     Location/Qualifiers
source                      1..222
                            mol_type = protein
                            organism = Serratia sp.
SEQUENCE: 414
MSLLLYGIVA EDTQLALEPD GSPHAGEEPM QLVKAATLAA LVKPCEADVS REPAAALAFG    60
QQIMHVHQQT TIIPIRYGCV LADEDAVTQH LLNHEAHYQT QLVELENCDE MGIRLSLASA   120
EDNAVTTPQA SGLDYLRSRK LAYAVPEHAE RQAALLNNAF TGLYRRHCAE ISMFNGQRTY   180
LLSYLVPRTG LQAFRDQFNT LANNMTDIGV ISGPWPPYNF AS                     222

SEQ ID NO: 415              moltype = AA   length = 138
FEATURE                     Location/Qualifiers
source                      1..138
                            mol_type = protein
                            organism = Serratia sp.
SEQUENCE: 415
MLLIDDILFS PVKGVMWIFR QIHELAEDEL AGEADRIRES LTDLYMLLET GQITEDEFEQ    60
QEAVLLDRLD ALDEEDDMLG DEPGDDEDDE YEEDDDEEDD DEEDDDDEDD DEDDDDEED   120
DDDDEDDDDE DEPEGTTK                                                138

SEQ ID NO: 416              moltype = AA   length = 637
FEATURE                     Location/Qualifiers
source                      1..637
                            mol_type = protein
                            organism = Serratia sp.
SEQUENCE: 416
MKPAIYPKFL LESPLKLVFF GGKGGVGKST CATSTALRLA QEQPQHHFLL VSTDPAHSLQ    60
```

```
NILSDLVLPK NLDVRELNAA ASLHEFKSQH EGVLKEIAYR GTVLDQNDVQ GLMDTALPGM    120
DELAAYLEIA EWIQKDTYYR IIIDTAPTGH TLRLLEMPDL IYRWLTALDT LLAKQRYIRK    180
RFAGDNRLDH LDHFLLDMND SLKAMHELVT DSTRCCFVLV MLAEAMSVEE SIDLAGALNQ    240
QRVFLSDLVV NRLFPENDCP TCCVERNRQM LALQNGYQRL PGHVFWTLPL LAIEPRGALL    300
HEFWSGVRLL DENEVMATTC HHQLPLRVES SISLPASTFR LLIFAGKGGV GKTTLACATA    360
LRLNSEYPEL RILLFSADPA HSLSDCLGVT LQQQPISVLV NIDAQEINAQ ADFDKIRQGY    420
RAELEAFLLD TLPNLDITFD REVLEHLLDL APPGLDEIMA LTAIMDHLDS GRYDMVIVDG    480
APSGHLLRLL ELPELIRDWL KQFFSLLLKY RKVMRFPHLS ERLVQLSREL KNLRALLQDT    540
KQTGLYAVTV PTHLALEKTY EMTCALQRLG LTANALFINQ ITPPSDCTLC QAITSRESLE    600
LKCADEMFPS QPHAQIFRQT EPTGLSKLKT LGSALFL                            637

SEQ ID NO: 417           moltype = AA   length = 115
FEATURE                  Location/Qualifiers
source                   1..115
                         mol_type = protein
                         organism = Serratia sp.
SEQUENCE: 417
MTTNQLSHHS PVFGPTSPAI QRPITEANRH KIDIDGERVR DGLAQLVLTL VKLLHELLER    60
QAIRRMDSGS LSDEEVERLG LALMRQAEEL THLCDVFGFK DDDLNLDLGP LGRLL         115

SEQ ID NO: 418           moltype = AA   length = 87
FEATURE                  Location/Qualifiers
source                   1..87
                         mol_type = protein
                         organism = Serratia sp.
SEQUENCE: 418
MVNTTNDINA ATRGLLLRMG NAWFEQDELR QAVDIYLKII EQYPDSKESK TAQTALLTIS    60
QRYERDGLFR LSLDILERVG EITPTSI                                       87

SEQ ID NO: 419           moltype = AA   length = 192
FEATURE                  Location/Qualifiers
source                   1..192
                         mol_type = protein
                         organism = Serratia sp.
SEQUENCE: 419
MRALIHPPII HSPKDLGTLS EAASHLRTET QTRAYLAAVE GFWTMITTTI EGLDLDYTHL    60
KLYQDGLPVC GKENEIVTDV ANAGSQNYKL LLTLQHKGAI LMGTESPELL LQERDLMTQL    120
LQSTEQTEAS LETAKTLLNR RDDYIAQRID ETLQDGEMAI LFLGLMHNIE AKLPADIVFI    180
QPLGKPPGGE SI                                                       192

SEQ ID NO: 420           moltype = AA   length = 160
FEATURE                  Location/Qualifiers
source                   1..160
                         mol_type = protein
                         organism = Serratia sp.
SEQUENCE: 420
MTGNVEGILR GLGDLVEKLV ETGEQIKRSG AFDIDTNDGK NAKAVYGFSI KMGLDGNQEN    60
RVEPFGNIRR DEQTGEATVQ EVSEPLVDVI EESDHVLVLA EMPGVADEDV QVELNGDILT    120
LHSERGSKKY HKEIVLPCSF DDKAMERSCR NGILEVKLGK                         160

SEQ ID NO: 421           moltype = AA   length = 720
FEATURE                  Location/Qualifiers
source                   1..720
                         mol_type = protein
                         organism = Serratia sp.
SEQUENCE: 421
MSEELKLKVA EALPKDAGRG YARLDPADMA RLNAVGDIV QLTSKKGTGI AKLMPTYPDM     60
RNKGIVQLDG LTRRNTSLSL DEKVQIEPAS CKHATQIVLI PTTITPNQRD LDYIGSLLDG    120
LPVQKGDLLR AHLFGSRSAD FKVESTIPDG AVLIDPTTTL VIGKSNAVGN SSHSTQRLSY    180
EDVGGLKNQV RRIREMIELP LRYPEVFERL GIDAPKGVLL SGPPGCGKTL IARIIAQETD    240
AQFFTISGPE IVHKFYGESE AHLRKIFEEA GRKGPSIIFL DEIDSIAPHR DKVVGDVEKR    300
IVAQLLALMD GLKNRGKVIV IAATNLPNAI DPALRRPGRF DREISIPIPD REGRREIIEI    360
HSTGMPLNAD VDLNVLADIT HGFVGADLEA LCREAAMSAL RRLLPEIDFS SAELPYDRLA    420
ELTVMMDDFR AALCEVSPSA IRELFVDIPD VRWEDVGGLD DVRRRLIESV EWPIKYEPLY    480
EQAGVKPPKG LLLAGPPGVG KTLIAKAVAN ESGVNVISVK GPALMSRYVG DSEKGVRELF    540
LKARQAAPCI IFLDEVDSVI PARNEGAIDS HVAERVLSQF LSEMDGLEEL KGVFVMGATN    600
RADLIDPAML RPGRFDEIIE LGLPDEDARR QILAVHLRNK PLGDNIHADD LAERCDGASG    660
AELAAVCNRA ALAALRRAIQ QSEEAVLSPS TVGETPVALT VRIEQHDFAE VIAEMFGDDA    720

SEQ ID NO: 422           moltype = AA   length = 71
FEATURE                  Location/Qualifiers
source                   1..71
                         mol_type = protein
                         organism = Anabaena flos-aquae
SEQUENCE: 422
MAVEKTNSSS SLAEVIDRIL DKGIVIDAWV RVSLVGIELL AIEARIVIAS VETYLKYAEA    60
VGLTQSAAVP A                                                        71

SEQ ID NO: 423           moltype = AA   length = 193
```

```
FEATURE                 Location/Qualifiers
source                  1..193
                        mol_type = protein
                        organism = Anabaena flos-aquae
SEQUENCE: 423
MISLMAKIRQ EHQSIAEKVA ELSLETREFL SVTTAKRQEQ AEKQAQELQA FYKDLQETSQ    60
QFLSETAQAR IAQAEKQAQE LLAFHKELQE TSQQFLSATA QARIAQAEKQ AQELLAFYQE   120
VRETSQQFLS ATAQARIAQA EKQAQELLAF HKELQETSQQ FLSATADART AQAKEQKESL   180
LKFRQDLFVS IFG                                                     193

SEQ ID NO: 424          moltype = AA   length = 335
FEATURE                 Location/Qualifiers
source                  1..335
                        mol_type = protein
                        organism = Anabaena flos-aquae
SEQUENCE: 424
MTTTKVNHKR AVLRLRPGQF VVTPAIERVA IRALRYLKSG FPVHLRGPAG TGKTTLAMHL    60
ANCLDRPVML LFGDDQFKSS DLIGSESGYT HKKVLDNYIH SVVKLEDEFK QNWVDSRLTL   120
ACREGFTLVY DEFNRSRPEV NNVLLSALEE KILSLPPSSN QPEYLSVNPQ FRVIFTSNPE   180
EYAGVHSTQD ALMDRLVTIS MPEPDEITQT EILIQKTNID RESANFIVRL VKSFRLATGA   240
EKTSGLRSCL MIAKVCADNN IPVTTESLDF PDIAIDILFN RSHLSMSEST NIFLELLDKF   300
SAEELEILNN RVTGDNDFLI DNSQFVSQQL AGQPN                             335

SEQ ID NO: 425          moltype = AA   length = 248
FEATURE                 Location/Qualifiers
source                  1..248
                        mol_type = protein
                        organism = Anabaena flos-aquae
SEQUENCE: 425
MLPTRPQTNS SRTINTSTQG STLADILERV LDKGIVIAGD ISISIASTEL VHIRIRLLIS    60
SVDKAKEMGI NWWESDPYLS TKAQRLVEEN QQLQHRLESL EAKLNSLTSS SVKEEIPLAA   120
DVKDDLYQTS AKIPSPVDTP IEVLDFQAQS SGGTPPYVNT SMEILDFQAQ TSAESSSPVG   180
STVEILDFQA QTSEESSSPV VSTVEILDFQ AQTSEESSSP VGSTVEILDF QAQTSEEIPS   240
SVDPAIDV                                                           248

SEQ ID NO: 426          moltype = AA   length = 155
FEATURE                 Location/Qualifiers
source                  1..155
                        mol_type = protein
                        organism = Anabaena flos-aquae
SEQUENCE: 426
MVCTPAENFN NSLTIASKPK NEAGLAPLLL TVLELVRQLM EAQVIRRMEE DLLSEPDLER    60
AADSLQKLEE QILHLCEMFE VDPADLNINL GEIGTLLPSS GSYYPGQPSS RPSVLELLDR   120
LLNTGIVVDG EIDLGIAQID LIHAKLRLVL TSKPI                             155

SEQ ID NO: 427          moltype = AA   length = 245
FEATURE                 Location/Qualifiers
source                  1..245
                        mol_type = protein
                        organism = Anabaena flos-aquae
SEQUENCE: 427
MSIPLYLYGI FPNTIPETLE LEGLDKQPVH SQVVDEFCFL YSEARQEKYL ASRRNLLTHE    60
KVLEQTMHAG FRVLLPLRFG LVVKDWETIM SQLINPHKDQ LNQLFQKLAG KREVSIKIFW   120
DAKAELQTMM ESHQDLKQQR DNMEGKKLSM EEVIQIGQLI EINLLARKQA VIEVFSQELN   180
PPAQEIVVSD PMTEEMIYNA AFLIPWESES EFSERVEVID QKFGDRLRIR YNNFTAPYTF   240
AQLDS                                                              245

SEQ ID NO: 428          moltype = AA   length = 119
FEATURE                 Location/Qualifiers
source                  1..119
                        mol_type = protein
                        organism = Anabaena flos-aquae
SEQUENCE: 428
MLTKLLLLPI MGPLNGVVWI AEQIQERTNT EFDAQENLHK QLLSLQLSFD IGEIGEEEFE    60
IQEEEILLKI QALEEEARLE LEAEQEEARL ELEAEQEDFE YPPQFTAEVN KDQHLVLLP   119

SEQ ID NO: 429          moltype = AA   length = 114
FEATURE                 Location/Qualifiers
source                  1..114
                        mol_type = protein
                        organism = Anabaena flos-aquae
SEQUENCE: 429
MIKNIQVFFM KTISNRSISR AKISTMPRPK SDASSQLDLY KMVTEKQRIQ RDMYSIKERM    60
GLLQQRLDIL NQQIEATEKT IHKLRQPHSN TAQNIVRSNI FVESNNYQTF EVEY        114

SEQ ID NO: 430          moltype = AA   length = 226
FEATURE                 Location/Qualifiers
source                  1..226
                        mol_type = protein
```

```
                            organism = Anabaena flos-aquae
SEQUENCE: 430
MELENLYTYA FLEIPSSPLI LPQGAANQVV LINGTELAAI VEPGIFLESF QNNDEKIIQM    60
ALSHDRVICE LFQQITVLPL RFGTYFTSTN NLLNHLKSHE KEYQNKLEKI NGKNEFTLKL   120
IPRMIEEIVP SEGGGKDYFL AKKQRYQNQN NFSIAQAAEK QNLIDLITKV NQLPVVVQEQ   180
EEQIQIYLLV SCQDKTLLLE QFLTWQKACP KWDLLLGDCL PPYHFI                 226

SEQ ID NO: 431              moltype = DNA   length = 267
FEATURE                     Location/Qualifiers
source                      1..267
                            mol_type = genomic DNA
                            organism = Bacillus megaterium
SEQUENCE: 431
atgagcatcc agaagtccac caacagcagc agcctggccg aagtgatcga ccggatcctg    60
gacaagggca tcgtgatcga cgccttcgcc agagtgtccg tcgtgggcat cgagatcctg   120
accatcgagg ccagagtcgt gatcgccagc gtggacacct ggctgagata tgccgaagcc   180
gtgggcctgc tgcgggacga cgtggaagaa aatggcctgc ccagcggag caacagctct    240
gagggacagc cccggttcag catctga                                       267

SEQ ID NO: 432              moltype = DNA   length = 927
FEATURE                     Location/Qualifiers
source                      1..927
                            mol_type = genomic DNA
                            organism = Bacillus megaterium
SEQUENCE: 432
atgaccgtgc tgaccgacaa gcggaagaag ggcagcggcg ccttcatcca ggacgacgag    60
acaaaagagg tgctgagcag agccctgagc tacctgaagt ccggctacag catccacttc   120
accggacctg ccggcggagg caagacatct ctggctagag ccctggccaa gaaacggaag   180
cggcccgtga tgctgatgca cggcaaccac gagctgaaca caaggacct gatcggcgat   240
ttcaccggct acaccagcaa gaaagtgatc gaccagtacg tgccggagcgt gtacaagaaa   300
gacgaacagg tgtccgagaa ctggcaggac ggcagactgc tggaagccgt gaagaatggc   360
tacaccctga tctacgacga gttcaccaga agcaagccgg ctaccaacaa catcttcctg   420
agcatcctgg aagagggcgt gctgccctg tacggcgtga agatgaccga cccttcgtg    480
cgcgtgcacc ccgacttcag agtgatcttc accagcaacc ccgccgagta tgccggccgtg   540
tacgatacc aggacgccct gctggaccgg ctgatcacca tgtttcatcga ctacaaggac   600
atcgaccggg aaaccgccat cctgaccgag aaaaccgacg tggaagagga cgaggccgg    660
accatcgtga ccctggtggc caacgtgcgg aacagaagcg cgcgacgagaa tagcagcggc   720
ctgagcctga gagccagcct gatgattgcc ccctggcca ccagcagga catccctatc     780
gatgccagcg acgaggactt ccagaccctg tgcatcgaca tcctgcacca ccccctgacc   840
aagtgcctgg acgaggaaaa cgccaagagc aaggccgaga agatcattct ggaagagtgc   900
aagaacatcg acaccgagga aaagtga                                       927

SEQ ID NO: 433              moltype = DNA   length = 768
FEATURE                     Location/Qualifiers
source                      1..768
                            mol_type = genomic DNA
                            organism = Bacillus megaterium
SEQUENCE: 433
atgagcgaga caaacgagac aggcatctac atcttcagcg ccatccagac cgacaaggac    60
gaggaattcg gcgccgtgga agtggaaggg accaaggccg agacattcct gatccggtac   120
aaggacgccg ccatggtggc cgccgaagtg cccatggaa tctaccaccc caaccggtac    180
aacctgctga tgccaccagaa tgccgtggcc gccatcatgg acaagaacga caccgtgatc   240
cccatcagct tcggcaacgt gttcaagagc aaagaggacg tgaaggtgct gctgaaaaac   300
ctgtaccccc agttcgagaa gctgttcccc gccatcaagg aaagatcga agtgggcctg   360
aaagtgatcg gcaagaaaga gtggctggaa aagaaagtga acgagaaccc cgagctggaa   420
aaagtgtccg ccagcgtgaa gggcaagagc gaggccgctg gctactacga gagaatccag   480
ctgggcggca tggcccagaa gatgttcacc agcctgcaga agaagtgaa accgacgtg    540
ttcagccccc tggaagaagc cgccgaggcc gccaaagcca atgagcctac aggcgagaca   600
atgctgctga acgccagctt cctgatcaac agagaggacg aggccaagtt cgacgaaaaa   660
gtgaatgagg cccacgagaa ctggaaggat aaggccgact ccactacag cggcccctgg    720
cccgcctaca acttcgtgaa catccggctg aaggtggaag agaagtga                768

SEQ ID NO: 434              moltype = DNA   length = 267
FEATURE                     Location/Qualifiers
source                      1..267
                            mol_type = genomic DNA
                            organism = Bacillus megaterium
SEQUENCE: 434
atgctgcaca agctcgtgac cgcccccatc aacctggtcg tgaagatcgg cgagaaggtg    60
caggaagagg ccgacaagca gctgtacgac ctgcccacca tccagcagaa gctgatccag   120
ctgcagatga tgttcgagct gggcgagatc cccgaggaag ccttccagga aaaagaggac   180
gagctgctga tgagatacga gatcgccaag cggcgcgaga tcgagcagtg ggaggaactg   240
acccagaagc ggaacgagga agctga                                        267

SEQ ID NO: 435              moltype = DNA   length = 810
FEATURE                     Location/Qualifiers
source                      1..810
                            mol_type = genomic DNA
                            organism = Bacillus megaterium
```

```
SEQUENCE: 435
atgggcgagc tgctgtacct gtacggcctg atccccacca aagaggccgc tgccatcgag    60
cccttcccat tctacaaggg cttcgacggc gagcacagcc tgtaccctat cgccttcgac   120
caagtgaccg ccgtggtgtt caagctggac gccgacacct acagcgagaa agtgatccag   180
gaaaagatgg aacaggacat gagctggctg caggaaaagg ccttccacca ccacgagaca   240
gtggccgccc tgtacgagga attcaccatc atcccctga agttctgcac catctataag    300
ggcgaggaat ccctgcaggc cgccatcgag atcaacaaag agaagatcga gaactccctg   360
accctgctgc agggcaacga ggaatggaac gtgaagatct actgcgacga caccgagctg   420
aagaagggca tcagcgagac aaacgagagc gtgaaggccg agaagcagga aatcagccgc   480
ctgagccccg gcagacagtt cttcgagaag aagaagattg accagctgat cgagaaagag   540
ctggaactgc acaagaacaa agtgtgcgag gaaatccacg acaagctgat tgagctgagc   600
ctgtacgact ccgtgaagaa gaactggtcc aaggacgtga ccggcgctgc gaacagatg    660
gcctggaaca gcgtgttcct gctgcccagc ctgcagatca ccaagttcgt gaacgagatc   720
gaggaactgc agcagcggct ggaaaacaag ggctggaagt tcgaagtgac cggcccctgg   780
cctccctacc acttcagcag ctttgcctga                                    810

SEQ ID NO: 436          moltype = DNA  length = 285
FEATURE                 Location/Qualifiers
source                  1..285
                        mol_type = genomic DNA
                        organism = Bacillus megaterium
SEQUENCE: 436
atgagcctga agcagagcat ggaaaacaag gatatcgccc tgatcgacat cctggacgtg    60
atcctggaca agggcgtggc catcaagggc gacctgatca tctctatcgc cggcgtggac   120
ctggtgtacc tggacctgag agtgctgatc tccagcgtgg aaaccctggt gcaggccaaa   180
gagggcaacc acaagcccat caccagcgag cagttcgaca gcagaaaga ggaactgatg    240
gacgccaccg gccagcccag caagtggaca atcctctgg gcagc                    285

SEQ ID NO: 437          moltype = DNA  length = 285
FEATURE                 Location/Qualifiers
source                  1..285
                        mol_type = genomic DNA
                        organism = Bacillus megaterium
SEQUENCE: 437
atgcagcccg tgtcccaggc caacggcaga atccacctgg atcccgatca ggccgaacag    60
ggactggccc agctcgtgat gaccgtgatc gagctgctgc ggcagatcgt ggaacggcac   120
gccatgagaa gagtggaagg cggcacccty accgacgagc agatcgagaa tctgggaatc   180
gccctgatga acctggaaga gaagatggac gagctgaaag aggtgttcgg actggacgcc   240
gaggacctga acatcgacct gggccctctg ggcagcctgc tgtga                   285

SEQ ID NO: 438          moltype = DNA  length = 303
FEATURE                 Location/Qualifiers
source                  1..303
                        mol_type = genomic DNA
                        organism = Bacillus megaterium
SEQUENCE: 438
atggccgtgg aacacaaacat gcagagcagc accatcgtgg acgtgctgga aaagatcctg    60
gacaagggcg tcgtgatcgc cggggacatc acagtgggaa tcgccgacgt ggaactgctg   120
accatcaaga tccggctgat cgtgccagc gtggacaagg ccaaagaaat cggcatggat    180
tggtgggaga acgaccccta cctgagcagc aagggcgcca acaacaaggc cctgaagag    240
gaaaacaaga tgctgcacga gcggctgaaa acactggaag agaagatcga cacaaagcgc   300
tga                                                                 303

SEQ ID NO: 439          moltype = DNA  length = 417
FEATURE                 Location/Qualifiers
source                  1..417
                        mol_type = genomic DNA
                        organism = Bacillus megaterium
SEQUENCE: 439
atgagcaccg gccccagctt cagcaccaag acaacaccc tggaatactt cgtgaaggcc     60
agcaacaagc acggcttcag cctggacatc agcctgaacg tgaacggggc cgtgatcagc   120
ggcaccatga tcagcgccaa agagtacttc gactacctga gcgagacatt cgaagagggc   180
agcgaggtgg cccaggccct gtctgagcag tttagcctgg ccagcgaggc ctccgagtct   240
aatggcgaag ccgaggccca cttcatccac ctgaagaaca tctacgctgt ctgcggcgac   300
agcaagagca ccccagcaa gggcaagatc ttctggcgcg caagatcgc cgaggtggac    360
ggattcttcc tgggaaagat cagcgacgcc aagtccacca gcaagaagtc cagctga     417

SEQ ID NO: 440          moltype = DNA  length = 508
FEATURE                 Location/Qualifiers
misc_feature            1..508
                        note = synthetic polynucleotide
source                  1..508
                        mol_type = other DNA
                        organism = synthetic construct
SEQUENCE: 440
cgttacataa cttacggtaa atggcccgcc tggctgaccg cccaacgacc cccgcccatt     60
gacgtcaata atgacgtatg ttcccatagt aacgccaata gggactttcc attgacgtca   120
atgggtggag tatttacggt aaactgccca cttggcagta catcaagtgt atcatatgcc   180
aagtacgccc cctattgacg tcaatgacgg taaatggccc gcctggcatt atgcccagta   240
```

```
catgacccta tgggactttc ctacttggca gtacatctac gtattagtca tcgctattac    300
catggtgatg cggttttggc agtacatcaa tgggcgtgga tagcggtttg actcacgggg    360
atttccaagt ctccacccca ttgacgtcaa tgggagtttg ttttggcacc aaaatcaacg    420
ggactttcca aaatgtcgta acaactccgc cccattgacg caaatgggcg gtaggcgtgt    480
acggtgggag gtctatataa gcagagct                                       508

SEQ ID NO: 441          moltype = DNA   length = 135
FEATURE                 Location/Qualifiers
misc_feature            1..135
                        note = synthetic polynucleotide
source                  1..135
                        mol_type = other DNA
                        organism = synthetic construct
SEQUENCE: 441
aacttgttta ttgcagctta taatggttac aaataaagca atagcatcac aaatttcaca     60
aataaagcat ttttttcact gcattctagt tgtggtttgt ccaaactcat caatgtatct    120
tatcatgtct ggatc                                                     135

SEQ ID NO: 442          moltype = AA   length = 24
FEATURE                 Location/Qualifiers
REGION                  1..24
                        note = synthetic polypeptide
source                  1..24
                        mol_type = protein
                        organism = synthetic construct
SEQUENCE: 442
GAPGSGATNF SLLKQAGDVE ENPG                                            24

SEQ ID NO: 443          moltype = DNA   length = 6675
FEATURE                 Location/Qualifiers
misc_feature            1..6675
                        note = synthetic polynucleotide
source                  1..6675
                        mol_type = other DNA
                        organism = synthetic construct
SEQUENCE: 443
cgttacataa cttacggtaa atggcccgcc tggctgaccg cccaacgacc cccgcccatt     60
gacgtcaata atgacgtatg ttcccatagt aacgccaata gggactttcc attgacgtca    120
atgggtggag tatttacggt aaactgccca cttggcagta catcaagtgt atcatatgcc    180
aagtacgccc cctattgacg tcaatgacgg taaatggccc gcctggcatt atgcccagta    240
catgacccta tgggactttc ctacttggca gtacatctac gtattagtca tcgctattac    300
catggtgatg cggttttggc agtacatcaa tgggcgtgga tagcggtttg actcacgggg    360
atttccaagt ctccacccca ttgacgtcaa tgggagtttg ttttggcacc aaaatcaacg    420
ggactttcca aaatgtcgta acaactccgc cccattgacg caaatgggcg gtaggcgtgt    480
acggtgggag gtctatataa gcagagctcg tttagtgaac cgtcagatcg cctggagacg    540
ccatccacgc tgttttgacc tccatagaag acaccgggac cgatccagcc tccggactct    600
agcctaggct tttgcaaaaa gctatttagg tgacactata gaaggtacgc ctgcaggtac    660
cgagctcgga tccagtaccc ttcaccatga ccgtgctgac cgacaagcgg aagaagggca    720
gcggcgcctt catccaggac gacgagacaa aagaggtgct gagcagagcc ctgagctacc    780
tgaagtccgc ctacagcatc cacttcaccg gacctgccgg cggaggcaag acatctctgg    840
ctagagccct ggccaagaaa cggaagcggc ccgtgatgct gatgcacggc aaccacgagc    900
tgaacaacaa ggacctgatc ggcgatttca ccggctacac cagcaaaaag gtgatcgacc    960
agtacgtgcg gagcgtgtac aagaaagacg aacaggtgtc cgagaactgg caggacggca   1020
gactgctgga agccgtgaag aatggctaca ccctgatcta cgacgagttc accagaagca   1080
agccgctac caacaaactc ttcctgagca tccttgagga gccgtgctg ccctcgtacg    1140
gcgtgaagat gaccgaccct ttcgtgcgcg tgcaccccga cttcagagtg atctttacca   1200
gcaacccgc cgagtatgcc ggcgtgtacg ataccaagga cgcctgctg gaccggctga   1260
tcaccatgtt catcgactac aaggacatcg accgggaaac cgctatcctg accgagaaaa   1320
ctgacgtgga agaagacgag gcccggacca tcgtgacccc ggtggccaac gtgcggaaca   1380
gaagcggcga cgagaatagc agcggcctga gcctgagagc cagcctgatg attgccaccc   1440
tggccaccca gcaggacatc cctatcgatg cagcgacga ggacttccag accctgtgca   1500
tcgacatcct gcaccaccc ctgaccaagt gcctggacga agaacgcc aagagcaagg   1560
ccgagaagat cattctcgaa gagtgcaaga catcgacac cgaggagaag ggtgccccgg   1620
gatctggcgc aacaaatttt agtcttttaa agcaggcagg agacgtcgaa gaaacccgcc   1680
gacccgtgag cgagacaaac gagacaggca tctacatctt cagcgccatc agacagaca   1740
aggatgagga attcggcgcc gtggaagtgg aagggaccaa ggctgagaca ttcctgatcc   1800
ggtataagga cgccgccatg gtggccgccg aagtgcccat gaagatctac cacccccacc   1860
ggcagaacct gctgatgcac cagaatgccg tggccgcac catgacaag aacgacaccg   1920
tgatccccat cagcttcggc aacgtgttca gagccaaga ggacgtgaag gtgctcctcg   1980
aaaacctgta ccccagttc gagaagctgt tcccgccat caaggaaaag atcgaagtgg   2040
gcctgaaggt gatcggcaag aaagagtggc tcgaaaagaa agtgaacgag acccccgagc   2100
tggaaaaagt gtccgccagc gtgaagggca gagcgaggc cgctggctac tacgagaa   2160
tccagctggg cggcatggcc cagaagatgt tcacaagcct gcagaagaa gtgaaacc   2220
acgtgttcag cccctggaa gaagcgcg aggccgccaa agccaatgag cctacaggcg   2280
aaacaatgct gctgaacgcc agcttcctga tcaacagaga ggatgaggcc aagttcgacg   2340
agaaagtcaa tgaggcccac gagaactgga ggataaggc cgactccac tacagcggcc   2400
cctgccccgc ctacaacttc gtgaacatcc ggctgaaggt ggaagagaag ggggcacctg   2460
gctcgggagc gaccaacttc tcattactca acaagccgg agacgttgag gagaatccag   2520
gccctgtgct gcacaagctc gtgaccgcc ccatcaacct ggtcgtgaag atcggcgaga   2580
```

```
aggtgcagga agaggccgac aagcagctgt acgacctgcc caccatccag cagaagctga   2640
tccagctgca gatgatgttc gagctgggcg agatccccga ggaagccttc caggaaaaag   2700
aggacgaact gctgatgaga tacgagatcg ccaagcggcg cgagattgag cagtgggaag   2760
aactgaccca gaagcggaat gaggaaagcg gtgcccggg atctggcgca acaaattta    2820
gtcttttaaa gcaggcagga gacgtcgagg aaaaccctgg acccgtgggc gagctgctgt   2880
acctctacgg cctgatcccc accaaagagg ccgctgctat cgagcccttc ccattctaca   2940
agggcttcga cggcgagcac agcctgtacc ctatcgcctt cgaccaagtg accgccgtgg   3000
tgttcaagct ggacgccgac acctacacgcg agaaagtgat ccaggaaaag atggaacagg   3060
acatgagctg gctgcaggaa aaggccttcc accaccagga gacagtggcc gccctgtatg   3120
aggaattcac catcatcccc ctgaagttct gcaccatcta agggaggag gaatccctgc   3180
aggccgccat cgagatcaac aaagagaaga tcgaaaactc cctgaccctg ctgcagggca   3240
acgaggaatg gaacgtgaag atctactgcg acgacaccga gctgaagaag ggcatcagcg   3300
agacaaacga gagcgtgaag gccaagaagc aggaaatcag ccacctgagc cccggcagac   3360
agttcttcga gaagaagaag attgaccagc tcatcgagaa agagctggaa ctgcacaaga   3420
acaaagtgtg cgaggaaatc cacgacaagc tgattgagct gagcctctac gactccgtga   3480
agaagaactg gtccaaggac gtgacaggcg ctgccgaaca gatggcctgg aacagcgtgt   3540
tcctgctgcc cagcctgcag atcaccaagt tcgtgaacga gatcgaggaa ctccagcagc   3600
ggctggagaa caagggatgg aagttcgaag tgaccggccc ctggcctccc taccacttca   3660
gcagctttgc cggggcacct ggctcggag cgaccaactt ctcattactc aaacaagccg    3720
gagacgttga ggagaatcca ggccctgtga gcctgaagca gagcatggag aataaggata   3780
tcgccctgat cgacatcctc gacgtgatcc tggacaaggg agtggccatc aagggcgacc   3840
tgatcatctc tatcgccggc gtggacctgg tgtacctgga tctgagagtg ctgatctcca   3900
gcgtggaaac cctggtgcag gccaagagg gcaaccacga gcccatcacc agcgagcagt   3960
tcgacaagca gaaagaggag ctgatggacg ccaccggcca gcccagcaag tggacaaatc   4020
ctctgggcag cggcgctccc gggtcaggtg ccacgaattt tcgttgttg aagcaagctg    4080
gggatgttga agagaaccca gggcctgtgc agcccgtgtc ccaggccaac agcagaatcc   4140
acctggatcc cgatcaggcc gaacaggac tggcccagct cgtgatgacc gtgatcgagc    4200
tgctgcggca gatcgtggaa cggcacgcca tgagaagagt ggaaggcggc accctgaccg   4260
acgagcagat cgagaatctg ggaatcgctc tgatgaacct ggaggagaag atggacgagc   4320
tgaaagaggt gttcggactg gacgcgtgagg atctgaacat cgacctgggc cctctgggca   4380
gcctgctggg tgccccggga tctggcgcaa caaattttag tcttttaaag caggcaggag   4440
acgtcgagga aaaccctgga cccgtggccg tggaacacaa catgcagagc agcaccatcg   4500
tggacgtgct ggaaagatc ctggacaagg gcgtcgtgat cgccggggac atcacagtgg    4560
aatcgccga cgtggaactg ctgaccatca agatccggct gatcgtggcc agcgtggaca    4620
aggccaaaga aatcggcatg gattggtggg agaacgaccc ctacctgagc agcaagggcg   4680
ccaacaacaa ggctctggaa gaggaaaaca agatgctgca cgagcggctg aaaacactgg    4740
aagagaagat cgagacaaag cgcggggcac ctggctcggg agcgaccaac ttctcattac    4800
tcaaacaagc cggagacgtt gaggagaatc caggccctgt gagcaccggc cccagcttca   4860
gcaccaagga caacacctg gaatacttcg tgaaggccaa caagcagcct ttagcc       4920
tcgacatcag cctgaacgtg aatggggccg tgattagcgg caccatgatc agcgccaaag   4980
agtacttcga ctacctgagc gagacattcg aagagggcag cgaagtggcc caggccctgt   5040
ctgagcagtt tagcctggct agcgaggcct ccgagtctaa tggcgaagcc gaggcccact   5100
tcatccacct gaagaacacc aagatctact gcggcgacag cagagcccccc agcaagg     5160
gcaagatctt ctggcgcggc aagatcgccg aggtggacgg attcttcctg gaaaaatca    5220
gcgacgccaa gtccaccagc aagaagtcca gcggcgctcc cgggtcaggt gccacgaatt   5280
tttcgttgtt gaagcaagct ggggatgttg aagagaaccc agggcctgtg gtgtccaagg   5340
gcgaggaact gttcaccggc gtggtgccca tcctggtgga actggatggc gacgtgaacg   5400
gccacaagtt cagcgtgtcc ggcgaggggc aaggcgacgc cacatacgga aagctgaccg   5460
tgaagttcat ctgcaccacc ggcaagctgc ccgtgccttg gcctaccctc gtgaccacac   5520
tgacctacgg cgtgcagtgc ttcgccagat acccgaccca catgaagcag cacgatttct   5580
tcaagcgcta catgcccgag ggctacgtgc aggaacggac catcttcttc aaggacgacg   5640
gcaactacaa gacaagagcc gaagtgaagt tcgaggggcga caccctcgtg aaccggatcg   5700
agctgaaggg catcgacttc aaagaggatg gcaacatcct gggccacaag ctggagtaca   5760
actacaacag ccacaaggtg tacatcaccg ccgacaagca gaaaaacggc atcaaagtga   5820
acttcaagac ccggcacaac atcgaggacg gcagcgtgca gctggccgac cactaccagc   5880
agaacacccc catcggagat ggccccgtgc tgctgcccga caaccactac ctgagcacac   5940
aaagcgccct gagcaaggac cccaacgaga gcgggacca catggtgctg ctggaatttg    6000
tgaccgccgc tggcatcacc ctgggcatgg acgagctgta caagtgactc gagtctagag   6060
ggcccgtgg ctgtaatcta ggatcccct cgaggggccc aagcttacgc gtgcatgcga    6120
cgtcatagct ctctccctat agtgagtcgt attataagct agcttgggat ctttgtgaag   6180
gaaccttact tctgtggtgt gacataattg gacaaactac ctacagagat ttaaagctct   6240
aaggtaaata taaattttt aagtgtataa tgtgttaaac tagctgcata tgcttgctgc    6300
ttgagagttt tgcttactga gtatgattta tgaaatatt atacacagga gctagtgatt    6360
ctaattgttt gtgtattta gattcacagt cccaaggctc atttcaggcc cctcagtcct   6420
cacagtctgt tcatgatcat aatcagccat accacatttg tagaggtttt acttgcttta   6480
aaaaacctcc cacacctccc cctgaacctg aaacataaaa tgaatgcaat tgttgttgtt   6540
aacttgttta ttgcagctta taatggttac aaataaagca atagcatcac aaattttcaca   6600
aataaagcat tttttcact gcattctagt tgtggtttgt ccaaactcat caatgtatct    6660
tatcatgtct ggatc                                                   6675

SEQ ID NO: 444          moltype = DNA   length = 4009
FEATURE                 Location/Qualifiers
misc_feature            1..4009
                        note = synthetic polynucleotide
source                  1..4009
                        mol_type = other DNA
                        organism = synthetic construct
SEQUENCE: 444
cgttacataa cttacggtaa atggcccgcc tggctgaccg cccaacgacc cccgcccatt   60
```

```
gacgtcaata atgacgtatg ttcccatagt aacgccaata gggactttcc attgacgtca   120
atgggtggag tatttacggt aaactgccca cttggcagta catcaagtgt atcatatgcc   180
aagtacgccc cctattgacg tcaatgacgg taaatggccc gcctggcatt atgcccagta   240
catgacctta tgggactttc ctacttggca gtacatctac gtattagtca tcgctattac   300
catggtgatg cggttttggc agtacatcaa tgggcgtgga tagcggtttg actcacgggg   360
atttccaagt ctccacccca ttgacgtcaa tgggagtttg ttttggcacc aaaatcaacg   420
ggactttcca aatgtcgta acaactccgc cccattgacg caaatgggcg gtaggcgtgt    480
acggtgggag gtctatataa gcagagctcg tttagtgaac cgtcagatcg cctggagacg   540
ccatccacgc tgttttgacc tccatagaag acaccgggac cgatccagcc tccggactct   600
agcctaggct tttgcaaaaa gctatttagg tgacactata gaaggtacgc ctgcaggtac   660
cgagctcgga tccagtaccc ttcaccatgg ccgtggaaca acatgcag agcagcacca    720
tcgtggacgt gctggaaaag atcctggaca agggcgtcgt gatcgccggg gacatcacag   780
tgggaatcgc cgacgtggaa ctgctgacca tcaagatccg gctgatcgtg gccagcgtgg   840
acaaggccaa agaaatcggc atggattggt gggagaactga cccctacctg agcagcaagg   900
gcgccaacaa caaggccctg gaagaggaaa acaagatgct gcacgagcgg ctgaaaacac   960
tggaagagaa gatcgagaca aagcgcggtg ccccgggatc tggcgcaaca aattttagtc  1020
tttttaaagca ggcaggagac gtcgaggaaa accctgacc cgtgagcgag acaaacgaga  1080
caggcatcta catcttcagc gccatccaga cagacaagga tgaggaattc ggcgccgtgg  1140
aagtggaagg gaccaaggct gagacattcc tgatccggta taaggacgcc gccatggtgg  1200
ccgccgaagt gcccatgaag atctaccacc ccaaccggca gaacctgctg atgcaccaga  1260
atgccgtggc cgccatcatg gacaagaacg acaccgtgat ccccatcagc ttcggcaacg  1320
tgttcaagag caaagaggac gtgaaggtgc tcctgaaaa cctgtacccc cagttcgaga  1380
agctgttccc cgccatcaag ggaaagatcg aagtgggcct gaaggtgatc ggcaagaaag  1440
agtggctcga aagaaagtg aacgagaacc ccgagctgga aaaagtgtcc gccagcgtga  1500
agggcaagag cgaggccgct ggctactacg agagaatcca gctgggcggc atggcccaga  1560
agatgttcac aagcctgcag aaagaagtga aaaccgactg gttcagccgc ctggaagagg  1620
ccgccgaggc cgccaagcc aatgagccta caggcgaaac aatgctgctg aacgccagct  1680
tcctgatcaa cagagaggat gaggccaagt cgacgagaa agtcaatgag gcccacgaga  1740
actgaaagga taaggccgac ttccactaca gcggcccctg gccgcctac aacttcgtga  1800
acatccggct gaaggtggaa gagaaggggg cacctgctgc gggagcgacc aacttctcat  1860
tactcaaaca agccggagac gttgaggaga atccaggccc tgtgctgcac aagctcgtga  1920
ccgcccccat caacctggtc gtgaagatcg gcgagaaggt gcaggaagag gccgacaagc  1980
agctgtacga cctgcccacc atccagcaga agctgatcca gctgcagatg atgttcgagc  2040
tgggcgagat ccccgaggaa gccttccagg aaaaagagga cgaactgctg atgagatacg  2100
agatccgcaa gcggcgcgag attgacgagt gggaagaact gacccagaag cggaatgagg  2160
aaagcggtgc cccgggatct ggcgcaacaa attttagtct tttaagcag gcaggagacg  2220
tcgaggaaaa ccctggaccc gtgggcgagc tgctgtacct ctacgcctg atccccacca  2280
aagaggccgc tgctatcgag cccttccat tctacaaggg cttcgacggc gagcacagcc  2340
tgtaccctat cgccttcgac caagtgaccg ccgtggtgt caagctggac gccgacacct  2400
acagcgagaa agtgatccag gaaaagatgg aacaggacat gagctggctg caggaaaagg  2460
ccttccacca ccacgagaca gtggccgccc tgtatgagga attcaccatc atcccctga  2520
agttctgcac catctctaag ggagaggaat ccctgcaggc cgccatcgag atcaacaaag  2580
agaagatcga aaactccctg accctgctgc agggcaacga ggaatggaac tgaagatct  2640
actgcgacga caccgagctg aagaagggca tcagcgagac aaacgagagc gtgaaggcca  2700
agaagcagga aatcagccac ctgagccccg cagacagtt cttcgagaag aagaagattg  2760
accagctcat cgagaaagag ctggaactgc acaagaacaa agtgtgcgag gaaatccacg  2820
acaagctgat tgagctgagc ctctacgact ccgtgaagaa gaactgtccc aaggacgtga  2880
caggcgctgc cgaacagatg gcctggaaca gcgtgttcct gctgcccagc ctgcagatca  2940
ccaagttcgt gaacgagatc gaggaactcc agcagcggct ggagaacaag ggatggaagt  3000
tcgaagtgac cggcccctgg cctccctacc acttcagcag ctttgccggg gcacctggct  3060
cgggacgac caacttctca ttactcaaac aagccggaga cgttgaggag aatccaggcc  3120
ctgtgcagcc cgtgtcccag gccaacggca gaatccacct ggatcccgat caggccgaac  3180
agggactggc ccagctcgtg atgaccgtga tcgagctgct gcggcagatc gtggaacggc  3240
acgccatgag aagagtggaa ggcggcaccc tgaccgacga gcagatcgag aatctgggaa  3300
tcgccctgat gaacctggaa gagaagatgg acgagtcaga aaggtgttc ggactggacg  3360
ccgaggacct gaacatcgac ctgggccctc tgggcagcct gctgtgataa tctagaggat  3420
ccctcgaggg gcccaagctt acgcgtgcat gcgacgtcat agctctctcc ctatagtgag  3480
tcgtattata agctagcttg ggatctttgt gaaggaacct tacttctgtg gtgtgacata  3540
attggacaaa ctacctacag agatttaaag tctaaggta aatataaaat ttttaagtgt  3600
ataatgtgtt aaactagctg catatgcttg ctgcttgaga gttttgctta ctgagtatga  3660
tttatgaaaa tattatacac aggagctagt gattctaatt gtttgtgtat ttagattca   3720
cagtcccaag gctcatttca ggcccctcag tcctcacagt ctgttcatga tcataatcag  3780
ccataccaca tttgtagagg tttacttgc tttaaaaaac ctcccacacc tccccctgaa   3840
cctgaaacat aaaatgaatg caattgttgt tgttaacttg tttattgcag cttataatgg  3900
ttacaaataa agcaatagca tcacaaattt cacaaataaa gcatttttt cactgcattc    3960
tagttgtggt ttgtccaaac tcatcaatgt atcttatcat gtctggatc                4009

SEQ ID NO: 445     moltype = DNA   length = 3371
FEATURE            Location/Qualifiers
misc_feature       1..3371
                   note = synthetic polynucleotide
source             1..3371
                   mol_type = other DNA
                   organism = synthetic construct
SEQUENCE: 445
ccctagaaag ataatcatat tgtgacgtac gttaaagata atcatgtgta aaattgacgc    60
atgtgtttta tcgtctgta tatcgaggtt tattattaa tttgaataga tattaagttt    120
tattatatttt acacttacat actaataata aattcaacaa acaattatt tatgtttatt    180
tatttattaa aaaaaacaaa aactcaaaat ttcttctata aagtaacaaa acttttatga   240
```

```
gggacagccc cccccccaaag cccccaggga tgtaattacg tccctcccccc gctaggggc   300
agcagcgagc cgcccgggcc tccgctccgg tccggcgctc ccccgcatc ccgagccgg     360
cagcgtgcgg ggacagcccg ggcacgggga aggtggcacg ggatcgcttt cctctgaacg   420
cttctcgctg ctctttgagc ctgcagacac ctgggggat acggggaaaa ggcctccacg    480
gccactagtt tcactcgagt ttactcccta tcagtgatag agaacgtatg aagagtttac   540
tccctatcag tgatagagaa cgtatgcaga ctttactccc tatcagtgat agagaacgta   600
taaggagttt actccctatc agtgatagag aacgtatgac cagttactc cctatcagtg    660
atagagaacg tatctacagt ttactcccta tcagtgatag agaacgtata tccagtttac   720
tccctatcag tgatagagaa cgtatgtcga ggtaggcgtg tacggtgggc gcctataaaa   780
gcagagctcg tttagtgaac cgtcagatcg cctggagcaa ttccacaaca cttttgtctt   840
atacttggta cctatgcatg ccaccatgag catccagaag tccaccaaca gcagcagcct   900
ggccgaagtg atcgaccgga tcctggacaa gggcatcgtg atcgacgcct cgcagagt    960
gtccgtcgtg ggcatcgaga tcctgaccat cgaggcagga tcgtgatcg ccagcgtgga   1020
cacctggctg agatatgccg aagccgtggg cctgctgcgg gacgacgtgg aagaaaatgg   1080
cctgcccgag cggagcaaca gctctgaggg acagccccgg ttcagcatct gaactaaatc   1140
gcactgtcgg cgtccccccc taacgttact ggccgaagcc gcttggaata aggccggtgt   1200
gcgtttgtct atatgttatt ttccaccata ttgccgtctt ttggcaatgt gagggcccgg   1260
aaacctggcc ctgtcttctt gacgagcatt cctagggtc tttcccctct cgccaaagga   1320
atgcaaggtc tgttgaatgt cgtgaaggaa gcagttcctc tggaagcttc ttgaagacaa   1380
acaacgtctg tagcgaccct ttgcaggcag cggaaccccc cacctggcga caggtgcctc   1440
tgcggccaaa agcacgtgt ataagataca cctgcaaagg cggcacaacc ccagtgccac    1500
gttgtgagtt ggatagttgt ggaaagagtc aaatggcttc cctcaagcgt attcaacaag   1560
gggctgaagg atgcccagaa ggtaccccat tgtatgggat ctgatctggg gcctcggtgc   1620
acatgcttta catgtgttta gtcgaggtta aaaaacgtct aggcccccg aaccacgggg    1680
acgtggtttt cctttgaaaa acacgatgat aatatgccca aaccatggt gagcaagggc    1740
gaggaggata acatgccat catcaaggag ttcatgcgct tcaaggtgca catggaggc    1800
tccgtgaacg gccacgagtt cgagatcgag ggcgagggcg agggccgccc ctacgagggc   1860
acccagaccg ccaagctgaa ggtgaccaag gcggccccc tgcccttcgc ctgggacatc    1920
ctgtccctc agttcatgta cggctccaag gcctacgtga agcaccccgc cgacatccc    1980
gactacttga agctgtcctt ccccgagggc ttcaagtggg agcgcgtgat gaacttcgag   2040
gacggcggcg tggtgaccgt gacccaggac tcctccctgc aggacggcga gttcatctac   2100
aaggtgaagc tgcgcggcac caacttcccc tccgacggcc ccgtaatgca gaagaagacc   2160
atgggctggg aggcctcctc cgagcggatg taccccgagg acggcgccct gaagggcgag   2220
atcaagcaga ggctgaagct gaaggacggc ggccactacg acgctgaggt caagaccacc   2280
tacaaggcca agaagcccgt gcagctgccc ggcgcctaca acgtcaacat caagttggac   2340
atcacctccc acaacgagga ctacaccatc gtgaacagt acgaacgcgc cgagggcgc    2400
cactccaccg gcggcatgga cgagctgtac aagtgaacta gttcgttaac taaacttgtt   2460
tattgcagct tataatggtt acaaataaag caatagcatc acaaatttca caaataaagc   2520
atttttttca ctgcattcta gttgtggttt gtccaaactc atcaatgtat cttatcatgt   2580
ctggaattga ctcaaatgat gtcaattagt ctatcagaag ctcatctggt ctcccttccg   2640
ggggacaaga catccctgtt taatatttaa acagcagtgt tcccaaactg ggttcttata   2700
tcccttgctc tggtcaacca ggttgcaggg tttcctgtcc tcacaggaac gaagtcccta   2760
aagaaacagt ggcagccagg tttagccccg gaattgacgt gattccttt ttagggccca   2820
ttggtatggc tttttccccg tatcccccca ggtgtctgca ggctcaaaga gcagcgagaa   2880
gcgttcagag gaaagcgatc ccgtgccacc ttccccgtgc ccgggctgtc cccgcacgct   2940
gccggctcgg ggatgcgggg ggagcgccgg accgagcgg agcccgggc ggctcgctgc    3000
tgcccctag cgggggaggg acgtaattac atccctgggg gctttgggg gggctgtcc     3060
ctgatatcta taacaagaaa atatatat aataagttat cacgtaagta gaacatgaaa    3120
taacaatata attatcgtat gagttaaatc ttaaagtca cgtaaagat aatcatgcgt    3180
cattttgact cacgcggtcg ttatagttca aaatcagtga cacttaccgc attgacaagc   3240
acgcctcacg ggagctccaa gcggcgactg agatgtccta aatgcacagc gacggattcg   3300
cgctatttag aaagagagag caatatttca agaatgcatg cgtcaatttt acgcagacta   3360
tctttctagg g                                                        3371
SEQ ID NO: 446       moltype = DNA  length = 7161
FEATURE              Location/Qualifiers
misc_feature         1..7161
                     note = synthetic polynucleotide
source               1..7161
                     mol_type = other DNA
                     organism = synthetic construct
SEQUENCE: 446
ccctagaaag ataatcatat tgtgacgtac gttaaagata atcatgtgta aaattgacgc     60
atgtgtttta tcggtctgta tatcgaggtt tatttattaa tttgaataga tattaagttg    120
tattatatt acacttacat actaataata aattcaacaa acaatttatt tatgtttatt    180
tatttattaa aaaaaacaaa aactcaaaat ttcttctata aagtaacaaa acttttatga    240
gggacagccc cccccaaag cccccaggga tgtaattacg tccctcccccc gctaggggc    300
agcagcgagc cgcccgggcc tccgctccgg tccggcgctc ccccgcatc ccgagccgg     360
cagcgtgcgg ggacagcccg ggcacgggga aggtggcacg ggatcgcttt cctctgaacg   420
cttctcgctg ctctttgagc ctgcagacac ctgggggat acggggaaaa ggcctccacg    480
gccactagtt tcactcgagt ttactcccta tcagtgatag agaacgtatg aagagtttac   540
tccctatcag tgatagagaa cgtatgcaga ctttactccc tatcagtgat agagaacgta   600
taaggagttt actccctatc agtgatagag aacgtatgac cagttactc cctatcagtg    660
atagagaacg tatctacagt ttactcccta tcagtgatag agaacgtata tccagtttac   720
tccctatcag tgatagagaa cgtatgtcga ggtaggcgtg tacggtgggc gcctataaaa   780
gcagagctcg tttagtgaac cgtcagatcg cctggagcaa ttccacaaca cttttgtctt   840
atacttggta cctatgcatg ccaccatgac cgtgctgacc gacaagcgga agaagggcag   900
cggcgccttc atccaggacg acgagacaaa agaggtgctg agcagagccc tgagctacct   960
gaagtccggc tacagcatcc acttcaccgg acctgccggc ggaggcaaga catctctggc   1020
```

```
tagagccctg gccaagaaac ggaagcggcc cgtgatgctg atgcacggca accacgagct    1080
gaacaacaag gacctgatcg gcgatttcac cggctacacc agcaaaaagg tgatcgacca    1140
gtacgtgcgg agcgtgtaca agaaagacga acaggtgtcc gagaactggc aggacggcag    1200
actgctggaa gccgtgaaga atggctacac cctgatctac gacgagttca ccagaagcaa    1260
gcccgctacc aacaacatct tcctgagcat ccttgaggag ggcgtgctgc ccctgtacgg    1320
cgtgaagatg accgacccett tcgtgcgcgt gcaccccgac ttcagagtga tctttaccag    1380
caaccccgcc gagtatgccg gcgtgtacga tacccaggac gccctgctgg accggctgat    1440
caccatgttc atcgactaca aggacatcga ccgggaaacc gctatcctga ccgagaaaac    1500
tgacgtggaa gaagacgagg cccggaccat cgtgaccctg gtggccaacg tgcggaacag    1560
aagcggcgac gagaatagca gcggcctgag cctgagagcc agcctgatga ttgccaccct    1620
ggccacccag caggacatcc ctatcgatgg cagcgacgag gacttccaga ccctgtgcat    1680
cgacatcctg caccacccc tgaccaagtg cctggacgaa gagaacgcca agagcaaggc    1740
cgagaagatc attctcgaag agtgcaagaa catcgacacc gaggagaagg gtgccccggg    1800
atctggcgca acaaattta gtcttttaaa gcaggcagga gacgtcgagg aaaacccctgg    1860
acccgtgagc gagacaaacg agacaggcat ctacatcttc agccgccatcc agacagacaa    1920
ggatgaggaa ttcggcgccg tggaagtgga agggaccaag gctgagacat tcctgatccg    1980
gtataaggac gccgccatgg tggccgccga agtgcccatg aagatctacc accccaaccg    2040
gcagaacctg ctgatgcacc agaatgcct ggccgccatc atggacaaga acgacaccgt    2100
gatccccatc agcttcggca acgtgttcaa gagcaaagag gacgtgaagg tgctcctgga    2160
aaacctgtac ccccagttcg agaagctgtt ccccgccatc aagggaaaga tcgaagtggg    2220
cctgaaggtg atcggcaaga aagagtggct cgaaaagaaa gtgaacgaga accccgagct    2280
ggaaaaagtg tccgccagcg tgaagggcaa gagcgaggcc gacgtcgagt ctggctact acgagagaat    2340
ccagctgggc ggcatggccc agaagatgtt cacaagcctg cagaaagaag tgaaaaccga    2400
cgtgttcagc cccctggaag aagccgccga ggccgccaaa gccaatgagc ctacaggcga    2460
aacaatgctg ctgaacgcca gcttcctgat caacagagag gatgaggcca agttcgacga    2520
gaaagtcaat gaggcccacg agaactggaa ggataaggcc gacttccact acaacggccc    2580
ctggccccgcc tacaacttcg tgaacatccg gctgaaggtg aagaagaagg ggcacctgg    2640
ctcgggagcg accaacttct cattactcaa acaagccgga gacgttgagg agaatccagg    2700
ccctgtgctg cacaagctcg tgaccgcccc catcaacctg gtcgtgaaga tcggcgagaa    2760
ggtgcaggaa gaggccgaca agcagctgta cgacctgccc accatccagc agaagctgtt    2820
ccagctgcag atgatgttcg agctgggcga gatccccgag gaagccttcc aggaaaaaga    2880
ggacgaactg ctgatgagat acgagatcgc caagcggcgc gagattgagc agtgggaaga    2940
actgacccag aagcggaatg aggaaagcgg tgccccggga tctggcgcaa caaattttag    3000
tcttttaaag caggcaggag acgtcgagga aaaaccctgga cccgtggggcg agctgctgta    3060
cctctacggc ctgatcccca ccaaagaggc cgctgctatc gagccctcc cattctacaa    3120
gggcttcgac ggcgagcaca gcctgtaccc tatcgcctc gaccaagtga ccgccgtggt    3180
gttcaagctg gacgccgaca cctacagcga gaaagtgatc caggaaaaga tggaacagga    3240
catgagctgg ctgcaggaaa aggccttcca ccaccacgac acagtggccg ccctgtatga    3300
ggaattcacc atcatcccc tgaagttctg caccatctat aagggagagg aatccctgca    3360
ggccgccatc gagatcaaca aagagaagat cgaaaactcc ctgacctgc tgcagggcaa    3420
cgaggaatgg aacgtgaaga tctactgcga cgacaccgag ctgaagaagg gcatcagcga    3480
gacaaacgag agcgtgaagg ccaagaagca ggaaatcagc cacctgagcc ccggcagaca    3540
gttcttcgag aagaagaaa ttgaccagct catcgagaaa gacgctgagc tgcacaagaa    3600
caaagtgtgc gaggaaatcc acgacaagct gattgagctg agcctctacg actccgtgaa    3660
gaagaactgg tccaaggacg tgacaggcgc tgccgaacag atggcctgga acagcgtgtt    3720
cctgctgccc agcctgcaga tcaccaagtt cgtgaacgag atcgaggaac tccagcagcg    3780
gctgcagaac aagggatgga gttcgaagt gaccggcccc tggctccct accacttcag    3840
cagctttgcc ggggcacctg gctcgggagc gaccaacttc tcattactca acaagccgga    3900
agacgttgag gagaatccag gccctgtgag cctgaagcag agcatggaga ataaggatat    3960
cgccctgatc gacatcctcg acgtgatcct ggacaaggga gtggcatca agggcgacct    4020
gatcatctct atcgccgcg tggacctggt gtacctggat ctgagagtga tgatctccag    4080
cgtggaaacc ctggtgcagg ccaaagaggg caaccacaaa cccatcacca gcgagcagtt    4140
cgacaagcag aaagaggagc tgatggacgc caccggccag cccagcaagt ggacaaatcc    4200
tctgggcagc ggcgctcccg ggtcaggtgc cacgaatttt tcgttgttga agcaagctgg    4260
ggatgttgaa gagaacccag gcctgtgca gcccgtgtcc caggccaacg gcagaatcca    4320
cctggatccc gatcaggccg aacaggac gccccagctc gtgatgaccg tgatcgagct    4380
gctgcggcag atcgtggaac ggcacgccat gagaagagtg gaaggcgca ccctgaccga    4440
cgagcagatc gagaatctgg gaatcgctct gatgaacctg gaggagaaga tggacgagct    4500
gaagagaggtg ttcggactgg acgctgagga tctgaacatc gacctgggcc tctgggcag    4560
cctgctgggt gcccgggat ctggcgcaac aaattttagt cttttaaaag aggcaggaga    4620
cgtcgaggaa aaccctggac ccgtggccgt ggaacacaac atgcagagca gcaccatcgt    4680
ggacgctg aaaagatcc tggacaaggg cgtcgtgatc gccggggaca tcacagtggg    4740
aatcgccgac gtggaactgc tgaccatcaa gatccggctg atcgtggcca gcgtggacaa    4800
ggccaaagaa atcggcatgg attggttgga gaacgacccc tacctgacgg caaggggcca    4860
caacaacaag gctctggaag aggaaaacaa gatgctgcac gagcggctga aaacactgga    4920
agagaagatc gagacaaagc gcggggcacc tggctcggga gcgaccaact tctcattact    4980
caaacaagcc ggagacgttg aggagaatcc aggccctgtg agcaccggcc ccagcttcag    5040
caccaaggac aacacccgg aatacttcgt gaaggccagc aacaagcacg gcttagcct    5100
cgacatcagc ctgaacgtga atggggccgt gattagcgc accatgatca gcgccaaga    5160
gtacttcgac tacctgagcg acattcga agagggcagc gaagtggccc aggccctgtc    5220
tgagcagttt agcctggcta gcgaggcct cgagtctaat ggcgaagccg aggcccactt    5280
catccacctg aagaacacca agatctactg cggcgacagc aagagcacc ccagcaaggg    5340
caagatcttc tggcgcggca agatcgccga ggtgacgga ttcttcctgg aaaaatcag    5400
cgacgccaag tccaccacga acaggcccag cggcgctcc agtcaggtg cacgaatttt    5460
tcgttgttga agcaagctgg ggatgttgaa agagaaccca ggcctgtgg tgtccaaggc    5520
cgaggaactg ttcaccggcg tggtcccat cctggtggaa ctggatggcg acgtgaacgg    5580
ccacaagttc agcgtgtccg gcgagggcga aggcgacgcc acatacggaa agctgaccct    5640
gaagttcatc tgcaccaccg gcaagctgcc cgtgccttgg cctaccctcg tgaccacact    5700
gacctacggc gtgcagtgct tcgccagata ccccgaccac atgaagcagc acgatttctt    5760
```

-continued

```
caagagcgcc atgcccgagg gctacgtgca ggaacggacc atcttcttca aggacgacgg    5820
caactacaag acaagagccg aagtgaagtt cgagggcgac accctcgtga accggatcga    5880
gctgaagggc atcgacttca agaggatgg caacatcctg gccacaagc tggagtacaa     5940
ctacaacagc cacaaggtgt acatcaccgc cgacaagcag aaaaacggca tcaaagtgaa    6000
cttcaagacc cggcacaaca tcgaggacgg cagcgtgcag ctggccgacc actaccagca    6060
gaacaccccc atcggagatg gccccgtgct gctgcccgac aaccactacc tgagcacaca    6120
aagcgccctg agcaaggacc ccaacgagaa gcgggaccac atggtgctgc tggaatttgt    6180
gaccgccgct ggcatcaccc tgggcatgga cgagctgtac aagtgaacta gttcgttaac    6240
taaacttgtt tattgcagct tataatggtt acaaataaag caatagcatc acaaatttca    6300
caaataaagc attttttca ctgcattcta gttgtggttt gtccaaactc atcaatgtat     6360
cttatcatgt ctggaattga ctcaaatgat gtcaattagt ctatcagaag ctcatctggt    6420
ctcccttccg ggggacaaga catccctgtt taatatttaa acagcagtgt tcccaaactg    6480
ggttcttata tcccttgctc tggtcaacca ggttgcaggg tttcctgtcc tcacaggaac    6540
gaagtcccta aagaaacagt ggcagccagg tttagccccg gaattgactg gattccttc     6600
ttagggccca ttggtatggc ttttttcccg tatcccccca ggtgtctgca ggctcaaaga    6660
gcagcgagaa gcgttcagag gaaagcgatc ccgtgccacc ttccccgtgc ccgggctgtc    6720
cccgcacgct gccggctcgg ggatgcgggg ggagcgccgg accggagcgg agccccgggc    6780
ggctcgctgc tgccccctag cgggggaggg acgtaattac atccctgggg gcttttgggg    6840
ggggctgtcc ctgatatcta taacaagaaa atatatatat aataagttat cacgtaagta    6900
gaacatgaaa taacaatata attatcgtat gagttaaatc ttaaaagtca cgtaaaagat    6960
aatcatgcgt cattttgact cacgcggtcg ttatagttca aaatcagtga cacttaccgc    7020
attgacaagc acgcctcacg ggagctccaa gcggcgactg agatgtccta aatgcacagc    7080
gacgattcg cgctatttag aaagagagag caatatttca agaatgcatg cgtcaatttt     7140
acgcagacta tctttctagg g                                              7161

SEQ ID NO: 447         moltype = DNA  length = 5617
FEATURE                Location/Qualifiers
misc_feature           1..5617
                       note = synthetic polynucleotide
source                 1..5617
                       mol_type = other DNA
                       organism = synthetic construct
SEQUENCE: 447
ccctagaaag ataatcatat tgtgacgtac gttaaagata atcatgtgta aaattgacgc      60
atgtgtttta tcggtctgta tatcgaggtt tatttattaa tttgaataga tattaagttt    120
tattatattt acacttacat actaataata aattcaacaa acaatttatt tatgtttatt    180
tatttattaa aaaaaacaaa aactcaaaat ttcttctata aagtaacaaa acttttatga    240
gggacagccc ccccccaaag ccccccaggga tgtaattacg tccctcccc gctaggggc     300
agcagcgagc cgcccggggc tccgctccgg tccggccgcatc ccgagccgg               360
cagcgtgcgg ggacagcccg ggcacgggga aggtggcacg ggatcgcttt cctctgaacg    420
cttctcgctg ctctttgagc ctgcagacac ctgggggat acggggaaaa ggcctccacg     480
gccactagtt ttccccgaaa agtgccacct gacgtcggca gtgaaaaaaa tgctttattt    540
gtgaaatttg tgatgctatt gctttatttg taaccattat aagctgcaat aaacaagtta    600
acaacaacaa ttgcattcat tttatgtttc aggttcaggg ggaggtgtgg gaggtttttt    660
aaagcaagta aaacctctac aaatgtggta tggctgatta tgatcctcta gacatatgct    720
gcagtcactt gtacagctca tccatgccca gggtgatgcc agcggcggtc cgaaattcca    780
gcagcaccat gtggtcccgc ttctcgttgg ggtccttgct cagcacgctc tgggtgctca    840
ggtagtggct atcaggcagc agcacgggc catctccgat gggggtgttc tgctggtagt     900
ggtcggccag ctgcacgctg ccatcttcca cgttgtgccg gatcttgaag ttcactttga    960
tgccgttttt ctgcttcacg gccatgatgt agatgttgtg gctgttgaag ttgtactcca   1020
gcttgtggcc caggatgttg ccgtcctctt tgaagtccac gcccttcagc tcgatccgat   1080
tcacgagggt gtcgccctcg aacttcactt cggctctggt cttgtaggtg ccgtcgtcct   1140
tgaagaagat ggtccgttcc tgcacgtagc cctcgggcat ggcgctcttg aagaaatcgt   1200
gctgcttcat gtggtcgggg tatctggcga agcactgcac gccgtgagac agtgtggtca   1260
cgagggtagg ccaaggcacg ggcagcttgc cggtggtgca gatgaacttc agggtcagct   1320
tgccatttgt ggcgtcgcct tcgccctctc cccgcacaga gaacttgtgg ccgttcacgt   1380
cgccatccag ttccaccagg atgggcacca cgccggtgaa cagttcctcg cccttggaca   1440
ccatggtgaa gggtactgga tccgagctcg gtacctgcag gcgtaccttc tatagtgtca   1500
cctaaatgcg atctgacggt tcactaaacg agctctgctt atataggcct cccaccgtac   1560
acgccacctc gacatactcg agtttactcc ctatcagtga tagagaacgt atgaagagtt   1620
tactccctat cagtgataga gaacgtatgc agactttact cccatcagt gatagagaac    1680
gtataaggag tttactccct atcagtgata gagaacgtat gaccagttta ctccctatca   1740
gtgatagaga acgtatctac agtttactcc ctatcagtga tagaacgt atatccagtt     1800
tactccctat cagtgataga acgtatgt cgaggtaggc gtgtacggtg ggcgcctata     1860
aaagcagagc tcgtttagtg aaccgtcaga tcgcctggag caattccaca acactttgt    1920
cttatacttg gtaccatgc atgccaccat ggccgtggaa cacaacatgc agagcagcac    1980
catcgtggac gtgctggaaa agatcctgga caagggcgtc gtgatcgccg ggacatcac    2040
agtgggaatc gccgacgtgg aactgctgac catcaagatc cggctgatcg tggccagcgt   2100
ggacaaggcc aaagaaatcg catggattg tgggagaac gaccccctacc gtgagcagcaa   2160
gggcgccaac aacaaggccc tggaagagga aaacaagatg ctgcacgagc ggctgaaaac   2220
actgaagag aagatcgaga caaagcgcgg tgccccggga tctggcgcaa caaattttag   2280
tcttttaaag caggcaggag acgtcgagga aaaccctgga cccgtgagcg agacaaacga   2340
gacaggcatc tacatcttca gcgccatcca gacagacaag gatgaggaat cggcgccgt    2400
ggaagtggaa ggggatcaagg ctgaagcatt cctgatcgtg tataaggacg agccatggt    2460
ggccgccgaa gtgccatga agatctacca ccccaaccgg cagaacctgc tgatgcacca    2520
gaatgccgtg gccgccatca tggacaagaa cgacaccgtg atccccatca gcttcggcaa   2580
cgtgttcaag agcaaagagg acgtgaaggt gctcctggaa aacctgtacc ccagttcga    2640
gaagctgttc cccgccatca agggaaagat cgaagtgggc ctgaaggtga tcggcaagaa   2700
agtggctc gaaaagaaag tgaacgagaa ccccgagctg gaaaaagtgt ccgccagcgt     2760
```

```
gaagggcaag agcgaggccg ctggctacta cgagagaatc cagctgggcg gcatggccca 2820
gaagatgttc acaagcctgc agaaagaagt gaaaaccgac gtgttcagcc ccctggaaga 2880
agccgccgag gccgccaaag ccaatgagcc tacaggcgaa acaatgctgc tgaacgccag 2940
cttcctgatc aacagagagg atgaggccaa gttcgacgag aaagtcaatg aggcccacga 3000
gaactggaag gataaggccg acttccacta cagcggcccc tggcccgcct acaacttcgt 3060
gaacatccgg ctgaaggtgg aagagaaggg ggcacctggc tcgggagcga ccaacttctc 3120
attactcaaa caagccggag acgttgagga gaatccaggc cctgtgctgc acaagctcgt 3180
gaccgccccc atcaacctgg tcgtgaagat cggcgagaag gtgcaggaag aggccgacaa 3240
gcagctgtac gacctgccca ccatccagca gaagctgatc cagctgcaga tgatgttcga 3300
gctgggcgag atccccgagg aagccttcca ggaaaaagag gacgaactgc tgatgagata 3360
cgagatcgcc aagcggcgcg agattgagca gtgggaagaa ctgacccaga gcggaatga 3420
ggaaagcggt gccccgggat ctggcgcaac aaatttttagt cttttaaagc aggcaggaga 3480
cgtcgaggaa aaccctggac ccgtgggcga gctgctgtac ctctacgcc tgatccccac 3540
caaagaggcc gctgctatcg agcccttccc attctacaag ggcttcgacg gcgagcacag 3600
cctgtaccct atcgccttcg accaagtgac cgccgtggtg ttcaagctgg acgccgcac 3660
ctacagcgag aaagtgatcc aggaaaagat ggaacaggac atgagctggc tgcaggaaaa 3720
ggccttccac caccacgaga cagtggccgc cctgtatgag gaattcacca tcatccccct 3780
gaagttctgc accatctata agggagagga atccctgcag gccgccatcg agatcaacaa 3840
agagaagatc gaaaactccc tgaccctgct gcagggcaac gaggaatgga acgtgaagat 3900
ctactgcgac gacaccgagc tgaagaaggg catcagcgag acaaacgaga gcgtgaaggc 3960
caagaagcag gaaatcagcc acctgagccc cggcagacag ttcttcgaga agaagaagat 4020
tgaccagctc atcgagaaag agctggaact gcacaagaac aaagtgtgcg agaaaatcca 4080
cgacaagctg attgagctga gcctctacga ctccgtgaag aagaactggt ccaaggacgt 4140
gacaggcgct gccgaacaga tggcctggaa cagcgtgttc ctgctgccca gcctgcagat 4200
caccaagttc gtgaacagga tcgaggaact ccagcagcgg ctggagaaca agggatggaa 4260
gttcgaagtg accggcccct ggcctcccta ccacttcagc agctttgccg gggcacctgg 4320
ctcgggagcg accaacttct cattactcaa acaagccgga gacgttgagg agaatccagg 4380
ccctgtgcag cccgtgtccc aggccaacgg cagaatccac ctggatcccg atcaggccga 4440
acagggactg gcccagctcg tgatgaccgt gatcgagctg ctgcggcaga tcgtggaacg 4500
gcacgccatg agaagagtgg aaggcggcac cctgaccgac gagcagatcg agaatctggg 4560
aatcgccctg atgaaccctg aagagaagat ggacgagctg aaagaggtgt tcggactggg 4620
cgccgaggac ctgaacatcg acctgggccc tctgggcagc ctgctgtgaa ctagttcgat 4680
accgtcgacc gttaactaaa cttgtttatt gcagcttata atggtacaa ataaagcaat 4740
agcatcacaa atttcacaaa taaagcattt ttttcactgc attctagttg tggtttgtcc 4800
aaactcatca atgtatctta tcatgtctgg aattgactca aatgatgtca attagtctat 4860
cagaagctca tctggtctcc cttccggggg acaagacatc cctgtttaat atttaaacag 4920
cagtgttccc aaactgggtt cttatatccc ttgctctggt caaccaggtt gcagggtttc 4980
ctgtcctcac aggaacgaag tccctaaaga aacagtggca gccaggttta gccccggaat 5040
tgactggatt ccttttttag ggcccattgg tatggctttt tccccgtatc ccccaggtg 5100
tctgcaggct caaagagcag cgagaagcgt tcagaggaaa gcgatcccgt gccaccttcc 5160
ccgtgccggg gctgtcccgc cacgctgccg gctcggggat gcggggggag cgccggaccg 5220
gagcggagcc ccgggcggct cgctgctgcc cctagcggg ggagggacgt aattacatcc 5280
ctgggggggg tggtccctga tatctataac aagaaaatat atatataata 5340
agttatcacg taagtagaac atgaaataac aatataatta tcgtatgagt taaatcttaa 5400
aagtcacgta aaagataatc atgcgtcatt ttgactcacg cggtcgttat agttcaaaat 5460
cagtgacact taccgcattg acaagcacgc ctcacgggag ctccaagcgg cgactgagat 5520
gtcctaaatg cacacgacg gattcgcgct atttagaaag agagagcaat atttcaagaa 5580
tgcatgcgtc aattttacgc agactatctt tctaggg 5617
```

SEQ ID NO: 448          moltype = DNA  length = 237
FEATURE                Location/Qualifiers
misc_feature       1..237
                      note = synthetic polynucleotide
source                 1..237
                      mol_type = other DNA
                      organism = synthetic construct
SEQUENCE: 448
```
ccctagaaag ataatcatat tgtgacgtac gttaaagata atcatgtgta aaattgacgc 60
atgtgtttta tcggtctgta tatcgaggtt tatttattaa tttgaataga tattaagttt 120
tattatattt acacttacat actaataata aattcaacaa acaatttatt tatgtttatt 180
tatttattaa aaaaaacaaa aactcaaaat ttcttctata aagtaacaaa actttta 237
```

SEQ ID NO: 449          moltype = DNA  length = 232
FEATURE                Location/Qualifiers
misc_feature       1..232
                      note = synthetic polynucleotide
source                 1..232
                      mol_type = other DNA
                      organism = synthetic construct
SEQUENCE: 449
```
gagggacagc cccccccaa agccccccagg gatgtaatta cgtccctccc ccgctagggg 60
gcagcagcga gccgcccggg gctccgctcc ggtccggcgc tcccccgca tccccgagcc 120
ggcagcgtgc ggggacagcc cgggcacggg gaaggtggca cgggatcgct ttcctctgaa 180
cgcttctcgc tgctctttga gcctgcagac acctgggggg atacgggaa aa 232
```

SEQ ID NO: 450          moltype = DNA  length = 350
FEATURE                Location/Qualifiers
misc_feature       1..350
                      note = synthetic polynucleotide

| | | |
|---|---|---|
| source | 1..350<br>mol_type = other DNA<br>organism = synthetic construct | |

SEQUENCE: 450
```
gagtttactc cctatcagtg atagagaacg tatgaagagt ttactcccta tcagtgatag    60
agaacgtatg cagactttac tccctatcag tgatagagaa cgtataagga gtttactccc   120
tatcagtgat agagaacgta tgaccagttt actccctatc agtgatagag aacgtatcta   180
cagtttactc cctatcagtg atagagaacg tatatccagt ttactcccta tcagtgatag   240
agaacgtatg tcgaggtagg cgtgtacggt gggcgcctat aaaagcagag ctcgtttagt   300
gaaccgtcag atcgcctgga gcaattccac aacactttttg tcttatactt               350
```

| | | |
|---|---|---|
| SEQ ID NO: 451<br>FEATURE<br>misc_feature<br>source | moltype = DNA length = 122<br>Location/Qualifiers<br>1..122<br>note = synthetic polynucleotide<br>1..122<br>mol_type = other DNA<br>organism = synthetic construct | |

SEQUENCE: 451
```
aacttgttta ttgcagctta taatggttac aaataaagca atagcatcac aaatttcaca    60
aataaagcat ttttttcact gcattctagt tgtggtttgt ccaaactcat caatgtatct   120
ta                                                                   122
```

| | | |
|---|---|---|
| SEQ ID NO: 452<br>FEATURE<br>misc_feature<br>source | moltype = DNA length = 231<br>Location/Qualifiers<br>1..231<br>note = synthetic polynucleotide<br>1..231<br>mol_type = other DNA<br>organism = synthetic construct | |

SEQUENCE: 452
```
ttttccccgt atcccccccag gtgtctgcag gctcaaagag cagcgagaag cgttcagagg    60
aaagcgatcc cgtgccacct tccccgtgcc cgggctgtcc ccgcacgctg ccggctcggg   120
gatgcggggg gagcgccgga ccggagcgga gccccgggcg gctcgctgct gccccctagc   180
gggggaggga cgtaattaca tccctggggg ctttgggggg gggctgtccc t             231
```

| | | |
|---|---|---|
| SEQ ID NO: 453<br>FEATURE<br>misc_feature<br>source | moltype = DNA length = 309<br>Location/Qualifiers<br>1..309<br>note = synthetic polynucleotide<br>1..309<br>mol_type = other DNA<br>organism = synthetic construct | |

SEQUENCE: 453
```
gatatctata acaagaaaat atatatataa taagttatca cgtaagtaga acatgaaata    60
acaatataat tatcgtatga gttaaatctt aaaagtcacg taaaagataa tcatgcgtca   120
ttttgactca cgcggtcgtt atagttcaaa atcagtgaca tctaccgcat tgacaagcac   180
gcctcacggg agctccaagc ggcgactgag atgtcctaaa tgcacagcga cggattcgca   240
ctatttagaa agagagagca atatttcaag aatgcatgcg tcaattttac gcagactatc   300
tttctaggg                                                           309
```

| | | |
|---|---|---|
| SEQ ID NO: 454<br>FEATURE<br>misc_feature<br>source | moltype = DNA length = 7535<br>Location/Qualifiers<br>1..7535<br>note = synthetic polynucleotide<br>1..7535<br>mol_type = other DNA<br>organism = synthetic construct | |

SEQUENCE: 454
```
cgttacataa cttacggtaa atggcccgcc tggctgaccg cccaacgacc cccgcccatt    60
gacgtcaata atgacgtatg ttcccatagt aacgccaata gggactttcc attgacgtca   120
atgggtggag tatttacggt aaactgccca cttggcagta catcaagtgt atcatatgcc   180
aagtacgccc cctattgacg tcaatgacgg taaatggccc gcctggcatt atgcccagta   240
catgacctta tgggactttc ctacttggca gtacatctac gtattagtca tcgctattac   300
catggtgatg cggttttggc agtacatcaa tgggcgtgga tagcggtttg actcacgggg   360
atttccaagt ctccacccca ttgacgtcaa tgggagtttg ttttggcacc aaaatcaacg   420
ggactttcca aaatgtcgta caactccgcc ccattgacgc aaatgggcg gtaggcgtgt   480
acggtggag gtctatataa gcagagctcg tttagtgaac cgtcagatcg cctggagacg   540
ccatccacgc tgttttgacc tccatagaag acaccgggac cgatccgcc tccggactct   600
agcctaggct tttgcaaaaa gctatttagg tgacactata aaggtacgcg ctgcaggtac   660
cgagctcgga tccagtaccc ttcaccatga gcatccagaa gtccaccaac agcagcagcc   720
tggccgaagt gatcgaccgg atcctggaca agggcatcgt gatcgacgcc ttcgccgag   780
tgtccgtcgt gggcatcgag atcctgacca tcgaggcag agtcgtgatc gccagcgtgg   840
acacctggct gagatatgcc gaagccgtgg gcctgctggg gaagaaaatg   900
gcctgcccga gcgagcaac agctctgagg acagcccccg gttcagcatc tgaactaaat   960
cgcactgtcg gcgtccccc taacgttac tggccgaagc gcttggaat aaggccggtg  1020
tgcgtttgtc tatatgttat tttccaccat attgccgtct tttggcaatg tgagggcccg  1080
gaaacctggc cctgtcttct tgacgagcat tcctaggggt ctttcccctc tcgccaaagg  1140
aatgcaaggt ctgttgaatg tcgtgaagga agcagttcct ctggaagctt cttgaagaca  1200
```

```
aacaacgtct gtagcgaccc tttgcaggca gcggaacccc ccacctgcg  acaggtgcct  1260
ctgcggccaa aagccacgtg tataagatac acctgcaaag gcggcacaac cccagtgcca  1320
cgttgtgagt tggatagttg tggaaagagt caaatggctc tcctcaagcg tattcaacaa  1380
ggggctgaag gatgcccaga aggtacccca ttgtatggga tctgatctgg ggcctcggtg  1440
cacatgcttt acatgtgttt agtcgaggtt aaaaaacgtc taggccccc  gaaccacggg  1500
gacgtggttt tcctttgaaa aacacgatga taatatggcc acaaccgtga ccgtgctgac  1560
cgacaagcgg aagaagggca gcggcgcctt catccaggac gacgagacaa aagaggtgct  1620
gagcagagcc ctgagctacc tgaagtccgg ctacagcatc cacttcaccg gacctgccgg  1680
cggaggcaag acatctctgg ctagagccct ggccaagaac cggaagcggc ccgtgatgct  1740
gatgcacggc aaccacgagc tgaacaacaa ggacctgatc ggcgatttca ccggctacac  1800
cagcaaaaag gtgatcgacc agtacgtgcg gagcgtgtac aagaaagacg aacaggtgtc  1860
cgagaactgg caggacggca gactgctgga agccgtgaag aatggctaca ccctgatcta  1920
cgacgagttc accagaagca agcccgctac caacaacatc ttcctgagca tccttgagga  1980
gggcgtgctg cccctgtacg gcgtgaagat gaccgaccct ttcgtgcgcg tgcacccga   2040
cttcagagtg atctttacca gcaacccgc  cgagtatgcc ggcgtgtacg ataccaggca  2100
cgccctgctg gaccggctga tcaccatgtt catcgactac aaggacatcg accgggaaac  2160
cgctatcctg accgagaaaa ctgacgtgga agaagacgag gcccggacca tcgtgaccct  2220
ggtgcgcaac gtgcggaaca gaagcggcga cgagaatagc agcggcctga gcctgagagc  2280
cagcctgatg attgccaccc tggccaccca gcaggacatc cctatcgatg gcagcgacga  2340
ggacttccag accctgtgca tcgacatcct gcaccacccc ctgaccaagt gcctggacga  2400
agagaacgcc aagagcaagg ccgagaagat cattctcgaa gagtgcaaga acatcgacac  2460
ccgaggagag ggtgccccgg gatctggcgc aacaaatttt agtcttttaa agcaggcagg  2520
agacgtcgag gaaaccctg  gacccgtgag cgagacaaac gagacaggca tctacatctt  2580
cagcgccatc cagacagaca aggatgagga attcggcgcc gtggaagtgg aagggaccaa  2640
ggctgagaca ttcctgatcc ggtataagga cgccgccatg gtgccgccg  aagtgcccat  2700
gaagatctac caccccaacc ggcagaacct gctgatgcac cagaatgccg tggccgccat  2760
catgcacaag aacgacaccg tgatccccat cagcttcggc aacgtgttca gagcaaaga   2820
ggacgtgaag gtgctcctgg aaaacctgta ccccagttc  gagaagctgt tccccgccat  2880
caagggaaag atcgaagtgg gcctgaaggt gatcggcaag aaagagtggc tcgaaaagaa  2940
agtgaacgag aaccccgagc tggaaaaagt gtccgccaag gtgaagggca agagcgaggc  3000
cgctggctac tacgagagaa tccagctggg cggcatggcc cagaagatgt tcacaagcct  3060
gcagaaagaa gtgaaaaccg acgtgttcag cccctggaa  gaagccgcc  aggccgccaa  3120
agccaatgag cctacaggcg aaacaatgct gctgaacgcc agcttcctga tcaacagaga  3180
ggatgaggcc aagttcgacg agaaagtcaa tgaggcccac gagaactgga aggataaggc  3240
cgacttccac tacagcggcc cctggccgc  ctacaacttc gtgaacatcc ggctgaaagt  3300
ggaagagaag ggggcacctg gctcgggagc gaccaacttc tcattactca aacaagccgg  3360
agacgttgag gagaatccag gccctgtgct gcacaagctc gtgaccgccc catcaacct   3420
ggtcgtgaag atcggcgaga aggtgcagga agaggccgac aagcagctgt acgacctgcc  3480
caccatccag cagaagctga tccagccgga gagctgggcg agatccccga                  3540
ggaagccttc caggaaaaag aggacgaact gctgatgaga tacgagatcg ccaagcggcg  3600
cgagattgag cagtgggaag aactgaccca gaagcggaat gaggaaagcg gtgccccggg  3660
atctggcgca acaaatttta gtcttttaaa gcaggcagga gacgtcgagg aaaaccctgg  3720
acccgtgggc gagctgctgt acctctacgg cctgatcccc accaaagagg ccgctgctat  3780
cgagcccttc ccattctaca agggcttcga cggcgagcac agcctgtacc ctatcgcctt  3840
cgaccaagtg accgccgtgg tgttcaagct ggacgccgac acctacagcg agaaagtgat  3900
ccaggaaaag atggaacagg acatgagctg gctgcaggaa aaggccttcc accaccacga  3960
gacagtggcc gccctgtatg aggaattcac catcatcccc ctgaagttct gcaccatcta  4020
taagggagag gaatccctgc aggccgccat cgagatcaac aaagagaaga tcgaaaactc  4080
cctgaccctg ctgcagggca cgaggaatg  gaacgtgaag atctactgcg acgacaccga  4140
gctgaagaag ggcatcagcg agacaaacga gagcgtgaag gccaagaagc aggaaatcag  4200
ccacctgagc cccggcagac agttcttcga gaagaagaag attgaccagc tcatcgagaa  4260
agagctggaa ctgcacaaga acaaagtgtg cgaggaaatc cacgacaagc tgattgagct  4320
gagcctctac gactccgtga agaagaactg gtccaaggac gtgacaggcg ctgccgaaca  4380
gatggcctgg aacagcgtgt tcctgctgcc cagcctgcag atcaccaagt tcgtgaacga  4440
gatccagaaa ctccagcagc ggctggagaa caagggatgg aagttcgaag tgaccggcca  4500
ctggcctccc taccacttca gcagctttgc cggggcacct ggctcggag  cgaccaactt  4560
ctcattactc aaacaagccg gagacgttga ggagaatcca ggccctgtga gcctgaagca  4620
gagcatggag aataaggata tcgccctgat cgacatcctc gacgtgatcc tggacaaggg  4680
agtggccatc aagggcgacc tgatcatctc tatccgcgc  gtggacctgg tgtacctgga  4740
tctgagagtg ctgatctcca gcgtggaaac cctggtcgac gccaaagagg gcaaccacaa  4800
gcccatcacc agcgagcagt cgacaagca  gaaagaggag ctgatgacga ccaccggcca  4860
gcccagcaag tggacaaatc ctctgggcag cggcgctccc gggtcaggtg ccacgaattt  4920
ttcgttgttg aagcaagctg gggatgttga agagaaccca gggcctgtgc agcccgtgtc  4980
ccaggccaac ggcagaatcc acctggatcc cgatcagctc gaacagggac tggccagct   5040
cgtgatgacc gtgatcgagc tgctgcggca gatcgtggaa cggcacgcca tgagaagagt  5100
ggaaggcggc accctgaccg acgagcagat cgagaatctg gaatcgctc  tgatgaacct  5160
ggaggagaag atgacgagc  tgaaaggt  gttcggactg gacgctgagg atctgaacat  5220
cgacctgggc cctctgggca gcctgctggg tgccccggga tctggcgcaa caaatttag   5280
tcttttaaag caggcaggag acgtcgagga aaaccctgg  cccgtgggc  tggaacacaa  5340
catgcagagc agcaccatcg tggacgtgct ggaaaagatc ctggacaagg gcgtcgtgat  5400
cgccggggac atcacagtgg gaatcgccga cgtggaactg ctgaccatca agatccggct  5460
gatcgtggcc agcgtggaca aggccaaaga aatcggcatg gattggtggg agaacgaccc  5520
ctacctgagc agcaagggcg ccaacaacaa ggctctggaa gaggaaaaca agatgctgca  5580
cgagcggctg aaaacactgg aagagaagat cgagacaagc cacggctcgg  agtggcaggg  5640
agcgaccaac ttctcattac tcaaacaagc cggagacgtt gaggagaatc caggccctgt  5700
gagcaccggc cccagcttca gcaccaagga caacaccctg gaatacttcg tgaaggcag   5760
caacaagcac ggctttagcc tcgacatcag cctgaacgtg aatggggccg tgattagcgg  5820
caccatgatc agcgccaaag agtacttcga ctacctgagc gagacattcg aagagggcag  5880
cgaagtggcc caggccctgt ctgagcagtt tagcctggct agcgaggcct ccgagtctaa  5940
```

```
tggcgaagcc gaggcccact tcatccacct gaagaacacc aagatctact gcggcgacag 6000
caagagcacc cccagcaagg gcaagatctt ctggcgcggc aagatcgccg aggtggacgg 6060
attcttcctg ggaaaaatca gcgacgccaa gtccaccagc aagaagtcca gcggcgctcc 6120
cgggtcaggt gccacgaatt tttcgttgtt gaagcaagct ggggatgttg aagagaaccc 6180
agggcctgtg gtgtccaagg gcgaggaact gttcaccggc gtggtgccca tcctggtgga 6240
actggatggc gacgtgaacg gccacaagtt cagcgtgtcc ggcgagggcg aaggcgacgc 6300
cacatacgga aagctgaccc tgaagttcat ctgcaccacc ggcaagctgc ccgtgccttg 6360
gcctaccctc gtgaccacac tgacctacgg cgtgcagtgc ttcgccagat accccgacca 6420
catgaagcag cacgatttct tcaagagcgc catgcccgag ggctacgtgc aggaacggac 6480
catcttcttc aaggacgacg gcaactacaa gacaagagcc gaagtgaagt tcgagggcga 6540
caccctcgtg aaccggatcg agctgaaggg catcgacttc aaagaggatg gcaacatcct 6600
gggccacaag ctggagtaca actacaacag ccacaaggtg tacatcaccg ccgacaagca 6660
gaaaaacggc atcaaagtga acttcaagac ccggcacaac atcgaggacg gcagcgtgca 6720
gctggccgac cactaccagc agaacacccc catcggagat ggccccgtgc tgctgcccga 6780
caaccactac ctgagcacac aaagcgcccc gagcaaggac cccaacgaga gcgggacca 6840
catggtgctg ctggaatttg tgaccgccgc tggcatcacc ctgggcatgg acgagctgta 6900
caagtgactc gagtctagag ggcccgtgg ctgtaatcta gaggatccct cgaggggccc 6960
aagcttacgc gtgcatgcga cgtcatagct ctctccctat agtgagtcgt attataagct 7020
agcttgggat ctttgtgaag gaaccttact tctgtggtgt gacataattg gacaaactac 7080
ctacagagat ttaaagctct aaggtaaata taaaattttt aagtgtataa tgtgttaaac 7140
tagctgcata tgcttgctgc ttgagagttt tgcttactga gtatgattta tgaaaatatt 7200
atacacagga gctagtgatt ctaattgttt gtgtatttta gattcacagt ccaaggctc 7260
atttcaggcc cctcagtcct cacagtctgt tcatgatcat aatcagccat accacatttg 7320
tagaggtttt acttgcttta aaaaacctcc cacacctccc cctgaacctg aaacataaaa 7380
tgaatgcaat tgttgttgtt aacttgttta ttgcagctta taatggttac aaataaagca 7440
atagcatcac aaatttcaca aataaagcat ttttttcact gcattctagt tgtggtttgt 7500
ccaaactcat caatgtatct tatcatgtct ggatc 7535

SEQ ID NO: 455            moltype = DNA  length = 4894
FEATURE                   Location/Qualifiers
misc_feature              1..4894
                          note = synthetic polynucleotide
source                    1..4894
                          mol_type = other DNA
                          organism = synthetic construct
SEQUENCE: 455
cgttacataa cttacggtaa atggcccgcc tggctgaccg cccaacgacc cccgcccatt 60
gacgtcaata atgacgtatg ttcccatagt aacgccaata gggactttcc attgacgtca 120
atgggtggag tatttacggt aaactgccca cttggcagta catcaagtgt atcatatgcc 180
aagtacgccc cctattgacg tcaatgacgg taaatggccc gcctggcatt atgcccagta 240
catgacctta tgggactttc ctacttggca gtacatctac gtattagtca tcgctattac 300
catggtgatg cggttttggc agtacatcaa tgggcgtgga tagcggtttg actcacgggg 360
atttccaagt ctccacccca ttgacgtcaa tgggagtttg ttttggcacc aaaatcaacg 420
ggactttcca aaatgtcgta acaactccgc cccattgacg caaatgggcg gtaggcgtgt 480
acggtgggag gtctatataa gcagagctcg tttagtgaac cgtcagatcg cctggagacg 540
ccatccacgc tgttttgacc tccatagaag acaccgggac cgatccagcc tccggactct 600
agcctaggct tttgcaaaaa gctatttagg tgacactata aaggtacgc ctgcaggtac 660
cgagctcgga tccagtaccc ttcaccatga gcatccagaa gtccaccaac agcagcagcc 720
tggccgaagt gatcgaccgg atcctggaca aagggcatcgt gatcgacgcc ttcgccgag 780
tgtccgtcgt gggcatcgag atcctgacca tcgaggccag agtcgtgatc gccagcgtgg 840
acacctggct gagatatgcc gaagccgtgg gcctgctgcg ggacagcccg gttcagcatc 900
gcctgcccga gcggagcaac agctctgagg gacagccccg gttcagcatc tgaactaaat 960
cgcactgtcg gcgtcccccc ctaacgttac tggccgaagc cgcttggaat aaggccggtg 1020
tgcgtttgtc tatatgttat tttccaccat attgccgtct tttggcaatg tgagggcccg 1080
gaaacctggc cctgtcttct tgacgagcat tcctaggggt cttcccctc tcgccaaagg 1140
aatgcaaggt ctgttgaatg tcgtgaagga agcagttcct ctggaagctt cttgaagaca 1200
aacaacgtct gtagcgaccc tttgcaggca gcggaacccc ccacctggcg acaggtgcct 1260
ctgcggccaa aagccacgtg tataagatac acctgcaaag gcggcacaac cccagtgcca 1320
cgttgtgagt tggatagttg tggaaagagt caaatggctc tcctcaagcg tattcaacaa 1380
ggggctgaag gatgcccaga aggtacccca ttgtatggga tctgatctgg ggcctcggtg 1440
cacatgcttt acatgtgttt agtcgaggtt aaaaaacgtc taggcccccc gaaccacggg 1500
gacgtggttt cctttgaaa aacacgatga taatatggcc acaaccgtgg ccgtggaaca 1560
caacatgcag agcagcacca tcgtggacgt gctggaaaaa tcctggacaa agggcgtcgt 1620
gatcgccggg gacatcacgt gggaatcgc cgacgtagta ctgctgacca tcaagatccg 1680
gctgatcgtg gccagcgtgg acaaggccaa agaaatcggc atggattggt gggagaacga 1740
cccctacctg agcagcaagg gcgccaacaa caaggccctg aagaggaaa acaagatgct 1800
gcacgagcgg ctgaaaacac tggaagagaa gatcgagaca aagcgcggtg ccccgggatc 1860
tggcgcaaca aatttagtc tttaaagca ggcaggagac gtcgaggaaa accctggacc 1920
cgtgagcgag acaaacgaga caggcatcta catcttcagc gccatccaga cagacaagga 1980
tgaggaattc ggcgccgtgg aagtggaagg gaccaaggct gagacattcc tgatccggta 2040
taaggacgcc gccatggtgg ccgcgaagt gcccatgaag atctaccacc ccaaccggca 2100
gaacctgcta atgaccaga atgccgtggc cgccatcatg acaagaacg acaccgtgat 2160
ccccatcagc ttcggcaacg tgttcaagag caaagaggac gtgaaggtgc tcctggaaaa 2220
cctgtaccc cagttcgaga agctgttccc cgccatcaag gaaaagatcg aagtgcaagt 2280
gaaggtgatc ggcaagaaag agtggctcga aaagaaagtg aacgagaacc cgagctgga 2340
aaagtgtcc gccagcgtga agggcaagag cgagggccgct ggctactacg agagaatcca 2400
gctgggcggc atgcccagag atgttcac aagcctgcag aaagagtga aaccgacgt 2460
gttcagcccc ctggaagaag ccgccgaggc cgccaaagcc aatgagccta caggcgaaac 2520
aatgctgctg aacgccagct tcctgatcaa cagagaggat gaggccaagt tcgacgagaa 2580
```

```
agtcaatgag gcccacgaga actggaagga taaggccgac ttccactaca gcggcccctg   2640
gcccgcctac aacttcgtga acatccggct gaaggtggaa gagaagggg cacctggctc   2700
gggagcgacc aacttctcat tactcaaaca agccggagac gttgaggaga atccaggccc   2760
tgtgctgcac aagctcgtga ccgcccccat caacctggtc gtgaagatcg gcgagaaggt   2820
gcaggaagag gccgacaagc agctgtacga cctgcccacc atccagcaga agctgatcca   2880
gctgcagatg atgttcgagc tgggcgagat ccccgaggag gccttccagg aaaaagagga   2940
cgaactgctg atgagatacg agatcgccaa gcggcgcgag attgagcagt gggaagaact   3000
gacccagaag cggaatgagg aaagcggtgc cccgggatct ggcgcaacaa atttagtct   3060
tttaaagcag gcaggagacg tcgaggaaaa ccctgaccc gtgggcgagc tgctgtacct   3120
ctacggcctg atccccacca aagaggccgc tgctatcgag cccttcccat tctacaaggg   3180
cttcgacggc gagcacagcc tgtaccctat cgccttcgac caagtgaccg ccgtggtgtt   3240
caagctggac gccgacacct acagcgagaa agtgatccag gaaaagatgg aacaggacat   3300
gagctggctg caggaaaagg ccttccacca ccacgagaca gtggccgccc tgtatgagga   3360
attcaccatc atcccctga agttctgcac catctataag ggagaggaat ccctgcaggc   3420
cgccatcgag atcaacaaag agaagatcga aaactccctg accctgctgc agggcaacga   3480
ggaatggaac gtgaagatct actgcgacga caccgagctg aagaagggca tcagcgagac   3540
aaacgagagc gtgaaggcca agaagcagga aatcagccac ctgagcccg gcagacagtt   3600
cttcgacaag aagaagattg accgctcat cgagaaagag ctggaactgc acaagaacaa   3660
agtgtgcgag gaaatccacg acaagctgat tgagctgagc ctctacgact ccgtgaagaa   3720
gaactggtcc aaggacgtga caggcgctgc cgaacagatg gcctggaaca gcgtgttcct   3780
gctgcccagc ctgcagatca ccaagttcgt gaacgagatc gaggaactcc agcagcggct   3840
ggagaacaag ggatggaagt tcgaagtgac cggcccctgg cctccctacc acttcagcag   3900
ctttgccggg gcacctggct cgggagcgac caacttctca ttactcaaac aagccggaga   3960
cgttgaggag aatccaggcc ctgtgcagcc cgtgtcccag gccaacggca gaatccacct   4020
ggatcccgat caggccgaac agggactggc ccagctcgtg atgaccgtga tcgagctgct   4080
gcggcagatc gtggaacggc acgccatgag aagagtggaa ggcggcaccc tgaccgacga   4140
gcagatcgag aatctgggaa tcgccctgat gaacctggaa gagaagatgg acgagctgaa   4200
agaggtgttc ggactggacg ccgaggacct gaacatcgac ctgggccctc tgggcagcct   4260
gctgtgatcg agtctagagg gccccgtggc tgtaatctag aggatccctc gaggggccca   4320
agcttacgcg tgcatgcgac gtcatagctc tctccctata gtgagtcgta ttataagcta   4380
gcttgggatc tttgtgaagg aaccttactt ctgtggtgtg acataattgg acaaactacc   4440
tacagagatt taaagctcta aggtaaatat aaattttta agtgtataat gtgttaaact   4500
agctgcatat gcttgctgct tgagagtttt gcttactgag tatgatttat gaaaatatta   4560
tacacaggag ctagtgattc taattgtttg tgtattttag attcacagtc ccaaggctca   4620
tttcaggccc ctcagtcctc acagtctgtt catgatcata atcagccata ccacatttgt   4680
agaggtttta cttgctttaa aaaacctccc acacctcccc ctgaacctga acataaaat   4740
gaatgcaatt gttgttgtta acttgtttat tgcagcttat aatggttaca aataaagcaa   4800
tagcatcaca aatttcacaa ataaagcatt ttttcactg cattctagtt gtggtttgtc   4860
caaactcatc aatgtatctt atcatgtctg gatc                                4894

SEQ ID NO: 456          moltype = AA  length = 127
FEATURE                 Location/Qualifiers
REGION                  1..127
                        note = synthetic polypeptide
source                  1..127
                        mol_type = protein
                        organism = synthetic construct
SEQUENCE: 456
MGSLTKLLLL PIMGPLNGVV WIAEQIQERT NTEFDAQENL HKQLLSLQLS FDIGEIGEEE    60
FEIQEEEILL KIQALEEEAR LELEAEQEEA RLELEAEQED FEYHLNSQQK LIKINISSCY  120
LSIDGRK                                                             127

SEQ ID NO: 457          moltype = AA  length = 60
FEATURE                 Location/Qualifiers
REGION                  1..60
                        note = synthetic polypeptide
source                  1..60
                        mol_type = protein
                        organism = synthetic construct
SEQUENCE: 457
MPVNKQYQDE QQQVSLCEAL DRVLNKGVVI VADITISVAN IDLIYLSLQA LVSSVEAKNR    60

SEQ ID NO: 458          moltype = AA  length = 61
FEATURE                 Location/Qualifiers
REGION                  1..61
                        note = synthetic polypeptide
source                  1..61
                        mol_type = protein
                        organism = synthetic construct
SEQUENCE: 458
MSGNKKLTHS TDSTTVADLL ERLLDKGVVI SGDIRIRLVE VELLTLEIRL LICSVDKAVE    60
M                                                                    61

SEQ ID NO: 459          moltype = AA  length = 72
FEATURE                 Location/Qualifiers
REGION                  1..72
                        note = synthetic polypeptide
source                  1..72
                        mol_type = protein
```

```
                         organism = synthetic construct
SEQUENCE: 459
MTVVPAQQTG GGGSSGLYDV LELVLDRGLV IDAFVRVSLV GIEILKIDVR VVVASVDTYL    60
RFAEACNRLD LE                                                       72

SEQ ID NO: 460           moltype = AA   length = 72
FEATURE                  Location/Qualifiers
REGION                   1..72
                         note = synthetic polypeptide
source                   1..72
                         mol_type = protein
                         organism = synthetic construct
SEQUENCE: 460
MITYDDEVVC APRAGTLYDV LELILDRGMV IDVFVRVSLV GIEILKVDAR IVVASVDTYL    60
RFAEACNRLD LE                                                       72

SEQ ID NO: 461           moltype = AA   length = 72
FEATURE                  Location/Qualifiers
REGION                   1..72
                         note = synthetic polypeptide
source                   1..72
                         mol_type = protein
                         organism = synthetic construct
SEQUENCE: 461
MTVSSQSMNR APKPSSLADV LDVVLDRGIV IDAYARVALV GIEVLTADAR VVIATVDTYL    60
RFAEAVNRLD LA                                                       72

SEQ ID NO: 462           moltype = AA   length = 61
FEATURE                  Location/Qualifiers
REGION                   1..61
                         note = synthetic polypeptide
source                   1..61
                         mol_type = protein
                         organism = synthetic construct
SEQUENCE: 462
MTINKSNDCS SLAEVVDRIL DKGVVIDVFA RISVIGIELI TIEARIVIAS VDTWLRYAEA    60
V                                                                   61

SEQ ID NO: 463           moltype = AA   length = 60
FEATURE                  Location/Qualifiers
REGION                   1..60
                         note = synthetic polypeptide
source                   1..60
                         mol_type = protein
                         organism = synthetic construct
SEQUENCE: 463
MVSQSPDSSS LAEVLDRILD KGIVVDTWAR VSLVGIEILA IEARVVVASV DTFLHYAEEI    60

SEQ ID NO: 464           moltype = AA   length = 58
FEATURE                  Location/Qualifiers
REGION                   1..58
                         note = synthetic polypeptide
source                   1..58
                         mol_type = protein
                         organism = synthetic construct
SEQUENCE: 464
MAQPDSSSLA EVLDRVLDKG VVVDVYARLS LVGIEILTVE ARVVAASVDT FLHYAEEI     58

SEQ ID NO: 465           moltype = AA   length = 58
FEATURE                  Location/Qualifiers
REGION                   1..58
                         note = synthetic polypeptide
source                   1..58
                         mol_type = protein
                         organism = synthetic construct
SEQUENCE: 465
MVQPDSSSLA EVLDRVLDKG VVVDVWARIS LVGIEILTVE ARVAASVDT FLHYAEEI      58

SEQ ID NO: 466           moltype = AA   length = 58
FEATURE                  Location/Qualifiers
REGION                   1..58
                         note = synthetic polypeptide
source                   1..58
                         mol_type = protein
                         organism = synthetic construct
SEQUENCE: 466
MAQPDSSGLA EVLDRVLDKG VVVDVWARVS LVGIEILTVE ARVVAASVDT FLHYAEEI     58

SEQ ID NO: 467           moltype = AA   length = 58
```

```
FEATURE                 Location/Qualifiers
REGION                  1..58
                        note = synthetic polypeptide
source                  1..58
                        mol_type = protein
                        organism = synthetic construct
SEQUENCE: 467
MAQPDSSSLA EVLDRVLDKG VVVDVWARIS LVGIEILTVE ARVVAASVDT FLHYAEEI        58

SEQ ID NO: 468          moltype = AA  length = 61
FEATURE                 Location/Qualifiers
REGION                  1..61
                        note = synthetic polypeptide
source                  1..61
                        mol_type = protein
                        organism = synthetic construct
SEQUENCE: 468
MSIQKSTDSS SLAEVIDRIL DKGIVIDAFA RVSLVGIEIL TIEARVVIAS VDTWLRYAEA      60
V                                                                      61

SEQ ID NO: 469          moltype = AA  length = 61
FEATURE                 Location/Qualifiers
REGION                  1..61
                        note = synthetic polypeptide
source                  1..61
                        mol_type = protein
                        organism = synthetic construct
SEQUENCE: 469
MSIQKSTNSS SLAEVIDRIL DKGIVIDAFA RVSVVGIEIL TIEARVVIAS VDTWLRYAEA      60
V                                                                      61

SEQ ID NO: 470          moltype = AA  length = 61
FEATURE                 Location/Qualifiers
REGION                  1..61
                        note = synthetic polypeptide
source                  1..61
                        mol_type = protein
                        organism = synthetic construct
SEQUENCE: 470
MAVEKTNSSS SLAEVIDRIL DKGIVIDAWV RVSLVGIELL AIEARIVIAS VETYLKYAEA      60
V                                                                      61

SEQ ID NO: 471          moltype = AA  length = 61
FEATURE                 Location/Qualifiers
REGION                  1..61
                        note = synthetic polypeptide
source                  1..61
                        mol_type = protein
                        organism = synthetic construct
SEQUENCE: 471
MAVEKTNSSS SLAEVIDRIL DKGIVIDAWA RVSLVGIELL AIEARVVIAS VETYLKYAEA      60
V                                                                      61

SEQ ID NO: 472          moltype = AA  length = 62
FEATURE                 Location/Qualifiers
REGION                  1..62
                        note = synthetic polypeptide
source                  1..62
                        mol_type = protein
                        organism = synthetic construct
SEQUENCE: 472
MAKVQKSTDS SSLAEVVDRI LDKGIVIDAW VKVSLVGIEL LSIEARVVIA SVETYLKYAE      60
AI                                                                     62

SEQ ID NO: 473          moltype = AA  length = 112
FEATURE                 Location/Qualifiers
source                  1..112
                        mol_type = protein
                        note = NIES-39
                        organism = Arthrospira platensis
SEQUENCE: 473
MRYKYHRQIQ PKLSAIPRQK SQANLYRNSY LLAVEKKRLT EELEVLQSRS HIIEQRLALI      60
EDQLGELEKD VTQLSVPPSP KPQNNLPVNN PEPPPQSNPT NSSHINTFMV DY             112

SEQ ID NO: 474          moltype =    length =
SEQUENCE: 474
000

SEQ ID NO: 475          moltype =    length =
```

```
SEQUENCE: 475
000

SEQ ID NO: 476          moltype =    length =
SEQUENCE: 476
000

SEQ ID NO: 477          moltype = DNA   length = 12
FEATURE                 Location/Qualifiers
misc_feature            1..12
                        note = synthetic polynucleotide
source                  1..12
                        mol_type = other DNA
                        organism = synthetic construct
SEQUENCE: 477
cccttcacca tg                                                              12

SEQ ID NO: 478          moltype =    length =
SEQUENCE: 478
000

SEQ ID NO: 479          moltype = DNA   length = 57
FEATURE                 Location/Qualifiers
misc_feature            1..57
                        note = synthetic polynucleotide
source                  1..57
                        mol_type = other DNA
                        organism = synthetic construct
SEQUENCE: 479
gctactaact tcagcctcct taaacaggcc ggcgacgtgg aagagaatcc tggctag             57

SEQ ID NO: 480          moltype = DNA   length = 18
FEATURE                 Location/Qualifiers
misc_feature            1..18
                        note = synthetic polynucleotide
source                  1..18
                        mol_type = other DNA
                        organism = synthetic construct
SEQUENCE: 480
ggagcgccag gttccggg                                                        18

SEQ ID NO: 481          moltype = DNA   length = 24
FEATURE                 Location/Qualifiers
source                  1..24
                        mol_type = other DNA
                        organism = Synthetic construct
SEQUENCE: 481
aaaatggccg cgcccagagc gtag                                                 24
```